US012503709B2

(12) United States Patent
Nandi et al.

(10) Patent No.: US 12,503,709 B2
(45) Date of Patent: Dec. 23, 2025

(54) POLIOVIRUS RECEPTOR (PVR/CD155) KNOCKOUT CELLS DERIVED FROM RD (HUMAN RHABDOMYOSARCOMA) CELL LINE BY CRISPR

(71) Applicant: INDIAN COUNCIL OF MEDICAL RESEARCH, New Delhi (IN)

(72) Inventors: S. S. Nandi, Mumbai (IN); Sonali Ankush Sawant, Mumbai (IN); Jagdish Mohan Deshpande, Mumbai (IN)

(73) Assignee: INDIAN COUNCIL OF MEDICAL RESEARCH, New Delhi (IN)

( * ) Notice: Subject to any disclaimer, the term of this patent is extended or adjusted under 35 U.S.C. 154(b) by 1261 days.

(21) Appl. No.: 17/275,991

(22) PCT Filed: Sep. 13, 2019

(86) PCT No.: PCT/IN2019/050671

§ 371 (c)(1),
(2) Date: Mar. 12, 2021

(87) PCT Pub. No.: WO2020/053897

PCT Pub. Date: Mar. 19, 2020

(65) Prior Publication Data

US 2022/0127643 A1 Apr. 28, 2022

(30) Foreign Application Priority Data

Sep. 14, 2018 (IN) ............................ 201811034727

(51) Int. Cl.

*C12N 15/90* (2006.01)
*C07K 14/705* (2006.01)
*C12N 9/22* (2006.01)
*C12N 15/11* (2006.01)

(52) U.S. Cl.

CPC ........ *C12N 15/90* (2013.01); *C07K 14/70596* (2013.01); *C12N 9/22* (2013.01); *C12N 15/111* (2013.01); *C12N 2310/20* (2017.05)

(58) Field of Classification Search

None

See application file for complete search history.

(56) References Cited

PUBLICATIONS

Koike et al. "The poliovirus receptor is produced both as membrane-bound and secreted form" (1990) EMBO J, vol. 9, No. 10, 3217-3224. (Year: 1990).*

Kim et al.; "CRISPR/Cas9-mediated gene knockout screens and target identification via whole-genome sequencing uncover host genes required for picornavirus infection;" J. Biol. Chem.; 2017; pp. 10664-10671; vol. 292, No. 25.

Li et al.; "CD155 loss enhances tumor suppression via combined host and tumor-intrinsic mechanisms;" The Journal of Clinical Investigation; 2018; pp. 2613-2625; vol. 128, No. 6.

Mehndiratta et al.; Poliomyelitis: Historical Facts, Epidemiology, and Current Challenges in Eradication; The Neurohospitalist; 2014; pp. 223-229; vol. 4, No. 4.

Louten; "The World of Viruses;" Chapter 1, Essential Human Virology; 2016; Elsevier Inc.

Oberste et al.; "Typing of Human Enteroviruses by Partial Sequencing of VP1;" Journal of Clinical Microbiology; 1999; pp. 1288-1293; vol. 37, No. 5.

Zell et al.; "ICTV Virus Taxonomy Profile: Picornaviridae;" Journal of General Virology; 2017; pp. 2421-2422; vol. 98.

Mcallister et al.; "Cultivation in Vitro of Cells Derived From a Human Rhabdomyosarcoma;" Cancer; 1969; pp. 520-526; vol. 24, No. 3.

Dec. 26, 2019 Search Report issued in International Patent Application No. PCT/IN2019/050671.

* cited by examiner

*Primary Examiner* — Teresa E Knight
(74) *Attorney, Agent, or Firm* — Oliff PLC

(57) ABSTRACT

A modified polio virus receptor (PVR/CD155) gene including one or more mutations in exons selected from exons 2, 3 and 4 of poliovirus receptor (PVR/CD155) gene having SEQ ID No.1. More specifically, cell lines including the modified gene and method of producing the same using clustered regularly interspaced short palindromic repeats (CRISPR) and CRISPR-associated protein 9 (CRISPR-Cas9) system. The cell line is refractory (non-permissive) to poliovirus and susceptible to most *Enteroviruses* and many other human viruses. Further, the cell line can be applied in the fields of research, diagnostic and therapy.

11 Claims, 45 Drawing Sheets

Specification includes a Sequence Listing.

FIG. 1

```
   1 aataaataac tttttagacc atatatttct tttttttttt tttttttttt tgagacagag
  61 tctcactctg ttgcccagac tggaatgcag tggcatgacg ttgactcact gtaacctcca
 121 cctcaagtga ttcagcctcc caagtagctg ggattacagg tgtgcacgac taccacccag
 181 ctaatttttg tgtttttagt acagatgggg tttcaccatg ttggccaggc tggtcttgaa
 241 ctcctgacct caaaagtgtg ggggaaagaa agagagatca gactgttact gtgtctatgt
 301 agaaaaagga agacataaga aactccattt tgatctgtac taagaaaaat tcttctgcct
 361 tgagatgctg ttaatctgta accctagccc caaccctgtg ctcgcagaaa cgtgtgctgt
 421 attgactcaa ggtttaatgg atttagggct gtgcaggatg tgctttggta aaaatgtgtt
 481 tgcaggcagt atgcttggta aaagtcattg ccattctcca gtctcaagta accagggaca
 541 ccatacactg cggaaggcag cagggacctc tgcccaagaa aacctgggta ttgtccaaga
 601 tttcccccac tgagacagcc tgagagatgg cctcgtggga agggaaagac ctgaccgtcc
 661 cccagcccga cacccataaa aggtctgtgc tgaggaggat tagtgaaaga ggaaggcctc
 721 tctgcagttg agataagagg agggcatctg tctgctgctc gtccctggga atggaatatc
 781 tcggtgtaaa acccgatcgt acattctatt tactgagata ggagaaaact gccttatggc
 841 tggaggtgag acacactggc agcaatactg ctctttactg cactgagata tttgtgtaaa
 901 gtcaaacata aatctggcct acgtgcacat ccaggcacag ctcctttcct taaatttatc
 961 tatgacaccg agtcctttgc tcacgttttc ctgctgaccc tctccccacc attaccctat
1021 agtcctgcca catccccctc accgagatag tagggatagt gatcaataaa tactgaggga
1081 actcagagac cagtgccggt gcaggtcctc acttgctgag caccggtccc ctgggcccac
1141 ttttcttcct ctatactttg tctctgtgtc ttatttcttt tctcagtctc tcgtctccac
1201 cttgtgagaa atactcagag gtgtggaggg gcaggccccc ttcaaaatga tccacccacc
1261 tcagcctccc aaagtgctgg gattacaggc atgagccacc atgcccagcc acatataact
1321 tatttctaaa taacttattt aactaacacc acatgatttt atgacccccct attttatgga
1381 tgagaaaaaa gaggcaagag aagcgatacc agttgcttag gattcccagc taccaattag
1441 tggaagcaga atttgaacca agggagtctc tggagccctc gttcccaatc tcctttctt
1501 cctctccatg tctttctttc tccccctgct cccaggcctc ctacatcaca cccttctgga
1561 caaagcttca catctgacat tttctttttt ggggtggaca gagtcttact ctgtcaccga
1621 ggctggaggg ccgtggcgca atcatggctc atggcagcct caaactcctg ggcttgaggg
1681 atcctccagc ctcagcctcc caagtagctg ggactatggg catgtgccac cacacctggc
1741 taatttttta atttttgtta gaaatacagg gggtgggggc atatctgaaa attttaaacc
1801 ttccctgact gccgtgagca tttctgggta gaagccactc cacgacctta ctttgctggc
1861 atgagtgctg gacagcaatt tggcaacatc ctctagacca caaatgtgca tggcctttgg
1921 cccagcaaat cagcttctgg gaataaatat gacagatact gttacataca tgggaaatgc
1981 catggacatg atgacccagg gaagcacagt ttgcaagtac aaaagggctg gaaacaccca
2041 aaaagcccat cccctgaaga cagtttcaaa aatgacggtg cattcatgta atggaatagt
2101 acacatttgt gaatgaatga atgaggtagc tcaatatatc tgcctatggg aaaatcacca
2161 agatatgttg ctaagtgaaa aacagaaaga tacagaataa tgctaccatt ttattttta
2221 atgggagagg gaagaataag gaaatggatt catatttgct taattacaca agcttcctga
2281 tgatcctttt ggatccagaa gtttgaaaac cacagcatca agaggatgcc cattgggcat
2341 ggtggctcac gcctgtaatc ccagcacttt gggaggctga ggagggtgga tcgcctaagt
2401 tcaggagttc gagaccagcc tggccaacat ggtgaaaccc catctctact aaaaacacaa
2461 aaaaattagc tgggtatggt ggtgcaggcc tgtaattcca gctacttggg aggctgaggc
2521 gcaagaatca cttaagcctg ggaggcggag gctgccgtga gccgagatca cgccattgca
2581 ctccagcttg ggagacagag caagactgtc tcaaaacaaa caaacacaca caaaaaataa
2641 gatgcccatt ggagatctcc attcactatt ttatcagatg atatttcagc acttgagtga
```

FIG. 1..continued

```
2701 agaaaatgtc tacaactggt ccaaacactc aaggaattta gactcttgac agagaaacac
2761 acagaagcaa gcagatatgc cccgaaccaa acttgctttt tcttctaagc ctgcttcttc
2821 ggagcagcct ctgaccctcc agggccctga gaggagtccc tggagccaca ggagcttggg
2881 agcccagaga agtgggggaa tcccagatgg tgacagcatc atccagagga ggaacataac
2941 gatggccaca gattcccaat ttggaaataa ctcagcaaaa caacactgac agaaaattca
3001 gagatttcca agagactagc ctccctgttt ccatttagaa attcacctac atacatccag
3061 ggtgagagac cccaagcatc agatgtgtca tacacaagca tcagatccaa gttagagagg
3121 gcacccgggg acagaaacct ccaagccagc caaaagccaa aggaaggatt ttacagaaag
3181 atacaggaat gtggggccag gcacagtggc tcatgcctgc aatcctagca ctttgggagg
3241 ccgaggtggg aggatcgctt gcggccagga attcaaggcc agcctgagca acatagcgag
3301 atcctatctc tacaacaaat ttaaaaacta gctgggtgtg atcacatatg cctgtggtcc
3361 caactaccca ggaggctgag gcaggagttg agcccaggag gtggaggctg caatgagcaa
3421 tgatggcgcc acttcactcc agcctcagtg aaatagtgag accctgtcta aaaataataa
3481 taaaaataaa aaacatataa agatgtcaga gcacagggac cagagctgtt agtcggcctc
3541 atggagaccc tggccaggac agccacctct ggggaccagg aagtctctca gtttctgtct
3601 ctgagggttt ggctctctga gtctctctgt cacctctcat ttctctctca tctccctctg
3661 tctatgctgt gtctctatct ctttcaatct ctctgtctct gtctcccagc ccttatctct
3721 gagtgtgtct gtttctctct catttctctc tctctctctc tctctttctc tctctctctt
3781 tctctctctc tctttctctc tccccccctcc ctcctcccct ctccctactg caggctggtc
3841 cataaccctt atcttcccca gacctgatgg agttctggta ttaatctgtt tatggtctgt
3901 ttccctccac tagaacacgg tcttcattaa aggcagagat ttttgtctgt cttattttct
3961 gctgtatacc cagtgcctgg gatactggct ggatcaataa atatatgctg aatgaagaat
4021 gaatgaatga ccattctcat gaacattatt atttgatgcc aactgtaaag caacaataat
4081 aataattgtc actgccactg ctgctattgt tggtatatca gctttttatt tagtacaaac
4141 tatatccccg aaattgagct aggcagtttc ttgtttaagt tttacagacc acgctgtgag
4201 gtaagtactg ttagtatgcc ctttttttctt tctttttgag acagagtctc actctgtcgc
4261 ccaggctgga gtgcagaggc ccgatcttgg ctcactgcaa cctctgcctc ccgggtacaa
4321 gtgattttcc tgtcttagcc tccccagtag ctgggattac aggcatgtgc caccatgccg
4381 gctaattttt gtatttttag taaagatggg tttttgccat gttggccagg ctggtcttga
4441 actcctggac ctctggtgat cctcctgcct cggcctccca aagtgctggg attacaggcg
4501 tcagccactg cgcttgctcc cccagccccc aaactttttt tttttttttt gagacaggtc
4561 tggctctgcc acccaagctg tagtgtagtg gcgcaatggt agctcactga agcctctaac
4621 tcctgggttc acacagtcct cctgcctcag cctcccaaaa tgctggaatt caggcctgag
4681 ccaccgcgcc ctactatgcc catttttcag ataaagaatc tgagggccct cgaggagaaa
4741 ccacttgccc aacatgagcc ctggtcttgt ctgaccccaa agcccatggg aagtttaggc
4801 tgcgtggaag gacagcctgg tgggctcagg atctgtccca tcacgagttg gaacctcagc
4861 tctgccactc ggcaaccgcg agccgttagt aagttgctga atctctccgt gtgcctccgt
4921 ttcctcacct ggaatgtggg cgacctcaca caggaagccg cctcttctag tgggcaccga
4981 cggagcgagc gcgcgtctgc agcgggactg agcgccggga gagacctgcg caggcgcagg
5041 cgcgcgggga gggccagcct gggtggccca ccccgcgcct ggcgggactg gccgccaact
5101 cccctccgct ccagtcactt gtctggagct tgaagaagtg ggtattcccc ttcccacccc
5161 aggcactgga ggagcggccc cccggggatt ccaggacctg agctccggga gctggactcg
5221 cagcgaccgc ggcagagcga gcgggcgccg ggaagcgagg agacgcccgc gggaggccca
5281 gctgctcgga gcaactggca tggcccgagc catggccgcc gcgtggccgc tgctgctggt
```

FIG. 1..continued 5341 ggcgctactg gtgctgtcct ggccaccccc aggaaccggt gagtgacccc cgcgcagtcc
(EXON 1)
5401 ggtggcccct gtctggctcc cagctccgca tccaggccgg gtactcgccc ccttgggttc
5461 ccgaagatga cggccccgcc cggcgccacc cacccccccat ctctgccccg gggttggaag
5521 gaacacggtg cgagggtgcg agggcaggac cctcctcttg gccacccgga gagcggtcgg
5581 agttgggtac agaaattcct cgaaattggc agcaacacgg gtcgggcaca agaccctcct
5641 ctgggcccct cggaaagggg atggagttgg gtgaggaaat ttcccaaaaa ggcaagtgaa
5701 tcccggaaaa tcagcagatg gtgacgcatg ccggattacc ttacccaggt tcctgctcag
5761 catacccagg ccataaccca gcagcgtgct ggcaggctgg gtctggacgg aggggatggt
5821 tgatgttggg gaggaggaca gtgggtgaca cttgacacca ttacccctct gacccccaat
5881 gtctgactcc aggggcctgg ccattcattc attctttcat tcttttttttt ttttttttga
5941 gacagtctca ctccatcacc caggctggag tgcagtgtcc tgctctcggc tcactgcagc
6001 ctcctcctcc cgagttcaag cgattctcct gcttcagcct cccgagtagc tcggattaca
6061 gacatgtgcc actatgcctg gctaatattt ttgtattttt agtagataca ggatttcacc
6121 atgttggcca ggctggtctc aaactcctga taaatatata tattatatat tattattata
6181 tattacatat tatagtaata tataataaaa atatataata tatattatag taatatataa
6241 tatataataa aatatataat atatattata gtaatatata atatataata aaatatataa
6301 tatatattat agtaatatat aatatattat aatatattat atatattatt ataatatata
6361 atatgtatat tatatattat atatattatt ataatatata atatgtatat tatatattat
6421 atatattatt ataatatata atatgtatta tgtattatat aattgataat atataataat
6481 atatttctta ataaatatat attaaatata ttatatattt ataacatata ttatttatat
6541 aataaataat atatatttta ttatacattt aaagagtaaa tagataacat attttattat
6601 ttatttatat gttttgtgta tatatatata tatatatata tatatatagt gcgtgtgtgc
6661 gtgtatgtgt gtgtgtgtat gagagagaca aggtcttgct ttgttgccca ggctggagtg
6721 cagtggtaca atcccggctc attgcaaact cgacttccca ggctcaagcg atcctctcac
6781 tgtggcttct ggagtagctg ggattatagg tgctcacctg gctaattttt tttgtatttt
6841 tggtagagac agggtttcgc tatgctgccc aggctggttg cagccaagca cagtggctca
6901 tgcctgtaat cccaacactt tgggaggctg tggtgggagg atcacttgag cttaggaatt
6961 caaaaccagc ctgggcaata tggcaagacc ccatctctac aaaaataatt aactaaataa
7021 aaatttaaaa ataaaaaaga atgcatagga ccatgtttat tagtgtcaat aagcgctgtc
7081 acattttgag gacctactat gtgctagggc ccttagcaga aagattttta tataggacct
7141 gggggattag aggtcagtct ctgaccgccc aagttcaaat cccacctctg ccactaaacc
7201 tctgtatgac ttggaggaca ctatactctg tgtcagtttc cctgtctgta aaatgatgtt
7261 aacagtagtg cttgcctcag gggggctatt tgaggattaa atgccaagat atatgtgaag
7321 cacccagaat agcccctgat ctgtgtcagc accctgtgag tgtccactgt tctaagtctc
7381 attttacaaa ctaggaaaaa gaatcagaga ggttaagtaa ccggcctgaa gctccacagc
7441 agaaaactga agggacccaa aactcctggg ctataattgc cttcctctcg tgcctcaatc
7501 ccccacattc ttccaaccag gacccaccca gagtaataat gcagtgtttc atggatttga
7561 agacccaaga tttctccccg ttttctacat tggggttatt ctaaccccta atggcaagtt
7621 gtgctataaa tgacaacagt catggtatgt gaaacctacg acactggtgc gatgaaaaag
7681 ttctgggcca ggtgcggtgg ctcatacctg taatcccagc actttgggag gccgtagtgg
7741 gaggatcact tgaggtcagg agttcaagac cagcctggcc aacatggtga aaccccatct
7801 ctgctaaaaa caaaaataca aaaaattagc caggtgtggt ggtgggagcc tgtcatccca
7861 gctacgcgga aagctgaggc aggagaaccg cttgaacccc agaggcagag cttgcagtga
7921 gcagagatcg cgccactgca ctccccctgg gcgacagaga gagactccgt ctcaaaaaaa

FIG. 1..continued

```
 7981 aaagagaaga aaagaaaaag ttctggcgct atatagtagt aacggttgca caatatcgtg
 8041 aaatgtacat agtgccactg aactgtatgc tttaaatgac ttaaatggta aatttagttt
 8101 tttaaccaca atatttacca caattttttta aatcagtgat gttgagattc agggaaatac
 8161 ggtaataata gaagaaatac ggtaataaat agccaaagtg aaggagcacg gccaagttgc
 8221 agaccatccc agacgccctt accctcctcg cctgccatgg ccccaactag tgccccagtt
 8281 cccccccccc ccacaccccca cggtccaccg gggatccagg gccccagcgt gcaagtgcac
 8341 gcccaggtgc ccgggctcct ggagcccctc cctatctagt ccaagaacgc cccgggtctg
 8401 acaccttctc ttcggttctc cgcaggggac gtcgtcgtgc aggcgcccac ccaggtgccc
 8461 ggcttcttgg gcgactccgt gacgctgccc tgctacctac aggtgcccaa catggaggtg
 8521 acgcatgtgt cacagctgac ttgggcgcgg catggtgaat ctggcagcat ggccgtcttc
 8581 caccaaacgc agggccccag ctattcggag tccaaacggc tggaattcgt ggcagccaga
 8641 ctgggcgcgg agctgcggaa tgcctcgctg aggatgttcg ggttgcgcgt agaggatgaa
 8701 ggcaactaca cctgcctgtt cgtcacgttc ccgcagggca gcaggagcgt ggatatctgg
 8761 ctccgagtgc ttggtgagca gggggttttg ggaggctga atgaaaggca gagacttggt
(EXON 2)
 8821 gggaggatca gggaagttgg caaagagcgg ggaggcctgg gagggaggga gattccctcc
 8881 acagcagatc ccctggggac aaaaggaggg ggcagcgcaa tgatgtgggg tggggtgggg
 8941 ggaggtgagt gggggagggg gctgcagggc aggaagaaag cagagatctc agggagtaag
 9001 gacccccaag cctgggatca gaaagccctg agggaggagg aggggtatat tggaaaggga
 9061 gctgggaggg gactgggaag gaagggagga ggcctgggtg gcctcttctg ggtccctcct
 9121 ttcctcatct gtaaaagggt tggtgacaac agcatcaccc ttggaaagct gtcctgagtg
 9181 tcatcactgc ctaggaaaga gtctgtctgc cccttggac tgtgtaccca tgagggcaga
 9241 accggggcta ttttgatcac tgctgggccc cagcactttc caccaaacaa tatttattga
 9301 gcacttatta tgtgccattc taagagcttt acctgcatat tctaattgcc tgtgattcca
 9361 tcattatcac ctgttgacag acaaggaaac tgaggcacag acttgcccaa gaccaaagct
 9421 gcagccttag ggcagcggcg cttcaccgct ggcccatgtg agccccttag agctgtcggt
 9481 tactgttact ttatctggtg aagaaggaga aagttgaaac agacagacag gaaagcaagg
 9541 atcctgatac ccaaaagagg aggggatcat gctttcattt tcatgagctc catgaagcct
 9601 tcctcttgga acttgagcaa gaagtctctg tgcctcagtt tcctcatctg tgggataggg
 9661 atcaccatga ggattcaaaa aaactgaccc tttttttttt tttgagatag tttagttctg
 9721 tcgcccaggc tggagtgcag tggtgtgatc atagtaggtc ctcactgcag cctggaactc
 9781 ctgggctcaa gggatgttcc taccctccct gtagctggaa ttacaggaat gtgccaccat
 9841 gcccaacttg ttttctgttt tgttttgttt tgttttgttt tctttttcttt ttaagcttat
 9901 gtgccaagaa ctattccaag cctgtgcatg agaaactcat gaaatgtcaa gggcttggaa
 9961 ctgtgcctag cacacaacac ccaaccaaag gcagctgttg tcactccagc aagcctggga
10021 ttctgggtat catggtttag gatgagggta aaacagaaac agtgagtcaa gttaaggaga
10081 aatcttcggt aaataatata ggtaatgatg gggaaggaag ttccaggttt gggaatcacc
10141 aggatgatga ttaagagatg gtcaaggtgg ttttggaagtc agacagactt tatgtgaaag
10201 cccagctctg ctgcttacag ctgtgtgacc atgggcaagt cacttccctt ctcaacttca
10261 gggctcaggc ttcctctcct ccactgagcc ccagaccagg ataacccccct ttgggtttcc
10321 cctttccagc cctgccctct ccgagtcatc actgcctagg aaagagtccg tctgcccccct
10381 tggactgtgt acccatgagg gcagaaccag ggctattttg gtcactgctg ggctccagca
10441 ctttccacca aacaatattt attgagcgct tattatatac cattctaaga gctttacctg
10501 catattctca ttgcctgtga tcccatcact atcccctgtc aacagacaag gaaactgagg
10561 cacagacttg cccaagacca cacagctgct cagggacaca gctgggattt aaaccatgcc
```

FIG. 1..continued 10621 attctgtatc tttttttttt tttttttttt gagacagaat ctcactctgt cgcccaggct
10681 ggagagcagt gacacaatct cagctcactg caacctccgc ctcccgagtt caagcaattc
10741 tctggtctca gcctcccaag taactgggat tactggcgtg tgccaccata ccctggctaa
10801 tttttaatag agacagtttc tccatgttgg ccaggctggt ctcgaactcc tgaccccaag
10861 tgatccaccc acctcagccc cccaaagttc tgggattata ggcgtgagcc accccgccca
10921 gcaaccatgc catcctgtac ccttaatgaa tgccccctc tgccacggag gggttcattg
10981 aatgacttgt tgcttttgtt cctcttccca gccaagcccc agaacacagc tgaggttcag
11041 aaggtccagc tcactggaga gccagtgccc atggcccgct gcgtctccac aggggtcgc
11101 ccgccagccc aaatcacctg gcactcagac ctgggcggga tgcccaatac gagccaggtg
11161 ccagggttcc tgtctggcac agtcactgtc accagcctct ggatattggt gccctcaagc
11221 caggtggacg gcaagaatgt gacctgcaag gtggagcacg agagctttga gaagcctcag
11281 ctgctgactg tgaacctcac cgtgtactgt gagtgtgccc aagtcagcga tggcaagaac
(EXON 3)
11341 ccctgccggg ctgcccccac cactgtctac actgactccc caaggcactg taggcattgc
11401 ttccatcatc tgcaccggct cccctgactc ctgtctacac gacccacccc cattgtctgc
11461 accagctccc ctgggccgta aacaacactg tccctattgt ctacaccagt ttacttgggc
11521 catagtcaat gctggtaccc agactgtctg ccctggctcc tctagcggct gtctgcacgg
11581 atacctgaca ctctgttgac tcccttgagc acagtctaca ctgcccctaa actgcctaca
11641 cccatttccc caggcaagta tccacaatga ccctccccac attgctacac tggttcttct
11701 ggccacgatc aacactgcct cccttattgt ctacacccac tcccttgtcc ttttctttct
11761 ttcctttttt tttttttttt tttgaaatag agtctcactc tgttacccag gctgcagtac
11821 agtggcatgt tctcggctca ctgtaacctc tgcctcccaa attcaggtgg ttctcctacc
11881 tcagcctccc aaatagctgg gattaaaggt gcacaccacc acacctggct aatttttgta
11941 tttttagtag agacagggtt tcatcatgtt ggccaggctg gtttcgaact cctgacctca
12001 ggtgatcggc ctgcctcagc ctcccaaagt atgctggaat tataggcatg agccactgtg
12061 cccggctttt tgttttgttt tgtttttcct ttggacaggg tctcgctctg tcacccaggc
12121 tggagtgtag gggcatgatc atggttccta cagcctcacc cttccaggct caagcaatcc
12181 ttctccctca gcctcccaag taactgggac tacaggtgca gccaccatgc ccggctaatt
12241 ttacagtttt tttctagaga gagttttgct gtgttgccca ggctggtctc aaactcctag
12301 gcttaagtga tcctcccgcc tcagtctccc gaagtgctga gattacaggc gtgagccact
12361 gcacctggcc ccttgtccat tttctacact gccttaccat tgtctacact ggctctcctg
12421 ggccacagac agcactaacc ccattgtcta caccacctat tttggccacc agctgtgggg
12481 tgttttcact gtctcccata gtgtctacac tggctcctat gacccactgtc tatgtaaaca
12541 ccccactttt tctacactgg ttctcctagg cactctctaa agtgccccct gacactgtct
12601 acactgactc cctggagaac tgtctgcatt cacctcccac attgtatcga ccagttcccc
12661 tgagccacga tcaactgtct ccgccgggtg ctagttgcat tgatcttctc acattgtttg
12721 tgctggctcc cctaagcagt gtctgcagag tcccccagtg tagtctccat gttcctctgc
12781 ccaatattgt ctacactggc tcatctacag gctatccagt ctcaccccac atcaccacac
12841 tggcctcctt gtgttctgtc tgcacagccc cctgacagca tctgtcctga ttctcctgca
12901 cagcgttacc tccaccagct ccctcatggc atcatcgaca ttgacaccca cacatttatc
12961 tccactgaca gccccaggac tctctaacca gtgctgtcta acagaaatag catgcaagct
13021 gcatatagga ttttaaattc tccagcggcc accccattaa aaaattaaaa gaaagaggcc
13081 aggcacggtg gctcacgcct gtaatcccag cactttggga ggccgaggca ggtggatcac
13141 ctgaggtcag gcattcaaga ccagcctgat caatgtggtg aaactctgtc ttcactaaaa
13201 aatacaaaaa ttagccaggc acggtggcgg gtgcctgtaa tcccagctac tcgggagact
13261 gaggcaggag aatcacttga acctgggagg cggagattgc aatgagcgag attacgccat

FIG. 1..continued

```
13321 tgcactccag cctgggcagc agagcaaaac tccatctcaa aaacaagaaa agaaagagat
13381 gaaatttatt tgtttattta tttatctatt tatttatttg agacggggtc ttactctgtc
13441 acccagactg gagtgcagtg gcacagctcc ctgcagcctc aacctcctgg gcttaagtga
13501 tcctcccacc tcagcctcag tctcctgagt agctgggact acaggcgtgt gacaccatgc
13561 ctagctaatt tttgtttttg tttttgtttt tgtttttttg ttttgtgatg aagtcttgct
13621 ctgtcaccca ggctagagtg cagtggcacg atctcaactc actgcagcct ccgcctctcg
13681 ggttcaagtg attctcctgc ctcagcctcc cgagtagctg ggattacaag ccctggccac
13741 agtgcccagc taatttttgt atttgtggta gagacgggat ttcaccatgt tggccaggct
13801 ggtctcaaac tcctgacctc gtgatccacc caccttggcc tcccaaattg ctgggattac
13861 agacgtgagc caccgcaccc ggcctatttt tatttttttct ggagacagga tctccctatg
13921 ttgcccaggc tggtctcaaa ctcctgggct caagtgatcc tcctgcctca acctcccaag
13981 gtactgggat tacaggcatg agccactgtg cctggccaaa attaattttt aataattgcc
14041 tttacttaac ccaatatacc taaaatatta tttcaacttg taattgtttt tttaaaatta
14101 ttcttgagat ctttcccatt tattttgtcc tagtaaagcc tttgaaatct ggtgtgtatt
14161 tcggcctggc tatatttcga gtgctcagta gtcacatgtg gccagtaggt gccatattgg
14221 acagcacaga tctagactaa gctcccacat catctacact ggctcatcca aatactgtct
14281 acacacatac acagagcctg tcttaatttc gtcagctccc ggggacacac tgtatatgtg
14341 ggggtgatct cacccccacc accacatttt caacactggc ccgacaatat agcatctgct
14401 gtaatattcc aacaccctgt ctacactgaa cccatcagta atatccacac aagctcttct
14461 agacatcatt catactgttc ctcccaccat tgtctatact gcttactccc cgccaggcaa
14521 ttggtacaca gattccctca ggtactgtct atactggagt ccctcaacac tgtcactggg
14581 tctgagcgag gaggagatct acactgactc ctacccctcg cccccgaata aaaccctgtc
14641 ccattggcct gcccccaagg acattgaaag gtcttcgctg tcaatcacgt atgggatggc
14701 tgagcagcag cctagagcag ggttatctgg gactctttcc tgcaggactt gtcagaacct
14761 tgaatacact gctgtgtgtt gtgagtggtc attgcctatg agtgagaaaa ggaggaggca
14821 ttttcctgca ggacacccaa gacatgcctg gtccaggcta cccaggaaag ctagtggaga
14881 aaagcagctc ctcagaagcc ttctccatgt ccccactgac caaggactcc taggcttctg
14941 ctctctgtgg caccccatct acctagactc ctcctaggcc tctccagctc ccgctgtttt
15001 ccaaatatcc ccgggccttt tcctgcagtg tcgtgaatcc cgcgtagccc caggcccccc
15061 aaagcctccc agtctctgaa cctctgtatc catttcctgc agacccccca gaggtatcca
15121 tctctggcta tgataacaac tggtaccttg gccagaatga ggccaccctg acctgcgatg
15181 ctcgcagcaa cccagagccc acaggctata attggagcac gtgagtcctg ggtctcaggg
(EXON 4)
15241 aggaggggct gggggtctgg atttctagca ctgagggagg aggggctggg ggcctggact
15301 cctgggactg agggagaagg ggctgggggc ccggacccct gggtctgagg gacgagaggc
15361 tgggagcccg gactcctggg tctgagggaa gaggggctgg gggtctggac ccctgggact
15421 gagagaggag gggctgggcc tggaccoctg ggtctgaggg aggaggggct gggggtctg
15481 gaccccctggg tctgagggag gagaagctgg gagcctggac ccctgggtct gaggcaggac
15541 agactggggc ctggactcct ggtctaagag aggagggaga ttcagaaaag agaaaaagag
15601 gaggttgact tcgggccccc agtgggggc atctctgttt tgacatctct gttttgcggt
15661 tgaggcgttt agcaggtggt tgaatcctgg ctggtggatg cacctgcttt ttggggtgtg
15721 cctgctctgt gcccggtact tcccccgaat cccatgtgac cccatgctgt gcacagtcag
15781 cagctgttgc cctgcccagg ttaaagacca gccacgagag ggcagaagcg gcccttgaat
15841 cagcgctcgg ctcccaaagct ggtcctccgc ctcttggcca agcttgtcta acctgcaggc
15901 cacatcattt gtaaactttc ttaaaacatt atgagacttt ttttttgcga atttttttag
15961 ctcattagct attgttagtg ttagtgtatt ttatgtatgg cccaggacag ttcttcttct
```

FIG. 1..continued 16021 tccaatgtgg cccggggaag ccaaaagatt ggacaccccc actctagact gtaaccacct
16081 caccgtcacc ttgtgtaacc tacttggtta tctctggatg gagcaagtac tatatatccc
16141 cattgtctag atgagaaagt tgaggctcac agcaataaga tttccccaga ttcacactga
16301 ggctgagatc aagagcaagg taagaaaaag gcaaagagat aatacataat tttataatac
16261 ataattttac ataaattaca taattttact gaaccgccct ttttttttaa agaaggggct
16321 ctgttgccga ggctggagtg cagtggcgtg atcatagctc actgcagcct ggacctccct
16381 gggctcaggt gatcctccca cctcagcctc ctgagtagct gggactacag gcacacgcca
16441 ccacactcag ctaattttgt tgtatttttt ttgcagagac agggttttgc cacattgccc
16501 aggctggtct gcaactcctg ggctcaagca atcaacccac ctcagcctcc taaagtgctg
16561 ggattacagg cgtgagccac ctcgcccagc cttaggtctt tttccttatt acaaaaataa
16621 cttgtgtcca ctgtagaaat atcaaacaat ttagttatga gcaaaaagaa gaaagtagtg
16681 cctatagttc aagtgtaccc agccacctcc agaaataccc agtgacccct tattatacat
16741 cctgtctttt ttctctctgt ttctaaacaa agactggaat tatgctgtac atataatttt
16801 gaacctttc gtctgtcttg tgaatacctt tccatgtcaa agcacataga tccacaactc
16861 cattttcccc cacgttgtat taggaagact gtcaaacata cagaaaaatc ataggaattt
16921 tccagtgaac acttaagatt ccaccacgtg gattcccctg ctaacatttt actgtgcttg
16981 ctttatcacg tttctgtgat tccttcagtc cctctattca tccatcaatc atattatgca
17041 tttcagagca cccccagctc tcctgctttt tttttttttt tttttttttt gaggcagggc
17101 ctcactctgt tgctcaggct gtagtgccgt ggcacaatca cagctcactg cagccttgaa
17161 ttcctgggct caagcgatcc tccagcttca gcctcccaga tagctgggac tacaggcaca
17221 caccaccacg cctggctaac ctggcccctt ttttagtgtt gctgggattc caccacttta
17281 aaaaaaaaat tcaaagaata gagacaggat ctcactatgt tgcccaggct ggtcttgaac
17341 tcctgtactc aagcagtcat ctcacctggg cctcccaaag ggcagggaag ggattccaac
17401 atatgtggat gtcatcagtt atttaaccag tccctagtag aggacacaga tgtcattttc
17461 cattttcaac tctgcaaatg ccatggtggt gtccatcccc actggtcact tgtcagcagt
17521 tgtccgtgga aggaattgcc ggtcaaaggt tttcaactgg tgtgatggtg cctttactgt
17581 cctgcctcaa agcaccgcaa ttcaggctct tgagccagat agctgcgttt gcatcccagc
17641 tctgcggagc acccaaagcc tgatgcttcc atctcctcca cctctgttca ttaaaccagt
17701 gttccttgac tacttactgt gtgccgggtg caattaacca acatacgttg gtcgataaaa
17761 cagaccaaat ttcctcccca tatagagctt ccattctagt ggtgaaagaa acaagaagca
17821 agataaagtg tgtagtgtgt gtgcaatggt gataaatacc atggagaaga caaagcagag
17881 aagggaatgg gactgggcgc catgactcat acctgtaatc ccagcacttt gggaggcaga
17941 gatgggagga tcacttgagg ctaggagttc aagaccagcc tggccaacat ggcgaaaccc
18001 catctctacc aaaaaagata caaaaattgg ccgggtgtgg tggcatgcac ctgtagtccc
18061 agctactcag gaggctgagg tgggaagatt ccatgcaccc aggaggtgga ggttgcagtg
18121 agtcaagatg gtgccactgc actccagcct gggtgacaga gtgagacgct gtctcaaaaa
18181 aataataatt aaataaatta aagagaaggg gatgggaagg gtgatcatca cagttgaaat
18241 agggtggcca agtgaggtgt tactaaggtg acatcccagc agaggcctga aggagatgag
18301 ggtgagctct gcgggtgcct aggggaaag cattccagca gagggaacag catgggcaaa
18361 cccatttcta tccatcagtc cctgcataag caaacacccct ggacacctaa ctggagagtt
18421 tgaggaccaa caaagaggcc actgtggatg cagaggcggg agcaaagggg agagtaatgg
18481 aaaacgtggg cagaggtagc aggggccaga tcacgtgggg cctgtgacac cagaagactt
18541 cggtttaact ctgagccagg ctaggccccc agagggtact gagctgaggt atgggaactg
18601 acttagggtt cacaggcgac ctctggtggc catgtgggga acagacgagg gggcgagggc
18661 agaaacggag cccagcgtgg aggcggctgc tgggggccgg gatgcacagc gccagagcag
18721 ggaggtaccg tggaagccct gaggagaggt gggattctgg atggatctta aggcggggcc

FIG. 1..continued

```
18781 gacatgattg gctaatgggt tgggtgtggg catgagagga agggaagagt tgggggggcct
18841 ccagagttgc tctccgctta tgctatagag ggcgtgaggg tttctgggca cgtagtgcgt
18901 gctcaatcac tgtcactccg gacctgcagc agaggccacc tcctcacctt tctgtctctc
18961 ccaggaccat gggtcccctg ccaccctttg ctgtggccca gggcgcccag ctcctgatcc
19021 gtcctgtgga caaaccaatc aacacaactt taatctgcaa cgtcaccaat gccctaggag
19081 ctcgccaggc agaactgacc gtccaggtca aaggtgagga actccctggg tgggaagaac
{EXON 5}
19141 agggaccaaa ggaagaggtc gaggcagggt tccctgtcta atgctctctg gctcccatcc
19201 ttctcctaag ccttctcaca aaaggaccag tggggccagc tttactcccc tgttaactcc
19261 atacctatat cactggtacc gttgttcagc tgcctggata cactccctcc acacacacag
19321 gttgggatag atgtggaatc cctctctctc agggactcag gcctttccaa atatattagg
19381 cagacctcta tcaattgcaa ttgacagaaa cacaaagtag tctaagcaaa aaaaaccaaa
19441 caaaacagga ctttattgaa aattcacctt caggtatggt tagatccagg ggctccaacc
19501 ttgtaaccca ggaactttta ttttatacat ctcttgtctc tgcttttcgt tatactggct
19561 ttattctcag gcaggctctg aagcaagatg gccctcggca gggacaggct cacattctac
19621 cagaatggca acagcaggag aaaaaacata ccactttcag taactgtagc catagtccca
19681 gggctggctc tcattggccc agcttaggcc acagcccacc tatgaaccaa tcatagcagc
19741 cagggagaat ggaatattct gattggccag gcctgtgtca aagtcccatt ctgggcacca
19801 gagggtggga tccattccac ctgaattaaa tagactgagg cagtggagtg gtggctccct
19861 aaggaaattc aagatgccat ttcaagaatg agggataaac cccaagagtt tccttaccta
19921 aatacctgtt tccttctctt tcagagggac ctcccagtga gcactcaggc atgtccccgta
19981 acgccatcat cttcctggtt ctgggaatcc tggtttttct gatcctgctg gggatcggga
20041 tttatttcta ttggtccaaa tgttcccgtg aggtcctttg gcactgtcat ctgtgtccct
20101 cgagtgagca tcaccagagc tgccgtaatt gagcacctac tacgggctct gtgctgagtc
{EXON 6}
20161 cttccagtgt gcctctcact gaatcctcac cccactgcca tgaggtttcc cccatttgac
20221 tgatgagggt gcagagccag ggagccttgt tcactggttc attgattaca tttacaaata
20281 ttatttacag agtgggagaa gagcgtatag ggtcttaatg ccatggtagg gactttggaa
20341 tttaattcag gtgatgtggg agtccctgcc agatggatgg agggtgaaat aatgcttaag
20401 ccctcagcct tactccatct gccttgttca ggagtgactc ctaggaggag gtggcaggaa
20461 ctggcacctc tgatcctcag ctctaaaagg gtctgatgct ttcacacctc aagagatttg
20521 cacaggccgt tcccctgcct ggagcaccct cccatggctc cttctggaga agtgtgccag
20581 ctcattctgt aatcagagga acgatgcttt gctgagcact gtctacatgc cactttgtat
20641 gtataacccc ctcgatttta atttttaatt tttttatta tttatgtatt tatttattta
20701 tttttgagac aggctctcac tgtcgcccag gctggagtgc agtggtgcga tctcggctca
20761 ctgtagcctt cacctcccag gttcaagcga ttctcatgcc tcagcctccc aaggagcggg
20821 gattacaggc acgcactact atgcccagca atttttgtat ttttaggaga gacagcgttt
20881 cgccatgttg gccaggctgg tctcaaaccc ctggtctcct gtgatccacc cgcctcagcc
20941 tcccaaagtg ctgggattac aggcatgagc caccacacct ggcctgtaca atctccttga
21001 atgcccacaa ccacccagca aagtggttct cccgtgagcc ccatgttaca gaggaggaag
21061 tatttgcttt gagagatgaa gttacctgcc aatggtcaaa cagctggaca tggttgttgg
21121 ggagaagaag ccagatcttt gactaccaag cttttccttc aaccactaaa caaagctgct
21181 cccttacaac ccaggcggat actgcctcgt ccaggaagcc ctccctgacc cccaagcatg
21241 agccaagcat ccactaggct ctcccactcc agccttgccc attctgggtc atcaccgtgg
21301 gggacttgtt tgtcatcccc agtggactgt gagccccaag atagcagacc tgaggctgtc
21361 actgtcatga ctgtgtcccc aggaccgcct accactgggc cgggcataaa agaggcactc
```

FIG. 1..continued

```
21421 gaggaagtgt ttgctgagtg attcaatgtg tcagctccag agccagactg cctgtatctg
21481 ggccctaaag ctactgcttg attagtgatg tcaccatagg caaatagctt aagctgtatg
21541 actcagtttc ctcatctgta aaatggggtg atggtaccta ataatacagt agagcactta
21601 acacagtagg tggcacatgg taagccacat actgagtatg tatttgctat gattgttatt
21661 gctattatta ctattattgt tattattaac ataaactgca caagagcagg ctttttgttt
21721 gtttgtttgt gttttgtttt gagacaagat cttgctctgt tgcccagact ggagtagtgc
21781 agtgatgtga tcttggctca ctgcagcctc aacctcccag gctcaggtga ttctcccacc
21841 tcagcctctc gagtagctgg gattataggc gtgcactccc acgcctggct aattttttat
21901 atttttagta gagatggagt ttcgttgtgt tgcccaagct ggtctcaaac tcctagactc
21961 cagcaatccg cccacctcag cctcccagag tgctggaatt ataggtgtga gccaccacgc
22021 ctggccaaga gcaggcattt ttatctgttt tgttcacagc tgtgtcccca gcacctagaa
22081 tgtacctggc acaaagtaga cattcaccat ttgctgaata atactactat ttgctaaata
22141 aacccctgtt gaatagtcta ggaaactgaa cacagagagg ttaagtcact tgtccaagtt
22201 cacacagctc ctaaaggaca gagatggaat ttgaacccat ccatctggtt ccagagccag
22261 gctcgatatt tatggatatt tcataaccaa gtgaataact ggatggctaa atccttagaa
22321 agcacaccct ccatccctgt ctgacacacg tgtataccat taagggaaat ggcaccccca
22381 tgtaatagca gaggcagaac ttgacatttt cagggccctg acacccaggc atgtcttctt
22441 cccatgcttc ccagcattat tccttcctga cgacttcccc tcctatttcc ccaggtacag
22501 agcatgccag cgcctcagct aatggggtaa gtgcagtgtt ggagctaagg agggtgtggg
```

(EXON 7)

```
22561 gtctgcacga actacagacc agacgtcttc agatgcccac ggcccggcct caggagcctg
22621 ggtctttttct cctggtgcct cgagcagcat ttcccaaccc ttcctgctgg gcggaatccc
22681 ctgtagagtt tgctaagacg cagccccaga cagtctggtc tgtgatgggg ccagggaatc
22741 tgcattttaa tatccgctct ctccccccctg ccccacgccc cttcaattcc acccatggcc
22801 acaccttgag aagcactgcc ctggcttcca gggagagagg aggggacggg cctgcagttc
22861 tttgcacatg gggcttcagt gggaagatgt ttgattttgt tcaaaagagc cccaaggcta
22921 aaatttgaaa accctcttct agcatgtctc ctattcagct gtgagcagag agaacagctc
22981 ttcccaggat ccacagacag agggcacaag gtgacagcgt cgggactgag aggggagaga
23041 gactggagct ggcaaggacg tgggcctcca gagttggacc cgaccccaat ggatgaagac
23101 cccctccaaa gagaccagcc tccctccctg tgccagacct caaaacgacg ggggcaggtg
23161 caagttcata ggtctccaag accaccctcc tttcatttgc tagaaggact cactagactc
23221 aggaaagctg ttaggctcac agttacagtt tattacagta aaaggacaga gattaagatc
23281 agcaaaggga ggaggtgcac agcacacgtt ccacgacaga tgaggcgacg gcttccatct
23341 gccctctccc agtggagcca tataggcagc acctgattct cacagcaaca tgtgacaaca
23401 tgcaagaagt actgccaata ctgccaacca gagcagctca ctcgagatct ttgtgtccag
23461 agtttttttgt ttgtcttgag acagggtctg gctctgttgg cagactagag tacagtggtg
23521 agatcacagt tcattgcagc cttgacttct caacgccaag tcatcctccc acctcagcct
23581 cctgagtagc tatgactaca ggtatgtgcc accacgtctg gctaatcttt ttatttatttg
23641 taaagtcgag gtttccctgt gttgcccagg ctggtcttga actcttggct ccaagtgata
23701 cttctgcctt ggcctcccaa agtgctgaat taagcagctc accatccaca cggctgacct
23761 catacatcaa gccaataccg tgtggcccaa gaccccccacc ataaatcaca tcattagcat
23821 gaaccaccca gagtggccca agactccaag atcagctacc aggcaggata ttccaagggc
23881 ttagagatga atgcccagga gctgaggata aagggcccga tctttctttg ggcaaggtta
23941 agcctttact gcatagcaga ccacacagaa gggtgtgggc caccagagaa ttttggtaaa
24001 aatttggcct ctggccttga gcttctaaat ctctgtatcc gtcagatctc tgtggttaca
24061 agaaacagcc actgaccctg gtcaccagag gctgcaattc aggccgcaag cagctgcctg
```

FIG. 1..continued

```
24121 gggggtgtcc aaggagcaga gaaaactact agatgtgaac ttgaagaagg ttgtcagctg
24181 cagccacttt ctgccagcat ctgcagccac tttctgccag catctgcagc cagcaagctg
24241 ggactggcag gaaataaccc acaaaagaag caaatgcaat ttccaacaca agggggaagg
24301 gatgcagggg gaggcagcgc tgcagttgct caggacacgc tcctatagga ccaagatgga
24361 tgcgacccaa gacccaggag gcccagctgc tcagtgcaac tgacaagtta aaaaggtcta
24421 tgatcttgag ggcagacagc agaattcctc ttataaagaa aactgtttgg gaaaatacgt
24481 tgagggagag aagaccttgg gccaagatgc taaatgggaa tgcaaagctt gagctgctct
24541 gcaagagaaa ataagcagga cagaggattt gctctggaca gagatggaag agccgggaac
24601 agagaagtgt ggggaagaga taggaaccag caggatggca ggggcaaagg gctcaagggt
24661 gaggaggcca gtgggacccc acagagttgg ggagataaag gaacattggt tgctttggtg
24721 gcacgtaagc tccttgtctg tctccagcac ccagaatctc attaaagctt atttattgta
24781 cctccagcgg ctgtgtgcaa tggggtcttt tgtggaaatc aaggagcaga caggtttcat
24841 gtgtactgtc accacgtggg atggaaccag aggcatggaa gcaagacgct aaatgaagag
24901 ggccataagg gctgggattc ccaggcacct taggaacagc ttgtcttttt ttttttcctc
24961 tccaaaaaaa atgtttaagg gacggtgtct cctgtcaccc aggctggagt gcaatggcac
25021 gatcatagct cattgcagcc tctaactccg ggctcaagc aatcctccca cctcagccta
25081 ccaagtagct gtgaccacag ctgcccctca ccatgctaag ctaatttttt taattagata
25141 gtacataaac gtcccaaaat tagaagataa aaagacatga gggatccatt ctaatttgtg
25201 tttggagtgt aatggtccag ctccattctt ctgcacatgg atatccagtt ttacacaaca
25261 ctgtgaatgt aatgaatgcc actgaatcat acactcaaaa atagctaaaa tggcaaattg
25321 tctgttatct ctttttaacc accatttttg aaaattaatt ataccaaaaa accattgaat
25381 agtgcacttt atttatttat ttatttgttt atttatttat ttattttaga aataagagtc
25441 tcactttgtt gcccaggctg gagtgcagtg gcgtgatcat ggctcattgc agcctcgacc
25501 tgctgggctc gggctatcct tccatctcag cctcccgagt agctgggact ataggtgggc
25561 gccaccccac ctggctaaat ctctttttaa cttttgtaga gataggcatc tcgctatgtt
25621 gcctaggctg ggctggaact cctgggctca agtgctcctc ctgccttggc ctcccaaagc
25681 gctaggatta cagatgtgag ccaccgcgcc caccctgaac cttacttttt ttgctcagtt
25741 tctggtaatt cagagaatgc ctcctgagtt gttctacacc cacctcatat tccatgggag
25801 ggctgtacag ggctttttta acgaggcctc taaggacagg catttgtatc ctttccagcc
25861 tttcactatt acaatgttgt agtgaataac tttacacact gtcatttatt ttactttttt
25921 ttttttttat tttagagaaa ggaatcttgc catcttgccc aggctggtct caaattcctg
25981 ggcccaaaca atcctcccgc cttggcctcc taaagtactg ggatttatag gcataagcca
26041 ccgtgcctgg ccaatgcaca ctgtcattta gctcatgtta acacctgagt gtaggacaca
26101 ctcctggagg tggaattgct gggccaaaga gtatgtttct tgtcattgtg atagatattg
26161 acaaatgaac cctcacagaa gttgtgctga gttctgttcc caccagcgac gtaggcgatg
26221 accttttctt ggagggaggg ggcatccttg gagtccacag agccaggaat ggagagtggg
26281 cccagaattt tggtataggt gttgtataaa cttatagtaa ggttaagaaa accgcaacta
26341 tccttatcag agacttggcg gggggcaggg tatgatggag atcataagga ggctaaaaca
26401 ctccacaccc tccctctgca ttgctcctgc acgggagtcg ggaatctttt caggttgata
26461 cgatctcacc ttgaggagct gtgaggtccc agaagcctct gggttgcaga ttgcttgggg
26521 tgaaaatgtc tgtgctactg aaatctaact ttttacaaaa aattacgggc tgggcgcagt
26581 ggctcacgcc tgtaatccca gcactttggg aggctgcagc gggtggatca cttgaggtaa
26641 ggagttcaag accagaccat agtgaaaccg tgtctctaca aaaaaaatta gccaggtgtg
26701 gtggtgcatg cttgtaatcc cagctactca gaaggctgag gtgggagaat cccttgaacc
26761 cgggaagtgg aggctggagt aaaccatgat cgagttactg cactccagcc tgggtgacaa
26821 gagtgagact ctgtctccaa aaaaaaaaaa aaaaaaaaaa aaactggatt gcctggctct
```

FIG. 1..continued

```
    26881 actccgggca cagcatgcag gcccagttct gctgctctgc tgtttgttct gctttcctcc
    26941 acatattggc atcaccctct ggtgccaaga tggctgctgc attccaggca tcacatccag
    27001 actcagaccc agagaagctg cccatcccta cctgggtgag cctttgtagg aacgagaaac
    27061 cgcatccagc agcagaaacc tcacccagca gcgtcttttc cggtctcatt caccagcgcc
    27121 gcccaccgct caaccaatcc ctggccaaaa gaatgggacc gcctggaagg ctggaccaaa
    27181 caggacctgc cctctggggc tggggagagg cccagatgaa ggctgcagga caggatggac
    27241 tcctagacct ctgttaccag cagtgactac ctctgtctgg gtggttggaa catgtttgaa
    27301 ttttattcta agtactgtct acaagttctg caataaacct tgactcttct tttaataatg
    27361 caaaaggaat cgaagtgatt gtttgaaagg gagaggaaga aagagagagg gagggaggga
(EXON 8)
    27421 agaatggagg gaggcaggga aggagacaga gagagtagaa tccagccacc ggaaaatcca
    27481 gaatagctgg ctttgcttaa tccatgcctg gaaataactg ctgggtttgc aacaacttct
    27541 ctcccggaga cagaccaagg aaactacaaa actgcaggaa ggattgaagg gccgggcaca
    27601 gtggctcacg cctgtaatcc caacactttg ggaggccgag gtggattgga tcacctgaga
    27661 tcaggagttc gagaccagcc tggccaacat ggtgaaacct cgtctctgct agaaatacaa
    27721 aaataagccg ggcgtggtgg cgtgcgccta tagtcccagc tactcgggag gctgaggcaa
    27781 gagaatcgct tgaacctggg aggtggaggt tgcagtgagc tgagatcgtg ccactgcact
    27841 ccagcttggg cgacagagtg agaatctgtc aggtggattc tgagggtact ctgaccccac
    27901 gaacccagca tgaaatcttc caggcattaa ggaacattga ggatgtggag gattggaaat
    27961 ccctccaggg aaaatacact tctcttgagc agggtcacga ggggtggggg caatgtggga
    28021 ggtggggcaa atccaaagac aaggtcaaca gcaataataa taataacaat gacaggcatt
    28081 tgttgcttgt tggctgggcc tcttgcatac agttctccca acatccctgt gaggtggtga
    28141 tgcttatccc cattctccag gggaggaggc tgaggcccag agaggtgaag tcgtgtgcca
    28201 caaaataccc cagccatatg gtggtagaac caagttttca gccagactca ccagctcaca
    28261 gcagagctgc cctggactct acagccattc agtgtatagc tgggccactc catcattcaa
    28321 ggcagttcaa cgtcaagatt cctgatttgc ctcaacctgg ggcctctaga agataccatc
    28381 acccccaaca agctgaagac gtgtgtccgg aacactcaga cacacacaaa gtgctatgga
    28441 tacaccacac cccgacctag ctgtctcttc ctgatggacc tcactgggta gaaatgcctg
    28501 gcaccgcctg cctcagatcc ctaggtcagc tctcactccc caatagaagt ttctgagatg
    28561 atgatgaaaa cgttctccat ctgtgctgtc caatggagta gccactgatc acttgaggct
    28621 agtgagcact tgaaggtggc tagtttgagg aactgcattt tttaatgcat ttaattttag
    28681 ttactttgaa tatatataca catatataca tttatatata catattcata cacatacatt
    28741 ttacatatat tttatatgta tatgtaatat atatataaat tatatatgta tatattttta
    28801 tatataaata tatattatat atttataaat atataaatat ataatatata ttatatagat
    28861 atataaatat aaatatatat tatatatata aatatataat atatattata taaatatata
    28921 taaattatat atttatatat ataatatata aattatataa attatatata tttatatata
    28981 atatataaat atatataaat tatataattt atatattata tataaattat atattttata
    29041 tataatatat acaatatata taaattatat ataatatata aatatatata aattatatat
    29101 aatatataaa atatatataa attatatata atatataaaa tatatataaa ttatataaat
    29161 ctatataaat atatactata ttataaatat agtatatatt tatatagatt tatattattt
    29221 atatagtata tattatatat ttatatgttt atgtatatat aaatatataa tatataaata
    29281 tatttatata ttatatattt atataatatt ttatataata tgttatatat ttttatataa
    29341 tatattatat atatttatat
```

Fig. 4

```
   1 aataaataac tttttagacc atatatttct tttttttttt tttttttttt tgagacagag
  61 tctcactctg ttgcccagac tggaatgcag tggcatgacg ttgactcact gtaacctcca
 121 cctcaagtga ttcagcctcc caagtagctg ggattacagg tgtgcacgac taccacccag
 181 ctaatttttg tgtttttagt acagatgggg tttcaccatg ttggccaggc tggtcttgaa
 241 ctcctgacct caaaagtgtg ggggaaagaa agagagatca gactgttact gtgtctatgt
 301 agaaaaagga agacataaga aactccattt tgatctgtac taagaaaaat tcttctgcct
 361 tgagatgctg ttaatctgta accctagccc caaccctgtg ctcgcagaaa cgtgtgctgt
 421 attgactcaa ggtttaatgg atttagggct gtgcaggatg tgctttggta aaaatgtgtt
 481 tgcaggcagt atgcttggta aaagtcattg ccattctcca gtctcaagta accagggaca
 541 ccatacactg cggaaggcag cagggacctc tgcccaagaa aacctgggta ttgtccaaga
 601 tttcccccac tgagacagcc tgagagatgg cctcgtggga agggaaagac ctgaccgtcc
 661 cccagcccga cacccataaa aggtctgtgc tgaggaggat tagtgaaaga ggaaggcctc
 721 tctgcagttg agataagagg agggcatctg tctgctgctc gtccctggga atggaatatc
 781 tcggtgtaaa acccgatcgt acattctatt tactgagata ggagaaaact gccttatggc
 841 tggaggtgag acacactggc agcaatactg ctctttactg cactgagata tttgtgtaaa
 901 gtcaaacata aatctggcct acgtgcacat ccaggcacag ctcctttcct taaatttatc
 961 tatgacaccg agtcctttgc tcacgttttc ctgctgaccc tctccccacc attaccctat
1021 agtcctgcca catccccctc accgagatag tagggatagt gatcaataaa tactgaggga
1081 actcagagac cagtgccggt gcaggtcctc acttgctgag caccggtccc ctgggcccac
1141 ttttcttcct ctatactttg tctctgtgtc ttatttcttt tctcagtctc tcgtctccac
1201 cttgtgagaa atactcagag gtgtggaggg gcaggccccc ttcaaaatga tccacccacc
1261 tcagcctccc aaagtgctgg gattacaggc atgagccacc atgcccagcc acatataact
1321 tatttctaaa taacttattt aactaacacc acatgatttt atgacccccct attttatgga
1381 tgagaaaaaa gaggcaagag aagcgatacc agttgcttag gattcccagc taccaattag
1441 tggaagcaga atttgaacca agggagtctc tggagccctc gttcccaatc tcctttttctt
1501 cctctccatg tctttctttc tccccctgct cccaggcctc ctacatcaca cccttctgga
1561 caaagcttca catctgacat tttctttttt ggggtggaca gagtcttact ctgtcaccga
1621 ggctggaggg ccgtggcgca atcatggctc atggcagcct caaactcctg ggcttgaggg
1681 atcctccagc ctcagcctcc caagtagctg ggactatggg catgtgccac cacacctggc
1741 taatttttta atttttttgta gaaatacagg gggtgggggc atatctgaaa attttaaacc
1801 ttccctgact gccgtgagca tttctgggta gaagccactc cacgacctta ctttgctggc
1861 atgagtgctg gacagcaatt tggcaacatc ctctagacca caaatgtgca tggcctttgg
1921 cccagcaaat cagcttctgg gaataaatat gacagatact gttacataca tgggaaatgc
1981 catggacatg atgacccagg gaagcacagt ttgcaagtac aaaagggctg gaaacaccca
2041 aaaagcccat cccctgaaga cagtttcaaa aatgacggtg cattcatgta atggaatagt
2101 acacatttgt gaatgaatga atgaggtagc tcaatatatc tgcctatggg aaaatcacca
2161 agatatgttg ctaagtgaaa aacagaaaga tacagaataa tgctaccatt ttattttttta
2221 atgggagagg gaagaataag gaaatggatt catatttgct taattacaca agcttcctga
2281 tgatcctttt ggatccagaa gtttgaaaac cacagcatca agaggatgcc cattgggcat
2341 ggtggctcac gcctgtaatc ccagcacttt gggaggctga ggagggtgga tcgcctaagt
2401 tcaggagttc gagaccagcc tggccaacat ggtgaaaccc catctctact aaaaacacaa
2461 aaaaattagc tgggtatggt ggtgcaggcc tgtaattcca gctacttggg aggctgaggc
2521 gcaagaatca cttaagcctg ggaggcggag gctgccgtga gccgagatca cgccattgca
2581 ctccagcttg ggagacagag caagactgtc tcaaaacaaa caaacacaca caaaaaaataa
2641 gatgcccatt ggagatctcc attcactatt ttatcagatg atatttcagc acttgagtga
```

FIG. 4..continued 3701 agaaaatgtc tacaactggt ccaaacactc aaggaattta gactcttgac agagaaacac 3761 acagaagcaa gcagatatgc cccgaaccaa acttgctttt tcttctaagc ctgcttcttc 3831 ggagcagcct ctgaccctcc agggccctga gaggagtccc tggagccaca ggagcttggg 2881 agcccagaga agtgggggaa tcccagatgg tgacagcatc atccagagga ggaacataac 2941 gatggccaca gattcccaat ttggaaataa ctcagcaaaa caacactgac agaaaattca 3001 gagatttcca agagactagc ctccctgttt ccatttagaa attcacctac atacatccag 3061 ggtgagagac cccaagcatc agatgtgtca tacacaagca tcagatccaa gttagagagg 3121 gcacccgggg acagaaacct ccaagccagc caaaagccaa aggaaggatt ttacagaaag 3181 atacaggaat gtggggccag gcacagtggc tcatgcctgc aatcctagca ctttgggagg 3241 ccgaggtggg aggatcgctt gcggccagga attcaaggcc agcctgagca acatagcgag 3301 atcctatctc tacaacaaat ttaaaaacta gctgggtgtg atcacatatg cctgtggtcc 3361 caactaccca ggaggctgag gcaggagttg agcccaggag gtggaggctg caatgagcaa 3421 tgatggcgcc acttcactcc agcctcagtg aaatagtgag accctgtcta aaaataataa 3481 taaaaataaa aaacatataa agatgtcaga gcacagggac cagagctgtt agtcggcctc 3541 atggagaccc tggccaggac agccacctct ggggaccagg aagtctctca gtttctgtct 3601 ctgagggttt ggctctctga gtctctctgt cacctctcat ttctctctca tctccctctg 3651 tctatgctgt gtctctatct ctttcaatct ctctgtctct gtctcccagc ccttatctct 3721 gagtgtgtct gtttctctct catttctctc tctctctctc tctctttctc tctctctctt 3781 tctctctctc tctttctctc tccccccctcc ctcctcccct ctccctactg caggctggtc 3841 cataaccctt atcttcccca gacctgatgg agttctggta ttaatctgtt tatggtctgt 3901 ttccctccac tagaacacgg tctttcattaa aggcagagat ttttgtctgt cttattttct 3961 gctgtatacc cagtgcctgg gatactggct ggatcaataa atatatgctg aatgaagaat 4021 gaatgaatga ccattctcat gaacattatt atttgatgcc aactgtaaag caacaataat 4081 aataattgtc actgccactg ctgctattgt tggtatatca gctttttatt tagtacaaac 4141 tatatccccg aaattgagct aggcagtttc ttgtttaagt tttacagacc acgctgtgag 4201 gtaagtactg ttagtatgcc cttttttctt tcttttttgag acagagtctc actctgtcgc 4261 ccaggctgga gtgcagaggc ccgatcttgg ctcactgcaa cctctgcctc ccgggtacaa 4321 gtgatttttcc tgtcttagcc tccccagtag ctgggattac aggcatgtgc caccatgccg 4381 gctaattttt gtatttttag taaagatggg tttttgccat gttggccagg ctggtcttga 4441 actcctggac ctctggtgat cctcctgcct cggcctccca aagtgctggg attacaggcg 4501 tcagccactg cgcttgctcc cccagccccc aaactttttt tttttttttt gagacaggtc 4561 tggctctgcc acccaagctg tagtgtagtg gcgcaatggt agctcactga agcctctaac 4621 tcctgggttc acacagtcct cctgcctcag cctccccaaaa tgctggaatt caggcctgag 4681 ccaccgcgcc ctactatgcc catttttcag ataaagaatc tgagggccct cgaggagaaa 4741 ccacttgccc aacatgagcc ctggtcttgt ctgaccccaa agcccatggg aagtttaggc 4801 tgcgtggaag gacagcctgg tgggctcagg atctgtccca tcacgagttg gaacctcagc 4861 tctgccactc ggcaaccgcg agccgttagt aagttgctga atctctccgt gtgcctccgt 4921 ttcctcacct ggaatgtggg cgacctcaca caggaagccg cctcttctag tgggcaccga 4981 cggagcgagc gcgcgtctgc agcgggactg agcgccggga gagacctgcg caggcgcagg 5041 cgcgcgggga gggccagcct gggtggccca ccccgcgcct ggcgggactg gccgccaact 5101 cccctccgct ccagtcactt gtctggagct tgaagaagtg ggtattcccc ttcccacccc 5161 aggcactgga ggagcggccc cccggggatt ccaggacctg agctccggga gctggactcg 5221 cagcgaccgc ggcagagcga gcgggcgccg ggaagcgagg agacgcccgc gggaggccca 5281 gctgctcgga gcaactggca tggcccgagc catggccgcc gcgtggccgc tgctgctggt 5341 ggcgctactg gtgctgtcct ggccaccccc aggaaccggt gagtgacccc cgcgcagtcc (EXON 1)

FIG. 4..continued

```
5401 ggtggcccct gtctggctcc cagctccgca tccaggccgg gtactcgccc ccttgggttc
5461 ccgaagatga cggccccgcc cggcgccacc cacccccat ctctgccccg gggttggaag
5521 gaacacggtg cgagggtgcg agggcaggac cctcctcttg gccaccccgga gagcggtcgg
5581 agttgggtac agaaattcct cgaaattggc agcaacacgg gtcgggcaca agaccctcct
5641 ctgggcccct cggaaagggg atggagttgg gtgaggaaat ttcccaaaaa ggcaagtgaa
5701 tcccggaaaa tcagcagatg gtgacgcatg ccggattacc ttacccaggt tcctgctcag
5761 catacccagg ccataaccca gcagcgtgct ggcaggctgg gtctggacgg aggggatggt
5821 tgatgttggg gaggaggaca gtgggtgaca cttgacacca ttacccctct gacccccaat
5881 gtctgactcc aggggcctgg ccattcattc atttctttcat tctttttttt ttttttttga
5941 gacagtctca ctccatcacc caggctggag tgcagtgtcc tgctctcggc tcactgcagc
6001 ctcctcctcc cgagttcaag cgattctcct gcttcagcct cccgagtagc tcggattaca
6061 gacatgtgcc actatgcctg gctaatattt ttgtattttt agtagataca ggatttcacc
6121 atgttggcca ggctggtctc aaactcctga taaatatata tattatatat tattattata
6181 tattacatat tatagtaata tataataaaa atatataata tatattatag taatatataa
6241 tatataataa aatatataat atatattata gtaatatata atatataata aaatatataa
6301 tatatattat agtaatatat aatatattat aatatattat atatattatt ataatatata
6361 atatgtatat tatatattat atatattatt ataatatata atatgtatat tatatattat
6421 atatattatt ataatatata atatgtatta tgtattatat aattgataat atataataat
6481 atatttctta ataaatatat attaaatata ttatatattt ataacatata ttatttatat
6541 aataaataat atatatttta ttatacattt aaagagtaaa tagataacat attttattat
6601 ttatttatat gttttgtgta tatatatata tatatatata tatatatagt gcgtgtgtgc
6661 gtgtatgtgt gtgtgtgtat gagagagaca aggtcttgct ttgttgccca ggctggagtg
6721 cagtggtaca atcccggctc attgcaaact cgacttccca ggctcaagcg atcctctcac
6781 tgtggcttct ggagtagctg ggattatagg tgctcacctg gctaattttt tttgtatttt
6841 tggtagagac agggtttcgc tatgctgccc aggctggttg cagccaagca cagtggctca
6901 tgcctgtaat cccaacactt tgggaggctg tggtgggagg atcacttgag cttaggaatt
6961 caaaaccagc ctgggcaata tggcaagacc ccatctctac aaaaataatt aactaaataa
7021 aaatttaaaa ataaaaaaga atgcatagga ccatgtttat tagtgtcaat aagcgctgtc
7081 acattttgag gacctactat gtgctagggc ccttagcaga aagattttta tataggacct
7141 gggggattag aggtcagtct ctgaccgccc aagttcaaat cccacctctg ccactaaacc
7201 tctgtatgac ttggaggaca ctatactctg tgtcagtttc cctgtctgta aaatgatgtt
7261 aacagtagtg cttgcctcag gggggctatt tgaggattaa atgccaagat atatgtgaag
7321 cacccagaat agcccctgat ctgtgtcagc accctgtgag tgtccactgt tctaagtctc
7381 attttacaaa ctaggaaaaa gaatcagaga ggttaagtaa ccggcctgaa gctccacagc
7441 agaaaactga agggacccaa aactcctggg ctataattgc cttcctctcg tgcctcaatc
7501 ccccacattc ttccaaccag gacccaccca gagtaataat gcagtgtttc atggatttga
7561 agacccaaga tttctccccg ttttctacat tggggttatt ctaaccccta atggcaagtt
7621 gtgctataaa tgacaacagt catggtatgt gaaacctacg acactggtgc gatgaaaaag
7681 ttctgggcca ggtgcggtgg ctcatacctg taatcccagc actttgggag gccgtagtgg
7741 gaggatcact tgaggtcagg agttcaagac cagcctggcc aacatggtga aaccccatct
7801 ctgctaaaaa caaaaataca aaaaattagc caggtgtggt ggtgggagcc tgtcatccca
7861 gctacgcgga aagctgaggc aggagaaccg cttgaacccc agaggcagag cttgcagtga
7921 gcagagatcg cgccactgca ctcccctgg gcgacagaga gagactccgt ctcaaaaaaa
7981 aaagagaaga aaagaaaaag ttctggcgct atatagtagt aacggttgca caatatcgtg
8041 aaatgtacat agtgccactg aactgtatgc tttaaatgac ttaaatggta aatttagttt
8101 tttaaccaca atatttacca caattttta aatcagtgat gttgagattc agggaaatac
```

FIG. 4..continued

```
 8161 ggtaataata gaagaaatac ggtaataaat agccaaagtg aaggagcacg gccaagttgc
 8221 agaccatccc agacgccctt accctcctcg cctgccatgg ccccaactag tgccccagtt
 8281 cccccteccc ccacacccca cggtccaccg gggatccagg gccccagcgt gcaagtgcac
 8341 gcccaggtgc ccgggctcct ggagcccctc cctatctagt ccaagaacgc cccgggtctg
 8401 acaccttctc ttcggttctc cgcaggggac gtcgtcgtgc aggcgcccac ccaggtgccc
 8461 ggcttcttgg gcgactccgt gacgctgccc tgctacctac aggtgcccaa catggaggtg
 8521 acgcatgtgt cacagctgac ttgggcgcgg catggtgaat ctggcagcat ggccgtcttc
 8581 caccaaacgc agggccccag ctattcggag tccaaacggc tggaattcgt ggcagccaga
 8641 ctgggcgcgg agctgcggaa tgcctcgctg aggatgttcg ggttgcgcgt agaggatgaa
 8701 ggcaactaca cctgcctgtt cgtcacgttc ccgcagggca gcaggagcgt ggatatctgg
 8761 ctccgagtgc ttggtgagca gggggtttg gggaggctga atgaaaggca gagacttggt
 8821 gggaggatca gggaagttgg caaagagcgg ggaggcctgg gagggaggga gattccctcc
 8881 acagcagatc ccctggggac aaaaggaggg ggcagcgcaa tgatgtgggg tggggtgggg
 8941 ggaggtgagt gggggagggg gctgcagggc aggaagaaag cagagatctc agggagtaag
 9001 gacccccaag cctgggatca gaaagccctg agggaggagg aggggtatat tggaaaggga
 9061 gctgggaggg gactgggaag gaagggagga ggcctgggtg gcctcttctg ggtccctcct
 9121 ttcctcatct gtaaaagggt tggtgacaac agcatcaccc ttggaaagct gtcctgagtg
 9181 tcatcactgc ctaggaaaga gtctgtctgc cccettggac tgtgtaccca tgagggcaga
 9241 accggggcta ttttgatcac tgctgggccc cagcactttc caccaaacaa tatttattga
 9301 gcacttatta tgtgccattc taagagcttt acctgcatat tctaattgcc tgtgattcca
 9361 tcattatcac ctgttgacag acaaggaaac tgaggcacag acttgcccaa gaccaaagct
 9421 gcagccttag ggcagcgggcg cttcaccgct ggcccatgtg agccccttag agctgtcggt
 9481 tactgttact ttatctggtg aagaaggaga aagttgaaac agacagacag gaaagcaagg
 9541 atcctgatac ccaaaagagg aggggatcat gctttcattt tcatgagctc catgaagcct
 9601 tcctcttgga acttgagcaa gaagtctctg tgcctcagtt tcctcatctg tgggataggg
 9661 atcaccatga ggattcaaaa aaactgaccc tttttttttt tttgagatag tttagttctg
 9721 tcgcccaggc tggagtgcag tggtgtgatc atagtaggtc ctcactgcag cctggaactc
 9781 ctgggctcaa gggatgttcc taccctccct gtagctggaa ttacaggaat gtgccaccat
 9841 gcccaacttg ttttctgttt tgttttgttt tgttttgttt tcttttcttt ttaagcttat
 9901 gtgccaagaa ctattccaag cctgtgcatg agaaactcat gaaatgtcaa gggcttggaa
 9961 ctgtgcctag cacacaacac ccaaccaaag gcagctgttg tcactccagc aagcctggga
10021 ttctgggtat catggtttag gatgagggta aaacagaaac agtgagtcaa gttaaggaga
10081 aatcttcggt aaataatata ggtaatgatg gggaaggaag ttccaggttt gggaatcacc
10141 aggatgatga ttaagagatg gtcaaggtgg ttttggagtc agacagactt tatgtgaaag
10201 cccagctctg ctgcttacag ctgtgtgacc atgggcaagt cacttccctt ctcaacttca
10261 gggctcaggc ttcctctcct ccactgagcc ccagaccagg ataacccccct ttgggtttcc
10321 cctttccagc cctgccctct ccgagtcatc actgcctagg aaagagtccg tctgccccct
10381 tggactgtgt acccatgagg gcagaaccag ggctattttg gtcactgctg ggctccagca
10441 cttttccacca aacaatattt attgagcgct tatttatatac cattctaaga gctttacctg
10501 catattctca ttgcctgtga tcccatcact atcccctgtc aacagacaag gaaactgagg
10561 cacagacttg cccaagacca cacagctgct cagggacaca gctgggattt aaaccatgcc
10621 attctgtatc tttttttttt tttttttttt gagacagaat ctcactctgt cgcccaggct
10681 ggagagcagt gacacaatct cagctcactg caacctccgc ctcccgagtt caagcaattc
10741 tctggtctca gcctcccaag taactgggat tactggcgtg tgcccaccata ccctggctaa
10801 tttttaatag agacagtttc tccatgttgg ccaggctggt ctcgaactcc tgaccccaag
10861 tgatccaccc acctcagccc cccaaagttc tgggattata ggcgtgagcc accccgccca
```

FIG. 4..continued 10921 gcaaccatgc catcctgtac ccttaatgaa tgcccccttc tgccacggag gggttcattg
10981 aatgacttgt tgcttttgtt cctcttccca gccaagcccc agaaca~~cagc tggggttcag~~
11041 ~~aaggtccagc tcactggaga gccagtgccc atggcccgct gcgtctccac aggggtcggc~~
11101 ~~ccgccagccc aaatcacctg gcact~~cagac ctgggcggga tgcccaatac gagccaggtg
11161 ccagggttcc tgtctggcac agtcactgtc accagcctct ggatattggt gccctcaagc
11221 caggtggacg gcaagaatgt gacctgcaag gtggagcacg agagctttga gaagcctcag
11281 ctgctgactg tgaacctcac cgtgtactgt gagtgtgccc aagtcagcga tggcaagaac
11341 ccctgccggg ctgcccccac cactgtctac actgactccc caaggcactg taggcattgc
11401 ttccatcatc tgcaccggct cccctgactc ctgtctacac gacccacccc cattgtctgc
11461 accagctccc ctgggccgta aacaacactg tccctattgt ctacaccagt ttacttgggc
11521 catagtcaat gctggtaccc agactgtctg ccctggctcc tctagcggct gtctgcacgg
11581 atacctgaca ctctgttgac tcccttgagc acagtctaca ctgcccctaa actgcctaca
11641 cccatttccc caggcaagta tcccacaatga ccctccccac attgctacac tggttcttct
11701 ggccacgatc aacactgcct cccttattgt ctacacccac tcccttgtcc ttttcttttct
11761 ttcctttttt tttttttttt tttgaaatag agtctcactc tgttacccag gctgcagtac
11821 agtggcatgt tctcggctca ctgtaacctc tgcctcccaa attcaggtgg ttctcctacc
11881 tcagcctccc aaatagctgg gattaaaggt gcacaccacc acacctggct aatttttgta
11941 tttttagtag agacagggtt tcatcatgtt ggccaggctg gtttcgaact cctgacctca
12001 ggtgatcggc ctgcctcagc ctcccaaagt atgctggaat tataggcatg agccactgtg
12061 cccggctttt tgttttgttt tgtttttcct ttggacaggg tctcgctctg tcacccaggc
12121 tggagtgtag gggcatgatc atggttccta cagcctcacc cttccaggct caagcaatcc
12181 ttctccctca gcctcccaag taactgggac tacaggtgca gccaccatgc ccggctaatt
12241 ttacagtttt tttctagaga gagttttgct gtgttgccca ggctggtctc aaactcctag
12301 gcttaagtga tcctcccgcc tcagtctccc gaagtgctga gattacaggc gtgagccact
12361 gcacctggcc cattgtccat tttctacact gccttaccat tgtctacact ggctctcctg
12421 ggccacagac agcactaacc ccattgtcta caccacctat tttggccacc agctgtgggg
12481 tgtttttcact gtctcccata gtgtctacac tggctcctat gaccactgtc tatgtaaaca
12541 ccccactttt tctacactgg ttctcctagg cactctctaa agtgccccct gacactgtct
12601 acactgactc cctggagaac tgtctgcatt cacctcccac attgtatcga ccagttcccc
12661 tgagccacga tcaactgtct ccgccgggtg ctagttgcat tgatcttctc acattgtttg
12721 tgctggctcc cctaagcagt gtctgcagag tccccccagtg tagtctccat gttcctctgc
12781 ccaatattgt ctacactggc tcatctacag gctatccagt ctcaccccac atcaccacac
12841 tggcctcctt gtgttctgtc tgcacagccc cctgacagca tctgtcctga ttctcctgca
12901 cagcgttacc tccaccagct ccctcatggc atcatcgaca ttgacaccca cacatttatc
12961 tccactgaca gccccaggac tctctaacca gtgctgtcta acagaaatag catgcaagct
13021 gcatatagga ttttaaattc tccagcggcc accccattaa aaaattaaaa gaaagaggcc
13081 aggcacggtg gctcacgcct gtaatcccag cactttggga ggccgaggca ggtggatcac
13141 ctgaggtcag gcattcaaga ccagcctgat caatgtggtg aaactctgtc ttcactaaaa
13201 aatacaaaaa ttagccaggc acggtggcgg gtgcctgtaa tcccagctac tcgggagact
13261 gaggcaggag aatcacttga acctgggagg cggagattgc aatgagcgag attacgccat
13321 tgcactccag cctgggcagc agagcaaaac tccatctcaa aaacaagaaa agaaagagat
13381 gaaatttatt tgtttattta tttatctatt tatttatttg agacggggtc ttactctgtc
13441 acccagactg gagtgcagtg gcacagctcc ctgcagcctc aacctcctgg gcttaagtga
13501 tcctcccacc tcagcctcag tctcctgagt agctgggact acaggcgtgt gacaccatgc
13561 ctagctaatt tttgtttttg tttttgtttt tgtttttttg ttttgtgatg aagtcttgct
13621 ctgtcaccca ggctagagtg cagtggcacg atctcaactc actgcagcct ccgcctctcg

FIG. 4..continued 13681 ggttcaagtg attctcctgc ctcagcctcc cgagtagctg ggattacaag ccctggccac
13741 agtgccccagc taatttttgt atttgtggta gagacgggat ttcaccatgt tggccaggct
13801 ggtctcaaac tcctgacctc gtgatccacc caccttggcc tcccaaattg ctgggattac
13861 agacgtgagc caccgcaccc ggcctatttt tatttttttct ggagacagga tctccctatg
13921 ttgcccaggc tggtctcaaa ctcctgggct caagtgatcc tcctgcctca acctcccaag
13981 gtactgggat tacaggcatg agccactgtg cctggccaaa attaattttt aataattgcc
14041 tttacttaac ccaatatacc taaaatatta tttcaacttg taattgtttt tttaaaatta
14101 ttcttgagat ctttcccatt tattttgtcc tagtaaagcc tttgaaatct ggtgtgtatt
14161 tcggcctggc tatatttcga gtgctcagta gtcacatgtg gccagtaggt gccatattgg
14221 acagcacaga tctagactaa gctcccacat catctacact ggctcatcca aatactgtct
14281 acacacatac acagagcctg tcttaatttc gtcagctccc ggggacacac tgtatatgtg
14341 ggggtgatct cacccccacc accacatttt caacactggc ccgacaatat agcatctgct
14401 gtaatattcc aacaccctgt ctacactgaa cccatcagta atatccacac aagctcttct
14461 agacatcatt catactgttc ctcccaccat tgtctatact gcttactccc cgccaggcaa
14521 ttggtacaca gattccctca ggtactgtct atactggagt ccctcaacac tgtcactggg
14581 tctgagcgag gaggagatct acactgactc ctacccctcg cccccgaata aaaccctgtc
14641 ccattggcct gcccccaagg acattgaaag gtcttcgctg tcaatcacgt atgggatggc
14701 tgagcagcag cctagagcag ggttatctgg gactctttcc tgcaggactt gtcagaacct
14761 tgaatacact gctgtgtgtt gtgagtggtc attgcctatg agtgagaaaa ggaggaggca
14821 ttttcctgca ggacacccaa gacatgcctg gtccaggcta cccaggaaag ctagtggaga
14881 aaagcagctc ctcagaagcc ttctccatgt ccccactgac caaggactcc taggcttctg
14941 ctctctgtgg caccccatct acctagactc ctcctaggcc tctccagctc ccgctgtttt
15001 ccaaatatcc ccgggccttt tcctgcagtg tcgtgaatcc cgcgtagccc caggcccccc
15061 aaagcctccc agtctctgaa cctctgtatc catttcctgc agacccccca gaggtatcca
15121 tctctggcta tgataacaac tggtaccttg gccagaatga ggccaccctg acctgcgatg
15181 ctcgcagcaa cccagagccc acaggctata attggagcac gtgagtcctg ggtctcaggg

(EXON 4)

15241 aggaggggct gggggtctgg atttctagca ctgagggagg aggggctggg ggcctggact
15301 cctgggactg agggagaagg ggctgggggc ccggacccct gggtctgagg gacgagaggc
15361 tgggagcccg gactcctggg tctgagggaa gaggggctgg gggtctggac ccctgggact
15421 gagagaggag gggctgggcc tggaccctg ggtctgaggg aggaggggct gggggtctg
15481 gacccctggg tctgagggag gagaagctgg gagcctggac ccctgggtct gaggcaggac
15541 agactggggc ctggactcct ggtctaagag aggagggaga ttcagaaaag agaaaaagag
15601 gaggttgact tcgggccccc agtgggggc atctctgttt tgacatctct gttttgcggt
15661 tgaggcgttt agcaggtggt tgaatcctgg ctggtggatg cacctgcttt ttggggtgtg
15721 cctgctctgt gccccggtact tcccccgaat cccatgtgac cccatgctgt gcacagttag
15781 cagctgttgc cctgcccagg ttaaagacca gccacgagag ggcagaagcg gcccttgaat
15841 cagcgctcgg ctccaaagct ggtcctccgc ctcttggcca agcttgtcta acctgcaggc
15901 cacatcattt gtaaactttc ttaaaacatt atgagacttt tttttgcga atttttttag
15961 ctcattagct attgttagtg ttagtgtatt ttatgtatgg cccaggacag ttcttcttct
16021 tccaatgtgg cccgggaag ccaaaagatt ggacaccccc actctagact gtaaccacct
16081 caccgtcacc ttgtgtaacc tacttggtta tctctggatg gagcaagtac tatatatccc
16141 cattgtctag atgagaaagt tgaggctcac agcaataaga tttccccaga ttcacactga
16201 ggctgagatc aagagcaagg taagaaaaag gcaaagagat aatacataat tttataatac
16261 ataattttac ataaattaca taattttact gaaccgccct ttttttttaa agaagggggct
16321 ctgttgccga ggctggagtg cagtggcgtg atcatagctc actgcagcct ggacctccct

FIG. 4..continued 16381 gggctcaggt gatcctccca cctcagcctc ctgagtagct gggactacag gcacacgcca 16441 ccacactcag ctaattttgt tgtatttttt ttgcagagac agggttttgc cacattgccc 16501 aggctggtct gcaactcctg ggctcaagca atcaacccac ctcagcctcc taaagtgctg 16561 ggattacagg cgtgagccac ctcgcccagc cttaggtctt tttccttatt acaaaaataa 16621 cttgtgtcca ctgtagaaat atcaaacaat ttagttatga gcaaaaagaa gaaagtagtg 16681 cctatagttc aagtgtaccc agccacctcc agaaataccc agtgacccct tattatacat 16741 cctgtctttt ttctctctgt ttctaaacaa agactggaat tatgctgtac atataatttt 16801 gaaccttttc gtctgtcttg tgaatacctt tccatgtcaa agcacataga tccacaactc 16861 cattttcccc cacgttgtat taggaagact gtcaaacata cagaaaaatc ataggaattt 16921 tccagtgaac acttaagatt ccaccacgtg gattcccctg ctaacatttt actgtgcttg 16981 ctttatcacg tttctgtgat tccttcagtc cctctattca tccatcaatc atattatgca 17041 tttcagagca cccccagctc tcctgctttt tttttttttt tttttttttt gaggcagggc 17101 ctcactctgt tgctcaggct gtagtgccgt ggcacaatca cagctcactg cagccttgaa 17161 ttcctgggct caagcgatcc tccagcttca gcctcccaga tagctgggac tacaggcaca 17221 caccaccacg cctggctaac ctggcccctt ttttagtgtt gctgggattc caccacttta 17281 aaaaaaaaat tcaaagaata gagacaggat ctcactatgt tgcccaggct ggtcttgaac 17341 tcctgtactc aagcagtcat ctcacctggg cctcccaaag ggcagggaag ggattccaac 17401 atatgtggat gtcatcagtt atttaaccag tccctagtag aggacacaga tgtcattttc 17461 cattttcaac tctgcaaatg ccatggtggt gtccatcccc actggtcact tgtcagcagt 17521 tgtccgtgga aggaattgcc ggtcaaaggt tttcaactgg tgtgatggtg cctttactgt 17581 cctgcctcaa agcaccgcaa ttcaggctct tgagccagat agctgcgttt gcatcccagc 17641 tctgcggagc acccaaagcc tgatgcttcc atctcctcca cctctgttca ttaaaccagt 17701 gttccttgac tacttactgt gtgccgggtg caattaacca acatacgttg gtcgataaaa 17761 cagaccaaat ttcctcccca tatagagctt ccattctagt ggtgaaagaa acaagaagca 17821 agataaagtg tgtagtgtgt gtgcaatggt gataaatacc atggagaaga caaagcagag 17881 aagggaatgg gactgggcgc catgactcat acctgtaatc ccagcacttt gggaggcaga 17941 gatgggagga tcacttgagg ctaggagttc aagaccagcc tggccaacat ggcgaaaccc 18001 catctctacc aaaaaagata caaaaattgg ccgggtgtgg tggcatgcac ctgtagtccc 18061 agctactcag gaggctgagg tgggaagatt ccatgcaccc aggaggtgga ggttgcagtg 18121 agtcaagatg gtgccactgc actccagcct gggtgacaga gtgagacgct gtctcaaaaa 18181 aataataatt aaataaatta aagagaaggg gatgggaagg gtgatcatca cagttgaaat 18241 agggtggcca agtgaggtgt tactaaggtg acatcccagc agaggcctga aggagatgag 18301 ggtgagctct gcgggtgcct aggggaaag cattccagca gagggaacag catgggcaaa 18361 cccatttcta tccatcagtc cctgcataag caaacaccct ggacacctaa ctggagagtt 18421 tgaggaccaa caaagaggcc actgtggatg cagaggcggg agcaaagggg agagtaatgg 18481 aaaacgtggg cagaggtagc aggggccaga tcacgtgggg cctgtgacac cagaagactt 18541 cggtttaact ctgagccagg ctaggccccc agagggtact gagctgaggt atgggaactg 18601 acttagggtt cacaggcgac ctctggtggc catgtgggga acagacgagg gggcgagggc 18661 agaaacggag cccagcgtgg aggcggctgc tggggccgg gatgcacagc gccagagcag 18721 ggaggtaccg tggaagccct gaggagaggt gggattctgg atggatctta aggcggggcc 18781 gacatgattg gctaatgggt tgggtgtggg catgagagga agggaagagt tggggggcct 18841 ccagagttgc tctccgctta tgctatagag ggcgtgaggg tttctgggca cgtagtgcgt 18901 gctcaatcac tgtcactccg gacctgcagc agaggccacc tcctcacctt tctgtctctc 18961 ccaggaccat gggtcccctg ccacccttg ctgtggccca gggcgcccag ctcctgatcc 19021 gtcctgtgga caaaccaatc aacacaactt taatctgcaa cgtcaccaat gccctaggag 19081 ctcgccaggc agaactgacc gtccaggtca aaggtgagga actccctggg tgggaagaac

FIG. 4..continued

(EXON 5)

19141 agggaccaaa ggaagaggtc gaggcagggt tccctgtcta atgctctctg gctcccatcc
19201 ttctcctaag ccttctcaca aaaggaccag tggggccagc tttactcccc tgttaactcc
19261 atacctatat cactggtacc gttgttcagc tgcctggata cactccctcc acacacacag
19321 gttgggatag atgtggaatc cctctctctc agggactcag gcctttccaa atatattagg
19381 cagacctcta tcaattgcaa ttgacagaaa cacaaagtag tctaagcaaa aaaaaccaaa
19441 caaaacagga ctttattgaa aattcacctt caggtatggt tagatccagg ggctccaacc
19501 ttgtaaccca ggaactttta ttttatacat ctcttgtctc tgcttttcgt tatactggct
19561 ttattctcag gcaggctctg aagcaagatg gccctcggca gggacaggct cacattctac
19621 cagaatggca acagcaggag aaaaaacata ccactttcag taactgtagc catagtccca
19681 gggctggctc tcattggccc agcttaggcc acagcccacc tatgaaccaa tcatagcagc
19741 cagggagaat ggaatattct gattggccag gcctgtgtca aagtcccatt ctgggcacca
19801 gagggtggga tccattccac ctgaattaaa tagactgagg cagtggagtg gtggctccct
19861 aaggaaattc aagatgccat ttcaagaatg agggataaac cccaagagtt tccttaccta
19921 aatacctgtt tccttctctt tcagagggac ctcccagtga gcactcaggc atgtcccgta
19981 acgccatcat cttcctggtt ctgggaatcc tggtttttct gatcctgctg gggatcggga
20041 tttatttcta ttggtccaaa tgttcccgtg aggtcctttg gcactgtcat ctgtgtccct
20101 cgagtgagca tcaccagagc tgccgtaatt gagcacctac tacgggctct gtgctgagtc

(EXON 6)

20161 cttccagtgt gcctctcact gaatcctcac cccactgcca tgaggtttcc cccatttgac
20221 tgatgagggt gcagagccag ggagccttgt tcactggttc attgattaca tttacaaata
20281 ttatttacag agtgggagaa gagcgtatag ggtcttaatg ccatggtagg gactttggaa
20341 tttaattcag gtgatgtggg agtccctgcc agatggatgg agggtgaaat aatgcttaag
20401 ccctcagcct tactccatct gccttgttca ggagtgactc ctaggaggag gtggcaggaa
20461 ctggcacctc tgatcctcag ctctaaaagg gtctgatgct ttcacacctc aagagatttg
20521 cacaggccgt tcccctgcct ggagcacccct cccatggctc cttctggaga agtgtgccag
20581 ctcattctgt aatcagagga acgatgcttt gctgagcact gtctacatgc cactttgtat
20641 gtataacccc ctcgatttta atttttaatt ttttttatta tttatgtatt tatttattta
20701 tttttgagac aggctctcac tgtcgcccag gctggagtgc agtggtgcga tctcggctca
20761 ctgtagcctt cacctcccag gttcaagcga ttctcatgcc tcagcctccc aaggagcggg
20821 gattacaggc acgcactact atgcccagca atttttgtat ttttaggaga gacagcgttt
20881 cgccatgttg gccaggctgg tctcaaaccc ctggtctcct gtgatccacc cgcctcagcc
20941 tcccaaagtg ctgggattac aggcatgagc caccacacct ggcctgtaca atctccttga
21001 atgcccacaa ccacccagca aagtggttct cccgtgagcc ccatgttaca gaggaggaag
21061 tatttgcttt gagagatgaa gttacctgcc aatggtcaaa cagctggaca tggttgttgg
21121 ggagaagaag ccagatcttt gactaccaag cttttccttc aaccactaaa caaagctgct
21181 cccttacaac ccaggcggat actgcctcgt ccaggaagcc ctccctgacc cccaagcatg
21241 agccaagcat ccactaggct ctcccactcc agccttgccc attctgggtc atcaccgtgg
21301 gggacttgtt tgtcatcccc agtggactgt gagccccaag atagcagacc tgaggctgtc
21361 actgtcatga ctgtgtcccc aggaccgcct accactgggc cgggcataaa agaggcactc
21421 gaggaagtgt ttgctgagtg attcaatgtg tcagctccag agccagactg cctgtatctg
21481 ggccctaaag ctactgcttg attagtgatg tcaccatagg caaatagctt aagctgtatg
21541 actcagtttc ctcatctgta aaatggggtg atggtaccta ataatacagt agagcactta
21601 acacagtagg tggcacatgg taagccacat actgagtatg tatttgctat gattgttatt
21661 gctattatta ctattattgt tattattaac ataaactgca caagagcagg ctttttgttt
21721 gtttgtttgt gttttgtttt gagacaagat cttgctctgt tgcccagact ggagtagtgc

FIG. 4..continued

```
21781 agtgatgtga tcttggctca ctgcagcctc aacctcccag gctcaggtga ttctcccacc
21841 tcagcctctc gagtagctgg gattataggc gtgcactccc acgcctggct aatttttttat
21901 atttttagta gagatggagt ttcgttgtgt tgcccaagct ggtctcaaac tcctagactc
21961 cagcaatccg cccacctcag cctcccagag tgctggaatt ataggtgtga gccaccacgc
22021 ctggccaaga gcaggcattt ttatctgttt tgttcacagc tgtgtcccca gcacctagaa
22081 tgtacctggc acaaagtaga cattcaccat ttgctgaata atactactat ttgctaaata
22141 aacccctgtt gaatagtcta ggaaactgaa cacagagagg ttaagtcact tgtccaagtt
22201 cacacagctc ctaaaggaca gagatggaat ttgaacccat ccatctggtt ccagagccag
22261 gctcgatatt tatggatatt tcataaccaa gtgaataact ggatggctaa atccttagaa
22321 agcacaccct ccatccctgt ctgacacacg tgtataccat taagggaaat ggcacccccca
22381 tgtaatagca gaggcagaac ttgacatttt cagggccctg acacccaggc atgtcttctt
22441 cccatgcttc ccagcattat tccttcctga cgacttcccc tcctatttcc ccaggtacag
22501 agcatgccag cgcctcagct aatggggtaa gtgcagtgtt ggagctaagg agggtgtggg
(EXON 7)
22561 gtctgcacga actacagacc agacgtcttc agatgcccac ggcccggcct caggagcctg
22621 ggtctttttct cctggtgcct cgagcagcat ttcccaaccc ttcctgctgg gcggaatccc
22681 ctgtagagtt tgctaagacg cagccccaga cagtctggtc tgtgatgggg ccagggaatc
22741 tgcattttaa tatccgctct ctccccccctg ccccacgccc cttcaattcc acccatggcc
22801 acaccttgag aagcactgcc ctggcttcca gggagagagg aggggacggg cctgcagttc
22861 tttgcacatg gggcttcagt gggaagatgt ttgattttgt tcaaaagagc cccaaggcta
22921 aaatttgaaa accctcttct agcatgtctc ctattcagct gtgagcagag agaacagctc
22981 ttcccaggat ccacagacag agggcacaag gtgacagcgt cgggactgag aggggagaga
23041 gactggagct ggcaaggacg tgggcctcca gagttggacc cgacccccaat ggatgaagac
23101 cccctccaaa gagaccagcc tccctccctg tgccagacct caaaacgacg gggcaggtg
23161 caagttcata ggtctccaag accaccctcc tttcatttgc tagaaggact cactagactc
23221 aggaaagctg ttaggctcac agttacagtt tattacagta aaaggacaga gattaagatc
23281 agcaaaggga ggaggtgcac agcacacgtt ccacgacaga tgaggcgacg gcttccatct
23341 gccctctccc agtggagcca tataggcagc acctgattct cacagcaaca tgtgacaaca
23401 tgcaagaagt actgccaata ctgccaacca gagcagctca ctcgagatct ttgtgtccag
23461 agtttttgt ttgtcttgag acagggtctg gctctgttgg cagactagag tacagtggtg
23521 agatcacagt tcattgcagc cttgacttct caacgccaag tcatcctccc acctcagcct
23581 cctgagtagc tatgactaca ggtatgtgcc accacgtctg gctaatcttt ttattatttg
23641 taaagtcgag gtttccctgt gttgcccagg ctggtcttga actcttggct ccaagtgata
23701 cttctgcctt ggcctcccaa agtgctgaat taagcagctc accatccaca cggctgacct
23761 catacatcaa gccaataccg tgtggcccaa gacccccacc ataaatcaca tcattagcat
23821 gaaccaccca gagtggccca agactccaag atcagctacc aggcaggata tttccaagggc
23881 ttagagatga atgcccagga gctgaggata aagggcccga tctttctttg ggcaaggtta
23941 agcctttact gcatagcaga ccacacagaa gggtgtgggc caccagagaa ttttggtaaa
24001 aatttggcct ctggccttga gcttctaaat ctctgtatcc gtcagatctc tgtggttaca
24061 agaaacagcc actgaccctg gtcaccagag gctgcaattc aggccgcaag cagctgcctg
24121 gggggtgtcc aaggagcaga gaaaactact agatgtgaac ttgaagaagg ttgtcagctg
24181 cagccacttt ctgccagcat ctgcagccac tttctgccag catctgcagc cagcaagctg
24241 ggactggcag gaaataaccc acaaaagaag caaatgcaat ttccaacaca aggggggaagg
24301 gatgcagggg gaggcagcgc tgcagttgct caggacacgc tcctatagga ccaagatgga
24361 tgcgacccaa gacccaggag gcccagctgc tcagtgcaac tgacaagtta aaaaggtcta
24421 tgatcttgag ggcagacagc agaattcctc ttataaagaa aactgtttgg gaaaatacgt
```

FIG. 4..continued 24481 tgagggagag aagaccttgg gccaagatgc taaatgggaa tgcaaagctt gagctgctct
24541 gcaagagaaa ataagcagga cagaggattt gctctggaca gagatggaag agccgggaac
24601 agagaagtgt ggggaagaga taggaaccag caggatggca ggggcaaagg gctcaagggt
24661 gaggaggcca gtgggacccc acagagttgg ggagataaag gaacattggt tgctttggtg
24721 gcacgtaagc tccttgtctg tctccagcac ccagaatctc attaaagctt atttattgta
24781 cctccagcgg ctgtgtgcaa tggggtcttt tgtggaaatc aaggagcaga caggtttcat
24841 gtgtactgtc accacgtggg atggaaccag aggcatggaa gcaagacgct aaatgaagag
24901 ggccataagg gctgggattc ccaggcacct taggaacagc ttgtcttttt tttttcctc
24961 tccaaaaaaa atgtttaagg gacggtgtct cctgtcaccc aggctggagt gcaatggcac
25021 gatcatagct cattgcagcc tctaactccg gggctcaagc aatcctccca cctcagccta
25081 ccaagtagct gtgaccacag ctgcccctca ccatgctaag ctaatttttt taattagata
25141 gtacataaac gtcccaaaat tagaagataa aaagacatga gggatccatt ctaatttgtg
25201 tttggagtgt aatggtccag ctccattctt ctgcacatgg atatccagtt ttacacaaca
25261 ctgtgaatgt aatgaatgcc actgaatcat acactcaaaa atagctaaaa tggcaaattg
25321 tctgttatct ctttttaacc accatttttg aaaattaatt ataccaaaaa accattgaat
25381 agtgcacttt atttatttat ttatttgttt atttatttat ttattttaga aataagagtc
25441 tcactttgtt gcccaggctg gagtgcagtg gcgtgatcat ggctcattgc agcctcgacc
25501 tgctgggctc gggctatcct tccatctcag cctcccgagt agctgggact ataggtgggc
25561 gccaccccac ctggctaaat ctctttttaa cttttgtaga gataggcatc tcgctatgtt
25621 gcctaggctg ggctggaact cctgggctca agtgctcctc ctgccttggc ctcccaaagc
25681 gctaggatta cagatgtgag ccaccgcgcc caccctgaac cttacttttt ttgctcagtt
25741 tctggtaatt cagagaatgc ctcctgagtt gttctacacc cacctcatat tccatgggag
25801 ggctgtacag ggcttttttta acgaggcctc taaggacagg catttgtatc ctttccagcc
25861 tttcactatt acaatgttgt agtgaataac tttacacact gtcatttatt ttactttttt
25921 ttttttttat tttagagaaa ggaatcttgc catcttgccc aggctggtct caaattcctg
25981 ggcccaaaca atcctcccgc cttggcctcc taaagtactg ggatttatag gcataagcca
26041 ccgtgcctgg ccaatgcaca ctgtcattta gctcatgtta acacctgagt gtaggacaca
26101 ctcctggagg tggaattgct gggccaaaga gtatgtttct tgtcattgtg atagatattg
26161 acaaatgaac cctcacagaa gttgtgctga gttctgttcc caccagcgac gtaggcgatg
26221 accttttttct ggagggaggg ggcatccttg gagtccacag agccaggaat ggagagtggg
26281 cccagaattt tggtataggt gttgtataaa cttatagtaa ggttaagaaa accgcaacta
26341 tccttatcag agacttggcg gggggcaggg tatgatggag atcataagga ggctaaaaca
26401 ctccacaccc tccctctgca ttgctcctgc acgggagtcg ggaatctttt caggttgata
26461 cgatctcacc ttgaggagct gtgaggtccc agaagcctct gggttgcaga ttgcttgggg
26521 tgaaaatgtc tgtgctactg aaatctaact ttttacaaaa aattacgggc tgggcgcagt
26581 ggctcacgcc tgtaatccca gcactttggg aggctgcagc gggtggatca cttgaggtaa
26641 ggagttcaag accagaccat agtgaaaccg tgtctctaca aaaaaattta gccaggtgtg
26701 gtggtgcatg cttgtaatcc cagctactca gaaggctgag gtgggagaat cccttgaacc
26761 cgggaagtgg aggctggagt aaaccatgat cgagttactg cactccagcc tgggtgacaa
26821 gagtgagact ctgtctccaa aaaaaaaaaa aaaaaaaaaa aaactggatt gcctggctct
26881 actccgggca cagcatgcag gcccagttct gctgctctgc tgtttgttct gctttcctcc
26941 acatattggc atcaccctct ggtgccaaga tggctgctgc attccaggca tcacatccag
27001 actcagaccc agagaagctg cccatcccta cctgggtgag cctttgtagg aacgagaaac
27061 cgcatccagc agcagaaacc tcacccagca gcgtcttttc cggtctcatt caccagcgcc
27121 gcccaccgct caaccaatcc ctggccaaaa gaatgggacc gcctggaagg ctggaccaaa
27181 caggacctgc cctctggggc tggggagagg cccagatgaa ggctgcagga caggatggac

FIG. 4..continued

```
27241 tcctagacct ctgttaccag cagtgactac ctctgtctgg gtggttggaa catgtttgaa
27301 ttttattcta agtactgtct acaagttctg caataaacct tgactcttct tttaataatg
27361 caaaaggaat cgaagtgatt gtttgaaagg gagaggaaga aagagagagg gagggaggga
{EXON 8}
27421 agaatggagg gaggcaggga aggagacaga gagagtagaa tccagccacc ggaaaatcca
27481 gaatagctgg ctttgcttaa tccatgcctg gaaataactg ctgggtttgc aacaacttct
27541 ctcccggaga cagaccaagg aaactacaaa actgcaggaa ggattgaagg gccgggcaca
27601 gtggctcacg cctgtaatcc caacactttg ggaggccgag gtggattgga tcacctgaga
27661 tcaggagttc gagaccagcc tggccaacat ggtgaaacct cgtctctgct agaaatacaa
27721 aaataagccg ggcgtggtgg cgtgcgccta tagtcccagc tactcgggag gctgaggcaa
27781 gagaatcgct tgaacctggg aggtggaggt tgcagtgagc tgagatcgtg ccactgcact
27841 ccagcttggg cgacagagtg agaatctgtc aggtggattc tgagggtact ctgaccccac
27901 gaacccagca tgaaatcttc caggcattaa ggaacattga ggatgtggag gattggaaat
27961 ccctccaggg aaaatacact tctcttgagc agggtcacga ggggtggggg caatgtggga
28021 ggtggggcaa atccaaagac aaggtcaaca gcaataataa taataacaat gacaggcatt
28081 tgttgcttgt tggctgggcc tcttgcatac agttctccca acatccctgt gaggtggtga
28141 tgcttatccc cattctccag gggaggaggc tgaggcccag agaggtgaag tcgtgtgcca
28201 caaaataccc cagccatatg gtggtagaac caagttttca gccagactca ccagctcaca
28261 gcagagctgc cctggactct acagccattc agtgtatagc tgggccactc catcattcaa
28321 ggcagttcaa cgtcaagatt cctgatttgc ctcaacctgg ggcctctaga agataccatc
28381 acccccaaca agctgaagac gtgtgtccgg aacactcaga cacacacaaa gtgctatgga
28441 tacacccacac cccgacctag ctgtctcttc ctgatggacc tcactgggta gaaatgcctg
28501 gcaccgcctg cctcagatcc ctaggtcagc tctcactccc caatagaagt ttctgagatg
28561 atgatgaaaa cgttctccat ctgtgctgtc caatggagta gccactgatc acttgaggct
28621 agtgagcact tgaaggtggc tagtttgagg aactgcattt tttaatgcat ttaattttag
28681 ttactttgaa tatatataca catatataca tttatatata catattcata cacatacatt
28741 ttacatatat tttatatgta tatgtaatat atatataaat tatatatgta tatattttta
28801 tatataaata tatattatat atttataaat atataaatat ataatatata ttatatagat
28861 atataaatat aaatatatat tatatatata aatatataat atatattata taaatatata
28921 taaattatat atttatatat ataatatata aattatataa attatatata tttatatata
28981 atatataaat atatataaat tatataattt atatattata tataaattat atattttata
29041 tataatatat acaatatata taaattatat ataatatata aatatatata aattatatat
29101 aatatataaa atatatataa attatatata atatataaaa tatatataaa ttatataaat
29161 ctatataaat atatactata ttataaatat agtatatatt tatatagatt tatattattt
29221 atatagtata tattatatat ttatatgttt atgtatatat aaatatataa tatataaata
29281 tatttatata ttatatattt atataatatt ttatataata tgttatatat ttttatataa
29341 tatattatat atatttatat
```

Fig. 5

```
agtcacttgt ctggagcttg aagaagtggg tattcccctt cccaccccag gcactggagg
        agcggccccc cggggattcc aggacctgag ctccgggagc tggactcgca gcgaccgcgg
        cagagcgagc gggcgccggg aagcgaggag acgcccgcgg gaggcccagc tgctcggagc
        aactggcatg gcccgagcca tggccgccgc gtggccgctg ctgctggtgg cgctactggt
        gctgtcctgg ccacccccag gaaccg(EXON 1)
                    ggga cgtcgtcgtg caggcgccca cccaggt~~gcc~~
    301 ~~cggcttcttg ggcgactccg tgacgctgcc ctgctacc~~ta caggtgccca acatggaggt
    361 gacgcatgtg tcacagctga cttgggcgcg gcatggtgaa tctggcagca tggccgtctt
    421 ccaccaaacg cagggcccca gctattcgga gtccaaacgg ctggaattcg tggcagccag
    481 actgggcgcg gagctgcgga atgcctcgct gaggatgttc gggttgcgcg tagaggatga
    541 aggcaactac acctgcctgt tcgtcacgtt cccgcagggc agcaggagcg tggatatctg
    601 gctccgagtg cttg
(41 nt deletion: ~~gcccggcttcttg ggcgactccg tgacgctgcc ctgctacc~~ in EXON 2)

                 ccaagc cccagaaca~~c agctgaggtt cagaaggtcc agctcactgg~~
    661 ~~agagccagtg cccatggccc gctgcgtctc cacaggggt cgccccgccag cccaaatcac~~
    721 ~~ctggcact~~ca gacctgggcg ggatgcccaa tacgagccag gtgccagggt tcctgtctgg
    781 cacagtcact gtcaccagcc tctggatatt ggtgccctca agccaggtgg acggcaagaa
    841 tgtgacctgc aaggtggagc acgagagctt tgagaagcct cagctgctga ctgtgaacct
    901 caccgtgtac t
(99 nt deletion: ~~c agctgaggtt cagaaggtcc agctcactggagagccagtg cccatggccc~~
~~gctgcgtctc cacaggggt cgccccgccag cccaaatcacctggcact~~ in EXON 3)
                 accccccag aggtatccat ctctggctat gataacaact ggtaccttgg
    961 ccagaatgag gccaccctga cctgcgatgc tcgcagcaac ccagagccca caggctataa
   1021 ttggagcac (EXON 4)
              g accatgggtc ccctgccacc ctttgctgtg gcccagggcg cccagctcct
   1081 gatccgtcct gtggacaaac caatcaacac aactttaatc tgcaacgtca ccaatgccct
   1141 aggagctcgc caggcagaac tgaccgtcca ggtcaaag (EXON 5)
                                      ag ggacctccca gtgagcactc
   1201 aggcatgtcc cgtaacgcca tcatcttcct ggttctggga atcctggttt ttctgatcct
   1261 gctggggatc gggatttatt tctattggtc caaatgttcc cgtgaggtcc tttggcactg
   1321 tcatctgtgt ccctcga (EXON 6)
                    gta cagagcatgc cagcgcctca gctaatgggg (EXON 7)
                                                c atgtctccta
   1381 ttcagctgtg agcagagaga acagctcttc ccaggatcca cagacagagg gcacaaggtg
   1441 acagcgtcgg gactgagagg ggagagagac tggagctggc aaggacgtgg gcctccagag
   1501 ttggacccga ccccaatgga tgaagacccc ctccaaagag accagcctcc ctccctgtgc
   1561 cagacctcaa aacgacgggg gcaggtgcaa gttcataggt ctccaagacc accctccttt
   1621 catttgctag aaggactcac tagactcagg aaagctgtta ggctcacagt tacagtttat
   1681 tacagtaaaa ggacagagat taagatcagc aaagggagga ggtgcacagc acacgttcca
   1741 cgacagatga ggcgacggct tccatctgcc ctctcccagt ggagccatat aggcagcacc
   1801 tgattctcac agcaacatgt gacaacatgc aagaagtact gccaatactg ccaaccagag
   1861 cagctcactc gagatctttg tgtccagagt tttttgtttg tcttgagaca gggtctggct
   1921 ctgttggcag actagagtac agtggtgaga tcacagttca ttgcagcctt gacttctcaa
   1981 cgccaagtca tcctcccacc tcagcctcct gagtagctat gactacaggt atgtgccacc
   2041 acgtctggct aatcttttta ttatttgtaa agtcgaggtt tccctgtgtt gcccaggctg
   2101 gtcttgaact cttggctcca agtgatactt ctgccttggc ctcccaaagt gctgaattaa
```

FIG. 5..continued

```
2161 gcagctcacc atccacacgg ctgacctcat acatcaagcc aataccgtgt ggcccaagac
2221 ccccacccata aatcacatca ttagcatgaa ccacccagag tggcccaaga ctccaagatc
2281 agctaccagg caggatattc caagggctta gagatgaatg cccaggagct gaggataaag
2341 ggcccgatct ttctttgggc aaggttaagc ctttactgca tagcagacca cacagaaggg
2401 tgtgggccac cagagaattt tggtaaaaat ttggcctctg gccttgagct tctaaatctc
2461 tgtatccgtc agatctctgt ggttacaaga aacagccact gaccctggtc accagaggct
2521 gcaattcagg ccgcaagcag ctgcctgggg ggtgtccaag gagcagagaa aactactaga
2581 tgtgaacttg aagaaggttg tcagctgcag ccactttctg ccagcatctg cagccacttt
2641 ctgccagcat ctgcagccag caagctggga ctggcaggaa ataaccccaca aaagaagcaa
2701 atgcaatttc caacacaagg gggaagggat gcagggggag gcagcgctgc agttgctcag
2761 gacacgctcc tataggacca agatggatgc gacccaagac ccaggaggcc cagctgctca
2821 gtgcaactga caagttaaaa aggtctatga tcttgagggc agacagcaga attcctctta
2881 taaagaaaac tgtttgggaa aatacgttga gggagagaag accttgggcc aagatgctaa
2941 atgggaatgc aaagcttgag ctgctctgca agagaaaata agcaggacag aggatttgct
3001 ctggacagag atggaagagc cgggaacaga gaagtgtggg gaagagatag gaaccagcag
3061 gatggcaggg gcaaagggct caagggtgag gaggccagtg ggacccccaca gagttgggga
3121 gataaaggaa cattggttgc tttggtggca cgtaagctcc ttgtctgtct ccagcacccca
3181 gaatctcatt aaagcttatt tattgtacct ccagcggctg tgtgcaatgg ggtcttttgt
3241 ggaaatcaag gagcagacag gtttcatgtg tactgtcacc acgtgggatg gaaccagagg
3301 catggaagca agacgctaaa tgaagagggc cataagggct gggattccca ggcaccttag
3361 gaacagcttg tctttttttt tttcctctcc aaaaaaaatg tttaagggac ggtgtctcct
3421 gtcacccagg ctggagtgca atggcacgat catagctcat tgcagcctct aactccgggg
3481 ctcaagcaat cctcccacct cagcctacca agtagctgtg accacagctg cccctcacca
3541 tgctaagcta atttttttaa ttagatagta cataaacgtc ccaaaattag aagataaaaa
3601 gacatgaggg atccattcta atttgtgttt ggagtgtaat ggtccagctc cattcttctg
3661 cacatggata tccagtttta cacaacactg tgaatgtaat gaatgccact gaatcataca
3721 ctcaaaaata gctaaaatgg caaattgtct gttatctctt tttaaccacc atttttgaaa
3781 attaattata ccaaaaaacc attgaatagt gcactttatt tatttattta tttgtttatt
3841 tatttattta ttttagaaat aagagtctca ctttgttgcc caggctggag tgcagtggcg
3901 tgatcatggc tcattgcagc ctcgacctgc tgggctcggg ctatccttcc atctcagcct
3961 cccgagtagc tgggactata ggtgggcgcc acccccacctg gctaaatctc tttttaactt
4021 ttgtagagat aggcatctcg ctatgttgcc taggctgggc tggaactcct gggctcaagt
4081 gctcctcctg ccttggcctc ccaaagcgct aggattacag atgtgagcca ccgcgcccac
4141 cctgaacctt actttttttg ctcagtttct ggtaattcag agaatgcctc ctgagttgtt
4201 ctacacccac ctcatattcc atgggagggc tgtacagggc tttttaacg aggcctctaa
4261 ggacaggcat ttgtatcctt tccagccttt cactattaca atgttgtagt gaataacttt
4321 acacactgtc atttatttta cttttttttt tttttatttt agagaaagga atcttgccat
4381 cttgcccagg ctggtctcaa attcctgggc ccaaacaatc ctcccgcctt ggcctcctaa
4441 agtactggga tttataggca taagccaccg tgcctggcca atgcacactg tcatttagct
4501 catgttaaca cctgagtgta ggacacactc ctggaggtgg aattgctggg ccaaagagta
4561 tgtttcttgt cattgtgata gatattgaca aatgaaccct cacagaagtt gtgctgagtt
4621 ctgttcccac cagcgacgta ggcgatgacc tttttctgga gggagggggc atccttggag
4681 tccacagagc caggaatgga gagtgggccc agaattttgg tataggtgtt gtataaactt
4741 atagtaaggt taagaaaacc gcaactatcc ttatcagaga cttggcgggg ggcagggtat
4801 gatggagatc ataaggaggc taaaacactc cacaccctcc ctctgcattg ctcctgcacg
4861 ggagtcggga atctttttcag gttgatacga tctcaccttg aggagctgtg aggtcccaga
4921 agcctctggg ttgcagattg cttggggtga aaatgtctgt gctactgaaa tctaactttt
4981 tacaaaaaat tacgggctgg gcgcagtggc tcacgcctgt aatcccagca ctttgggagg
5041 ctgcagcggg tggatcactt gaggtaagga gttcaagacc agaccatagt gaaaccgtgt
5101 ctctacaaaa aaaattagcc aggtgtggtg gtgcatgctt gtaatcccag ctactcagaa
5161 ggctgaggtg ggagaatccc ttgaacccgg gaagtggagg ctggagtaaa ccatgatcga
5221 gttactgcac tccagcctgg gtgacaagag tgagactctg tctccaaaaa aaaaaaaaaa
```

FIG. 5..continued

```
5281 aaaaaaaaaa ctggattgcc tggctctact ccgggcacag catgcaggcc cagttctgct
5341 gctctgctgt ttgttctgct ttcctccaca tattggcatc accctctggt gccaagatgg
5401 ctgctgcatt ccaggcatca catccagact cagacccaga gaagctgccc atccctacct
5461 gggtgagcct ttgtaggaac gagaaaccgc atccagcagc agaaacctca cccagcagcg
5521 tcttttccgg tctcattcac cagcgccgcc caccgctcaa ccaatccctg gccaaaagaa
5581 tgggaccgcc tggaaggctg gaccaaacag gacctgccct ctggggctgg ggagaggccc
5641 agatgaaggc tgcaggacag gatggactcc tagacctctg ttaccagcag tgactacctc
5701 tgtctgggtg gttggaacat gtttgaattt tattctaagt actgtctaca agttctgcaa
5761 taaaccttga ctcttctttt aataatgcaa aa (EXON 8)
```

Figure 6

```
   1 agtcacttgt ctggagcttg aagaagtggg tattcccctt cccaccccag gcactggagg
  61 agcggccccc cggggattcc aggacctgag ctccgggagc tggactcgca gcgaccgcgg
 121 cagagcgagc gggcgccggg aagcgaggag acgcccgcgg gaggcccagc tgctcggagc
 181 aactggcatg gcccgagcca tggccgccgc gtggccgctg ctgctggtgg cgctactggt
 241 gctgtcctgg ccacccccag gaaccg (EXON 1)
                                ggga cgtcgtcgtg caggcgccca cccaggtgcc
 301 cggcttcttg ggcgactccg tgacgctgcc ctgctaccta caggtgccca acatggaggt
 361 gacgcatgtg tcacagctga cttgggcgcg gcatggtgaa tctggcagca tggccgtctt
 421 ccaccaaacg cagggcccca gctattcgga gtccaaacgg ctggaattcg tggcagccag
 481 actgggcgcg gagctgcgga atgcctcgct gaggatgttc gggttgcgcg tagaggatga
 541 aggcaactac acctgcctgt tcgtcacgtt cccgcagggc agcaggagcg tggatatctg
 601 gctccgagtg cttg (EXON 2)
                      ccaagc cccagaacac agctgaggtt cagaaggtcc agctcactgg
 661 agagccagtg cccatggccc gctgcgtctc cacagggggt cgcccgccag cccaaatcac
 721 ctggcactca gacctgggcg ggatgcccaa tacgagccag gtgccagggt tcctgtctgg
 781 cacagtcact gtcaccagcc tctggatatt ggtgccctca agccaggtgg acggcaagaa
 841 tgtgacctgc aaggtggagc acgagagctt tgagaagcct cagctgctga ctgtgaacct
 901 caccgtgtac t (EXON3)
                   accccccag aggtatccat ctctggctat gataacaact ggtaccttgg
 961 ccagaatgag gccaccctga cctgcgatgc tcgcagcaac ccagagccca caggctataa
1021 ttggagcac (EXON 4)
                         g accatgggtc ccctgccacc ctttgctgtg gcccagggcg cccagctcct
1081 gatccgtcct gtggacaaac caatcaacac aactttaatc tgcaacgtca ccaatgccct
1141 aggagctcgc caggcagaac tgaccgtcca ggtcaaag (EXON 5)
                                                  ag ggacctccca gtgagcactc
1201 aggcatgtcc cgtaacgcca tcatcttcct ggttctggga atcctggttt ttctgatcct
1261 gctggggatc gggatttatt tctattggtc caaatgttcc cgtgaggtcc tttggcactg
1321 tcatctgtgt ccctcga (EXON 6)
                               gta cagagcatgc cagcgcctca gctaatgggg (EXON 7)
                                                                 c atgtctccta
1381 ttcagctgtg agcagagaga acagctcttc ccaggatcca cagacagagg gcacaaggtg
1441 acagcgtcgg gactgagagg ggagagagac tggagctggc aaggacgtgg gcctccagag
1501 ttggacccga ccccaatgga tgaagacccc ctccaaagag accagcctcc ctccctgtgc
1561 cagacctcaa aacgacgggg gcaggtgcaa gttcataggt ctccaagacc accctccttt
1621 catttgctag aaggactcac tagactcagg aaagctgtta ggctcacagt tacagtttat
```

FIG. 6..continued

```
1681 tacagtaaaa ggacagagat taagatcagc aaagggagga ggtgcacagc acacgttcca
1741 cgacagatga ggcgacggct tccatctgcc ctctcccagt ggagccatat aggcagcacc
1801 tgattctcac agcaacatgt gacaacatgc aagaagtact gccaatactg ccaaccagag
1861 cagctcactc gagatctttg tgtccagagt tttttgtttg tcttgagaca gggtctggct
1921 ctgttggcag actagagtac agtggtgaga tcacagttca ttgcagcctt gacttctcaa
1981 cgccaagtca tcctcccacc tcagcctcct gagtagctat gactacaggt atgtgccacc
2041 acgtctggct aatcttttta ttatttgtaa agtcgaggtt tccctgtgtt gcccaggctg
2101 gtcttgaact cttggctcca agtgatactt ctgccttggc ctcccaaagt gctgaattaa
2161 gcagctcacc atccacacgg ctgacctcat acatcaagcc aataccgtgt ggcccaagac
2221 ccccacccata aatcacatca ttagcatgaa ccacccagag tggcccaaga ctccaagatc
2281 agctaccagg caggatattc caagggctta gagatgaatg cccaggagct gaggataaag
2341 ggcccgatct ttctttgggc aaggttaagc ctttactgca tagcagacca cacagaaggg
2401 tgtgggccac cagagaattt tggtaaaaat ttggcctctg gccttgagct tctaaatctc
2461 tgtatccgtc agatctctgt ggttacaaga aacagccact gaccctggtc accagaggct
2521 gcaattcagg ccgcaagcag ctgcctgggg ggtgtccaag gagcagagaa aactactaga
2581 tgtgaacttg aagaaggttg tcagctgcag ccactttctg ccagcatctg cagccacttt
2641 ctgccagcat ctgcagccag caagctggga ctggcaggaa ataacccaca aaagaagcaa
2701 atgcaatttc caacacaagg gggaagggat gcaggggggag gcagcgctgc agttgctcag
2761 gacacgctcc tataggacca agatggatgc gacccaagac ccaggaggcc cagctgctca
2821 gtgcaactga caagttaaaa aggtctatga tcttgagggc agacagcaga attcctctta
2881 taaagaaaac tgtttgggaa aatacgttga gggagagaag accttgggcc aagatgctaa
2941 atgggaatgc aaagcttgag ctgctctgca agagaaaata agcaggacag aggatttgct
3001 ctggacagag atggaagagc cgggaacaga gaagtgtggg gaagagatag gaaccagcag
3061 gatggcaggg gcaaagggct caagggtgag gaggccagtg ggaccccaca gagttgggga
3121 gataaaggaa cattggttgc tttggtggca cgtaagctcc ttgtctgtct ccagcaccca
3181 gaatctcatt aaagcttatt tattgtacct ccagcggctg tgtgcaatgg ggtcttttgt
3241 ggaaatcaag gagcagacag gtttcatgtg tactgtcacc acgtgggatg gaaccagagg
3301 catggaagca agacgctaaa tgaagagggc cataagggct gggattccca ggcaccttag
3361 gaacagcttg tctttttttt tttcctctcc aaaaaaaatg tttaagggac ggtgtctcct
3421 gtcacccagg ctggagtgca atggcacgat catagctcat tgcagcctct aactccgggg
3481 ctcaagcaat cctcccacct cagcctacca agtagctgtg accacagctg cccctcacca
3541 tgctaagcta atttttttaa ttagatagta cataaacgtc ccaaaattag aagataaaaa
3601 gacatgaggg atccattcta atttgtgttt ggagtgtaat ggtccagctc cattcttctg
3661 cacatggata tccagtttta cacaacactg tgaatgtaat gaatgccact gaatcataca
3721 ctcaaaaata gctaaaatgg caaattgtct gttatctctt tttaaccacc attttttgaaa
3781 attaattata ccaaaaaacc attgaatagt gcactttatt tatttattta tttgtttatt
3841 tatttattta ttttagaaat aagagtctca ctttgttgcc caggctggag tgcagtggcg
3901 tgatcatggc tcattgcagc ctcgacctgc tgggctcggg ctatccttcc atctcagcct
3961 cccgagtagc tgggactata ggtgggcgcc accccacctg gctaaatctc tttttaactt
4021 ttgtagagat aggcatctcg ctatgttgcc taggctgggc tggaactcct gggctcaagt
4081 gctcctcctg ccttggcctc ccaaagcgct aggattacag atgtgagcca ccgcgcccac
4141 cctgaacctt actttttttg ctcagtttct ggtaattcag agaatgcctc ctgagttgtt
4201 ctacacccac ctcatattcc atgggagggc tgtacagggc tttttaacg aggcctctaa
4261 ggacaggcat ttgtatcctt tccagccttt cactattaca atgttgtagt gaataacttt
4321 acacactgtc atttatttta cttttttttt tttttatttt agagaaagga atcttgccat
4381 cttgcccagg ctggtctcaa attcctgggc ccaaacaatc ctcccgcctt ggcctcctaa
4441 agtactggga tttataggca taagccaccg tgcctggcca atgcacactg tcatttagct
4501 catgttaaca cctgagtgta ggacacactc ctggaggtgg aattgctggg ccaaagagta
4561 tgtttcttgt cattgtgata gatattgaca aatgaacccct cacagaagtt gtgctgagtt
4621 ctgttcccac cagcgacgta ggcgatgacc tttttctgga gggaggggc atccttggag
4681 tccacagagc caggaatgga gagtgggccc agaattttgg tataggtgtt gtataaactt
4741 atagtaaggt taagaaaacc gcaactatcc ttatcagaga cttggcgggg ggcagggtat
```

FIG. 6..continued

```
4801 gatggagatc ataaggaggc taaaacactc cacaccctcc ctctgcattg ctcctgcacg
4861 ggagtcggga atcttttcag gttgatacga tctcaccttg aggagctgtg aggtcccaga
4921 agcctctggg ttgcagattg cttggggtga aaatgtctgt gctactgaaa tctaactttt
4981 tacaaaaaat tacgggctgg gcgcagtggc tcacgcctgt aatcccagca ctttgggagg
5041 ctgcagcggg tggatcactt gaggtaagga gttcaagacc agaccatagt gaaaccgtgt
5101 ctctacaaaa aaaattagcc aggtgtggtg gtgcatgctt gtaatcccag ctactcagaa
5161 ggctgaggtg ggagaatccc ttgaacccgg gaagtggagg ctggagtaaa ccatgatcga
5221 gttactgcac tccagcctgg gtgacaagag tgagactctg tctccaaaaa aaaaaaaaaa
5281 aaaaaaaaaa ctggattgcc tggctctact ccgggcacag catgcaggcc cagttctgct
5341 gctctgctgt ttgttctgct ttcctccaca tattggcatc accctctggt gccaagatgg
5401 ctgctgcatt ccaggcatca catccagact cagacccaga gaagctgccc atccctacct
5461 gggtgagcct ttgtaggaac gagaaaccgc atccagcagc agaaacctca cccagcagcg
5521 tcttttccgg tctcattcac cagcgccgcc caccgctcaa ccaatccctg gccaaaagaa
5581 tgggaccgcc tggaaggctg gaccaaacag gacctgccct ctggggctgg ggagaggccc
5641 agatgaaggc tgcaggacag gatggactcc tagacctctg ttaccagcag tgactacctc
5701 tgtctgggtg gttggaacat gtttgaattt tattctaagt actgtctaca agttctgcaa
5761 taaaccttga ctcttctttt aataatgcaa aa (EXON 8)
```

Figure 7

```
   1 aataaataac tttttagacc atatatttct tttttttttt tttttttttt tgagacagag
  61 tctcactctg ttgcccagac tggaatgcag tggcatgacg ttgactcact gtaacctcca
 121 cctcaagtga ttcagcctcc caagtagctg ggattacagg tgtgcacgac taccacccag
 181 ctaatttttg tgtttttagt acagatgggg tttcaccatg ttggccaggc tggtcttgaa
 241 ctcctgacct caaaagtgtg ggggaaagaa agagagatca gactgttact gtgtctatgt
 301 agaaaaagga agacataaga aactccattt tgatctgtac taagaaaaat tcttctgcct
 361 tgagatgctg ttaatctgta accctagccc caaccctgtg ctcgcagaaa cgtgtgctgt
 421 attgactcaa ggtttaatgg atttagggct gtgcaggatg tgctttggta aaaatgtgtt
 481 tgcaggcagt atgcttggta aaagtcattg ccattctcca gtctcaagta accagggaca
 541 ccatacactg cggaaggcag cagggacctc tgcccaagaa aacctgggta ttgtccaaga
 601 tttcccccac tgagacagcc tgagagatgg cctcgtggga agggaaagac ctgaccgtcc
 661 cccagcccga cacccataaa aggtctgtgc tgaggaggat tagtgaaaga ggaaggcctc
 721 tctgcagttg agataagagg agggcatctg tctgctgctc gtccctggga atggaatatc
 781 tcggtgtaaa acccgatcgt acattctatt tactgagata ggagaaaact gccttatggc
 841 tggaggtgag acacactggc agcaatactg ctctttactg cactgagata tttgtgtaaa
 901 gtcaaacata aatctggcct acgtgcacat ccaggcacag ctcctttcct taaatttatc
 961 tatgacaccg agtcctttgc tcacgttttc ctgctgaccc tctccccacc attaccctat
1021 agtcctgcca catccccctc accgagatag tagggatagt gatcaataaa tactgaggga
1081 actcagagac cagtgccggt gcaggtcctc acttgctgag caccggtccc ctgggcccac
1141 ttttcttcct ctatactttg tctctgtgtc ttatttcttt tctcagtctc tcgtctccac
1201 cttgtgagaa atactcagag gtgtggaggg gcaggccccc ttcaaaatga tccacccacc
1261 tcagcctccc aaagtgctgg gattacaggc atgagccacc atgcccagcc acatataact
1321 tatttctaaa taacttattt aactaacacc acatgatttt atgaccccct attttatgga
1381 tgagaaaaaa gaggcaagag aagcgatacc agttgcttag gattcccagc taccaattag
1441 tggaagcaga atttgaacca agggagtctc tggagccctc gttcccaatc tccttttctt
1501 cctctccatg tctttctttc tccccctgct cccaggcctc ctacatcaca cccttctgga
1561 caaagcttca catctgacat tttctttttt ggggtggaca gagtcttact ctgtcaccga
1621 ggctggaggg ccgtggcgca atcatggctc atggcagcct caaactcctg ggcttgaggg
1681 atcctccagc ctcagcctcc caagtagctg ggactatggg catgtgccac cacacctggc
1741 taatttttta attttttgta gaaatacagg gggtgggggc atatctgaaa attttaaacc
1801 ttccctgact gccgtgagca tttctgggta gaagccactc cacgacctta ctttgctggc
1861 atgagtgctg gacagcaatt tggcaacatc ctctagacca caaatgtgca tggcctttgg
1921 cccagcaaat cagcttctgg gaataaatat gacagatact gttacataca tgggaaatgc
1981 catggacatg atgacccagg gaagcacagt ttgcaagtac aaaagggctg gaaacaccca
2041 aaaagcccat cccctgaaga cagtttcaaa aatgacggtg cattcatgta atggaatagt
2101 acacatttgt gaatgaatga atgaggtagc tcaatatatc tgcctatggg aaaatcacca
2161 agatatgttg ctaagtgaaa aacagaaaga tacagaataa tgctaccatt ttatttttta
2221 atgggagagg gaagaataag gaaatggatt catatttgct taattacaca agcttcctga
2281 tgatcctttt ggatccagaa gtttgaaaac cacagcatca agaggatgcc cattgggcat
2341 ggtggctcac gcctgtaatc ccagcacttt gggaggctga ggagggtgga tcgcctaagt
2401 tcaggagttc gagaccagcc tggccaacat ggtgaaaccc catctctact aaaaacacaa
2461 aaaaattagc tgggtatggt ggtgcaggcc tgtaattcca gctacttggg aggctgaggc
2521 gcaagaatca cttaagcctg ggaggcggag gctgccgtga gccgagatca cgccattgca
```

FIG. 7..continued 2581 ctccagcttg ggagacagag caagactgtc tcaaaacaaa caaacacaca caaaaaataa
2641 gatgcccatt ggagatctcc attcactatt ttatcagatg atatttcagc acttgagtga
2701 agaaaatgtc tacaactggt ccaaacactc aaggaattta gactcttgac agagaaacac
2761 acagaagcaa gcagatatgc cccgaaccaa acttgctttt tcttctaagc ctgcttcttc
2821 ggagcagcct ctgaccctcc agggccctga gaggagtccc tggagccaca ggagcttggg
2881 agcccagaga agtgggggaa tcccagatgg tgacagcatc atccagagga ggaacataac
2941 gatggccaca gattcccaat ttggaaataa ctcagcaaaa caacactgac agaaaattca
3001 gagatttcca agagactagc ctccctgttt ccatttagaa attcacctac atacatccag
3061 ggtgagagac cccaagcatc agatgtgtca tacacaagca tcagatccaa gttagagagg
3121 gcaccccggg acagaaacct ccaagccagc caaaagccaa aggaaggatt ttacagaaag
3181 atacaggaat gtggggccag gcacagtggc tcatgcctgc aatcctagca ctttgggagg
3241 ccgaggtggg aggatcgctt gcggccagga attcaaggcc agcctgagca acatagcgag
3301 atcctatctc tacaacaaat ttaaaaacta gctgggtgtg atcacatatg cctgtggtcc
3361 caactaccca ggaggctgag gcaggagttg agcccaggag gtggaggctg caatgagcaa
3421 tgatggcgcc acttcactcc agcctcagtg aaatagtgag accctgtcta aaaataataa
3481 taaaaataaa aaacatataa agatgtcaga gcacagggac cagagctgtt agtcggcctc
3541 atggagaccc tggccaggac agccacctct ggggaccagg aagtctctca gtttctgtct
3601 ctgagggttt ggctctctga gtctctctgt cacctctcat ttctctctca tctccctctg
3661 tctatgctgt gtctctatct ctttcaatct ctctgtctct gtctcccagc ccttatctct
3721 gagtgtgtct gtttctctct catttctctc tctctctctc tctctttctc tctctctctt
3781 tctctctctc tctttctctc tccccccctcc ctcctcccct ctccctactg caggctggtc
3841 cataaccctt atcttcccca gacctgatgg agttctggta ttaatctgtt tatggtctgt
3901 ttccctccac tagaacacgg tcttcattaa aggcagagat ttttgtctgt cttattttct
3961 gctgtatacc cagtgcctgg gatactggct ggatcaataa atatatgctg aatgaagaat
4021 gaatgaatga ccatttctcat gaacattatt atttgatgcc aactgtaaag caacaataat
4081 aataattgtc actgccactg ctgctattgt tggtatatca gctttttatt tagtacaaac
4141 tatatccccg aaattgagct aggcagtttc ttgtttaagt tttacagacc acgctgtgag
4201 gtaagtactg ttagtatgcc cttttttctt tctttttgag acagagtctc actctgtcgc
4261 ccaggctgga gtgcagaggc ccgatcttgg ctcactgcaa cctctgcctc ccgggtacaa
4321 gtgattttcc tgtcttagcc tccccagtag ctgggattac aggcatgtgc caccatgccg
4381 gctaattttt gtatttttag taaagatggg tttttgccat gttggccagg ctggtcttga
4441 actcctggac ctctggtgat cctcctgcct cggcctccca aagtgctggg attacaggcg
4501 tcagccactg cgcttgctcc cccagccccc aaactttttt tttttttttt gagacaggtc
4561 tggctctgcc acccaagctg tagtgtagtg gcgcaatggt agctcactga agcctctaac
4621 tcctgggttc acacagtcct cctgcctcag cctcccaaaa tgctggaatt caggcctgag
4681 ccaccgcgcc ctactatgcc catttttcag ataaagaatc tgagggccct cgaggagaaa
4741 ccacttgccc aacatgagcc ctggtcttgt ctgaccccaa agcccatggg aagtttaggc
4801 tgcgtggaag gacagcctgg tgggctcagg atctgtccca tcacgagttg gaacctcagc
4861 tctgccactc ggcaaccgcg agccgttagt aagttgctga atctctccgt gtgcctccgt
4921 ttcctcacct ggaatgtggg cgacctcaca caggaagccg cctcttctag tgggcaccga
4981 cggagcgagc gcgcgtctgc agcgggactg agcgccggga gagacctgcg caggcgcagg
5041 cgcgcgggga gggccagcct gggtggccca ccccgcgcct ggcgggactg gccgccaact
5101 cccctccgct ccagtcactt gtctggagct tgaagaagtg ggtattcccc ttcccacccc
5161 aggcactgga ggagcggccc cccggggatt ccaggacctg agctccggga gctggactcg
5221 cagcgacccgc ggcagagcga gcgggcgccg ggaagcgagg agacgcccgc gggaggccca
5281 gctgctcgga gcaactggca tggcccgagc catggccgcc gcgtggccgc tgctgctggt

FIG. 7..continued 5341 ggcgctactg gtgctgtcct ggccaccccc aggaaccggt gagtgacccc cgcgcagtcc
(EXON 1)
5401 ggtggcccct gtctggctcc cagctccgca tccaggccgg gtactcgccc ccttgggttc
5461 ccgaagatga cggcccgcc cggcgccacc cacccccat ctctgccccg gggttggaag
5521 gaacacggtg cgagggtgcg agggcaggac cctcctcttg gccacccgga gagcggtcgg
5581 agttgggtac agaaattcct cgaaattggc agcaacacgg gtcgggcaca agaccctcct
5641 ctgggcccct cggaaagggg atggagttgg gtgaggaaat ttcccaaaaa ggcaagtgaa
5701 tcccggaaaa tcagcagatg gtgacgcatg ccggattacc ttacccaggt tcctgctcag
5761 catacccagg ccataaccca gcagcgtgct ggcaggctgg gtctggacgg aggggatggt
5821 tgatgttggg gaggaggaca gtgggtgaca cttgacacca ttacccctct gacccccaat
5881 gtctgactcc aggggcctgg ccattcattc attctttcat tctttttttt ttttttttga
5941 gacagtctca ctccatcacc caggctggag tgcagtgtcc tgctctcggc tcactgcagc
6001 ctcctcctcc cgagttcaag cgattctcct gcttcagcct cccgagtagc tcggattaca
6061 gacatgtgcc actatgcctg gctaatattt ttgtattttt agtagataca ggatttcacc
6121 atgttggcca ggctggtctc aaactcctga taaatatata tattatatat tattattata
6181 tattacatat tatagtaata tataataaaa atatataata tatattatag taatatataa
6241 tatataataa aatatataat atatattata gtaatatata atatataata aaatatataa
6301 tatatattat agtaatatat aatatattat aatatattat atatattatt ataatatata
6361 atatgtatat tatatattat atatattatt ataatatata atatgtatat tatatattat
6421 atatattatt ataatatata atatgtatta tgtattatat aattgataat atataataat
6481 atatttctta ataaatatat attaaatata ttatatattt ataacatata ttatttatat
6541 aataaataat atatatttta ttatacattt aaagagtaaa tagataacat attttattat
6601 ttatttatat gttttgtgta tatatatata tatatatata tatatatagt gcgtgtgtgc
6661 gtgtatgtgt gtgtgtgtat gagagagaca aggtcttgct ttgttgccca ggctggagtg
6721 cagtggtaca atcccggctc attgcaaact cgacttccca ggctcaagcg atcctctcac
6781 tgtggcttct ggagtagctg ggattatagg tgctcacctg gctaattttt tttgtatttt
6841 tggtagagac agggtttcgc tatgctgccc aggctggttg cagccaagca cagtggctca
6901 tgcctgtaat cccaacactt tgggaggctg tggtgggagg atcacttgag cttaggaatt
6961 caaaaccagc ctgggcaata tggcaagacc ccatctctac aaaaataatt aactaaataa
7021 aaatttaaaa ataaaaaaga atgcatagga ccatgtttat tagtgtcaat aagcgctgtc
7081 acattttgag gacctactat gtgctagggc ccttagcaga aagattttta tataggacct
7141 gggggattag aggtcagtct ctgaccgccc aagttcaaat cccacctctg ccactaaacc
7201 tctgtatgac ttggaggaca ctatactctg tgtcagtttc cctgtctgta aaatgatgtt
7261 aacagtagtg cttgcctcag gggggctatt tgaggattaa atgccaagat atatgtgaag
7321 cacccagaat agcccctgat ctgtgtcagc accctgtgag tgtccactgt tctaagtctc
7381 attttacaaa ctaggaaaaa gaatcagaga ggttaagtaa ccggcctgaa gctccacagc
7441 agaaaactga agggacccaa aactcctggg ctataattgc cttcctctcg tgcctcaatc
7501 ccccacattc ttccaaccag gacccaccca gagtaataat gcagtgtttc atggatttga
7561 agacccaaga tttctccccg ttttctacat tggggttatt ctaaccccta atggcaagtt
7621 gtgctataaa tgacaacagt catggtatgt gaaacctacg acactggtgc gatgaaaaag
7681 ttctgggcca ggtgcggtgg ctcatacctg taatcccagc actttgggag gccgtagtgg
7741 gaggatcact tgaggtcagg agttcaagac cagcctggcc aacatggtga aaccccatct
7801 ctgctaaaaa caaaaataca aaaaattagc caggtgtggt ggtgggagcc tgtcatccca
7861 gctacgcgga aagctgaggc aggagaaccg cttgaacccc agaggcagag cttgcagtga
7921 gcagagatcg cgccactgca ctcccccctgg gcgacagaga gagactccgt ctcaaaaaaa
7981 aaagagaaga aaagaaaaag ttctggcgct atatagtagt aacggttgca caatatcgtg

FIG. 7..continued 8041 aaatgtacat agtgccactg aactgtatgc tttaaatgac ttaaatggta aatttagttt
8101 tttaaccaca atatttacca caattttta aatcagtgat gttgagattc agggaaatac
8161 ggtaataata gaagaaatac ggtaataaat agccaaagtg aaggagcacg gccaagttgc
8221 agaccatccc agacgccctt accctcctcg cctgccatgg ccccaactag tgccccagtt
8281 ccccctcccc ccacacccca cggtccaccg gggatccagg gccccagcgt gcaagtgcac
8341 gcccaggtgc ccgggctcct ggagcccctc cctatctagt ccaagaacgc cccgggtctg
8401 acaccttctc ttcggttctc cgcaggggac gtcgtcgtgc aggcgcccac ccaggtgccc
8461 ggcttcttgg gcgactcc~~gt gacgctgccc tgctacc~~ttac aggtgcccaa catggaggtg
8521 acgcatgtgt cacagctgac ttgggcgcgg catggtgaat ctggcagcat ggccgtcttc
8581 caccaaacgc agggccccag ctattcggag tccaaacggc tggaattcgt ggcagccaga
8641 ctgggcgcgg agctgcggaa tgcctcgctg aggatgttcg ggttgcgcgt agaggatgaa
8701 ggcaactaca cctgcctgtt cgtcacgttc ccgcagggca gcaggagcgt ggatatctgg
8761 ctccgagtgc ttg (19 bp deletion, 1 bp insertion) Exon 2
gtgagca gggggttttg gggaggctga atgaaaggca gagacttggt
8821 gggaggatca gggaagttgg caaagagcgg ggaggcctgg gagggaggga gattccctcc
8881 acagcagatc ccctggggac aaaaggaggg ggcagcgcaa tgatgtgggg tggggtgggg
8941 ggaggtgagt gggggggaggg gctgcagggc aggaagaaag cagagatctc agggagtaag
9001 gacccccaag cctgggatca gaaagccctg agggaggagg aggggtatat tggaaaggga
9061 gctgggaggg gactgggaag gaagggagga ggcctgggtg gcctcttctg ggtccctcct
9121 ttcctcatct gtaaaagggt tggtgacaac agcatcaccc ttggaaagct gtcctgagtg
9181 tcatcactgc ctaggaaaga gtctgtctgc ccccttggac tgtgtaccca tgagggcaga
9241 accggggcta ttttgatcac tgctgggccc cagcactttc caccaaacaa tatttattga
9301 gcacttatta tgtgccattc taagagcttt acctgcatat tctaattgcc tgtgattcca
9361 tcattatcac ctgttgacag acaaggaaac tgaggcacag acttgcccaa gaccaaagct
9421 gcagccttag ggcagcggcg cttcaccgct ggcccatgtg agccccttag agctgtcggt
9481 tactgttact ttatctggtg aagaaggaga aagttgaaac agacagacag gaaagcaagg
9541 atcctgatac ccaaaagagg aggggatcat gctttcattt tcatgagctc catgaagcct
9601 tcctcttgga acttgagcaa gaagtctctg tgcctcagtt tcctcatctg tgggataggg
9661 atcaccatga ggattcaaaa aaactgaccc tttttttttt tttgagatag tttagttctg
9721 tcgcccaggc tggagtgcag tggtgtgatc atagtaggtc ctcactgcag cctggaactc
9781 ctgggctcaa gggatgttcc taccctccct gtagctggaa ttacaggaat gtgccaccat
9841 gcccaacttg ttttctgttt tgttttgttt tgttttgttt tcttttcttt ttaagcttat
9901 gtgccaagaa ctattccaag cctgtgcatg agaaactcat gaaatgtcaa gggcttggaa
9961 ctgtgcctag cacacaacac ccaaccaaag gcagctgttg tcactccagc aagcctggga
10021 ttctgggtat catggtttag gatgagggta aaacagaaac agtgagtcaa gttaaggaga
10081 aatcttcggt aaataatata ggtaatgatg gggaaggaag ttccaggttt gggaatcacc
10141 aggatgatga ttaagagatg gtcaaggtgg ttttggagtc agacagactt tatgtgaaag
10201 cccagctctg ctgcttacag ctgtgtgacc atgggcaagt cacttccctt ctcaacttca
10261 gggctcaggc ttcctctcct ccactgagcc ccagaccagg ataaccccct ttgggtttcc
10321 cctttccagc cctgccctct ccgagtcatc actgcctagg aaagagtccg tctgccccct
10381 tggactgtgt acccatgagg gcagaaccag ggctattttg gtcactgctg ggctccagca
10441 ctttccacca aacaatattt attgagcgct tattatatac cattctaaga gctttacctg
10501 catattctca ttgcctgtga tcccatcact atcccctgtc aacagacaag gaaactgagg
10561 cacagacttg cccaagacca cacagctgct cagggacaca gctgggattt aaaccatgcc
10621 attctgtatc tttttttttt tttttttttt gagacagaat ctcactctgt cgcccaggct
10681 ggagagcagt gacacaatct cagctcactg caacctccgc ctcccgagtt caagcaattc

FIG. 7..continued

```
10741 tctggtctca gcctcccaag taactgggat tactggcgtg tgccaccata ccctggctaa
10801 tttttaatag agacagtttc tccatgttgg ccaggctggt ctcgaactcc tgaccccaag
10861 tgatccaccc acctcagccc cccaaagttc tgggattata ggcgtgagcc accccgccca
10921 gcaaccatgc catcctgtac ccttaatgaa tgcccccttc tgccacggag gggttcattg
10981 aatgacttgt tgcttttgtt cctcttccca gccaagcccc agaaca~~cagc tgaggtccag~~
~~11041 caggtccagc tcactggaga gccagtgccc atggcccgct gcgtctccac aggggtcgcc~~
~~11101 ccgcccagcc aaatcacctg gccct~~cagac ctgggcggga tgcccaatac gagccaggtg
11161 ccagggttcc tgtctggcac agtcactgtc accagcctct ggatattggt gccctcaagc
11221 caggtggacg gcaagaatgt gacctgcaag gtggagcacg agagctttga gaagcctcag
11281 ctgctgactg tgaacctcac cgtgtact (99 bp deletion) Exon 3
gt gagtgtgccc aagtcagcga tggcaagaac
11341 ccctgccggg ctgcccccac cactgtctac actgactccc caaggcactg taggcattgc
11401 ttccatcatc tgcaccggct cccctgactc ctgtctacac gacccacccc cattgtctgc
11461 accagctccc ctgggccgta aacaacactg tccctattgt ctacaccagt ttacttgggc
11521 catagtcaat gctggtaccc agactgtctg ccctggctcc tctagcggct gtctgcacgg
11581 atacctgaca ctctgttgac tcccttgagc acagtctaca ctgcccctaa actgcctaca
11641 cccatttccc caggcaagta tccacaatga ccctccccac attgctacac tggttcttct
11701 ggccacgatc aacactgcct cccttattgt ctacacccac tcccttgtcc ttttcttcct
11761 ttcctttttt tttttttttt tttgaaatag agtctcactc tgttacccag gctgcagtac
11821 agtggcatgt tctcggctca ctgtaacctc tgcctcccaa attcaggtgg ttctcctacc
11881 tcagcctccc aaatagctgg gattaaaggt gcacaccacc acacctggct aatttttgta
11941 tttttagtag agacagggtt tcatcatgtt ggccaggctg gtttcgaact cctgacctca
12001 ggtgatcggc ctgcctcagc ctcccaaagt atgctggaat tataggcatg agccactgtg
12061 cccggctttt tgttttgttt tgtttttcct ttggacaggg tctcgctctg tcacccaggc
12121 tggagtgtag ggcatgatc atggttccta cagcctcacc cttccaggct caagcaatcc
12181 ttctccctca gcctcccaag taactgggac tacaggtgca gccaccatgc ccggctaatt
12241 ttacagtttt tttctagaga gagttttgct gtgttgccca ggctggtctc aaactcctag
12301 gcttaagtga tcctcccgcc tcagtctccc gaagtgctga gattacaggc gtgagccact
12361 gcacctggcc ccttgtccat tttctacact gccttaccat tgtctacact ggctctcctg
12421 ggccacagac agcactaacc ccattgtcta caccacctat tttggccacc agctgtgggg
12481 tgttttcact gtctcccata gtgtctacac tggctcctat gaccactgtc tatgtaaaca
12541 ccccactttt tctacactgg ttctcctagg cactctctaa agtgcccccct gacactgtct
12601 acactgactc cctggagaac tgtctgcatt cacctcccac attgtatcga ccagttcccc
12661 tgagccacga tcaactgtct ccgccgggtg ctagttgcat tgatcttctc acattgtttg
12721 tgctggctcc cctaagcagt gtctgcagag tcccccagtg tagtctccat gttcctctgc
12781 ccaatattgt ctacactggc tcatctacag gctatccagt ctcaccccac atcaccacac
12841 tggcctcctt gtgttctgtc tgcacagccc cctgacagca tctgtcctga ttctcctgca
12901 cagcgttacc tccaccagct ccctcatggc atcatcgaca ttgacaccca cacatttatc
12961 tccactgaca gccccaggac tctctaacca gtgctgtcta acagaaatag catgcaagct
13021 gcatatagga ttttaaattc tccagcggcc accccattaa aaaattaaaa gaaagaggcc
13081 aggcacggtg gctcacgcct gtaatcccag cactttggga ggccgaggca ggtggatcac
13141 ctgaggtcag gcattcaaga ccagcctgat caatgtggtg aaactctgtc ttcactaaaa
13201 aatacaaaaa ttagccaggc acggtggcgg gtgcctgtaa tcccagctac tcgggagact
13261 gaggcaggag aatcacttga acctgggagg cggagattgc aatgagcgag attacgccat
13321 tgcactccag cctgggcagc agagcaaaac tccatctcaa aaacaagaaa agaaagagat
13381 gaaatttatt tgtttattta tttatctatt tatttatttg agacggggtc ttactctgtc
```

FIG. 7..continued

```
13441 acccagactg gagtgcagtg gcacagctcc ctgcagcctc aacctcctgg gcttaagtga
13501 tcctcccacc tcagcctcag tctcctgagt agctgggact acaggcgtgt gacaccatgc
13561 ctagctaatt tttgtttttg tttttgtttt tgtttttttg ttttgtgatg aagtcttgct
13621 ctgtcaccca ggctagagtg cagtggcacg atctcaactc actgcagcct ccgcctctcg
13681 ggttcaagtg attctcctgc ctcagcctcc cgagtagctg ggattacaag ccctggccac
13741 agtgcccagc taatttttgt atttgtggta gagacgggat ttcaccatgt tggccaggct
13801 ggtctcaaac tcctgacctc gtgatccacc caccttggcc tcccaaattg ctgggattac
13861 agacgtgagc caccgcaccc ggcctatttt tatttttttct ggagacagga tctccctatg
13921 ttgcccaggc tggtctcaaa ctcctgggct caagtgatcc tcctgcctca acctcccaag
13981 gtactgggat tacaggcatg agccactgtg cctggccaaa attaattttt aataattgcc
14041 tttacttaac ccaatatacc taaaatatta tttcaacttg taattgtttt tttaaaatta
14101 ttcttgagat ctttcccatt tattttgtcc tagtaaagcc tttgaaatct ggtgtgtatt
14161 tcggcctggc tatatttcga gtgctcagta gtcacatgtg gccagtaggt gccatattgg
14221 acagcacaga tctagactaa gctcccacat catctacact ggctcatcca aatactgtct
14281 acacacatac acagagcctg tcttaatttc gtcagctccc ggggacacac tgtatatgtg
14341 ggggtgatct caccccccacc acccacatttt caacactggc ccgacaatat agcatctgct
14401 gtaatattcc aacaccctgt ctacactgaa cccatcagta atatccacac aagctcttct
14461 agacatcatt catactgttc ctcccaccat tgtctatact gcttactccc cgccaggcaa
14521 ttggtacaca gattccctca ggtactgtct atactggagt ccctcaacac tgtcactggg
14581 tctgagcgag gaggagatct acactgactc ctacccctcg cccccgaata aaaccctgtc
14641 ccattggcct gccccaagg acattgaaag gtcttcgctg tcaatcacgt atgggatggc
14701 tgagcagcag cctagagcag ggttatctgg gactctttcc tgcaggactt gtcagaacct
14761 tgaatacact gctgtgtgtt gtgagtggtc attgcctatg agtgagaaaa ggaggaggca
14821 ttttcctgca ggacacccaa gacatgcctg gtccaggcta cccaggaaag ctagtggaga
14881 aaagcagctc ctcagaagcc ttctccatgt ccccactgac caaggactcc taggcttctg
14941 ctctctgtgg caccccatct acctagactc ctcctaggcc tctccagctc ccgctgtttt
15001 ccaaatatcc ccgggccttt tcctgcagtg tcgtgaatcc cgcgtagccc caggcccccc
15061 aaagcctccc agtctctgaa cctctgtatc catttcctgc agaccccccca gaggtatcca
15121 tctctggcta tgataacaac tggtaccttg gccagaatga ggccaccctg acctgcgatg
15181 ctcgcagcaa cccagagccc acaggctata attggagcac Exon 4
gtgagtcctg ggtctcaggg
15241 aggagggggct gggggtctgg atttctagca ctgagggagg aggggctggg ggcctggact
15301 cctgggactg agggagaagg ggctgggggc ccggacccct gggtctgagg gacgagaggc
15361 tgggagcccg gactcctggg tctgagggaa gaggggctgg gggtctggac ccctgggact
15421 gagagaggag gggctgggcc tggacccctg ggtctgaggg aggaggggct ggggggtctg
15481 gacccctggg tctgagggag gagaagctgg gagcctggac ccctgggtct gaggcaggac
15541 agactggggc ctggactcct ggtctaagag aggagggaga ttcagaaaag agaaaaagag
15601 gaggttgact tcgggccccc agtgggggc atctctgttt tgacatctct gttttgcggt
15661 tgaggcgttt agcaggtggt tgaatcctgg ctggtggatg cacctgcttt ttggggtgtg
15721 cctgctctgt gccccggtact tcccccgaat cccatgtgac cccatgctgt gcacagtcag
15781 cagctgttgc cctgcccagg ttaaagacca gccacgagag ggcagaagcg gcccttgaat
15841 cagcgctcgg ctccaaagct ggtcctccgc ctcttggcca agcttgtcta acctgcaggc
15901 cacatcattt gtaaactttc ttaaaacatt atgagacttt ttttttgcga atttttttag
15961 ctcattagct attgttagtg ttagtgtatt ttatgtatgg cccaggacag ttcttcttct
16021 tccaatgtgg cccggggaag ccaaaagatt ggacaccccc actctagact gtaaccacct
16081 caccgtcacc ttgtgtaacc tacttggtta tctctggatg gagcaagtac tatatatccc
```

FIG. 7..continued

```
16141 cattgtctag atgagaaagt tgaggctcac agcaataaga tttccccaga ttcacactga
16201 ggctgagatc aagagcaagg taagaaaaag gcaaagagat aatacataat tttataatac
16261 ataattttac ataaattaca taattttact gaaccgccct ttttttttaa agaaggggct
16321 ctgttgccga ggctggagtg cagtggcgtg atcatagctc actgcagcct ggacctccct
16381 gggctcaggt gatcctccca cctcagcctc ctgagtagct gggactacag gcacacgcca
16441 ccacactcag ctaattttgt tgtatttttt ttgcagagac agggttttgc cacattgccc
16501 aggctggtct gcaactcctg ggctcaagca atcaacccac ctcagcctcc taaagtgctg
16561 ggattacagg cgtgagccac ctcgcccagc cttaggtctt tttccttatt acaaaaataa
16621 cttgtgtcca ctgtagaaat atcaaacaat ttagttatga gcaaaaagaa gaaagtagtg
16681 cctatagttc aagtgtaccc agccacctcc agaaataccc agtgacccct tattatacat
16741 cctgtctttt ttctctctgt ttctaaacaa agactggaat tatgctgtac atataatttt
16801 gaaccttttc gtctgtcttg tgaatacctt tccatgtcaa agcacataga tcccacaactc
16861 cattttcccc cacgttgtat taggaagact gtcaaacata cagaaaaatc ataggaattt
16921 tccagtgaac acttaagatt ccaccacgtg gattcccctg ctaacatttt actgtgcttg
16981 ctttatcacg tttctgtgat tccttcagtc cctctattca tccatcaatc atattatgca
17041 tttcagagca cccccagctc tcctgctttt tttttttttt tttttttttt gaggcagggc
17101 ctcactctgt tgctcaggct gtagtgccgt ggcacaatca cagctcactg cagccttgaa
17161 ttcctgggct caagcgatcc tccagcttca gcctcccaga tagctgggac tacaggcaca
17221 caccaccacg cctggctaac ctggcccctt ttttagtgtt gctgggattc caccacttta
17281 aaaaaaaaat tcaaagaata gagacaggat ctcactatgt tgcccaggct ggtcttgaac
17341 tcctgtactc aagcagtcat ctcacctggg cctcccaaag ggcagggaag ggattccaac
17401 atatgtggat gtcatcagtt atttaaccag tccctagtag aggacacaga tgtcattttc
17461 cattttcaac tctgcaaatg ccatggtggt gtccatcccc actggtcact tgtcagcagt
17521 tgtccgtgga aggaattgcc ggtcaaaggt tttcaactgg tgtgatggtg cctttactgt
17581 cctgcctcaa agcaccgcaa ttcaggctct tgagccagat agctgcgttt gcatcccagc
17641 tctgcggagc acccaaagcc tgatgcttcc atctcctcca cctctgttca ttaaaccagt
17701 gttccttgac tacttactgt gtgccgggtg caattaacca acatacgttg gtcgataaaa
17761 cagaccaaat ttcctcccca tatagagctt ccattctagt ggtgaaagaa acaagaagca
17821 agataaagtg tgtagtgtgt gtgcaatggt gataaatacc atggagaaga caaagcagag
17881 aagggaatgg gactgggcgc catgactcat acctgtaatc ccagcacttt gggaggcaga
17941 gatgggagga tcacttgagg ctaggagttc aagaccagcc tggccaacat ggcgaaaccc
18001 catctctacc aaaaaagata caaaaattgg ccgggtgtgg tggcatgcac ctgtagtccc
18061 agctactcag gaggctgagg tgggaagatt ccatgcaccc aggaggtgga ggttgcagtg
18121 agtcaagatg gtgccactgc actccagcct gggtgacaga gtgagacgct gtctcaaaaa
18181 aataataatt aaataaatta aagagaaggg gatgggaagg gtgatcatca cagttgaaat
18241 agggtggcca agtgaggtgt tactaaggtg acatcccagc agaggcctga aggagatgag
18301 ggtgagctct gcgggtgcct aggggaaag cattccagca gagggaacag catgggcaaa
18361 cccatttcta tccatcagtc cctgcataag caaacaccct ggacacctaa ctggagagtt
18421 tgaggaccaa caaagaggcc actgtggatg cagaggcggg agcaaagggg agagtaatgg
18481 aaaacgtggg cagaggtagc aggggccaga tcacgtgggg cctgtgacac cagaagactt
18541 cggtttaact ctgagccagg ctaggccccc agagggtact gagctgaggt atgggaactg
18601 acttagggtt cacaggcgac ctctggtggc catgtgggga acagacgagg gggcgagggc
18661 agaaacggag cccagcgtgg aggcggctgc tgggggccgg gatgcacagc gccagagcag
18721 ggaggtaccg tggaagccct gaggagaggt gggattctgg atggatctta aggcggggcc
18781 gacatgattg gctaatgggt tgggtgtggg catgagagga agggaagagt tgggggggcct
18841 ccagagttgc tctccgctta tgctatagag ggcgtgaggg tttctgggca cgtagtgcgt
```

FIG. 7..continued 18901 gctcaatcac tgtcactccg gacctgcagc agaggccacc tcctcacctt tctgtctctc
18961 ccaggaccat gggtcccctg ccaccctttg ctgtggccca gggcgcccag ctcctgatcc
19021 gtcctgtgga caaaccaatc aacacaactt taatctgcaa cgtcaccaat gccctaggag
19081 ctcgccaggc agaactgacc gtccaggtca aaggtgagga actccctggg tgggaagaac
(EXON 5)
19141 agggaccaaa ggaagaggtc gaggcagggt tccctgtcta atgctctctg gctcccatcc
19201 ttctcctaag ccttctcaca aaaggaccag tggggccagc tttactcccc tgttaactcc
19261 atacctatat cactggtacc gttgttcagc tgcctggata cactccctcc acacacacag
19321 gttgggatag atgtggaatc cctctctctc agggactcag gcctttccaa atatattagg
19381 cagacctcta tcaattgcaa ttgacagaaa cacaaagtag tctaagcaaa aaaaaccaaa
19441 caaaacagga ctttattgaa aattcacctt caggtatggt tagatccagg ggctccaacc
19501 ttgtaaccca ggaactttta ttttatacat ctcttgtctc tgcttttcgt tatactggct
19561 ttattctcag gcaggctctg aagcaagatg gccctcggca gggacaggct cacattctac
19621 cagaatggca acagcaggag aaaaaacata ccactttcag taactgtagc catagtccca
19681 gggctggctc tcattggccc agcttaggcc acagcccacc tatgaaccaa tcatagcagc
19741 cagggagaat ggaatattct gattggccag gcctgtgtca aagtcccatt ctgggcacca
19801 gagggtggga tccattccac ctgaattaaa tagactgagg cagtggagtg gtggctccct
19861 aaggaaattc aagatgccat ttcaagaatg agggataaac cccaagagtt tccttaccta
19921 aatacctgtt tccttctctt tcagagggac ctcccagtga gcactcaggc atgtcccgta
19981 acgccatcat cttcctggtt ctgggaatcc tggtttttct gatcctgctg gggatcggga
20041 tttatttcta ttggtccaaa tgttcccgtg aggtcctttg gcactgtcat ctgtgtccct
20101 cgagtgagca tcaccagagc tgccgtaatt gagcacctac tacgggctct gtgctgagtc
(EXON 6)
20161 cttccagtgt gcctctcact gaatcctcac cccactgcca tgaggtttcc cccatttgac
20221 tgatgagggt gcagagccag ggagccttgt tcactggttc attgattaca tttacaaata
20281 ttatttacag agtgggagaa gagcgtatag ggtcttaatg ccatggtagg gactttggaa
20341 tttaattcag gtgatgtggg agtccctgcc agatggatgg agggtgaaat aatgcttaag
20401 ccctcagcct tactccatct gccttgttca ggagtgactc ctaggaggag gtggcaggaa
20461 ctggcacctc tgatcctcag ctctaaaagg gtctgatgct ttcacacctc aagagatttg
20521 cacaggccgt tcccctgcct ggagcaccct cccatggctc cttctggaga agtgtgccag
20581 ctcattctgt aatcagagga acgatgcttt gctgagcact gtctacatgc cactttgtat
20641 gtataacccc ctcgatttta atttttaatt tttttatta tttatgtatt tatttattta
20701 tttttgagac aggctctcac tgtcgcccag gctggagtgc agtggtgcga tctcggctca
20761 ctgtagcctt cacctcccag gttcaagcga ttctcatgcc tcagcctccc aaggagcggg
20821 gattacaggc acgcactact atgcccagca atttttgtat ttttaggaga gacagcgttt
20881 cgccatgttg gccaggctgg tctcaaaccc ctggtctcct gtgatccacc cgcctcagcc
20941 tcccaaagtg ctgggattac aggcatgagc caccacacct ggcctgtaca atctccttga
21001 atgcccacaa ccacccagca aagtggttct cccgtgagcc ccatgttaca gaggaggaag
21061 tatttgcttt gagagatgaa gttacctgcc aatggtcaaa cagctggaca tggttgttgg
21121 ggagaagaag ccagatcttt gactaccaag cttttccttc aaccactaaa caaagctgct
21181 cccttacaac ccaggcggat actgcctcgt ccaggaagcc ctccctgacc cccaagcatg
21241 agccaagcat ccactaggct ctcccactcc agccttgccc attctgggtc atcaccgtgg
21301 gggacttgtt tgtcatcccc agtggactgt gagccccaag atagcagacc tgaggctgtc
21361 actgtcatga ctgtgtcccc aggaccgcct accactgggc cgggcataaa agaggcactc
21421 gaggaagtgt ttgctgagtg attcaatgtg tcagctccag agccagactg cctgtatctg
21481 ggccctaaag ctactgcttg attagtgatg tcaccatagg caaatagctt aagctgtatg

FIG. 7..continued 21541 actcagtttc ctcatctgta aaatggggtg atggtaccta ataatacagt agagcactta
21601 acacagtagg tggcacatgg taagccacat actgagtatg tatttgctat gattgttatt
21661 gctattatta ctattattgt tattattaac ataaactgca caagagcagg ctttttgttt
21721 gtttgtttgt gttttgtttt gagacaagat cttgctctgt tgcccagact ggagtagtgc
21781 agtgatgtga tcttggctca ctgcagcctc aacctcccag gctcaggtga ttctcccacc
21841 tcagcctctc gagtagctgg gattataggc gtgcactccc acgcctggct aatttttat
21901 atttttagta gagatggagt ttcgttgtgt tgcccaagct ggtctcaaac tcctagactc
21961 cagcaatccg cccacctcag cctcccagag tgctggaatt ataggtgtga gccaccacgc
22021 ctggccaaga gcaggcattt ttatctgttt tgttcacagc tgtgtcccca gcacctagaa
22081 tgtacctggc acaaagtaga cattcaccat ttgctgaata atactactat ttgctaaata
22141 aacccctgtt gaatagtcta ggaaactgaa cacagagagg ttaagtcact tgtccaagtt
22201 cacacagctc ctaaaggaca gagatggaat ttgaacccat ccatctggtt ccagagccag
22261 gctcgatatt tatggatatt tcataaccaa gtgaataact ggatggctaa atccttagaa
22321 agcacaccct ccatccctgt ctgacacacg tgtataccat taagggaaat ggcaccccca
22381 tgtaatagca gaggcagaac ttgacatttt cagggccctg acacccaggc atgtcttctt
22441 cccatgcttc ccagcattat tccttcctga cgacttcccc tcctatttcc ccaggtacag
22501 agcatgccag cgcctcagct aatggggtaa gtgcagtgtt ggagctaagg agggtgtggg
(EXON 7)
22561 gtctgcacga actacagacc agacgtcttc agatgcccac ggcccggcct caggagcctg
22621 ggtcttttct cctggtgcct cgagcagcat ttcccaaccc ttcctgctgg gcggaatccc
22681 ctgtagagtt tgctaagacg cagccccaga cagtctggtc tgtgatgggg ccagggaatc
22741 tgcattttaa tatccgctct ctcccccctg ccccacgccc cttcaattcc acccatggcc
22801 acaccttgag aagcactgcc ctggcttcca gggagagagg aggggacggg cctgcagttc
22861 tttgcacatg gggcttcagt gggaagatgt ttgattttgt tcaaaagagc cccaaggcta
22921 aaatttgaaa accctcttct agcatgtctc ctattcagct gtgagcagag agaacagctc
22981 ttcccaggat ccacagacag agggcacaag gtgacagcgt cgggactgag aggggagaga
23041 gactggagct ggcaaggacg tgggcctcca gagttggacc cgaccccaat ggatgaagac
23101 cccctccaaa gagaccagcc tccctccctg tgccagacct caaaacgacg gggcaggtg
23161 caagttcata ggtctccaag accaccctcc tttcatttgc tagaaggact cactagactc
23221 aggaaagctg ttaggctcac agttacagtt tattacagta aaaggacaga gattaagatc
23281 agcaaaggga ggaggtgcac agcacacgtt ccacgacaga tgaggcgacg gcttccatct
23341 gccctctccc agtggagcca tataggcagc acctgattct cacagcaaca tgtgacaaca
23401 tgcaagaagt actgccaata ctgccaacca gagcagctca ctcgagatct ttgtgtccag
23461 agtttttttgt ttgtcttgag acagggtctg gctctgttgg cagactagag tacagtggtg
23521 agatcacagt tcattgcagc cttgacttct caacgccaag tcatcctccc acctcagcct
23581 cctgagtagc tatgactaca ggtatgtgcc accacgtctg gctaatcttt ttattatttg
23641 taaagtcgag gtttccctgt gttgcccagg ctggtcttga actcttggct ccaagtgata
23701 cttctgcctt ggcctcccaa agtgctgaat taagcagctc accatccaca cggctgacct
23761 catacatcaa gccaataccg tgtggcccaa gacccccacc ataaatcaca tcattagcat
23821 gaaccaccca gagtggccca agactccaag atcagctacc aggcaggata ttccaagggc
23881 ttagagatga atgcccagga gctgaggata aagggcccga tctttctttg ggcaaggtta
23941 agcctttact gcatagcaga ccacacagaa gggtgtgggc caccagagaa ttttggtaaa
24001 aatttggcct ctggccttga gcttctaaat ctctgtatcc gtcagatctc tgtggttaca
24061 agaaacagcc actgaccctg gtcaccagag gctgcaattc aggccgcaag cagctgcctg
24121 gggggtgtcc aaggagcaga gaaaactact agatgtgaac ttgaagaagg ttgtcagctg
24181 cagccacttt ctgccagcat ctgcagccac tttctgccag catctgcagc cagcaagctg

FIG. 7..continued

```
24241 ggactggcag gaaataaccc acaaaagaag caaatgcaat ttccaacaca aggggaagg
24301 gatgcagggg gaggcagcgc tgcagttgct caggacacgc tcctatagga ccaagatgga
24361 tgcgacccaa gacccaggag gcccagctgc tcagtgcaac tgacaagtta aaaaggtcta
24421 tgatcttgag ggcagacagc agaattcctc ttataaagaa aactgtttgg gaaaatacgt
24481 tgagggagag aagaccttgg gccaagatgc taaatgggaa tgcaaagctt gagctgctct
24541 gcaagagaaa ataagcagga cagaggattt gctctggaca gagatggaag agccgggaac
24601 agagaagtgt ggggaagaga taggaaccag caggatggca ggggcaaagg gctcaagggt
24661 gaggaggcca gtgggacccc acagagttgg ggagataaag gaacattggt tgctttggtg
24721 gcacgtaagc tccttgtctg tctccagcac ccagaatctc attaaagctt atttattgta
24781 cctccagcgg ctgtgtgcaa tggggtcttt tgtggaaatc aaggagcaga caggtttcat
24841 gtgtactgtc accacgtggg atggaaccag aggcatggaa gcaagacgct aaatgaagag
24901 ggccataagg gctgggattc ccaggcacct taggaacagc ttgtcttttt tttttcctc
24961 tccaaaaaaa atgtttaagg gacggtgtct cctgtcaccc aggctggagt gcaatggcac
25021 gatcatagct cattgcagcc tctaactccg ggctcaagc aatcctccca cctcagccta
25081 ccaagtagct gtgaccacag ctgcccctca ccatgctaag ctaatttttt taattagata
25141 gtacataaac gtcccaaaat tagaagataa aaagacatga gggatccatt ctaatttgtg
25201 tttggagtgt aatggtccag ctccattctt ctgcacatgg atatccagtt ttacacaaca
25261 ctgtgaatgt aatgaatgcc actgaatcat acactcaaaa atagctaaaa tggcaaattg
25321 tctgttatct ctttttaacc accatttttg aaaattaatt ataccaaaaa accattgaat
25381 agtgcacttt atttatttat ttatttgttt atttatttat ttattttaga aataagagtc
25441 tcactttgtt gcccaggctg gagtgcagtg gcgtgatcat ggctcattgc agcctcgacc
25501 tgctgggctc gggctatcct tccatctcag cctcccgagt agctgggact ataggtgggc
25561 gccaccccac ctggctaaat ctctttttaa cttttgtaga gataggcatc tcgctatgtt
25621 gcctaggctg ggctggaact cctgggctca agtgctcctc ctgccttggc ctcccaaagc
25681 gctaggatta cagatgtgag ccaccgcgcc caccctgaac cttacttttt ttgctcagtt
25741 tctggtaatt cagagaatgc ctcctgagtt gttctacacc cacctcatat tccatgggag
25801 ggctgtacag ggcttttta acgaggcctc taaggacagg catttgtatc ctttccagcc
25861 tttcactatt acaatgttgt agtgaataac tttacacact gtcatttatt ttactttttt
25921 ttttttttat tttagagaaa ggaatcttgc catcttgccc aggctggtct caaattcctg
25981 ggcccaaaca atcctcccgc cttggcctcc taaagtactg ggatttatag gcataagcca
26041 ccgtgcctgg ccaatgcaca ctgtcattta gctcatgtta acacctgagt gtaggacaca
26101 ctcctggagg tggaattgct gggccaaaga gtatgtttct tgtcattgtg atagatattg
26161 acaaatgaac cctcacagaa gttgtgctga gttctgttcc caccagcgac gtaggcgatg
26221 accttttttct ggagggaggg ggcatccttg gagtccacag agccaggaat ggagagtggg
26281 cccagaattt tggtataggt gttgtataaa cttatagtaa ggttaagaaa accgcaacta
26341 tccttatcag agacttggcg gggggcaggg tatgatggag atcataagga ggctaaaaca
26401 ctcccacacc tccctctgca ttgctcctgc acgggagtcg ggaatctttt caggttgata
26461 cgatctcacc ttgaggagct gtgaggtccc agaagcctct gggttgcaga ttgcttgggg
26521 tgaaaatgtc tgtgctactg aaatctaact ttttacaaaa aattacgggc tgggcgcagt
26581 ggctcacgcc tgtaatccca gcactttggg aggctgcagc gggtggatca cttgaggtaa
26641 ggagttcaag accagaccat agtgaaaccg tgtctctaca aaaaaaatta gccaggtgtg
26701 gtggtgcatg cttgtaatcc cagctactca gaaggctgag gtgggagaat cccttgaacc
26761 cgggaagtgg aggctggagt aaaccatgat cgagttactg cactccagcc tgggtgacaa
26821 gagtgagact ctgtctccaa aaaaaaaaaa aaaaaaaaaa aaactggatt gcctggctct
26881 actccgggca cagcatgcag gcccagttct gctgctctgc tgtttgttct gctttcctcc
26941 acatattggc atcaccctct ggtgccaaga tggctgctgc attccaggca tcacatccag
```

FIG. 7..continued

```
27001 actcagaccc agagaagctg cccatcccta cctgggtgag cctttgtagg aacgagaaac
27061 cgcatccagc agcagaaacc tcacccagca gcgtcttttc cggtctcatt caccagcgcc
27121 gcccaccgct caaccaatcc ctggccaaaa gaatgggacc gcctggaagg ctggaccaaa
27181 caggacctgc cctctggggc tggggagagg cccagatgaa ggctgcagga caggatggac
27241 tcctagacct ctgttaccag cagtgactac ctctgtctgg gtggttggaa catgtttgaa
27301 ttttattcta agtactgtct acaagttctg caataaacct tgactcttct tttaataatg
27361 caaaaggaat cgaagtgatt gtttgaaagg gagaggaaga aagagagagg gagggaggga
{EXON 8}
27421 agaatggagg gaggcaggga aggagacaga gagagtagaa tccagccacc ggaaaatcca
27481 gaatagctgg ctttgcttaa tccatgcctg gaaataactg ctgggtttgc aacaacttct
27541 ctcccggaga cagaccaagg aaactacaaa actgcaggaa ggattgaagg gccgggcaca
27601 gtggctcacg cctgtaatcc caacactttg ggaggccgag gtggattgga tcacctgaga
27661 tcaggagttc gagaccagcc tggccaacat ggtgaaacct cgtctctgct agaaatacaa
27721 aaataagccg ggcgtggtgg cgtgcgccta tagtcccagc tactcgggag gctgaggcaa
27781 gagaatcgct tgaacctggg aggtggaggt tgcagtgagc tgagatcgtg ccactgcact
27841 ccagcttggg cgacagagtg agaatctgtc aggtggattc tgagggtact ctgaccccac
27901 gaacccagca tgaaatcttc caggcattaa ggaacattga ggatgtggag gattggaaat
27961 ccctccaggg aaaatacact tctcttgagc agggtcacga ggggtggggg caatgtggga
28021 ggtggggcaa atccaaagac aaggtcaaca gcaataataa taataacaat gacaggcatt
28081 tgttgcttgt tggctgggcc tcttgcatac agttctccca acatccctgt gaggtggtga
28141 tgcttatccc cattctccag gggaggaggc tgaggcccag agaggtgaag tcgtgtgcca
28201 caaaataccc cagccatatg gtggtagaac caagttttca gccagactca ccagctcaca
28261 gcagagctgc cctggactct acagccattc agtgtatagc tgggccactc catcattcaa
28321 ggcagttcaa cgtcaagatt cctgatttgc ctcaacctgg ggcctctaga agataccatc
28381 acccccaaca agctgaagac gtgtgtccgg aacactcaga cacacacaaa gtgctatgga
28441 tacacccacac cccgacctag ctgtctcttc ctgatggacc tcactgggta gaaatgcctg
28501 gcacccgcctg cctcagatcc ctaggtcagc tctcactccc caatagaagt ttctgagatg
28561 atgatgaaaa cgttctccat ctgtgctgtc caatggagta gccactgatc acttgaggct
28621 agtgagcact tgaaggtggc tagtttgagg aactgcattt tttaatgcat ttaattttag
28681 ttactttgaa tatatataca catatataca tttatatata catattcata cacatacatt
28741 ttacatatat tttatatgta tatgtaatat atatataaat tatatatgta tatattttta
28801 tatataaata tatattatat atttataaat atataaatat ataatatata ttatatagat
28861 atataaatat aaatatatat tatatatata aatatataat atatattata taaatatata
28921 taaattatat atttatatat ataatatata aattatataa attatatata tttatatata
28981 atatataaat atatataaat tatataattt atatattata tataaattat atattttata
29041 tataatatat acaatatata taaattatat ataatatata aatatatata aattatatat
29101 aatatataaa atatatataa attatatata atatataaaa tatatataaa ttatataaat
29161 ctatataaat atatactata ttataaatat agtatatatt tatatagatt tatattattt
29221 atataqtata tattatatat ttatatqttt atqtatatat aaatatataa tatataaata
29281 tatttatata ttatatattt atataatatt ttatataata tgttatatat ttttatataa
29341 tatattatat atatttatat
```

Figure 8

1 agtcacttgt ctggagcttg aagaagtggg tattcccctt cccaccccag gcactggagg
61 agcggccccc cggggattcc aggacctgag ctccgggagc tggactcgca gcgaccgcgg
121 cagagcgagc gggcgccggg aagcgaggag acgcccgcgg gaggcccagc tgctcggagc
181 aactggcatg gcccgagcca tggccgccgc gtggccgctg ctgctggtgg cgctactggt
241 gctgtcctgg ccacccccag gaaccg (EXON 1)
ggga cgtcgtcgtg caggcgccca cccaggtgcc
301 cggcttcttg ggcgactcc~~g tgacgctgcc ctgctacct~~ta caggtgccca acatggaggt
361 gacgcatgtg tcacagctga cttgggcgcg gcatggtgaa tctggcagca tggccgtctt
421 ccaccaaacg cagggcccca gctattcgga gtccaaacgg ctggaattcg tggcagccag
481 actgggcgcg gagctgcgga atgcctcgct gaggatgttc gggttgcgcg tagaggatga
541 aggcaactac acctgcctgt tcgtcacgtt cccgcagggc agcaggagcg tggatatctg
601 gctccgagtg cttg (19 bp deletion and 1 bp insertion EXON 2)
ccaagc cccagaaca~~c agctgaggtt cagaaggtcc agctcactgg~~
~~661 agagccagtg cccatggccc gctgcgtctc cacaggggt cgcccgccag cccaaatcac~~
~~721 ctggcact~~ca gacctgggcg ggatgcccaa tacgagccag gtgccagggt tcctgtctgg
781 cacagtcact gtcaccagcc tctggatatt ggtgccctca agccaggtgg acggcaagaa
841 tgtgacctgc aaggtggagc acgagagctt tgagaagcct cagctgctga ctgtgaacct
901 caccgtgtac t (99 bp deletion EXON 3)
accccccag aggtatccat ctctggctat gataacaact ggtaccttgg
961 ccagaatgag gccaccctga cctgcgatgc tcgcagcaac ccagagccca caggctataa
1021 ttggagcac (EXON 4)
g accatgggtc ccctgccacc ctttgctgtg gcccagggcg cccagctcct
1081 gatccgtcct gtggacaaac caatcaacac aactttaatc tgcaacgtca ccaatgccct
1141 aggagctcgc caggcagaac tgaccgtcca ggtcaaag (EXON 5)
ag ggacctccca gtgagcactc
1201 aggcatgtcc cgtaacgcca tcatcttcct ggttctggga atcctggttt ttctgatcct
1261 gctggggatc gggatttatt tctattggtc caaatgttcc cgtgaggtcc tttggcactg
1321 tcatctgtgt ccctcga (EXON 6)
gta cagagcatgc cagcgcctca gctaatggg (EXON 7)
c atgtctccta
1381 ttcagctgtg agcagagaga acagctcttc ccaggatcca cagacagagg gcacaaggtg
1441 acagcgtcgg gactgagagg ggagagagac tggagctggc aaggacgtgg gcctccagag
1501 ttggacccga ccccaatgga tgaagacccc ctccaaagag accagcctcc ctccctgtgc
1561 cagacctcaa aacgacgggg gcaggtgcaa gttcataggt ctccaagacc accctccttt
1621 catttgctag aaggactcac tagactcagg aaagctgtta ggctcacagt tacagtttat
1681 tacagtaaaa ggacagagat taagatcagc aaagggagga ggtgcacagc acacgttcca
1741 cgacagatga ggcgacggct tccatctgcc ctctcccagt ggagccatat aggcagcacc
1801 tgattctcac agcaacatgt gacaacatgc aagaagtact gccaatactg ccaaccagag
1861 cagctcactc gagatctttg tgtccagagt tttttgtttg tcttgagaca gggtctggct
1921 ctgttggcag actagagtac agtggtgaga tcacagttca ttgcagcctt gacttctcaa
1981 cgccaagtca tcctcccacc tcagcctcct gagtagctat gactacaggt atgtgccacc
2041 acgtctggct aatcttttta ttatttgtaa agtcgaggtt tccctgtgtt gcccaggctg
2101 gtcttgaact cttggctcca agtgatactt ctgccttggc ctcccaaagt gctgaattaa
2161 gcagctcacc atccacacgg ctgacctcat acatcaagcc aataccgtgt ggcccaagac
2221 ccccaccata aatcacatca ttagcatgaa ccacccagag tggcccaaga ctccaagatc
2281 agctaccagg caggatattc caagggctta gagatgaatg cccaggagct gaggataaag
2341 ggcccgatct ttctttgggc aaggttaagc ctttactgca tagcagacca cacagaaggg
2401 tgtgggccac cagagaattt tggtaaaaat ttggcctctg gccttgagct tctaaatctc
2461 tgtatccgtc agatctctgt ggttacaaga aacagccact gaccctggtc accagaggct
2521 gcaattcagg ccgcaagcag ctgcctgggg ggtgtccaag gagcagagaa aactactaga

FIG. 8..continued 2581 tgtgaacttg aagaaggttg tcagctgcag ccactttctg ccagcatctg cagccacttt
2641 ctgccagcat ctgcagccag caagctggga ctggcaggaa ataaccccaca aaagaagcaa
2701 atgcaatttc caacacaagg gggaagggat gcagggggag gcagcgctgc agttgctcag
2761 gacacgctcc tataggacca agatggatgc gacccaagac ccaggaggcc cagctgctca
2821 gtgcaactga caagttaaaa aggtctatga tcttgagggc agacagcaga attcctctta
2881 taaagaaaac tgtttgggaa aatacgttga gggagagaag accttgggcc aagatgctaa
2941 atgggaatgc aaagcttgag ctgctctgca agagaaaata agcaggacag aggatttgct
3001 ctggacagag atggaagagc cgggaacaga gaagtgtggg gaagagatag gaaccagcag
3061 gatggcaggg gcaaagggct caagggtgag gaggccagtg ggaccccaca gagttgggga
3121 gataaaggaa cattggttgc tttggtggca cgtaagctcc ttgtctgtct ccagcaccca
3181 gaatctcatt aaagcttatt tattgtacct ccagcggctg tgtgcaatgg ggtcttttgt
3241 ggaaatcaag gagcagacag gtttcatgtg tactgtcacc acgtgggatg gaaccagagg
3301 catggaagca agacgctaaa tgaagagggc cataagggct gggattccca ggcaccttag
3361 gaacagcttg tctttttttt tttcctctcc aaaaaaaatg tttaagggac ggtgtctcct
3421 gtcacccagg ctggagtgca atggcacgat catagctcat tgcagcctct aactccgggg
3481 ctcaagcaat cctcccacct cagcctacca agtagctgtg accacagctg cccctcacca
3541 tgctaagcta attttttttaa ttagatagta cataaacgtc ccaaaattag aagataaaaa
3601 gacatgaggg atccattcta atttgtgttt ggagtgtaat ggtccagctc cattcttctg
3661 cacatggata tccagtttta cacaacactg tgaatgtaat gaatgccact gaatcataca
3721 ctcaaaaata gctaaaatgg caaattgtct gttatctctt tttaaccacc atttttgaaa
3781 attaattata ccaaaaaacc attgaatagt gcactttatt tatttattta tttgtttatt
3841 tatttattta ttttagaaat aagagtctca ctttgttgcc caggctggag tgcagtggcg
3901 tgatcatggc tcattgcagc ctcgacctgc tgggctcggg ctatccttcc atctcagcct
3961 cccgagtagc tgggactata ggtgggcgcc accccacctg gctaaatctc tttttaactt
4021 ttgtagagat aggcatctcg ctatgttgcc taggctgggc tggaactcct gggctcaagt
4081 gctcctcctg ccttggcctc ccaaagcgct aggattacag atgtgagcca ccgcgcccac
4141 cctgaacctt actttttttg ctcagtttct ggtaattcag agaatgcctc ctgagttgtt
4201 ctacacccac ctcatattcc atgggagggc tgtacagggc tttttaacg aggcctctaa
4261 ggacaggcat ttgtatcctt tccagccttt cactattaca atgttgtagt gaataacttt
4321 acacactgtc atttatttta cttttttttt tttttatttt agagaaagga atcttgccat
4381 cttgcccagg ctggtctcaa attcctgggc ccaaacaatc ctcccgcctt ggcctcctaa
4441 agtactggga tttataggca taagccaccg tgcctggcca atgcacactg tcatttagct
4501 catgttaaca cctgagtgta ggacacactc ctggaggtgg aattgctggg ccaaagagta
4561 tgtttcttgt cattgtgata gatattgaca aatgaaccct cacagaagtt gtgctgagtt
4621 ctgttcccac cagcgacgta ggcgatgacc tttttctgga gggagggggc atccttggag
4681 tccacagagc caggaatgga gagtgggccc agaattttgg tataggtgtt gtataaactt
4741 atagtaaggt taagaaaacc gcaactatcc ttatcagaga cttggcgggg ggcagggtat
4801 gatggagatc ataaggaggc taaaacactc cacaccctcc ctctgcattg ctcctgcacg
4861 ggagtcggga atcttttcag gttgatacga tctcaccttg aggagctgtg aggtcccaga
4921 agcctctggg ttgcagattg cttggggtga aaatgtctgt gctactgaaa tctaactttt
4981 tacaaaaaat tacgggctgg gcgcagtggc tcacgcctgt aatcccagca ctttgggagg
5041 ctgcagcggg tggatcactt gaggtaagga gttcaagacc agaccatagt gaaaccgtgt
5101 ctctacaaaa aaaattagcc aggtgtggtg gtgcatgctt gtaatcccag ctactcagaa
5161 ggctgaggtg ggagaatccc ttgaacccgg gaagtggagg ctggagtaaa ccatgatcga
5221 gttactgcac tccagcctgg gtgacaagag tgagactctg tctccaaaaa aaaaaaaaaa
5281 aaaaaaaaaa ctggattgcc tggctctact ccgggcacag catgcaggcc cagttctgct
5341 gctctgctgt ttgttctgct ttcctccaca tattggcatc accctctggt gccaagatgg
5401 ctgctgcatt ccaggcatca catccagact cagacccaga gaagctgccc atccctacct
5461 gggtgagcct ttgtaggaac gagaaaccgc atccagcagc agaaacctca cccagcagcg
5521 tcttttccgg tctcattcac cagcgccgcc caccgctcaa ccaatccctg gccaaaagaa
5581 tgggaccgcc tggaaggctg gaccaaacag gacctgccct ctggggctgg ggagaggccc
5641 agatgaaggc tgcaggacag gatggactcc tagacctctg ttaccagcag tgactacctc

FIG. 8..continued

```
5701 tgtctgggtg gttggaacat gtttgaattt tattctaagt actgtctaca agttctgcaa
5761 taaaccttga ctcttctttt aataatgcaa aa {EXON 8}
```

POLIOVIRUS RECEPTOR (PVR/CD155) KNOCKOUT CELLS DERIVED FROM RD (HUMAN RHABDOMYOSARCOMA) CELL LINE BY CRISPR

The present application contains a Sequence Listing that has been submitted electronically in ASCII format and is hereby incorporated by reference in its entirety. The ASCII copy, created on Jan. 12, 2022, is named Substitute Sequence Listing_ST25.txt and is 464,026 bytes in size.

TECHNICAL FIELD

The present disclosure relates to the field of genetic engineering and genome editing. Specifically, the present disclosure provides a modified polio virus receptor (PVR/CD155) gene. More specifically, the present invention provides cell lines comprising said modified gene and method of producing the same using clustered regularly interspaced short palindromic repeats (CRISPR) and CRISPR-associated protein 9 (CRISPR-Cas9) system. The said cell line is refractory (non-permissive) to poliovirus and susceptible to most *Enteroviruses* and many other human viruses. Further, use of said cell line is research, diagnostic and therapy.

BACKGROUND ART

Genus *Enterovirus* of the Picornaviridae family of single stranded positive sense RNA viruses contain more than 100 different human *Enterovirus* types grouped into four species namely EV-A, EV -B, EV-C and EV-D. Human *Enteroviruses* cause a variety of diseases from mild diarrhoeas to encephalitis, aseptic meningitis, acute flaccid paralysis, poliomyelitis, hand foot and mouth disease, acute haemorrhagic conjunctivitis, pancreatitis and cardiovascular diseases mainly in infants and children. Most *Enteroviruses* can be cultured in cell lines of human and monkey origins. A few *Enteroviruses* can also be cultured in murine cells. *Enteroviruses* utilize a variety of different cell surface receptors to infect cells. Cell tropism is dependent on the differential expression of the receptors on the cells in different tissues.

Poliomyelitis or polio (derived from greek words 'polios' meaning grey and 'myelos' meaning matter) had a tragic legacy of paralysis and deformity. It is most significant among the history for its epidemic outbreak (Mehndiratta et al., 2014, Louten J., 2016). The disease causes inflammation of grey matter of spinal cord which results in paralysis, also known as paralytic poliomyelitis. It is also called infantile paralysis because it mainly paralyzes young children below 5 years. It causes non-curable paralysis. The causative agent is Poliovirus belongs to subtype *Enterovirus* C (Oberste et al., 1999, Zell et al., ICTV report). It has three serotypes PV1, PV2, and PV3. Polio virus infects only humans without animal reservoir and have shorter life span in the environment. Children can be protected from this disease by providing them lifelong immunity through effective and inexpensive vaccines. Unlike other diseases, polio can be eradicated completely by cessation of wild polio transmission and immunization with Polio vaccines.

Polioviruses are unique in the sense that they use CD155, a member of immunoglobulin superfamily, as their sole cell surface receptor for cellular entry. Most importantly, no other *Enterovirus* uses CD155 as its cell receptor. Other cellular functions of CD155 are not yet well defined. These may include cell adhesion, cell mobility, innate immunity and cancer biology among others.

Poliovirus is on the verge of global eradication. Wild poliovirus 2 has been globally eradicated, wild poliovirus 3 has not been detected anywhere in the world for the past 5 years. Four out of the six WHO Regions have been certified polio free. African Region (AFR) is polio-free for more than 3 years. Wild poliovirus 1 is still endemic in Pakistan and Afghanistan, the last 2 countries to stop wild poliovirus transmission. There were 33 wild poliovirus confirmed polio cases in the two countries in 2018. As of date 59 cases of wild poliovirus 1 have been reported in Pakistan (n=47) and Afghanistan (n=12). In 2016, type 2 polio vaccine (Sabin) was withdrawn from the routine immunization schedule in all OPV using countries. The WHO has recommended cessation of use of live attenuated poliovirus vaccines (Sabin) for polio immunization soon after stopping the last wild poliovirus transmission to achieve completely polio free world.

World Health Organization (WHO) launched Global Poliovirus Eradication Initiative (GPEI) in 1998 with a view to eradicate polio globally. 350,000 annual cases of wild poliovirus were reported from 125 countries in 1988. However, in 2018, only 33 cases were reported by two countries - Pakistan and Afghanistan. The eradication progress for polio has been serotype-specific. Wild polio virus 2 eradicated in 2015, after its last cases identified in India in 1999, wild polio virus 3 lastly detected in 2012. As of 31 July 2019, 59 cases have been reported for wild type polio virus 1 from two countries Pakistan (n=47) and Afghanistan (n=12).

The live weakened virus originally contained in the oral polio vaccine (OPV), can mutate while multiplying in the host. This mutant virus has potential to cause paralysis and can spread causing cVDPV. In the past, there have been outbreaks reported in certain regions due to Vaccine derived poliovirus cases. Due to eradication of wild type poliovirus 2, it has been considered for containment. Type2 have also been removed from the OPV, which caused over 90% of cVDPV cases since the eradication of WPV2 in 1999. Due to risk of introduction of vaccine derived poliovirus in circulation have led to the usage of Intravenous Polio vaccine (IPV) in many countries.

Since, globally wild polio exists in the small geographic area and only type 1 wild poliovirus strains appears to be in circulation, WHO has initiated Polio Endgame Strategy. The Polio eradication and endgame strategic plan 2013-2018 was developed. According to this plan following objective needs to be achieved:

1. Cessation of wild Polio transmission
2. Cessation of use of OPV to eliminate the risks of vaccine-associated paralytic poliomyelitis (VAPP), immunodeficiency-associated vaccine-derived poliovirus (iVDPV) and outbreaks of circulating vaccine-derived poliovirus
3. Containment measures to avoid the risks of a facility-associated reintroduction of virus into the polio-free community in post-eradication period.

Thus, WHO Polio Endgame Strategy provides guidelines called as Global Action Plan for safe handling and containment of poliovirus infectious and potentially infectious materials. After two successive editions of GAP (2004 & 2009), the third edition of Global Action Plan (GAPIII) was endorsed in 2014 by WHO Strategic Advisory Group of Experts.

GAPIII provides guidance as quoted in the manual "to minimize poliovirus facility-associated risk after type specific eradication of wild polioviruses and sequential cessation of oral polio vaccine use". The manual also states that "all facilities but specifically those that could/don't know if they are collecting, handling or storing poliovirus. These include facilities that are not purposefully using and manipulating poliovirus for research, diagnostics and or/vaccine production but rather, might inadvertently be working with the virus through poliovirus potentially infectious material (PV PIM). The guidance aims to help facilities identify PV PIM and eliminate or minimize risks of handling and storing such material".

The guidance provides list for PV PIM such as fecal, nasopharyngeal, or sewage samples collected in a time and place where wild polioviruses vaccine-derived, or OPV derived viruses were circulating or oral polio vaccines were in use. Research facilities with a high probability of storing such materials include those working with rotavirus or other enteric agents, hepatitis viruses, influenza/respiratory viruses, and measles virus. Other facilities could include those conducting nutrition research or environmental facilities. The guidance aims to help these facilities identify PV PIM and eliminate or minimize risks of handling and store such materials, so that poliovirus is not accidentally or deliberately released into the environment. Under the laboratory hazards, inoculation of the samples in PV-permissive cells would result in increased PV content up to 108 CCID50/ml unknowingly. Thus, laboratories wanting to culture viruses from PV PIM like human fecal samples, human throat secretions and environmental waters in poliovirus permissive cell lines will have to establish biosafety and bio-risk management systems and obtain verification/certification by National Containment Authority. This may prove very expensive for the laboratories.

This necessitates for poliovirus non-permissive cell line supporting growth of a variety of different viruses (enteric/respiratory viruses) but not poliovirus.

Cell lines derived from human and monkey tissues are routinely used for diagnosis, isolation and research. Human Rhabdomyosarcoma (RD) cell line, carcinoma of larynx (Hep-2), carcinoma of cervix (HeLa), human diploid cell strains as well as monkey kidney cell lines (Vero, BGM, LLCMK2 etc.) are the most useful cells in virology research laboratories worldwide. There are several other cell lines derived from humans for special purposes. These cell express cell surface receptors for Polio and *Enteroviruses* as well as many other enteric and respiratory viruses. RD Cell line is most widely used in virology laboratories for *Enterovirus* diagnostics and research.

Human rhabdomyosarcoma (RD), carcinoma of larynx (Hep-2), carcinoma of cervix (HeLa), human diploid cell strains as well as monkey kidney cell lines (Vero, BGM, LLCMK2 etc.) are the most useful cells in *Enterovirus* research laboratories worldwide. There are several other cell lines derived from humans for special purposes. These cell express cell surface receptors for Polio and *Enteroviruses* as well as many other enteric and respiratory viruses. The most preferred in the laboratory use is RD. It is a continuous cell line established from rhabdomyosarcoma obtained from pelvic mass of 7-year-old female by McAllister et al in 1969. The cells are used for growth of a number of human viruses. The RD cells are highly susceptible to poliovirus and other *Enteroviruses* (non-polio *Enteroviruses*/NPEV). RD cells have been recommended for poliovirus isolation in Global Polio Network Laboratories.

The RD cell line naturally expresses the receptor for polio on the extracellular region of the cell. Apart from being a viral receptor CD155 also devises a role in cellular activities such as cell migration and invasion, tumour immunity and as biomarker for cancer. The receptor is found in both soluble and transmembrane form. CD155 is used as viral receptor only by poliovirus among the other *Enteroviruses*. Thus, it is a unique receptor for poliovirus attachment and binding.

In order to meet the requirement as set forth in the art, the present invention provides modified polio virus receptor (PVR/CD155) gene. More specifically, the present invention provides cell lines comprising said modified gene and method of producing the same using clustered regularly interspaced short palindromic repeats (CRISPR) and CRISPR-associated protein 9 (CRISPR-Cas9) system. The said cell line is refractory (non-permissive) to poliovirus and susceptible to most *Enteroviruses* and many other human viruses. The cell line is authenticated for growth of polio by collaborating with three National Polio Laboratories.

OBJECTIVES

It is; therefore, the primary object of the present invention is to provide modified sequence comprising one or more mutations in exons selected from exons 2, 3 and 4 of poliovirus receptor (PVR/CD155) gene having SEQ ID No.1.

The present invention further aims to provides a cell line is refractory (non-permissive) to poliovirus and susceptible to most *Enteroviruses* and many other human viruses.

The present invention aims to provides a method for producing a cell line of the present invention, wherein, said method comprises the steps of:

- modifying one or more target exons of a gene in the cell by introducing three or more kinds of guide RNAs selected from SEQ ID NO 19-23 and their oligonucleotides having sequences set forth in SEQ ID Nos. 24-33 for said target gene using the clustered regularly interspaced short palindromic repeats (CRISPR) and CRISPR-associated protein 9 (CRISPR-Cas9) system;
- knocking out one or more target exons of the gene by (i) causing five kinds of guide RNAs to target each of the one or more kinds of target exons of the gene and then (ii) causing a Cas protein to cut each of the one or more kinds of target exons of the gene;
- sequencing the cell strains to confirm the knock-out using primers.

As another objective, the present invention provides use of the modified nucleotide sequence of the present invention, wherein said modified sequence can be used for research, therapy, diagnosis and screening.

SUMMARY

The present disclosure is related to a modified polio virus receptor (PVR/CD155) gene. Said gene comprises one or more mutations in exons selected from exons 2, 3 and 4 of poliovirus receptor (PVR/CD155) gene having SEQ ID No.1. More specifically, the present invention provides cell lines comprising said modified gene and method of producing the same using clustered regularly interspaced short palindromic repeats (CRISPR) and CRISPR-associated protein 9 (CRISPR-Cas9) system. The said cell line is refractory (non-permissive) to poliovirus and susceptible to most *Enteroviruses* and many other human viruses. Further, use of said cell line is research, diagnostic and therapy.

BRIEF DESCRIPTION OF DRAWINGS

The disclosure may be more fully understood by reading the following detailed description of the embodiment, with reference made to the accompanying drawings as follows:

FIG. 1 shows the sequence of PVR/CD155 highlighting each of the exons with respect to their positions in the sequence.

FIG. 4 shows the complete Sequence of CD155/PVR for RD-SJ40 cell line (Deletion/insertion has been shown in proper regions).

FIG. 5 shows modified RD-SJ40 mRNA sequence.

FIG. 6 shows Homo sapiens poliovirus receptor (PVR), transcript variant 1, mRNA;

FIG. 7 shows modified RD-SJ35 sequence;

FIG. 8 shows modified RD-SJ35 mRNA sequence;

DETAILED DESCRIPTION

Figure 2:
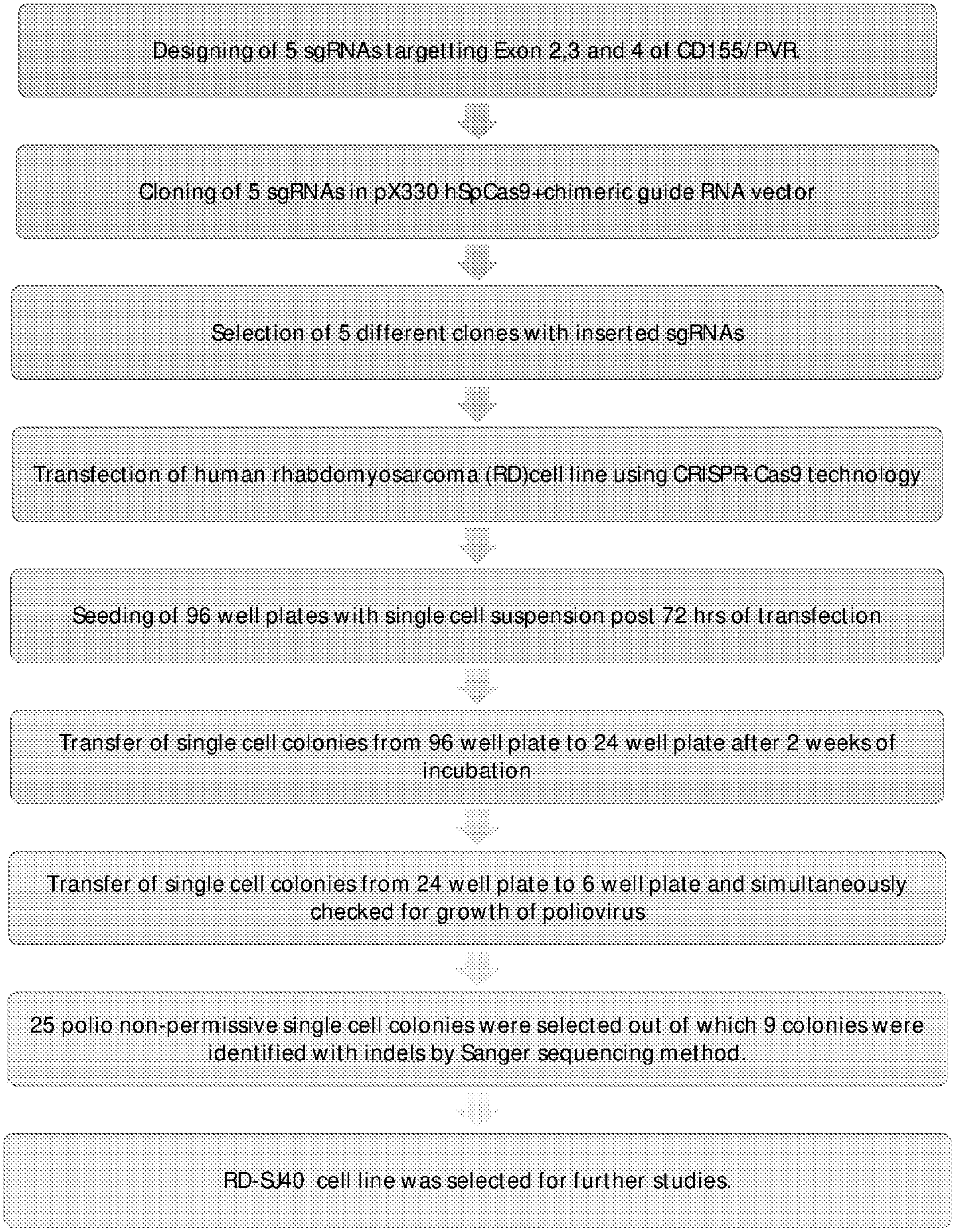
FIG. 2 shows the flow chart of conducting the process of obtaining desired cell line.
Figure 3:
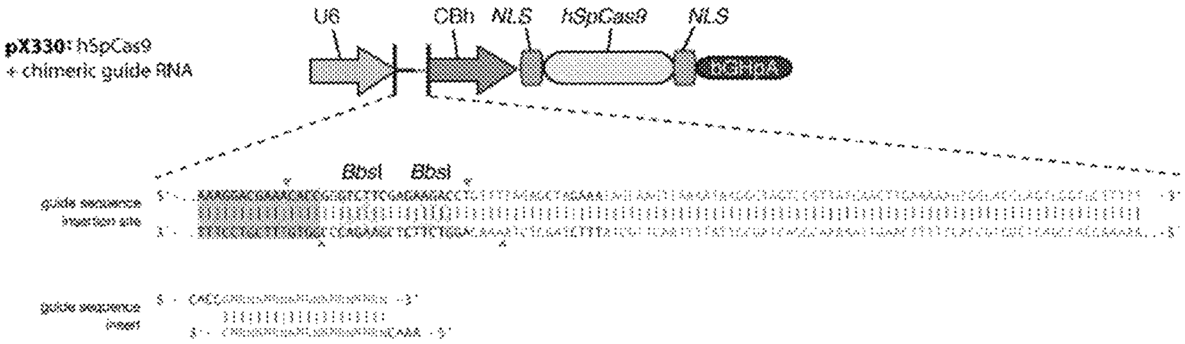
FIG. 3 shows the construct design.
Figure 9:
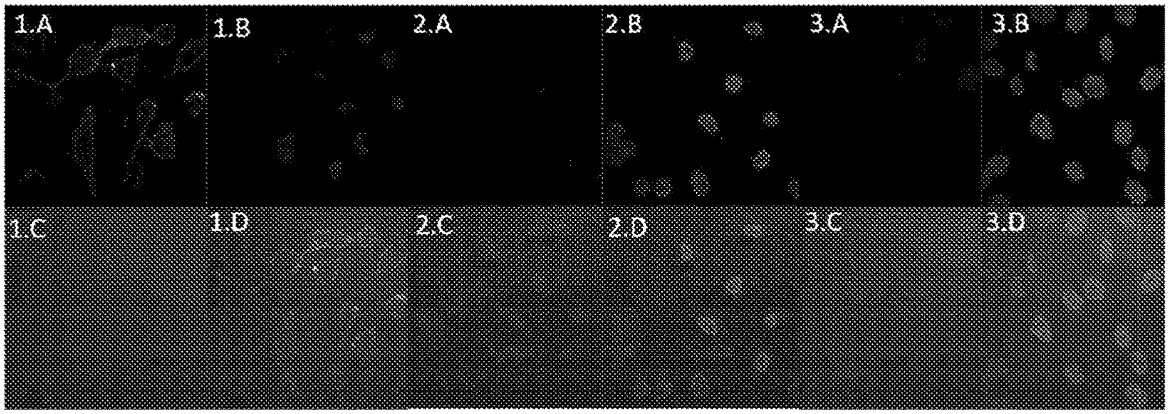
FIG. 9 shows Immunofluorescence assay: Anti-CD155 antibody was used for detection of CD155 gene. 1 shows RD cell line used as control, 2 shows RD-SJ35 cells, 3 shows RD-SJ40 cells; A: Immunofluorescence of CD155 using mouse anti CD155 monoclonal antibody stained with Alexa488.B: DAPI staining of the cell nuclei. C: DIC image D: Overlap of A+B.
Figure 10:
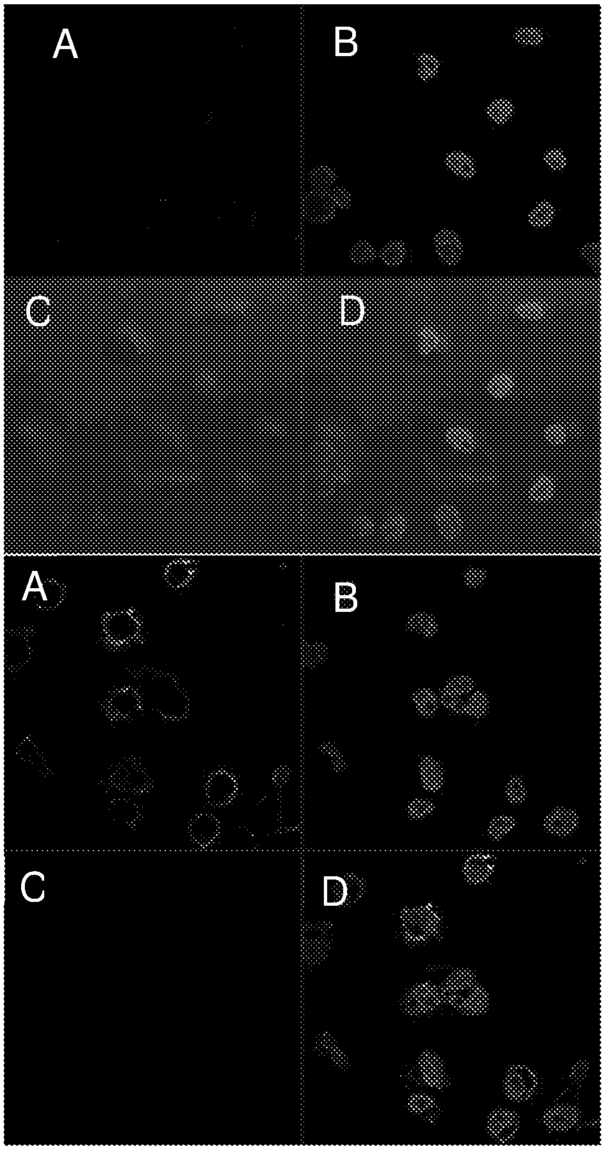
FIG. 10 shows Immunofluorescence staining of CD155 cell surface receptor on RD-SJ40 cells and RD (original). Anti-CD155 mouse monoclonal antibodies and Alexa488 labeled anti-mouse Ig antibodies were used for visualization of CD155 on the cell surface by confocal microscopy (Zeiss). Cell nuclei were also stained with DAPI. Each Panel shows a) CD155 immunofluorescence staining b) DAPI staining, c) DIC and d) Overlap of CD155 immunofluorescence and DAPI staining. Top panel CD155 Knockout RD cells. Lower panel RD (original) cells

The details of one or more embodiments of the invention are set forth in the accompanying description below including specific details of the best mode contemplated by the inventors for carrying out the invention. The embodiments of the invention which are apparent to one skilled in the art after reading the present disclosure and on applying the common general knowledge of the technical field are within the scope of this invention.

DEFINITIONS:

The use of "comprise", "comprises", "comprising", "contain", "contains", "containing", "include", "includes", and "including" are not intended to be limiting. It is to be understood that both the foregoing general description and this detailed description are exemplary and explanatory only and are not restrictive.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art.

Hereinafter, the terms used in this invention are described in more detail.

The term "batch culture' used in this invention indicates the method of culture that continues until the first supplied raw materials are all consumed without additional Supply, with which the concentration of substrates, the concentration of metabolites, and the density of cells are changed continuously over the culture time.

The term "knockout", "elimination', and "deletion' in this invention can be used interchangeably. This term means any addition or loss of a target gene sequence of cell genome so that the protein expression mediated by the target gene is completely removed.

The term "clone' and "cell line' can be used interchange ably, which both indicate a cell group having the same characteristics.

In this invention, "CRISPR is the system composed of sgRNA (guide RNA) complementarily binding to the target genome and Cas9 protein that can cut the genome gene by binding to sgRNA and the target genome simultaneously. As a result, when sgRNA vector and Cas9 vector are expressed temporarily in cells together at the same time, SgRNA and Cas9 protein are produced to change gS gene sequence, leading to the Suppression of the GS protein expression The present invention provides a modified polio virus receptor (PVR/CD155) gene. More specifically, the present invention provides cell lines comprising said modified gene and method of producing the same using clustered regularly interspaced short palindromic repeats (CRISPR) and CRISPR-associated protein 9 (CRISPR-Cas9) system. The said cell line is refractory (non-permissive) to poliovirus and susceptible to most *Enteroviruses* and many other human viruses. The cell line is authenticated for growth of polio by collaborating with three National Polio Laboratories.

In an embodiment, the present invention provides Modified nucleotide sequences comprising one or more changes (insertion/ deletion) exons selected from exon2, exon3 and/ or exon 4 of poliovirus receptor (PVR/CD155) gene having SEQ ID No.1.

In another embodiment, said changes are achieved through deletion and/or insertion.

In yet another embodiment said sequence is selected from SEQ ID No. 2-10. The same have been explained in the below table:

TABLE 1

| Sr.no. | Cell line | SEQ ID complete modified genome | SEQ ID mRNA |
|---|---|---|---|
| 1 | RD-SJ1 | 2 | 48 |
| 2 | RD-SJ4 | 3 | 49 |
| 3 | RD-SJ15 | 4 | 50 |
| 4 | RD-SJ23 | 5 | 51 |
| 5 | RD-SJ28 | 6 | 52 |
| 6 | RD-SJ30 | 7 | 53 |
| 7 | RD-SJ35 | 8 | 54 |
| 8 | RD-SJ37 | 9 | 55 |
| 9 | RD-SJ40 | 10 | 56 |

In another embodiment, said exon 2 has SEQ ID No.12.

In a further embodiment said exon 3 has SEQ ID No.13.

In a further embodiment said exon 4 has SEQ ID No.14.

In an aspect, the present invention provides a genetically engineered cell strains comprising the modified nucleotide sequences of the present invention, wherein said cell strains, RD-SJ1, RD-SJ4, RDSJ15, RD-SJ23, RD-SJ 28, RD-SJ30, RD-SJ35, RD-SJ37 and RD-SJ40 are derived from RD cell line of human rhabdomyosarcoma.

In one embodiment, said cell strain is refractory (non-permissive) to poliovirus and susceptible to most *Enteroviruses* and many other human viruses.

The cell strain RD-SJ40, one of the nine strains is being sent for deposition at ATCC (USA) with an Account 131466A. The details will be provided in due course.

In another aspect, the present invention provides a method for producing a cell line of the present invention, wherein, said method comprises the steps of:

- modifying one or more target exons of a gene in the cell by introducing three or more kinds of guide RNAs selected from SEQ ID NO 19-23 and their oligonucleotides having sequences set forth in SEQ ID Nos. 24-33 for said target gene using the clustered regularly interspaced short palindromic repeats (CRISPR) and CRISPR-associated protein 9 (CRISPR-Cas9) system;
- knocking out one or more target exons of the gene by (i) causing five kinds of guide RNAs to target each of the one or more kinds of target exons of the gene and then (ii) causing a Cas protein to cut each of the one or more kinds of target exons of the gene;
- sequencing the cell strains to confirm the knock-out using primers.

In an embodiment, said primers have sequences set forth in SEQ ID Nos. 34-47.

In another embodiment, the target exons of the gene have sequence selected from SEQ ID Nos. 11-18.

In yet another embodiment, the worked/modified cell strain is RD cell strain of human rhabdomyosarcoma (RD).

In one aspect, the present provides use of the modified nucleotide sequence of the present invention, wherein said modified sequence can be used for research, therapy, diagnosis and screening.

The exons sequences are provided below in which the mutations were introduced:

Example 2: Design and Cloning of Single Guide RNA (sgRNA)

The study targeted three exon regions of CD155. Accordingly, five sgRNAs were designed—two sgRNAs for Exon2, two sgRNAs for Exon3 and, one sgRNA for Exon4 of CD155 gene (NG_008781.2). In order to relegate the off-target effects and to extend the specificity, sgRNA sequences with high scores for on-target activity were selected. The reverse complement (rc) of each guide sequence were determined. Addition of "CACC" before the 20-mer guide sequence and "AAAC" before the guide's reverse complement for cloning into the pX330 vector was done (Addgene, Plasmid 48138, Middlesex, UK). The five sgRNA obtained were cloned and expressed in pX330 vector. The confirmation of integrated sgRNA clones was done by sequencing, using U6 promoter forward primer: CGTAACTTGAAAGTATTTCGATTTCTTGGC. The selected clones were used for CRISPR/Cas9 experiments.

Example 3: Transfection of RD Cells

RD cells were seeded into 6-well plate with cell density of $6\times10^5$ cells per well. All the five sgRNA clones were pooled together at concentration of 900 ng. The transfection was carried out after 24 h of incubation i.e 70-80% confluent cells as per Lipofectamine CRISPRMAX Reagent Cas9 Nuclease Transfection Protocol (Thermo Scientific). After 72 h incubation at 37° C., 5% $CO_2$; single cell suspension was prepared in a growth medium containing puromycin (2 μg/ml). 96 well plates were seeded with cell suspension, after 3 weeks selection of monoclonal colonies was done.

TABLE 2

CD155 Exon regions

| Exon | Region | Nucleotides | Amino acids | SEQ ID. NOs |
|---|---|---|---|---|
| Exon 1 (5001nt . . . 5378nt) | 5' UTR and leader sequence | 81 | 27 | 11 |
| Exon 2 (8426nt . . . 8773nt) | Domain 1 | 348 | 116 | 12 |
| Exon 3 (11012nt . . . 11308nt) | Domain 2 | 297 | 99 | 13 |
| Exon 4 (15103nt . . . 15220nt) | | 117 | 39 | 14 |
| Exon 5 (18965nt . . . 19113nt) | Domain 3 | 147 | 49 | 15 |
| Exon 6 (19945nt . . . 20103nt) | Trans membrane region | 159 | 53 | 16 |
| Exon 7 (22495nt . . . 22526nt) | Cytoplasmic region | 30 | 10 | 17 |
| Exon 8 (22943nt . . . 27364nt) | 3' UTR and C-terminus region | 72 | 24 | 18 |

EXAMPLE

The following examples and advantages of the present invention are provided for the purpose of illustration only and are not intended to limit the scope of the present invention.

Example 1: Cell Culture

Rhabdomyosarcoma cell line (RD) was attained from CDC. RD and Rhabdomyosarcoma knockout (RD-KO)-CD155 cell lines were maintained in Dulbecco' s modified Eagle's Medium (DMEM) supplemented with 10% fetal bovine serum, 3% Glutamine, 1M HEPES, 7.5% sodium bicarbonate, penicillin, and streptomycin. Incubated at 37° C. humidified incubator with 5% $CO_2$.

Example 4: Screening and Selection of RD-KO-CD155 Cells

Polio type1-sabin like (NIBSC 10/164, grown in RD) was used for infection to screen for the polio resistant cells. Each monoclonal colonies were grown in triplicates in 96 well plates. Infection was carried out on 90% confluent cells with 100 $TCID_{50}$. Plates were incubated at 37° C., 5% $CO_2$ for 5 days and examined for cytopathic effect (CPE). Back titration was performed using RD cell line, to check the virus titer used in the experiment. Cells showing no CPE were selected as poliovirus resistant cells. After the initial screening, the selected cells were tested against Polio type3-Sabin like 100 $TCID_{50}$ and Non-Polio *Enterovirus* (infection dose) and checked for the CPE. The list of NPEVs used are provided below.

TABLE 3

| Sr. No. | Virus | Enterovirus Species | RD | RD-SJ35 | RD-SJ40 |
|---|---|---|---|---|---|
| 1 | CV-A2 Fleetwood | Enterovirus A | + | + | + |
| 2 | CV-A3 Olson | Enterovirus A | + | + | + |
| 3 | CV-A5 Swartz | Enterovirus A | + | + | + |
| 4 | CV-A6 Gdula | Enterovirus A | + | + | + |
| 5 | CV-A7 ABIV USSR | Enterovirus A | + | + | + |
| 6 | CV-A9 Griggs | Enterovirus B | + | + | + |
| 7 | CV-A10 Kowalik | Enterovirus A | + | + | + |
| 8 | CVA11 Belgium | Enterovirus C | + | + | + |
| 9 | CVA14 G-14 | Enterovirus A | + | + | + |
| 10 | CVA15 G-9 | Enterovirus A | + | + | + |
| 11 | CVA16 G-10 | Enterovirus A | + | + | + |
| 12 | CVA21 Kvykendall | Enterovirus C | + | + | + |
| 13 | CVA22 Chulman | Enterovirus C | + | + | + |
| 14 | CVA24 6357 | Enterovirus C | + | + | + |
| 15 | E-4 RIVM | Enterovirus B | + | + | + |
| 16 | E-6 RIVM | Enterovirus B | + | + | + |
| 17 | E-11 RIVM | Enterovirus B | + | + | + |
| 18 | E-13 Delcarmen | Enterovirus B | + | + | + |
| 19 | E-30 Bastianni | Enterovirus B | + | + | + |
| 20 | CV-B4 Tilo | Enterovirus B | + | + | + |
| 21 | CV-B5 Deuk | Enterovirus B | + | + | + |
| 22 | EV-A71 BrCr | Enterovirus A | + | + | + |
| 23 | CV-B1 Dekking | Enterovirus B | + | + | + |
| 24 | CV-B3 Nancy | Enterovirus B | + | + | + |
| 25 | CB6 Schmitt | Enterovirus B | + | + | + |
| 26 | EV88 (Isolate) | Enterovirus B | + | + | + |
| 27 | EV76 (Isolate) | Enterovirus A | + | + | + |
| 28 | EV114 (Isolate) | Enterovirus A | + | + | + |
| 29 | EV121 (Isolate) | Enterovirus J | + | + | + |
| 30 | Poliovirus 1 (Sabin) | Enterovirus C | + | − | − |
| 31 | Poliovirus 3 (Sabin) | Enterovirus C | + | − | − |

+ Cytopathic effect (CPE) and virus growth
− No cytopathic effect (CPE)

Example 5: Detection of Insertion/Deletion (Indels) by Sequencing 14 primers were designed flanking the targeted exon regions (Exon 2, Exon 3 and, Exon4) of CD155 gene. Extraction of genomic DNA was performed as per Phire Tissue Direct PCR kit (Thermo Scientific). PCR products were electrophoresed using 1% agarose gel, desired bands were purified using the QIAquick Gel Extraction Kit (Qiagen). The PCR purified DNA was sequenced using both forward and reverse primer as described in BigDye Terminator v3.1 Cycle Sequencing Kit. Cycle sequencing product was purified using BigDye X terminator Purification Kit (Thermo Scientific). The sequence data generated was resolved on ABI 3130x1 Genetic Analyzer and analyzed by Sequencher v.5.4. (Gene Codes, USA). RD cell line was used as a control for validating the primers. The list of target specific primer and sequencing primers are provided in the below tables.

TABLE 4

List of sgRNA designed for the CRISPR/Cas9 experiment.

| Sr. no. | Target Exon | Sequence | SEQ ID NO. | PAM sequence |
|---|---|---|---|---|
| 1. | Exon3 | AATCACCTGGCACTCAGACC | 19 | TGG |
| 2. | Exon2 | CAGGCGCCCACCCAGGTGCC | 20 | CGG |
| 3. | Exon2 | GACGCTGCCCTGCTACCTAC | 21 | AGG |
| 4. | Exon3 | CAAGCCCCAGAACACAGCTG | 22 | AGG |
| 5. | Exon4 | CTGGTACCTTGGCCAGAATG | 23 | AGG |

Designing the Guide Sequence Into the sgRNA Scaffold

To clone the guide sequence into the sgRNA scaffold, synthesize two oligos of the form:

5'-CACCGNNNNNNNNNNNNNNNNNNN-3'

3'-CNNNNNNNNNNNNNNNNNNNCAAA-5'

To clone in your target sequence, synthesize two partially complementary oligos with 4nt overhangs compatible for cloning into the vector. "N" and "n" represent complementary nucleotides.

5'-CACCGNNNNNNNNNNNNNNNNNNN-3'

5'-AAACnnnnnnnnnnnnnnnnnnnC-3'

When annealed oligos form double stranded DNA with overhangs for cloning into BbsI site in px330.

5'-CACCGNNNNNNNNNNNNNNNNNNN-3'

3'-CNNNNNNNNNNNNNNNNNNNCAAA-5'

Forward primer:
5'-CACCGNNNNNNNNNNNNNNNNNNN-3'

Reverse primer:
5'-AAACnnnnnnnnnnnnnnnnnnnC-3'

Note: 1) make sure The PAM site is not included in the sgRNA sequence.

2) Added CACCG to forward oligo(if there is Gin the 5' site, just add CACC).

3) Designed the oligo 2, Get reverse complementary sequence of forward oligo, then added aaac to 5', c to 3' site.

TABLE 5

List of oligos for the 5 sgRNAs designed:

| Sr. No. | sgRNA | Forward/Reverse sequence | Sequence | SEQ ID NO. |
|---|---|---|---|---|
| 1 | 1st sgRNA | Forward Sequence for Cloning | 5'**CACCG**AATCACCTGGCACTCAGACC3' | 24 |
| 2 | NIV (Exon 3) | Reverse Sequence for Cloning | 5'**AAAC** GGTCTGAGTGCCAGGTGATTC3' | 25 |
| 3 | 2nd sgRNA | Forward Sequence for Cloning | 5'**CACCG** CAGGCGCCCACCCAGGTGCC3' | 26 |
| 4 | NIV (Exon 2) | Reverse Sequence for Cloning | 5'**AAAC** GGCACCTGGGTGGGCGCCTGC3' | 27 |
| 5 | 3rd sgRNA | Forward Sequence for Cloning | 5'**CACCG** ACGCTGCCCTGCTACCTAC3' | 28 |
| 6 | NIV (Exon 2) | Reverse Sequence for Cloning | 5'**AAACG** TAGGTAGCAGGGCAGCGTCC3' | 29 |
| 7 | 4th sgRNA | Forward Sequence for Cloning | 5'**CACCG** CAAGCCCCAGAACACAGCTG3' | 30 |
| 8 | NIV (Exon 3) | Reverse Sequence for Cloning | 5'**AAAC** CAGCTGTGTTCTGGGGCTTGC3' | 31 |
| 9 | 5th sgRNA | Forward Sequence for Cloning | 5'**CACCG** CTGGTACCTTGGCCAGAATG3' | 32 |
| 10 | NIV (Exon 4) | Reverse Sequence for Cloning | 5'**AAAC** CATTCTGGCCAAGGTACCAGC3' | 33 |

Example 6: Immunofluorescence

The expression of CD155 protein on cell membrane of engineered RD-SJ40 cell line was detected by immunofluorescence. Primary antibody used was anti-CD155 antibody (Santacruz, Ab-B-6 sc514623, 1:100) and secondary antibody used was tagged with Alexa Fluor 488 (Invitrogen, A11029, 1:200). RD cells were used as control. Protocol obtained from the manufacturer was used.

Example 7: Cell Line Validation

The RD-SJ40 cell line was validated by three NPLs—BJMC Ahmedabad, KIPM Chennai, and SGPGI Lucknow. Stool samples of Acute Flaccid Paralysis (AFP) cases were tested on the RD-SJ40 cell line. The samples which showed CPE in RD-SJ40 cell line were processed for identification of NPEVs. Viral RNA was isolated using Qiagen Viral RNA isolation kit. cDNA was prepared from the RNA isolated and PCR protocol was performed as per the standard Protocol obtained from CDC. The primers used for sequencing were specific to NPEVs. The sequences were obtained by Sanger sequencing and analyzed using Sequencher v.5.4. (Gene Codes, USA). The sequences generated were identified using Blast tool, NCBI.

Results

The engineered RD-KO-CD155 cell line wherein the CD155 gene is perpetually edited from the genome of RD cell line. The knockout cell line was established by designing five sgRNAs targeting exon2 (Domain1, variable region), exon3 (Domain2, constant region1) and exon4 (Domain3, constant region2). RD cell line naturally express CD155 receptor on its surface and is highly susceptible to polio and majority of the non-polio *Enteroviruses*. Upon transfection monoclonal colonies were infected with Polio type1-Sabin like (NIBSC, grown in RD), colonies showing no cytopathic effect were selected as they were resistant to growth for poliovirus. The colonies showing no viral growth confirms that the CRISPR/Cas9 has successfully modified the poliovirus receptor. The colonies resistant to poliovirus were considered as knockout for CD155. Sanger sequencing was performed to analyze the regions hampered by the sgRNAs. The sequencing data for nine clones were obtained showing indels at exon2 and exon3. The table below summarizes the same:

TABLE 6

| Sr. no. | Cell line | SEQ ID complete genome | SEQ ID mRNA | Exon 2 | Exon 3 | Exon 4 |
|---|---|---|---|---|---|---|
| 1 | RD-SJ1 | 2 | 48 | No in/del | 1 nt deletion<br>11026 nt<br>3 nt mismatch<br>11027 nt . . . 11029 nt<br>*<u>a</u>ctt*<br>11 nt mismatch<br>11129 nt . . . 11139 nt<br>1 nt deletion<br>11140 nt<br>*cccaaatcacc*<br><u>a</u> | No in/del |

TABLE 6-continued

| Sr.no. | Cell line | SEQ ID complete genome | SEQ ID mRNA | Exon 2 | Exon 3 | Exon 4 |
|---|---|---|---|---|---|---|
| 2 | RD-SJ4 | 3 | 49 | No in/del | 99 nt deletion<br>11027 nt . . . 11125 nt<br>cagc tgaggttcag<br>aaggtccagc<br>tcactggaga<br>gccagtgccc<br>atggcccgct<br>gcgtctccac<br>agggggtcgc<br>ccgccagccc<br>aaatcacctg gcact | No in/del |
| 3 | RD-SJ15 | 4 | 50 | 40 nt deletion<br>8457 nt . . . 8496 nt<br>gccc<br>ggcttcttgg<br>gcgactccgt<br>gacgctgccc<br>tgctac | 99 nt deletion<br>11027 nt . . . 11125 nt<br>cagc tgaggttcag<br>aaggtccagc<br>tcactggaga<br>gccagtgccc<br>atggcccgct<br>gcgtctccac<br>agggggtcgc<br>ccgccagccc<br>aaatcacctg gcact | No in/del |
| 4 | RD-SJ23 | 5 | 51 | 1 nt deletion<br>8497 nt<br>c | 99 nt deletion<br>11027 nt . . . 11125 nt<br>cagc tgaggttcag<br>aaggtccagc<br>tcactggaga<br>gccagtgccc<br>atggcccgct<br>gcgtctccac<br>agggggtcgc<br>ccgccagccc<br>aaatcacctg gcact | No in/del |
| 5 | RD-SJ28 | 6 | 52 | No in/del | 99 nt deletion<br>11027 nt . . . 11125 nt<br>cagc tgaggttcag<br>aaggtccagc<br>tcactggaga<br>gccagtgccc<br>atggcccgct<br>gcgtctccac<br>agggggtcgc<br>ccgccagccc<br>aaatcacctg gcact | No in/del |
| 6 | RD-SJ30 | 7 | 53 | No in/del | 99 nt deletion<br>11027 nt . . . 11125 nt<br>cagc tgaggttcag<br>aaggtccagc<br>tcactggaga<br>gccagtgccc<br>atggcccgct<br>gcgtctccac<br>agggggtcgc<br>ccgccagccc<br>aaatcacctg gcact | No in/del |
| 7 | RD-SJ35 | 8 | 54 | 19 nt deletion<br>8479 nt . . . 8497 nt<br>1 nt insertion<br>8498 nt<br>gt<br>gacgctgccc<br>tgctacct | 99 nt deletion<br>11027 nt....11125 nt<br>cagc tgaggttcag<br>aaggtccagc<br>tcactggaga<br>gccagtgccc<br>atggcccgct<br>gcgtctccac<br>agggggtcgc<br>ccgccagccc<br>aaatcacctg gcact | No in/del |

TABLE 6-continued

| Sr.no. | Cell line | SEQ ID complete genome | SEQ ID mRNA | Exon 2 | Exon 3 | Exon 4 |
|---|---|---|---|---|---|---|
| 8 | RD-SJ37 | 9 | 55 | No in/del | 99 nt deletion<br>11027 nt . . . 11125 nt<br>cagc tgaggttcag<br>aaggtccagc<br>tcactggaga<br>gccagtgccc<br>atggcccgct<br>gcgtctccac<br>agggggtcgc<br>ccgccagccc<br>aaatcacctg gcact | 3 nt mis match<br>15155 nt . . . 15157 nt<br>*ccc* |
| 9 | RD-SJ40 | 10 | 56 | 41 nt deletion<br>8457 nt . . . 8497 nt<br>gccc<br>ggcttcttgg<br>gcgactccgt<br>gacgctgccc<br>gcgtctccac<br>tgctacc | 99 nt deletion<br>11027 nt . . . 11125 nt<br>cagc tgaggttcag<br>aaggtccagc<br>tcactggaga<br>gccagtgccc<br>atggcccgct<br>agggggtcgc<br>ccgccagccc<br>aaatcacctg gcact | No in/del |

underlined sequence represents deleted sequences;
italic sequences represent mismatch sequences;
bold sequence represents inserted sequences (insertion may be due to self-cell repair mechanism)

The curated and annotated sequence having accession number—NG_008781.2 (SEQ ID NO. 1) was used in the present invention as reference sequence for the PVR/CD155 protein. The indels obtained were compared to the Reference Sequence of the PVR protein expressed in humans was obtained from the RefSeq database of NCBI. The nucleotide region for the three exons are mentioned here—exon 2 is 8426 nucleotides to 8773 nucleotides; exon 3 is 11012 nucleotides to 11308 nucleotide and exon 4 is 15103 nucleotide to 15220 nucleotide.

In, RD-SJ35 the exon 2 has 19 nucleotide deletion from 8479 nucleotide to 8497 nucleotide and 1 nucleotide insertion at 8498. The exon 3 has 99 nucleotide deletion from 11027 nucleotide to 11125 nucleotides. The exon 4 has no indels. In, RD-SJ40 the exon 2 has 41 nucleotide deletion from 8457 nucleotide to 8497 nucleotides. The exon 3 has 99 nucleotide deletion from 11027 nucleotide to 11125 nucleotides. The exon 4 has no indels. The indels marked are provided in the table 5 above.

The exon 2 region codes for domainl which is essential for the attachment and binding of poliovirus to the cell. The exon 3 and exon 4 region codes for domain2 which is known to structurally support domain 1 but has no role in the infection process. The sequencing data suggests that the CD155 receptor in RD-SJ35 and RD-SJ40 cell line has indels in the region of domain 1 and domain 2 Immunofluorescence assay was performed to detect extracellular expression of the receptor. Antibody against CD155 was used for detection. The parent RD cell line was taken as control. The two cell lines RD-SJ35 and RD-SJ40 did not express the receptor on the outer surface of the cell when compared to the RD cell line which was used as control. Thus, the two RD knockout cell lines were confirmed to have defunct CD155 gene (FIG. 7).

After the establishment of PVR/CD155 knockout RD cell line, it was essential to check whether the cell line has not lost any characteristics essential for NPEVs infection. The two cell lines, RD-SJ35and RD-SJ40 were infected with two Polio strains—Polio type1-Sabin like (NIB SC, grown in RD) and Polio type3-Sabin like (NIBSC, grown in RD) and 29 NPEVs from different groups. The two cell lines showed viral infection for all 29 NPEVs and no infection was observed by the two polio strains. Results for the test is shown in Table no. 1. It can be concluded that the cell lines support growth of NPEVs and is non permissive to Polio. Thus, it is safe to use the cell line in Non-polio *Enterovirus* working laboratories as per the GAPIII regulations.

Of the two-cell line only one was validated by the three National Polio Laboratories (NPLs), who are part of the Polio Surveillance Project. The validation was conducted after National Immunization Day of Polio (NID), India held on 11 Mar. 2019. The validation of the RD-SJ40 cell line was conducted post NID as this increases the chance for the detection of Poliovirus. The three labs selected for validation were B.J Medical College (BJMC) Ahmedabad, Sanjay Gandhi Postgraduate Institute of Medical Sciences (SGPGI) Lucknow and King Institute of Preventive Medicine and Research (KIPM) Chennai situated in India. The three labs routinely test stool samples of Acute Flaccid Paralysis (AFP) cases. The laboratory simultaneously inoculated the stool extract in RD, L2OB and RD-SJ40 cell line.

The newly PVR/CD155 Knockout cell line was tested against 626 samples across three Polio network labs. Out of which 55 (8.78%) samples were Polio positives which had grown in RD and L20B (specific for Polio) cell line but not in PVR/CD155 knock out cell line. NPEV's which were 45 (7.19%) had grown in RD and PVR/CD155 knock out cell line but not in L2OB which is specific for Polio. The viral isolates which showed growth in RD-SJ40 cell line were sequenced for identification of viral strains. As per the Sanger sequencing method, the viral strains were detected to be NPEVs. (Table 1).

TABLE 7

Comparison of RD, L20B and RD-SJ40 cell line for growth of poliovirus.

| CPE result combinations | CPE Combination code | SGPGI | KIPM | BJMC | Row Total | CPE Combination code Virus isolation |
|---|---|---|---|---|---|---|
| L20B−/RD−/RD-SJ40− | 1 | 145 | 198 | 167 | 510 | Negative |
| L20B+/RD+/RL+/ RD-SJ40− | 2 | 33 | 9 | 11 | 53 | Polio |
| L20B−/RD+/RL+/RD-SJ40− | 3 | 0 | 0 | 2 | 2 | Polio |
| L20B+/RD−/RD-SJ40− | 4 | 0 | 0 | 1 | 1 | Polio? |
| L20B−RD+/RL−/RD-SJ40+ | 5 | 18 | 11 | 15 | 44 | NPEV |
| L20B−/RD+/RL−/RD-SJ40− | 6 | 2 | 0 | 0 | 2 | NPEVon RD |
| L20B−/RD+/RL+/RD-SJ40+ | 7 | 0 | 0 | 1 | 1 | NPEV L20B growing |
| L20B−/RD−/RD-SJ40+ | 8 | 7 | 3 | 3 | 13 | NPEV on RD-SJ40 |
| L20B+/RD−/RD-SJ40+ | 9 | 0 | 0 | 0 | 0 | Unknown? |
| COLUMN TOTAL | | 205 | 221 | 200 | 626 | |

RD-SJ40 = PVR/CD155 knockout RD cell line

Example 8: PVR/CD155 Protein

The protein encoding gene consists of 8 exons. The sequence encoding region for each exon in the RefSeq sequence (NG_008781.2) is provided as FIG. 1 showing the exons underlined.

The exon 1 codes for 5' untranslated region and signal peptide from 5001 nucleotide to 5378 nucleotides. The exon 2 codes for domain 1 from 8426 nucleotide to 8773 nucleotides. The exon 3 and exon 4 codes for domain 2, the position of exon 3 is from 11012 nucleotide to 11308 nucleotide and exon 4 is from 15103 nucleotide to 15220 nucleotides. The exon 5 codes for domain 3 from 18965 nucleotide to 19113 nucleotides. The exon 6 codes for transmembrane region from 19945 nucleotide to 20103 nucleotides. The exon 7 codes for cytoplasmic region from 22495 nucleotide to 22526 nucleotides. The exon 8 codes for 3'untranslated region and C-terminus region from 22943 nucleotide to 27364 nucleotides.

The PVR/CD155 mRNA sequence was used as the reference sequence for mRNA transcript. The PVR protein has four variant sequences available in the database. The sequence used in our studies is PVR expressed in humans, transcript variant 1, mRNA. The accession number obtained from the NCBI database—NM_006505. This sequence only has 8 exons of the protein. The sequence encoding region for each exon in the Reference sequence (NM_006505.5) is listed in FIG. 5.

The exon 1 codes for 5' untranslated region and signal peptide from 1 nucleotide to 266 nucleotides. The exon 2 codes for domain 1 from 267 nucleotide to 614 nucleotides. The exon 3 and exon 4 codes for domain 2, the position of exon 3 is from 615 nucleotide to 911 nucleotide and exon 4 is from 912 nucleotide to 1029 nucleotide. The exon 5 codes for domain 3 from 1030 nucleotide to 1178 nucleotide.

The exon 6 codes for transmembrane region from 1179 nucleotide to 1337 nucleotide. The exon 7 codes for cytoplasmic region from 1338 nucleotide to 1369 nucleotide. The exon 8 codes for 3'untranslated region and C-terminus region from 1370 nucleotide to 5792 nucleotides.

The mRNA sequence of PVR is provided in FIG. 5.

Example 9: RD-SJ40

The Reference Sequence for the PVR protein expressed in humans was obtained from the RefSeq database of NCBI. The curated and annotated sequence having accession number—NG_008781.2 was used for our studies as reference sequence for the PVR/CD155 protein. This sequence consists of introns and exons. The sequence encoding region for each exon along with the mutations are shown in FIG. 6.

The exon 1 codes for 5' untranslated region and signal peptide from 5001 nucleotide to 5378 nucleotides. The exon 2 codes for domain 1 from 8426 nucleotide to 8773 nucleotides with 41 nucleotide deletion at 8457 nucleotides to 8497 nucleotides. The exon 3 and exon 4 codes for domain 2, the position of exon 3 is from 11012 nucleotide to 11308 nucleotides with 99 nucleotide deletion at 11027 nucleotides to 11125 nucleotide and exon 4 is from 15103 nucleotide to 15220 nucleotides. The exon 5 codes for domain 3 from 18965 nucleotide to 19113 nucleotides. The exon 6 codes for transmembrane region from 19945 nucleotide to 20103 nucleotides. The exon 7 codes for cytoplasmic region from 22495 nucleotide to 22526 nucleotides. The exon 8 codes for 3'untranslated region and C-terminus region from 22943 nucleotide to 27364 nucleotides.

The sequence of PVR is provided in the FIG. 4 highlighting each of the exons with respect to their positions in the sequence.

The PVR/CD155 mRNA sequence was used as the reference sequence for mRNA transcript. The PVR protein has four variant sequences available in the database. The sequence used in our studies is PVR expressed in humans, transcript variant 1, mRNA. The accession number obtained from the NCBI database—NM_006505.5. This sequence only has 8 exons of the protein. The sequence encoding region for each exon along with mutation is listed FIG. 5.

The exon 1 codes for 5' untranslated region and signal peptide from 1 nucleotide to 266 nucleotides. The exon 2 codes for domain 1 from 267 nucleotide to 614 nucleotides with 41 nucleotide deletion at 298 nucleotides to 338 nucleotides. The exon 3 and exon 4 codes for domain 2, the position of exon 3 is from 615 nucleotide to 911 nucleotide with 99 nucleotide deletion at 630 nucleotides to 728 nucleotide and exon 4 is from 912 nucleotide to 1029 nucleotide. The exon 5 codes for domain 3 from 1030 nucleotide to 1178 nucleotide. The exon 6 codes for transmembrane region from 1179 nucleotide to 1337 nucleotide. The exon 7 codes for cytoplasmic region from 1338 nucleotide to 1369 nucleotide. The exon 8 codes for 3'untranslated region and C-terminus region from 1370 nucleotide to 5792 nucleotides.

The mRNA sequence of PVR is provided in FIG. 6 highlighting deletion of nucleotide.

Example: RD-SJ35

The Reference Sequence for the PVR protein expressed in humans was obtained from the RefSeq database of NCBI. The curated and annotated sequence having accession number—NG_008781.2 was used for our studies as reference sequence for the PVR/CD155 protein. This sequence consists of introns and exons. The sequence encoding region for each exon along with the mutations are shown in FIG. 8.

The exon 1 codes for 5' untranslated region and signal peptide from 5001 nucleotide to 5378 nucleotides. The exon 2 codes for domain 1 from 8426 nucleotide to 8773 nucleotides with 19 nucleotide deletion at 8479 nucleotides to 8497 nucleotide and 1 nucleotide insertion at 8498. The exon 3 and exon 4 codes for domain 2, the position of exon 3 is from 11012 nucleotide to 11308 nucleotides with 99 nucleotide deletion at 11027 nucleotides to 11125 nucleotide and exon 4 is from 15103 nucleotide to 15220 nucleotides. The exon 5 codes for domain 3 from 18965 nucleotide to 19113 nucleotides. The exon 6 codes for transmembrane region from 19945 nucleotide to 20103 nucleotides. The exon 7 codes for cytoplasmic region from 22495 nucleotide to 22526 nucleotides. The exon 8 codes for 3'untranslated region and C-terminus region from 22943 nucleotide to 27364 nucleotides.

The sequence of PVR is provided in FIG. 7 highlighting each of the exons with respect to their positions in the sequence.

The PVR/CD155 mRNA sequence was used as the reference sequence for mRNA transcript. The PVR protein has four variant sequences available in the database. The sequence used in our studies is PVR expressed in humans, transcript variant 1, mRNA. The accession number obtained from the NCBI database—NM_006505.5. This sequence only has 8 exons of the protein. The sequence encoding region for each exon along with mutation is listed FIG. 8.

The exon 1 codes for 5' untranslated region and signal peptide from 1 nucleotide to 266 nucleotides. The exon 2 codes for domain 1 from 267 nucleotide to 614 nucleotides with 19 nucleotide deletion at 320 nucleotide to 339 nucleotide and insertion at 340 nucleotide. The exon 3 and exon 4 codes for domain 2, the position of exon 3 is from 615 nucleotide to 911 nucleotide with 99 nucleotide deletion at 630 nucleotides to 728 nucleotide and exon 4 is from 912 nucleotide to 1029 nucleotide. The exon 5 codes for domain 3 from 1030 nucleotide to 1178 nucleotide. The exon 6 codes for transmembrane region from 1179 nucleotide to 1337 nucleotide. The exon 7 codes for cytoplasmic region from 1338 nucleotide to 1369 nucleotide. The exon 8 codes for 3'untranslated region and C-terminus region from 1370 nucleotide to 5792 nucleotides.

The mRNA sequence of PVR is provided in FIG. 8 highlighting deletion of nucleotide.

ADVANTAGES OF THE PRESENT INVENTION

The CD155/PVR knockout cells RD-SJ40 (poliovirus non-permissive cell line) will be used safely in all non-polio laboratories wanting to grow non-polio *Enteroviruses* from clinical samples (stool or respiratory secretions) for diagnostic purposes and research without the fear of poliovirus growth as inadvertent contamination. The CD155/PVR knockout RD-SJ40 cells will find wide applications in laboratories worldwide.

The modified sequence of the present invention has the advantage of being used in various research;

The present invention is cost effective, simple and find its uses in various research, diagnostic processes.

The invention claimed is:

1. A modified poliovirus receptor (PVR/CD 155) gene comprising a sequence selected from SEQ ID Nos. 2-10.

2. A genetically engineered cell strain comprising the modified poliovirus receptor (PVR/CD 155) gene as claimed in claim 1, wherein the genetically engineered cell strain is selected from the group consisting of RD-SJ1, RD-SJ4, RDSJ15, RD-SJ23, RD-SJ 28, RD-SJ30, RD-SJ35, RD-SJ37 and RD-SJ40, wherein the genetically engineered cell strain is derived from RD (Rhabdomyosarcoma) cell line of human rhabdomyosarcoma.

3. The genetically engineered cell strain as claimed in claim 2, wherein the genetically engineered cell strain is refractory (non-permissive) to poliovirus and susceptible to enteroviruses and human viruses.

4. A method for producing the genetically engineered cell strain as claimed in claim 2, the method comprising:

modifying one or more target exons of a gene in the cell by introducing three or more guide RNAs selected from SEQ ID Nos. 19-23 and their oligonucleotides having sequences set forth in SEQ ID Nos. 24-33 for the target gene using the clustered regularly interspaced short palindromic repeats (CRISPR) and CRISPR-associated protein 9 (CRISPR-Cas9) system;

knocking out one or more target exons of the gene by (i) causing five kinds of the three or more guide RNAs to target each of the one or more kinds of-target exons of the gene and then (ii) causing a Cas protein to cut each of the one or more kinds of target exons of the gene; and sequencing the cell strain to confirm the knock-out using primers.

5. The method as claimed in claim 4, wherein the primers have sequences set forth in SEQ ID Nos. 34-47.

6. The method as claimed in claim 4, wherein the CRISPR-Cas9 system is a system including three or more guide RNAs for each of the one or more target genes.

7. The method as claimed in claim 4, wherein the target exons of gene have sequence selected from SEQ ID Nos. 11-18.

8. The method as claimed in claim 4, wherein the modified cell strain is a RD cell strain of human rhabdomyosarcoma.

9. A method comprising applying the modified poliovirus receptor (PVR/CD 155) gene as claimed in claim 1 for research.

10. The genetically engineered cell strain as claimed in claim 2, wherein the genetically engineered cell strain comprises one or more target exons modified by introducing three or more kinds of guide RNAs selected from the group consisting of SEQ ID-NO Nos. 19-23.

11. The genetically engineered cell strain as claimed in claim 2, wherein the genetically engineered cell strain is a knock-out cell line, and wherein primer sequences used for sequencing knock-out cell line are selected from the group consisting of SEQ ID Nos. 34-47.

* * * * *

SEQUENCE LISTING

```
<160> NUMBER OF SEQ ID NOS: 56

<210> SEQ ID NO 1
<211> LENGTH: 29360
<212> TYPE: DNA
<213> ORGANISM: Homo sapiens

<400> SEQUENCE: 1

aataaataac tttttagacc atatatttct ttttttttt ttttttttt tgagacagag      60

tctcactctg ttgcccagac tggaatgcag tggcatgacg ttgactcact gtaacctcca    120

cctcaagtga ttcagcctcc caagtagctg ggattacagg tgtgcacgac taccacccag    180

ctaatttttg tgtttttagt acagatgggg tttcaccatg ttggccaggc tggtcttgaa    240

ctcctgacct caaaagtgtg ggggaaagaa agagagatca gactgttact gtgtctatgt    300

agaaaaagga agacataaga aactccattt tgatctgtac taagaaaaat tcttctgcct    360

tgagatgctg ttaatctgta accctagccc caaccctgtg ctcgcagaaa cgtgtgctgt    420

attgactcaa ggtttaatgg atttagggct gtgcaggatg tgctttggta aaaatgtgtt    480
```

```
tgcaggcagt atgcttggta aaagtcattg ccattctcca gtctcaagta accagggaca    540
ccatacactg cggaaggcag cagggacctc tgcccaagaa aacctgggta ttgtccaaga    600
tttcccccac tgagacagcc tgagagatgg cctcgtggga agggaaagac ctgaccgtcc    660
cccagcccga cacccataaa aggtctgtgc tgaggaggat tagtgaaaga ggaaggcctc    720
tctgcagttg agataagagg agggcatctg tctgctgctc gtccctggga atggaatatc    780
tcggtgtaaa acccgatcgt acattctatt tactgagata ggagaaaact gccttatggc    840
tggaggtgag acacactggc agcaatactg ctctttactg cactgagata tttgtgtaaa    900
gtcaaacata aatctggcct acgtgcacat ccaggcacag ctcctttcct taaatttatc    960
tatgacaccg agtcctttgc tcacgttttc ctgctgaccc tctccccacc attaccctat   1020
agtcctgcca catcccccct accgagatag tagggatagt gatcaataaa tactgaggga   1080
actcagagac cagtgccggt gcaggtcctc acttgctgag caccggtccc ctgggcccac   1140
ttttcttcct ctatactttg tctctgtgtc ttatttcttt tctcagtctc tcgtctccac   1200
cttgtgagaa atactcagag gtgtggaggg gcaggccccc ttcaaaatga tccacccacc   1260
tcagcctccc aaagtgctgg gattacaggc atgagccacc atgcccagcc acatataact   1320
tatttctaaa taacttattt aactaacacc acatgatttt atgacccccct attttatgga  1380
tgagaaaaaa gaggcaagag aagcgatacc agttgcttag gattcccagc taccaattag   1440
tggaagcaga atttgaacca agggagtctc tggagccctc gttcccaatc tccttttctt   1500
cctctccatg tctttctttc tccccctgct cccaggcctc ctacatcaca cccttctgga   1560
caaagcttca catctgacat tttcttttttt ggggtggaca gagtcttact ctgtcaccga  1620
ggctggaggg ccgtggcgca atcatggctc atggcagcct caaactcctg ggcttgaggg   1680
atcctccagc ctcagcctcc caagtagctg ggactatggg catgtgccac cacacctggc   1740
taattttttta attttttgta gaaatacagg gggtgggggc atatctgaaa attttaaacc  1800
ttccctgact gccgtgagca tttctgggta gaagccactc cacgacctta ctttgctggc   1860
atgagtgctg gacagcaatt tggcaacatc ctctagacca caaatgtgca tggcctttgg   1920
cccagcaaat cagcttctgg gaataaatat gacagatact gttacataca tgggaaatgc   1980
catggacatg atgacccagg gaagcacagt ttgcaagtac aaaagggctg gaaacaccca   2040
aaaagcccat cccctgaaga cagtttcaaa aatgacggtg cattcatgta atggaatagt   2100
acacatttgt gaatgaatga atgaggtagc tcaatatatc tgcctatggg aaaatcacca   2160
agatatgttg ctaagtgaaa aacagaaaga tacagaataa tgctaccatt ttattttttta  2220
atgggagagg gaagaataag gaaatggatt catatttgct taattacaca agcttcctga   2280
tgatcctttt ggatccagaa gtttgaaaac cacagcatca agaggatgcc cattgggcat   2340
ggtggctcac gcctgtaatc ccagcacttt gggaggctga ggagggtgga tcgcctaagt   2400
tcaggagttc gagaccagcc tggccaacat ggtgaaaccc catctctact aaaaacacaa   2460
aaaaattagc tgggtatggt ggtgcaggcc tgtaattcca gctacttggg aggctgaggc   2520
gcaagaatca cttaagcctg ggaggcggag gctgccgtga gccgagatca cgccattgca   2580
ctccagcttg ggagacagag caagactgtc tcaaaacaaa caaacacaca caaaaaataa   2640
gatgcccatt ggagatctcc attcactatt ttatcagatg atatttcagc acttgagtga   2700
agaaaatgtc tacaactggt ccaaacactc aaggaattta gactcttgac agagaaacac   2760
acagaagcaa gcagatatgc cccgaaccaa acttgctttt tcttctaagc ctgcttcttc   2820
ggagcagcct ctgaccctcc agggccctga gaggagtccc tggagccaca ggagcttggg   2880
```

-continued

```
agcccagaga agtgggggaa tcccagatgg tgacagcatc atccagagga ggaacataac   2940
gatggccaca gattcccaat ttggaaataa ctcagcaaaa caacactgac agaaaattca   3000
gagatttcca agagactagc ctccctgttt ccatttagaa attcacctac atacatccag   3060
ggtgagagac cccaagcatc agatgtgtca tacacaagca tcagatccaa gttagagagg   3120
gcacccgggg acagaaacct ccaagccagc caaaagccaa aggaaggatt ttacagaaag   3180
atacaggaat gtggggccag gcacagtggc tcatgcctgc aatcctagca ctttgggagg   3240
ccgaggtggg aggatcgctt gcggccagga attcaaggcc agcctgagca acatagcgag   3300
atcctatctc tacaacaaat ttaaaaacta gctgggtgtg atcacatatg cctgtggtcc   3360
caactaccca ggaggctgag gcaggagttg agcccaggag gtggaggctg caatgagcaa   3420
tgatggcgcc acttcactcc agcctcagtg aaatagtgag accctgtcta aaaataataa   3480
taaaaataaa aaacatataa agatgtcaga gcacagggac cagagctgtt agtcggcctc   3540
atggagaccc tggccaggac agccacctct ggggaccagg aagtctctca gtttctgtct   3600
ctgagggttt ggctctctga gtctctctgt cacctctcat ttctctctca tctccctctg   3660
tctatgctgt gtctctatct ctttcaatct ctctgtctct gtctcccagc ccttatctct   3720
gagtgtgtct gtttctctct catttctctc tctctctctc tctctttctc tctctctctt   3780
tctctctctc tctttctctc tccccccctcc ctcctcccct ctccctactg caggctggtc   3840
cataaccctt atcttcccca gacctgatgg agttctggta ttaatctgtt tatggtctgt   3900
ttccctccac tagaacacgg tcttcattaa aggcagagat ttttgtctgt cttattttct   3960
gctgtatacc cagtgcctgg gatactggct ggatcaataa atatatgctg aatgaagaat   4020
gaatgaatga ccattctcat gaacattatt atttgatgcc aactgtaaag caacaataat   4080
aataattgtc actgccactg ctgctattgt tggtatatca gctttttatt tagtacaaac   4140
tatatccccg aaattgagct aggcagtttc ttgtttaagt tttacagacc acgctgtgag   4200
gtaagtactg ttagtatgcc ctttttttctt tctttttgag acagagtctc actctgtcgc   4260
ccaggctgga gtgcagaggc ccgatcttgg ctcactgcaa cctctgcctc ccgggtacaa   4320
gtgattttcc tgtcttagcc tccccagtag ctgggattac aggcatgtgc caccatgccg   4380
gctaattttt gtatttttag taaagatggg tttttgccat gttggccagg ctggtcttga   4440
actcctggac ctctggtgat cctcctgcct cggcctccca aagtgctggg attacaggcg   4500
tcagccactg cgcttgctcc cccagccccc aaactttttt tttttttttt gagacaggtc   4560
tggctctgcc acccaagctg tagtgtagtg gcgcaatggt agctcactga agcctctaac   4620
tcctgggttc acacagtcct cctgcctcag cctcccaaaa tgctggaatt caggcctgag   4680
ccaccgcgcc ctactatgcc catttttcag ataaagaatc tgagggccct cgaggagaaa   4740
ccacttgccc aacatgagcc ctggtcttgt ctgaccccaa agcccatggg aagtttaggc   4800
tgcgtggaag gacagcctgg tgggctcagg atctgtccca tcacgagttg gaacctcagc   4860
tctgccactc ggcaaccgcg agccgttagt aagttgctga atctctccgt gtgcctccgt   4920
ttcctcacct ggaatgtggg cgacctcaca caggaagccg cctcttctag tgggcaccga   4980
cggagcgagc gcgcgtctgc agcgggactg agcgccggga gagacctgcg caggcgcagg   5040
cgcgcgggga gggccagcct gggtggccca ccccgcgcct ggcgggactg gccgccaact   5100
cccctccgct ccagtcactt gtctggagct tgaagaagtg ggtattcccc ttcccacccc   5160
aggcactgga ggagcggccc cccggggatt ccaggacctg agctccggga gctggactcg   5220
```

cagcgaccgc ggcagagcga gcgggcgccg ggaagcgagg agacgcccgc gggaggccca 5280
gctgctcgga gcaactggca tggcccgagc catggccgcc gcgtggccgc tgctgctggt 5340
ggcgctactg gtgctgtcct ggccaccccc aggaaccggt gagtgacccc cgcgcagtcc 5400
ggtggcccct gtctggctcc cagctccgca tccaggccgg gtactcgccc ccttgggttc 5460
ccgaagatga cggccccgcc cggcgccacc caccccccat ctctgccccg gggttggaag 5520
gaacacggtg cgagggtgcg agggcaggac cctcctcttg gccacccgga gagcggtcgg 5580
agttgggtac agaaattcct cgaaattggc agcaacacgg gtcgggcaca agaccctcct 5640
ctgggcccct cggaaagggg atggagttgg gtgaggaaat ttcccaaaaa ggcaagtgaa 5700
tcccggaaaa tcagcagatg gtgacgcatg ccggattacc ttacccaggt tcctgctcag 5760
catacccagg ccataaccca gcagcgtgct ggcaggctgg gtctggacgg aggggatggt 5820
tgatgttggg gaggaggaca gtgggtgaca cttgacacca ttacccctct gacccccaat 5880
gtctgactcc aggggcctgg ccattcattc attctttcat tctttttttt ttttttttga 5940
gacagtctca ctccatcacc caggctggag tgcagtgtcc tgctctcggc tcactgcagc 6000
ctcctcctcc cgagttcaag cgattctcct gcttcagcct cccgagtagc tcggattaca 6060
gacatgtgcc actatgcctg gctaatattt ttgtattttt agtagataca ggatttcacc 6120
atgttggcca ggctggtctc aaactcctga taaatatata tattatatat tattattata 6180
tattacatat tatagtaata tataataaaa atatataata tatattatag taatatataa 6240
tatataataa aatatataat atatattata gtaatatata atatataata aaatatataa 6300
tatatattat agtaatatat aatatattat aatatattat atatattatt ataatatata 6360
atatgtatat tatatattat atatattatt ataatatata atatgtatat tatatattat 6420
atatattatt ataatatata atatgtatta tgtattatat aattgataat atataataat 6480
atatttctta ataaatatat attaaatata ttatatattt ataacatata ttatttatat 6540
aataaataat atatatttta ttatacattt aaagagtaaa tagataacat attttattat 6600
ttatttatat gttttgtgta tatatatata tatatatata tatatatagt gcgtgtgtgc 6660
gtgtatgtgt gtgtgtgtat gagagagaca aggtcttgct ttgttgccca ggctggagtg 6720
cagtggtaca atcccggctc attgcaaact cgacttccca ggctcaagcg atcctctcac 6780
tgtggcttct ggagtagctg ggattatagg tgctcacctg gctaattttt tttgtatttt 6840
tggtagagac agggtttcgc tatgctgccc aggctggttg cagccaagca cagtggctca 6900
tgcctgtaat cccaacactt tgggaggctg tggtgggagg atcacttgag cttaggaatt 6960
caaaaccagc ctgggcaata tggcaagacc ccatctctac aaaaataatt aactaaataa 7020
aaatttaaaa ataaaaaaga atgcatagga ccatgtttat tagtgtcaat aagcgctgtc 7080
acattttgag gacctactat gtgctagggc ccttagcaga aagattttta tataggacct 7140
gggggattag aggtcagtct ctgaccgccc aagttcaaat cccacctctg ccactaaacc 7200
tctgtatgac ttggaggaca ctatactctg tgtcagtttc cctgtctgta aaatgatgtt 7260
aacagtagtg cttgcctcag gggggctatt tgaggattaa atgccaagat atatgtgaag 7320
cacccagaat agcccctgat ctgtgtcagc accctgtgag tgtccactgt tctaagtctc 7380
attttacaaa ctaggaaaaa gaatcagaga ggttaagtaa ccggcctgaa gctccacagc 7440
agaaaactga agggacccaa aactcctggg ctataattgc cttcctctcg tgcctcaatc 7500
ccccacattc ttccaaccag gacccaccca gagtaataat gcagtgtttc atggatttga 7560
agacccaaga tttctccccg ttttctacat tggggttatt ctaaccccta atggcaagtt 7620

```
gtgctataaa tgacaacagt catggtatgt gaaacctacg acactggtgc gatgaaaaag   7680
ttctgggcca ggtgcggtgg ctcatacctg taatcccagc actttgggag gccgtagtgg   7740
gaggatcact tgaggtcagg agttcaagac cagcctggcc aacatggtga aaccccatct   7800
ctgctaaaaa caaaaataca aaaaattagc caggtgtggt ggtgggagcc tgtcatccca   7860
gctacgcgga aagctgaggc aggagaaccg cttgaacccc agaggcagag cttgcagtga   7920
gcagagatcg cgccactgca ctccccctgg gcgacagaga gagactccgt ctcaaaaaaa   7980
aaagagaaga aaagaaaaag ttctggcgct atatagtagt aacggttgca caatatcgtg   8040
aaatgtacat agtgccactg aactgtatgc tttaaatgac ttaaatggta aatttagttt   8100
tttaaccaca atatttacca caattttttta aatcagtgat gttgagattc agggaaatac   8160
ggtaataata gaagaaatac ggtaataaat agccaaagtg aaggagcacg gccaagttgc   8220
agaccatccc agacgccctt accctcctcg cctgccatgg ccccaactag tgccccagtt   8280
ccccctcccc ccacacccca cggtccaccg gggatccagg gccccagcgt gcaagtgcac   8340
gcccaggtgc ccgggctcct ggagcccctc cctatctagt ccaagaacgc cccgggtctg   8400
acaccttctc ttcggttctc cgcaggggac gtcgtcgtgc aggcgcccac ccaggtgccc   8460
ggcttcttgg gcgactccgt gacgctgccc tgctacctac aggtgcccaa catggaggtg   8520
acgcatgtgt cacagctgac ttgggcgcgg catggtgaat ctggcagcat ggccgtcttc   8580
caccaaacgc agggccccag ctattcggag tccaaacggc tggaattcgt ggcagccaga   8640
ctgggcgcgg agctgcggaa tgcctcgctg aggatgttcg ggttgcgcgt agaggatgaa   8700
ggcaactaca cctgcctgtt cgtcacgttc ccgcagggca gcaggagcgt ggatatctgg   8760
ctccgagtgc ttggtgagca gggggttttg gggaggctga atgaaaggca gagacttggt   8820
gggaggatca gggaagttgg caaagagcgg ggaggcctgg gagggaggga gattccctcc   8880
acagcagatc ccctggggac aaaaggaggg ggcagcgcaa tgatgtgggg tggggtgggg   8940
ggaggtgagt ggggggaggg gctgcagggc aggaagaaag cagagatctc agggagtaag   9000
gacccccaag cctgggatca gaaagccctg agggaggagg aggggtatat tggaaaggga   9060
gctgggaggg gactgggaag gaagggagga ggcctgggtg gcctcttctg ggtccctcct   9120
ttcctcatct gtaaaagggt tggtgacaac agcatcaccc ttggaaagct gtcctgagtg   9180
tcatcactgc ctaggaaaga gtctgtctgc ccccttggac tgtgtaccca tgagggcaga   9240
accggggcta ttttgatcac tgctgggccc cagcactttc caccaaacaa tatttattga   9300
gcacttatta tgtgccattc taagagcttt acctgcatat tctaattgcc tgtgattcca   9360
tcattatcac ctgttgacag acaaggaaac tgaggcacag acttgcccaa gaccaaagct   9420
gcagccttag ggcagcggcg cttcaccgct ggcccatgtg agccccttag agctgtcggt   9480
tactgttact ttatctggtg aagaaggaga aagttgaaac agacagacag gaaagcaagg   9540
atcctgatac ccaaaagagg aggggatcat gctttcattt tcatgagctc catgaagcct   9600
tcctcttgga acttgagcaa gaagtctctg tgcctcagtt tcctcatctg tgggataggg   9660
atcaccatga ggattcaaaa aaactgaccc tttttttttt tttgagatag tttagttctg   9720
tcgcccaggc tggagtgcag tggtgtgatc atagtaggtc ctcactgcag cctggaactc   9780
ctgggctcaa gggatgttcc taccctccct gtagctggaa ttacaggaat gtgccaccat   9840
gcccaacttg ttttctgttt tgttttgttt tgttttgttt tcttttcttt ttaagcttat   9900
gtgccaagaa ctattccaag cctgtgcatg agaaactcat gaaatgtcaa gggcttggaa   9960
```

-continued ctgtgcctag cacacaacac ccaaccaaag gcagctgttg tcactccagc aagcctggga 10020
ttctgggtat catggtttag gatgagggta aaacagaaac agtgagtcaa gttaaggaga 10080
aatcttcggt aaataatata ggtaatgatg gggaaggaag ttccaggttt gggaatcacc 10140
aggatgatga ttaagagatg gtcaaggtgg ttttggagtc agacagactt tatgtgaaag 10200
cccagctctg ctgcttacag ctgtgtgacc atgggcaagt cacttccctt ctcaacttca 10260
gggctcaggc ttcctctcct ccactgagcc ccagaccagg ataacccct ttgggtttcc 10320 cctttccagc cctgccctct ccgagtcatc actgcctagg aaagagtccg tctgcccccct 10380 tggactgtgt acccatgagg gcagaaccag ggctattttg gtcactgctg ggctccagca 10440
ctttccacca aacaatattt attgagcgct tattatatac cattctaaga gctttacctg 10500
catattctca ttgcctgtga tcccatcact atcccctgtc aacagacaag gaaactgagg 10560
cacagacttg cccaagacca cacagctgct cagggacaca gctgggattt aaaccatgcc 10620
attctgtatc tttttttttt tttttttttt gagacagaat ctcactctgt cgcccaggct 10680
ggagagcagt gacacaatct cagctcactg caacctccgc ctcccgagtt caagcaattc 10740
tctggtctca gcctcccaag taactgggat tactggcgtg tgccaccata ccctggctaa 10800
tttttaatag agacagtttc tccatgttgg ccaggctggt ctcgaactcc tgaccccaag 10860
tgatccaccc acctcagccc cccaaagttc tgggattata ggcgtgagcc accccgccca 10920
gcaaccatgc catcctgtac ccttaatgaa tgccccccttc tgccacggag gggttcattg 10980
aatgacttgt tgcttttgtt cctcttccca gccaagcccc agaacacagc tgaggttcag 11040
aaggtccagc tcactggaga gccagtgccc atggcccgct gcgtctccac agggggtcgc 11100
ccgccagccc aaatcacctg gcactcagac ctgggcggga tgcccaatac gagccaggtg 11160
ccagggttcc tgtctggcac agtcactgtc accagcctct ggatattggt gccctcaagc 11220
caggtggacg gcaagaatgt gacctgcaag gtggagcacg agagctttga gaagcctcag 11280
ctgctgactg tgaacctcac cgtgtactgt gagtgtgccc aagtcagcga tggcaagaac 11340
ccctgccggg ctgcccccac cactgtctac actgactccc caaggcactg taggcattgc 11400
ttccatcatc tgcaccggct cccctgactc ctgtctacac gacccacccc cattgtctgc 11460
accagctccc ctgggccgta aacaacactg tccctattgt ctacaccagt ttacttgggc 11520
catagtcaat gctggtaccc agactgtctg ccctggctcc tctagcggct gtctgcacgg 11580
atacctgaca ctctgttgac tcccttgagc acagtctaca ctgcccctaa actgcctaca 11640
cccatttccc caggcaagta tccacaatga ccctccccac attgctacac tggttcttct 11700
ggccacgatc aacactgcct cccttattgt ctacacccac tcccttgtcc ttttctttct 11760
ttcctttttt tttttttttt tttgaaatag agtctcactc tgttacccag gctgcagtac 11820
agtggcatgt tctcggctca ctgtaacctc tgcctcccaa attcaggtgg ttctcctacc 11880
tcagcctccc aaatagctgg gattaaaggt gcacaccacc acacctggct aatttttgta 11940
tttttagtag agacagggtt tcatcatgtt ggccaggctg gtttcgaact cctgacctca 12000
ggtgatcggc ctgcctcagc ctcccaaagt atgctggaat tataggcatg agccactgtg 12060
cccggctttt tgttttgttt tgtttttcct ttggacaggg tctcgctctg tcacccaggc 12120
tggagtgtag gggcatgatc atggttccta cagcctcacc cttccaggct caagcaatcc 12180
ttctccctca gcctcccaag taactgggac tacaggtgca gccaccatgc ccggctaatt 12240
ttacagtttt tttctagaga gagttttgct gtgttgccca ggctggtctc aaactcctag 12300
gcttaagtga tcctcccgcc tcagtctccc gaagtgctga gattacaggc gtgagccact 12360
gcacctggcc ccttgtccat tttctacact gccttaccat tgtctacact ggctctcctg 12420
ggccacagac agcactaacc ccattgtcta caccacctat tttggccacc agctgtgggg 12480
tgttttcact gtctcccata gtgtctacac tggctcctat gaccactgtc tatgtaaaca 12540
ccccactttt tctacactgg ttctcctagg cactctctaa agtgccccct gacactgtct 12600
acactgactc cctggagaac tgtctgcatt cacctcccac attgtatcga ccagttcccc 12660
tgagccacga tcaactgtct ccgccgggtg ctagttgcat tgatcttctc acattgtttg 12720
tgctggctcc cctaagcagt gtctgcagag tcccccagtg tagtctccat gttcctctgc 12780
ccaatattgt ctacactggc tcatctacag gctatccagt ctcaccccac atcaccacac 12840
tggcctcctt gtgttctgtc tgcacagccc cctgacagca tctgtcctga ttctcctgca 12900
cagcgttacc tccaccagct ccctcatggc atcatcgaca ttgacaccca cacatttatc 12960
tccactgaca gccccaggac tctctaacca gtgctgtcta acagaaatag catgcaagct 13020
gcatatagga ttttaaattc tccagcggcc accccattaa aaaattaaaa gaaagaggcc 13080
aggcacggtg gctcacgcct gtaatcccag cactttggga ggccgaggca ggtggatcac 13140
ctgaggtcag gcattcaaga ccagcctgat caatgtggtg aaactctgtc ttcactaaaa 13200
aatacaaaaa ttagccaggc acggtggcgg gtgcctgtaa tcccagctac tcgggagact 13260
gaggcaggag aatcacttga acctgggagg cggagattgc aatgagcgag attacgccat 13320
tgcactccag cctgggcagc agagcaaaac tccatctcaa aaacaagaaa agaaagagat 13380
gaaatttatt tgtttattta tttatctatt tatttatttg agacggggtc ttactctgtc 13440
acccagactg gagtgcagtg gcacagctcc ctgcagcctc aacctcctgg gcttaagtga 13500
tcctcccacc tcagcctcag tctcctgagt agctgggact acaggcgtgt gacaccatgc 13560
ctagctaatt tttgtttttg tttttgtttt tgtttttttg ttttgtgatg aagtcttgct 13620
ctgtcaccca ggctagagtg cagtggcacg atctcaactc actgcagcct ccgcctctcg 13680
ggttcaagtg attctcctgc ctcagcctcc cgagtagctg ggattacaag ccctggccac 13740
agtgcccagc taatttttgt atttgtggta gagacgggat ttcaccatgt tggccaggct 13800
ggtctcaaac tcctgacctc gtgatccacc caccttggcc tcccaaattg ctgggattac 13860
agacgtgagc caccgcaccc ggcctatttt tattttttct ggagacagga tctccctatg 13920
ttgcccaggc tggtctcaaa ctcctgggct caagtgatcc tcctgcctca acctcccaag 13980
gtactgggat tacaggcatg agccactgtg cctggccaaa attaattttt aataattgcc 14040
tttacttaac ccaatatacc taaaatatta tttcaacttg taattgtttt tttaaaatta 14100
ttcttgagat ctttcccatt tattttgtcc tagtaaagcc tttgaaatct ggtgtgtatt 14160
tcggcctggc tatatttcga gtgctcagta gtcacatgtg gccagtaggt gccatattgg 14220
acagcacaga tctagactaa gctcccacat catctacact ggctcatcca aatactgtct 14280
acacacatac acagagcctg tcttaatttc gtcagctccc ggggacacac tgtatatgtg 14340
ggggtgatct cacccccacc accacatttt caacactggc ccgacaatat agcatctgct 14400
gtaatattcc aacaccctgt ctacactgaa cccatcagta atatccacac aagctcttct 14460
agacatcatt catactgttc ctcccaccat tgtctatact gcttactccc cgccaggcaa 14520
ttggtacaca gattccctca ggtactgtct atactggagt ccctcaacac tgtcactggg 14580
tctgagcgag gaggagatct acactgactc ctacccctcg cccccgaata aaaccctgtc 14640
ccattggcct gcccccaagg acattgaaag gtcttcgctg tcaatcacgt atgggatggc 14700
tgagcagcag cctagagcag ggttatctgg gactctttcc tgcaggactt gtcagaacct 14760
tgaatacact gctgtgtgtt gtgagtggtc attgcctatg agtgagaaaa ggaggaggca 14820
ttttcctgca ggacacccaa gacatgcctg gtccaggcta cccaggaaag ctagtggaga 14880
aaagcagctc ctcagaagcc ttctccatgt ccccactgac caaggactcc taggcttctg 14940
ctctctgtgg caccccatct acctagactc ctcctaggcc tctccagctc ccgctgtttt 15000
ccaaatatcc ccgggccttt tcctgcagtg tcgtgaatcc cgcgtagccc caggcccccc 15060
aaagcctccc agtctctgaa cctctgtatc catttcctgc agacccccca gaggtatcca 15120
tctctggcta tgataacaac tggtaccttg gccagaatga ggccaccctg acctgcgatg 15180
ctcgcagcaa cccagagccc acaggctata attggagcac gtgagtcctg ggtctcaggg 15240
aggaggggct gggggtctgg atttctagca ctgagggagg aggggctggg ggcctggact 15300
cctgggactg agggagaagg ggctgggggc ccggacccct gggtctgagg gacgagaggc 15360
tgggagcccg gactcctggg tctgagggaa gaggggctgg gggtctggac ccctgggact 15420
gagagaggag gggctgggcc tggacccctg ggtctgaggg aggaggggct ggggggtctg 15480
gacccctggg tctgagggag gagaagctgg gagcctggac ccctgggtct gaggcaggac 15540
agactggggc ctggactcct ggtctaagag aggagggaga ttcagaaaag agaaaaagag 15600
gaggttgact tcgggccccc agtgggggc atctctgttt tgacatctct gttttgcggt 15660
tgaggcgttt agcaggtggt tgaatcctgg ctggtggatg cacctgcttt ttggggtgtg 15720
cctgctctgt gcccggtact tcccccgaat cccatgtgac cccatgctgt gcacagtcag 15780
cagctgttgc cctgcccagg ttaaagacca gccacgagag ggcagaagcg gcccttgaat 15840
cagcgctcgg ctccaaagct ggtcctccgc ctcttggcca agcttgtcta acctgcaggc 15900
cacatcattt gtaaactttc ttaaaacatt atgagacttt ttttttgcga attttttttag 15960
ctcattagct attgttagtg ttagtgtatt ttatgtatgg cccaggacag ttcttcttct 16020
tccaatgtgg cccggggaag ccaaaagatt ggacaccccc actctagact gtaaccacct 16080
caccgtcacc ttgtgtaacc tacttggtta tctctggatg gagcaagtac tatatatccc 16140
cattgtctag atgagaaagt tgaggctcac agcaataaga tttccccaga ttcacactga 16200
ggctgagatc aagagcaagg taagaaaaag gcaaagagat aatacataat tttataatac 16260
ataattttac ataaattaca taattttact gaaccgccct ttttttttaa agaaggggct 16320
ctgttgccga ggctggagtg cagtggcgtg atcatagctc actgcagcct ggacctccct 16380
gggctcaggt gatcctccca cctcagcctc ctgagtagct gggactacag gcacacgcca 16440
ccacactcag ctaattttgt tgtatttttt ttgcagagac agggttttgc cacattgccc 16500
aggctggtct gcaactcctg ggctcaagca atcaacccac ctcagcctcc taaagtgctg 16560
ggattacagg cgtgagccac ctcgcccagc cttaggtctt tttccttatt acaaaaataa 16620
cttgtgtcca ctgtagaaat atcaaacaat ttagttatga gcaaaaagaa gaaagtagtg 16680
cctatagttc aagtgtaccc agccacctcc agaaataccc agtgacccct tattatacat 16740
cctgtctttt ttctctctgt ttctaaacaa agactggaat tatgctgtac atataatttt 16800
gaacctttc gtctgtcttg tgaatacctt tccatgtcaa agcacataga tccacaactc 16860
cattttcccc cacgttgtat taggaagact gtcaaacata cagaaaaatc ataggaattt 16920
tccagtgaac acttaagatt ccaccacgtg gattcccctg ctaacatttt actgtgcttg 16980
ctttatcacg tttctgtgat tccttcagtc cctctattca tccatcaatc atattatgca 17040
tttcagagca cccccagctc tcctgctttt tttttttttt tttttttttt gaggcagggc 17100
ctcactctgt tgctcaggct gtagtgccgt ggcacaatca cagctcactg cagccttgaa 17160
ttcctgggct caagcgatcc tccagcttca gcctcccaga tagctgggac tacaggcaca 17220
caccaccacg cctggctaac ctggcccctt ttttagtgtt gctgggattc caccacttta 17280
aaaaaaaaat tcaaagaata gagacaggat ctcactatgt tgcccaggct ggtcttgaac 17340
tcctgtactc aagcagtcat ctcacctggg cctcccaaag ggcagggaag ggattccaac 17400
atatgtggat gtcatcagtt atttaaccag tccctagtag aggacacaga tgtcattttc 17460
cattttcaac tctgcaaatg ccatggtggt gtccatcccc actggtcact tgtcagcagt 17520
tgtccgtgga aggaattgcc ggtcaaaggt tttcaactgg tgtgatggtg cctttactgt 17580
cctgcctcaa agcaccgcaa ttcaggctct tgagccagat agctgcgttt gcatcccagc 17640
tctgcggagc acccaaagcc tgatgcttcc atctcctcca cctctgttca ttaaaccagt 17700
gttccttgac tacttactgt gtgccgggtg caattaacca acatacgttg gtcgataaaa 17760
cagaccaaat ttcctcccca tatagagctt ccattctagt ggtgaaagaa acaagaagca 17820
agataaagtg tgtagtgtgt gtgcaatggt gataaatacc atggagaaga caaagcagag 17880
aagggaatgg gactgggcgc catgactcat acctgtaatc ccagcacttt gggaggcaga 17940
gatgggagga tcacttgagg ctaggagttc aagaccagcc tggccaacat ggcgaaaccc 18000
catctctacc aaaaaagata caaaaattgg ccgggtgtgg tggcatgcac ctgtagtccc 18060
agctactcag gaggctgagg tgggaagatt ccatgcaccc aggaggtgga ggttgcagtg 18120
agtcaagatg gtgccactgc actccagcct gggtgacaga gtgagacgct gtctcaaaaa 18180
aataataatt aaataaatta aagagaaggg gatgggaagg gtgatcatca cagttgaaat 18240
agggtggcca agtgaggtgt tactaaggtg acatcccagc agaggcctga aggagatgag 18300
ggtgagctct gcgggtgcct agggggaaag cattccagca gagggaacag catgggcaaa 18360
cccatttcta tccatcagtc cctgcataag caaacaccct ggacacctaa ctggagagtt 18420
tgaggaccaa caaagaggcc actgtggatg cagaggcggg agcaaagggg agagtaatgg 18480
aaaacgtggg cagaggtagc aggggccaga tcacgtgggg cctgtgacac cagaagactt 18540
cggtttaact ctgagccagg ctaggccccc agagggtact gagctgaggt atgggaactg 18600
acttagggtt cacaggcgac ctctggtggc catgtgggga acagacgagg gggcgagggc 18660
agaaacggag cccagcgtgg aggcggctgc tgggggccgg gatgcacagc gccagagcag 18720
ggaggtaccg tggaagccct gaggagaggt gggattctgg atggatctta aggcggggcc 18780
gacatgattg gctaatgggt tgggtgtggg catgagagga agggaagagt tggggggcct 18840
ccagagttgc tctccgctta tgctatagag ggcgtgaggg tttctgggca cgtagtgcgt 18900
gctcaatcac tgtcactccg gacctgcagc agaggccacc tcctcacctt tctgtctctc 18960
ccaggaccat gggtcccctg ccaccctttg ctgtggccca gggcgcccag ctcctgatcc 19020
gtcctgtgga caaaccaatc aacacaactt taatctgcaa cgtcaccaat gccctaggag 19080
ctcgccaggc agaactgacc gtccaggtca aaggtgagga actccctggg tgggaagaac 19140
agggaccaaa ggaagaggtc gaggcagggt tccctgtcta atgctctctg gctcccatcc 19200
ttctcctaag ccttctcaca aaaggaccag tggggccagc tttactcccc tgttaactcc 19260
atacctatat cactggtacc gttgttcagc tgcctggata cactccctcc acacacacag 19320
gttgggatag atgtggaatc cctctctctc agggactcag gcctttccaa atatattagg 19380
cagacctcta tcaattgcaa ttgacagaaa cacaaagtag tctaagcaaa aaaaaccaaa 19440
caaaacagga ctttattgaa aattcacctt caggtatggt tagatccagg ggctccaacc 19500
ttgtaaccca ggaactttta ttttatacat ctcttgtctc tgcttttcgt tatactggct 19560
ttattctcag gcaggctctg aagcaagatg gccctcggca gggacaggct cacattctac 19620
cagaatggca acagcaggag aaaaaacata ccactttcag taactgtagc catagtccca 19680
gggctggctc tcattggccc agcttaggcc acagcccacc tatgaaccaa tcatagcagc 19740
cagggagaat ggaatattct gattggccag gcctgtgtca aagtcccatt ctgggcacca 19800
gagggtggga tccattccac ctgaattaaa tagactgagg cagtggagtg gtggctccct 19860
aaggaaattc aagatgccat ttcaagaatg agggataaac cccaagagtt tccttaccta 19920
aatacctgtt tccttctctt tcagagggac ctcccagtga gcactcaggc atgtcccgta 19980
acgccatcat cttcctggtt ctgggaatcc tggtttttct gatcctgctg gggatcggga 20040
tttatttcta ttggtccaaa tgttcccgtg aggtcctttg gcactgtcat ctgtgtccct 20100
cgagtgagca tcaccagagc tgccgtaatt gagcacctac tacgggctct gtgctgagtc 20160
cttccagtgt gcctctcact gaatcctcac cccactgcca tgaggtttcc cccatttgac 20220
tgatgagggt gcagagccag ggagccttgt tcactggttc attgattaca tttacaaata 20280
ttatttacag agtgggagaa gagcgtatag ggtcttaatg ccatggtagg gactttggaa 20340
tttaattcag gtgatgtggg agtccctgcc agatggatgg agggtgaaat aatgcttaag 20400
ccctcagcct tactccatct gccttgttca ggagtgactc ctaggaggag gtggcaggaa 20460
ctggcacctc tgatcctcag ctctaaaagg gtctgatgct ttcacacctc aagagatttg 20520
cacaggccgt tcccctgcct ggagcaccct cccatggctc cttctggaga agtgtgccag 20580
ctcattctgt aatcagagga acgatgcttt gctgagcact gtctacatgc cactttgtat 20640
gtataacccc ctcgatttta atttttaatt tttttatta tttatgtatt tatttattta 20700
tttttgagac aggctctcac tgtcgcccag gctggagtgc agtggtgcga tctcggctca 20760
ctgtagcctt cacctcccag gttcaagcga ttctcatgcc tcagcctccc aaggagcggg 20820
gattacaggc acgcactact atgcccagca atttttgtat ttttaggaga gacagcgttt 20880
cgccatgttg gccaggctgg tctcaaaccc ctggtctcct gtgatccacc cgcctcagcc 20940
tcccaaagtg ctgggattac aggcatgagc caccacacct ggcctgtaca atctccttga 21000
atgcccacaa ccacccagca aagtggttct cccgtgagcc ccatgttaca gaggaggaag 21060
tatttgcttt gagagatgaa gttacctgcc aatggtcaaa cagctggaca tggttgttgg 21120
ggagaagaag ccagatcttt gactaccaag cttttccttc aaccactaaa caaagctgct 21180
cccttacaac ccaggcggat actgcctcgt ccaggaagcc ctccctgacc cccaagcatg 21240
agccaagcat ccactaggct ctcccactcc agccttgccc attctgggtc atcaccgtgg 21300
gggacttgtt tgtcatcccc agtggactgt gagccccaag atagcagacc tgaggctgtc 21360
actgtcatga ctgtgtcccc aggaccgcct accactgggc cgggcataaa agaggcactc 21420
gaggaagtgt ttgctgagtg attcaatgtg tcagctccag agccagactg cctgtatctg 21480
ggccctaaag ctactgcttg attagtgatg tcaccatagg caaatagctt aagctgtatg 21540
actcagtttc ctcatctgta aaatggggtg atggtaccta ataatacagt agagcactta 21600
acacagtagg tggcacatgg taagccacat actgagtatg tatttgctat gattgttatt 21660
gctattatta ctattattgt tattattaac ataaactgca caagagcagg ctttttgttt 21720
gtttgtttgt gttttgtttt gagacaagat cttgctctgt tgcccagact ggagtagtgc 21780
agtgatgtga tcttggctca ctgcagcctc aacctcccag gctcaggtga ttctcccacc 21840

```
tcagcctctc gagtagctgg gattataggc gtgcactccc acgcctggct aatttttat  21900
atttttagta gagatggagt ttcgttgtgt tgcccaagct ggtctcaaac tcctagactc  21960
cagcaatccg cccacctcag cctcccagag tgctggaatt ataggtgtga gccaccacgc  22020
ctggccaaga gcaggcattt ttatctgttt tgttcacagc tgtgtcccca gcacctagaa  22080
tgtacctggc acaaagtaga cattcaccat ttgctgaata atactactat ttgctaaata  22140
aacccctgtt gaatagtcta ggaaactgaa cacagagagg ttaagtcact tgtccaagtt  22200
cacacagctc ctaaaggaca gagatggaat ttgaacccat ccatctggtt ccagagccag  22260
gctcgatatt tatggatatt tcataaccaa gtgaataact ggatggctaa atccttagaa  22320
agcacaccct ccatccctgt ctgacacacg tgtataccat taagggaaat ggcaccccca  22380
tgtaatagca gaggcagaac ttgacatttt cagggccctg acacccaggc atgtcttctt  22440
cccatgcttc ccagcattat tccttcctga cgacttcccc tcctatttcc ccaggtacag  22500
agcatgccag cgcctcagct aatggggtaa gtgcagtgtt ggagctaagg agggtgtggg  22560
gtctgcacga actacagacc agacgtcttc agatgcccac ggcccggcct caggagcctg  22620
ggtcttttct cctggtgcct cgagcagcat ttcccaaccc ttcctgctgg gcggaatccc  22680
ctgtagagtt tgctaagacg cagccccaga cagtctggtc tgtgatgggg ccagggaatc  22740
tgcattttaa tatccgctct ctccccccctg ccccacgccc cttcaattcc acccatggcc  22800
acaccttgag aagcactgcc ctggcttcca gggagagagg aggggacggg cctgcagttc  22860
tttgcacatg gggcttcagt gggaagatgt ttgattttgt tcaaaagagc cccaaggcta  22920
aaatttgaaa accctcttct agcatgtctc ctattcagct gtgagcagag agaacagctc  22980
ttcccaggat ccacagacag agggcacaag gtgacagcgt cgggactgag aggggagaga  23040
gactggagct ggcaaggacg tggcctcca gagttggacc cgaccccaat ggatgaagac  23100
cccctccaaa gagaccagcc tccctccctg tgccagacct caaaacgacg ggggcaggtg  23160
caagttcata ggtctccaag accaccctcc tttcatttgc tagaaggact cactagactc  23220
aggaaagctg ttaggctcac agttacagtt tattacagta aaaggacaga gattaagatc  23280
agcaaaggga ggaggtgcac agcacacgtt ccacgacaga tgaggcgacg gcttccatct  23340
gccctctccc agtggagcca tataggcagc acctgattct cacagcaaca tgtgacaaca  23400
tgcaagaagt actgccaata ctgccaacca gagcagctca ctcgagatct ttgtgtccag  23460
agtttttgt ttgtcttgag acagggtctg gctctgttgg cagactagag tacagtggtg  23520
agatcacagt tcattgcagc cttgacttct caacgccaag tcatcctccc acctcagcct  23580
cctgagtagc tatgactaca ggtatgtgcc accacgtctg gctaatcttt ttattatttg  23640
taaagtcgag gtttccctgt gttgcccagg ctggtcttga actcttggct ccaagtgata  23700
cttctgcctt ggcctcccaa agtgctgaat taagcagctc accatccaca cggctgacct  23760
catacatcaa gccaataccg tgtggcccaa gacccccacc ataaatcaca tcattagcat  23820
gaaccaccca gagtggccca agactccaag atcagctacc aggcaggata ttccaagggc  23880
ttagagatga atgcccagga gctgaggata aagggcccga tctttctttg ggcaaggtta  23940
agcctttact gcatagcaga ccacacagaa gggtgtgggc caccagagaa ttttggtaaa  24000
aatttggcct ctggccttga gcttctaaat ctctgtatcc gtcagatctc tgtggttaca  24060
agaaacagcc actgaccctg gtcaccagag gctgcaattc aggccgcaag cagctgcctg  24120
gggggtgtcc aaggagcaga gaaaactact agatgtgaac ttgaagaagg ttgtcagctg  24180
```

```
cagccacttt ctgccagcat ctgcagccac tttctgccag catctgcagc cagcaagctg  24240
ggactggcag gaaataaccc acaaaagaag caaatgcaat ttccaacaca agggggaagg  24300
gatgcagggg gaggcagcgc tgcagttgct caggacacgc tcctatagga ccaagatgga  24360
tgcgacccaa gacccaggag gcccagctgc tcagtgcaac tgacaagtta aaaaggtcta  24420
tgatcttgag ggcagacagc agaattcctc ttataaagaa aactgtttgg gaaaatacgt  24480
tgagggagag aagaccttgg gccaagatgc taaatgggaa tgcaaagctt gagctgctct  24540
gcaagagaaa ataagcagga cagaggattt gctctggaca gagatggaag agccgggaac  24600
agagaagtgt ggggaagaga taggaaccag caggatggca ggggcaaagg gctcaagggt  24660
gaggaggcca gtgggacccc acagagttgg ggagataaag gaacattggt tgctttggtg  24720
gcacgtaagc tccttgtctg tctccagcac ccagaatctc attaaagctt atttattgta  24780
cctccagcgg ctgtgtgcaa tggggtcttt tgtggaaatc aaggagcaga caggtttcat  24840
gtgtactgtc accacgtggg atggaaccag aggcatggaa gcaagacgct aaatgaagag  24900
ggccataagg gctgggattc ccaggcacct taggaacagc ttgtcttttt tttttcctc  24960
tccaaaaaaa atgtttaagg gacggtgtct cctgtcaccc aggctggagt gcaatggcac  25020
gatcatagct cattgcagcc tctaactccg gggctcaagc aatcctccca cctcagccta  25080
ccaagtagct gtgaccacag ctgcccctca ccatgctaag ctaatttttt taattagata  25140
gtacataaac gtcccaaaat tagaagataa aaagacatga gggatccatt ctaatttgtg  25200
tttggagtgt aatggtccag ctccattctt ctgcacatgg atatccagtt ttacacaaca  25260
ctgtgaatgt aatgaatgcc actgaatcat acactcaaaa atagctaaaa tggcaaattg  25320
tctgttatct ctttttaacc accatttttg aaaattaatt ataccaaaaa accattgaat  25380
agtgcacttt atttatttat ttatttgttt atttatttat ttattttaga aataagagtc  25440
tcactttgtt gcccaggctg gagtgcagtg gcgtgatcat ggctcattgc agcctcgacc  25500
tgctgggctc gggctatcct tccatctcag cctcccgagt agctgggact ataggtgggc  25560
gccaccccac ctggctaaat ctctttttaa cttttgtaga gataggcatc tcgctatgtt  25620
gcctaggctg ggctggaact cctgggctca agtgctcctc ctgccttggc ctcccaaagc  25680
gctaggatta cagatgtgag ccaccgcgcc caccctgaac cttacttttt ttgctcagtt  25740
tctggtaatt cagagaatgc ctcctgagtt gttctacacc cacctcatat tccatgggag  25800
ggctgtacag ggctttttta acgaggcctc taaggacagg catttgtatc ctttccagcc  25860
tttcactatt acaatgttgt agtgaataac tttacacact gtcatttatt ttactttttt  25920
ttttttttat tttagagaaa ggaatcttgc catcttgccc aggctggtct caaattcctg  25980
ggcccaaaca atcctcccgc cttggcctcc taaagtactg ggatttatag gcataagcca  26040
ccgtgcctgg ccaatgcaca ctgtcattta gctcatgtta acacctgagt gtaggacaca  26100
ctcctggagg tggaattgct gggccaaaga gtatgtttct tgtcattgtg atagatattg  26160
acaaatgaac cctcacagaa gttgtgctga gttctgttcc caccagcgac gtaggcgatg  26220
accttttct ggagggaggg ggcatccttg gagtccacag agccaggaat ggagagtggg  26280
cccagaattt tggtataggt gttgtataaa cttatagtaa ggttaagaaa accgcaacta  26340
tccttatcag agacttggcg gggggcaggg tatgatggag atcataagga ggctaaaaca  26400
ctccacaccc tccctctgca ttgctcctgc acgggagtcg ggaatctttt caggttgata  26460
cgatctcacc ttgaggagct gtgaggtccc agaagcctct gggttgcaga ttgcttgggg  26520
tgaaaatgtc tgtgctactg aaatctaact ttttacaaaa aattacgggc tgggcgcagt  26580
```

```
ggctcacgcc tgtaatccca gcactttggg aggctgcagc gggtggatca cttgaggtaa  26640
ggagttcaag accagaccat agtgaaaccg tgtctctaca aaaaaaatta gccaggtgtg  26700
gtggtgcatg cttgtaatcc cagctactca gaaggctgag gtgggagaat cccttgaacc  26760
cgggaagtgg aggctggagt aaaccatgat cgagttactg cactccagcc tgggtgacaa  26820
gagtgagact ctgtctccaa aaaaaaaaaa aaaaaaaaaa aaactggatt gcctggctct  26880
actccgggca cagcatgcag gcccagttct gctgctctgc tgtttgttct gctttcctcc  26940
acatattggc atcaccctct ggtgccaaga tggctgctgc attccaggca tcacatccag  27000
actcagaccc agagaagctg cccatcccta cctgggtgag cctttgtagg aacgagaaac  27060
cgcatccagc agcagaaacc tcacccagca gcgtcttttc cggtctcatt caccagcgcc  27120
gcccaccgct caaccaatcc ctggccaaaa gaatgggacc gcctggaagg ctggaccaaa  27180
caggacctgc cctctggggc tggggagagg cccagatgaa ggctgcagga caggatggac  27240
tcctagacct ctgttaccag cagtgactac ctctgtctgg gtggttggaa catgtttgaa  27300
ttttattcta agtactgtct acaagttctg caataaacct tgactcttct tttaataatg  27360
caaaaggaat cgaagtgatt gtttgaaagg gagaggaaga aagagagagg gagggaggga  27420
agaatggagg gaggcaggga aggagacaga gagagtagaa tccagccacc ggaaaatcca  27480
gaatagctgg ctttgcttaa tccatgcctg gaaataactg ctgggtttgc aacaacttct  27540
ctcccggaga cagaccaagg aaactacaaa actgcaggaa ggattgaagg gccgggcaca  27600
gtggctcacg cctgtaatcc caacactttg ggaggccgag gtggattgga tcacctgaga  27660
tcaggagttc gagaccagcc tggccaacat ggtgaaacct cgtctctgct agaaatacaa  27720
aaataagccg ggcgtggtgg cgtgcgccta tagtcccagc tactcgggag gctgaggcaa  27780
gagaatcgct tgaacctggg aggtggaggt tgcagtgagc tgagatcgtg ccactgcact  27840
ccagcttggg cgacagagtg agaatctgtc aggtggattc tgagggtact ctgaccccac  27900
gaacccagca tgaaatcttc caggcattaa ggaacattga ggatgtggag gattggaaat  27960
ccctccaggg aaaatacact tctcttgagc agggtcacga ggggtggggg caatgtggga  28020
ggtggggcaa atccaaagac aaggtcaaca gcaataataa taataacaat gacaggcatt  28080
tgttgcttgt tggctgggcc tcttgcatac agttctccca acatccctgt gaggtggtga  28140
tgcttatccc cattctccag gggaggaggc tgaggcccag agaggtgaag tcgtgtgcca  28200
caaaataccc cagccatatg gtggtagaac caagttttca gccagactca ccagctcaca  28260
gcagagctgc cctggactct acagccattc agtgtatagc tgggccactc catcattcaa  28320
ggcagttcaa cgtcaagatt cctgatttgc ctcaacctgg ggcctctaga agataccatc  28380
acccccaaca agctgaagac gtgtgtccgg aacactcaga cacacacaaa gtgctatgga  28440
tacaccacac cccgacctag ctgtctcttc ctgatggacc tcactgggta gaaatgcctg  28500
gcaccgcctg cctcagatcc ctaggtcagc tctcactccc caatagaagt ttctgagatg  28560
atgatgaaaa cgttctccat ctgtgctgtc caatggagta gccactgatc acttgaggct  28620
agtgagcact tgaaggtggc tagtttgagg aactgcattt tttaatgcat ttaattttag  28680
ttactttgaa tatatataca catatataca tttatatata catattcata cacatacatt  28740
ttacatatat tttatatgta tatgtaatat atatataaat tatatatgta tatattttta  28800
tatataaata tatattatat atttataaat atataaatat ataatatata ttatatagat  28860
atataaatat aaatatatat tatatatata aatatataat atatattata taaatatata  28920
```

```
taaattatat atttatatat ataatatata aattatataa attatatata tttatatata  28980

atatataaat atatataaat tatataattt atatattata tataaattat atattttata  29040

tataatatat acaatatata taaattatat ataatatata aatatatata aattatatat  29100

aatatataaa atatatataa attatatata atatataaaa tatatataaa ttatataaat  29160

ctatataaat atatactata ttataaatat agtatatatt tatatagatt tatattattt  29220

atatagtata tattatatat ttatatgttt atgtatatat aaatatataa tatataaata  29280

tatttatata ttatatattt atataatatt ttatataata tgttatatat ttttatataa  29340

tatattatat atatttatat                                              29360
```

<210> SEQ ID NO 2
<211> LENGTH: 29358
<212> TYPE: DNA
<213> ORGANISM: Artificial Sequence
<220> FEATURE:
<223> OTHER INFORMATION: modified gene

<400> SEQUENCE: 2

```
aataaataac tttttagacc atatatttct tttttttttt tttttttttt tgagacagag     60

tctcactctg ttgcccagac tggaatgcag tggcatgacg ttgactcact gtaacctcca    120

cctcaagtga ttcagcctcc caagtagctg ggattacagg tgtgcacgac taccacccag    180

ctaatttttg tgtttttagt acagatgggg tttcaccatg ttggccaggc tggtcttgaa    240

ctcctgacct caaaagtgtg ggggaaagaa agagagatca gactgttact gtgtctatgt    300

agaaaaagga agacataaga aactccattt tgatctgtac taagaaaaat tcttctgcct    360

tgagatgctg ttaatctgta accctagccc caaccctgtg ctcgcagaaa cgtgtgctgt    420

attgactcaa ggtttaatgg atttagggct gtgcaggatg tgctttggta aaaatgtgtt    480

tgcaggcagt atgcttggta aaagtcattg ccattctcca gtctcaagta accagggaca    540

ccatacactg cggaaggcag cagggacctc tgcccaagaa aacctgggta ttgtccaaga    600

tttcccccac tgagacagcc tgagagatgg cctcgtggga agggaaagac ctgaccgtcc    660

cccagcccga cacccataaa aggtctgtgc tgaggaggat tagtgaaaga ggaaggcctc    720

tctgcagttg agataagagg agggcatctg tctgctgctc gtccctggga atggaatatc    780

tcggtgtaaa acccgatcgt acattctatt tactgagata ggagaaaact gccttatggc    840

tggaggtgag acacactggc agcaatactg ctctttactg cactgagata tttgtgtaaa    900

gtcaaacata aatctggcct acgtgcacat ccaggcacag ctcctttcct taaatttatc    960

tatgacaccg agtcctttgc tcacgttttc ctgctgaccc tctccccacc attaccctat   1020

agtcctgcca catccccctc accgagatag tagggatagt gatcaataaa tactgaggga   1080

actcagagac cagtgccggt gcaggtcctc acttgctgag caccggtccc ctgggcccac   1140

ttttcttcct ctatactttg tctctgtgtc ttatttcttt tctcagtctc tcgtctccac   1200

cttgtgagaa atactcagag gtgtggaggg gcaggccccc ttcaaaatga tccacccacc   1260

tcagcctccc aaagtgctgg gattacaggc atgagccacc atgcccagcc acatataact   1320

tatttctaaa taacttattt aactaacacc acatgatttt atgaccccct attttatgga   1380

tgagaaaaaa gaggcaagag aagcgatacc agttgcttag gattcccagc taccaattag   1440

tggaagcaga atttgaacca agggagtctc tggagccctc gttcccaatc tccttttctt   1500

cctctccatg tctttctttc tccccctgct cccaggcctc ctacatcaca cccttctgga   1560

caaagcttca catctgacat tttctttttt ggggtggaca gagtcttact ctgtcaccga   1620
```

```
ggctggaggg ccgtggcgca atcatggctc atggcagcct caaactcctg ggcttgaggg   1680
atcctccagc ctcagcctcc caagtagctg ggactatggg catgtgccac cacacctggc   1740
taattttta atttttgta gaaatacagg gggtgggggc atatctgaaa attttaaacc   1800
ttccctgact gccgtgagca tttctgggta gaagccactc cacgacctta ctttgctggc   1860
atgagtgctg gacagcaatt tggcaacatc ctctagacca caaatgtgca tggcctttgg   1920
cccagcaaat cagcttctgg gaataaatat gacagatact gttacataca tgggaaatgc   1980
catggacatg atgacccagg gaagcacagt ttgcaagtac aaaagggctg gaaacaccca   2040
aaaagcccat cccctgaaga cagtttcaaa aatgacggtg cattcatgta atggaatagt   2100
acacatttgt gaatgaatga atgaggtagc tcaatatatc tgcctatggg aaaatcacca   2160
agatatgttg ctaagtgaaa aacagaaaga tacagaataa tgctaccatt ttattttta   2220
atgggagagg gaagaataag gaaatggatt catatttgct taattacaca agcttcctga   2280
tgatcctttt ggatccagaa gtttgaaaac cacagcatca agaggatgcc cattgggcat   2340
ggtggctcac gcctgtaatc ccagcacttt gggaggctga ggagggtgga tcgcctaagt   2400
tcaggagttc gagaccagcc tggccaacat ggtgaaaccc catctctact aaaaacacaa   2460
aaaaattagc tgggtatggt ggtgcaggcc tgtaattcca gctacttggg aggctgaggc   2520
gcaagaatca cttaagcctg ggaggcggag gctgccgtga gccgagatca cgccattgca   2580
ctccagcttg ggagacagag caagactgtc tcaaaacaaa caaacacaca caaaaaataa   2640
gatgcccatt ggagatctcc attcactatt ttatcagatg atatttcagc acttgagtga   2700
agaaaatgtc tacaactggt ccaaacactc aaggaattta gactcttgac agagaaacac   2760
acagaagcaa gcagatatgc cccgaaccaa acttgctttt tcttctaagc ctgcttcttc   2820
ggagcagcct ctgaccctcc agggccctga gaggagtccc tggagccaca ggagcttggg   2880
agcccagaga agtgggggaa tcccagatgg tgacagcatc atccagagga ggaacataac   2940
gatggccaca gattcccaat ttggaaataa ctcagcaaaa caacactgac agaaaattca   3000
gagatttcca agagactagc ctccctgttt ccatttagaa attcacctac atacatccag   3060
ggtgagagac cccaagcatc agatgtgtca tacacaagca tcagatccaa gttagagagg   3120
gcacccgggg acagaaacct ccaagccagc caaaagccaa aggaaggatt ttacagaaag   3180
atacaggaat gtggggccag gcacagtggc tcatgcctgc aatcctagca ctttgggagg   3240
ccgaggtggg aggatcgctt gcggccagga attcaaggcc agcctgagca acatagcgag   3300
atcctatctc tacaacaaat ttaaaaacta gctgggtgtg atcacatatg cctgtggtcc   3360
caactaccca ggaggctgag gcaggagttg agcccaggag gtggaggctg caatgagcaa   3420
tgatggcgcc acttcactcc agcctcagtg aaatagtgag accctgtcta aaaataataa   3480
taaaaataaa aaacatataa agatgtcaga gcacagggac cagagctgtt agtcggcctc   3540
atggagaccc tggccaggac agccacctct ggggaccagg aagtctctca gtttctgtct   3600
ctgagggttt ggctctctga gtctctctgt cacctctcat ttctctctca tctccctctg   3660
tctatgctgt gtctctatct ctttcaatct ctctgtctct gtctcccagc ccttatctct   3720
gagtgtgtct gtttctctct catttctctc tctctctctc tctctttctc tctctctctt   3780
tctctctctc tctttctctc tccccccctcc ctcctcccct ctccctactg caggctggtc   3840
cataaccctt atcttcccca gacctgatgg agttctggta ttaatctgtt tatggtctgt   3900
ttccctccac tagaacacgg tcttcattaa aggcagagat ttttgtctgt cttattttct   3960
```

gctgtatacc cagtgcctgg gatactggct ggatcaataa atatatgctg aatgaagaat 4020
gaatgaatga ccattctcat gaacattatt atttgatgcc aactgtaaag caacaataat 4080
aataattgtc actgccactg ctgctattgt tggtatatca gctttttatt tagtacaaac 4140
tatatccccg aaattgagct aggcagtttc ttgtttaagt tttacagacc acgctgtgag 4200
gtaagtactg ttagtatgcc ctttttttctt tctttttgag acagagtctc actctgtcgc 4260
ccaggctgga gtgcagaggc ccgatcttgg ctcactgcaa cctctgcctc ccgggtacaa 4320
gtgattttcc tgtcttagcc tccccagtag ctgggattac aggcatgtgc caccatgccg 4380
gctaattttt gtatttttag taaagatggg tttttgccat gttggccagg ctggtcttga 4440
actcctggac ctctggtgat cctcctgcct cggcctccca aagtgctggg attacaggcg 4500
tcagccactg cgcttgctcc cccagccccc aaactttttt tttttttttt gagacaggtc 4560
tggctctgcc acccaagctg tagtgtagtg gcgcaatggt agctcactga agcctctaac 4620
tcctgggttc acacagtcct cctgcctcag cctcccaaaa tgctggaatt caggcctgag 4680
ccaccgcgcc ctactatgcc catttttcag ataaagaatc tgagggccct cgaggagaaa 4740
ccacttgccc aacatgagcc ctggtcttgt ctgaccccaa agcccatggg aagtttaggc 4800
tgcgtggaag gacagcctgg tgggctcagg atctgtccca tcacgagttg gaacctcagc 4860
tctgccactc ggcaaccgcg agccgttagt aagttgctga atctctccgt gtgcctccgt 4920
ttcctcacct ggaatgtggg cgacctcaca caggaagccg cctcttctag tgggcaccga 4980
cggagcgagc gcgcgtctgc agcgggactg agcgccggga gagacctgcg caggcgcagg 5040
cgcgcgggga gggccagcct gggtggccca ccccgcgcct ggcgggactg gccgccaact 5100
cccctccgct ccagtcactt gtctggagct tgaagaagtg ggtattcccc ttcccacccc 5160
aggcactgga ggagcggccc cccggggatt ccaggacctg agctccggga gctggactcg 5220
cagcgaccgc ggcagagcga gcgggcgccg ggaagcgagg agacgcccgc gggaggccca 5280
gctgctcgga gcaactggca tggcccgagc catggccgcc gcgtggccgc tgctgctggt 5340
ggcgctactg gtgctgtcct ggccaccccc aggaaccggt gagtgacccc cgcgcagtcc 5400
ggtggcccct gtctggctcc cagctccgca tccaggccgg gtactcgccc ccttgggttc 5460
ccgaagatga cggccccgcc cggcgccacc caccccccat ctctgccccg gggttggaag 5520
gaacacggtg cgagggtgcg agggcaggac cctcctcttg gccacccgga gagcggtcgg 5580
agttgggtac agaaattcct cgaaattggc agcaacacgg gtcgggcaca agaccctcct 5640
ctgggcccct cggaaagggg atggagttgg gtgaggaaat ttcccaaaaa ggcaagtgaa 5700
tcccggaaaa tcagcagatg gtgacgcatg ccggattacc ttacccaggt tcctgctcag 5760
catacccagg ccataaccca gcagcgtgct ggcaggctgg gtctggacgg aggggatggt 5820
tgatgttggg gaggaggaca gtgggtgaca cttgacacca ttacccctct gacccccaat 5880
gtctgactcc aggggcctgg ccattcattc attctttcat tctttttttt tttttttga 5940 gacagtctca ctccatcacc caggctggag tgcagtgtcc tgctctcggc tcactgcagc 6000
ctcctcctcc cgagttcaag cgattctcct gcttcagcct cccgagtagc tcggattaca 6060
gacatgtgcc actatgcctg gctaatattt ttgtattttt agtagataca ggatttcacc 6120
atgttggcca ggctggtctc aaactcctga taaatatata tattatatat tattattata 6180
tattacatat tatagtaata tataataaaa atatataata tatattatag taatatataa 6240
tatataataa aatatataat atatattata gtaatatata atatataata aaatatataa 6300
tatatattat agtaatatat aatatattat aatatattat atatattatt ataatatata 6360
atatgtatat tatatattat atatattatt ataatatata atatgtatat tatatattat 6420
atatattatt ataatatata atatgtatta tgtattatat aattgataat atataataat 6480
atatttctta ataaatatat attaaatata ttatatattt ataacatata ttatttatat 6540
aataaataat atatatttta ttatacattt aaagagtaaa tagataacat attttattat 6600
ttatttatat gttttgtgta tatatatata tatatatata tatatatagt gcgtgtgtgc 6660
gtgtatgtgt gtgtgtgtat gagagagaca aggtcttgct ttgttgccca ggctggagtg 6720
cagtggtaca atcccggctc attgcaaact cgacttccca ggctcaagcg atcctctcac 6780
tgtggcttct ggagtagctg ggattatagg tgctcacctg gctaattttt tttgtatttt 6840
tggtagagac agggtttcgc tatgctgccc aggctggttg cagccaagca cagtggctca 6900
tgcctgtaat cccaacactt tgggaggctg tggtgggagg atcacttgag cttaggaatt 6960
caaaaccagc ctgggcaata tggcaagacc ccatctctac aaaaataatt aactaaataa 7020
aaatttaaaa ataaaaaaga atgcatagga ccatgtttat tagtgtcaat aagcgctgtc 7080
acattttgag gacctactat gtgctagggc ccttagcaga aagattttta tataggacct 7140
gggggattag aggtcagtct ctgaccgccc aagttcaaat cccacctctg ccactaaacc 7200
tctgtatgac ttggaggaca ctatactctg tgtcagtttc cctgtctgta aaatgatgtt 7260
aacagtagtg cttgcctcag gggggctatt tgaggattaa atgccaagat atatgtgaag 7320
cacccagaat agcccctgat ctgtgtcagc accctgtgag tgtccactgt tctaagtctc 7380
attttacaaa ctaggaaaaa gaatcagaga ggttaagtaa ccggcctgaa gctccacagc 7440
agaaaactga agggacccaa aactcctggg ctataattgc cttcctctcg tgcctcaatc 7500
ccccacattc ttccaaccag gacccaccca gagtaataat gcagtgtttc atggatttga 7560
agacccaaga tttctccccg ttttctacat tggggttatt ctaaccccta atggcaagtt 7620
gtgctataaa tgacaacagt catggtatgt gaaacctacg acactggtgc gatgaaaaag 7680
ttctgggcca ggtgcggtgg ctcatacctg taatcccagc actttgggag gccgtagtgg 7740
gaggatcact tgaggtcagg agttcaagac cagcctggcc aacatggtga aaccccatct 7800
ctgctaaaaa caaaaataca aaaaattagc caggtgtggt ggtgggagcc tgtcatccca 7860
gctacgcgga aagctgaggc aggagaaccg cttgaacccc agaggcagag cttgcagtga 7920
gcagagatcg cgccactgca ctccccctgg gcgacagaga gagactccgt ctcaaaaaaa 7980
aaagagaaga aaagaaaaag ttctggcgct atatagtagt aacggttgca caatatcgtg 8040
aaatgtacat agtgccactg aactgtatgc tttaaatgac ttaaatggta aatttagttt 8100
tttaaccaca atatttacca caatttttta aatcagtgat gttgagattc agggaaatac 8160
ggtaataata gaagaaatac ggtaataaat agccaaagtg aaggagcacg gccaagttgc 8220
agaccatccc agacgccctt accctcctcg cctgccatgg ccccaactag tgccccagtt 8280
ccccctcccc ccacacccca cggtccaccg gggatccagg gccccagcgt gcaagtgcac 8340
gcccaggtgc ccgggctcct ggagcccctc cctatctagt ccaagaacgc cccgggtctg 8400
acaccttctc ttcggttctc cgcaggggac gtcgtcgtgc aggcgcccac ccaggtgccc 8460
ggcttcttgg gcgactccgt gacgctgccc tgctacctac aggtgcccaa catggaggtg 8520
acgcatgtgt cacagctgac ttgggcgcgg catggtgaat ctggcagcat ggccgtcttc 8580
caccaaacgc agggccccag ctattcggag tccaaacggc tggaattcgt ggcagccaga 8640
ctgggcgcgg agctgcggaa tgcctcgctg aggatgttcg ggttgcgcgt agaggatgaa 8700
ggcaactaca cctgcctgtt cgtcacgttc ccgcagggca gcaggagcgt ggatatctgg 8760
ctccgagtgc ttggtgagca gggggttttg gggaggctga atgaaaggca gagacttggt 8820
gggaggatca gggaagttgg caaagagcgg ggaggcctgg gagggaggga gattccctcc 8880
acagcagatc ccctggggac aaaaggaggg ggcagcgcaa tgatgtgggg tggggtgggg 8940
ggaggtgagt ggggggaggg gctgcagggc aggaagaaag cagagatctc agggagtaag 9000
gacccccaag cctgggatca gaaagccctg agggaggagg aggggtatat tggaaaggga 9060
gctgggaggg gactgggaag gaagggagga ggcctgggtg gcctcttctg ggtccctcct 9120
ttcctcatct gtaaaagggt tggtgacaac agcatcaccc ttggaaagct gtcctgagtg 9180
tcatcactgc ctaggaaaga gtctgtctgc cccctggac tgtgtaccca tgagggcaga 9240
accggggcta ttttgatcac tgctgggccc cagcactttc caccaaacaa tatttattga 9300
gcacttatta tgtgccattc taagagcttt acctgcatat tctaattgcc tgtgattcca 9360
tcattatcac ctgttgacag acaaggaaac tgaggcacag acttgcccaa gaccaaagct 9420
gcagccttag ggcagcggcg cttcaccgct ggcccatgtg agccccttag agctgtcggt 9480
tactgttact ttatctggtg aagaaggaga aagttgaaac agacagacag gaaagcaagg 9540
atcctgatac ccaaaagagg aggggatcat gctttcattt tcatgagctc catgaagcct 9600
tcctcttgga acttgagcaa gaagtctctg tgcctcagtt tcctcatctg tgggataggg 9660
atcaccatga ggattcaaaa aaactgaccc ttttttttt tttgagatag tttagttctg 9720
tcgcccaggc tggagtgcag tggtgtgatc atagtaggtc ctcactgcag cctggaactc 9780
ctgggctcaa gggatgttcc taccctccct gtagctggaa ttacaggaat gtgccaccat 9840
gcccaacttg ttttctgttt tgttttgttt tgttttgttt tcttttcttt ttaagcttat 9900
gtgccaagaa ctattccaag cctgtgcatg agaaactcat gaaatgtcaa gggcttggaa 9960
ctgtgcctag cacacaacac ccaaccaaag gcagctgttg tcactccagc aagcctggga 10020
ttctgggtat catggtttag gatgagggta aaacagaaac agtgagtcaa gttaaggaga 10080
aatcttcggt aaataatata ggtaatgatg gggaaggaag ttccaggttt gggaatcacc 10140
aggatgatga ttaagagatg gtcaaggtgg ttttggagtc agacagactt tatgtgaaag 10200
cccagctctg ctgcttacag ctgtgtgacc atgggcaagt cacttccctt ctcaacttca 10260
gggctcaggc ttcctctcct ccactgagcc ccagaccagg ataacccccct ttgggtttcc 10320
cctttccagc cctgccctct ccgagtcatc actgcctagg aaagagtccg tctgccccct 10380
tggactgtgt acccatgagg gcagaaccag ggctattttg gtcactgctg ggctccagca 10440
ctttccacca aacaatattt attgagcgct tattatatac cattctaaga gctttacctg 10500
catattctca ttgcctgtga tcccatcact atcccctgtc aacagacaag gaaactgagg 10560
cacagacttg cccaagacca cacagctgct cagggacaca gctgggattt aaaccatgcc 10620
attctgtatc ttttttttt ttttttttt gagacagaat ctcactctgt cgcccaggct 10680
ggagagcagt gacacaatct cagctcactg caacctccgc ctcccgagtt caagcaattc 10740
tctggtctca gcctcccaag taactgggat tactggcgtg tgccaccata ccctggctaa 10800
tttttaatag agacagtttc tccatgttgg ccaggctggt ctcgaactcc tgaccccaag 10860
tgatccaccc acctcagccc cccaaagttc tgggattata ggcgtgagcc accccgccca 10920
gcaaccatgc catcctgtac ccttaatgaa tgccccccttc tgccacggag gggttcattg 10980
aatgacttgt tgcttttgtt cctcttccca gccaagcccc agaaccttct gaggttcaga 11040
aggtccagct cactggagag ccagtgccca tggcccgctg cgtctccaca gggggtcgcc 11100
cgccagccca aatcacctgg cactcagccc aaatcacctg cccaatacga gccaggtgcc 11160
agggttcctg tctggcacag tcactgtcac cagcctctgg atattggtgc cctcaagcca 11220
ggtggacggc aagaatgtga cctgcaaggt ggagcacgag agctttgaga agcctcagct 11280
gctgactgtg aacctcaccg tgtactgtga gtgtgcccaa gtcagcgatg gcaagaaccc 11340
ctgccgggct gcccccacca ctgtctacac tgactcccca aggcactgta ggcattgctt 11400
ccatcatctg caccggctcc cctgactcct gtctacacga cccacccccca ttgtctgcac 11460
cagctcccct gggccgtaaa caacactgtc cctattgtct acaccagttt acttgggcca 11520
tagtcaatgc tggtacccag actgtctgcc ctggctcctc tagcggctgt ctgcacggat 11580
acctgacact ctgttgactc ccttgagcac agtctacact gcccctaaac tgcctacacc 11640
catttcccca ggcaagtatc cacaatgacc ctccccacat tgctacactg gttcttctgg 11700
ccacgatcaa cactgcctcc cttattgtct acacccactc ccttgtcctt ttctttcttt 11760
cctttttttt tttttttttt tgaaatagag tctcactctg ttacccaggc tgcagtacag 11820
tggcatgttc tcggctcact gtaacctctg cctcccaaat tcaggtggtt ctcctacctc 11880
agcctcccaa atagctggga ttaaaggtgc acaccaccac acctggctaa tttttgtatt 11940
tttagtagag acagggtttc atcatgttgg ccaggctggt ttcgaactcc tgacctcagg 12000
tgatcggcct gcctcagcct cccaaagtat gctggaatta taggcatgag ccactgtgcc 12060
cggctttttg ttttgttttg tttttccttt ggacagggtc tcgctctgtc acccaggctg 12120
gagtgtaggg gcatgatcat ggttcctaca gcctcaccct tccaggctca agcaatcctt 12180
ctccctcagc ctcccaagta actgggacta caggtgcagc caccatgccc ggctaatttt 12240
acagtttttt tctagagaga gttttgctgt gttgcccagg ctggtctcaa actcctaggc 12300
ttaagtgatc ctcccgcctc agtctcccga agtgctgaga ttacaggcgt gagccactgc 12360
acctggcccc ttgtccattt tctacactgc cttaccattg tctacactgg ctctcctggg 12420
ccacagacag cactaacccc attgtctaca ccacctattt tggccaccag ctgtggggtg 12480
ttttcactgt ctcccatagt gtctacactg gctcctatga ccactgtcta tgtaaacacc 12540
ccactttttc tacactggtt ctcctaggca ctctctaaag tgccccctga cactgtctac 12600
actgactccc tggagaactg tctgcattca cctcccacat tgtatcgacc agttcccctg 12660
agccacgatc aactgtctcc gccgggtgct agttgcattg atcttctcac attgtttgtg 12720
ctggctcccc taagcagtgt ctgcagagtc ccccagtgta gtctccatgt tcctctgccc 12780
aatattgtct acactggctc atctacaggc tatccagtct caccccacat caccacactg 12840
gcctccttgt gttctgtctg cacagccccc tgacagcatc tgtcctgatt ctcctgcaca 12900
gcgttacctc caccagctcc ctcatggcat catcgacatt gacacccaca catttatctc 12960
cactgacagc cccaggactc tctaaccagt gctgtctaac agaaatagca tgcaagctgc 13020
atataggatt ttaaattctc cagcggccac cccattaaaa aattaaaaga aagaggccag 13080
gcacggtggc tcacgcctgt aatcccagca ctttgggagg ccgaggcagg tggatcacct 13140
gaggtcaggc attcaagacc agcctgatca atgtggtgaa actctgtctt cactaaaaaa 13200
tacaaaaatt agccaggcac ggtggcgggt gcctgtaatc ccagctactc gggagactga 13260
ggcaggagaa tcacttgaac ctgggaggcg gagattgcaa tgagcgagat tacgccattg 13320
cactccagcc tgggcagcag agcaaaactc catctcaaaa acaagaaaag aaagagatga 13380
aatttatttg tttatttatt tatctattta tttatttgag acggggtctt actctgtcac 13440

```
ccagactgga gtgcagtggc acagctccct gcagcctcaa cctcctgggc ttaagtgatc  13500
ctcccacctc agcctcagtc tcctgagtag ctgggactac aggcgtgtga caccatgcct  13560
agctaatttt tgtttttgtt tttgtttttg tttttttgtt ttgtgatgaa gtcttgctct  13620
gtcacccagg ctagagtgca gtggcacgat ctcaactcac tgcagcctcc gcctctcggg  13680
ttcaagtgat tctcctgcct cagcctcccg agtagctggg attacaagcc ctggccacag  13740
tgcccagcta atttttgtat ttgtggtaga gacgggattt caccatgttg gccaggctgg  13800
tctcaaactc ctgacctcgt gatccaccca ccttggcctc ccaaattgct gggattacag  13860
acgtgagcca ccgcacccgg cctattttta ttttttctgg agacaggatc tccctatgtt  13920
gcccaggctg gtctcaaact cctgggctca agtgatcctc ctgcctcaac ctcccaaggt  13980
actgggatta caggcatgag ccactgtgcc tggccaaaat taatttttaa taattgcctt  14040
tacttaaccc aatataccta aaatattatt tcaacttgta attgtttttt taaaattatt  14100
cttgagatct ttcccattta ttttgtccta gtaaagcctt tgaaatctgg tgtgtatttc  14160
ggcctggcta tatttcgagt gctcagtagt cacatgtggc cagtaggtgc catattggac  14220
agcacagatc tagactaagc tcccacatca tctacactgg ctcatccaaa tactgtctac  14280
acacatacac agagcctgtc ttaatttcgt cagctcccgg ggacacactg tatatgtggg  14340
ggtgatctca cccccaccac cacattttca acactggccc gacaatatag catctgctgt  14400
aatattccaa caccctgtct acactgaacc catcagtaat atccacacaa gctcttctag  14460
acatcattca tactgttcct cccaccattg tctatactgc ttactccccg ccaggcaatt  14520
ggtacacaga ttccctcagg tactgtctat actggagtcc ctcaacactg tcactgggtc  14580
tgagcgagga ggagatctac actgactcct accccctcgcc cccgaataaa accctgtccc  14640
attggcctgc ccccaaggac attgaaaggt cttcgctgtc aatcacgtat gggatggctg  14700
agcagcagcc tagagcaggg ttatctggga ctctttcctg caggacttgt cagaaccttg  14760
aatacactgc tgtgtgttgt gagtggtcat tgcctatgag tgagaaaagg aggaggcatt  14820
ttcctgcagg acacccaaga catgcctggt ccaggctacc caggaaagct agtggagaaa  14880
agcagctcct cagaagcctt ctccatgtcc ccactgacca aggactccta ggcttctgct  14940
ctctgtggca ccccatctac ctagactcct cctaggcctc tccagctccc gctgttttcc  15000
aaatatcccc gggccttttc ctgcagtgtc gtgaatcccg cgtagcccca ggccccccaa  15060
agcctcccag tctctgaacc tctgtatcca tttcctgcag accccccaga ggtatccatc  15120
tctggctatg ataacaactg gtaccttggc cagaatgagg ccaccctgac ctgcgatgct  15180
cgcagcaacc cagagcccac aggctataat tggagcacgt gagtcctggg tctcagggag  15240
gaggggctgg gggtctggat ttctagcact gagggaggag gggctggggg cctggactcc  15300
tgggactgag ggagaagggg ctgggggccc ggacccctgg gtctgaggga cgagaggctg  15360
ggagcccgga ctcctgggtc tgagggaaga ggggctgggg gtctggaccc ctgggactga  15420
gagaggaggg gctgggcctg gacccctggg tctgagggag gaggggctgg ggggtctgga  15480
cccctgggtc tgagggagga gaagctggga gcctggaccc ctgggtctga ggcaggacag  15540
actggggcct ggactcctgg tctaagagag gagggagatt cagaaaagag aaaaagagga  15600
ggttgacttc gggcccccag tggggggcat ctctgttttg acatctctgt tttgcggttg  15660
aggcgtttag caggtggttg aatcctggct ggtggatgca cctgcttttt ggggtgtgcc  15720
tgctctgtgc ccggtacttc cccgaatcc catgtgaccc catgctgtgc acagtcagca  15780
gctgttgccc tgcccaggtt aaagaccagc cacgagaggg cagaagcggc ccttgaatca  15840
```

gcgctcggct ccaaagctgg tcctccgcct cttggccaag cttgtctaac ctgcaggcca 15900
catcatttgt aaactttctt aaaacattat gagacttttt ttttgcgaat ttttttagct 15960
cattagctat tgttagtgtt agtgtatttt atgtatggcc caggacagtt cttcttcttc 16020
caatgtggcc cggggaagcc aaaagattgg acacccccac tctagactgt aaccacctca 16080
ccgtcacctt gtgtaaccta cttggttatc tctggatgga gcaagtacta tatatcccca 16140
ttgtctagat gagaaagttg aggctcacag caataagatt tccccagatt cacactgagg 16200
ctgagatcaa gagcaaggta agaaaaaggc aaagagataa tacataattt tataatacat 16260
aattttacat aaattacata attttactga accgcccttt ttttttaaag aaggggctct 16320
gttgccgagg ctggagtgca gtggcgtgat catagctcac tgcagcctgg acctccctgg 16380
gctcaggtga tcctcccacc tcagcctcct gagtagctgg gactacaggc acacgccacc 16440
acactcagct aattttgttg tatttttttt gcagagacag ggttttgcca cattgcccag 16500
gctggtctgc aactcctggg ctcaagcaat caacccacct cagcctccta aagtgctggg 16560
attacaggcg tgagccacct cgcccagcct taggtctttt tccttattac aaaaataact 16620
tgtgtccact gtagaaatat caaacaattt agttatgagc aaaaagaaga aagtagtgcc 16680
tatagttcaa gtgtacccag ccacctccag aaatacccag tgacccctta ttatacatcc 16740
tgtctttttt ctctctgttt ctaaacaaag actggaatta tgctgtacat ataattttga 16800 acctttttcgt ctgtcttgtg aataccttttc catgtcaaag cacatagatc cacaactcca 16860
ttttccccca cgttgtatta ggaagactgt caaacataca gaaaaatcat aggaattttc 16920
cagtgaacac ttaagattcc accacgtgga ttcccctgct aacattttac tgtgcttgct 16980
ttatcacgtt tctgtgattc cttcagtccc tctattcatc catcaatcat attatgcatt 17040
tcagagcacc cccagctctc ctgctttttt tttttttttt tttttttga ggcagggcct 17100 cactctgttg ctcaggctgt agtgccgtgg cacaatcaca gctcactgca gccttgaatt 17160
cctgggctca agcgatcctc cagcttcagc ctcccagata gctgggacta caggcacaca 17220
ccaccacgcc tggctaacct ggcccctttt ttagtgttgc tgggattcca ccactttaaa 17280
aaaaaaattc aaagaataga gacaggatct cactatgttg cccaggctgg tcttgaactc 17340
ctgtactcaa gcagtcatct cacctgggcc tcccaaaggg cagggaaggg attccaacat 17400
atgtggatgt catcagttat ttaaccagtc cctagtagag gacacagatg tcattttcca 17460
ttttcaactc tgcaaatgcc atggtggtgt ccatccccac tggtcacttg tcagcagttg 17520
tccgtggaag gaattgccgg tcaaaggttt tcaactggtg tgatggtgcc tttactgtcc 17580
tgcctcaaag caccgcaatt caggctcttg agccagatag ctgcgtttgc atcccagctc 17640
tgcggagcac ccaaagcctg atgcttccat ctcctccacc tctgttcatt aaaccagtgt 17700
tccttgacta cttactgtgt gccgggtgca attaaccaac atacgttggt cgataaaaca 17760
gaccaaattt cctccccata tagagcttcc attctagtgg tgaaagaaac aagaagcaag 17820
ataaagtgtg tagtgtgtgt gcaatggtga taaataccat ggagaagaca aagcagagaa 17880
gggaatggga ctgggcgcca tgactcatac ctgtaatccc agcactttgg gaggcagaga 17940
tgggaggatc acttgaggct aggagttcaa gaccagcctg gccaacatgg cgaaacccca 18000
tctctaccaa aaaagataca aaaattggcc gggtgtggtg gcatgcacct gtagtcccag 18060
ctactcagga ggctgaggtg ggaagattcc atgcacccag gaggtggagg ttgcagtgag 18120
tcaagatggt gccactgcac tccagcctgg gtgacagagt gagacgctgt ctcaaaaaaa 18180

```
taataattaa ataaattaaa gagaagggga tgggaagggt gatcatcaca gttgaaatag  18240
ggtggccaag tgaggtgtta ctaaggtgac atcccagcag aggcctgaag gagatgaggg  18300
tgagctctgc gggtgcctag ggggaaagca ttccagcaga gggaacagca tgggcaaacc  18360
catttctatc catcagtccc tgcataagca aacaccctgg acacctaact ggagagtttg  18420
aggaccaaca aagaggccac tgtggatgca gaggcgggag caaaggggag agtaatggaa  18480
aacgtgggca gaggtagcag gggccagatc acgtggggcc tgtgacacca gaagacttcg  18540
gtttaactct gagccaggct aggcccccag agggtactga gctgaggtat gggaactgac  18600
ttagggttca caggcgacct ctggtggcca tgtggggaac agacgagggg gcgagggcag  18660
aaacggagcc cagcgtggag gcggctgctg gggcgggga tgcacagcgc cagagcaggg  18720
aggtaccgtg gaagccctga ggagaggtgg gattctggat ggatcttaag gcggggccga  18780
catgattggc taatgggttg ggtgtgggca tgagaggaag ggaagagttg gggggcctcc  18840
agagttgctc tccgcttatg ctatagaggg cgtgagggtt tctgggcacg tagtgcgtgc  18900
tcaatcactg tcactccgga cctgcagcag aggccacctc ctcacctttc tgtctctccc  18960
aggaccatgg gtcccctgcc accctttgct gtggcccagg gcgcccagct cctgatccgt  19020
cctgtggaca aaccaatcaa cacaacttta atctgcaacg tcaccaatgc cctaggagct  19080
cgccaggcag aactgaccgt ccaggtcaaa ggtgaggaac tccctgggtg ggaagaacag  19140
ggaccaaagg aagaggtcga ggcagggttc cctgtctaat gctctctggc tcccatcctt  19200
ctcctaagcc ttctcacaaa aggaccagtg gggccagctt tactcccctg ttaactccat  19260
acctatatca ctggtaccgt tgttcagctg cctggataca ctccctccac acacacaggt  19320
tgggatagat gtggaatccc tctctctcag ggactcaggc ctttccaaat atattaggca  19380
gacctctatc aattgcaatt gacagaaaca caaagtagtc taagcaaaaa aaaccaaaca  19440
aaacaggact ttattgaaaa ttcaccttca ggtatggtta gatccagggg ctccaacctt  19500
gtaacccagg aacttttatt ttatacatct cttgtctctg cttttcgtta tactggcttt  19560
attctcaggc aggctctgaa gcaagatggc cctcggcagg gacaggctca cattctacca  19620
gaatggcaac agcaggagaa aaaacatacc actttcagta actgtagcca tagtcccagg  19680
gctggctctc attggcccag cttaggccac agcccaccta tgaaccaatc atagcagcca  19740
gggagaatgg aatattctga ttggccaggc ctgtgtcaaa gtcccattct gggcaccaga  19800
gggtgggatc cattccacct gaattaaata gactgaggca gtggagtggt ggctccctaa  19860
ggaaattcaa gatgccattt caagaatgag ggataaaccc caagagtttc cttacctaaa  19920
tacctgtttc cttctctttc agagggacct cccagtgagc actcaggcat gtcccgtaac  19980
gccatcatct tcctggttct gggaatcctg gtttttctga tcctgctggg gatcgggatt  20040
tatttctatt ggtccaaatg ttcccgtgag gtcctttggc actgtcatct gtgtccctcg  20100
agtgagcatc accagagctg ccgtaattga gcacctacta cgggctctgt gctgagtcct  20160
tccagtgtgc ctctcactga atcctcaccc cactgccatg aggtttcccc catttgactg  20220
atgagggtgc agagccaggg agccttgttc actggttcat tgattacatt tacaaatatt  20280
atttacagag tgggagaaga gcgtataggg tcttaatgcc atggtaggga ctttggaatt  20340
taattcaggt gatgtgggag tccctgccag atggatggag ggtgaaataa tgcttaagcc  20400
ctcagcctta ctccatctgc cttgttcagg agtgactcct aggaggaggt ggcaggaact  20460
ggcacctctg atcctcagct ctaaaagggt ctgatgcttt cacacctcaa gagatttgca  20520
caggccgttc ccctgcctgg agcaccctcc catggctcct tctggagaag tgtgccagct  20580
```

cattctgtaa tcagaggaac gatgctttgc tgagcactgt ctacatgcca ctttgtatgt 20640
ataacccccct cgattttaat ttttaatttt ttttattatt tatgtattta tttatttatt 20700
tttgagacag gctctcactg tcgcccaggc tggagtgcag tggtgcgatc tcggctcact 20760
gtagccttca cctcccaggt tcaagcgatt ctcatgcctc agcctcccaa ggagcgggga 20820
ttacaggcac gcactactat gcccagcaat ttttgtattt ttaggagaga cagcgtttcg 20880
ccatgttggc caggctggtc tcaaacccct ggtctcctgt gatccacccg cctcagcctc 20940
ccaaagtgct gggattacag gcatgagcca ccacacctgg cctgtacaat ctccttgaat 21000
gcccacaacc acccagcaaa gtggttctcc cgtgagcccc atgttacaga ggaggaagta 21060
tttgctttga gagatgaagt tacctgccaa tggtcaaaca gctggacatg gttgttgggg 21120
agaagaagcc agatctttga ctaccaagct tttccttcaa ccactaaaca aagctgctcc 21180
cttacaaccc aggcggatac tgcctcgtcc aggaagccct ccctgacccc caagcatgag 21240
ccaagcatcc actaggctct cccactccag ccttgcccat tctgggtcat caccgtgggg 21300
gacttgtttg tcatccccag tggactgtga gccccaagat agcagacctg aggctgtcac 21360
tgtcatgact gtgtccccag gaccgcctac cactgggccg ggcataaaag aggcactcga 21420
ggaagtgttt gctgagtgat tcaatgtgtc agctccagag ccagactgcc tgtatctggg 21480
ccctaaagct actgcttgat tagtgatgtc accataggca aatagcttaa gctgtatgac 21540
tcagtttcct catctgtaaa atggggtgat ggtacctaat aatacagtag agcacttaac 21600
acagtaggtg gcacatggta agccacatac tgagtatgta tttgctatga ttgttattgc 21660
tattattact attattgtta ttattaacat aaactgcaca agagcaggct ttttgtttgt 21720
ttgtttgtgt tttgttttga gacaagatct tgctctgttg cccagactgg agtagtgcag 21780
tgatgtgatc ttggctcact gcagcctcaa cctcccaggc tcaggtgatt ctcccacctc 21840
agcctctcga gtagctggga ttataggcgt gcactcccac gcctggctaa tttttttatat 21900
ttttagtaga gatggagttt cgttgtgttg cccaagctgg tctcaaactc ctagactcca 21960
gcaatccgcc cacctcagcc tcccagagtg ctggaattat aggtgtgagc caccacgcct 22020
ggccaagagc aggcattttt atctgttttg ttcacagctg tgtccccagc acctagaatg 22080
tacctggcac aaagtagaca ttcaccattt gctgaataat actactattt gctaaataaa 22140
cccctgttga atagtctagg aaactgaaca cagagaggtt aagtcacttg tccaagttca 22200
cacagctcct aaaggacaga gatggaattt gaacccatcc atctggttcc agagccaggc 22260
tcgatattta tggatatttc ataaccaagt gaataactgg atggctaaat ccttagaaag 22320
cacaccctcc atccctgtct gacacacgtg tataccatta agggaaatgg cacccccatg 22380
taatagcaga ggcagaactt gacattttca gggccctgac acccaggcat gtcttcttcc 22440
catgcttccc agcattattc cttcctgacg acttcccctc ctatttcccc aggtacagag 22500
catgccagcg cctcagctaa tggggtaagt gcagtgttgg agctaaggag ggtgtggggt 22560
ctgcacgaac tacagaccag acgtcttcag atgcccacgg cccggcctca ggagcctggg 22620
tcttttctcc tggtgcctcg agcagcattt cccaaccctt cctgctgggc ggaatcccct 22680
gtagagtttg ctaagacgca gccccagaca gtctggtctg tgatggggcc agggaatctg 22740
cattttaata tccgctctct cccccctgcc ccacgcccct tcaattccac ccatggccac 22800
accttgagaa gcactgccct ggcttccagg gagagaggag gggacgggcc tgcagttctt 22860
tgcacatggg gcttcagtgg gaagatgttt gattttgttc aaaagagccc caaggctaaa 22920

-continued atttgaaaac cctcttctag catgtctcct attcagctgt gagcagagag aacagctctt 22980
cccaggatcc acagacagag ggcacaaggt gacagcgtcg ggactgagag gggagagaga 23040
ctggagctgg caaggacgtg ggcctccaga gttggacccg accccaatgg atgaagaccc 23100
cctccaaaga gaccagcctc cctccctgtg ccagacctca aaacgacggg ggcaggtgca 23160
agttcatagg tctccaagac caccctcctt tcatttgcta gaaggactca ctagactcag 23220
gaaagctgtt aggctcacag ttacagttta ttacagtaaa aggacagaga ttaagatcag 23280
caaagggagg aggtgcacag cacacgttcc acgacagatg aggcgacggc ttccatctgc 23340
cctctcccag tggagccata taggcagcac ctgattctca cagcaacatg tgacaacatg 23400
caagaagtac tgccaatact gccaaccaga gcagctcact cgagatcttt gtgtccagag 23460
ttttttgttt gtcttgagac agggtctggc tctgttggca gactagagta cagtggtgag 23520
atcacagttc attgcagcct tgacttctca acgccaagtc atcctcccac ctcagcctcc 23580
tgagtagcta tgactacagg tatgtgccac cacgtctggc taatcttttt attatttgta 23640
aagtcgaggt ttccctgtgt tgcccaggct ggtcttgaac tcttggctcc aagtgatact 23700
tctgccttgg cctcccaaag tgctgaatta agcagctcac catccacacg gctgacctca 23760
tacatcaagc caataccgtg tggcccaaga cccccaccat aaatcacatc attagcatga 23820
accacccaga gtggcccaag actccaagat cagctaccag gcaggatatt ccaagggctt 23880
agagatgaat gcccaggagc tgaggataaa gggcccgatc tttctttggg caaggttaag 23940
cctttactgc atagcagacc acacagaagg gtgtgggcca ccagagaatt ttggtaaaaa 24000
tttggcctct ggccttgagc ttctaaatct ctgtatccgt cagatctctg tggttacaag 24060
aaacagccac tgaccctggt caccagaggc tgcaattcag gccgcaagca gctgcctggg 24120
gggtgtccaa ggagcagaga aaactactag atgtgaactt gaagaaggtt gtcagctgca 24180
gccactttct gccagcatct gcagccactt tctgccagca tctgcagcca gcaagctggg 24240
actggcagga aataacccac aaaagaagca aatgcaattt ccaacacaag ggggaaggga 24300
tgcaggggga ggcagcgctg cagttgctca ggacacgctc ctataggacc aagatggatg 24360
cgacccaaga cccaggaggc ccagctgctc agtgcaactg acaagttaaa aaggtctatg 24420
atcttgaggg cagacagcag aattcctctt ataaagaaaa ctgtttggga aaatacgttg 24480
agggagagaa gaccttgggc caagatgcta aatgggaatg caaagcttga gctgctctgc 24540
aagagaaaat aagcaggaca gaggatttgc tctggacaga gatggaagag ccgggaacag 24600
agaagtgtgg ggaagagata ggaaccagca ggatggcagg ggcaaagggc tcaagggtga 24660
ggaggccagt gggaccccac agagttgggg agataaagga acattggttg ctttggtggc 24720
acgtaagctc cttgtctgtc tccagcaccc agaatctcat taaagcttat ttattgtacc 24780
tccagcggct gtgtgcaatg gggtcttttg tggaaatcaa ggagcagaca ggtttcatgt 24840
gtactgtcac cacgtgggat ggaaccagag gcatggaagc aagacgctaa atgaagaggg 24900
ccataagggc tgggattccc aggcacctta ggaacagctt gtcttttttt ttttcctctc 24960
caaaaaaaat gtttaaggga cggtgtctcc tgtcacccag gctggagtgc aatggcacga 25020
tcatagctca ttgcagcctc taactccggg gctcaagcaa tcctcccacc tcagcctacc 25080
aagtagctgt gaccacagct gcccctcacc atgctaagct aatttttta attagatagt 25140 acataaacgt cccaaaatta gaagataaaa agacatgagg gatccattct aatttgtgtt 25200
tggagtgtaa tggtccagct ccattcttct gcacatggat atccagtttt acacaacact 25260
gtgaatgtaa tgaatgccac tgaatcatac actcaaaaat agctaaaatg gcaaattgtc 25320
tgttatctct ttttaaccac catttttgaa aattaattat accaaaaaac cattgaatag 25380
tgcactttat ttatttattt atttgtttat ttatttattt attttagaaa taagagtctc 25440
actttgttgc ccaggctgga gtgcagtggc gtgatcatgg ctcattgcag cctcgacctg 25500
ctgggctcgg gctatccttc catctcagcc tcccgagtag ctgggactat aggtgggcgc 25560
caccccacct ggctaaatct ctttttaact tttgtagaga taggcatctc gctatgttgc 25620
ctaggctggg ctggaactcc tgggctcaag tgctcctcct gccttggcct cccaaagcgc 25680
taggattaca gatgtgagcc accgcgccca ccctgaacct tacttttttt gctcagtttc 25740
tggtaattca gagaatgcct cctgagttgt tctacaccca cctcatattc catgggaggg 25800
ctgtacaggg ctttttttaac gaggcctcta aggacaggca tttgtatcct ttccagcctt 25860
tcactattac aatgttgtag tgaataactt tacacactgt catttatttt actttttttt 25920
tttttatttt tagagaaagg aatcttgcca tcttgcccag gctggtctca aattcctggg 25980
cccaaacaat cctcccgcct tggcctccta aagtactggg atttataggc ataagccacc 26040
gtgcctggcc aatgcacact gtcatttagc tcatgttaac acctgagtgt aggacacact 26100
cctggaggtg gaattgctgg gccaaagagt atgtttcttg tcattgtgat agatattgac 26160
aaatgaaccc tcacagaagt tgtgctgagt tctgttccca ccagcgacgt aggcgatgac 26220
ctttttctgg agggaggggg catccttgga gtccacagag ccaggaatgg agagtgggcc 26280
cagaattttg gtataggtgt tgtataaact tatagtaagg ttaagaaaac cgcaactatc 26340
cttatcagag acttggcggg gggcagggta tgatggagat cataaggagg ctaaaacact 26400
ccacaccctc cctctgcatt gctcctgcac gggagtcggg aatcttttca ggttgatacg 26460
atctcacctt gaggagctgt gaggtcccag aagcctctgg gttgcagatt gcttggggtg 26520
aaaatgtctg tgctactgaa atctaacttt ttacaaaaaa ttacgggctg ggcgcagtgg 26580
ctcacgcctg taatcccagc actttgggag gctgcagcgg gtggatcact tgaggtaagg 26640
agttcaagac cagaccatag tgaaaccgtg tctctacaaa aaaaattagc caggtgtggt 26700
ggtgcatgct tgtaatccca gctactcaga aggctgaggt gggagaatcc cttgaacccg 26760
ggaagtggag gctggagtaa accatgatcg agttactgca ctccagcctg ggtgacaaga 26820
gtgagactct gtctccaaaa aaaaaaaaaa aaaaaaaaaa actggattgc ctggctctac 26880
tccgggcaca gcatgcaggc ccagttctgc tgctctgctg tttgttctgc tttcctccac 26940
atattggcat caccctctgg tgccaagatg gctgctgcat tccaggcatc acatccagac 27000
tcagacccag agaagctgcc catccctacc tgggtgagcc tttgtaggaa cgagaaaccg 27060
catccagcag cagaaacctc acccagcagc gtcttttccg gtctcattca ccagcgccgc 27120
ccaccgctca accaatccct ggccaaaaga atgggaccgc ctggaaggct ggaccaaaca 27180
ggacctgccc tctggggctg gggagaggcc cagatgaagg ctgcaggaca ggatggactc 27240
ctagacctct gttaccagca gtgactacct ctgtctgggt ggttggaaca tgtttgaatt 27300
ttattctaag tactgtctac aagttctgca ataaaccttg actcttcttt taataatgca 27360
aaaggaatcg aagtgattgt ttgaaaggga gaggaagaaa gagagaggga gggagggaag 27420
aatggaggga ggcagggaag gagacagaga gagtagaatc cagccaccgg aaaatccaga 27480
atagctggct ttgcttaatc catgcctgga aataactgct gggtttgcaa caacttctct 27540
cccggagaca gaccaaggaa actacaaaac tgcaggaagg attgaagggc cgggcacagt 27600
ggctcacgcc tgtaatccca acactttggg aggccgaggt ggattggatc acctgagatc 27660

```
aggagttcga gaccagcctg gccaacatgg tgaaacctcg tctctgctag aaatacaaaa  27720
ataagccggg cgtggtggcg tgcgcctata gtcccagcta ctcgggaggc tgaggcaaga  27780
gaatcgcttg aacctgggag gtggaggttg cagtgagctg agatcgtgcc actgcactcc  27840
agcttgggcg acagagtgag aatctgtcag gtggattctg agggtactct gaccccacga  27900
acccagcatg aaatcttcca ggcattaagg aacattgagg atgtggagga ttggaaatcc  27960
ctccagggaa aatacacttc tcttgagcag ggtcacgagg ggtgggggca atgtgggagg  28020
tggggcaaat ccaaagacaa ggtcaacagc aataataata ataacaatga caggcatttg  28080
ttgcttgttg gctgggcctc ttgcatacag ttctcccaac atccctgtga ggtggtgatg  28140
cttatcccca ttctccaggg gaggaggctg aggcccagag aggtgaagtc gtgtgccaca  28200
aaatacccca gccatatggt ggtagaacca agttttcagc cagactcacc agctcacagc  28260
agagctgccc tggactctac agccattcag tgtatagctg ggccactcca tcattcaagg  28320
cagttcaacg tcaagattcc tgatttgcct caacctgggg cctctagaag ataccatcac  28380
ccccaacaag ctgaagacgt gtgtccggaa cactcagaca cacacaaagt gctatggata  28440
caccacaccc cgacctagct gtctcttcct gatggacctc actgggtaga aatgcctggc  28500
accgcctgcc tcagatccct aggtcagctc tcactcccca atagaagttt ctgagatgat  28560
gatgaaaacg ttctccatct gtgctgtcca atggagtagc cactgatcac ttgaggctag  28620
tgagcacttg aaggtggcta gtttgaggaa ctgcattttt taatgcattt aattttagtt  28680
actttgaata tatatacaca tatatacatt tatatataca tattcataca catacatttt  28740
acatatattt tatatgtata tgtaatatat atataaatta tatatgtata tatttttata  28800
tataaatata tattatatat ttataaatat ataaatatat aatatatatt atatagatat  28860
ataaatataa atatatatta tatatataaa tatataatat atattatata aatatatata  28920
aattatatat ttatatatat aatatataaa ttatataaat tatatatatt tatatataat  28980
atataaatat atataaatta tataatttat atattatata taaattatat attttatata  29040
taatatatac aatatatata aattatatat aatatataaa tatatataaa ttatatataa  29100
tatataaaat atatataaat tatatataat atataaaata tatataaatt atataaatct  29160
atataaatat atactatatt ataaatatag tatatattta tatagattta tattatttat  29220
atagtatata ttatatattt atatgtttat gtatatataa atatataata tataaatata  29280
tttatatatt atatatttat ataatatttt atataatatg ttatatattt ttatataata  29340
tattatatat atttatat                                                29358
```

<210> SEQ ID NO 3
<211> LENGTH: 29261
<212> TYPE: DNA
<213> ORGANISM: Artificial Sequence
<220> FEATURE:
<223> OTHER INFORMATION: modified gene

<400> SEQUENCE: 3

```
aataaataac tttttagacc atatatttct tttttttttt tttttttttt tgagacagag     60
tctcactctg ttgcccagac tggaatgcag tggcatgacg ttgactcact gtaacctcca    120
cctcaagtga ttcagcctcc caagtagctg ggattacagg tgtgcacgac taccacccag    180
ctaatttttg tgtttttagt acagatgggg tttcaccatg ttggccaggc tggtcttgaa    240
ctcctgacct caaaagtgtg ggggaaagaa agagagatca gactgttact gtgtctatgt    300
agaaaaagga agacataaga aactccattt tgatctgtac taagaaaaat tcttctgcct    360
```

-continued

```
tgagatgctg ttaatctgta accctagccc caaccctgtg ctcgcagaaa cgtgtgctgt    420
attgactcaa ggtttaatgg atttagggct gtgcaggatg tgctttggta aaaatgtgtt    480
tgcaggcagt atgcttggta aaagtcattg ccattctcca gtctcaagta accagggaca    540
ccatacactg cggaaggcag cagggacctc tgcccaagaa aacctgggta ttgtccaaga    600
tttcccccac tgagacagcc tgagagatgg cctcgtggga agggaaagac ctgaccgtcc    660
cccagcccga cacccataaa aggtctgtgc tgaggaggat tagtgaaaga ggaaggcctc    720
tctgcagttg agataagagg agggcatctg tctgctgctc gtccctggga atggaatatc    780
tcggtgtaaa acccgatcgt acattctatt tactgagata ggagaaaact gccttatggc    840
tggaggtgag acacactggc agcaatactg ctctttactg cactgagata tttgtgtaaa    900
gtcaaacata aatctggcct acgtgcacat ccaggcacag ctcctttcct taaatttatc    960
tatgacaccg agtcctttgc tcacgttttc ctgctgaccc tctccccacc attaccctat   1020
agtcctgcca catccccctc accgagatag tagggatagt gatcaataaa tactgaggga   1080
actcagagac cagtgccggt gcaggtcctc acttgctgag caccggtccc ctgggcccac   1140
ttttcttcct ctatactttg tctctgtgtc ttatttcttt tctcagtctc tcgtctccac   1200
cttgtgagaa atactcagag gtgtggaggg gcaggccccc ttcaaaatga tccacccacc   1260
tcagcctccc aaagtgctgg gattacaggc atgagccacc atgcccagcc acatataact   1320
tatttctaaa taacttattt aactaacacc acatgatttt atgacccccct attttatgga   1380
tgagaaaaaa gaggcaagag aagcgatacc agttgcttag gattcccagc taccaattag   1440
tggaagcaga atttgaacca agggagtctc tggagccctc gttcccaatc tccttttctt   1500
cctctccatg tctttctttc tccccctgct cccaggcctc ctacatcaca cccttctgga   1560
caaagcttca catctgacat tttctttttt ggggtggaca gagtcttact ctgtcaccga   1620
ggctggaggg ccgtggcgca atcatggctc atggcagcct caaactcctg ggcttgaggg   1680
atcctccagc ctcagcctcc caagtagctg ggactatggg catgtgccac cacacctggc   1740
taatttttta atttttttgta gaaatacagg gggtgggggc atatctgaaa attttaaacc   1800
ttccctgact gccgtgagca tttctgggta gaagccactc cacgacctta ctttgctggc   1860
atgagtgctg gacagcaatt tggcaacatc ctctagacca caaatgtgca tggcctttgg   1920
cccagcaaat cagcttctgg gaataaatat gacagatact gttacataca tgggaaatgc   1980
catggacatg atgacccagg gaagcacagt ttgcaagtac aaaagggctg gaaacaccca   2040
aaaagcccat cccctgaaga cagtttcaaa aatgacggtg cattcatgta atggaatagt   2100
acacatttgt gaatgaatga atgaggtagc tcaatatatc tgcctatggg aaaatcacca   2160
agatatgttg ctaagtgaaa aacagaaaga tacagaataa tgctaccatt ttattttta   2220
atgggagagg gaagaataag gaaatggatt catatttgct taattacaca agcttcctga   2280
tgatcctttt ggatccagaa gtttgaaaac cacagcatca agaggatgcc cattgggcat   2340
ggtggctcac gcctgtaatc ccagcacttt gggaggctga ggagggtgga tcgcctaagt   2400
tcaggagttc gagaccagcc tggccaacat ggtgaaaccc catctctact aaaaacacaa   2460
aaaaattagc tgggtatggt ggtgcaggcc tgtaattcca gctacttggg aggctgaggc   2520
gcaagaatca cttaagcctg ggaggcggag gctgccgtga gccgagatca cgccattgca   2580
ctccagcttg ggagacagag caagactgtc tcaaaacaaa caaacacaca caaaaaaataa   2640
gatgcccatt ggagatctcc attcactatt ttatcagatg atatttcagc acttgagtga   2700
```

```
agaaaatgtc tacaactggt ccaaacactc aaggaattta gactcttgac agagaaacac   2760
acagaagcaa gcagatatgc cccgaaccaa acttgctttt tcttctaagc ctgcttcttc   2820
ggagcagcct ctgaccctcc agggccctga gaggagtccc tggagccaca ggagcttggg   2880
agcccagaga agtgggggaa tcccagatgg tgacagcatc atccagagga ggaacataac   2940
gatggccaca gattcccaat ttggaaataa ctcagcaaaa caacactgac agaaaattca   3000
gagatttcca agagactagc ctccctgttt ccatttagaa attcacctac atacatccag   3060
ggtgagagac cccaagcatc agatgtgtca tacacaagca tcagatccaa gttagagagg   3120
gcacccgggg acagaaacct ccaagccagc caaaagccaa aggaaggatt ttacagaaag   3180
atacaggaat gtggggccag gcacagtggc tcatgcctgc aatcctagca ctttgggagg   3240
ccgaggtggg aggatcgctt gcggccagga attcaaggcc agcctgagca acatagcgag   3300
atcctatctc tacaacaaat ttaaaaacta gctgggtgtg atcacatatg cctgtggtcc   3360
caactaccca ggaggctgag gcaggagttg agcccaggag gtggaggctg caatgagcaa   3420
tgatggcgcc acttcactcc agcctcagtg aaatagtgag accctgtcta aaaataataa   3480
taaaaataaa aaacatataa agatgtcaga gcacagggac cagagctgtt agtcggcctc   3540
atggagaccc tggccaggac agccacctct ggggaccagg aagtctctca gtttctgtct   3600
ctgagggttt ggctctctga gtctctctgt cacctctcat ttctctctca tctccctctg   3660
tctatgctgt gtctctatct ctttcaatct ctctgtctct gtctcccagc ccttatctct   3720
gagtgtgtct gtttctctct catttctctc tctctctctc tctctttctc tctctctctt   3780
tctctctctc tctttctctc tccccccctcc ctcctcccct ctccctactg caggctggtc   3840
cataaccctt atcttcccca gacctgatgg agttctggta ttaatctgtt tatggtctgt   3900
ttccctccac tagaacacgg tcttcattaa aggcagagat ttttgtctgt cttattttct   3960
gctgtatacc cagtgcctgg gatactggct ggatcaataa atatatgctg aatgaagaat   4020
gaatgaatga ccattctcat gaacattatt atttgatgcc aactgtaaag caacaataat   4080
aataattgtc actgccactg ctgctattgt tggtatatca gctttttatt tagtacaaac   4140
tatatccccg aaattgagct aggcagtttc ttgtttaagt tttacagacc acgctgtgag   4200
gtaagtactg ttagtatgcc ctttttcttt tctttttgag acagagtctc actctgtcgc   4260
ccaggctgga gtgcagaggc ccgatcttgg ctcactgcaa cctctgcctc ccgggtacaa   4320
gtgattttcc tgtcttagcc tccccagtag ctgggattac aggcatgtgc caccatgccg   4380
gctaattttt gtatttttag taaagatggg tttttgccat gttggccagg ctggtcttga   4440
actcctggac ctctggtgat cctcctgcct cggcctccca aagtgctggg attacaggcg   4500
tcagccactg cgcttgctcc cccagccccc aaactttttt tttttttttt gagacaggtc   4560
tggctctgcc acccaagctg tagtgtagtg gcgcaatggt agctcactga agcctctaac   4620
tcctgggttc acacagtcct cctgcctcag cctcccaaaa tgctggaatt caggcctgag   4680
ccaccgcgcc ctactatgcc catttttcag ataaagaatc tgagggccct cgaggagaaa   4740
ccacttgccc aacatgagcc ctggtcttgt ctgaccccaa agcccatggg aagtttaggc   4800
tgcgtggaag gacagcctgg tgggctcagg atctgtccca tcacgagttg gaacctcagc   4860
tctgccactc ggcaaccgcg agccgttagt aagttgctga atctctccgt gtgcctccgt   4920
ttcctcacct ggaatgtggg cgacctcaca caggaagccg cctcttctag tgggcaccga   4980
cggagcgagc gcgcgtctgc agcgggactg agcgccggga gagacctgcg caggcgcagg   5040
cgcgcgggga gggccagcct gggtggccca ccccgcgcct ggcgggactg gccgccaact   5100
```

```
ccccctccgct ccagtcactt gtctggagct tgaagaagtg ggtattcccc ttcccacccc   5160
aggcactgga ggagcggccc cccggggatt ccaggacctg agctccggga gctggactcg   5220
cagcgaccgc ggcagagcga gcgggcgccg ggaagcgagg agacgcccgc gggaggccca   5280
gctgctcgga gcaactggca tggcccgagc catggccgcc gcgtggccgc tgctgctggt   5340
ggcgctactg gtgctgtcct ggccaccccc aggaaccggt gagtgacccc cgcgcagtcc   5400
ggtggcccct gtctggctcc cagctccgca tccaggccgg gtactcgccc ccttgggttc   5460
ccgaagatga cggccccgcc cggcgccacc caccccccat ctctgccccg gggttggaag   5520
gaacacggtg cgagggtgcg agggcaggac cctcctcttg gccacccgga gagcggtcgg   5580
agttgggtac agaaattcct cgaaattggc agcaacacgg gtcgggcaca agaccctcct   5640
ctgggcccct cggaaagggg atggagttgg gtgaggaaat ttcccaaaaa ggcaagtgaa   5700
tcccggaaaa tcagcagatg gtgacgcatg ccggattacc ttacccaggt tcctgctcag   5760
catacccagg ccataaccca gcagcgtgct ggcaggctgg gtctggacgg aggggatggt   5820
tgatgttggg gaggaggaca gtgggtgaca cttgacacca ttacccctct gacccccaat   5880
gtctgactcc aggggcctgg ccattcattc attctttcat tcttttttt ttttttttga   5940
gacagtctca ctccatcacc caggctggag tgcagtgtcc tgctctcggc tcactgcagc   6000
ctcctcctcc cgagttcaag cgattctcct gcttcagcct cccgagtagc tcggattaca   6060
gacatgtgcc actatgcctg gctaatattt ttgtattttt agtagataca ggatttcacc   6120
atgttggcca ggctggtctc aaactcctga taaatatata tattatatat tattattata   6180
tattacatat tatagtaata tataataaaa atatataata tatattatag taatatataa   6240
tatataataa aatatataat atatattata gtaatatata atatataata aaatatataa   6300
tatatattat agtaatatat aatatattat aatatattat atatattatt ataatatata   6360
atatgtatat tatatattat atatattatt ataatatata atatgtatat tatatattat   6420
atatattatt ataatatata atatgtatta tgtattatat aattgataat atataataat   6480
atatttctta ataaatatat attaaatata ttatatattt ataacatata ttatttatat   6540
aataaataat atatatttta ttatacattt aaagagtaaa tagataacat attttattat   6600
ttatttatat gttttgtgta tatatatata tatatatata tatatatagt gcgtgtgtgc   6660
gtgtatgtgt gtgtgtgtat gagagagaca aggtcttgct ttgttgccca ggctggagtg   6720
cagtggtaca atcccggctc attgcaaact cgacttccca ggctcaagcg atcctctcac   6780
tgtggcttct ggagtagctg ggattatagg tgctcacctg gctaattttt tttgtatttt   6840
tggtagagac agggtttcgc tatgctgccc aggctggttg cagccaagca cagtggctca   6900
tgcctgtaat cccaacactt tgggaggctg tggtgggagg atcacttgag cttaggaatt   6960
caaaaccagc ctgggcaata tggcaagacc ccatctctac aaaaataatt aactaaataa   7020
aaatttaaaa ataaaaaaga atgcatagga ccatgtttat tagtgtcaat aagcgctgtc   7080
acattttgag gacctactat gtgctagggc ccttagcaga aagattttta tataggacct   7140
gggggattag aggtcagtct ctgaccgccc aagttcaaat cccacctctg ccactaaacc   7200
tctgtatgac ttggaggaca ctatactctg tgtcagtttc cctgtctgta aaatgatgtt   7260
aacagtagtg cttgcctcag gggggctatt tgaggattaa atgccaagat atatgtgaag   7320
cacccagaat agcccctgat ctgtgtcagc accctgtgag tgtccactgt tctaagtctc   7380
attttacaaa ctaggaaaaa gaatcagaga ggttaagtaa ccggcctgaa gctccacagc   7440
```

agaaaactga agggacccaa aactcctggg ctataattgc cttcctctcg tgcctcaatc 7500
ccccacattc ttccaaccag gacccaccca gagtaataat gcagtgtttc atggatttga 7560
agacccaaga tttctccccg ttttctacat tggggttatt ctaacccccta atggcaagtt 7620 gtgctataaa tgacaacagt catggtatgt gaaacctacg acactggtgc gatgaaaaag 7680
ttctgggcca ggtgcggtgg ctcatacctg taatcccagc actttgggag gccgtagtgg 7740
gaggatcact tgaggtcagg agttcaagac cagcctggcc aacatggtga aaccccatct 7800
ctgctaaaaa caaaaataca aaaaattagc caggtgtggt ggtgggagcc tgtcatccca 7860
gctacgcgga aagctgaggc aggagaaccg cttgaacccc agaggcagag cttgcagtga 7920
gcagagatcg cgccactgca ctccccctgg gcgacagaga gagactccgt ctcaaaaaaa 7980
aaagagaaga aaagaaaaag ttctggcgct atatagtagt aacggttgca caatatcgtg 8040
aaatgtacat agtgccactg aactgtatgc tttaaatgac ttaaatggta aatttagttt 8100
tttaaccaca atatttacca caatttttta aatcagtgat gttgagattc agggaaatac 8160
ggtaataata gaagaaatac ggtaataaat agccaaagtg aaggagcacg gccaagttgc 8220
agaccatccc agacgccctt accctcctcg cctgccatgg ccccaactag tgccccagtt 8280
ccccctcccc ccacacccca cggtccaccg gggatccagg gccccagcgt gcaagtgcac 8340
gcccaggtgc ccgggctcct ggagcccctc cctatctagt ccaagaacgc cccgggtctg 8400
acaccttctc ttcggttctc cgcaggggac gtcgtcgtgc aggcgcccac ccaggtgccc 8460
ggcttcttgg gcgactccgt gacgctgccc tgctacctac aggtgcccaa catggaggtg 8520
acgcatgtgt cacagctgac ttgggcgcgg catggtgaat ctggcagcat ggccgtcttc 8580
caccaaacgc agggccccag ctattcggag tccaaacggc tggaattcgt ggcagccaga 8640
ctgggcgcgg agctgcggaa tgcctcgctg aggatgttcg ggttgcgcgt agaggatgaa 8700
ggcaactaca cctgcctgtt cgtcacgttc ccgcagggca gcaggagcgt ggatatctgg 8760
ctccgagtgc ttggtgagca gggggttttg gggaggctga atgaaaggca gagacttggt 8820
gggaggatca gggaagttgg caaagagcgg ggaggcctgg gagggaggga gattccctcc 8880
acagcagatc ccctggggac aaaaggaggg ggcagcgcaa tgatgtgggg tggggtgggg 8940
ggaggtgagt ggggggaggg gctgcagggc aggaagaaag cagagatctc agggagtaag 9000
gacccccaag cctgggatca gaaagccctg agggaggagg aggggtatat tggaaaggga 9060
gctgggaggg gactgggaag gaagggagga ggcctgggtg gcctcttctg ggtccctcct 9120
ttcctcatct gtaaaagggt tggtgacaac agcatcaccc ttggaaagct gtcctgagtg 9180
tcatcactgc ctaggaaaga gtctgtctgc cccccttggac tgtgtaccca tgagggcaga 9240
accggggcta ttttgatcac tgctgggccc cagcactttc caccaaacaa tatttattga 9300
gcacttatta tgtgccattc taagagcttt acctgcatat tctaattgcc tgtgattcca 9360
tcattatcac ctgttgacag acaaggaaac tgaggcacag acttgcccaa gaccaaagct 9420
gcagccttag ggcagcggcg cttcaccgct ggcccatgtg agccccttag agctgtcggt 9480
tactgttact ttatctggtg aagaaggaga aagttgaaac agacagacag gaaagcaagg 9540
atcctgatac ccaaaagagg aggggatcat gctttcattt tcatgagctc catgaagcct 9600
tcctcttgga acttgagcaa gaagtctctg tgcctcagtt tcctcatctg tgggataggg 9660
atcaccatga ggattcaaaa aaactgaccc tttttttttt tttgagatag tttagttctg 9720
tcgcccaggc tggagtgcag tggtgtgatc atagtaggtc ctcactgcag cctggaactc 9780
ctgggctcaa gggatgttcc taccctccct gtagctggaa ttacaggaat gtgccaccat 9840
gcccaacttg ttttctgttt tgttttgttt tgttttgttt tcttttcttt ttaagcttat 9900
gtgccaagaa ctattccaag cctgtgcatg agaaactcat gaaatgtcaa gggcttggaa 9960
ctgtgcctag cacacaacac ccaaccaaag gcagctgttg tcactccagc aagcctggga 10020
ttctgggtat catggtttag gatgagggta aaacagaaac agtgagtcaa gttaaggaga 10080
aatcttcggt aaataatata ggtaatgatg gggaaggaag ttccaggttt gggaatcacc 10140
aggatgatga ttaagagatg gtcaaggtgg ttttggagtc agacagactt tatgtgaaag 10200
cccagctctg ctgcttacag ctgtgtgacc atgggcaagt cacttccctt ctcaacttca 10260
gggctcaggc ttcctctcct ccactgagcc ccagaccagg ataacccccct ttgggtttcc 10320
cctttccagc cctgccctct ccgagtcatc actgcctagg aaagagtccg tctgcccccct 10380
tggactgtgt acccatgagg gcagaaccag ggctattttg gtcactgctg ggctccagca 10440
ctttccacca aacaatattt attgagcgct tattatatac cattctaaga gctttacctg 10500
catattctca ttgcctgtga tcccatcact atcccctgtc aacagacaag gaaactgagg 10560
cacagacttg cccaagacca cacagctgct cagggacaca gctgggattt aaaccatgcc 10620
attctgtatc tttttttttt tttttttttt gagacagaat ctcactctgt cgcccaggct 10680
ggagagcagt gacacaatct cagctcactg caacctccgc ctcccgagtt caagcaattc 10740
tctggtctca gcctcccaag taactgggat tactggcgtg tgccaccata ccctggctaa 10800
tttttaatag agacagtttc tccatgttgg ccaggctggt ctcgaactcc tgaccccaag 10860
tgatccaccc acctcagccc cccaaagttc tgggattata ggcgtgagcc accccgccca 10920
gcaaccatgc catcctgtac ccttaatgaa tgccccccttc tgccacggag gggttcattg 10980
aatgacttgt tgcttttgtt cctcttccca gccaagcccc agaacacaga cctgggcggg 11040
atgcccaata cgagccaggt gccagggttc ctgtctggca cagtcactgt caccagcctc 11100
tggatattgg tgccctcaag ccaggtggac ggcaagaatg tgacctgcaa ggtggagcac 11160
gagagctttg agaagcctca gctgctgact gtgaacctca ccgtgtactg tgagtgtgcc 11220
caagtcagcg atggcaagaa cccctgccgg gctgcccccca ccactgtcta cactgactcc 11280
ccaaggcact gtaggcattg cttccatcat ctgcaccggc tcccctgact cctgtctaca 11340
cgacccaccc ccattgtctg caccagctcc cctgggccgt aaacaacact gtccctattg 11400
tctacaccag tttacttggg ccatagtcaa tgctggtacc cagactgtct gccctggctc 11460
ctctagcggc tgtctgcacg gatacctgac actctgttga ctcccttgag cacagtctac 11520
actgccccta aactgcctac acccatttcc ccaggcaagt atccacaatg accctcccca 11580
cattgctaca ctggttcttc tggccacgat caacactgcc tcccttattg tctacaccca 11640
ctcccttgtc cttttctttc tttccttttt tttttttttt ttttgaaata gagtctcact 11700
ctgttaccca ggctgcagta cagtggcatg ttctcggctc actgtaacct ctgcctccca 11760
aattcaggtg gttctcctac ctcagcctcc caaatagctg ggattaaagg tgcacaccac 11820
cacacctggc taatttttgt atttttagta gagacagggt ttcatcatgt tggccaggct 11880
ggtttcgaac tcctgacctc aggtgatcgg cctgcctcag cctcccaaag tatgctggaa 11940
ttataggcat gagccactgt gcccggcttt ttgttttgtt ttgtttttcc tttggacagg 12000
gtctcgctct gtcacccagg ctggagtgta ggggcatgat catggttcct acagcctcac 12060
ccttccaggc tcaagcaatc cttctccctc agcctcccaa gtaactggga ctacaggtgc 12120
agccaccatg cccggctaat tttacagttt ttttctagag agagttttgc tgtgttgccc 12180

```
aggctggtct caaactccta ggcttaagtg atcctcccgc ctcagtctcc cgaagtgctg  12240
agattacagg cgtgagccac tgcacctggc cccttgtcca ttttctacac tgccttacca  12300
ttgtctacac tggctctcct gggccacaga cagcactaac cccattgtct acaccaccta  12360
ttttggccac cagctgtggg gtgttttcac tgtctcccat agtgtctaca ctggctccta  12420
tgaccactgt ctatgtaaac accccacttt ttctacactg gttctcctag gcactctcta  12480
aagtgccccc tgacactgtc tacactgact ccctggagaa ctgtctgcat tcacctccca  12540
cattgtatcg accagttccc ctgagccacg atcaactgtc tccgccgggt gctagttgca  12600
ttgatcttct cacattgttt gtgctggctc ccctaagcag tgtctgcaga gtccccccagt  12660
gtagtctcca tgttcctctg cccaatattg tctacactgg ctcatctaca ggctatccag  12720
tctcacccca catcaccaca ctggcctcct tgtgttctgt ctgcacagcc ccctgacagc  12780
atctgtcctg attctcctgc acagcgttac ctccaccagc tccctcatgg catcatcgac  12840
attgacaccc acacatttat ctccactgac agccccagga ctctctaacc agtgctgtct  12900
aacagaaata gcatgcaagc tgcatatagg attttaaatt ctccagcggc caccccatta  12960
aaaaattaaa agaaagaggc caggcacggt ggctcacgcc tgtaatccca gcactttggg  13020
aggccgaggc aggtggatca cctgaggtca ggcattcaag accagcctga tcaatgtggt  13080
gaaactctgt cttcactaaa aaatacaaaa attagccagg cacggtggcg ggtgcctgta  13140
atcccagcta ctcgggagac tgaggcagga gaatcacttg aacctgggag gcggagattg  13200
caatgagcga gattacgcca ttgcactcca gcctgggcag cagagcaaaa ctccatctca  13260
aaaacaagaa aagaaagaga tgaaatttat ttgtttattt atttatctat ttatttattt  13320
gagacggggt cttactctgt cacccagact ggagtgcagt ggcacagctc cctgcagcct  13380
caacctcctg ggcttaagtg atcctcccac ctcagcctca gtctcctgag tagctgggac  13440
tacaggcgtg tgacaccatg cctagctaat tttgttttt gtttttgttt ttgttttttt  13500
gttttgtgat gaagtcttgc tctgtcaccc aggctagagt gcagtggcac gatctcaact  13560
cactgcagcc tccgcctctc gggttcaagt gattctcctg cctcagcctc ccgagtagct  13620
gggattacaa gccctggcca cagtgcccag ctaatttttg tatttgtggt agagacggga  13680
tttcaccatg ttggccaggc tggtctcaaa ctcctgacct cgtgatccac ccaccttggc  13740
ctcccaaatt gctgggatta cagacgtgag ccaccgcacc cggcctattt ttattttttc  13800
tggagacagg atctccctat gttgcccagg ctggtctcaa actcctgggc tcaagtgatc  13860
ctcctgcctc aacctcccaa ggtactggga ttacaggcat gagccactgt gcctggccaa  13920
aattaatttt taataattgc ctttacttaa cccaatatac ctaaaatatt atttcaactt  13980
gtaattgttt ttttaaaatt attcttgaga tctttcccat ttattttgtc ctagtaaagc  14040
ctttgaaatc tggtgtgtat ttcggcctgg ctatatttcg agtgctcagt agtcacatgt  14100
ggccagtagg tgccatattg gacagcacag atctagacta agctcccaca tcatctacac  14160
tggctcatcc aaatactgtc tacacacata cacagagcct gtcttaattt cgtcagctcc  14220
cggggacaca ctgtatatgt gggggtgatc tcacccccac caccacattt tcaacactgg  14280
cccgacaata tagcatctgc tgtaatattc caacaccctg tctacactga acccatcagt  14340
aatatccaca caagctcttc tagacatcat tcatactgtt cctcccacca ttgtctatac  14400
tgcttactcc ccgccaggca attggtacac agattccctc aggtactgtc tatactggag  14460
tccctcaaca ctgtcactgg gtctgagcga ggaggagatc tacactgact cctacccctc  14520
gcccccgaat aaaaccctgt cccattggcc tgcccccaag gacattgaaa ggtcttcgct  14580
```

```
gtcaatcacg tatgggatgg ctgagcagca gcctagagca gggttatctg ggactctttc  14640
ctgcaggact tgtcagaacc ttgaatacac tgctgtgtgt tgtgagtggt cattgcctat  14700
gagtgagaaa aggaggaggc attttcctgc aggacaccca agacatgcct ggtccaggct  14760
acccaggaaa gctagtggag aaaagcagct cctcagaagc cttctccatg tccccactga  14820
ccaaggactc ctaggcttct gctctctgtg gcaccccatc tacctagact cctcctaggc  14880
ctctccagct cccgctgttt tccaaatatc cccgggcctt ttcctgcagt gtcgtgaatc  14940
ccgcgtagcc ccaggccccc caaagcctcc cagtctctga acctctgtat ccatttcctg  15000
cagacccccc agaggtatcc atctctggct atgataacaa ctggtacctt ggccagaatg  15060
aggccaccct gacctgcgat gctcgcagca acccagagcc cacaggctat aattggagca  15120
cgtgagtcct gggtctcagg gaggaggggc tgggggtctg gatttctagc actgagggag  15180
gaggggctgg gggcctggac tcctgggact gagggagaag gggctggggg cccggacccc  15240
tgggtctgag ggacgagagg ctgggagccc ggactcctgg gtctgaggga agaggggctg  15300
ggggtctgga cccctgggac tgagagagga ggggctgggc ctggacccct gggtctgagg  15360
gaggaggggc tggggggtct ggacccctgg gtctgaggga ggagaagctg ggagcctgga  15420
cccctgggtc tgaggcagga cagactgggg cctggactcc tggtctaaga gaggagggag  15480
attcagaaaa gagaaaaaga ggaggttgac ttcgggcccc cagtgggggg catctctgtt  15540
ttgacatctc tgttttgcgg ttgaggcgtt tagcaggtgg ttgaatcctg gctggtggat  15600
gcacctgctt tttggggtgt gcctgctctg tgcccggtac ttcccccgaa tcccatgtga  15660
ccccatgctg tgcacagtca gcagctgttg ccctgcccag gttaaagacc agccacgaga  15720
gggcagaagc ggcccttgaa tcagcgctcg gctccaaagc tggtcctccg cctcttggcc  15780
aagcttgtct aacctgcagg ccacatcatt tgtaaacttt cttaaaacat tatgagactt  15840
tttttttgcg aattttttta gctcattagc tattgttagt gttagtgtat tttatgtatg  15900
gcccaggaca gttcttcttc ttccaatgtg gcccggggaa gccaaaagat tggacacccc  15960
cactctagac tgtaaccacc tcaccgtcac cttgtgtaac ctacttggtt atctctggat  16020
ggagcaagta ctatatatcc ccattgtcta gatgagaaag ttgaggctca cagcaataag  16080
atttccccag attcacactg aggctgagat caagagcaag gtaagaaaaa ggcaaagaga  16140
taatacataa ttttataata cataatttta cataaattac ataattttac tgaaccgccc  16200
ttttttttta aagaaggggc tctgttgccg aggctggagt gcagtggcgt gatcatagct  16260
cactgcagcc tggacctccc tgggctcagg tgatcctccc acctcagcct cctgagtagc  16320
tgggactaca ggcacacgcc accacactca gctaattttg ttgtattttt tttgcagaga  16380
cagggttttg ccacattgcc caggctggtc tgcaactcct gggctcaagc aatcaaccca  16440
cctcagcctc ctaaagtgct gggattacag gcgtgagcca cctcgcccag ccttaggtct  16500
ttttccttat tacaaaaata acttgtgtcc actgtagaaa tatcaaacaa tttagttatg  16560
agcaaaaaga agaaagtagt gcctatagtt caagtgtacc cagccacctc cagaaatacc  16620
cagtgacccc ttattataca tcctgtcttt tttctctctg tttctaaaca aagactggaa  16680
ttatgctgta catataattt tgaacctttt cgtctgtctt gtgaatacct ttccatgtca  16740
aagcacatag atccacaact ccattttccc ccacgttgta ttaggaagac tgtcaaacat  16800
acagaaaaat cataggaatt ttccagtgaa cacttaagat tccaccacgt ggattcccct  16860
gctaacattt tactgtgctt gctttatcac gtttctgtga ttccttcagt ccctctattc  16920
```

```
atccatcaat catattatgc atttcagagc acccccagct ctcctgcttt tttttttttt  16980
tttttttttt tgaggcaggg cctcactctg ttgctcaggc tgtagtgccg tggcacaatc  17040
acagctcact gcagccttga attcctgggc tcaagcgatc ctccagcttc agcctcccag  17100
atagctggga ctacaggcac acaccaccac gcctggctaa cctggcccct tttttagtgt  17160
tgctgggatt ccaccacttt aaaaaaaaaa ttcaaagaat agagacagga tctcactatg  17220
ttgcccaggc tggtcttgaa ctcctgtact caagcagtca tctcacctgg gcctcccaaa  17280
gggcagggaa gggattccaa catatgtgga tgtcatcagt tatttaacca gtccctagta  17340
gaggacacag atgtcatttt ccattttcaa ctctgcaaat gccatggtgg tgtccatccc  17400
cactggtcac ttgtcagcag ttgtccgtgg aaggaattgc cggtcaaagg ttttcaactg  17460
gtgtgatggt gcctttactg tcctgcctca aagcaccgca attcaggctc ttgagccaga  17520
tagctgcgtt tgcatcccag ctctgcggag cacccaaagc ctgatgcttc catctcctcc  17580
acctctgttc attaaaccag tgttccttga ctacttactg tgtgccgggt gcaattaacc  17640
aacatacgtt ggtcgataaa acagaccaaa tttcctcccc atatagagct tccattctag  17700
tggtgaaaga aacaagaagc aagataaagt gtgtagtgtg tgtgcaatgg tgataaatac  17760
catggagaag acaaagcaga gaagggaatg ggactgggcg ccatgactca tacctgtaat  17820
cccagcactt tgggaggcag agatgggagg atcacttgag gctaggagtt caagaccagc  17880
ctggccaaca tggcgaaacc ccatctctac caaaaaagat acaaaaattg gccgggtgtg  17940
gtggcatgca cctgtagtcc cagctactca ggaggctgag gtgggaagat tccatgcacc  18000
caggaggtgg aggttgcagt gagtcaagat ggtgccactg cactccagcc tgggtgacag  18060
agtgagacgc tgtctcaaaa aaataataat taaataaatt aaagagaagg ggatgggaag  18120
ggtgatcatc acagttgaaa tagggtggcc aagtgaggtg ttactaaggt gacatcccag  18180
cagaggcctg aaggagatga gggtgagctc tgcgggtgcc taggggggaaa gcattccagc  18240
agagggaaca gcatgggcaa acccatttct atccatcagt ccctgcataa gcaaacaccc  18300
tggacaccta actggagagt ttgaggacca acaaagaggc cactgtggat gcagaggcgg  18360
gagcaaaggg gagagtaatg gaaaacgtgg gcagaggtag caggggccag atcacgtggg  18420
gcctgtgaca ccagaagact tcggtttaac tctgagccag gctaggcccc cagagggtac  18480
tgagctgagg tatgggaact gacttagggt tcacaggcga cctctggtgg ccatgtgggg  18540
aacagacgag ggggcgaggg cagaaacgga gcccagcgtg gaggcggctg ctgggggccg  18600
ggatgcacag cgccagagca gggaggtacc gtggaagccc tgaggagagg tgggattctg  18660
gatggatctt aaggcggggc cgacatgatt ggctaatggg ttgggtgtgg gcatgagagg  18720
aagggaagag ttggggggcc tccagagttg ctctccgctt atgctataga gggcgtgagg  18780
gtttctgggc acgtagtgcg tgctcaatca ctgtcactcc ggacctgcag cagaggccac  18840
ctcctcacct ttctgtctct cccaggacca tgggtcccct gccacccttt gctgtggccc  18900
agggcgccca gctcctgatc cgtcctgtgg acaaaccaat caacacaact ttaatctgca  18960
acgtcaccaa tgccctagga gctcgccagg cagaactgac cgtccaggtc aaaggtgagg  19020
aactccctgg gtgggaagaa cagggaccaa aggaagaggt cgaggcaggg ttccctgtct  19080
aatgctctct ggctcccatc cttctcctaa gccttctcac aaaaggacca gtggggccag  19140
ctttactccc ctgttaactc catacctata tcactggtac cgttgttcag ctgcctggat  19200
acactccctc cacacacaca ggttgggata gatgtggaat ccctctctct cagggactca  19260
ggcctttcca aatatattag gcagacctct atcaattgca attgacagaa acacaaagta  19320
```

```
gtctaagcaa aaaaaaccaa acaaaacagg actttattga aaattcacct tcaggtatgg  19380
ttagatccag ggctccaac cttgtaaccc aggaactttt attttataca tctcttgtct  19440
ctgcttttcg ttatactggc tttattctca ggcaggctct gaagcaagat ggccctcggc  19500
agggacaggc tcacattcta ccagaatggc aacagcagga gaaaaaacat accactttca  19560
gtaactgtag ccatagtccc agggctggct ctcattggcc cagcttaggc cacagcccac  19620
ctatgaacca atcatagcag ccagggagaa tggaatattc tgattggcca ggcctgtgtc  19680
aaagtcccat tctgggcacc agagggtggg atccattcca cctgaattaa atagactgag  19740
gcagtggagt ggtggctccc taaggaaatt caagatgcca tttcaagaat gagggataaa  19800
ccccaagagt ttccttacct aaatacctgt ttccttctct ttcagaggga cctcccagtg  19860
agcactcagg catgtcccgt aacgccatca tcttcctggt tctgggaatc ctggtttttc  19920
tgatcctgct ggggatcggg atttatttct attggtccaa atgttcccgt gaggtccttt  19980
ggcactgtca tctgtgtccc tcgagtgagc atcaccagag ctgccgtaat tgagcaccta  20040
ctacgggctc tgtgctgagt ccttccagtg tgcctctcac tgaatcctca ccccactgcc  20100
atgaggtttc ccccatttga ctgatgaggg tgcagagcca gggagccttg ttcactggtt  20160
cattgattac atttacaaat attatttaca gagtgggaga agagcgtata gggtcttaat  20220
gccatggtag ggactttgga atttaattca ggtgatgtgg gagtccctgc cagatggatg  20280
gagggtgaaa taatgcttaa gccctcagcc ttactccatc tgccttgttc aggagtgact  20340
cctaggagga ggtggcagga actggcacct ctgatcctca gctctaaaag ggtctgatgc  20400
tttcacacct caagagattt gcacaggccg ttcccctgcc tggagcaccc tcccatggct  20460
ccttctggag aagtgtgcca gctcattctg taatcagagg aacgatgctt tgctgagcac  20520
tgtctacatg ccactttgta tgtataaccc cctcgatttt aatttttaat ttttttttatt  20580
atttatgtat ttatttattt atttttgaga caggctctca ctgtcgccca ggctggagtg  20640
cagtggtgcg atctcggctc actgtagcct tcacctccca ggttcaagcg attctcatgc  20700
ctcagcctcc caaggagcgg ggattacagg cacgcactac tatgcccagc aatttttgta  20760
tttttaggag agacagcgtt tcgccatgtt ggccaggctg gtctcaaacc cctggtctcc  20820
tgtgatccac ccgcctcagc ctcccaaagt gctgggatta caggcatgag ccaccacacc  20880
tggcctgtac aatctccttg aatgcccaca accacccagc aaagtggttc tcccgtgagc  20940
cccatgttac agaggaggaa gtatttgctt tgagagatga agttacctgc caatggtcaa  21000
acagctggac atggttgttg gggagaagaa gccagatctt tgactaccaa gcttttcctt  21060
caaccactaa acaaagctgc tcccttacaa cccaggcgga tactgcctcg tccaggaagc  21120
cctccctgac ccccaagcat gagccaagca tccactaggc tctcccactc cagccttgcc  21180
cattctgggt catcaccgtg ggggacttgt ttgtcatccc cagtggactg tgagccccaa  21240
gatagcagac ctgaggctgt cactgtcatg actgtgtccc caggaccgcc taccactggg  21300
ccgggcataa aagaggcact cgaggaagtg tttgctgagt gattcaatgt gtcagctcca  21360
gagccagact gcctgtatct gggccctaaa gctactgctt gattagtgat gtcaccatag  21420
gcaaatagct taagctgtat gactcagttt cctcatctgt aaaatggggt gatggtacct  21480
aataatacag tagagcactt aacacagtag gtggcacatg gtaagccaca tactgagtat  21540
gtatttgcta tgattgttat tgctattatt actattattg ttattattaa cataaactgc  21600
acaagagcag gctttttgtt tgtttgtttg tgttttgttt tgagacaaga tcttgctctg  21660
```

```
ttgcccagac tggagtagtg cagtgatgtg atcttggctc actgcagcct caacctccca  21720
ggctcaggtg attctcccac ctcagcctct cgagtagctg ggattatagg cgtgcactcc  21780
cacgcctggc taattttttta tatttttagt agagatggag tttcgttgtg ttgcccaagc  21840
tggtctcaaa ctcctagact ccagcaatcc gcccacctca gcctcccaga gtgctggaat  21900
tataggtgtg agccaccacg cctggccaag agcaggcatt tttatctgtt ttgttcacag  21960
ctgtgtcccc agcacctaga atgtacctgg cacaaagtag acattcacca tttgctgaat  22020
aatactacta tttgctaaat aaacccctgt tgaatagtct aggaaactga acacagagag  22080
gttaagtcac ttgtccaagt tcacacagct cctaaaggac agagatggaa tttgaaccca  22140
tccatctggt tccagagcca ggctcgatat ttatggatat ttcataacca agtgaataac  22200
tggatggcta aatccttaga aagcacaccc tccatccctg tctgacacac gtgtatacca  22260
ttaagggaaa tggcaccccc atgtaatagc agaggcagaa cttgacattt tcagggccct  22320
gacacccagg catgtcttct tcccatgctt cccagcatta ttccttcctg acgacttccc  22380
ctcctatttc cccaggtaca gagcatgcca gcgcctcagc taatggggta agtgcagtgt  22440
tggagctaag gagggtgtgg ggtctgcacg aactacagac cagacgtctt cagatgccca  22500
cggcccggcc tcaggagcct gggtcttttc tcctggtgcc tcgagcagca tttcccaacc  22560
cttcctgctg ggcggaatcc cctgtagagt ttgctaagac gcagccccag acagtctggt  22620
ctgtgatggg gccagggaat ctgcatttta atatccgctc tctccccccct gccccacgcc  22680
ccttcaattc cacccatggc cacaccttga gaagcactgc cctggcttcc agggagagag  22740
gaggggacgg gcctgcagtt ctttgcacat ggggcttcag tgggaagatg tttgattttg  22800
ttcaaaagag ccccaaggct aaaatttgaa aaccctcttc tagcatgtct cctattcagc  22860
tgtgagcaga gagaacagct cttcccagga tccacagaca gagggcacaa ggtgacagcg  22920
tcgggactga gaggggagag agactggagc tggcaaggac gtgggcctcc agagttggac  22980
ccgaccccaa tggatgaaga ccccctccaa agagaccagc ctccctccct gtgccagacc  23040
tcaaaacgac gggggcaggt gcaagttcat aggtctccaa gaccaccctc ctttcatttg  23100
ctagaaggac tcactagact caggaaagct gttaggctca cagttacagt ttattacagt  23160
aaaaggacag agattaagat cagcaaaggg aggaggtgca cagcacacgt tccacgacag  23220
atgaggcgac ggcttccatc tgccctctcc cagtggagcc atataggcag cacctgattc  23280
tcacagcaac atgtgacaac atgcaagaag tactgccaat actgccaacc agagcagctc  23340
actcgagatc tttgtgtcca gagttttttg tttgtcttga gacagggtct ggctctgttg  23400
gcagactaga gtacagtggt gagatcacag ttcattgcag ccttgacttc tcaacgccaa  23460
gtcatcctcc cacctcagcc tcctgagtag ctatgactac aggtatgtgc caccacgtct  23520
ggctaatctt tttattattt gtaaagtcga ggtttccctg tgttgcccag gctggtcttg  23580
aactcttggc tccaagtgat acttctgcct tggcctccca aagtgctgaa ttaagcagct  23640
caccatccac acggctgacc tcatacatca agccaatacc gtgtggccca agacccccac  23700
cataaatcac atcattagca tgaaccaccc agagtggccc aagactccaa gatcagctac  23760
caggcaggat attccaaggg cttagagatg aatgcccagg agctgaggat aaagggcccg  23820
atctttcttt gggcaaggtt aagcctttac tgcatagcag accacacaga agggtgtggg  23880
ccaccagaga attttggtaa aaatttggcc tctggccttg agcttctaaa tctctgtatc  23940
cgtcagatct ctgtggttac aagaaacagc cactgaccct ggtcaccaga ggctgcaatt  24000
caggccgcaa gcagctgcct ggggggtgtc caaggagcag agaaaactac tagatgtgaa  24060
```

cttgaagaag gttgtcagct gcagccactt tctgccagca tctgcagcca ctttctgcca 24120
gcatctgcag ccagcaagct gggactggca ggaaataacc cacaaaagaa gcaaatgcaa 24180
tttccaacac aagggggaag ggatgcaggg ggaggcagcg ctgcagttgc tcaggacacg 24240
ctcctatagg accaagatgg atgcgaccca agacccagga ggcccagctg ctcagtgcaa 24300
ctgacaagtt aaaaaggtct atgatcttga gggcagacag cagaattcct cttataaaga 24360
aaactgtttg ggaaaatacg ttgagggaga gaagaccttg ggccaagatg ctaaatggga 24420
atgcaaagct tgagctgctc tgcaagagaa aataagcagg acagaggatt tgctctggac 24480
agagatggaa gagccgggaa cagagaagtg tggggaagag ataggaacca gcaggatggc 24540
aggggcaaag ggctcaaggg tgaggaggcc agtgggaccc cacagagttg gggagataaa 24600
ggaacattgg ttgctttggt ggcacgtaag ctccttgtct gtctccagca cccagaatct 24660
cattaaagct tatttattgt acctccagcg gctgtgtgca atggggtctt ttgtggaaat 24720
caaggagcag acaggtttca tgtgtactgt caccacgtgg gatggaacca gaggcatgga 24780
agcaagacgc taaatgaaga gggccataag ggctgggatt cccaggcacc ttaggaacag 24840
cttgtctttt ttttttcct ctccaaaaaa aatgtttaag ggacggtgtc tcctgtcacc 24900
caggctggag tgcaatggca cgatcatagc tcattgcagc ctctaactcc ggggctcaag 24960
caatcctccc acctcagcct accaagtagc tgtgaccaca gctgcccctc accatgctaa 25020
gctaattttt ttaattagat agtacataaa cgtcccaaaa ttagaagata aaaagacatg 25080
agggatccat tctaatttgt gtttggagtg taatggtcca gctccattct tctgcacatg 25140
gatatccagt tttacacaac actgtgaatg taatgaatgc cactgaatca tacactcaaa 25200
aatagctaaa atggcaaatt gtctgttatc tctttttaac caccattttt gaaaattaat 25260
tataccaaaa aaccattgaa tagtgcactt tatttattta tttatttgtt tatttattta 25320
tttattttag aaataagagt ctcactttgt tgcccaggct ggagtgcagt ggcgtgatca 25380
tggctcattg cagcctcgac ctgctgggct cgggctatcc ttccatctca gcctcccgag 25440
tagctgggac tataggtggg cgccacccca cctggctaaa tctcttttta acttttgtag 25500
agataggcat ctcgctatgt tgcctaggct gggctggaac tcctgggctc aagtgctcct 25560
cctgccttgg cctcccaaag cgctaggatt acagatgtga gccaccgcgc ccaccctgaa 25620
ccttactttt tttgctcagt ttctggtaat tcagagaatg cctcctgagt tgttctacac 25680
ccacctcata ttccatggga gggctgtaca gggctttttt aacgaggcct ctaaggacag 25740
gcatttgtat cctttccagc ctttcactat tacaatgttg tagtgaataa ctttacacac 25800
tgtcatttat tttacttttt ttttttttta ttttagagaa aggaatcttg ccatcttgcc 25860
caggctggtc tcaaattcct gggcccaaac aatcctcccg ccttggcctc ctaaagtact 25920
gggatttata ggcataagcc accgtgcctg gccaatgcac actgtcattt agctcatgtt 25980
aacacctgag tgtaggacac actcctggag gtggaattgc tgggccaaag agtatgtttc 26040
ttgtcattgt gatagatatt gacaaatgaa ccctcacaga agttgtgctg agttctgttc 26100
ccaccagcga cgtaggcgat gaccttttc tggagggagg gggcatcctt ggagtccaca 26160
gagccaggaa tggagagtgg gcccagaatt ttggtatagg tgttgtataa acttatagta 26220
aggttaagaa aaccgcaact atccttatca gagacttggc ggggggcagg gtatgatgga 26280
gatcataagg aggctaaaac actccacacc ctccctctgc attgctcctg cacgggagtc 26340
gggaatcttt tcaggttgat acgatctcac cttgaggagc tgtgaggtcc cagaagcctc 26400

```
tgggttgcag attgcttggg gtgaaaatgt ctgtgctact gaaatctaac tttttacaaa  26460
aaattacggg ctgggcgcag tggctcacgc ctgtaatccc agcactttgg gaggctgcag  26520
cgggtggatc acttgaggta aggagttcaa gaccagacca tagtgaaacc gtgtctctac  26580
aaaaaaaatt agccaggtgt ggtggtgcat gcttgtaatc ccagctactc agaaggctga  26640
ggtgggagaa tcccttgaac ccgggaagtg gaggctggag taaaccatga tcgagttact  26700
gcactccagc ctgggtgaca agagtgagac tctgtctcca aaaaaaaaaa aaaaaaaaaa  26760
aaaactggat tgcctggctc tactccgggc acagcatgca ggcccagttc tgctgctctg  26820
ctgtttgttc tgctttcctc cacatattgg catcaccctc tggtgccaag atggctgctg  26880
cattccaggc atcacatcca gactcagacc cagagaagct gcccatccct acctgggtga  26940
gcctttgtag gaacgagaaa ccgcatccag cagcagaaac ctcacccagc agcgtctttt  27000
ccggtctcat tcaccagcgc cgcccaccgc tcaaccaatc cctggccaaa agaatgggac  27060
cgcctggaag gctggaccaa acaggacctg ccctctgggg ctggggagag gcccagatga  27120
aggctgcagg acaggatgga ctcctagacc tctgttacca gcagtgacta cctctgtctg  27180
ggtggttgga acatgtttga attttattct aagtactgtc tacaagttct gcaataaacc  27240
ttgactcttc ttttaataat gcaaaaggaa tcgaagtgat tgtttgaaag ggagaggaag  27300
aaagagagag ggagggaggg aagaatggag ggaggcaggg aaggagacag agagagtaga  27360
atccagccac cggaaaatcc agaatagctg gctttgctta atccatgcct ggaaataact  27420
gctgggtttg caacaacttc tctcccggag acagaccaag gaaactacaa aactgcagga  27480
aggattgaag ggccgggcac agtggctcac gcctgtaatc ccaacacttt gggaggccga  27540
ggtggattgg atcacctgag atcaggagtt cgagaccagc ctggccaaca tggtgaaacc  27600
tcgtctctgc tagaaataca aaaataagcc gggcgtggtg gcgtgcgcct atagtcccag  27660
ctactcggga ggctgaggca agagaatcgc ttgaacctgg gaggtggagg ttgcagtgag  27720
ctgagatcgt gccactgcac tccagcttgg gcgacagagt gagaatctgt caggtggatt  27780
ctgagggtac tctgacccca cgaacccagc atgaaatctt ccaggcatta aggaacattg  27840
aggatgtgga ggattggaaa tccctccagg gaaaatacac ttctcttgag cagggtcacg  27900
aggggtgggg gcaatgtggg aggtggggca aatccaaaga caaggtcaac agcaataata  27960
ataataacaa tgacaggcat ttgttgcttg ttggctgggc ctcttgcata cagttctccc  28020
aacatccctg tgaggtggtg atgcttatcc ccattctcca ggggaggagg ctgaggccca  28080
gagaggtgaa gtcgtgtgcc acaaaatacc ccagccatat ggtggtagaa ccaagttttc  28140
agccagactc accagctcac agcagagctg ccctggactc tacagccatt cagtgtatag  28200
ctgggccact ccatcattca aggcagttca acgtcaagat tcctgatttg cctcaacctg  28260
gggcctctag aagataccat cacccccaac aagctgaaga cgtgtgtccg gaacactcag  28320
acacacacaa agtgctatgg atacaccaca ccccgaccta gctgtctctt cctgatggac  28380
ctcactgggt agaaatgcct ggcaccgcct gcctcagatc cctaggtcag ctctcactcc  28440
ccaatagaag tttctgagat gatgatgaaa acgttctcca tctgtgctgt ccaatggagt  28500
agccactgat cacttgaggc tagtgagcac ttgaaggtgg ctagtttgag gaactgcatt  28560
ttttaatgca tttaatttta gttactttga atatatatac acatatatac atttatatat  28620
acatattcat acacatacat tttacatata ttttatatgt atatgtaata tatatataaa  28680
ttatatatgt atatattttt atatataaat atatattata tatttataaa tatataaata  28740
tataatatat attatataga tatataaata taaatatata ttatatatat aaatatataa  28800
```

tatatattat ataaatatat ataaattata tatttatata tataatatat aaattatata 28860
aattatatat atttatatat aatatataaa tatatataaa ttatataatt tatatattat 28920
atataaatta tatattttat atataatata tacaatatat ataaattata tataatatat 28980
aaatatatat aaattatata taatatataa aatatatata aattatatat aatatataaa 29040
atatatataa attatataaa tctatataaa tatatactat attataaata tagtatatat 29100
ttatatagat ttatattatt tatatagtat atattatata tttatatgtt tatgtatata 29160
taaatatata atatataaat atatttatat attatatatt tatataatat tttatataat 29220
atgttatata tttttatata atatattata tatatttata t 29261

<210> SEQ ID NO 4
<211> LENGTH: 29221
<212> TYPE: DNA
<213> ORGANISM: Artificial Sequence
<220> FEATURE:
<223> OTHER INFORMATION: modified gene

<400> SEQUENCE: 4
aataaataac tttttagacc atatatttct tttttttttt tttttttttt tgagacagag 60
tctcactctg ttgcccagac tggaatgcag tggcatgacg ttgactcact gtaacctcca 120
cctcaagtga ttcagcctcc caagtagctg ggattacagg tgtgcacgac taccacccag 180
ctaatttttg tgtttttagt acagatgggg tttcaccatg ttggccaggc tggtcttgaa 240
ctcctgacct caaaagtgtg ggggaaagaa agagagatca gactgttact gtgtctatgt 300
agaaaaagga agacataaga aactccattt tgatctgtac taagaaaaat tcttctgcct 360
tgagatgctg ttaatctgta accctagccc caaccctgtg ctcgcagaaa cgtgtgctgt 420
attgactcaa ggtttaatgg atttagggct gtgcaggatg tgctttggta aaaatgtgtt 480
tgcaggcagt atgcttggta aaagtcattg ccattctcca gtctcaagta accagggaca 540
ccatacactg cggaaggcag cagggacctc tgcccaagaa aacctgggta ttgtccaaga 600
tttcccccac tgagacagcc tgagagatgg cctcgtggga agggaaagac ctgaccgtcc 660
cccagcccga cacccataaa aggtctgtgc tgaggaggat tagtgaaaga ggaaggcctc 720
tctgcagttg agataagagg agggcatctg tctgctgctc gtccctggga atggaatatc 780
tcggtgtaaa acccgatcgt acattctatt tactgagata ggagaaaact gccttatggc 840
tggaggtgag acacactggc agcaatactg ctctttactg cactgagata tttgtgtaaa 900
gtcaaacata aatctggcct acgtgcacat ccaggcacag ctcctttcct taaatttatc 960
tatgacaccg agtcctttgc tcacgttttc ctgctgaccc tctccccacc attaccctat 1020
agtcctgcca catccccctc accgagatag tagggatagt gatcaataaa tactgaggga 1080
actcagagac cagtgccggt gcaggtcctc acttgctgag caccggtccc ctgggcccac 1140
ttttcttcct ctatactttg tctctgtgtc ttatttcttt tctcagtctc tcgtctccac 1200
cttgtgagaa atactcagag gtgtggaggg gcaggccccc ttcaaaatga tccacccacc 1260
tcagcctccc aaagtgctgg gattacaggc atgagccacc atgcccagcc acatataact 1320
tatttctaaa taacttattt aactaacacc acatgatttt atgacccccct attttatgga 1380 tgagaaaaaa gaggcaagag aagcgatacc agttgcttag gattcccagc taccaattag 1440
tggaagcaga atttgaacca agggagtctc tggagccctc gttcccaatc tccttttctt 1500
cctctccatg tctttctttc tccccctgct cccaggcctc ctacatcaca cccttctgga 1560

```
caaagcttca catctgacat tttctttttt ggggtggaca gagtcttact ctgtcaccga   1620
ggctggaggg ccgtggcgca atcatggctc atggcagcct caaactcctg ggcttgaggg   1680
atcctccagc ctcagcctcc caagtagctg ggactatggg catgtgccac cacacctggc   1740
taattttta atttttgta gaaatacagg gggtgggggc atatctgaaa attttaaacc   1800
ttccctgact gccgtgagca tttctgggta gaagccactc cacgacctta ctttgctggc   1860
atgagtgctg gacagcaatt tggcaacatc ctctagacca caaatgtgca tggcctttgg   1920
cccagcaaat cagcttctgg gaataaatat gacagatact gttacataca tgggaaatgc   1980
catggacatg atgacccagg gaagcacagt ttgcaagtac aaaagggctg gaaacaccca   2040
aaaagcccat cccctgaaga cagtttcaaa aatgacggtg cattcatgta atggaatagt   2100
acacatttgt gaatgaatga atgaggtagc tcaatatatc tgcctatggg aaaatcacca   2160
agatatgttg ctaagtgaaa aacagaaaga tacagaataa tgctaccatt ttattttta   2220
atgggagagg gaagaataag gaaatggatt catatttgct taattacaca agcttcctga   2280
tgatcctttt ggatccagaa gtttgaaaac cacagcatca agaggatgcc cattgggcat   2340
ggtggctcac gcctgtaatc ccagcacttt gggaggctga ggagggtgga tcgcctaagt   2400
tcaggagttc gagaccagcc tggccaacat ggtgaaaccc catctctact aaaaacacaa   2460
aaaaattagc tgggtatggt ggtgcaggcc tgtaattcca gctacttggg aggctgaggc   2520
gcaagaatca cttaagcctg ggaggcggag gctgccgtga gccgagatca cgccattgca   2580
ctccagcttg ggagacagag caagactgtc tcaaaacaaa caaacacaca caaaaaataa   2640
gatgcccatt ggagatctcc attcactatt ttatcagatg atatttcagc acttgagtga   2700
agaaaatgtc tacaactggt ccaaacactc aaggaattta gactcttgac agagaaacac   2760
acagaagcaa gcagatatgc cccgaaccaa acttgctttt tcttctaagc ctgcttcttc   2820
ggagcagcct ctgaccctcc agggccctga gaggagtccc tggagccaca ggagcttggg   2880
agcccagaga agtgggggaa tcccagatgg tgacagcatc atccagagga ggaacataac   2940
gatggccaca gattcccaat ttggaaataa ctcagcaaaa caacactgac agaaaattca   3000
gagatttcca agagactagc ctccctgttt ccatttagaa attcacctac atacatccag   3060
ggtgagagac cccaagcatc agatgtgtca tacacaagca tcagatccaa gttagagagg   3120
gcacccgggg acagaaacct ccaagccagc caaaagccaa aggaaggatt ttacagaaag   3180
atacaggaat gtggggccag gcacagtggc tcatgcctgc aatcctagca ctttgggagg   3240
ccgaggtggg aggatcgctt gcggccagga attcaaggcc agcctgagca acatagcgag   3300
atcctatctc tacaacaaat ttaaaaacta gctgggtgtg atcacatatg cctgtggtcc   3360
caactaccca ggaggctgag gcaggagttg agcccaggag gtggaggctg caatgagcaa   3420
tgatggcgcc acttcactcc agcctcagtg aaatagtgag accctgtcta aaaataataa   3480
taaaaataaa aaacatataa agatgtcaga gcacagggac cagagctgtt agtcggcctc   3540
atggagaccc tggccaggac agccacctct ggggaccagg aagtctctca gtttctgtct   3600
ctgagggttt ggctctctga gtctctctgt cacctctcat ttctctctca tctccctctg   3660
tctatgctgt gtctctatct ctttcaatct ctctgtctct gtctcccagc ccttatctct   3720
gagtgtgtct gtttctctct catttctctc tctctctctc tctctttctc tctctctctt   3780
tctctctctc tctttctctc tccccccctcc ctcctcccct ctccctactg caggctggtc   3840
cataaccctt atcttcccca gacctgatgg agttctggta ttaatctgtt tatggtctgt   3900
ttccctccac tagaacacgg tcttcattaa aggcagagat ttttgtctgt cttattttct   3960
```

```
gctgtatacc cagtgcctgg gatactggct ggatcaataa atatatgctg aatgaagaat   4020
gaatgaatga ccattctcat gaacattatt atttgatgcc aactgtaaag caacaataat   4080
aataattgtc actgccactg ctgctattgt tggtatatca gctttttatt tagtacaaac   4140
tatatccccg aaattgagct aggcagtttc ttgtttaagt tttacagacc acgctgtgag   4200
gtaagtactg ttagtatgcc cttttttctt tctttttgag acagagtctc actctgtcgc   4260
ccaggctgga gtgcagaggc ccgatcttgg ctcactgcaa cctctgcctc ccgggtacaa   4320
gtgattttcc tgtcttagcc tccccagtag ctgggattac aggcatgtgc caccatgccg   4380
gctaattttt gtatttttag taaagatggg tttttgccat gttggccagg ctggtcttga   4440
actcctggac ctctggtgat cctcctgcct cggcctccca aagtgctggg attacaggcg   4500
tcagccactg cgcttgctcc cccagccccc aaactttttt tttttttttt gagacaggtc   4560
tggctctgcc acccaagctg tagtgtagtg gcgcaatggt agctcactga agcctctaac   4620
tcctgggttc acacagtcct cctgcctcag cctcccaaaa tgctggaatt caggcctgag   4680
ccaccgcgcc ctactatgcc catttttcag ataaagaatc tgagggccct cgaggagaaa   4740
ccacttgccc aacatgagcc ctggtcttgt ctgaccccaa agcccatggg aagtttaggc   4800
tgcgtggaag gacagcctgg tgggctcagg atctgtccca tcacgagttg gaacctcagc   4860
tctgccactc ggcaaccgcg agccgttagt aagttgctga atctctccgt gtgcctccgt   4920
ttcctcacct ggaatgtggg cgacctcaca caggaagccg cctcttctag tgggcaccga   4980
cggagcgagc gcgcgtctgc agcgggactg agcgccggga gagacctgcg caggcgcagg   5040
cgcgcgggga gggccagcct gggtggccca ccccgcgcct ggcgggactg gccgccaact   5100
cccctccgct ccagtcactt gtctggagct tgaagaagtg ggtattcccc ttcccacccc   5160
aggcactgga ggagcggccc cccggggatt ccaggacctg agctccggga gctggactcg   5220
cagcgaccgc ggcagagcga gcgggcgccg ggaagcgagg agacgcccgc gggaggccca   5280
gctgctcgga gcaactggca tggcccgagc catggccgcc gcgtggccgc tgctgctggt   5340
ggcgctactg gtgctgtcct ggccaccccc aggaaccggt gagtgacccc cgcgcagtcc   5400
ggtggcccct gtctggctcc cagctccgca tccaggccgg gtactcgccc ccttgggttc   5460
ccgaagatga cggccccgcc cggcgccacc caccccccat ctctgccccg gggttggaag   5520
gaacacggtg cgagggtgcg agggcaggac cctcctcttg gccacccgga gagcggtcgg   5580
agttgggtac agaaattcct cgaaattggc agcaacacgg gtcgggcaca agaccctcct   5640
ctgggcccct cggaaagggg atggagttgg gtgaggaaat ttcccaaaaa ggcaagtgaa   5700
tcccggaaaa tcagcagatg gtgacgcatg ccggattacc ttacccaggt tcctgctcag   5760
catacccagg ccataaccca gcagcgtgct ggcaggctgg gtctggacgg aggggatggt   5820
tgatgttggg gaggaggaca gtgggtgaca cttgacacca ttacccctct gacccccaat   5880
gtctgactcc aggggcctgg ccattcattc attctttcat tctttttttt tttttttga    5940
gacagtctca ctccatcacc caggctggag tgcagtgtcc tgctctcggc tcactgcagc   6000
ctcctcctcc cgagttcaag cgattctcct gcttcagcct cccgagtagc tcggattaca   6060
gacatgtgcc actatgcctg gctaatattt ttgtattttt agtagataca ggatttcacc   6120
atgttggcca ggctggtctc aaactcctga taaatatata tattatatat tattattata   6180
tattacatat tatagtaata tataataaaa atatataata tatattatag taatatataa   6240
tatataataa aatatataat atatattata gtaatatata atatataata aaatatataa   6300
```

```
tatatattat agtaatatat aatatattat aatatattat atatattatt ataatatata   6360
atatgtatat tatatattat atatattatt ataatatata atatgtatat tatatattat   6420
atatattatt ataatatata atatgtatta tgtattatat aattgataat atataataat   6480
atatttctta ataaatatat attaaatata ttatatattt ataacatata ttatttatat   6540
aataaataat atatatttta ttatacattt aaagagtaaa tagataacat attttattat   6600
ttatttatat gttttgtgta tatatatata tatatatata tatatatagt gcgtgtgtgc   6660
gtgtatgtgt gtgtgtgtat gagagagaca aggtcttgct ttgttgccca ggctggagtg   6720
cagtggtaca atcccggctc attgcaaact cgacttccca ggctcaagcg atcctctcac   6780
tgtggcttct ggagtagctg ggattatagg tgctcacctg gctaattttt tttgtatttt   6840
tggtagagac agggtttcgc tatgctgccc aggctggttg cagccaagca cagtggctca   6900
tgcctgtaat cccaacactt tgggaggctg tggtgggagg atcacttgag cttaggaatt   6960
caaaaccagc ctgggcaata tggcaagacc ccatctctac aaaaataatt aactaaataa   7020
aaatttaaaa ataaaaaaga atgcatagga ccatgtttat tagtgtcaat aagcgctgtc   7080
acattttgag gacctactat gtgctagggc ccttagcaga aagattttta tataggacct   7140
gggggattag aggtcagtct ctgaccgccc aagttcaaat cccacctctg ccactaaacc   7200
tctgtatgac ttggaggaca ctatactctg tgtcagtttc cctgtctgta aaatgatgtt   7260
aacagtagtg cttgcctcag gggggctatt tgaggattaa atgccaagat atatgtgaag   7320
cacccagaat agcccctgat ctgtgtcagc accctgtgag tgtccactgt tctaagtctc   7380
attttacaaa ctaggaaaaa gaatcagaga ggttaagtaa ccggcctgaa gctccacagc   7440
agaaaactga agggacccaa aactcctggg ctataattgc cttcctctcg tgcctcaatc   7500
ccccacattc ttccaaccag gacccaccca gagtaataat gcagtgtttc atggatttga   7560
agacccaaga tttctccccg ttttctacat tggggttatt ctaaccccta atggcaagtt   7620
gtgctataaa tgacaacagt catggtatgt gaaacctacg acactggtgc gatgaaaaag   7680
ttctgggcca ggtgcggtgg ctcatacctg taatcccagc actttgggag gccgtagtgg   7740
gaggatcact tgaggtcagg agttcaagac cagcctggcc aacatggtga aaccccatct   7800
ctgctaaaaa caaaaataca aaaaattagc caggtgtggt ggtgggagcc tgtcatccca   7860
gctacgcgga aagctgaggc aggagaaccg cttgaacccc agaggcagag cttgcagtga   7920
gcagagatcg cgccactgca ctccccctgg gcgacagaga gagactccgt ctcaaaaaaa   7980
aaagagaaga aaagaaaaag ttctggcgct atatagtagt aacggttgca caatatcgtg   8040
aaatgtacat agtgccactg aactgtatgc tttaaatgac ttaaatggta aatttagttt   8100
tttaaccaca atatttacca caattttttta aatcagtgat gttgagattc agggaaatac   8160
ggtaataata gaagaaatac ggtaataaat agccaaagtg aaggagcacg gccaagttgc   8220
agaccatccc agacgccctt accctcctcg cctgccatgg ccccaactag tgccccagtt   8280
ccccctcccc ccacacccca cggtccaccg gggatccagg gccccagcgt gcaagtgcac   8340
gcccaggtgc ccgggctcct ggagcccctc cctatctagt ccaagaacgc cccgggtctg   8400
acaccttctc ttcggttctc cgcaggggac gtcgtcgtgc aggcgcccac ccaggtctac   8460
aggtgcccaa catggaggtg acgcatgtgt cacagctgac ttgggcgcgg catggtgaat   8520
ctggcagcat ggccgtcttc caccaaacgc agggccccag ctattcggag tccaaacggc   8580
tggaattcgt ggcagccaga ctgggcgcgg agctgcggaa tgcctcgctg aggatgttcg   8640
ggttgcgcgt agaggatgaa ggcaactaca cctgcctgtt cgtcacgttc ccgcagggca   8700
```

```
gcaggagcgt ggatatctgg ctccgagtgc ttggtgagca gggggttttg gggaggctga   8760
atgaaaggca gagacttggt gggaggatca gggaagttgg caaagagcgg ggaggcctgg   8820
gagggaggga gattccctcc acagcagatc ccctggggac aaaaggaggg ggcagcgcaa   8880
tgatgtgggg tggggtgggg ggaggtgagt ggggggaggg gctgcagggc aggaagaaag   8940
cagagatctc agggagtaag gacccccaag cctgggatca gaaagccctg agggaggagg   9000
aggggtatat tggaaaggga gctgggaggg gactgggaag gaagggagga ggcctgggtg   9060
gcctcttctg ggtccctcct ttcctcatct gtaaaagggt tggtgacaac agcatcaccc   9120
ttggaaagct gtcctgagtg tcatcactgc ctaggaaaga gtctgtctgc cccccttggac  9180
tgtgtaccca tgagggcaga accggggcta ttttgatcac tgctgggccc cagcactttc   9240
caccaaacaa tatttattga gcacttatta tgtgccattc taagagcttt acctgcatat   9300
tctaattgcc tgtgattcca tcattatcac ctgttgacag acaaggaaac tgaggcacag   9360
acttgcccaa gaccaaagct gcagccttag ggcagcggcg cttcaccgct ggcccatgtg   9420
agccccttag agctgtcggt tactgttact ttatctggtg aagaaggaga aagttgaaac   9480
agacagacag gaaagcaagg atcctgatac ccaaaagagg aggggatcat gctttcattt   9540
tcatgagctc catgaagcct tcctcttgga acttgagcaa gaagtctctg tgcctcagtt   9600
tcctcatctg tgggataggg atcaccatga ggattcaaaa aaactgaccc tttttttttt   9660
tttgagatag tttagttctg tcgcccaggc tggagtgcag tggtgtgatc atagtaggtc   9720
ctcactgcag cctggaactc ctgggctcaa gggatgttcc taccctccct gtagctggaa   9780
ttacaggaat gtgccaccat gcccaacttg ttttctgttt tgttttgttt tgttttgttt   9840
tcttttcttt ttaagcttat gtgccaagaa ctattccaag cctgtgcatg agaaactcat   9900
gaaatgtcaa gggcttggaa ctgtgcctag cacacaacac ccaaccaaag gcagctgttg   9960
tcactccagc aagcctggga ttctgggtat catggtttag gatgagggta aaacagaaac  10020
agtgagtcaa gttaaggaga aatcttcggt aaataatata ggtaatgatg gggaaggaag  10080
ttccaggttt gggaatcacc aggatgatga ttaagagatg gtcaaggtgg ttttggagtc  10140
agacagactt tatgtgaaag cccagctctg ctgcttacag ctgtgtgacc atgggcaagt  10200
cacttccctt ctcaacttca gggctcaggc ttcctctcct ccactgagcc ccagaccagg  10260
ataacccccct ttgggtttcc cctttccagc cctgccctct ccgagtcatc actgcctagg  10320
aaagagtccg tctgcccccct tggactgtgt acccatgagg gcagaaccag ggctattttg  10380
gtcactgctg ggctccagca ctttccacca aacaatattt attgagcgct tattatatac  10440
cattctaaga gctttacctg catattctca ttgcctgtga tcccatcact atcccctgtc  10500
aacagacaag gaaactgagg cacagacttg cccaagacca cacagctgct cagggacaca  10560
gctgggattt aaaccatgcc attctgtatc tttttttttt tttttttttt gagacagaat  10620
ctcactctgt cgcccaggct ggagagcagt gacacaatct cagctcactg caacctccgc  10680
ctcccgagtt caagcaattc tctggtctca gcctcccaag taactgggat tactggcgtg  10740
tgccaccata ccctggctaa tttttaatag agacagtttc tccatgttgg ccaggctggt  10800
ctcgaactcc tgaccccaag tgatccaccc acctcagccc cccaaagttc tgggattata  10860
ggcgtgagcc accccgccca gcaaccatgc catcctgtac ccttaatgaa tgccccccttc  10920
tgccacggag gggttcattg aatgacttgt tgcttttgtt cctcttccca gccaagcccc  10980
agaacacaga cctgggcggg atgcccaata cgagccaggt gccagggttc ctgtctggca  11040
```

```
cagtcactgt caccagcctc tggatattgg tgccctcaag ccaggtggac ggcaagaatg  11100
tgacctgcaa ggtggagcac gagagctttg agaagcctca gctgctgact gtgaacctca  11160
ccgtgtactg tgagtgtgcc caagtcagcg atggcaagaa cccctgccgg gctgccccca  11220
ccactgtcta cactgactcc ccaaggcact gtaggcattg cttccatcat ctgcaccggc  11280
tcccctgact cctgtctaca cgacccaccc ccattgtctg caccagctcc cctgggccgt  11340
aaacaacact gtccctattg tctacaccag tttacttggg ccatagtcaa tgctggtacc  11400
cagactgtct gccctggctc ctctagcggc tgtctgcacg gatacctgac actctgttga  11460
ctcccttgag cacagtctac actgccccta aactgcctac acccatttcc ccaggcaagt  11520
atccacaatg accctcccca cattgctaca ctggttcttc tggccacgat caacactgcc  11580
tcccttattg tctacaccca ctcccttgtc cttttctttc tttccttttt tttttttttt  11640
ttttgaaata gagtctcact ctgttaccca ggctgcagta cagtggcatg ttctcggctc  11700
actgtaacct ctgcctccca aattcaggtg gttctcctac ctcagcctcc caaatagctg  11760
ggattaaagg tgcacaccac cacacctggc taatttttgt atttttagta gagacagggt  11820
ttcatcatgt tggccaggct ggtttcgaac tcctgacctc aggtgatcgg cctgcctcag  11880
cctcccaaag tatgctggaa ttataggcat gagccactgt gcccggcttt ttgttttgtt  11940
ttgtttttcc tttggacagg gtctcgctct gtcacccagg ctggagtgta ggggcatgat  12000
catggttcct acagcctcac ccttccaggc tcaagcaatc cttctccctc agcctcccaa  12060
gtaactggga ctacaggtgc agccaccatg cccggctaat tttacagttt ttttctagag  12120
agagttttgc tgtgttgccc aggctggtct caaactccta ggcttaagtg atcctcccgc  12180
ctcagtctcc cgaagtgctg agattacagg cgtgagccac tgcacctggc cccttgtcca  12240
ttttctacac tgccttacca ttgtctacac tggctctcct gggccacaga cagcactaac  12300
cccattgtct acaccaccta ttttggccac cagctgtggg gtgttttcac tgtctcccat  12360
agtgtctaca ctggctccta tgaccactgt ctatgtaaac accccacttt ttctacactg  12420
gttctcctag gcactctcta aagtgccccc tgacactgtc tacactgact ccctggagaa  12480
ctgtctgcat tcacctccca cattgtatcg accagttccc ctgagccacg atcaactgtc  12540
tccgccgggt gctagttgca ttgatcttct cacattgttt gtgctggctc ccctaagcag  12600
tgtctgcaga gtcccccagt gtagtctcca tgttcctctg cccaatattg tctacactgg  12660
ctcatctaca ggctatccag tctcacccca catcaccaca ctggcctcct tgtgttctgt  12720
ctgcacagcc ccctgacagc atctgtcctg attctcctgc acagcgttac ctccaccagc  12780
tccctcatgg catcatcgac attgacaccc acacatttat ctccactgac agccccagga  12840
ctctctaacc agtgctgtct aacagaaata gcatgcaagc tgcatatagg attttaaatt  12900
ctccagcggc caccccatta aaaaattaaa agaaagaggc caggcacggt ggctcacgcc  12960
tgtaatccca gcactttggg aggccgaggc aggtggatca cctgaggtca ggcattcaag  13020
accagcctga tcaatgtggt gaaactctgt cttcactaaa aaatacaaaa attagccagg  13080
cacggtggcg ggtgcctgta atcccagcta ctcgggagac tgaggcagga gaatcacttg  13140
aacctgggag gcggagattg caatgagcga gattacgcca ttgcactcca gcctgggcag  13200
cagagcaaaa ctccatctca aaaacaagaa aagaaagaga tgaaatttat ttgtttattt  13260
atttatctat ttatttattt gagacggggt cttactctgt cacccagact ggagtgcagt  13320
ggcacagctc cctgcagcct caacctcctg ggcttaagtg atcctcccac ctcagcctca  13380
gtctcctgag tagctgggac tacaggcgtg tgacaccatg cctagctaat tttgttttt  13440
```

gtttttgttt ttgttttttt gttttgtgat gaagtcttgc tctgtcaccc aggctagagt 13500
gcagtggcac gatctcaact cactgcagcc tccgcctctc gggttcaagt gattctcctg 13560
cctcagcctc ccgagtagct gggattacaa gccctggcca cagtgcccag ctaatttttg 13620
tatttgtggt agagacggga tttcaccatg ttggccaggc tggtctcaaa ctcctgacct 13680
cgtgatccac ccaccttggc ctcccaaatt gctgggatta cagacgtgag ccaccgcacc 13740
cggcctattt ttattttttc tggagacagg atctccctat gttgcccagg ctggtctcaa 13800
actcctgggc tcaagtgatc ctcctgcctc aacctcccaa ggtactggga ttacaggcat 13860
gagccactgt gcctggccaa aattaatttt taataattgc ctttacttaa cccaatatac 13920
ctaaaatatt atttcaactt gtaattgttt ttttaaaatt attcttgaga tctttcccat 13980
ttattttgtc ctagtaaagc ctttgaaatc tggtgtgtat ttcggcctgg ctatatttcg 14040
agtgctcagt agtcacatgt ggccagtagg tgccatattg gacagcacag atctagacta 14100
agctcccaca tcatctacac tggctcatcc aaatactgtc tacacacata cacagagcct 14160
gtcttaattt cgtcagctcc cggggacaca ctgtatatgt gggggtgatc tcaccccccac 14220 caccacattt tcaacactgg cccgacaata tagcatctgc tgtaatattc caacaccctg 14280
tctacactga acccatcagt aatatccaca caagctcttc tagacatcat tcatactgtt 14340
cctcccacca ttgtctatac tgcttactcc ccgccaggca attggtacac agattccctc 14400
aggtactgtc tatactggag tccctcaaca ctgtcactgg gtctgagcga ggaggagatc 14460
tacactgact cctacccctc gcccccgaat aaaaccctgt cccattggcc tgcccccaag 14520
gacattgaaa ggtcttcgct gtcaatcacg tatgggatgg ctgagcagca gcctagagca 14580
gggttatctg ggactctttc ctgcaggact tgtcagaacc ttgaatacac tgctgtgtgt 14640
tgtgagtggt cattgcctat gagtgagaaa aggaggaggc attttcctgc aggacaccca 14700
agacatgcct ggtccaggct acccaggaaa gctagtggag aaaagcagct cctcagaagc 14760
cttctccatg tccccactga ccaaggactc ctaggcttct gctctctgtg gcaccccatc 14820
tacctagact cctcctaggc ctctccagct cccgctgttt tccaaatatc cccgggcctt 14880
ttcctgcagt gtcgtgaatc ccgcgtagcc ccaggccccc caaagcctcc cagtctctga 14940
acctctgtat ccatttcctg cagacccccc agaggtatcc atctctggct atgataacaa 15000
ctggtacctt ggccagaatg aggccaccct gacctgcgat gctcgcagca acccagagcc 15060
cacaggctat aattggagca cgtgagtcct gggtctcagg gaggaggggc tgggggtctg 15120
gatttctagc actgagggag gaggggctgg gggcctggac tcctgggact gagggagaag 15180
gggctggggg cccggacccc tgggtctgag ggacgagagg ctgggagccc ggactcctgg 15240
gtctgaggga agaggggctg ggggtctgga cccctgggac tgagagagga ggggctgggc 15300
ctggacccct gggtctgagg gaggaggggc tggggggtct ggacccctgg gtctgaggga 15360
ggagaagctg ggagcctgga cccctgggtc tgaggcagga cagactgggg cctggactcc 15420
tggtctaaga gaggagggag attcagaaaa gagaaaaaga ggaggttgac ttcgggcccc 15480
cagtgggggg catctctgtt ttgacatctc tgttttgcgg ttgaggcgtt tagcaggtgg 15540
ttgaatcctg gctggtggat gcacctgctt tttggggtgt gcctgctctg tgcccggtac 15600
ttcccccgaa tcccatgtga ccccatgctg tgcacagtca gcagctgttg ccctgcccag 15660
gttaaagacc agccacgaga gggcagaagc ggcccttgaa tcagcgctcg gctccaaagc 15720
tggtcctccg cctcttggcc aagcttgtct aacctgcagg ccacatcatt tgtaaacttt 15780

```
cttaaaacat tatgagactt tttttttgcg aatttttta gctcattagc tattgttagt  15840
gttagtgtat tttatgtatg gcccaggaca gttcttcttc ttccaatgtg gcccggggaa  15900
gccaaaagat tggacacccc cactctagac tgtaaccacc tcaccgtcac cttgtgtaac  15960
ctacttggtt atctctggat ggagcaagta ctatatatcc ccattgtcta gatgagaaag  16020
ttgaggctca cagcaataag atttccccag attcacactg aggctgagat caagagcaag  16080
gtaagaaaaa ggcaaagaga taatacataa ttttataata cataatttta cataaattac  16140
ataattttac tgaaccgccc ttttttttta aagaaggggc tctgttgccg aggctggagt  16200
gcagtggcgt gatcatagct cactgcagcc tggacctccc tgggctcagg tgatcctccc  16260
acctcagcct cctgagtagc tgggactaca ggcacacgcc accacactca gctaattttg  16320
ttgtattttt tttgcagaga cagggttttg ccacattgcc caggctggtc tgcaactcct  16380
gggctcaagc aatcaaccca cctcagcctc ctaaagtgct gggattacag gcgtgagcca  16440
cctcgcccag ccttaggtct ttttccttat tacaaaaata acttgtgtcc actgtagaaa  16500
tatcaaacaa tttagttatg agcaaaaaga agaaagtagt gcctatagtt caagtgtacc  16560
cagccacctc cagaaatacc cagtgacccc ttattataca tcctgtcttt tttctctctg  16620
tttctaaaca aagactggaa ttatgctgta catataattt tgaacctttt cgtctgtctt  16680
gtgaatacct ttccatgtca aagcacatag atccacaact ccattttccc ccacgttgta  16740
ttaggaagac tgtcaaacat acagaaaaat cataggaatt ttccagtgaa cacttaagat  16800
tccaccacgt ggattcccct gctaacattt tactgtgctt gctttatcac gtttctgtga  16860
ttccttcagt ccctctattc atccatcaat catattatgc atttcagagc acccccagct  16920
ctcctgcttt tttttttttt ttttttttt tgaggcaggg cctcactctg ttgctcaggc  16980
tgtagtgccg tggcacaatc acagctcact gcagccttga attcctgggc tcaagcgatc  17040
ctccagcttc agcctcccag atagctggga ctacaggcac acaccaccac gcctggctaa  17100
cctggcccct tttttagtgt tgctgggatt ccaccacttt aaaaaaaaaa ttcaaagaat  17160
agagacagga tctcactatg ttgcccaggc tggtcttgaa ctcctgtact caagcagtca  17220
tctcacctgg gcctcccaaa gggcagggaa gggattccaa catatgtgga tgtcatcagt  17280
tatttaacca gtccctagta gaggacacag atgtcatttt ccattttcaa ctctgcaaat  17340
gccatggtgg tgtccatccc cactggtcac ttgtcagcag ttgtccgtgg aaggaattgc  17400
cggtcaaagg ttttcaactg gtgtgatggt gcctttactg tcctgcctca aagcaccgca  17460
attcaggctc ttgagccaga tagctgcgtt tgcatcccag ctctgcggag cacccaaagc  17520
ctgatgcttc catctcctcc acctctgttc attaaaccag tgttccttga ctacttactg  17580
tgtgccgggt gcaattaacc aacatacgtt ggtcgataaa acagaccaaa tttcctcccc  17640
atatagagct tccattctag tggtgaaaga aacaagaagc aagataaagt gtgtagtgtg  17700
tgtgcaatgg tgataaatac catggagaag acaaagcaga gaagggaatg ggactgggcg  17760
ccatgactca tacctgtaat cccagcactt tgggaggcag agatgggagg atcacttgag  17820
gctaggagtt caagaccagc ctggccaaca tggcgaaacc ccatctctac caaaaaagat  17880
acaaaaattg gccgggtgtg gtggcatgca cctgtagtcc cagctactca ggaggctgag  17940
gtgggaagat tccatgcacc caggaggtgg aggttgcagt gagtcaagat ggtgccactg  18000
cactccagcc tgggtgacag agtgagacgc tgtctcaaaa aaataataat taaataaatt  18060
aaagagaagg ggatgggaag ggtgatcatc acagttgaaa tagggtggcc aagtgaggtg  18120
ttactaaggt gacatcccag cagaggcctg aaggagatga gggtgagctc tgcgggtgcc  18180
```

tagggggaaa gcattccagc agagggaaca gcatgggcaa acccatttct atccatcagt 18240
ccctgcataa gcaaacaccc tggacaccta actggagagt ttgaggacca acaaagaggc 18300
cactgtggat gcagaggcgg gagcaaaggg gagagtaatg gaaaacgtgg gcagaggtag 18360
caggggccag atcacgtggg gcctgtgaca ccagaagact tcggtttaac tctgagccag 18420
gctaggcccc cagagggtac tgagctgagg tatgggaact gacttagggt tcacaggcga 18480
cctctggtgg ccatgtgggg aacagacgag ggggcgaggg cagaaacgga gcccagcgtg 18540
gaggcggctg ctgggggccg ggatgcacag cgccagagca gggaggtacc gtggaagccc 18600
tgaggagagg tgggattctg gatggatctt aaggcggggc cgacatgatt ggctaatggg 18660
ttgggtgtgg gcatgagagg aagggaagag ttggggggcc tccagagttg ctctccgctt 18720
atgctataga gggcgtgagg gtttctgggc acgtagtgcg tgctcaatca ctgtcactcc 18780
ggacctgcag cagaggccac ctcctcacct ttctgtctct cccaggacca tgggtcccct 18840
gccacccttt gctgtggccc agggcgccca gctcctgatc cgtcctgtgg acaaaccaat 18900
caacacaact ttaatctgca acgtcaccaa tgccctagga gctcgccagg cagaactgac 18960
cgtccaggtc aaaggtgagg aactccctgg gtgggaagaa cagggaccaa aggaagaggt 19020
cgaggcaggg ttccctgtct aatgctctct ggctcccatc cttctcctaa gccttctcac 19080
aaaaggacca gtggggccag ctttactccc ctgttaactc catacctata tcactggtac 19140
cgttgttcag ctgcctggat acactccctc cacacacaca ggttgggata gatgtggaat 19200
ccctctctct cagggactca ggcctttcca aatatattag gcagacctct atcaattgca 19260
attgacagaa acacaaagta gtctaagcaa aaaaaaccaa acaaaacagg actttattga 19320
aaattcacct tcaggtatgg ttagatccag gggctccaac cttgtaaccc aggaactttt 19380
attttataca tctcttgtct ctgcttttcg ttatactggc tttattctca ggcaggctct 19440
gaagcaagat ggccctcggc agggacaggc tcacattcta ccagaatggc aacagcagga 19500
gaaaaaacat accactttca gtaactgtag ccatagtccc agggctggct ctcattggcc 19560
cagcttaggc cacagcccac ctatgaacca atcatagcag ccagggagaa tggaatattc 19620
tgattggcca ggcctgtgtc aaagtcccat tctgggcacc agagggtggg atccattcca 19680
cctgaattaa atagactgag gcagtggagt ggtggctccc taaggaaatt caagatgcca 19740
tttcaagaat gagggataaa ccccaagagt ttccttacct aaatacctgt ttccttctct 19800
ttcagaggga cctcccagtg agcactcagg catgtcccgt aacgccatca tcttcctggt 19860
tctgggaatc ctggtttttc tgatcctgct ggggatcggg atttatttct attggtccaa 19920
atgttcccgt gaggtccttt ggcactgtca tctgtgtccc tcgagtgagc atcaccagag 19980
ctgccgtaat tgagcaccta ctacgggctc tgtgctgagt ccttccagtg tgcctctcac 20040
tgaatcctca ccccactgcc atgaggtttc ccccatttga ctgatgaggg tgcagagcca 20100
gggagccttg ttcactggtt cattgattac atttacaaat attatttaca gagtgggaga 20160
agagcgtata gggtcttaat gccatggtag ggactttgga atttaattca ggtgatgtgg 20220
gagtccctgc cagatggatg gagggtgaaa taatgcttaa gccctcagcc ttactccatc 20280
tgccttgttc aggagtgact cctaggagga ggtggcagga actggcacct ctgatcctca 20340
gctctaaaag ggtctgatgc tttcacacct caagagattt gcacaggccg ttcccctgcc 20400
tggagcaccc tcccatggct ccttctggag aagtgtgcca gctcattctg taatcagagg 20460
aacgatgctt tgctgagcac tgtctacatg ccactttgta tgtataaccc cctcgatttt 20520
aatttttaat ttttttttatt atttatgtat ttatttattt atttttgaga caggctctca 20580
ctgtcgccca ggctggagtg cagtggtgcg atctcggctc actgtagcct tcacctccca 20640
ggttcaagcg attctcatgc ctcagcctcc caaggagcgg ggattacagg cacgcactac 20700
tatgcccagc aatttttgta tttttaggag agacagcgtt tcgccatgtt ggccaggctg 20760
gtctcaaacc cctggtctcc tgtgatccac ccgcctcagc ctcccaaagt gctgggatta 20820
caggcatgag ccaccacacc tggcctgtac aatctccttg aatgcccaca accacccagc 20880
aaagtggttc tcccgtgagc cccatgttac agaggaggaa gtatttgctt tgagagatga 20940
agttacctgc caatggtcaa acagctggac atggttgttg gggagaagaa gccagatctt 21000
tgactaccaa gcttttcctt caaccactaa acaaagctgc tcccttacaa cccaggcgga 21060
tactgcctcg tccaggaagc cctccctgac ccccaagcat gagccaagca tccactaggc 21120
tctcccactc cagccttgcc cattctgggt catcaccgtg ggggacttgt ttgtcatccc 21180
cagtggactg tgagccccaa gatagcagac ctgaggctgt cactgtcatg actgtgtccc 21240
caggaccgcc taccactggg ccgggcataa aagaggcact cgaggaagtg tttgctgagt 21300
gattcaatgt gtcagctcca gagccagact gcctgtatct gggccctaaa gctactgctt 21360
gattagtgat gtcaccatag gcaaatagct taagctgtat gactcagttt cctcatctgt 21420
aaaatggggt gatggtacct aataatacag tagagcactt aacacagtag gtggcacatg 21480
gtaagccaca tactgagtat gtatttgcta tgattgttat tgctattatt actattattg 21540
ttattattaa cataaactgc acaagagcag gctttttgtt tgtttgtttg tgttttgttt 21600
tgagacaaga tcttgctctg ttgcccagac tggagtagtg cagtgatgtg atcttggctc 21660
actgcagcct caacctccca ggctcaggtg attctcccac ctcagcctct cgagtagctg 21720
ggattatagg cgtgcactcc cacgcctggc taattttttta tatttttagt agagatggag 21780
tttcgttgtg ttgcccaagc tggtctcaaa ctcctagact ccagcaatcc gcccacctca 21840
gcctcccaga gtgctggaat tataggtgtg agccaccacg cctggccaag agcaggcatt 21900
tttatctgtt ttgttcacag ctgtgtcccc agcacctaga atgtacctgg cacaaagtag 21960
acattcacca tttgctgaat aatactacta tttgctaaat aaacccctgt tgaatagtct 22020
aggaaactga acacagagag gttaagtcac ttgtccaagt tcacacagct cctaaaggac 22080
agagatggaa tttgaaccca tccatctggt tccagagcca ggctcgatat tttatggatat 22140 ttcataacca agtgaataac tggatggcta aatccttaga aagcacaccc tccatccctg 22200
tctgacacac gtgtatacca ttaagggaaa tggcaccccc atgtaatagc agaggcagaa 22260
cttgacattt tcagggccct gacacccagg catgtcttct tcccatgctt cccagcatta 22320
ttccttcctg acgacttccc ctcctatttc cccaggtaca gagcatgcca gcgcctcagc 22380
taatggggta agtgcagtgt tggagctaag gagggtgtgg ggtctgcacg aactacagac 22440
cagacgtctt cagatgccca cggcccggcc tcaggagcct gggtcttttc tcctggtgcc 22500
tcgagcagca tttcccaacc cttcctgctg ggcggaatcc cctgtagagt ttgctaagac 22560
gcagccccag acagtctggt ctgtgatggg gccagggaat ctgcatttta atatccgctc 22620 tctccccccct gccccacgcc ccttcaattc cacccatggc cacaccttga gaagcactgc 22680
cctggcttcc agggagagag gaggggacgg gcctgcagtt ctttgcacat ggggcttcag 22740
tgggaagatg tttgattttg ttcaaaagag ccccaaggct aaaatttgaa aaccctcttc 22800
tagcatgtct cctattcagc tgtgagcaga gagaacagct cttcccagga tccacagaca 22860
gagggcacaa ggtgacagcg tcgggactga gaggggagag agactggagc tggcaaggac 22920
gtgggcctcc agagttggac ccgaccccaa tggatgaaga ccccctccaa agagaccagc 22980
ctccctccct gtgccagacc tcaaaacgac gggggcaggt gcaagttcat aggtctccaa 23040
gaccaccctc ctttcatttg ctagaaggac tcactagact caggaaagct gttaggctca 23100
cagttacagt ttattacagt aaaaggacag agattaagat cagcaaaggg aggaggtgca 23160
cagcacacgt tccacgacag atgaggcgac ggcttccatc tgccctctcc cagtggagcc 23220
atataggcag cacctgattc tcacagcaac atgtgacaac atgcaagaag tactgccaat 23280
actgccaacc agagcagctc actcgagatc tttgtgtcca gagtttttttg tttgtcttga 23340
gacagggtct ggctctgttg gcagactaga gtacagtggt gagatcacag ttcattgcag 23400
ccttgacttc tcaacgccaa gtcatcctcc cacctcagcc tcctgagtag ctatgactac 23460
aggtatgtgc caccacgtct ggctaatctt tttattattt gtaaagtcga ggtttccctg 23520
tgttgcccag gctggtcttg aactcttggc tccaagtgat acttctgcct tggcctccca 23580
aagtgctgaa ttaagcagct caccatccac acggctgacc tcatacatca agccaatacc 23640
gtgtggccca agacccccac cataaatcac atcattagca tgaaccaccc agagtggccc 23700
aagactccaa gatcagctac caggcaggat attccaaggg cttagagatg aatgcccagg 23760
agctgaggat aaagggcccg atctttcttt gggcaaggtt aagcctttac tgcatagcag 23820
accacacaga agggtgtggg ccaccagaga attttggtaa aaatttggcc tctggccttg 23880
agcttctaaa tctctgtatc cgtcagatct ctgtggttac aagaaacagc cactgaccct 23940
ggtcaccaga ggctgcaatt caggccgcaa gcagctgcct gggggtgtc caaggagcag 24000
agaaaactac tagatgtgaa cttgaagaag gttgtcagct gcagccactt tctgccagca 24060
tctgcagcca ctttctgcca gcatctgcag ccagcaagct gggactggca ggaaataacc 24120
cacaaaagaa gcaaatgcaa tttccaacac aagggggaag ggatgcaggg ggaggcagcg 24180
ctgcagttgc tcaggacacg ctcctatagg accaagatgg atgcgaccca agacccagga 24240
ggcccagctg ctcagtgcaa ctgacaagtt aaaaaggtct atgatcttga gggcagacag 24300
cagaattcct cttataaaga aaactgtttg ggaaaatacg ttgagggaga gaagaccttg 24360
ggccaagatg ctaaatggga atgcaaagct tgagctgctc tgcaagagaa aataagcagg 24420
acagaggatt tgctctggac agagatggaa gagccgggaa cagagaagtg tggggaagag 24480
ataggaacca gcaggatggc aggggcaaag ggctcaaggg tgaggaggcc agtgggaccc 24540
cacagagttg gggagataaa ggaacattgg ttgctttggt ggcacgtaag ctccttgtct 24600
gtctccagca cccagaatct cattaaagct tatttattgt acctccagcg gctgtgtgca 24660
atggggtctt ttgtggaaat caaggagcag acaggtttca tgtgtactgt caccacgtgg 24720
gatggaacca gaggcatgga agcaagacgc taaatgaaga gggccataag ggctgggatt 24780
cccaggcacc ttaggaacag cttgtctttt tttttttcct ctccaaaaaa aatgtttaag 24840
ggacggtgtc tcctgtcacc caggctggag tgcaatggca cgatcatagc tcattgcagc 24900
ctctaactcc ggggctcaag caatcctccc acctcagcct accaagtagc tgtgaccaca 24960
gctgcccctc accatgctaa gctaattttt ttaattagat agtacataaa cgtcccaaaa 25020
ttagaagata aaaagacatg agggatccat tctaatttgt gtttggagtg taatggtcca 25080
gctccattct tctgcacatg gatatccagt tttacacaac actgtgaatg taatgaatgc 25140
cactgaatca tacactcaaa aatagctaaa atggcaaatt gtctgttatc tctttttaac 25200
caccattttt gaaaattaat tataccaaaa aaccattgaa tagtgcactt tatttattta 25260

```
tttatttgtt tatttattta tttattttag aaataagagt ctcactttgt tgcccaggct  25320
ggagtgcagt ggcgtgatca tggctcattg cagcctcgac ctgctgggct cgggctatcc  25380
ttccatctca gcctcccgag tagctgggac tataggtggg cgccacccca cctggctaaa  25440
tctcttttta acttttgtag agataggcat ctcgctatgt tgcctaggct gggctggaac  25500
tcctgggctc aagtgctcct cctgccttgg cctcccaaag cgctaggatt acagatgtga  25560
gccaccgcgc ccaccctgaa ccttactttt tttgctcagt ttctggtaat tcagagaatg  25620
cctcctgagt tgttctacac ccacctcata ttccatggga gggctgtaca gggctttttt  25680
aacgaggcct ctaaggacag gcatttgtat cctttccagc ctttcactat tacaatgttg  25740
tagtgaataa ctttacacac tgtcatttat tttacttttt ttttttttta ttttagagaa  25800
aggaatcttg ccatcttgcc caggctggtc tcaaattcct gggcccaaac aatcctcccg  25860
ccttggcctc ctaaagtact gggatttata ggcataagcc accgtgcctg gccaatgcac  25920
actgtcattt agctcatgtt aacacctgag tgtaggacac actcctggag gtggaattgc  25980
tgggccaaag agtatgtttc ttgtcattgt gatagatatt gacaaatgaa ccctcacaga  26040
agttgtgctg agttctgttc ccaccagcga cgtaggcgat gacctttttc tggagggagg  26100
gggcatcctt ggagtccaca gagccaggaa tggagagtgg gcccagaatt ttggtatagg  26160
tgttgtataa acttatagta aggttaagaa aaccgcaact atccttatca gagacttggc  26220
ggggggcagg gtatgatgga gatcataagg aggctaaaac actccacacc ctccctctgc  26280
attgctcctg cacgggagtc gggaatcttt tcaggttgat acgatctcac cttgaggagc  26340
tgtgaggtcc cagaagcctc tgggttgcag attgcttggg gtgaaaatgt ctgtgctact  26400
gaaatctaac tttttacaaa aaattacggg ctgggcgcag tggctcacgc ctgtaatccc  26460
agcactttgg gaggctgcag cgggtggatc acttgaggta aggagttcaa gaccagacca  26520
tagtgaaacc gtgtctctac aaaaaaaatt agccaggtgt ggtggtgcat gcttgtaatc  26580
ccagctactc agaaggctga ggtgggagaa tcccttgaac ccgggaagtg gaggctggag  26640
taaaccatga tcgagttact gcactccagc ctgggtgaca agagtgagac tctgtctcca  26700
aaaaaaaaaa aaaaaaaaaa aaaactggat tgcctggctc tactccgggc acagcatgca  26760
ggcccagttc tgctgctctg ctgtttgttc tgctttcctc cacatattgg catcaccctc  26820
tggtgccaag atggctgctg cattccaggc atcacatcca gactcagacc cagagaagct  26880
gcccatccct acctgggtga gcctttgtag gaacgagaaa ccgcatccag cagcagaaac  26940
ctcacccagc agcgtctttt ccggtctcat tcaccagcgc cgcccaccgc tcaaccaatc  27000
cctggccaaa agaatgggac cgcctggaag gctggaccaa acaggacctg ccctctgggg  27060
ctggggagag gcccagatga aggctgcagg acaggatgga ctcctagacc tctgttacca  27120
gcagtgacta cctctgtctg ggtggttgga acatgtttga attttattct aagtactgtc  27180
tacaagttct gcaataaacc ttgactcttc ttttaataat gcaaaaggaa tcgaagtgat  27240
tgtttgaaag ggagaggaag aaagagagag ggagggaggg aagaatggag ggaggcaggg  27300
aaggagacag agagagtaga atccagccac cggaaaatcc agaatagctg gctttgctta  27360
atccatgcct ggaaataact gctgggtttg caacaacttc tctcccggag acagaccaag  27420
gaaactacaa aactgcagga aggattgaag ggccgggcac agtggctcac gcctgtaatc  27480
ccaacacttt gggaggccga ggtggattgg atcacctgag atcaggagtt cgagaccagc  27540
ctggccaaca tggtgaaacc tcgtctctgc tagaaataca aaaataagcc gggcgtggtg  27600
gcgtgcgcct atagtcccag ctactcggga ggctgaggca agagaatcgc ttgaacctgg  27660
```

gaggtggagg ttgcagtgag ctgagatcgt gccactgcac tccagcttgg gcgacagagt 27720
gagaatctgt caggtggatt ctgagggtac tctgacccca cgaacccagc atgaaatctt 27780
ccaggcatta aggaacattg aggatgtgga ggattggaaa tccctccagg gaaaatacac 27840
ttctcttgag cagggtcacg aggggtgggg gcaatgtggg aggtggggca aatccaaaga 27900
caaggtcaac agcaataata ataataacaa tgacaggcat ttgttgcttg ttggctgggc 27960
ctcttgcata cagttctccc aacatccctg tgaggtggtg atgcttatcc ccattctcca 28020
ggggaggagg ctgaggccca gagaggtgaa gtcgtgtgcc acaaaatacc ccagccatat 28080
ggtggtagaa ccaagttttc agccagactc accagctcac agcagagctg ccctggactc 28140
tacagccatt cagtgtatag ctgggccact ccatcattca aggcagttca acgtcaagat 28200
tcctgatttg cctcaacctg gggcctctag aagataccat caccccccaac aagctgaaga 28260 cgtgtgtccg gaacactcag acacacacaa agtgctatgg atacaccaca ccccgaccta 28320
gctgtctctt cctgatggac ctcactgggt agaaatgcct ggcaccgcct gcctcagatc 28380
cctaggtcag ctctcactcc ccaatagaag tttctgagat gatgatgaaa acgttctcca 28440
tctgtgctgt ccaatggagt agccactgat cacttgaggc tagtgagcac ttgaaggtgg 28500
ctagtttgag gaactgcatt ttttaatgca tttaatttta gttactttga atatatatac 28560
acatatatac atttatatat acatattcat acacatacat tttacatata ttttatatgt 28620
atatgtaata tatatataaa ttatatatgt atatattttt atatataaat atatattata 28680
tatttataaa tatataaata tataatatat attatataga tatataaata taaatatata 28740
ttatatatat aaatatataa tatatattat ataaatatat ataaattata tatttatata 28800
tataatatat aaattatata aattatatat atttatatat aatatataaa tatatataaa 28860
ttatataatt tatatattat atataaatta tatattttat atataatata tacaatatat 28920
ataaattata tataatatat aaatatatat aaattatata taatatataa aatatatata 28980
aattatatat aatatataaa atatatataa attatataaa tctatataaa tatatactat 29040
attataaata tagtatatat ttatatagat ttatattatt tatatagtat atattatata 29100
tttatatgtt tatgtatata taaatatata atatataaat atatttatat attatatatt 29160
tatataatat tttatataat atgttatata tttttatata atatattata tatatttata 29220
t 29221

<210> SEQ ID NO 5
<211> LENGTH: 29260
<212> TYPE: DNA
<213> ORGANISM: Artificial Sequence
<220> FEATURE:
<223> OTHER INFORMATION: modified gene

<400> SEQUENCE: 5
aataaataac tttttagacc atatatttct tttttttttt tttttttttt tgagacagag 60
tctcactctg ttgcccagac tggaatgcag tggcatgacg ttgactcact gtaacctcca 120
cctcaagtga ttcagcctcc caagtagctg ggattacagg tgtgcacgac taccacccag 180
ctaatttttg tgtttttagt acagatgggg tttcaccatg ttggccaggc tggtcttgaa 240
ctcctgacct caaaagtgtg ggggaaagaa agagagatca gactgttact gtgtctatgt 300
agaaaaagga agacataaga aactccattt tgatctgtac taagaaaaat tcttctgcct 360
tgagatgctg ttaatctgta accctagccc caaccctgtg ctcgcagaaa cgtgtgctgt 420

```
attgactcaa ggtttaatgg atttagggct gtgcaggatg tgctttggta aaaatgtgtt    480
tgcaggcagt atgcttggta aaagtcattg ccattctcca gtctcaagta accagggaca    540
ccatacactg cggaaggcag cagggacctc tgcccaagaa aacctgggta ttgtccaaga    600
tttcccccac tgagacagcc tgagagatgg cctcgtggga agggaaagac ctgaccgtcc    660
cccagcccga cacccataaa aggtctgtgc tgaggaggat tagtgaaaga ggaaggcctc    720
tctgcagttg agataagagg agggcatctg tctgctgctc gtccctggga atggaatatc    780
tcggtgtaaa acccgatcgt acattctatt tactgagata ggagaaaact gccttatggc    840
tggaggtgag acacactggc agcaatactg ctctttactg cactgagata tttgtgtaaa    900
gtcaaacata aatctggcct acgtgcacat ccaggcacag ctcctttcct taaatttatc    960
tatgacaccg agtcctttgc tcacgttttc ctgctgaccc tctccccacc attaccctat   1020
agtcctgcca catcccctc accgagatag tagggatagt gatcaataaa tactgaggga   1080
actcagagac cagtgccggt gcaggtcctc acttgctgag caccggtccc ctgggcccac   1140
ttttcttcct ctatactttg tctctgtgtc ttatttcttt tctcagtctc tcgtctccac   1200
cttgtgagaa atactcagag gtgtggaggg gcaggccccc ttcaaaatga tccacccacc   1260
tcagcctccc aaagtgctgg gattacaggc atgagccacc atgcccagcc acatataact   1320
tatttctaaa taacttattt aactaacacc acatgatttt atgacccct attttatgga   1380
tgagaaaaaa gaggcaagag aagcgatacc agttgcttag gattcccagc taccaattag   1440
tggaagcaga atttgaacca agggagtctc tggagccctc gttcccaatc tccttttctt   1500
cctctccatg tctttctttc tccccctgct cccaggcctc ctacatcaca cccttctgga   1560
caaagcttca catctgacat tttctttttt ggggtggaca gagtcttact ctgtcaccga   1620
ggctggaggg ccgtggcgca atcatggctc atggcagcct caaactcctg ggcttgaggg   1680
atcctccagc ctcagcctcc caagtagctg ggactatggg catgtgccac cacacctggc   1740
taattttta attttttgta gaaatacagg gggtgggggc atatctgaaa attttaaacc   1800
ttccctgact gccgtgagca tttctgggta gaagccactc cacgacctta ctttgctggc   1860
atgagtgctg gacagcaatt tggcaacatc ctctagacca caaatgtgca tggcctttgg   1920
cccagcaaat cagcttctgg gaataaatat gacagatact gttacataca tgggaaatgc   1980
catggacatg atgacccagg gaagcacagt ttgcaagtac aaaagggctg gaaacaccca   2040
aaaagcccat cccctgaaga cagtttcaaa aatgacggtg cattcatgta atggaatagt   2100
acacatttgt gaatgaatga atgaggtagc tcaatatatc tgcctatggg aaaatcacca   2160
agatatgttg ctaagtgaaa aacagaaaga tacagaataa tgctaccatt ttatttttta   2220
atgggagagg gaagaataag gaaatggatt catatttgct taattacaca agcttcctga   2280
tgatcctttt ggatccagaa gtttgaaaac cacagcatca agaggatgcc cattgggcat   2340
ggtggctcac gcctgtaatc ccagcacttt gggaggctga ggagggtgga tcgcctaagt   2400
tcaggagttc gagaccagcc tggccaacat ggtgaaaccc catctctact aaaaacacaa   2460
aaaaattagc tgggtatggt ggtgcaggcc tgtaattcca gctacttggg aggctgaggc   2520
gcaagaatca cttaagcctg ggaggcggag gctgccgtga gccgagatca cgccattgca   2580
ctccagcttg ggagacagag caagactgtc tcaaaacaaa caaacacaca caaaaaaataa   2640
gatgcccatt ggagatctcc attcactatt ttatcagatg atatttcagc acttgagtga   2700
agaaaatgtc tacaactggt ccaaacactc aaggaattta gactcttgac agagaaacac   2760
acagaagcaa gcagatatgc cccgaaccaa acttgctttt tcttctaagc ctgcttcttc   2820
```

```
ggagcagcct ctgaccctcc agggccctga gaggagtccc tggagccaca ggagcttggg   2880
agcccagaga agtgggggaa tcccagatgg tgacagcatc atccagagga ggaacataac   2940
gatggccaca gattcccaat ttggaaataa ctcagcaaaa caacactgac agaaaattca   3000
gagatttcca agagactagc ctccctgttt ccatttagaa attcacctac atacatccag   3060
ggtgagagac cccaagcatc agatgtgtca tacacaagca tcagatccaa gttagagagg   3120
gcacccgggg acagaaacct ccaagccagc caaaagccaa aggaaggatt ttacagaaag   3180
atacaggaat gtggggccag gcacagtggc tcatgcctgc aatcctagca ctttgggagg   3240
ccgaggtggg aggatcgctt gcggccagga attcaaggcc agcctgagca acatagcgag   3300
atcctatctc tacaacaaat ttaaaaacta gctgggtgtg atcacatatg cctgtggtcc   3360
caactaccca ggaggctgag gcaggagttg agcccaggag gtggaggctg caatgagcaa   3420
tgatggcgcc acttcactcc agcctcagtg aaatagtgag accctgtcta aaaataataa   3480
taaaaataaa aaacatataa agatgtcaga gcacagggac cagagctgtt agtcggcctc   3540
atggagaccc tggccaggac agccacctct ggggaccagg aagtctctca gtttctgtct   3600
ctgagggttt ggctctctga gtctctctgt cacctctcat ttctctctca tctccctctg   3660
tctatgctgt gtctctatct ctttcaatct ctctgtctct gtctcccagc ccttatctct   3720
gagtgtgtct gtttctctct catttctctc tctctctctc tctctttctc tctctctctt   3780
tctctctctc tctttctctc tccccctcc ctcctcccct ctccctactg caggctggtc   3840
cataaccctt atcttcccca gacctgatgg agttctggta ttaatctgtt tatggtctgt   3900
ttccctccac tagaacacgg tcttcattaa aggcagagat ttttgtctgt cttattttct   3960
gctgtatacc cagtgcctgg gatactggct ggatcaataa atatatgctg aatgaagaat   4020
gaatgaatga ccattctcat gaacattatt atttgatgcc aactgtaaag caacaataat   4080
aataattgtc actgccactg ctgctattgt tggtatatca gctttttatt tagtacaaac   4140
tatatccccg aaattgagct aggcagtttc ttgtttaagt tttacagacc acgctgtgag   4200
gtaagtactg ttagtatgcc cttttttctt tctttttgag acagagtctc actctgtcgc   4260
ccaggctgga gtgcagaggc ccgatcttgg ctcactgcaa cctctgcctc ccgggtacaa   4320
gtgattttcc tgtcttagcc tccccagtag ctgggattac aggcatgtgc caccatgccg   4380
gctaattttt gtatttttag taaagatggg tttttgccat gttggccagg ctggtcttga   4440
actcctggac ctctggtgat cctcctgcct cggcctccca aagtgctggg attacaggcg   4500
tcagccactg cgcttgctcc cccagccccc aaactttttt tttttttttt gagacaggtc   4560
tggctctgcc acccaagctg tagtgtagtg gcgcaatggt agctcactga agcctctaac   4620
tcctgggttc acacagtcct cctgcctcag cctcccaaaa tgctggaatt caggcctgag   4680
ccaccgcgcc ctactatgcc catttttcag ataaagaatc tgagggccct cgaggagaaa   4740
ccacttgccc aacatgagcc ctggtcttgt ctgaccccaa agcccatggg aagtttaggc   4800
tgcgtggaag gacagcctgg tgggctcagg atctgtccca tcacgagttg gaacctcagc   4860
tctgccactc ggcaaccgcg agccgttagt aagttgctga atctctccgt gtgcctccgt   4920
ttcctcacct ggaatgtggg cgacctcaca caggaagccg cctcttctag tgggcaccga   4980
cggagcgagc gcgcgtctgc agcgggactg agcgccggga gagacctgcg caggcgcagg   5040
cgcgcgggga gggccagcct gggtggccca ccccgcgcct ggcgggactg gccgccaact   5100
cccctccgct ccagtcactt gtctggagct tgaagaagtg ggtattcccc ttcccacccc   5160
```

-continued

```
aggcactgga ggagcggccc cccggggatt ccaggacctg agctccggga gctggactcg   5220

cagcgaccgc ggcagagcga gcgggcgccg ggaagcgagg agacgcccgc gggaggccca   5280

gctgctcgga gcaactggca tggcccgagc catggccgcc gcgtggccgc tgctgctggt   5340

ggcgctactg gtgctgtcct ggccaccccc aggaaccggt gagtgacccc cgcgcagtcc   5400

ggtggcccct gtctggctcc cagctccgca tccaggccgg gtactcgccc ccttgggttc   5460

ccgaagatga cggccccgcc cggcgccacc caccccccat ctctgccccg gggttggaag   5520

gaacacggtg cgagggtgcg agggcaggac cctcctcttg gccacccgga gagcggtcgg   5580

agttgggtac agaaattcct cgaaattggc agcaacacgg gtcgggcaca agaccctcct   5640

ctgggcccct cggaaagggg atggagttgg gtgaggaaat ttcccaaaaa ggcaagtgaa   5700

tcccggaaaa tcagcagatg gtgacgcatg ccggattacc ttacccaggt tcctgctcag   5760

catacccagg ccataaccca gcagcgtgct ggcaggctgg gtctggacgg aggggatggt   5820

tgatgttggg gaggaggaca gtgggtgaca cttgacacca ttacccctct gacccccaat   5880

gtctgactcc aggggcctgg ccattcattc attctttcat tctttttttt ttttttttga   5940

gacagtctca ctccatcacc caggctggag tgcagtgtcc tgctctcggc tcactgcagc   6000

ctcctcctcc cgagttcaag cgattctcct gcttcagcct cccgagtagc tcggattaca   6060

gacatgtgcc actatgcctg gctaatattt ttgtattttt agtagataca ggatttcacc   6120

atgttggcca ggctggtctc aaactcctga taaatatata tattatatat tattattata   6180

tattacatat tatagtaata tataataaaa atatataata tatattatag taatatataa   6240

tatataataa aatatataat atatattata gtaatatata atatataata aaatatataa   6300

tatatattat agtaatatat aatatattat aatatattat atatattatt ataatatata   6360

atatgtatat tatatattat atatattatt ataatatata atatgtatat tatatattat   6420

atatattatt ataatatata atatgtatta tgtattatat aattgataat atataataat   6480

atatttctta ataaatatat attaaatata ttatatattt ataacatata ttatttatat   6540

aataaataat atatatttta ttatacattt aaagagtaaa tagataacat attttattat   6600

ttatttatat gttttgtgta tatatatata tatatatata tatatatagt gcgtgtgtgc   6660

gtgtatgtgt gtgtgtgtat gagagagaca aggtcttgct ttgttgccca ggctggagtg   6720

cagtggtaca atcccggctc attgcaaact cgacttccca ggctcaagcg atcctctcac   6780

tgtggcttct ggagtagctg ggattatagg tgctcacctg gctaattttt tttgtatttt   6840

tggtagagac agggtttcgc tatgctgccc aggctggttg cagccaagca cagtggctca   6900

tgcctgtaat cccaacactt tgggaggctg tggtgggagg atcacttgag cttaggaatt   6960

caaaaccagc ctgggcaata tggcaagacc ccatctctac aaaaataatt aactaaataa   7020

aaatttaaaa ataaaaaaga atgcatagga ccatgtttat tagtgtcaat aagcgctgtc   7080

acattttgag gacctactat gtgctagggc ccttagcaga aagattttta tataggacct   7140

gggggattag aggtcagtct ctgaccgccc aagttcaaat cccacctctg ccactaaacc   7200

tctgtatgac ttggaggaca ctatactctg tgtcagtttc cctgtctgta aaatgatgtt   7260

aacagtagtg cttgcctcag gggggctatt tgaggattaa atgccaagat atatgtgaag   7320

cacccagaat agcccctgat ctgtgtcagc accctgtgag tgtccactgt tctaagtctc   7380

attttacaaa ctaggaaaaa gaatcagaga ggttaagtaa ccggcctgaa gctccacagc   7440

agaaaactga agggacccaa aactcctggg ctataattgc cttcctctcg tgcctcaatc   7500

ccccacattc ttccaaccag gacccaccca gagtaataat gcagtgtttc atggatttga   7560
```

agacccaaga tttctccccg ttttctacat tggggttatt ctaaccccta atggcaagtt 7620
gtgctataaa tgacaacagt catggtatgt gaaacctacg acactggtgc gatgaaaaag 7680
ttctgggcca ggtgcggtgg ctcatacctg taatcccagc actttgggag gccgtagtgg 7740
gaggatcact tgaggtcagg agttcaagac cagcctggcc aacatggtga aaccccatct 7800
ctgctaaaaa caaaaataca aaaaattagc caggtgtggt ggtgggagcc tgtcatccca 7860
gctacgcgga aagctgaggc aggagaaccg cttgaacccc agaggcagag cttgcagtga 7920
gcagagatcg cgccactgca ctccccctgg gcgacagaga gagactccgt ctcaaaaaaa 7980
aaagagaaga aaagaaaaag ttctggcgct atatagtagt aacggttgca caatatcgtg 8040
aaatgtacat agtgccactg aactgtatgc tttaaatgac ttaaatggta aatttagttt 8100
tttaaccaca atatttacca caattttta aatcagtgat gttgagattc agggaaatac 8160
ggtaataata gaagaaatac ggtaataaat agccaaagtg aaggagcacg gccaagttgc 8220
agaccatccc agacgccctt accctcctcg cctgccatgg ccccaactag tgccccagtt 8280
ccccctcccc ccacacccca cggtccaccg gggatccagg gccccagcgt gcaagtgcac 8340
gcccaggtgc ccgggctcct ggagcccctc cctatctagt ccaagaacgc cccgggtctg 8400
acaccttctc ttcggttctc cgcaggggac gtcgtcgtgc aggcgcccac ccaggtgccc 8460
ggcttcttgg gcgactccgt gacgctgccc tgctactaca ggtgcccaac atggaggtga 8520
cgcatgtgtc acagctgact tgggcgcggc atggtgaatc tggcagcatg gccgtcttcc 8580
accaaacgca gggccccagc tattcggagt ccaaacggct ggaattcgtg gcagccagac 8640
tgggcgcgga gctgcggaat gcctcgctga ggatgttcgg gttgcgcgta gaggatgaag 8700
gcaactacac ctgcctgttc gtcacgttcc cgcagggcag caggagcgtg gatatctggc 8760
tccgagtgct tggtgagcag gggtttggg ggaggctgaa tgaaaggcag agacttggtg 8820
ggaggatcag ggaagttggc aaagagcggg gaggcctggg agggagggag attccctcca 8880
cagcagatcc cctggggaca aaaggagggg gcagcgcaat gatgtggggt ggggtggggg 8940
gaggtgagtg gggggagggg ctgcagggca ggaagaaagc agagatctca gggagtaagg 9000
acccccaagc ctgggatcag aaagccctga gggaggagga ggggtatatt ggaaagggag 9060
ctgggagggg actgggaagg aagggaggag gcctgggtgg cctcttctgg gtccctcctt 9120
tcctcatctg taaaagggtt ggtgacaaca gcatcaccct tggaaagctg tcctgagtgt 9180
catcactgcc taggaaagag tctgtctgcc cccttggact gtgtacccat gagggcagaa 9240
ccggggctat tttgatcact gctgggcccc agcactttcc accaaacaat atttattgag 9300
cacttattat gtgccattct aagagcttta cctgcatatt ctaattgcct gtgattccat 9360
cattatcacc tgttgacaga caaggaaact gaggcacaga cttgcccaag accaaagctg 9420
cagccttagg gcagcggcgc ttcaccgctg gcccatgtga gcccccttaga gctgtcggtt 9480
actgttactt tatctggtga agaaggagaa agttgaaaca gacagacagg aaagcaagga 9540
tcctgatacc caaaagagga ggggatcatg ctttcatttt catgagctcc atgaagcctt 9600
cctcttggaa cttgagcaag aagtctctgt gcctcagttt cctcatctgt gggataggga 9660
tcaccatgag gattcaaaaa aactgaccct tttttttttt ttgagatagt ttagttctgt 9720
cgcccaggct ggagtgcagt ggtgtgatca tagtaggtcc tcactgcagc ctggaactcc 9780
tgggctcaag ggatgttcct accctccctg tagctggaat tacaggaatg tgccaccatg 9840
cccaacttgt tttctgtttt gttttgtttt gttttgtttt cttttctttt taagcttatg 9900

```
tgccaagaac tattccaagc ctgtgcatga gaaactcatg aaatgtcaag ggcttggaac   9960
tgtgcctagc acacaacacc caaccaaagg cagctgttgt cactccagca agcctgggat  10020
tctgggtatc atggtttagg atgagggtaa aacagaaaca gtgagtcaag ttaaggagaa  10080
atcttcggta aataatatag gtaatgatgg ggaaggaagt tccaggtttg ggaatcacca  10140
ggatgatgat taagagatgg tcaaggtggt tttggagtca gacagacttt atgtgaaagc  10200
ccagctctgc tgcttacagc tgtgtgacca tgggcaagtc acttcccttc tcaacttcag  10260
ggctcaggct tcctctcctc cactgagccc cagaccagga taacccctt tgggtttccc   10320
ctttccagcc ctgccctctc cgagtcatca ctgcctagga aagagtccgt ctgcccccctt  10380
ggactgtgta cccatgaggg cagaaccagg gctattttgg tcactgctgg gctccagcac  10440
tttccaccaa acaatattta ttgagcgctt attatatacc attctaagag ctttacctgc  10500
atattctcat tgcctgtgat cccatcacta tcccctgtca acagacaagg aaactgaggc  10560
acagacttgc ccaagaccac acagctgctc agggacacag ctgggattta aaccatgcca  10620
ttctgtatct tttttttttt tttttttttg agacagaatc tcactctgtc gcccaggctg  10680
gagagcagtg acacaatctc agctcactgc aacctccgcc tcccgagttc aagcaattct  10740
ctggtctcag cctcccaagt aactgggatt actggcgtgt gccaccatac cctggctaat  10800
ttttaataga gacagtttct ccatgttggc caggctggtc tcgaactcct gaccccaagt  10860
gatccaccca cctcagcccc ccaaagttct gggattatag gcgtgagcca ccccgcccag  10920
caaccatgcc atcctgtacc cttaatgaat gccccccttct gccacggagg ggttcattga  10980
atgacttgtt gcttttgttc ctcttcccag ccaagcccca gaacacagac ctgggcggga  11040
tgcccaatac gagccaggtg ccagggttcc tgtctggcac agtcactgtc accagcctct  11100
ggatattggt gccctcaagc caggtggacg gcaagaatgt gacctgcaag gtggagcacg  11160
agagctttga gaagcctcag ctgctgactg tgaacctcac cgtgtactgt gagtgtgccc  11220
aagtcagcga tggcaagaac ccctgccggg ctgcccccac cactgtctac actgactccc  11280
caaggcactg taggcattgc ttccatcatc tgcaccggct cccctgactc ctgtctacac  11340
gacccacccc cattgtctgc accagctccc ctgggccgta aacaacactg tccctattgt  11400
ctacaccagt ttacttgggc catagtcaat gctggtaccc agactgtctg ccctggctcc  11460
tctagcggct gtctgcacgg atacctgaca ctctgttgac tcccttgagc acagtctaca  11520
ctgccccctaa actgcctaca cccatttccc caggcaagta tccacaatga ccctccccac  11580
attgctacac tggttcttct ggccacgatc aacactgcct cccttattgt ctacacccac  11640
tcccttgtcc ttttctttct ttcctttttt tttttttttt tttgaaatag agtctcactc  11700
tgttacccag gctgcagtac agtggcatgt tctcggctca ctgtaacctc tgcctcccaa  11760
attcaggtgg ttctcctacc tcagcctccc aaatagctgg gattaaaggt gcacaccacc  11820
acacctggct aatttttgta tttttagtag agacagggtt tcatcatgtt ggccaggctg  11880
gtttcgaact cctgacctca ggtgatcggc ctgcctcagc ctcccaaagt atgctggaat  11940
tataggcatg agccactgtg cccggctttt tgttttgttt tgtttttcct ttggacaggg  12000
tctcgctctg tcacccaggc tggagtgtag gggcatgatc atggttccta cagcctcacc  12060
cttccaggct caagcaatcc ttctccctca gcctcccaag taactgggac tacaggtgca  12120
gccaccatgc ccggctaatt ttacagtttt tttctagaga gagttttgct gtgttgccca  12180
ggctggtctc aaactcctag gcttaagtga tcctcccgcc tcagtctccc gaagtgctga  12240
gattacaggc gtgagccact gcacctggcc ccttgtccat tttctacact gccttaccat  12300
```

tgtctacact ggctctcctg ggccacagac agcactaacc ccattgtcta caccacctat 12360
tttggccacc agctgtgggg tgttttcact gtctcccata gtgtctacac tggctcctat 12420
gaccactgtc tatgtaaaca ccccactttt tctacactgg ttctcctagg cactctctaa 12480
agtgcccccct gacactgtct acactgactc cctggagaac tgtctgcatt cacctcccac 12540
attgtatcga ccagttcccc tgagccacga tcaactgtct ccgccgggtg ctagttgcat 12600
tgatcttctc acattgtttg tgctggctcc cctaagcagt gtctgcagag tcccccagtg 12660
tagtctccat gttcctctgc ccaatattgt ctacactggc tcatctacag gctatccagt 12720
ctcaccccac atcaccacac tggcctcctt gtgttctgtc tgcacagccc cctgacagca 12780
tctgtcctga ttctcctgca cagcgttacc tccaccagct ccctcatggc atcatcgaca 12840
ttgacaccca cacatttatc tccactgaca gccccaggac tctctaacca gtgctgtcta 12900
acagaaatag catgcaagct gcatatagga ttttaaattc tccagcggcc accccattaa 12960
aaaattaaaa gaaagaggcc aggcacggtg gctcacgcct gtaatcccag cactttggga 13020
ggccgaggca ggtggatcac ctgaggtcag gcattcaaga ccagcctgat caatgtggtg 13080
aaactctgtc ttcactaaaa aatacaaaaa ttagccaggc acggtggcgg gtgcctgtaa 13140
tcccagctac tcgggagact gaggcaggag aatcacttga acctgggagg cggagattgc 13200
aatgagcgag attacgccat tgcactccag cctgggcagc agagcaaaac tccatctcaa 13260
aaacaagaaa agaaagagat gaaatttatt tgtttattta tttatctatt tatttatttg 13320
agacggggtc ttactctgtc acccagactg gagtgcagtg gcacagctcc ctgcagcctc 13380
aacctcctgg gcttaagtga tcctcccacc tcagcctcag tctcctgagt agctgggact 13440
acaggcgtgt gacaccatgc ctagctaatt tttgtttttg tttttgtttt tgtttttttg 13500
ttttgtgatg aagtcttgct ctgtcaccca ggctagagtg cagtggcacg atctcaactc 13560
actgcagcct ccgcctctcg ggttcaagtg attctcctgc ctcagcctcc cgagtagctg 13620
ggattacaag ccctggccac agtgcccagc taatttttgt atttgtggta gagacgggat 13680
ttcaccatgt tggccaggct ggtctcaaac tcctgacctc gtgatccacc caccttggcc 13740
tcccaaattg ctgggattac agacgtgagc caccgcaccc ggcctatttt tatttttttct 13800
ggagacagga tctccctatg ttgcccaggc tggtctcaaa ctcctgggct caagtgatcc 13860
tcctgcctca acctcccaag gtactgggat tacaggcatg agccactgtg cctggccaaa 13920
attaattttt aataattgcc tttacttaac ccaatatacc taaaatatta tttcaacttg 13980
taattgtttt tttaaaatta ttcttgagat ctttcccatt tattttgtcc tagtaaagcc 14040
tttgaaatct ggtgtgtatt tcggcctggc tatatttcga gtgctcagta gtcacatgtg 14100
gccagtaggt gccatattgg acagcacaga tctagactaa gctcccacat catctacact 14160
ggctcatcca aatactgtct acacacatac acagagcctg tcttaatttc gtcagctccc 14220
ggggacacac tgtatatgtg ggggtgatct cacccccacc accacatttt caacactggc 14280
ccgacaatat agcatctgct gtaatattcc aacaccctgt ctacactgaa cccatcagta 14340
atatccacac aagctcttct agacatcatt catactgttc ctcccaccat tgtctatact 14400
gcttactccc cgccaggcaa ttggtacaca gattccctca ggtactgtct atactggagt 14460
ccctcaacac tgtcactggg tctgagcgag gaggagatct acactgactc ctacccctcg 14520
cccccgaata aaaccctgtc ccattggcct gcccccaagg acattgaaag gtcttcgctg 14580
tcaatcacgt atgggatggc tgagcagcag cctagagcag ggttatctgg gactctttcc 14640
tgcaggactt gtcagaacct tgaatacact gctgtgtgtt gtgagtggtc attgcctatg 14700
agtgagaaaa ggaggaggca ttttcctgca ggacacccaa gacatgcctg gtccaggcta 14760
cccaggaaag ctagtggaga aaagcagctc ctcagaagcc ttctccatgt ccccactgac 14820
caaggactcc taggcttctg ctctctgtgg caccccatct acctagactc ctcctaggcc 14880
tctccagctc ccgctgtttt ccaaatatcc ccgggccttt tcctgcagtg tcgtgaatcc 14940
cgcgtagccc caggcccccc aaagcctccc agtctctgaa cctctgtatc catttcctgc 15000
agacccccca gaggtatcca tctctggcta tgataacaac tggtaccttg gccagaatga 15060
ggccaccctg acctgcgatg ctcgcagcaa cccagagccc acaggctata attggagcac 15120
gtgagtcctg ggtctcaggg aggaggggct gggggtctgg atttctagca ctgagggagg 15180
aggggctggg ggcctggact cctgggactg agggagaagg ggctgggggc ccggacccct 15240
gggtctgagg gacgagaggc tgggagcccg gactcctggg tctgagggaa gaggggctgg 15300
gggtctggac ccctgggact gagagaggag gggctgggcc tggacccctg ggtctgaggg 15360
aggaggggct ggggggtctg gacccctggg tctgagggag gagaagctgg gagcctggac 15420
ccctgggtct gaggcaggac agactggggc ctggactcct ggtctaagag aggagggaga 15480
ttcagaaaag agaaaaagag gaggttgact tcgggccccc agtgggggc atctctgttt 15540 tgacatctct gttttgcggt tgaggcgttt agcaggtggt tgaatcctgg ctggtggatg 15600
cacctgcttt ttggggtgtg cctgctctgt gcccggtact tcccccgaat cccatgtgac 15660
cccatgctgt gcacagtcag cagctgttgc cctgcccagg ttaaagacca gccacgagag 15720
ggcagaagcg gcccttgaat cagcgctcgg ctccaaagct ggtcctccgc ctcttggcca 15780
agcttgtcta acctgcaggc cacatcattt gtaaactttc ttaaaacatt atgagacttt 15840
ttttttgcga attttttag ctcattagct attgttagtg ttagtgtatt ttatgtatgg 15900
cccaggacag ttcttcttct tccaatgtgg cccggggaag ccaaaagatt ggacaccccc 15960
actctagact gtaaccacct caccgtcacc ttgtgtaacc tacttggtta tctctggatg 16020
gagcaagtac tatatatccc cattgtctag atgagaaagt tgaggctcac agcaataaga 16080
tttccccaga ttcacactga ggctgagatc aagagcaagg taagaaaaag gcaaagagat 16140
aatacataat tttataatac ataattttac ataaattaca taattttact gaaccgccct 16200
ttttttttaa agaaggggct ctgttgccga ggctggagtg cagtggcgtg atcatagctc 16260
actgcagcct ggacctccct gggctcaggt gatcctccca cctcagcctc ctgagtagct 16320
gggactacag gcacacgcca ccacactcag ctaattttgt tgtatttttt ttgcagagac 16380
agggttttgc cacattgccc aggctggtct gcaactcctg ggctcaagca atcaacccac 16440
ctcagcctcc taaagtgctg ggattacagg cgtgagccac ctcgcccagc cttaggtctt 16500
tttccttatt acaaaaataa cttgtgtcca ctgtagaaat atcaaacaat ttagttatga 16560
gcaaaaagaa gaaagtagtg cctatagttc aagtgtaccc agccacctcc agaaataccc 16620
agtgacccct tattatacat cctgtctttt ttctctctgt ttctaaacaa agactggaat 16680
tatgctgtac atataatttt gaacctttc gtctgtcttg tgaatacctt tccatgtcaa 16740
agcacataga tccacaactc cattttcccc cacgttgtat taggaagact gtcaaacata 16800
cagaaaaatc ataggaattt tccagtgaac acttaagatt ccaccacgtg gattcccctg 16860
ctaacatttt actgtgcttg ctttatcacg tttctgtgat tccttcagtc cctctattca 16920
tccatcaatc atattatgca tttcagagca cccccagctc tcctgctttt tttttttttt 16980 ttttttttt gaggcagggc ctcactctgt tgctcaggct gtagtgccgt ggcacaatca 17040
cagctcactg cagccttgaa ttcctgggct caagcgatcc tccagcttca gcctcccaga 17100
tagctgggac tacaggcaca caccaccacg cctggctaac ctggcccctt ttttagtgtt 17160
gctgggattc caccacttta aaaaaaaaat tcaaagaata gagacaggat ctcactatgt 17220
tgcccaggct ggtcttgaac tcctgtactc aagcagtcat ctcacctggg cctcccaaag 17280
ggcagggaag ggattccaac atatgtggat gtcatcagtt atttaaccag tccctagtag 17340
aggacacaga tgtcattttc cattttcaac tctgcaaatg ccatggtggt gtccatcccc 17400
actggtcact tgtcagcagt tgtccgtgga aggaattgcc ggtcaaaggt tttcaactgg 17460
tgtgatggtg cctttactgt cctgcctcaa agcaccgcaa ttcaggctct tgagccagat 17520
agctgcgttt gcatcccagc tctgcggagc acccaaagcc tgatgcttcc atctcctcca 17580
cctctgttca ttaaaccagt gttccttgac tacttactgt gtgccgggtg caattaacca 17640
acatacgttg gtcgataaaa cagaccaaat ttcctcccca tatagagctt ccattctagt 17700
ggtgaaagaa acaagaagca agataaagtg tgtagtgtgt gtgcaatggt gataaatacc 17760
atggagaaga caaagcagag aagggaatgg gactgggcgc catgactcat acctgtaatc 17820
ccagcacttt gggaggcaga gatgggagga tcacttgagg ctaggagttc aagaccagcc 17880
tggccaacat ggcgaaaccc catctctacc aaaaaagata caaaaattgg ccgggtgtgg 17940
tggcatgcac ctgtagtccc agctactcag gaggctgagg tgggaagatt ccatgcaccc 18000
aggaggtgga ggttgcagtg agtcaagatg gtgccactgc actccagcct gggtgacaga 18060
gtgagacgct gtctcaaaaa aataataatt aaataaatta aagagaaggg gatgggaagg 18120
gtgatcatca cagttgaaat agggtggcca agtgaggtgt tactaaggtg acatcccagc 18180
agaggcctga aggagatgag ggtgagctct gcgggtgcct agggggaaag cattccagca 18240
gagggaacag catgggcaaa cccatttcta tccatcagtc cctgcataag caaacaccct 18300
ggacacctaa ctggagagtt tgaggaccaa caaagaggcc actgtggatg cagaggcggg 18360
agcaaagggg agagtaatgg aaaacgtggg cagaggtagc aggggccaga tcacgtgggg 18420
cctgtgacac cagaagactt cggtttaact ctgagccagg ctaggccccc agagggtact 18480
gagctgaggt atgggaactg acttagggtt cacaggcgac ctctggtggc catgtgggga 18540
acagacgagg gggcgagggc agaaacggag cccagcgtgg aggcggctgc tgggggccgg 18600
gatgcacagc gccagagcag ggaggtaccg tggaagccct gaggagaggt gggattctgg 18660
atggatctta aggcggggcc gacatgattg gctaatgggt tgggtgtggg catgagagga 18720
agggaagagt tggggggcct ccagagttgc tctccgctta tgctatagag ggcgtgaggg 18780
tttctgggca cgtagtgcgt gctcaatcac tgtcactccg gacctgcagc agaggccacc 18840
tcctcacctt tctgtctctc ccaggaccat gggtcccctg ccaccctttg ctgtggccca 18900
gggcgcccag ctcctgatcc gtcctgtgga caaaccaatc aacacaactt taatctgcaa 18960
cgtcaccaat gccctaggag ctcgccaggc agaactgacc gtccaggtca aaggtgagga 19020
actccctggg tgggaagaac agggaccaaa ggaagaggtc gaggcagggt tccctgtcta 19080
atgctctctg gctcccatcc ttctcctaag ccttctcaca aaaggaccag tggggccagc 19140
tttactcccc tgttaactcc atacctatat cactggtacc gttgttcagc tgcctggata 19200
cactccctcc acacacacag gttgggatag atgtggaatc cctctctctc agggactcag 19260
gcctttccaa atatattagg cagacctcta tcaattgcaa ttgacagaaa cacaaagtag 19320
tctaagcaaa aaaaaccaaa caaaacagga ctttattgaa aattcacctt caggtatggt 19380

```
tagatccagg ggctccaacc ttgtaaccca ggaactttta ttttatacat ctcttgtctc  19440
tgcttttcgt tatactggct ttattctcag gcaggctctg aagcaagatg gccctcggca  19500
gggacaggct cacattctac cagaatggca acagcaggag aaaaaacata ccactttcag  19560
taactgtagc catagtccca gggctggctc tcattggccc agcttaggcc acagcccacc  19620
tatgaaccaa tcatagcagc cagggagaat ggaatattct gattggccag gcctgtgtca  19680
aagtcccatt ctgggcacca gagggtggga tccattccac ctgaattaaa tagactgagg  19740
cagtggagtg gtggctccct aaggaaattc aagatgccat ttcaagaatg agggataaac  19800
cccaagagtt tccttaccta aatacctgtt tccttctctt tcagagggac ctcccagtga  19860
gcactcaggc atgtcccgta acgccatcat cttcctggtt ctgggaatcc tggtttttct  19920
gatcctgctg gggatcggga tttatttcta ttggtccaaa tgttcccgtg aggtcctttg  19980
gcactgtcat ctgtgtccct cgagtgagca tcaccagagc tgccgtaatt gagcacctac  20040
tacgggctct gtgctgagtc cttccagtgt gcctctcact gaatcctcac cccactgcca  20100
tgaggtttcc cccatttgac tgatgagggt gcagagccag ggagccttgt tcactggttc  20160
attgattaca tttacaaata ttatttacag agtgggagaa gagcgtatag ggtcttaatg  20220
ccatggtagg gactttggaa tttaattcag gtgatgtggg agtccctgcc agatggatgg  20280
agggtgaaat aatgcttaag ccctcagcct tactccatct gccttgttca ggagtgactc  20340
ctaggaggag gtggcaggaa ctggcacctc tgatcctcag ctctaaaagg gtctgatgct  20400
ttcacacctc aagagatttg cacaggccgt tcccctgcct ggagcaccct cccatggctc  20460
cttctggaga agtgtgccag ctcattctgt aatcagagga acgatgcttt gctgagcact  20520
gtctacatgc cactttgtat gtataacccc ctcgatttta atttttaatt tttttttatta  20580
tttatgtatt tatttattta tttttgagac aggctctcac tgtcgcccag gctggagtgc  20640
agtggtgcga tctcggctca ctgtagcctt cacctcccag gttcaagcga ttctcatgcc  20700
tcagcctccc aaggagcggg gattacaggc acgcactact atgcccagca atttttgtat  20760
ttttaggaga gacagcgttt cgccatgttg gccaggctgg tctcaaaccc ctggtctcct  20820
gtgatccacc cgcctcagcc tcccaaagtg ctgggattac aggcatgagc caccacacct  20880
ggcctgtaca atctccttga atgcccacaa ccacccagca aagtggttct cccgtgagcc  20940
ccatgttaca gaggaggaag tatttgcttt gagagatgaa gttacctgcc aatggtcaaa  21000
cagctggaca tggttgttgg ggagaagaag ccagatcttt gactaccaag cttttccttc  21060
aaccactaaa caaagctgct cccttacaac ccaggcggat actgcctcgt ccaggaagcc  21120
ctccctgacc cccaagcatg agccaagcat ccactaggct ctcccactcc agccttgccc  21180
attctgggtc atcaccgtgg gggacttgtt tgtcatcccc agtggactgt gagccccaag  21240
atagcagacc tgaggctgtc actgtcatga ctgtgtcccc aggaccgcct accactgggc  21300
cgggcataaa agaggcactc gaggaagtgt ttgctgagtg attcaatgtg tcagctccag  21360
agccagactg cctgtatctg ggccctaaag ctactgcttg attagtgatg tcaccatagg  21420
caaatagctt aagctgtatg actcagtttc ctcatctgta aaatggggtg atggtaccta  21480
ataatacagt agagcactta acacagtagg tggcacatgg taagccacat actgagtatg  21540
tatttgctat gattgttatt gctattatta ctattattgt tattattaac ataaactgca  21600
caagagcagg ctttttgttt gtttgtttgt gttttgtttt gagacaagat cttgctctgt  21660
tgcccagact ggagtagtgc agtgatgtga tcttggctca ctgcagcctc aacctcccag  21720
gctcaggtga ttctcccacc tcagcctctc gagtagctgg gattataggc gtgcactccc  21780
```

acgcctggct aattttttat atttttagta gagatggagt ttcgttgtgt tgcccaagct 21840
ggtctcaaac tcctagactc cagcaatccg cccacctcag cctcccagag tgctggaatt 21900
ataggtgtga gccaccacgc ctggccaaga gcaggcattt ttatctgttt tgttcacagc 21960
tgtgtcccca gcacctagaa tgtacctggc acaaagtaga cattcaccat ttgctgaata 22020
atactactat ttgctaaata aacccctgtt gaatagtcta ggaaactgaa cacagagagg 22080
ttaagtcact tgtccaagtt cacacagctc ctaaaggaca gagatggaat ttgaacccat 22140
ccatctggtt ccagagccag gctcgatatt tatggatatt tcataaccaa gtgaataact 22200
ggatggctaa atccttagaa agcacaccct ccatccctgt ctgacacacg tgtataccat 22260
taagggaaat ggcaccccca tgtaatagca gaggcagaac ttgacatttt cagggccctg 22320
acacccaggc atgtcttctt cccatgcttc ccagcattat tccttcctga cgacttcccc 22380
tcctatttcc ccaggtacag agcatgccag cgcctcagct aatggggtaa gtgcagtgtt 22440
ggagctaagg agggtgtggg gtctgcacga actacagacc agacgtcttc agatgcccac 22500
ggcccggcct caggagcctg ggtcttttct cctggtgcct cgagcagcat ttcccaaccc 22560
ttcctgctgg gcggaatccc ctgtagagtt tgctaagacg cagccccaga cagtctggtc 22620
tgtgatgggg ccagggaatc tgcattttaa tatccgctct ctccccccctg ccccacgccc 22680
cttcaattcc acccatggcc acaccttgag aagcactgcc ctggcttcca gggagagagg 22740
aggggacggg cctgcagttc tttgcacatg gggcttcagt gggaagatgt ttgattttgt 22800
tcaaaagagc cccaaggcta aaatttgaaa accctcttct agcatgtctc ctattcagct 22860
gtgagcagag agaacagctc ttcccaggat ccacagacag agggcacaag gtgacagcgt 22920
cgggactgag aggggagaga gactggagct ggcaaggacg tgggcctcca gagttggacc 22980
cgaccccaat ggatgaagac cccctccaaa gagaccagcc tccctccctg tgccagacct 23040
caaaacgacg gggcaggtg caagttcata ggtctccaag accaccctcc tttcatttgc 23100
tagaaggact cactagactc aggaaagctg ttaggctcac agttacagtt tattacagta 23160
aaaggacaga gattaagatc agcaaaggga ggaggtgcac agcacacgtt ccacgacaga 23220
tgaggcgacg gcttccatct gccctctccc agtggagcca tataggcagc acctgattct 23280
cacagcaaca tgtgacaaca tgcaagaagt actgccaata ctgccaacca gagcagctca 23340
ctcgagatct ttgtgtccag agttttttgt ttgtcttgag acagggtctg gctctgttgg 23400
cagactagag tacagtggtg agatcacagt tcattgcagc cttgacttct caacgccaag 23460
tcatcctccc acctcagcct cctgagtagc tatgactaca ggtatgtgcc accacgtctg 23520
gctaatcttt ttattatttg taaagtcgag gtttccctgt gttgcccagg ctggtcttga 23580
actcttggct ccaagtgata cttctgcctt ggcctcccaa agtgctgaat taagcagctc 23640
accatccaca cggctgacct catacatcaa gccaataccg tgtggcccaa gacccccacc 23700
ataaatcaca tcattagcat gaaccaccca gagtggccca agactccaag atcagctacc 23760
aggcaggata ttccaagggc ttagagatga atgcccagga gctgaggata aagggcccga 23820
tctttctttg ggcaaggtta agcctttact gcatagcaga ccacacagaa gggtgtgggc 23880
caccagagaa ttttggtaaa aatttggcct ctggccttga gcttctaaat ctctgtatcc 23940
gtcagatctc tgtggttaca agaaacagcc actgaccctg gtcaccagag gctgcaattc 24000
aggccgcaag cagctgcctg gggggtgtcc aaggagcaga gaaaactact agatgtgaac 24060
ttgaagaagg ttgtcagctg cagccacttt ctgccagcat ctgcagccac tttctgccag 24120
catctgcagc cagcaagctg ggactggcag gaaataaccc acaaaagaag caaatgcaat 24180
ttccaacaca agggggaagg gatgcagggg gaggcagcgc tgcagttgct caggacacgc 24240
tcctatagga ccaagatgga tgcgacccaa gacccaggag gcccagctgc tcagtgcaac 24300
tgacaagtta aaaaggtcta tgatcttgag ggcagacagc agaattcctc ttataaagaa 24360
aactgtttgg gaaaatacgt tgagggagag aagaccttgg gccaagatgc taaatgggaa 24420
tgcaaagctt gagctgctct gcaagagaaa ataagcagga cagaggattt gctctggaca 24480
gagatggaag agccgggaac agagaagtgt ggggaagaga taggaaccag caggatggca 24540
ggggcaaagg gctcaagggt gaggaggcca gtgggacccc acagagttgg ggagataaag 24600
gaacattggt tgctttggtg gcacgtaagc tccttgtctg tctccagcac ccagaatctc 24660
attaaagctt atttattgta cctccagcgg ctgtgtgcaa tggggtcttt tgtggaaatc 24720
aaggagcaga caggtttcat gtgtactgtc accacgtggg atggaaccag aggcatggaa 24780
gcaagacgct aaatgaagag ggccataagg gctgggattc ccaggcacct taggaacagc 24840
ttgtcttttt tttttcctc tccaaaaaaa atgtttaagg gacggtgtct cctgtcaccc 24900
aggctggagt gcaatggcac gatcatagct cattgcagcc tctaactccg gggctcaagc 24960
aatcctccca cctcagccta ccaagtagct gtgaccacag ctgcccctca ccatgctaag 25020
ctaatttttt taattagata gtacataaac gtcccaaaat tagaagataa aaagacatga 25080
gggatccatt ctaatttgtg tttggagtgt aatggtccag ctccattctt ctgcacatgg 25140
atatccagtt ttacacaaca ctgtgaatgt aatgaatgcc actgaatcat acactcaaaa 25200
atagctaaaa tggcaaattg tctgttatct ctttttaacc accattttg aaaattaatt 25260 ataccaaaaa accattgaat agtgcacttt atttatttat ttatttgttt atttatttat 25320
ttattttaga aataagagtc tcactttgtt gcccaggctg gagtgcagtg gcgtgatcat 25380
ggctcattgc agcctcgacc tgctgggctc gggctatcct tccatctcag cctcccgagt 25440
agctgggact ataggtgggc gccaccccac ctggctaaat ctctttttaa cttttgtaga 25500
gataggcatc tcgctatgtt gcctaggctg ggctggaact cctgggctca agtgctcctc 25560
ctgccttggc ctcccaaagc gctaggatta cagatgtgag ccaccgcgcc caccctgaac 25620
cttacttttt ttgctcagtt tctggtaatt cagagaatgc ctcctgagtt gttctacacc 25680
cacctcatat tccatgggag ggctgtacag ggctttttta acgaggcctc taaggacagg 25740
catttgtatc ctttccagcc tttcactatt acaatgttgt agtgaataac tttacacact 25800
gtcatttatt ttactttttt ttttttttat tttagagaaa ggaatcttgc catcttgccc 25860
aggctggtct caaattcctg ggcccaaaca atcctcccgc cttggcctcc taaagtactg 25920
ggatttatag gcataagcca ccgtgcctgg ccaatgcaca ctgtcattta gctcatgtta 25980
acacctgagt gtaggacaca ctcctggagg tggaattgct gggccaaaga gtatgtttct 26040
tgtcattgtg atagatattg acaaatgaac cctcacagaa gttgtgctga gttctgttcc 26100
caccagcgac gtaggcgatg acctttttct ggagggaggg ggcatccttg gagtccacag 26160
agccaggaat ggagagtggg cccagaattt tggtataggt gttgtataaa cttatagtaa 26220
ggttaagaaa accgcaacta tccttatcag agacttggcg gggggcaggg tatgatggag 26280
atcataagga ggctaaaaca ctccacaccc tccctctgca ttgctcctgc acgggagtcg 26340
ggaatctttt caggttgata cgatctcacc ttgaggagct gtgaggtccc agaagcctct 26400
gggttgcaga ttgcttgggg tgaaaatgtc tgtgctactg aaatctaact ttttacaaaa 26460
aattacgggc tgggcgcagt ggctcacgcc tgtaatccca gcactttggg aggctgcagc 26520

```
gggtggatca cttgaggtaa ggagttcaag accagaccat agtgaaaccg tgtctctaca  26580
aaaaaaatta gccaggtgtg gtggtgcatg cttgtaatcc cagctactca gaaggctgag  26640
gtgggagaat cccttgaacc cgggaagtgg aggctggagt aaaccatgat cgagttactg  26700
cactccagcc tgggtgacaa gagtgagact ctgtctccaa aaaaaaaaaa aaaaaaaaaa  26760
aaactggatt gcctggctct actccgggca cagcatgcag gcccagttct gctgctctgc  26820
tgtttgttct gctttcctcc acatattggc atcaccctct ggtgccaaga tggctgctgc  26880
attccaggca tcacatccag actcagaccc agagaagctg cccatcccta cctgggtgag  26940
cctttgtagg aacgagaaac cgcatccagc agcagaaacc tcacccagca gcgtcttttc  27000
cggtctcatt caccagcgcc gcccaccgct caaccaatcc ctggccaaaa gaatgggacc  27060
gcctggaagg ctggaccaaa caggacctgc cctctggggc tggggagagg cccagatgaa  27120
ggctgcagga caggatggac tcctagacct ctgttaccag cagtgactac ctctgtctgg  27180
gtggttggaa catgtttgaa ttttattcta agtactgtct acaagttctg caataaacct  27240
tgactcttct tttaataatg caaaaggaat cgaagtgatt gtttgaaagg gagaggaaga  27300
aagagagagg gagggaggga agaatggagg gaggcaggga aggagacaga gagagtagaa  27360
tccagccacc ggaaaatcca gaatagctgg ctttgcttaa tccatgcctg gaaataactg  27420
ctgggtttgc aacaacttct ctcccggaga cagaccaagg aaactacaaa actgcaggaa  27480
ggattgaagg gccgggcaca gtggctcacg cctgtaatcc caacactttg ggaggccgag  27540
gtggattgga tcacctgaga tcaggagttc gagaccagcc tggccaacat ggtgaaacct  27600
cgtctctgct agaaatacaa aaataagccg ggcgtggtgg cgtgcgccta tagtcccagc  27660
tactcgggag gctgaggcaa gagaatcgct tgaacctggg aggtggaggt tgcagtgagc  27720
tgagatcgtg ccactgcact ccagcttggg cgacagagtg agaatctgtc aggtggattc  27780
tgagggtact ctgaccccac gaacccagca tgaaatcttc caggcattaa ggaacattga  27840
ggatgtggag gattggaaat ccctccaggg aaaatacact tctcttgagc agggtcacga  27900
ggggtggggg caatgtggga ggtggggcaa atccaaagac aaggtcaaca gcaataataa  27960
taataacaat gacaggcatt tgttgcttgt tggctgggcc tcttgcatac agttctccca  28020
acatccctgt gaggtggtga tgcttatccc cattctccag gggaggaggc tgaggcccag  28080
agaggtgaag tcgtgtgcca caaaataccc cagccatatg gtggtagaac caagttttca  28140
gccagactca ccagctcaca gcagagctgc cctggactct acagccattc agtgtatagc  28200
tgggccactc catcattcaa ggcagttcaa cgtcaagatt cctgatttgc ctcaacctgg  28260
ggcctctaga agataccatc acccccaaca agctgaagac gtgtgtccgg aacactcaga  28320
cacacacaaa gtgctatgga tacaccacac cccgacctag ctgtctcttc ctgatggacc  28380
tcactgggta gaaatgcctg gcaccgcctg cctcagatcc ctaggtcagc tctcactccc  28440
caatagaagt ttctgagatg atgatgaaaa cgttctccat ctgtgctgtc caatggagta  28500
gccactgatc acttgaggct agtgagcact tgaaggtggc tagtttgagg aactgcattt  28560
tttaatgcat ttaattttag ttactttgaa tatatataca catatataca tttatatata  28620
catattcata cacatacatt ttacatatat tttatatgta tatgtaatat atatataaat  28680
tatatatgta tatattttta tatataaata tatattatat atttataaat atataaatat  28740
ataatatata ttatatagat atataaatat aaatatatat tatatatata aatatataat  28800
atatattata taaatatata taaattatat atttatatat ataatatata aattatataa  28860
```

```
attatatata tttatatata atatataaat atatataaat tatataattt atatattata  28920

tataaattat atattttata tataatatat acaatatata taaattatat ataatatata  28980

aatatatata aattatatat aatatataaa atatatataa attatatata atatataaaa  29040

tatatataaa ttatataaat ctatataaat atatactata ttataaatat agtatatatt  29100

tatatagatt tatattattt atatagtata tattatatat ttatatgttt atgtatatat  29160

aaatatataa tatataaata tatttatata ttatatattt atataatatt ttatataata  29220

tgttatatat ttttatataa tatattatat atatttatat                        29260
```

<210> SEQ ID NO 6
<211> LENGTH: 29261
<212> TYPE: DNA
<213> ORGANISM: Artificial Sequence
<220> FEATURE:
<223> OTHER INFORMATION: modified gene

<400> SEQUENCE: 6

```
aataaataac tttttagacc atatatttct tttttttttt tttttttttt tgagacagag     60

tctcactctg ttgcccagac tggaatgcag tggcatgacg ttgactcact gtaacctcca    120

cctcaagtga ttcagcctcc caagtagctg ggattacagg tgtgcacgac taccacccag    180

ctaatttttg tgtttttagt acagatgggg tttcaccatg ttggccaggc tggtcttgaa    240

ctcctgacct caaaagtgtg ggggaaagaa agagagatca gactgttact gtgtctatgt    300

agaaaaagga agacataaga aactccattt tgatctgtac taagaaaaat tcttctgcct    360

tgagatgctg ttaatctgta accctagccc caaccctgtg ctcgcagaaa cgtgtgctgt    420

attgactcaa ggtttaatgg atttagggct gtgcaggatg tgctttggta aaaatgtgtt    480

tgcaggcagt atgcttggta aaagtcattg ccattctcca gtctcaagta accagggaca    540

ccatacactg cggaaggcag cagggacctc tgcccaagaa aacctgggta ttgtccaaga    600

tttcccccac tgagacagcc tgagagatgg cctcgtggga agggaaagac ctgaccgtcc    660

cccagcccga cacccataaa aggtctgtgc tgaggaggat tagtgaaaga ggaaggcctc    720

tctgcagttg agataagagg agggcatctg tctgctgctc gtccctggga atggaatatc    780

tcggtgtaaa acccgatcgt acattctatt tactgagata ggagaaaact gccttatggc    840

tggaggtgag acacactggc agcaatactg ctctttactg cactgagata tttgtgtaaa    900

gtcaaacata aatctggcct acgtgcacat ccaggcacag ctcctttcct taaatttatc    960

tatgacaccg agtcctttgc tcacgttttc ctgctgaccc tctccccacc attaccctat   1020

agtcctgcca catccccctc accgagatag tagggatagt gatcaataaa tactgaggga   1080

actcagagac cagtgccggt gcaggtcctc acttgctgag caccggtccc ctgggcccac   1140

ttttcttcct ctatactttg tctctgtgtc ttatttcttt tctcagtctc tcgtctccac   1200

cttgtgagaa atactcagag gtgtggaggg gcaggccccc ttcaaaatga tccacccacc   1260

tcagcctccc aaagtgctgg gattacaggc atgagccacc atgcccagcc acatataact   1320

tatttctaaa taacttattt aactaacacc acatgatttt atgacccccct attttatgga   1380

tgagaaaaaa gaggcaagag aagcgatacc agttgcttag gattcccagc taccaattag   1440

tggaagcaga atttgaacca agggagtctc tggagccctc gttcccaatc tccttttctt   1500

cctctccatg tctttctttc tccccctgct cccaggcctc ctacatcaca cccttctgga   1560

caaagcttca catctgacat tttctttttt ggggtggaca gagtcttact ctgtcaccga   1620

ggctggaggg ccgtggcgca atcatggctc atggcagcct caaactcctg ggcttgaggg   1680
```

atcctccagc ctcagcctcc caagtagctg ggactatggg catgtgccac cacacctggc 1740
taatttttta attttttgta gaaatacagg gggtgggggc atatctgaaa attttaaacc 1800
ttccctgact gccgtgagca tttctgggta gaagccactc cacgacctta ctttgctggc 1860
atgagtgctg gacagcaatt tggcaacatc ctctagacca caaatgtgca tggcctttgg 1920
cccagcaaat cagcttctgg gaataaatat gacagatact gttacataca tgggaaatgc 1980
catggacatg atgacccagg gaagcacagt ttgcaagtac aaaagggctg gaaacaccca 2040
aaaagcccat cccctgaaga cagtttcaaa aatgacggtg cattcatgta atggaatagt 2100
acacatttgt gaatgaatga atgaggtagc tcaatatatc tgcctatggg aaaatcacca 2160
agatatgttg ctaagtgaaa aacagaaaga tacagaataa tgctaccatt ttattttta 2220
atgggagagg gaagaataag gaaatggatt catatttgct taattacaca agcttcctga 2280
tgatcctttt ggatccagaa gtttgaaaac cacagcatca agaggatgcc cattgggcat 2340
ggtggctcac gcctgtaatc ccagcacttt gggaggctga ggagggtgga tcgcctaagt 2400
tcaggagttc gagaccagcc tggccaacat ggtgaaaccc catctctact aaaaacacaa 2460
aaaaattagc tgggtatggt ggtgcaggcc tgtaattcca gctacttggg aggctgaggc 2520
gcaagaatca cttaagcctg ggaggcggag gctgccgtga gccgagatca cgccattgca 2580
ctccagcttg ggagacagag caagactgtc tcaaaacaaa caaacacaca caaaaaataa 2640
gatgcccatt ggagatctcc attcactatt ttatcagatg atatttcagc acttgagtga 2700
agaaaatgtc tacaactggt ccaaacactc aaggaattta gactcttgac agagaaacac 2760
acagaagcaa gcagatatgc cccgaaccaa acttgctttt tcttctaagc ctgcttcttc 2820
ggagcagcct ctgaccctcc agggccctga gaggagtccc tggagccaca ggagcttggg 2880
agcccagaga agtgggggaa tcccagatgg tgacagcatc atccagagga ggaacataac 2940
gatggccaca gattcccaat ttggaaataa ctcagcaaaa caacactgac agaaaattca 3000
gagatttcca agagactagc ctccctgttt ccatttagaa attcacctac atacatccag 3060
ggtgagagac cccaagcatc agatgtgtca tacacaagca tcagatccaa gttagagagg 3120
gcacccgggg acagaaacct ccaagccagc caaaagccaa aggaaggatt ttacagaaag 3180
atacaggaat gtggggccag gcacagtggc tcatgcctgc aatcctagca ctttgggagg 3240
ccgaggtggg aggatcgctt gcggccagga attcaaggcc agcctgagca acatagcgag 3300
atcctatctc tacaacaaat ttaaaaacta gctgggtgtg atcacatatg cctgtggtcc 3360
caactaccca ggaggctgag gcaggagttg agcccaggag gtggaggctg caatgagcaa 3420
tgatggcgcc acttcactcc agcctcagtg aaatagtgag accctgtcta aaaataataa 3480
taaaaataaa aaacatataa agatgtcaga gcacagggac cagagctgtt agtcggcctc 3540
atggagaccc tggccaggac agccacctct ggggaccagg aagtctctca gtttctgtct 3600
ctgagggttt ggctctctga gtctctctgt cacctctcat ttctctctca tctccctctg 3660
tctatgctgt gtctctatct ctttcaatct ctctgtctct gtctcccagc ccttatctct 3720
gagtgtgtct gtttctctct catttctctc tctctctctc tctctttctc tctctctctt 3780
tctctctctc tctttctctc tccccccctcc ctcctcccct ctccctactg caggctggtc 3840
cataaccctt atcttcccca gacctgatgg agttctggta ttaatctgtt tatggtctgt 3900
ttccctccac tagaacacgg tcttcattaa aggcagagat ttttgtctgt cttattttct 3960
gctgtatacc cagtgcctgg gatactggct ggatcaataa atatatgctg aatgaagaat 4020

-continued

```
gaatgaatga ccattctcat gaacattatt atttgatgcc aactgtaaag caacaataat   4080
aataattgtc actgccactg ctgctattgt tggtatatca gctttttatt tagtacaaac   4140
tatatccccg aaattgagct aggcagtttc ttgtttaagt tttacagacc acgctgtgag   4200
gtaagtactg ttagtatgcc ctttttttctt tctttttgag acagagtctc actctgtcgc   4260
ccaggctgga gtgcagaggc ccgatcttgg ctcactgcaa cctctgcctc ccgggtacaa   4320
gtgattttcc tgtcttagcc tccccagtag ctgggattac aggcatgtgc caccatgccg   4380
gctaattttt gtatttttag taaagatggg tttttgccat gttggccagg ctggtcttga   4440
actcctggac ctctggtgat cctcctgcct cggcctccca aagtgctggg attacaggcg   4500
tcagccactg cgcttgctcc cccagccccc aaactttttt tttttttttt gagacaggtc   4560
tggctctgcc acccaagctg tagtgtagtg gcgcaatggt agctcactga agcctctaac   4620
tcctgggttc acacagtcct cctgcctcag cctcccaaaa tgctggaatt caggcctgag   4680
ccaccgcgcc ctactatgcc catttttcag ataaagaatc tgagggccct cgaggagaaa   4740
ccacttgccc aacatgagcc ctggtcttgt ctgaccccaa agcccatggg aagtttaggc   4800
tgcgtggaag gacagcctgg tgggctcagg atctgtccca tcacgagttg gaacctcagc   4860
tctgccactc ggcaaccgcg agccgttagt aagttgctga atctctccgt gtgcctccgt   4920
ttcctcacct ggaatgtggg cgacctcaca caggaagccg cctcttctag tgggcaccga   4980
cggagcgagc gcgcgtctgc agcgggactg agcgccggga gagacctgcg caggcgcagg   5040
cgcgcgggga gggccagcct gggtggccca ccccgcgcct ggcgggactg gccgccaact   5100
cccctccgct ccagtcactt gtctggagct tgaagaagtg ggtattcccc ttcccacccc   5160
aggcactgga ggagcggccc cccggggatt ccaggacctg agctccggga gctggactcg   5220
cagcgaccgc ggcagagcga gcgggcgccg ggaagcgagg agacgcccgc gggaggccca   5280
gctgctcgga gcaactggca tggcccgagc catggccgcc gcgtggccgc tgctgctggt   5340
ggcgctactg gtgctgtcct ggccaccccc aggaaccggt gagtgacccc cgcgcagtcc   5400
ggtggcccct gtctggctcc cagctccgca tccaggccgg gtactcgccc ccttgggttc   5460
ccgaagatga cggccccgcc cggcgccacc caccccccat ctctgccccg gggttggaag   5520
gaacacggtg cgagggtgcg agggcaggac cctcctcttg gccacccgga gagcggtcgg   5580
agttgggtac agaaattcct cgaaattggc agcaacacgg gtcgggcaca agaccctcct   5640
ctgggcccct cggaaagggg atggagttgg gtgaggaaat ttcccaaaaa ggcaagtgaa   5700
tcccggaaaa tcagcagatg gtgacgcatg ccggattacc ttacccaggt tcctgctcag   5760
catacccagg ccataaccca gcagcgtgct ggcaggctgg gtctggacgg aggggatggt   5820
tgatgttggg gaggaggaca gtgggtgaca cttgacacca ttacccctct gacccccaat   5880
gtctgactcc aggggcctgg ccattcattc attctttcat tctttttttt ttttttttga   5940
gacagtctca ctccatcacc caggctggag tgcagtgtcc tgctctcggc tcactgcagc   6000
ctcctcctcc cgagttcaag cgattctcct gcttcagcct cccgagtagc tcggattaca   6060
gacatgtgcc actatgcctg gctaatattt ttgtattttt agtagataca ggatttcacc   6120
atgttggcca ggctggtctc aaactcctga taaatatata tattatatat tattattata   6180
tattacatat tatagtaata tataataaaa atatataata tatattatag taatatataa   6240
tatataataa aatatataat atatattata gtaatatata atatataata aaatatataa   6300
tatatattat agtaatatat aatatattat aatatattat atatattatt ataatatata   6360
atatgtatat tatatattat atatattatt ataatatata atatgtatat tatatattat   6420
```

atatattatt ataatatata atatgtatta tgtattatat aattgataat atataataat 6480
atatttctta ataaatatat attaaatata ttatatattt ataacatata ttatttatat 6540
aataaataat atatatttta ttatacattt aaagagtaaa tagataacat attttattat 6600
ttatttatat gttttgtgta tatatatata tatatatata tatatatagt gcgtgtgtgc 6660
gtgtatgtgt gtgtgtgtat gagagagaca aggtcttgct ttgttgccca ggctggagtg 6720
cagtggtaca atcccggctc attgcaaact cgacttccca ggctcaagcg atcctctcac 6780
tgtggcttct ggagtagctg ggattatagg tgctcacctg gctaattttt tttgtatttt 6840
tggtagagac agggtttcgc tatgctgccc aggctggttg cagccaagca cagtggctca 6900
tgcctgtaat cccaacactt tgggaggctg tggtgggagg atcacttgag cttaggaatt 6960
caaaaccagc ctgggcaata tggcaagacc ccatctctac aaaaataatt aactaaataa 7020
aaatttaaaa ataaaaaaga atgcatagga ccatgtttat tagtgtcaat aagcgctgtc 7080
acattttgag gacctactat gtgctagggc ccttagcaga aagattttta tataggacct 7140
gggggattag aggtcagtct ctgaccgccc aagttcaaat cccacctctg ccactaaacc 7200
tctgtatgac ttggaggaca ctatactctg tgtcagtttc cctgtctgta aaatgatgtt 7260
aacagtagtg cttgcctcag gggggctatt tgaggattaa atgccaagat atatgtgaag 7320
cacccagaat agcccctgat ctgtgtcagc accctgtgag tgtccactgt tctaagtctc 7380
attttacaaa ctaggaaaaa gaatcagaga ggttaagtaa ccggcctgaa gctccacagc 7440
agaaaactga agggacccaa aactcctggg ctataattgc cttcctctcg tgcctcaatc 7500
ccccacattc ttccaaccag gacccaccca gagtaataat gcagtgtttc atggatttga 7560
agacccaaga tttctccccg ttttctacat tggggttatt ctaaccccta atggcaagtt 7620
gtgctataaa tgacaacagt catggtatgt gaaacctacg acactggtgc gatgaaaaag 7680
ttctgggcca ggtgcggtgg ctcatacctg taatcccagc actttgggag gccgtagtgg 7740
gaggatcact tgaggtcagg agttcaagac cagcctggcc aacatggtga aaccccatct 7800
ctgctaaaaa caaaaataca aaaaattagc caggtgtggt ggtgggagcc tgtcatccca 7860
gctacgcgga aagctgaggc aggagaaccg cttgaacccc agaggcagag cttgcagtga 7920
gcagagatcg cgccactgca ctcccccctgg gcgacagaga gagactccgt ctcaaaaaaa 7980
aaagagaaga aaagaaaaag ttctggcgct atatagtagt aacggttgca caatatcgtg 8040
aaatgtacat agtgccactg aactgtatgc tttaaatgac ttaaatggta aatttagttt 8100
tttaaccaca atatttacca caatttttta aatcagtgat gttgagattc agggaaatac 8160
ggtaataata gaagaaatac ggtaataaat agccaaagtg aaggagcacg gccaagttgc 8220
agaccatccc agacgccctt accctcctcg cctgccatgg ccccaactag tgccccagtt 8280 cccccctcccc ccacacccca cggtccaccg gggatccagg gccccagcgt gcaagtgcac 8340
gcccaggtgc ccgggctcct ggagcccctc cctatctagt ccaagaacgc cccgggtctg 8400
acaccttctc ttcggttctc cgcaggggac gtcgtcgtgc aggcgcccac ccaggtgccc 8460
ggcttcttgg gcgactccgt gacgctgccc tgctacctac aggtgcccaa catggaggtg 8520
acgcatgtgt cacagctgac ttgggcgcgg catggtgaat ctggcagcat ggccgtcttc 8580
caccaaacgc agggccccag ctattcggag tccaaacggc tggaattcgt ggcagccaga 8640
ctgggcgcgg agctgcggaa tgcctcgctg aggatgttcg ggttgcgcgt agaggatgaa 8700
ggcaactaca cctgcctgtt cgtcacgttc ccgcagggca gcaggagcgt ggatatctgg 8760

-continued

```
ctccgagtgc ttggtgagca gggggttttg gggaggctga atgaaaggca gagacttggt   8820
gggaggatca gggaagttgg caaagagcgg ggaggcctgg gagggaggga gattccctcc   8880
acagcagatc ccctggggac aaaaggaggg ggcagcgcaa tgatgtgggg tggggtgggg   8940
ggaggtgagt ggggggaggg gctgcagggc aggaagaaag cagagatctc agggagtaag   9000
gacccccaag cctgggatca gaaagccctg agggaggagg aggggtatat tggaaaggga   9060
gctgggaggg gactgggaag gaagggagga ggcctgggtg gcctcttctg ggtccctcct   9120
ttcctcatct gtaaaagggt tggtgacaac agcatcaccc ttggaaagct gtcctgagtg   9180
tcatcactgc ctaggaaaga gtctgtctgc cccccttggac tgtgtaccca tgagggcaga   9240
accggggcta ttttgatcac tgctgggccc cagcactttc caccaaacaa tatttattga   9300
gcacttatta tgtgccattc taagagcttt acctgcatat tctaattgcc tgtgattcca   9360
tcattatcac ctgttgacag acaaggaaac tgaggcacag acttgcccaa gaccaaagct   9420
gcagccttag ggcagcggcg cttcaccgct ggcccatgtg agccccttag agctgtcggt   9480
tactgttact ttatctggtg aagaaggaga aagttgaaac agacagacag gaaagcaagg   9540
atcctgatac ccaaaagagg aggggatcat gctttcattt tcatgagctc catgaagcct   9600
tcctcttgga acttgagcaa gaagtctctg tgcctcagtt tcctcatctg tgggataggg   9660
atcaccatga ggattcaaaa aaactgaccc ttttttttt tttgagatag tttagttctg   9720
tcgcccaggc tggagtgcag tggtgtgatc atagtaggtc ctcactgcag cctggaactc   9780
ctgggctcaa gggatgttcc taccctccct gtagctggaa ttacaggaat gtgccaccat   9840
gcccaacttg ttttctgttt tgttttgttt tgttttgttt tcttttcttt ttaagcttat   9900
gtgccaagaa ctattccaag cctgtgcatg agaaactcat gaaatgtcaa gggcttggaa   9960
ctgtgcctag cacacaacac ccaaccaaag gcagctgttg tcactccagc aagcctggga  10020
ttctgggtat catggtttag gatgagggta aaacagaaac agtgagtcaa gttaaggaga  10080
aatcttcggt aaataatata ggtaatgatg gggaaggaag ttccaggttt gggaatcacc  10140
aggatgatga ttaagagatg gtcaaggtgg ttttggagtc agacagactt tatgtgaaag  10200
cccagctctg ctgcttacag ctgtgtgacc atgggcaagt cacttccctt ctcaacttca  10260
gggctcaggc ttcctctcct ccactgagcc ccagaccagg ataacccccct ttgggtttcc  10320
cctttccagc cctgccctct ccgagtcatc actgcctagg aaagagtccg tctgcccccct  10380
tggactgtgt acccatgagg gcagaaccag ggctattttg gtcactgctg ggctccagca  10440
ctttccacca aacaatattt attgagcgct tattatatac cattctaaga gctttacctg  10500
catattctca ttgcctgtga tcccatcact atcccctgtc aacagacaag gaaactgagg  10560
cacagacttg cccaagacca cacagctgct cagggacaca gctgggattt aaaccatgcc  10620
attctgtatc ttttttttt ttttttttt gagacagaat ctcactctgt cgcccaggct  10680
ggagagcagt gacacaatct cagctcactg caacctccgc ctcccgagtt caagcaattc  10740
tctggtctca gcctcccaag taactgggat tactggcgtg tgccaccata ccctggctaa  10800
tttttaatag agacagtttc tccatgttgg ccaggctggt ctcgaactcc tgaccccaag  10860
tgatccaccc acctcagccc cccaaagttc tgggattata ggcgtgagcc accccgccca  10920
gcaaccatgc catcctgtac ccttaatgaa tgccccccttc tgccacggag gggttcattg  10980
aatgacttgt tgcttttgtt cctcttccca gccaagcccc agaacacaga cctgggcggg  11040
atgcccaata cgagccaggt gccagggttc ctgtctggca cagtcactgt caccagcctc  11100
tggatattgg tgccctcaag ccaggtggac ggcaagaatg tgacctgcaa ggtggagcac  11160
```

gagagctttg agaagcctca gctgctgact gtgaacctca ccgtgtactg tgagtgtgcc 11220
caagtcagcg atggcaagaa cccctgccgg gctgccccca ccactgtcta cactgactcc 11280
ccaaggcact gtaggcattg cttccatcat ctgcaccggc tcccctgact cctgtctaca 11340
cgacccaccc ccattgtctg caccagctcc cctgggccgt aaacaacact gtccctattg 11400
tctacaccag tttacttggg ccatagtcaa tgctggtacc cagactgtct gccctggctc 11460
ctctagcggc tgtctgcacg gatacctgac actctgttga ctcccttgag cacagtctac 11520
actgccccta aactgcctac acccatttcc ccaggcaagt atccacaatg accctcccca 11580
cattgctaca ctggttcttc tggccacgat caacactgcc tcccttattg tctacaccca 11640
ctcccttgtc cttttctttc tttccttttt tttttttttt ttttgaaata gagtctcact 11700
ctgttaccca ggctgcagta cagtggcatg ttctcggctc actgtaacct ctgcctccca 11760
aattcaggtg gttctcctac ctcagcctcc caaatagctg ggattaaagg tgcacaccac 11820
cacacctggc taatttttgt atttttagta gagacagggt ttcatcatgt tggccaggct 11880
ggtttcgaac tcctgacctc aggtgatcgg cctgcctcag cctcccaaag tatgctggaa 11940
ttataggcat gagccactgt gcccggcttt ttgttttgtt ttgtttttcc tttggacagg 12000
gtctcgctct gtcacccagg ctggagtgta ggggcatgat catggttcct acagcctcac 12060
ccttccaggc tcaagcaatc cttctccctc agcctcccaa gtaactggga ctacaggtgc 12120
agccaccatg cccggctaat tttacagttt ttttctagag agagttttgc tgtgttgccc 12180
aggctggtct caaactccta ggcttaagtg atcctcccgc ctcagtctcc cgaagtgctg 12240
agattacagg cgtgagccac tgcacctggc cccttgtcca ttttctacac tgccttacca 12300
ttgtctacac tggctctcct gggccacaga cagcactaac cccattgtct acaccaccta 12360
ttttggccac cagctgtggg gtgttttcac tgtctcccat agtgtctaca ctggctccta 12420
tgaccactgt ctatgtaaac accccacttt ttctacactg gttctcctag gcactctcta 12480
aagtgccccc tgacactgtc tacactgact ccctggagaa ctgtctgcat tcacctccca 12540
cattgtatcg accagttccc ctgagccacg atcaactgtc tccgccgggt gctagttgca 12600
ttgatcttct cacattgttt gtgctggctc ccctaagcag tgtctgcaga gtcccccagt 12660
gtagtctcca tgttcctctg cccaatattg tctacactgg ctcatctaca ggctatccag 12720
tctcacccca catcaccaca ctggcctcct tgtgttctgt ctgcacagcc ccctgacagc 12780
atctgtcctg attctcctgc acagcgttac ctccaccagc tccctcatgg catcatcgac 12840
attgacaccc acacatttat ctccactgac agccccagga ctctctaacc agtgctgtct 12900
aacagaaata gcatgcaagc tgcatatagg attttaaatt ctccagcggc caccccatta 12960
aaaaattaaa agaaagaggc caggcacggt ggctcacgcc tgtaatccca gcactttggg 13020
aggccgaggc aggtggatca cctgaggtca ggcattcaag accagcctga tcaatgtggt 13080
gaaactctgt cttcactaaa aaatacaaaa attagccagg cacggtggcg ggtgcctgta 13140
atcccagcta ctcgggagac tgaggcagga gaatcacttg aacctgggag gcggagattg 13200
caatgagcga gattacgcca ttgcactcca gcctgggcag cagagcaaaa ctccatctca 13260
aaaacaagaa aagaaagaga tgaaatttat ttgtttattt atttatctat ttatttattt 13320
gagacggggt cttactctgt cacccagact ggagtgcagt ggcacagctc cctgcagcct 13380
caacctcctg ggcttaagtg atcctcccac ctcagcctca gtctcctgag tagctgggac 13440
tacaggcgtg tgacaccatg cctagctaat tttgttttt gtttttgttt ttgttttttt 13500

```
gttttgtgat gaagtcttgc tctgtcaccc aggctagagt gcagtggcac gatctcaact  13560
cactgcagcc tccgcctctc gggttcaagt gattctcctg cctcagcctc ccgagtagct  13620
gggattacaa gccctggcca cagtgcccag ctaatttttg tatttgtggt agagacggga  13680
tttcaccatg ttggccaggc tggtctcaaa ctcctgacct cgtgatccac ccaccttggc  13740
ctcccaaatt gctgggatta cagacgtgag ccaccgcacc cggcctattt ttattttttc  13800
tggagacagg atctccctat gttgcccagg ctggtctcaa actcctgggc tcaagtgatc  13860
ctcctgcctc aacctcccaa ggtactggga ttacaggcat gagccactgt gcctggccaa  13920
aattaatttt taataattgc ctttacttaa cccaatatac ctaaaatatt atttcaactt  13980
gtaattgttt ttttaaaatt attcttgaga tctttcccat ttattttgtc ctagtaaagc  14040
ctttgaaatc tggtgtgtat ttcggcctgg ctatatttcg agtgctcagt agtcacatgt  14100
ggccagtagg tgccatattg gacagcacag atctagacta agctcccaca tcatctacac  14160
tggctcatcc aaatactgtc tacacacata cacagagcct gtcttaattt cgtcagctcc  14220
cggggacaca ctgtatatgt gggggtgatc tcacccccac caccacattt tcaacactgg  14280
cccgacaata tagcatctgc tgtaatattc caacaccctg tctacactga acccatcagt  14340
aatatccaca caagctcttc tagacatcat tcatactgtt cctcccacca ttgtctatac  14400
tgcttactcc ccgccaggca attggtacac agattccctc aggtactgtc tatactggag  14460
tccctcaaca ctgtcactgg gtctgagcga ggaggagatc tacactgact cctacccctc  14520
gcccccgaat aaaaccctgt cccattggcc tgcccccaag gacattgaaa ggtcttcgct  14580
gtcaatcacg tatgggatgg ctgagcagca gcctagagca gggttatctg ggactctttc  14640
ctgcaggact tgtcagaacc ttgaatacac tgctgtgtgt tgtgagtggt cattgcctat  14700
gagtgagaaa aggaggaggc attttcctgc aggacaccca agacatgcct ggtccaggct  14760
acccaggaaa gctagtggag aaaagcagct cctcagaagc cttctccatg tccccactga  14820
ccaaggactc ctaggcttct gctctctgtg gcaccccatc tacctagact cctcctaggc  14880
ctctccagct cccgctgttt tccaaatatc cccgggcctt ttcctgcagt gtcgtgaatc  14940
ccgcgtagcc ccaggccccc caaagcctcc cagtctctga acctctgtat ccatttcctg  15000
cagacccccc agaggtatcc atctctggct atgataacaa ctggtacctt ggccagaatg  15060
aggccacccct gacctgcgat gctcgcagca acccagagcc cacaggctat aattggagca  15120
cgtgagtcct gggtctcagg gaggaggggc tgggggtctg gatttctagc actgagggag  15180
gaggggctgg gggcctggac tcctgggact gagggagaag gggctggggg cccggacccc  15240
tgggtctgag ggacgagagg ctgggagccc ggactcctgg gtctgaggga agaggggctg  15300
ggggtctgga cccctgggac tgagagagga ggggctgggc ctggacccct gggtctgagg  15360
gaggaggggc tggggggtct ggacccctgg gtctgaggga ggagaagctg ggagcctgga  15420
cccctgggtc tgaggcagga cagactgggg cctggactcc tggtctaaga gaggagggag  15480
attcagaaaa gagaaaaaga ggaggttgac ttcgggcccc cagtgggggg catctctgtt  15540
ttgacatctc tgttttgcgg ttgaggcgtt tagcaggtgg ttgaatcctg gctggtggat  15600
gcacctgctt tttggggtgt gcctgctctg tgcccggtac ttcccccgaa tcccatgtga  15660
ccccatgctg tgcacagtca gcagctgttg ccctgcccag gttaaagacc agccacgaga  15720
gggcagaagc ggcccttgaa tcagcgctcg gctccaaagc tggtcctccg cctcttggcc  15780
aagcttgtct aacctgcagg ccacatcatt tgtaaacttt cttaaaacat tatgagactt  15840
tttttttgcg aatttttta gctcattagc tattgttagt gttagtgtat tttatgtatg  15900
```

```
gcccaggaca gttcttcttc ttccaatgtg gcccggggaa gccaaaagat tggacacccc  15960
cactctagac tgtaaccacc tcaccgtcac cttgtgtaac ctacttggtt atctctggat  16020
ggagcaagta ctatatatcc ccattgtcta gatgagaaag ttgaggctca cagcaataag  16080
atttccccag attcacactg aggctgagat caagagcaag gtaagaaaaa ggcaaagaga  16140
taatacataa ttttataata cataatttta cataaattac ataattttac tgaaccgccc  16200
ttttttttta aagaaggggc tctgttgccg aggctggagt gcagtggcgt gatcatagct  16260
cactgcagcc tggacctccc tgggctcagg tgatcctccc acctcagcct cctgagtagc  16320
tgggactaca ggcacacgcc accacactca gctaattttg ttgtattttt tttgcagaga  16380
cagggttttg ccacattgcc caggctggtc tgcaactcct gggctcaagc aatcaaccca  16440
cctcagcctc ctaaagtgct gggattacag gcgtgagcca cctcgcccag ccttaggtct  16500
ttttccttat tacaaaaata acttgtgtcc actgtagaaa tatcaaacaa tttagttatg  16560
agcaaaaaga agaaagtagt gcctatagtt caagtgtacc cagccacctc cagaaatacc  16620
cagtgacccc ttattataca tcctgtcttt tttctctctg tttctaaaca aagactggaa  16680
ttatgctgta catataattt tgaacctttt cgtctgtctt gtgaatacct ttccatgtca  16740
aagcacatag atccacaact ccattttccc ccacgttgta ttaggaagac tgtcaaacat  16800
acagaaaaat cataggaatt ttccagtgaa cacttaagat tccaccacgt ggattcccct  16860
gctaacattt tactgtgctt gctttatcac gtttctgtga ttccttcagt ccctctattc  16920
atccatcaat catattatgc atttcagagc acccccagct ctcctgcttt tttttttttt  16980
tttttttttt tgaggcaggg cctcactctg ttgctcaggc tgtagtgccg tggcacaatc  17040
acagctcact gcagccttga attcctgggc tcaagcgatc ctccagcttc agcctcccag  17100
atagctggga ctacaggcac acaccaccac gcctggctaa cctggcccct tttttagtgt  17160
tgctgggatt ccaccacttt aaaaaaaaaa ttcaaagaat agagacagga tctcactatg  17220
ttgcccaggc tggtcttgaa ctcctgtact caagcagtca tctcacctgg gcctcccaaa  17280
gggcagggaa gggattccaa catatgtgga tgtcatcagt tatttaacca gtccctagta  17340
gaggacacag atgtcatttt ccattttcaa ctctgcaaat gccatggtgg tgtccatccc  17400
cactggtcac ttgtcagcag ttgtccgtgg aaggaattgc cggtcaaagg ttttcaactg  17460
gtgtgatggt gcctttactg tcctgcctca aagcaccgca attcaggctc ttgagccaga  17520
tagctgcgtt tgcatcccag ctctgcggag cacccaaagc ctgatgcttc catctcctcc  17580
acctctgttc attaaaccag tgttccttga ctacttactg tgtgccgggt gcaattaacc  17640
aacatacgtt ggtcgataaa acagaccaaa tttcctcccc atatagagct tccattctag  17700
tggtgaaaga aacaagaagc aagataaagt gtgtagtgtg tgtgcaatgg tgataaatac  17760
catggagaag acaaagcaga gaagggaatg ggactgggcg ccatgactca tacctgtaat  17820
cccagcactt tgggaggcag agatgggagg atcacttgag gctaggagtt caagaccagc  17880
ctggccaaca tggcgaaacc ccatctctac caaaaaagat acaaaaattg gccgggtgtg  17940
gtggcatgca cctgtagtcc cagctactca ggaggctgag gtgggaagat tccatgcacc  18000
caggaggtgg aggttgcagt gagtcaagat ggtgccactg cactccagcc tgggtgacag  18060
agtgagacgc tgtctcaaaa aaataataat taaataaatt aaagagaagg ggatgggaag  18120
ggtgatcatc acagttgaaa tagggtggcc aagtgaggtg ttactaaggt gacatcccag  18180
cagaggcctg aaggagatga gggtgagctc tgcgggtgcc tagggggaaa gcattccagc  18240
```

agagggaaca gcatgggcaa acccatttct atccatcagt ccctgcataa gcaaacaccc 18300
tggacaccta actggagagt ttgaggacca acaaagaggc cactgtggat gcagaggcgg 18360
gagcaaaggg gagagtaatg gaaaacgtgg gcagaggtag caggggccag atcacgtggg 18420
gcctgtgaca ccagaagact tcggtttaac tctgagccag gctaggcccc cagagggtac 18480
tgagctgagg tatgggaact gacttagggt tcacaggcga cctctggtgg ccatgtgggg 18540
aacagacgag gggcgaggg cagaaacgga gcccagcgtg gaggcggctg ctgggggccg 18600
ggatgcacag cgccagagca gggaggtacc gtggaagccc tgaggagagg tgggattctg 18660
gatggatctt aaggcggggc cgacatgatt ggctaatggg ttgggtgtgg gcatgagagg 18720
aagggaagag ttggggggcc tccagagttg ctctccgctt atgctataga gggcgtgagg 18780
gtttctgggc acgtagtgcg tgctcaatca ctgtcactcc ggacctgcag cagaggccac 18840
ctcctcacct ttctgtctct cccaggacca tgggtcccct gccacccttt gctgtggccc 18900
agggcgccca gctcctgatc cgtcctgtgg acaaaccaat caacacaact ttaatctgca 18960
acgtcaccaa tgccctagga gctcgccagg cagaactgac cgtccaggtc aaaggtgagg 19020
aactccctgg gtgggaagaa cagggaccaa aggaagaggt cgaggcaggg ttccctgtct 19080
aatgctctct ggctcccatc cttctcctaa gccttctcac aaaaggacca gtggggccag 19140
ctttactccc ctgttaactc catacctata tcactggtac cgttgttcag ctgcctggat 19200
acactccctc cacacacaca ggttgggata gatgtggaat ccctctctct cagggactca 19260
ggcctttcca aatatattag gcagacctct atcaattgca attgacagaa acacaaagta 19320
gtctaagcaa aaaaaaccaa acaaaacagg actttattga aaattcacct tcaggtatgg 19380
ttagatccag gggctccaac cttgtaaccc aggaactttt attttataca tctcttgtct 19440
ctgcttttcg ttatactggc tttattctca ggcaggctct gaagcaagat ggccctcggc 19500
agggacaggc tcacattcta ccagaatggc aacagcagga gaaaaaacat accactttca 19560
gtaactgtag ccatagtccc agggctggct ctcattggcc cagcttaggc cacagcccac 19620
ctatgaacca atcatagcag ccagggagaa tggaatattc tgattggcca ggcctgtgtc 19680
aaagtcccat tctgggcacc agagggtggg atccattcca cctgaattaa atagactgag 19740
gcagtggagt ggtggctccc taaggaaatt caagatgcca tttcaagaat gagggataaa 19800
ccccaagagt ttccttacct aaatacctgt ttccttctct ttcagaggga cctcccagtg 19860
agcactcagg catgtcccgt aacgccatca tcttcctggt tctgggaatc ctggtttttc 19920
tgatcctgct ggggatcggg atttatttct attggtccaa atgttcccgt gaggtccttt 19980
ggcactgtca tctgtgtccc tcgagtgagc atcaccagag ctgccgtaat tgagcaccta 20040
ctacgggctc tgtgctgagt ccttccagtg tgcctctcac tgaatcctca ccccactgcc 20100
atgaggtttc ccccatttga ctgatgaggg tgcagagcca gggagccttg ttcactggtt 20160
cattgattac atttacaaat attatttaca gagtgggaga agagcgtata gggtcttaat 20220
gccatggtag ggactttgga atttaattca ggtgatgtgg gagtccctgc cagatggatg 20280
gagggtgaaa taatgcttaa gccctcagcc ttactccatc tgccttgttc aggagtgact 20340
cctaggagga ggtggcagga actggcacct ctgatcctca gctctaaaag ggtctgatgc 20400
tttcacacct caagagattt gcacaggccg ttcccctgcc tggagcaccc tcccatggct 20460
ccttctggag aagtgtgcca gctcattctg taatcagagg aacgatgctt tgctgagcac 20520
tgtctacatg ccactttgta tgtataaccc cctcgatttt aatttttaat tttttttatt 20580
atttatgtat ttatttattt atttttgaga caggctctca ctgtcgccca ggctggagtg 20640
cagtggtgcg atctcggctc actgtagcct tcacctccca ggttcaagcg attctcatgc 20700
ctcagcctcc caaggagcgg ggattacagg cacgcactac tatgcccagc aatttttgta 20760
tttttaggag agacagcgtt tcgccatgtt ggccaggctg gtctcaaacc cctggtctcc 20820
tgtgatccac ccgcctcagc ctcccaaagt gctgggatta caggcatgag ccaccacacc 20880
tggcctgtac aatctccttg aatgcccaca accacccagc aaagtggttc tcccgtgagc 20940
cccatgttac agaggaggaa gtatttgctt tgagagatga agttacctgc caatggtcaa 21000
acagctggac atggttgttg gggagaagaa gccagatctt tgactaccaa gcttttcctt 21060
caaccactaa acaaagctgc tcccttacaa cccaggcgga tactgcctcg tccaggaagc 21120
cctccctgac ccccaagcat gagccaagca tccactaggc tctcccactc cagccttgcc 21180
cattctgggt catcaccgtg gggacttgt ttgtcatccc cagtggactg tgagccccaa 21240
gatagcagac ctgaggctgt cactgtcatg actgtgtccc caggaccgcc taccactggg 21300
ccgggcataa aagaggcact cgaggaagtg tttgctgagt gattcaatgt gtcagctcca 21360
gagccagact gcctgtatct gggccctaaa gctactgctt gattagtgat gtcaccatag 21420
gcaaatagct taagctgtat gactcagttt cctcatctgt aaaatggggt gatggtacct 21480
aataatacag tagagcactt aacacagtag gtggcacatg gtaagccaca tactgagtat 21540
gtatttgcta tgattgttat tgctattatt actattattg ttattattaa cataaactgc 21600
acaagagcag gctttttgtt tgtttgtttg tgttttgttt tgagacaaga tcttgctctg 21660
ttgcccagac tggagtagtg cagtgatgtg atcttggctc actgcagcct caacctccca 21720
ggctcaggtg attctcccac ctcagcctct cgagtagctg ggattatagg cgtgcactcc 21780
cacgcctggc taattttta tatttttagt agagatggag tttcgttgtg ttgcccaagc 21840
tggtctcaaa ctcctagact ccagcaatcc gcccacctca gcctcccaga gtgctggaat 21900
tataggtgtg agccaccacg cctggccaag agcaggcatt tttatctgtt ttgttcacag 21960
ctgtgtcccc agcacctaga atgtacctgg cacaaagtag acattcacca tttgctgaat 22020
aatactacta tttgctaaat aaacccctgt tgaatagtct aggaaactga acacagagag 22080
gttaagtcac ttgtccaagt tcacacagct cctaaaggac agagatggaa tttgaaccca 22140
tccatctggt tccagagcca ggctcgatat ttatggatat ttcataacca agtgaataac 22200
tggatggcta aatccttaga aagcacaccc tccatccctg tctgacacac gtgtatacca 22260
ttaagggaaa tggcacccc atgtaatagc agaggcagaa cttgacattt tcagggccct 22320
gacacccagg catgtcttct tcccatgctt cccagcatta ttccttcctg acgacttccc 22380
ctcctatttc cccaggtaca gagcatgcca gcgcctcagc taatggggta agtgcagtgt 22440
tggagctaag gagggtgtgg ggtctgcacg aactacagac cagacgtctt cagatgccca 22500
cggcccggcc tcaggagcct gggtcttttc tcctggtgcc tcgagcagca tttcccaacc 22560
cttcctgctg ggcggaatcc cctgtagagt ttgctaagac gcagccccag acagtctggt 22620
ctgtgatggg gccagggaat ctgcatttta atatccgctc tctcccccct gccccacgcc 22680
ccttcaattc cacccatggc cacaccttga gaagcactgc cctggcttcc agggagagag 22740
gaggggacgg gcctgcagtt ctttgcacat ggggcttcag tgggaagatg tttgattttg 22800
ttcaaaagag ccccaaggct aaaatttgaa aaccctcttc tagcatgtct cctattcagc 22860
tgtgagcaga gagaacagct cttcccagga tccacagaca gagggcacaa ggtgacagcg 22920
tcgggactga gaggggagag agactggagc tggcaaggac gtgggcctcc agagttggac 22980
ccgaccccaa tggatgaaga ccccctccaa agagaccagc ctccctccct gtgccagacc 23040
tcaaaacgac gggggcaggt gcaagttcat aggtctccaa gaccaccctc ctttcatttg 23100
ctagaaggac tcactagact caggaaagct gttaggctca cagttacagt ttattacagt 23160
aaaaggacag agattaagat cagcaaaggg aggaggtgca cagcacacgt tccacgacag 23220
atgaggcgac ggcttccatc tgccctctcc cagtggagcc atataggcag cacctgattc 23280
tcacagcaac atgtgacaac atgcaagaag tactgccaat actgccaacc agagcagctc 23340
actcgagatc tttgtgtcca gagtttttttg tttgtcttga gacagggtct ggctctgttg 23400
gcagactaga gtacagtggt gagatcacag ttcattgcag ccttgacttc tcaacgccaa 23460
gtcatcctcc cacctcagcc tcctgagtag ctatgactac aggtatgtgc caccacgtct 23520
ggctaatctt tttattattt gtaaagtcga ggtttccctg tgttgcccag gctggtcttg 23580
aactcttggc tccaagtgat acttctgcct tggcctccca aagtgctgaa ttaagcagct 23640
caccatccac acggctgacc tcatacatca agccaatacc gtgtggccca agaccccac 23700
cataaatcac atcattagca tgaaccaccc agagtggccc aagactccaa gatcagctac 23760
caggcaggat attccaaggg cttagagatg aatgcccagg agctgaggat aaagggcccg 23820
atctttcttt gggcaaggtt aagcctttac tgcatagcag accacacaga agggtgtggg 23880
ccaccagaga attttggtaa aaatttggcc tctggccttg agcttctaaa tctctgtatc 23940
cgtcagatct ctgtggttac aagaaacagc cactgaccct ggtcaccaga ggctgcaatt 24000
caggccgcaa gcagctgcct gggggtgtc caaggagcag agaaaactac tagatgtgaa 24060
cttgaagaag gttgtcagct gcagccactt tctgccagca tctgcagcca ctttctgcca 24120
gcatctgcag ccagcaagct gggactggca ggaaataacc cacaaaagaa gcaaatgcaa 24180
tttccaacac aagggggaag ggatgcaggg ggaggcagcg ctgcagttgc tcaggacacg 24240
ctcctatagg accaagatgg atgcgaccca agacccagga ggcccagctg ctcagtgcaa 24300
ctgacaagtt aaaaaggtct atgatcttga gggcagacag cagaattcct cttataaaga 24360
aaactgtttg ggaaaatacg ttgagggaga gaagaccttg ggccaagatg ctaaatggga 24420
atgcaaagct tgagctgctc tgcaagagaa aataagcagg acagaggatt tgctctggac 24480
agagatggaa gagccgggaa cagagaagtg tggggaagag ataggaacca gcaggatggc 24540
aggggcaaag ggctcaaggg tgaggaggcc agtgggaccc cacagagttg ggagataaa 24600
ggaacattgg ttgctttggt ggcacgtaag ctccttgtct gtctccagca cccagaatct 24660
cattaaagct tatttattgt acctccagcg gctgtgtgca atggggtctt ttgtggaaat 24720
caaggagcag acaggtttca tgtgtactgt caccacgtgg gatggaacca gaggcatgga 24780
agcaagacgc taaatgaaga gggccataag ggctgggatt cccaggcacc ttaggaacag 24840
cttgtctttt ttttttcct ctccaaaaaa aatgtttaag ggacggtgtc tcctgtcacc 24900
caggctggag tgcaatggca cgatcatagc tcattgcagc ctctaactcc ggggctcaag 24960
caatcctccc acctcagcct accaagtagc tgtgaccaca gctgccccte accatgctaa 25020
gctaattttt ttaattagat agtacataaa cgtcccaaaa ttagaagata aaaagacatg 25080
agggatccat tctaatttgt gtttggagtg taatggtcca gctccattct tctgcacatg 25140
gatatccagt tttacacaac actgtgaatg taatgaatgc cactgaatca tacactcaaa 25200
aatagctaaa atggcaaatt gtctgttatc tctttttaac caccattttt gaaaattaat 25260
tataccaaaa aaccattgaa tagtgcactt tatttattta tttatttgtt tatttattta 25320
tttattttag aaataagagt ctcactttgt tgcccaggct ggagtgcagt ggcgtgatca 25380

```
tggctcattg cagcctcgac ctgctgggct cgggctatcc ttccatctca gcctcccgag  25440
tagctgggac tataggtggg cgccacccca cctggctaaa tctcttttta acttttgtag  25500
agataggcat ctcgctatgt tgcctaggct gggctggaac tcctgggctc aagtgctcct  25560
cctgccttgg cctcccaaag cgctaggatt acagatgtga gccaccgcgc ccaccctgaa  25620
ccttactttt tttgctcagt ttctggtaat tcagagaatg cctcctgagt tgttctacac  25680
ccacctcata ttccatggga gggctgtaca gggctttttt aacgaggcct ctaaggacag  25740
gcatttgtat cctttccagc ctttcactat tacaatgttg tagtgaataa ctttacacac  25800
tgtcatttat tttactttt ttttttttta ttttagagaa aggaatcttg ccatcttgcc  25860
caggctggtc tcaaattcct gggcccaaac aatcctcccg ccttggcctc ctaaagtact  25920
gggatttata ggcataagcc accgtgcctg gccaatgcac actgtcattt agctcatgtt  25980
aacacctgag tgtaggacac actcctggag gtggaattgc tgggccaaag agtatgtttc  26040
ttgtcattgt gatagatatt gacaaatgaa ccctcacaga agttgtgctg agttctgttc  26100
ccaccagcga cgtaggcgat gacctttttc tggagggagg gggcatcctt ggagtccaca  26160
gagccaggaa tggagagtgg gcccagaatt ttggtatagg tgttgtataa acttatagta  26220
aggttaagaa aaccgcaact atccttatca gagacttggc ggggggcagg gtatgatgga  26280
gatcataagg aggctaaaac actccacacc ctccctctgc attgctcctg cacgggagtc  26340
gggaatcttt tcaggttgat acgatctcac cttgaggagc tgtgaggtcc cagaagcctc  26400
tgggttgcag attgcttggg gtgaaaatgt ctgtgctact gaaatctaac tttttacaaa  26460
aaattacggg ctgggcgcag tggctcacgc ctgtaatccc agcactttgg gaggctgcag  26520
cgggtggatc acttgaggta aggagttcaa gaccagacca tagtgaaacc gtgtctctac  26580
aaaaaaaatt agccaggtgt ggtggtgcat gcttgtaatc ccagctactc agaaggctga  26640
ggtgggagaa tcccttgaac ccgggaagtg gaggctggag taaaccatga tcgagttact  26700
gcactccagc ctgggtgaca agagtgagac tctgtctcca aaaaaaaaaa aaaaaaaaaa  26760
aaaactggat tgcctggctc tactccgggc acagcatgca ggcccagttc tgctgctctg  26820
ctgtttgttc tgctttcctc cacatattgg catcaccctc tggtgccaag atggctgctg  26880
cattccaggc atcacatcca gactcagacc cagagaagct gcccatccct acctgggtga  26940
gcctttgtag gaacgagaaa ccgcatccag cagcagaaac ctcacccagc agcgtctttt  27000
ccggtctcat tcaccagcgc cgcccaccgc tcaaccaatc cctggccaaa agaatgggac  27060
cgcctggaag gctggaccaa acaggacctg ccctctgggg ctggggagag gcccagatga  27120
aggctgcagg acaggatgga ctcctagacc tctgttacca gcagtgacta cctctgtctg  27180
ggtggttgga acatgtttga attttattct aagtactgtc tacaagttct gcaataaacc  27240
ttgactcttc ttttaataat gcaaaaggaa tcgaagtgat tgtttgaaag ggagaggaag  27300
aaagagagag ggagggaggg aagaatggag ggaggcaggg aaggagacag agagagtaga  27360
atccagccac cggaaaatcc agaatagctg gctttgctta atccatgcct ggaaataact  27420
gctgggtttg caacaacttc tctcccggag acagaccaag gaaactacaa aactgcagga  27480
aggattgaag ggccgggcac agtggctcac gcctgtaatc ccaacacttt gggaggccga  27540
ggtggattgg atcacctgag atcaggagtt cgagaccagc ctggccaaca tggtgaaacc  27600
tcgtctctgc tagaaataca aaaataagcc gggcgtggtg gcgtgcgcct atagtcccag  27660
ctactcggga ggctgaggca agagaatcgc ttgaacctgg gaggtggagg ttgcagtgag  27720
```

ctgagatcgt gccactgcac tccagcttgg gcgacagagt gagaatctgt caggtggatt 27780
ctgagggtac tctgacccca cgaacccagc atgaaatctt ccaggcatta aggaacattg 27840
aggatgtgga ggattggaaa tccctccagg gaaaatacac ttctcttgag cagggtcacg 27900
aggggtgggg gcaatgtggg aggtggggca aatccaaaga caaggtcaac agcaataata 27960
ataataacaa tgacaggcat ttgttgcttg ttggctgggc ctcttgcata cagttctccc 28020
aacatccctg tgaggtggtg atgcttatcc ccattctcca ggggaggagg ctgaggccca 28080
gagaggtgaa gtcgtgtgcc acaaaatacc ccagccatat ggtggtagaa ccaagttttc 28140
agccagactc accagctcac agcagagctg ccctggactc tacagccatt cagtgtatag 28200
ctgggccact ccatcattca aggcagttca acgtcaagat tcctgatttg cctcaacctg 28260
gggcctctag aagataccat cacccccaac aagctgaaga cgtgtgtccg gaacactcag 28320
acacacacaa agtgctatgg atacaccaca ccccgaccta gctgtctctt cctgatggac 28380
ctcactgggt agaaatgcct ggcaccgcct gcctcagatc cctaggtcag ctctcactcc 28440
ccaatagaag tttctgagat gatgatgaaa acgttctcca tctgtgctgt ccaatggagt 28500
agccactgat cacttgaggc tagtgagcac ttgaaggtgg ctagtttgag gaactgcatt 28560
ttttaatgca tttaatttta gttactttga atatatatac acatatatac atttatatat 28620
acatattcat acacatacat tttacatata ttttatatgt atatgtaata tatatataaa 28680
ttatatatgt atatattttt atatataaat atatattata tatttataaa tatataaata 28740
tataatatat attatataga tatataaata taaatatata ttatatatat aaatatataa 28800
tatatattat ataaatatat ataaattata tatttatata tataatatat aaattatata 28860
aattatatat atttatatat aatatataaa tatatataaa ttatataatt tatatattat 28920
atataaatta tatattttat atataatata tacaatatat ataaattata tataatatat 28980
aaatatatat aaattatata taatatataa aatatatata aattatatat aatatataaa 29040
atatatataa attatataaa tctatataaa tatatactat attataaata tagtatatat 29100
ttatatagat ttatattatt tatatagtat atattatata tttatatgtt tatgtatata 29160
taaatatata atatataaat atatttatat attatatatt tatataatat tttatataat 29220
atgttatata tttttatata atatattata tatatttata t 29261

<210> SEQ ID NO 7
<211> LENGTH: 29261
<212> TYPE: DNA
<213> ORGANISM: Artificial Sequence
<220> FEATURE:
<223> OTHER INFORMATION: modified gene

<400> SEQUENCE: 7
aataaataac tttttagacc atatatttct tttttttttt tttttttttt tgagacagag 60
tctcactctg ttgcccagac tggaatgcag tggcatgacg ttgactcact gtaacctcca 120
cctcaagtga ttcagcctcc caagtagctg ggattacagg tgtgcacgac taccacccag 180
ctaatttttg tgtttttagt acagatgggg tttcaccatg ttggccaggc tggtcttgaa 240
ctcctgacct caaaagtgtg ggggaaagaa agagagatca gactgttact gtgtctatgt 300
agaaaaagga agacataaga aactccattt tgatctgtac taagaaaaat tcttctgcct 360
tgagatgctg ttaatctgta accctagccc caaccctgtg ctcgcagaaa cgtgtgctgt 420
attgactcaa ggtttaatgg atttagggct gtgcaggatg tgctttggta aaaatgtgtt 480
tgcaggcagt atgcttggta aaagtcattg ccattctcca gtctcaagta accagggaca 540

```
ccatacactg cggaaggcag cagggacctc tgcccaagaa aacctgggta ttgtccaaga    600
tttcccccac tgagacagcc tgagagatgg cctcgtggga agggaaagac ctgaccgtcc    660
cccagcccga cacccataaa aggtctgtgc tgaggaggat tagtgaaaga ggaaggcctc    720
tctgcagttg agataagagg agggcatctg tctgctgctc gtccctggga atggaatatc    780
tcggtgtaaa acccgatcgt acattctatt tactgagata ggagaaaact gccttatggc    840
tggaggtgag acacactggc agcaatactg ctctttactg cactgagata tttgtgtaaa    900
gtcaaacata aatctggcct acgtgcacat ccaggcacag ctcctttcct taaatttatc    960
tatgacaccg agtcctttgc tcacgttttc ctgctgaccc tctccccacc attaccctat   1020
agtcctgcca catccccctc accgagatag tagggatagt gatcaataaa tactgaggga   1080
actcagagac cagtgccggt gcaggtcctc acttgctgag caccggtccc ctgggcccac   1140
ttttcttcct ctatactttg tctctgtgtc ttatttcttt tctcagtctc tcgtctccac   1200
cttgtgagaa atactcagag gtgtggaggg gcaggccccc ttcaaaatga tccacccacc   1260
tcagcctccc aaagtgctgg gattacaggc atgagccacc atgcccagcc acatataact   1320
tatttctaaa taacttattt aactaacacc acatgatttt atgacccccct attttatgga   1380
tgagaaaaaa gaggcaagag aagcgatacc agttgcttag gattcccagc taccaattag   1440
tggaagcaga atttgaacca agggagtctc tggagccctc gttcccaatc tccttttctt   1500
cctctccatg tctttctttc tccccctgct cccaggcctc ctacatcaca cccttctgga   1560
caaagcttca catctgacat tttctttttt ggggtggaca gagtcttact ctgtcaccga   1620
ggctggaggg ccgtggcgca atcatggctc atggcagcct caaactcctg ggcttgaggg   1680
atcctccagc ctcagcctcc caagtagctg ggactatggg catgtgccac cacacctggc   1740
taattttta atttttgta gaaatacagg gggtgggggc atatctgaaa attttaaacc   1800
ttccctgact gccgtgagca tttctgggta gaagccactc cacgacctta ctttgctggc   1860
atgagtgctg gacagcaatt tggcaacatc ctctagacca caaatgtgca tggcctttgg   1920
cccagcaaat cagcttctgg gaataaatat gacagatact gttacataca tgggaaatgc   1980
catggacatg atgacccagg gaagcacagt ttgcaagtac aaaagggctg gaaacaccca   2040
aaaagcccat cccctgaaga cagtttcaaa aatgacggtg cattcatgta atggaatagt   2100
acacatttgt gaatgaatga atgaggtagc tcaatatatc tgcctatggg aaaatcacca   2160
agatatgttg ctaagtgaaa aacagaaaga tacagaataa tgctaccatt ttattttta   2220
atgggagagg gaagaataag gaaatggatt catatttgct taattacaca agcttcctga   2280
tgatcctttt ggatccagaa gtttgaaaac cacagcatca agaggatgcc cattgggcat   2340
ggtggctcac gcctgtaatc ccagcacttt gggaggctga ggagggtgga tcgcctaagt   2400
tcaggagttc gagaccagcc tggccaacat ggtgaaaccc catctctact aaaaacacaa   2460
aaaaattagc tgggtatggt ggtgcaggcc tgtaattcca gctacttggg aggctgaggc   2520
gcaagaatca cttaagcctg ggaggcggag gctgccgtga gccgagatca cgccattgca   2580
ctccagcttg ggagacagag caagactgtc tcaaaacaaa caaacacaca caaaaaataa   2640
gatgcccatt ggagatctcc attcactatt ttatcagatg atatttcagc acttgagtga   2700
agaaaatgtc tacaactggt ccaaacactc aaggaattta gactcttgac agagaaacac   2760
acagaagcaa gcagatatgc cccgaaccaa acttgctttt tcttctaagc ctgcttcttc   2820
ggagcagcct ctgaccctcc agggccctga gaggagtccc tggagccaca ggagcttggg   2880
```

```
agcccagaga agtgggggaa tcccagatgg tgacagcatc atccagagga ggaacataac   2940
gatggccaca gattcccaat ttggaaataa ctcagcaaaa caacactgac agaaaattca   3000
gagatttcca agagactagc ctccctgttt ccatttagaa attcacctac atacatccag   3060
ggtgagagac cccaagcatc agatgtgtca tacacaagca tcagatccaa gttagagagg   3120
gcacccgggg acagaaacct ccaagccagc caaaagccaa aggaaggatt ttacagaaag   3180
atacaggaat gtggggccag gcacagtggc tcatgcctgc aatcctagca ctttgggagg   3240
ccgaggtggg aggatcgctt gcggccagga attcaaggcc agcctgagca acatagcgag   3300
atcctatctc tacaacaaat ttaaaaacta gctgggtgtg atcacatatg cctgtggtcc   3360
caactaccca ggaggctgag gcaggagttg agcccaggag gtggaggctg caatgagcaa   3420
tgatggcgcc acttcactcc agcctcagtg aaatagtgag accctgtcta aaaataataa   3480
taaaaataaa aaacatataa agatgtcaga gcacagggac cagagctgtt agtcggcctc   3540
atggagaccc tggccaggac agccacctct ggggaccagg aagtctctca gtttctgtct   3600
ctgagggttt ggctctctga gtctctctgt cacctctcat ttctctctca tctccctctg   3660
tctatgctgt gtctctatct ctttcaatct ctctgtctct gtctcccagc ccttatctct   3720
gagtgtgtct gtttctctct catttctctc tctctctctc tctctttctc tctctctctt   3780
tctctctctc tctttctctc tccccctcc ctcctcccct ctccctactg caggctggtc    3840
cataaccctt atcttcccca gacctgatgg agttctggta ttaatctgtt tatggtctgt   3900
ttccctccac tagaacacgg tcttcattaa aggcagagat ttttgtctgt cttattttct   3960
gctgtatacc cagtgcctgg gatactggct ggatcaataa atatatgctg aatgaagaat   4020
gaatgaatga ccattctcat gaacattatt atttgatgcc aactgtaaag caacaataat   4080
aataattgtc actgccactg ctgctattgt tggtatatca gctttttatt tagtacaaac   4140
tatatccccg aaattgagct aggcagtttc ttgtttaagt tttacagacc acgctgtgag   4200
gtaagtactg ttagtatgcc ctttttcttt tctttttgag acagagtctc actctgtcgc   4260
ccaggctgga gtgcagaggc ccgatcttgg ctcactgcaa cctctgcctc ccgggtacaa   4320
gtgattttcc tgtcttagcc tccccagtag ctgggattac aggcatgtgc caccatgccg   4380
gctaattttt gtatttttag taaagatggg tttttgccat gttggccagg ctggtcttga   4440
actcctggac ctctggtgat cctcctgcct cggcctccca aagtgctggg attacaggcg   4500
tcagccactg cgcttgctcc cccagccccc aaactttttt tttttttttt gagacaggtc   4560
tggctctgcc acccaagctg tagtgtagtg gcgcaatggt agctcactga agcctctaac   4620
tcctgggttc acacagtcct cctgcctcag cctcccaaaa tgctggaatt caggcctgag   4680
ccaccgcgcc ctactatgcc catttttcag ataaagaatc tgagggccct cgaggagaaa   4740
ccacttgccc aacatgagcc ctggtcttgt ctgaccccaa agcccatggg aagtttaggc   4800
tgcgtggaag gacagcctgg tgggctcagg atctgtccca tcacgagttg gaacctcagc   4860
tctgccactc ggcaaccgcg agccgttagt aagttgctga atctctccgt gtgcctccgt   4920
ttcctcacct ggaatgtggg cgacctcaca caggaagccg cctcttctag tgggcaccga   4980
cggagcgagc gcgcgtctgc agcgggactg agcgccggga gagacctgcg caggcgcagg   5040
cgcgcgggga gggccagcct gggtggccca ccccgcgcct ggcgggactg gccgccaact   5100
cccctccgct ccagtcactt gtctggagct tgaagaagtg ggtattcccc ttcccacccc   5160
aggcactgga ggagcggccc cccggggatt ccaggacctg agctccggga gctggactcg   5220
cagcgaccgc ggcagagcga gcgggcgccg ggaagcgagg agacgcccgc gggaggccca   5280
```

```
gctgctcgga gcaactggca tggcccgagc catggccgcc gcgtggccgc tgctgctggt   5340
ggcgctactg gtgctgtcct ggccaccccc aggaaccggt gagtgacccc cgcgcagtcc   5400
ggtggcccct gtctggctcc cagctccgca tccaggccgg gtactcgccc ccttgggttc   5460
ccgaagatga cggccccgcc cggcgccacc caccccccat ctctgccccg gggttggaag   5520
gaacacggtg cgagggtgcg agggcaggac cctcctcttg gccacccgga gagcggtcgg   5580
agttgggtac agaaattcct cgaaattggc agcaacacgg gtcgggcaca agaccctcct   5640
ctgggcccct cggaaagggg atggagttgg gtgaggaaat ttcccaaaaa ggcaagtgaa   5700
tcccggaaaa tcagcagatg gtgacgcatg ccggattacc ttacccaggt tcctgctcag   5760
catacccagg ccataaccca gcagcgtgct ggcaggctgg gtctggacgg aggggatggt   5820
tgatgttggg gaggaggaca gtgggtgaca cttgacacca ttacccctct gacccccaat   5880
gtctgactcc aggggcctgg ccattcattc attctttcat tcttttttttt ttttttttga   5940
gacagtctca ctccatcacc caggctggag tgcagtgtcc tgctctcggc tcactgcagc   6000
ctcctcctcc cgagttcaag cgattctcct gcttcagcct cccgagtagc tcggattaca   6060
gacatgtgcc actatgcctg gctaatattt ttgtattttt agtagataca ggatttcacc   6120
atgttggcca ggctggtctc aaactcctga taaatatata tattatatat tattattata   6180
tattacatat tatagtaata tataataaaa atatataata tatattatag taatatataa   6240
tatataataa aatatataat atatattata gtaatatata atatataata aaatatataa   6300
tatatattat agtaatatat aatatattat aatatattat atatattatt ataatatata   6360
atatgtatat tatatattat atatattatt ataatatata atatgtatat tatatattat   6420
atatattatt ataatatata atatgtatta tgtattatat aattgataat atataataat   6480
atatttctta ataaatatat attaaatata ttatatattt ataacatata ttatttatat   6540
aataaataat atatatttta ttatacattt aaagagtaaa tagataacat attttattat   6600
ttatttatat gttttgtgta tatatatata tatatatata tatatatagt gcgtgtgtgc   6660
gtgtatgtgt gtgtgtgtat gagagagaca aggtcttgct ttgttgccca ggctggagtg   6720
cagtggtaca atcccggctc attgcaaact cgacttccca ggctcaagcg atcctctcac   6780
tgtggcttct ggagtagctg ggattatagg tgctcacctg gctaattttt tttgtatttt   6840
tggtagagac agggtttcgc tatgctgccc aggctggttg cagccaagca cagtggctca   6900
tgcctgtaat cccaacactt tgggaggctg tggtgggagg atcacttgag cttaggaatt   6960
caaaaccagc ctgggcaata tggcaagacc ccatctctac aaaaataatt aactaaataa   7020
aaatttaaaa ataaaaaaga atgcatagga ccatgtttat tagtgtcaat aagcgctgtc   7080
acattttgag gacctactat gtgctagggc ccttagcaga aagattttta tataggacct   7140
gggggattag aggtcagtct ctgaccgccc aagttcaaat cccacctctg ccactaaacc   7200
tctgtatgac ttggaggaca ctatactctg tgtcagtttc cctgtctgta aaatgatgtt   7260
aacagtagtg cttgcctcag gggggctatt tgaggattaa atgccaagat atatgtgaag   7320
cacccagaat agcccctgat ctgtgtcagc accctgtgag tgtccactgt tctaagtctc   7380
attttacaaa ctaggaaaaa gaatcagaga ggttaagtaa ccggcctgaa gctccacagc   7440
agaaaactga agggacccaa aactcctggg ctataattgc cttcctctcg tgcctcaatc   7500
ccccacattc ttccaaccag gacccaccca gagtaataat gcagtgtttc atggatttga   7560
agacccaaga tttctccccg ttttctacat tggggttatt ctaaccccta atggcaagtt   7620
```

```
gtgctataaa tgacaacagt catggtatgt gaaacctacg acactggtgc gatgaaaaag   7680
ttctgggcca ggtgcggtgg ctcatacctg taatcccagc actttgggag gccgtagtgg   7740
gaggatcact tgaggtcagg agttcaagac cagcctggcc aacatggtga aaccccatct   7800
ctgctaaaaa caaaaataca aaaaattagc caggtgtggt ggtgggagcc tgtcatccca   7860
gctacgcgga aagctgaggc aggagaaccg cttgaacccc agaggcagag cttgcagtga   7920
gcagagatcg cgccactgca ctccccctgg gcgacagaga gagactccgt ctcaaaaaaa   7980
aaagagaaga aaagaaaaag ttctggcgct atatagtagt aacggttgca caatatcgtg   8040
aaatgtacat agtgccactg aactgtatgc tttaaatgac ttaaatggta aatttagttt   8100
tttaaccaca atatttacca caattttttta aatcagtgat gttgagattc agggaaatac   8160
ggtaataata gaagaaatac ggtaataaat agccaaagtg aaggagcacg gccaagttgc   8220
agaccatccc agacgccctt accctcctcg cctgccatgg ccccaactag tgccccagtt   8280
ccccctcccc ccacacccca cggtccaccg gggatccagg gccccagcgt gcaagtgcac   8340
gcccaggtgc ccgggctcct ggagcccctc cctatctagt ccaagaacgc cccgggtctg   8400
acaccttctc ttcggttctc cgcaggggac gtcgtcgtgc aggcgcccac ccaggtgccc   8460
ggcttcttgg gcgactccgt gacgctgccc tgctacctac aggtgcccaa catggaggtg   8520
acgcatgtgt cacagctgac ttgggcgcgg catggtgaat ctggcagcat ggccgtcttc   8580
caccaaacgc agggccccag ctattcggag tccaaacggc tggaattcgt ggcagccaga   8640
ctgggcgcgg agctgcggaa tgcctcgctg aggatgttcg ggttgcgcgt agaggatgaa   8700
ggcaactaca cctgcctgtt cgtcacgttc ccgcagggca gcaggagcgt ggatatctgg   8760
ctccgagtgc ttggtgagca gggggttttg gggaggctga atgaaaggca gagacttggt   8820
gggaggatca gggaagttgg caaagagcgg ggaggcctgg gagggaggga gattccctcc   8880
acagcagatc ccctggggac aaaaggaggg ggcagcgcaa tgatgtgggg tggggtgggg   8940
ggaggtgagt ggggggaggg gctgcagggc aggaagaaag cagagatctc agggagtaag   9000
gacccccaag cctgggatca gaaagccctg agggaggagg aggggtatat tggaaaggga   9060
gctgggaggg gactgggaag gaagggagga ggcctgggtg gcctcttctg ggtccctcct   9120
ttcctcatct gtaaaagggt tggtgacaac agcatcaccc ttggaaagct gtcctgagtg   9180
tcatcactgc ctaggaaaga gtctgtctgc cccccttggac tgtgtaccca tgagggcaga   9240
accggggcta ttttgatcac tgctgggccc cagcactttc caccaaacaa tatttattga   9300
gcacttatta tgtgccattc taagagcttt acctgcatat tctaattgcc tgtgattcca   9360
tcattatcac ctgttgacag acaaggaaac tgaggcacag acttgcccaa gaccaaagct   9420
gcagccttag ggcagcggcg cttcaccgct ggcccatgtg agccccttag agctgtcggt   9480
tactgttact ttatctggtg aagaaggaga aagttgaaac agacagacag gaaagcaagg   9540
atcctgatac ccaaaagagg aggggatcat gctttcattt tcatgagctc catgaagcct   9600
tcctcttgga acttgagcaa gaagtctctg tgcctcagtt tcctcatctg tgggataggg   9660
atcaccatga ggattcaaaa aaactgaccc ttttttttttt tttgagatag tttagttctg   9720
tcgcccaggc tggagtgcag tggtgtgatc atagtaggtc ctcactgcag cctggaactc   9780
ctgggctcaa gggatgttcc taccctccct gtagctggaa ttacaggaat gtgccaccat   9840
gcccaacttg ttttctgttt tgttttgttt tgttttgttt tcttttcttt ttaagcttat   9900
gtgccaagaa ctattccaag cctgtgcatg agaaactcat gaaatgtcaa gggcttggaa   9960
ctgtgcctag cacacaacac ccaaccaaag gcagctgttg tcactccagc aagcctggga  10020
```

```
ttctgggtat catggtttag gatgagggta aaacagaaac agtgagtcaa gttaaggaga  10080
aatcttcggt aaataatata ggtaatgatg gggaaggaag ttccaggttt gggaatcacc  10140
aggatgatga ttaagagatg gtcaaggtgg ttttggagtc agacagactt tatgtgaaag  10200
cccagctctg ctgcttacag ctgtgtgacc atgggcaagt cacttccctt ctcaacttca  10260
gggctcaggc ttcctctcct ccactgagcc ccagaccagg ataaccccct ttgggtttcc  10320
cctttccagc cctgccctct ccgagtcatc actgcctagg aaagagtccg tctgccccct  10380
tggactgtgt acccatgagg gcagaaccag ggctattttg gtcactgctg ggctccagca  10440
ctttccacca aacaatattt attgagcgct tattatatac cattctaaga gctttacctg  10500
catattctca ttgcctgtga tcccatcact atcccctgtc aacagacaag gaaactgagg  10560
cacagacttg cccaagacca cacagctgct cagggacaca gctgggattt aaaccatgcc  10620
attctgtatc tttttttttt tttttttttt gagacagaat ctcactctgt cgcccaggct  10680
ggagagcagt gacacaatct cagctcactg caacctccgc ctcccgagtt caagcaattc  10740
tctggtctca gcctcccaag taactgggat tactggcgtg tgccaccata ccctggctaa  10800
tttttaatag agacagtttc tccatgttgg ccaggctggt ctcgaactcc tgaccccaag  10860
tgatccaccc acctcagccc cccaaagttc tgggattata ggcgtgagcc accccgccca  10920
gcaaccatgc catcctgtac ccttaatgaa tgcccccttc tgccacggag gggttcattg  10980
aatgacttgt tgcttttgtt cctcttccca gccaagcccc agaacacaga cctgggcggg  11040
atgcccaata cgagccaggt gccagggttc ctgtctggca cagtcactgt caccagcctc  11100
tggatattgg tgccctcaag ccaggtggac ggcaagaatg tgacctgcaa ggtggagcac  11160
gagagctttg agaagcctca gctgctgact gtgaacctca ccgtgtactg tgagtgtgcc  11220
caagtcagcg atggcaagaa cccctgccgg gctgccccca ccactgtcta cactgactcc  11280
ccaaggcact gtaggcattg cttccatcat ctgcaccggc tcccctgact cctgtctaca  11340
cgacccaccc ccattgtctg caccagctcc cctgggccgt aaacaacact gtccctattg  11400
tctacaccag tttacttggg ccatagtcaa tgctggtacc cagactgtct gccctggctc  11460
ctctagcggc tgtctgcacg gatacctgac actctgttga ctcccttgag cacagtctac  11520
actgccccta aactgcctac acccatttcc ccaggcaagt atccacaatg accctcccca  11580
cattgctaca ctggttcttc tggccacgat caacactgcc tcccttattg tctacaccca  11640
ctcccttgtc cttttctttc tttccttttt tttttttttt ttttgaaata gagtctcact  11700
ctgttaccca ggctgcagta cagtggcatg ttctcggctc actgtaacct ctgcctccca  11760
aattcaggtg gttctcctac ctcagcctcc caaatagctg ggattaaagg tgcacaccac  11820
cacacctggc taatttttgt atttttagta gagacagggt ttcatcatgt tggccaggct  11880
ggtttcgaac tcctgacctc aggtgatcgg cctgcctcag cctcccaaag tatgctggaa  11940
ttataggcat gagccactgt gcccggcttt ttgttttgtt ttgtttttcc tttggacagg  12000
gtctcgctct gtcacccagg ctggagtgta ggggcatgat catggttcct acagcctcac  12060
ccttccaggc tcaagcaatc cttctccctc agcctcccaa gtaactggga ctacaggtgc  12120
agccaccatg cccggctaat tttacagttt ttttctagag agagttttgc tgtgttgccc  12180
aggctggtct caaactccta ggcttaagtg atcctcccgc ctcagtctcc cgaagtgctg  12240
agattacagg cgtgagccac tgcacctggc cccttgtcca ttttctacac tgccttacca  12300
ttgtctacac tggctctcct gggccacaga cagcactaac cccattgtct acaccaccta  12360
```

ttttggccac cagctgtggg gtgttttcac tgtctcccat agtgtctaca ctggctccta 12420
tgaccactgt ctatgtaaac accccacttt ttctacactg gttctcctag gcactctcta 12480
aagtgccccc tgacactgtc tacactgact ccctggagaa ctgtctgcat tcacctccca 12540
cattgtatcg accagttccc ctgagccacg atcaactgtc tccgccgggt gctagttgca 12600
ttgatcttct cacattgttt gtgctggctc ccctaagcag tgtctgcaga gtcccccagt 12660
gtagtctcca tgttcctctg cccaatattg tctacactgg ctcatctaca ggctatccag 12720
tctcacccca catcaccaca ctggcctcct tgtgttctgt ctgcacagcc ccctgacagc 12780
atctgtcctg attctcctgc acagcgttac ctccaccagc tccctcatgg catcatcgac 12840
attgacaccc acacatttat ctccactgac agccccagga ctctctaacc agtgctgtct 12900
aacagaaata gcatgcaagc tgcatatagg attttaaatt ctccagcggc caccccatta 12960
aaaaattaaa agaaagaggc caggcacggt ggctcacgcc tgtaatccca gcactttggg 13020
aggccgaggc aggtggatca cctgaggtca ggcattcaag accagcctga tcaatgtggt 13080
gaaactctgt cttcactaaa aaatacaaaa attagccagg cacggtggcg ggtgcctgta 13140
atcccagcta ctcgggagac tgaggcagga gaatcacttg aacctgggag gcggagattg 13200
caatgagcga gattacgcca ttgcactcca gcctgggcag cagagcaaaa ctccatctca 13260
aaaacaagaa aagaaagaga tgaaatttat ttgtttattt atttatctat ttatttattt 13320
gagacggggt cttactctgt cacccagact ggagtgcagt ggcacagctc cctgcagcct 13380
caacctcctg ggcttaagtg atcctcccac ctcagcctca gtctcctgag tagctgggac 13440
tacaggcgtg tgacaccatg cctagctaat ttttgttttt gtttttgttt ttgttttttt 13500
gttttgtgat gaagtcttgc tctgtcaccc aggctagagt gcagtggcac gatctcaact 13560
cactgcagcc tccgcctctc gggttcaagt gattctcctg cctcagcctc ccgagtagct 13620
gggattacaa gccctggcca cagtgcccag ctaatttttg tatttgtggt agagacggga 13680
tttcaccatg ttggccaggc tggtctcaaa ctcctgacct cgtgatccac ccaccttggc 13740
ctcccaaatt gctgggatta cagacgtgag ccaccgcacc cggcctattt ttattttttc 13800
tggagacagg atctccctat gttgcccagg ctggtctcaa actcctgggc tcaagtgatc 13860
ctcctgcctc aacctcccaa ggtactggga ttacaggcat gagccactgt gcctggccaa 13920
aattaatttt taataattgc ctttacttaa cccaatatac ctaaaatatt atttcaactt 13980
gtaattgttt ttttaaaatt attcttgaga tctttcccat ttattttgtc ctagtaaagc 14040
ctttgaaatc tggtgtgtat ttcggcctgg ctatatttcg agtgctcagt agtcacatgt 14100
ggccagtagg tgccatattg gacagcacag atctagacta agctcccaca tcatctacac 14160
tggctcatcc aaatactgtc tacacacata cacagagcct gtcttaattt cgtcagctcc 14220
cggggacaca ctgtatatgt gggggtgatc tcacccccac caccacattt tcaacactgg 14280
cccgacaata tagcatctgc tgtaatattc caacaccctg tctacactga acccatcagt 14340
aatatccaca caagctcttc tagacatcat tcatactgtt cctcccacca ttgtctatac 14400
tgcttactcc ccgccaggca attggtacac agattccctc aggtactgtc tatactggag 14460
tccctcaaca ctgtcactgg gtctgagcga ggaggagatc tacactgact cctacccctc 14520
gcccccgaat aaaaccctgt cccattggcc tgcccccaag gacattgaaa ggtcttcgct 14580
gtcaatcacg tatgggatgg ctgagcagca gcctagagca gggttatctg ggactctttc 14640
ctgcaggact tgtcagaacc ttgaatacac tgctgtgtgt tgtgagtggt cattgcctat 14700
gagtgagaaa aggaggaggc atttcctgc aggacaccca agacatgcct ggtccaggct 14760

```
acccaggaaa gctagtggag aaaagcagct cctcagaagc cttctccatg tccccactga  14820
ccaaggactc ctaggcttct gctctctgtg gcaccccatc tacctagact cctcctaggc  14880
ctctccagct cccgctgttt tccaaatatc cccgggcctt ttcctgcagt gtcgtgaatc  14940
ccgcgtagcc ccaggccccc caaagcctcc cagtctctga acctctgtat ccatttcctg  15000
cagacccccc agaggtatcc atctctggct atgataacaa ctggtacctt ggccagaatg  15060
aggccaccct gacctgcgat gctcgcagca acccagagcc cacaggctat aattggagca  15120
cgtgagtcct gggtctcagg gaggaggggc tgggggtctg gatttctagc actgagggag  15180
gaggggctgg gggcctggac tcctgggact gagggagaag gggctggggg cccggacccc  15240
tgggtctgag ggacgagagg ctgggagccc ggactcctgg gtctgaggga agaggggctg  15300
ggggtctgga cccctgggac tgagagagga ggggctgggc ctggacccct gggtctgagg  15360
gaggaggggc tggggggtct ggacccctgg gtctgaggga ggagaagctg ggagcctgga  15420
cccctgggtc tgaggcagga cagactgggg cctggactcc tggtctaaga gaggagggag  15480
attcagaaaa gagaaaaaga ggaggttgac ttcgggcccc cagtgggggg catctctgtt  15540
ttgacatctc tgttttgcgg ttgaggcgtt tagcaggtgg ttgaatcctg gctggtggat  15600
gcacctgctt tttggggtgt gcctgctctg tgcccggtac ttcccccgaa tcccatgtga  15660
ccccatgctg tgcacagtca gcagctgttg ccctgcccag gttaaagacc agccacgaga  15720
gggcagaagc ggcccttgaa tcagcgctcg gctccaaagc tggtcctccg cctcttggcc  15780
aagcttgtct aacctgcagg ccacatcatt tgtaaacttt cttaaaacat tatgagactt  15840
tttttttgcg aatttttta gctcattagc tattgttagt gttagtgtat tttatgtatg  15900
gcccaggaca gttcttcttc ttccaatgtg gcccggggaa gccaaaagat tggacacccc  15960
cactctagac tgtaaccacc tcaccgtcac cttgtgtaac ctacttggtt atctctggat  16020
ggagcaagta ctatatatcc ccattgtcta gatgagaaag ttgaggctca cagcaataag  16080
atttccccag attcacactg aggctgagat caagagcaag gtaagaaaaa ggcaaagaga  16140
taatacataa ttttataata cataatttta cataaattac ataattttac tgaaccgccc  16200
ttttttttta aagaaggggc tctgttgccg aggctggagt gcagtggcgt gatcatagct  16260
cactgcagcc tggacctccc tgggctcagg tgatcctccc acctcagcct cctgagtagc  16320
tgggactaca ggcacacgcc accacactca gctaattttg ttgtattttt tttgcagaga  16380
cagggttttg ccacattgcc caggctggtc tgcaactcct gggctcaagc aatcaaccca  16440
cctcagcctc ctaaagtgct gggattacag gcgtgagcca cctcgcccag ccttaggtct  16500
ttttccttat tacaaaaata acttgtgtcc actgtagaaa tatcaaacaa tttagttatg  16560
agcaaaaaga agaaagtagt gcctatagtt caagtgtacc cagccacctc cagaaatacc  16620
cagtgacccc ttattataca tcctgtcttt tttctctctg tttctaaaca aagactggaa  16680
ttatgctgta catataattt tgaacctttt cgtctgtctt gtgaatacct ttccatgtca  16740
aagcacatag atccacaact ccattttccc ccacgttgta ttaggaagac tgtcaaacat  16800
acagaaaaat cataggaatt ttccagtgaa cacttaagat tccaccacgt ggattcccct  16860
gctaacattt tactgtgctt gctttatcac gtttctgtga ttccttcagt ccctctattc  16920
atccatcaat catattatgc atttcagagc acccccagct ctcctgcttt tttttttttt  16980
tttttttttt tgaggcaggg cctcactctg ttgctcaggc tgtagtgccg tggcacaatc  17040
acagctcact gcagccttga attcctgggc tcaagcgatc ctccagcttc agcctcccag  17100
```

atagctggga ctacaggcac acaccaccac gcctggctaa cctggcccct tttttagtgt 17160
tgctgggatt ccaccacttt aaaaaaaaaa ttcaaagaat agagacagga tctcactatg 17220
ttgcccaggc tggtcttgaa ctcctgtact caagcagtca tctcacctgg cctcccaaa 17280 gggcagggaa gggattccaa catatgtgga tgtcatcagt tatttaacca gtccctagta 17340
gaggacacag atgtcatttt ccattttcaa ctctgcaaat gccatggtgg tgtccatccc 17400
cactggtcac ttgtcagcag ttgtccgtgg aaggaattgc cggtcaaagg ttttcaactg 17460
gtgtgatggt gcctttactg tcctgcctca aagcaccgca attcaggctc ttgagccaga 17520
tagctgcgtt tgcatcccag ctctgcggag cacccaaagc ctgatgcttc catctcctcc 17580
acctctgttc attaaaccag tgttccttga ctacttactg tgtgccgggt gcaattaacc 17640
aacatacgtt ggtcgataaa acagaccaaa tttcctcccc atatagagct tccattctag 17700
tggtgaaaga aacaagaagc aagataaagt gtgtagtgtg tgtgcaatgg tgataaatac 17760
catggagaag acaaagcaga gaagggaatg ggactgggcg ccatgactca tacctgtaat 17820
cccagcactt tgggaggcag agatgggagg atcacttgag gctaggagtt caagaccagc 17880
ctggccaaca tggcgaaacc ccatctctac caaaaaagat acaaaaattg gccgggtgtg 17940
gtggcatgca cctgtagtcc cagctactca ggaggctgag gtgggaagat tccatgcacc 18000
caggaggtgg aggttgcagt gagtcaagat ggtgccactg cactccagcc tgggtgacag 18060
agtgagacgc tgtctcaaaa aaataataat taaataaatt aaagagaagg ggatgggaag 18120
ggtgatcatc acagttgaaa tagggtggcc aagtgaggtg ttactaaggt gacatcccag 18180
cagaggcctg aaggagatga gggtgagctc tgcgggtgcc tagggggaaa gcattccagc 18240
agagggaaca gcatgggcaa acccatttct atccatcagt ccctgcataa gcaaacaccc 18300
tggacaccta actggagagt ttgaggacca acaaagaggc cactgtggat gcagaggcgg 18360
gagcaaaggg gagagtaatg gaaaacgtgg gcagaggtag caggggccag atcacgtggg 18420
gcctgtgaca ccagaagact tcggtttaac tctgagccag gctaggcccc cagagggtac 18480
tgagctgagg tatgggaact gacttagggt tcacaggcga cctctggtgg ccatgtgggg 18540
aacagacgag ggggcgaggg cagaaacgga gcccagcgtg gaggcggctg ctgggggccg 18600
ggatgcacag cgccagagca gggaggtacc gtggaagccc tgaggagagg tgggattctg 18660
gatggatctt aaggcggggc cgacatgatt ggctaatggg ttgggtgtgg gcatgagagg 18720
aagggaagag ttggggggcc tccagagttg ctctccgctt atgctataga gggcgtgagg 18780
gtttctgggc acgtagtgcg tgctcaatca ctgtcactcc ggacctgcag cagaggccac 18840
ctcctcacct ttctgtctct cccaggacca tgggtcccct gccacccttt gctgtggccc 18900
agggcgccca gctcctgatc cgtcctgtgg acaaaccaat caacacaact ttaatctgca 18960
acgtcaccaa tgccctagga gctcgccagg cagaactgac cgtccaggtc aaaggtgagg 19020
aactccctgg gtgggaagaa cagggaccaa aggaagaggt cgaggcaggg ttccctgtct 19080
aatgctctct ggctcccatc cttctcctaa gccttctcac aaaaggacca gtggggccag 19140
ctttactccc ctgttaactc catacctata tcactggtac cgttgttcag ctgcctggat 19200
acactccctc cacacacaca ggttgggata gatgtggaat ccctctctct cagggactca 19260
ggcctttcca aatatattag gcagacctct atcaattgca attgacagaa acacaaagta 19320
gtctaagcaa aaaaaaccaa acaaaacagg actttattga aaattcacct tcaggtatgg 19380
ttagatccag gggctccaac cttgtaaccc aggaactttt attttataca tctcttgtct 19440
ctgcttttcg ttatactggc tttattctca ggcaggctct gaagcaagat ggccctcggc 19500
agggacaggc tcacattcta ccagaatggc aacagcagga gaaaaaacat accactttca 19560
gtaactgtag ccatagtccc agggctggct ctcattggcc cagcttaggc cacagcccac 19620
ctatgaacca atcatagcag ccagggagaa tggaatattc tgattggcca ggcctgtgtc 19680
aaagtcccat tctgggcacc agagggtggg atccattcca cctgaattaa atagactgag 19740
gcagtggagt ggtggctccc taaggaaatt caagatgcca tttcaagaat gagggataaa 19800
ccccaagagt ttccttacct aaatacctgt ttccttctct ttcagaggga cctcccagtg 19860
agcactcagg catgtcccgt aacgccatca tcttcctggt tctgggaatc ctggtttttc 19920
tgatcctgct ggggatcggg atttatttct attggtccaa atgttcccgt gaggtccttt 19980
ggcactgtca tctgtgtccc tcgagtgagc atcaccagag ctgccgtaat tgagcaccta 20040
ctacgggctc tgtgctgagt ccttccagtg tgcctctcac tgaatcctca ccccactgcc 20100
atgaggtttc ccccatttga ctgatgaggg tgcagagcca gggagccttg ttcactggtt 20160
cattgattac atttacaaat attatttaca gagtgggaga agagcgtata gggtcttaat 20220
gccatggtag ggactttgga atttaattca ggtgatgtgg gagtccctgc cagatggatg 20280
gagggtgaaa taatgcttaa gccctcagcc ttactccatc tgccttgttc aggagtgact 20340
cctaggagga ggtggcagga actggcacct ctgatcctca gctctaaaag ggtctgatgc 20400
tttcacacct caagagattt gcacaggccg ttcccctgcc tggagcaccc tcccatggct 20460
ccttctggag aagtgtgcca gctcattctg taatcagagg aacgatgctt tgctgagcac 20520
tgtctacatg ccactttgta tgtataaccc cctcgatttt aatttttaat ttttttttatt 20580
atttatgtat ttatttattt atttttgaga caggctctca ctgtcgccca ggctggagtg 20640
cagtggtgcg atctcggctc actgtagcct tcacctccca ggttcaagcg attctcatgc 20700
ctcagcctcc caaggagcgg ggattacagg cacgcactac tatgcccagc aatttttgta 20760
tttttaggag agacagcgtt tcgccatgtt ggccaggctg gtctcaaacc cctggtctcc 20820
tgtgatccac ccgcctcagc ctcccaaagt gctgggatta caggcatgag ccaccacacc 20880
tggcctgtac aatctccttg aatgcccaca accacccagc aaagtggttc tcccgtgagc 20940
cccatgttac agaggaggaa gtatttgctt tgagagatga agttacctgc caatggtcaa 21000
acagctggac atggttgttg ggagaagaa gccagatctt tgactaccaa gcttttcctt 21060
caaccactaa acaaagctgc tcccttacaa cccaggcgga tactgcctcg tccaggaagc 21120
cctccctgac ccccaagcat gagccaagca tccactaggc tctcccactc cagccttgcc 21180
cattctgggt catcaccgtg gggacttgt ttgtcatccc cagtggactg tgagccccaa 21240
gatagcagac ctgaggctgt cactgtcatg actgtgtccc caggaccgcc taccactggg 21300
ccgggcataa aagaggcact cgaggaagtg tttgctgagt gattcaatgt gtcagctcca 21360
gagccagact gcctgtatct gggccctaaa gctactgctt gattagtgat gtcaccatag 21420
gcaaatagct taagctgtat gactcagttt cctcatctgt aaaatggggt gatggtacct 21480
aataatacag tagagcactt aacacagtag gtggcacatg gtaagccaca tactgagtat 21540
gtatttgcta tgattgttat tgctattatt actattattg ttattattaa cataaactgc 21600
acaagagcag gctttttgtt tgtttgtttg tgttttgttt tgagacaaga tcttgctctg 21660
ttgcccagac tggagtagtg cagtgatgtg atcttggctc actgcagcct caacctccca 21720
ggctcaggtg attctcccac ctcagcctct cgagtagctg ggattatagg cgtgcactcc 21780
cacgcctggc taattttttta tatttttagt agagatggag tttcgttgtg ttgcccaagc 21840

```
tggtctcaaa ctcctagact ccagcaatcc gcccacctca gcctcccaga gtgctggaat  21900
tataggtgtg agccaccacg cctggccaag agcaggcatt tttatctgtt ttgttcacag  21960
ctgtgtcccc agcacctaga atgtacctgg cacaaagtag acattcacca tttgctgaat  22020
aatactacta tttgctaaat aaacccctgt tgaatagtct aggaaactga acacagagag  22080
gttaagtcac ttgtccaagt tcacacagct cctaaaggac agagatggaa tttgaaccca  22140
tccatctggt tccagagcca ggctcgatat ttatggatat ttcataacca agtgaataac  22200
tggatggcta aatccttaga aagcacaccc tccatccctg tctgacacac gtgtatacca  22260
ttaagggaaa tggcaccccc atgtaatagc agaggcagaa cttgacattt tcagggccct  22320
gacacccagg catgtcttct tcccatgctt cccagcatta ttccttcctg acgacttccc  22380
ctcctatttc cccaggtaca gagcatgcca gcgcctcagc taatggggta agtgcagtgt  22440
tggagctaag gagggtgtgg ggtctgcacg aactacagac cagacgtctt cagatgccca  22500
cggcccggcc tcaggagcct gggtcttttc tcctggtgcc tcgagcagca tttcccaacc  22560
cttcctgctg ggcggaatcc cctgtagagt ttgctaagac gcagccccag acagtctggt  22620
ctgtgatggg gccagggaat ctgcatttta atatccgctc tctccccccct gccccacgcc  22680
ccttcaattc cacccatggc cacaccttga gaagcactgc cctggcttcc agggagagag  22740
gaggggacgg gcctgcagtt ctttgcacat ggggcttcag tgggaagatg tttgattttg  22800
ttcaaaagag ccccaaggct aaaatttgaa aaccctcttc tagcatgtct cctattcagc  22860
tgtgagcaga gagaacagct cttcccagga tccacagaca gagggcacaa ggtgacagcg  22920
tcgggactga gaggggagag agactggagc tggcaaggac gtgggcctcc agagttggac  22980
ccgaccccaa tggatgaaga ccccctccaa agagaccagc ctccctccct gtgccagacc  23040
tcaaaacgac gggggcaggt gcaagttcat aggtctccaa gaccaccctc ctttcatttg  23100
ctagaaggac tcactagact caggaaagct gttaggctca cagttacagt ttattacagt  23160
aaaaggacag agattaagat cagcaaaggg aggaggtgca cagcacacgt tccacgacag  23220
atgaggcgac ggcttccatc tgccctctcc cagtggagcc atataggcag cacctgattc  23280
tcacagcaac atgtgacaac atgcaagaag tactgccaat actgccaacc agagcagctc  23340
actcgagatc tttgtgtcca gagtttttttg tttgtcttga gacagggtct ggctctgttg  23400
gcagactaga gtacagtggt gagatcacag ttcattgcag ccttgacttc tcaacgccaa  23460
gtcatcctcc cacctcagcc tcctgagtag ctatgactac aggtatgtgc caccacgtct  23520
ggctaatctt tttattattt gtaaagtcga ggtttccctg tgttgcccag gctggtcttg  23580
aactcttggc tccaagtgat acttctgcct tggcctccca aagtgctgaa ttaagcagct  23640
caccatccac acggctgacc tcatacatca agccaatacc gtgtggccca agacccccac  23700
cataaatcac atcattagca tgaaccaccc agagtggccc aagactccaa gatcagctac  23760
caggcaggat attccaaggg cttagagatg aatgcccagg agctgaggat aaagggcccg  23820
atctttcttt gggcaaggtt aagcctttac tgcatagcag accacacaga agggtgtggg  23880
ccaccagaga attttggtaa aaatttggcc tctggccttg agcttctaaa tctctgtatc  23940
cgtcagatct ctgtggttac aagaaacagc cactgaccct ggtcaccaga ggctgcaatt  24000
caggccgcaa gcagctgcct ggggggtgtc caaggagcag agaaaactac tagatgtgaa  24060
cttgaagaag gttgtcagct gcagccactt tctgccagca tctgcagcca ctttctgcca  24120
gcatctgcag ccagcaagct gggactggca ggaaataacc cacaaaagaa gcaaatgcaa  24180
tttccaacac aagggggaag ggatgcaggg ggaggcagcg ctgcagttgc tcaggacacg  24240
```

ctcctatagg accaagatgg atgcgaccca agacccagga ggcccagctg ctcagtgcaa 24300
ctgacaagtt aaaaaggtct atgatcttga gggcagacag cagaattcct cttataaaga 24360
aaactgtttg ggaaaatacg ttgagggaga gaagaccttg ggccaagatg ctaaatggga 24420
atgcaaagct tgagctgctc tgcaagagaa aataagcagg acagaggatt tgctctggac 24480
agagatggaa gagccgggaa cagagaagtg tggggaagag ataggaacca gcaggatggc 24540
aggggcaaag ggctcaaggg tgaggaggcc agtgggaccc cacagagttg ggagataaa 24600
ggaacattgg ttgctttggt ggcacgtaag ctccttgtct gtctccagca cccagaatct 24660
cattaaagct tatttattgt acctccagcg gctgtgtgca atggggtctt ttgtggaaat 24720
caaggagcag acaggtttca tgtgtactgt caccacgtgg gatggaacca gaggcatgga 24780
agcaagacgc taaatgaaga gggccataag ggctgggatt cccaggcacc ttaggaacag 24840
cttgtctttt tttttttcct ctccaaaaaa aatgtttaag ggacggtgtc tcctgtcacc 24900
caggctggag tgcaatggca cgatcatagc tcattgcagc ctctaactcc ggggctcaag 24960
caatcctccc acctcagcct accaagtagc tgtgaccaca gctgcccctc accatgctaa 25020
gctaattttt ttaattagat agtacataaa cgtcccaaaa ttagaagata aaaagacatg 25080
agggatccat tctaatttgt gtttggagtg taatggtcca gctccattct tctgcacatg 25140
gatatccagt tttacacaac actgtgaatg taatgaatgc cactgaatca tacactcaaa 25200
aatagctaaa atggcaaatt gtctgttatc tctttttaac caccattttt gaaaattaat 25260
tataccaaaa aaccattgaa tagtgcactt tatttattta tttatttgtt tatttattta 25320
tttattttag aaataagagt ctcactttgt tgcccaggct ggagtgcagt ggcgtgatca 25380
tggctcattg cagcctcgac ctgctgggct cgggctatcc ttccatctca gcctcccgag 25440
tagctgggac tataggtggg cgccacccca cctggctaaa tctcttttta acttttgtag 25500
agataggcat ctcgctatgt tgcctaggct gggctggaac tcctgggctc aagtgctcct 25560
cctgccttgg cctcccaaag cgctaggatt acagatgtga gccaccgcgc ccaccctgaa 25620
ccttactttt tttgctcagt ttctggtaat tcagagaatg cctcctgagt tgttctacac 25680
ccacctcata ttccatggga gggctgtaca gggctttttt aacgaggcct ctaaggacag 25740
gcatttgtat cctttccagc ctttcactat tacaatgttg tagtgaataa ctttacacac 25800
tgtcatttat tttacttttt ttttttttta ttttagagaa aggaatcttg ccatcttgcc 25860
caggctggtc tcaaattcct gggcccaaac aatcctcccg ccttggcctc ctaaagtact 25920
gggatttata ggcataagcc accgtgcctg gccaatgcac actgtcattt agctcatgtt 25980
aacacctgag tgtaggacac actcctggag gtggaattgc tgggccaaag agtatgtttc 26040
ttgtcattgt gatagatatt gacaaatgaa ccctcacaga agttgtgctg agttctgttc 26100
ccaccagcga cgtaggcgat gaccttttc tggagggagg gggcatcctt ggagtccaca 26160
gagccaggaa tggagagtgg gcccagaatt ttggtatagg tgttgtataa acttatagta 26220
aggttaagaa aaccgcaact atccttatca gagacttggc ggggggcagg gtatgatgga 26280
gatcataagg aggctaaaac actccacacc ctccctctgc attgctcctg cacgggagtc 26340
gggaatcttt tcaggttgat acgatctcac cttgaggagc tgtgaggtcc cagaagcctc 26400
tgggttgcag attgcttggg gtgaaaatgt ctgtgctact gaaatctaac tttttacaaa 26460
aaattacggg ctgggcgcag tggctcacgc ctgtaatccc agcactttgg gaggctgcag 26520
cgggtggatc acttgaggta aggagttcaa gaccagacca tagtgaaacc gtgtctctac 26580

-continued aaaaaaaatt agccaggtgt ggtggtgcat gcttgtaatc ccagctactc agaaggctga 26640
ggtgggagaa tcccttgaac ccgggaagtg gaggctggag taaaccatga tcgagttact 26700
gcactccagc ctgggtgaca agagtgagac tctgtctcca aaaaaaaaaa aaaaaaaaaa 26760
aaaactggat tgcctggctc tactccgggc acagcatgca ggcccagttc tgctgctctg 26820
ctgtttgttc tgctttcctc cacatattgg catcaccctc tggtgccaag atggctgctg 26880
cattccaggc atcacatcca gactcagacc cagagaagct gcccatccct acctgggtga 26940
gcctttgtag gaacgagaaa ccgcatccag cagcagaaac ctcacccagc agcgtctttt 27000
ccggtctcat tcaccagcgc cgcccaccgc tcaaccaatc cctggccaaa agaatgggac 27060
cgcctggaag gctggaccaa acaggacctg ccctctgggg ctggggagag gcccagatga 27120
aggctgcagg acaggatgga ctcctagacc tctgttacca gcagtgacta cctctgtctg 27180
ggtggttgga acatgtttga attttattct aagtactgtc tacaagttct gcaataaacc 27240
ttgactcttc ttttaataat gcaaaaggaa tcgaagtgat tgtttgaaag ggagaggaag 27300
aaagagagag ggagggaggg aagaatggag ggaggcaggg aaggagacag agagagtaga 27360
atccagccac cggaaaatcc agaatagctg gctttgctta atccatgcct ggaaataact 27420
gctgggtttg caacaacttc tctcccggag acagaccaag gaaactacaa aactgcagga 27480
aggattgaag ggccgggcac agtggctcac gcctgtaatc ccaacacttt gggaggccga 27540
ggtggattgg atcacctgag atcaggagtt cgagaccagc ctggccaaca tggtgaaacc 27600
tcgtctctgc tagaaataca aaaataagcc gggcgtggtg gcgtgcgcct atagtcccag 27660
ctactcggga ggctgaggca agagaatcgc ttgaacctgg gaggtggagg ttgcagtgag 27720
ctgagatcgt gccactgcac tccagcttgg gcgacagagt gagaatctgt caggtggatt 27780
ctgagggtac tctgacccca cgaacccagc atgaaatctt ccaggcatta aggaacattg 27840
aggatgtgga ggattggaaa tccctccagg gaaaatacac ttctcttgag cagggtcacg 27900
aggggtgggg gcaatgtggg aggtggggca aatccaaaga caaggtcaac agcaataata 27960
ataataacaa tgacaggcat ttgttgcttg ttggctgggc ctcttgcata cagttctccc 28020
aacatccctg tgaggtggtg atgcttatcc ccattctcca ggggaggagg ctgaggccca 28080
gagaggtgaa gtcgtgtgcc acaaaatacc ccagccatat ggtggtagaa ccaagttttc 28140
agccagactc accagctcac agcagagctg ccctggactc tacagccatt cagtgtatag 28200
ctgggccact ccatcattca aggcagttca acgtcaagat tcctgatttg cctcaacctg 28260
gggcctctag aagataccat cacccccaac aagctgaaga cgtgtgtccg gaacactcag 28320
acacacacaa agtgctatgg atacaccaca ccccgaccta gctgtctctt cctgatggac 28380
ctcactgggt agaaatgcct ggcaccgcct gcctcagatc cctaggtcag ctctcactcc 28440
ccaatagaag tttctgagat gatgatgaaa acgttctcca tctgtgctgt ccaatggagt 28500
agccactgat cacttgaggc tagtgagcac ttgaaggtgg ctagtttgag gaactgcatt 28560
ttttaatgca tttaatttta gttactttga atatatatac acatatatac atttatatat 28620
acatattcat acacatacat tttacatata ttttatatgt atatgtaata tatatataaa 28680
ttatatatgt atatattttt atatataaat atatattata tatttataaa tatataaata 28740
tataatatat attatataga tatataaata taaatatata ttatatatat aaatatataa 28800
tatatattat ataaatatat ataaattata tatttatata tataatatat aaattatata 28860
aattatatat atttatatat aatatataaa tatatataaa ttatataatt tatatattat 28920
atataaatta tatattttat atataatata tacaatatat ataaattata tataatatat 28980
aaatatatat aaattatata taatatataa aatatatata aattatatat aatatataaa 29040
atatatataa attatataaa tctatataaa tatatactat attataaata tagtatatat 29100
ttatatagat ttatattatt tatatagtat atattatata tttatatgtt tatgtatata 29160
taaatatata atatataaat atatttatat attatatatt tatataatat tttatataat 29220
atgttatata tttttatata atatattata tatatttata t 29261

<210> SEQ ID NO 8
<211> LENGTH: 29243
<212> TYPE: DNA
<213> ORGANISM: Artificial Sequence
<220> FEATURE:
<223> OTHER INFORMATION: modified gene

<400> SEQUENCE: 8
aataaataac tttttagacc atatatttct tttttttttt tttttttttt tgagacagag 60
tctcactctg ttgcccagac tggaatgcag tggcatgacg ttgactcact gtaacctcca 120
cctcaagtga ttcagcctcc caagtagctg ggattacagg tgtgcacgac taccacccag 180
ctaatttttg tgtttttagt acagatgggg tttcaccatg ttggccaggc tggtcttgaa 240
ctcctgacct caaaagtgtg ggggaaagaa agagagatca gactgttact gtgtctatgt 300
agaaaaagga agacataaga aactccattt tgatctgtac taagaaaaat tcttctgcct 360
tgagatgctg ttaatctgta accctagccc caaccctgtg ctcgcagaaa cgtgtgctgt 420
attgactcaa ggtttaatgg atttagggct gtgcaggatg tgctttggta aaaatgtgtt 480
tgcaggcagt atgcttggta aaagtcattg ccattctcca gtctcaagta accagggaca 540
ccatacactg cggaaggcag cagggacctc tgcccaagaa aacctgggta ttgtccaaga 600
tttcccccac tgagacagcc tgagagatgg cctcgtggga agggaaagac ctgaccgtcc 660
cccagcccga cacccataaa aggtctgtgc tgaggaggat tagtgaaaga ggaaggcctc 720
tctgcagttg agataagagg agggcatctg tctgctgctc gtccctggga atggaatatc 780
tcggtgtaaa acccgatcgt acattctatt tactgagata ggagaaaact gccttatggc 840
tggaggtgag acacactggc agcaatactg ctctttactg cactgagata tttgtgtaaa 900
gtcaaacata aatctggcct acgtgcacat ccaggcacag ctcctttcct taaatttatc 960
tatgacaccg agtcctttgc tcacgttttc ctgctgaccc tctccccacc attaccctat 1020
agtcctgcca catccccctc accgagatag tagggatagt gatcaataaa tactgaggga 1080
actcagagac cagtgccggt gcaggtcctc acttgctgag caccggtccc ctgggcccac 1140
ttttcttcct ctatactttg tctctgtgtc ttatttcttt tctcagtctc tcgtctccac 1200
cttgtgagaa atactcagag gtgtggaggg gcaggccccc ttcaaaatga tccacccacc 1260
tcagcctccc aaagtgctgg gattacaggc atgagccacc atgcccagcc acatataact 1320
tatttctaaa taacttattt aactaacacc acatgatttt atgacccccct attttatgga 1380 tgagaaaaaa gaggcaagag aagcgatacc agttgcttag gattcccagc taccaattag 1440
tggaagcaga atttgaacca agggagtctc tggagccctc gttcccaatc tccttttctt 1500
cctctccatg tctttctttc tccccctgct cccaggcctc ctacatcaca cccttctgga 1560
caaagcttca catctgacat tttctttttt ggggtggaca gagtcttact ctgtcaccga 1620
ggctggaggg ccgtggcgca atcatggctc atggcagcct caaactcctg ggcttgaggg 1680
atcctccagc ctcagcctcc caagtagctg ggactatggg catgtgccac cacacctggc 1740

```
taatttttta atttttgta gaaatacagg gggtgggggc atatctgaaa attttaaacc   1800
ttccctgact gccgtgagca tttctgggta gaagccactc cacgacctta ctttgctggc   1860
atgagtgctg gacagcaatt tggcaacatc ctctagacca caaatgtgca tggcctttgg   1920
cccagcaaat cagcttctgg gaataaatat gacagatact gttacataca tgggaaatgc   1980
catggacatg atgacccagg gaagcacagt ttgcaagtac aaaagggctg gaaacaccca   2040
aaaagcccat cccctgaaga cagtttcaaa aatgacggtg cattcatgta atggaatagt   2100
acacatttgt gaatgaatga atgaggtagc tcaatatatc tgcctatggg aaaatcacca   2160
agatatgttg ctaagtgaaa aacagaaaga tacagaataa tgctaccatt ttatttttta   2220
atgggagagg gaagaataag gaaatggatt catatttgct taattacaca agcttcctga   2280
tgatcctttt ggatccagaa gtttgaaaac cacagcatca agaggatgcc cattgggcat   2340
ggtggctcac gcctgtaatc ccagcacttt gggaggctga ggagggtgga tcgcctaagt   2400
tcaggagttc gagaccagcc tggccaacat ggtgaaaccc catctctact aaaaacacaa   2460
aaaaattagc tgggtatggt ggtgcaggcc tgtaattcca gctacttggg aggctgaggc   2520
gcaagaatca cttaagcctg ggaggcggag gctgccgtga gccgagatca cgccattgca   2580
ctccagcttg ggagacagag caagactgtc tcaaaacaaa caaacacaca caaaaaaataa   2640
gatgcccatt ggagatctcc attcactatt ttatcagatg atatttcagc acttgagtga   2700
agaaaatgtc tacaactggt ccaaacactc aaggaattta gactcttgac agagaaacac   2760
acagaagcaa gcagatatgc cccgaaccaa acttgctttt tcttctaagc ctgcttcttc   2820
ggagcagcct ctgaccctcc agggccctga gaggagtccc tggagccaca ggagcttggg   2880
agcccagaga agtgggggaa tcccagatgg tgacagcatc atccagagga ggaacataac   2940
gatggccaca gattcccaat ttggaaataa ctcagcaaaa caacactgac agaaaattca   3000
gagatttcca agagactagc ctccctgttt ccatttagaa attcacctac atacatccag   3060
ggtgagagac cccaagcatc agatgtgtca tacacaagca tcagatccaa gttagagagg   3120
gcacccgggg acagaaacct ccaagccagc caaaagccaa aggaaggatt ttacagaaag   3180
atacaggaat gtggggccag gcacagtggc tcatgcctgc aatcctagca ctttgggagg   3240
ccgaggtggg aggatcgctt gcggccagga attcaaggcc agcctgagca acatagcgag   3300
atcctatctc tacaacaaat ttaaaaacta gctgggtgtg atcacatatg cctgtggtcc   3360
caactaccca ggaggctgag gcaggagttg agcccaggag gtggaggctg caatgagcaa   3420
tgatggcgcc acttcactcc agcctcagtg aaatagtgag accctgtcta aaaataataa   3480
taaaaataaa aaacatataa agatgtcaga gcacagggac cagagctgtt agtcggcctc   3540
atggagaccc tggccaggac agccacctct ggggaccagg aagtctctca gtttctgtct   3600
ctgagggttt ggctctctga gtctctctgt cacctctcat ttctctctca tctccctctg   3660
tctatgctgt gtctctatct ctttcaatct ctctgtctct gtctcccagc ccttatctct   3720
gagtgtgtct gtttctctct catttctctc tctctctctc tctctttctc tctctctctt   3780
tctctctctc tctttctctc tccccccctcc ctcctcccct ctccctactg caggctggtc   3840
cataaccctt atcttcccca gacctgatgg agttctggta ttaatctgtt tatggtctgt   3900
ttccctccac tagaacacgg tcttcattaa aggcagagat ttttgtctgt cttattttct   3960
gctgtatacc cagtgcctgg gatactggct ggatcaataa atatatgctg aatgaagaat   4020
gaatgaatga ccattctcat gaacattatt atttgatgcc aactgtaaag caacaataat   4080
aataattgtc actgccactg ctgctattgt tggtatatca gctttttatt tagtacaaac   4140
```

```
tatatccccg aaattgagct aggcagtttc ttgtttaagt tttacagacc acgctgtgag   4200
gtaagtactg ttagtatgcc cttttttctt tctttttgag acagagtctc actctgtcgc   4260
ccaggctgga gtgcagaggc ccgatcttgg ctcactgcaa cctctgcctc ccgggtacaa   4320
gtgattttcc tgtcttagcc tccccagtag ctgggattac aggcatgtgc caccatgccg   4380
gctaattttt gtatttttag taaagatggg tttttgccat gttggccagg ctggtcttga   4440
actcctggac ctctggtgat cctcctgcct cggcctccca aagtgctggg attacaggcg   4500
tcagccactg cgcttgctcc cccagccccc aaactttttt tttttttttt gagacaggtc   4560
tggctctgcc acccaagctg tagtgtagtg gcgcaatggt agctcactga agcctctaac   4620
tcctgggttc acacagtcct cctgcctcag cctcccaaaa tgctggaatt caggcctgag   4680
ccaccgcgcc ctactatgcc catttttcag ataaagaatc tgagggccct cgaggagaaa   4740
ccacttgccc aacatgagcc ctggtcttgt ctgaccccaa agcccatggg aagtttaggc   4800
tgcgtggaag gacagcctgg tgggctcagg atctgtccca tcacgagttg gaacctcagc   4860
tctgccactc ggcaaccgcg agccgttagt aagttgctga atctctccgt gtgcctccgt   4920
ttcctcacct ggaatgtggg cgacctcaca caggaagccg cctcttctag tgggcaccga   4980
cggagcgagc gcgcgtctgc agcgggactg agcgccggga gagacctgcg caggcgcagg   5040
cgcgcgggga gggccagcct gggtggccca ccccgcgcct ggcgggactg gccgccaact   5100
cccctccgct ccagtcactt gtctggagct tgaagaagtg ggtattcccc ttcccacccc   5160
aggcactgga ggagcggccc cccggggatt ccaggacctg agctccggga gctggactcg   5220
cagcgaccgc ggcagagcga gcgggcgccg ggaagcgagg agacgcccgc gggaggccca   5280
gctgctcgga gcaactggca tggcccgagc catggccgcc gcgtggccgc tgctgctggt   5340
ggcgctactg gtgctgtcct ggccaccccc aggaaccggt gagtgacccc cgcgcagtcc   5400
ggtggcccct gtctggctcc cagctccgca tccaggccgg gtactcgccc ccttgggttc   5460
ccgaagatga cggccccgcc cggcgccacc cacccccat ctctgccccg gggttggaag    5520
gaacacggtg cgagggtgcg agggcaggac cctcctcttg gccacccgga gagcggtcgg   5580
agttgggtac agaaattcct cgaaattggc agcaacacgg gtcgggcaca agaccctcct   5640
ctgggcccct cggaaagggg atggagttgg gtgaggaaat ttcccaaaaa ggcaagtgaa   5700
tcccggaaaa tcagcagatg gtgacgcatg ccggattacc ttacccaggt tcctgctcag   5760
catacccagg ccataaccca gcagcgtgct ggcaggctgg gtctggacgg aggggatggt   5820
tgatgttggg gaggaggaca gtgggtgaca cttgacacca ttacccctct gacccccaat   5880
gtctgactcc aggggcctgg ccattcattc attctttcat tctttttttt tttttttga    5940
gacagtctca ctccatcacc caggctggag tgcagtgtcc tgctctcggc tcactgcagc   6000
ctcctcctcc cgagttcaag cgattctcct gcttcagcct cccgagtagc tcggattaca   6060
gacatgtgcc actatgcctg gctaatattt ttgtattttt agtagataca ggatttcacc   6120
atgttggcca ggctggtctc aaactcctga taaatatata tattatatat tattattata   6180
tattacatat tatagtaata tataataaaa atatataata tatattatag taatatataa   6240
tatataataa aatatataat atatattata gtaatatata atatataata aaatatataa   6300
tatatattat agtaatatat aatatattat aatatattat atatattatt ataatatata   6360
atatgtatat tatatattat atatattatt ataatatata atatgtatat tatatattat   6420
atatattatt ataatatata atatgtatta tgtattatat aattgataat atataataat   6480
```

```
atatttctta ataaatatat attaaatata ttatatattt ataacatata ttatttatat   6540
aataaataat atatatttta ttatacattt aaagagtaaa tagataacat attttattat   6600
ttatttatat gttttgtgta tatatatata tatatatata tatatatagt gcgtgtgtgc   6660
gtgtatgtgt gtgtgtgtat gagagagaca aggtcttgct ttgttgccca ggctggagtg   6720
cagtggtaca atcccggctc attgcaaact cgacttccca ggctcaagcg atcctctcac   6780
tgtggcttct ggagtagctg ggattatagg tgctcacctg gctaattttt tttgtatttt   6840
tggtagagac agggtttcgc tatgctgccc aggctggttg cagccaagca cagtggctca   6900
tgcctgtaat cccaacactt tgggaggctg tggtgggagg atcacttgag cttaggaatt   6960
caaaaccagc ctgggcaata tggcaagacc ccatctctac aaaaataatt aactaaataa   7020
aaatttaaaa ataaaaaaga atgcatagga ccatgtttat tagtgtcaat aagcgctgtc   7080
acattttgag gacctactat gtgctagggc ccttagcaga aagattttta tataggacct   7140
gggggattag aggtcagtct ctgaccgccc aagttcaaat cccacctctg ccactaaacc   7200
tctgtatgac ttggaggaca ctatactctg tgtcagtttc cctgtctgta aaatgatgtt   7260
aacagtagtg cttgcctcag gggggctatt tgaggattaa atgccaagat atatgtgaag   7320
cacccagaat agcccctgat ctgtgtcagc accctgtgag tgtccactgt tctaagtctc   7380
attttacaaa ctaggaaaaa gaatcagaga ggttaagtaa ccggcctgaa gctccacagc   7440
agaaaactga agggacccaa aactcctggg ctataattgc cttcctctcg tgcctcaatc   7500
ccccacattc ttccaaccag gacccaccca gagtaataat gcagtgtttc atggatttga   7560
agacccaaga tttctccccg ttttctacat tggggttatt ctaaccccta atggcaagtt   7620
gtgctataaa tgacaacagt catggtatgt gaaacctacg acactggtgc gatgaaaaag   7680
ttctgggcca ggtgcggtgg ctcatacctg taatcccagc actttgggag gccgtagtgg   7740
gaggatcact tgaggtcagg agttcaagac cagcctggcc aacatggtga aaccccatct   7800
ctgctaaaaa caaaaataca aaaaattagc caggtgtggt ggtgggagcc tgtcatccca   7860
gctacgcgga aagctgaggc aggagaaccg cttgaacccc agaggcagag cttgcagtga   7920
gcagagatcg cgccactgca ctccccctgg gcgacagaga gagactccgt ctcaaaaaaa   7980
aaagagaaga aaagaaaaag ttctggcgct atatagtagt aacggttgca caatatcgtg   8040
aaatgtacat agtgccactg aactgtatgc tttaaatgac ttaaatggta aatttagttt   8100
tttaaccaca atatttacca caattttttta aatcagtgat gttgagattc agggaaatac   8160
ggtaataata gaagaaatac ggtaataaat agccaaagtg aaggagcacg gccaagttgc   8220
agaccatccc agacgccctt accctcctcg cctgccatgg ccccaactag tgccccagtt   8280
ccccctcccc ccacacccca cggtccaccg gggatccagg gccccagcgt gcaagtgcac   8340
gcccaggtgc ccgggctcct ggagcccctc cctatctagt ccaagaacgc cccgggtctg   8400
acaccttctc ttcggttctc cgcaggggac gtcgtcgtgc aggcgcccac ccaggtgccc   8460
ggcttcttgg gcgactcctt acaggtgccc aacatggagg tgacgcatgt gtcacagctg   8520
acttgggcgc ggcatggtga atctggcagc atggccgtct tccaccaaac gcagggcccc   8580
agctattcgg agtccaaacg gctggaattc gtggcagcca gactgggcgc ggagctgcgg   8640
aatgcctcgc tgaggatgtt cgggttgcgc gtagaggatg aaggcaacta cacctgcctg   8700
ttcgtcacgt tcccgcaggg cagcaggagc gtggatatct ggctccgagt gcttggtgag   8760
cagggggttt tggggaggct gaatgaaagg cagagacttg gtgggaggat cagggaagtt   8820
ggcaaagagc ggggaggcct gggagggagg gagattccct ccacagcaga tcccctgggg   8880
```

acaaaaggag ggggcagcgc aatgatgtgg ggtggggtgg ggggaggtga gtggggggag 8940
gggctgcagg gcaggaagaa agcagagatc tcagggagta aggacccccca agcctgggat 9000
cagaaagccc tgagggagga ggaggggtat attggaaagg gagctgggag gggactggga 9060
aggaagggag gaggcctggg tggcctcttc tgggtccctc ctttcctcat ctgtaaaagg 9120
gttggtgaca acagcatcac ccttggaaag ctgtcctgag tgtcatcact gcctaggaaa 9180
gagtctgtct gccccccttgg actgtgtacc catgagggca gaaccggggc tattttgatc 9240
actgctgggc cccagcactt tccaccaaac aatatttatt gagcacttat tatgtgccat 9300
tctaagagct ttacctgcat attctaattg cctgtgattc catcattatc acctgttgac 9360
agacaaggaa actgaggcac agacttgccc aagaccaaag ctgcagcctt agggcagcgg 9420
cgcttcaccg ctggcccatg tgagcccctt agagctgtcg gttactgtta ctttatctgg 9480
tgaagaagga gaaagttgaa acagacagac aggaaagcaa ggatcctgat acccaaaaga 9540
ggaggggatc atgctttcat tttcatgagc tccatgaagc cttcctcttg gaacttgagc 9600
aagaagtctc tgtgcctcag tttcctcatc tgtgggatag ggatcaccat gaggattcaa 9660
aaaaactgac cctttttttt tttttgagat agtttagttc tgtcgcccag gctggagtgc 9720
agtggtgtga tcatagtagg tcctcactgc agcctggaac tcctgggctc aagggatgtt 9780
cctaccctcc ctgtagctgg aattacagga atgtgccacc atgcccaact tgttttctgt 9840
tttgttttgt tttgttttgt tttcttttct ttttaagctt atgtgccaag aactattcca 9900
agcctgtgca tgagaaactc atgaaatgtc aagggcttgg aactgtgcct agcacacaac 9960
acccaaccaa aggcagctgt tgtcactcca gcaagcctgg gattctgggt atcatggttt 10020
aggatgaggg taaaacagaa acagtgagtc aagttaagga gaaatcttcg gtaaataata 10080
taggtaatga tggggaagga agttccaggt ttgggaatca ccaggatgat gattaagaga 10140
tggtcaaggt ggttttggag tcagacagac tttatgtgaa agcccagctc tgctgcttac 10200
agctgtgtga ccatgggcaa gtcacttccc ttctcaactt cagggctcag gcttcctctc 10260
ctccactgag ccccagacca ggataacccc ctttgggttt ccccttttcca gccctgccct 10320
ctccgagtca tcactgccta ggaaagagtc cgtctgcccc cttggactgt gtacccatga 10380
gggcagaacc agggctattt tggtcactgc tgggctccag cactttccac caaacaatat 10440
ttattgagcg cttattatat accattctaa gagctttacc tgcatattct cattgcctgt 10500
gatcccatca ctatcccctg tcaacagaca aggaaactga ggcacagact tgcccaagac 10560
cacacagctg ctcagggaca cagctgggat ttaaaccatg ccattctgta tctttttttt 10620
tttttttttt ttgagacaga atctcactct gtcgcccagg ctggagagca gtgacacaat 10680
ctcagctcac tgcaacctcc gcctcccgag ttcaagcaat tctctggtct cagcctccca 10740
agtaactggg attactggcg tgtgccacca taccctggct aatttttaat agagacagtt 10800
tctccatgtt ggccaggctg gtctcgaact cctgacccca agtgatccac ccacctcagc 10860
cccccaaagt tctgggatta taggcgtgag ccacccccgcc cagcaaccat gccatcctgt 10920
acccttaatg aatgcccccct tctgccacgg aggggttcat tgaatgactt gttgcttttg 10980
ttcctcttcc cagccaagcc ccagaacaca gacctgggcg ggatgcccaa tacgagccag 11040
gtgccagggt tcctgtctgg cacagtcact gtcaccagcc tctggatatt ggtgccctca 11100
agccaggtgg acggcaagaa tgtgacctgc aaggtggagc acgagagctt tgagaagcct 11160
cagctgctga ctgtgaacct caccgtgtac tgtgagtgtg cccaagtcag cgatggcaag 11220

```
aacccctgcc gggctgcccc caccactgtc tacactgact ccccaaggca ctgtaggcat  11280
tgcttccatc atctgcaccg gctcccctga ctcctgtcta cacgacccac ccccattgtc  11340
tgcaccagct cccctgggcc gtaaacaaca ctgtccctat tgtctacacc agtttacttg  11400
ggccatagtc aatgctggta cccagactgt ctgccctggc tcctctagcg gctgtctgca  11460
cggatacctg acactctgtt gactcccttg agcacagtct acactgcccc taaactgcct  11520
acacccattt ccccaggcaa gtatccacaa tgaccctccc cacattgcta cactggttct  11580
tctggccacg atcaacactg cctcccttat tgtctacacc cactcccttg tccttttctt  11640
tctttccttt tttttttttt ttttttgaaa tagagtctca ctctgttacc caggctgcag  11700
tacagtggca tgttctcggc tcactgtaac ctctgcctcc caaattcagg tggttctcct  11760
acctcagcct cccaaatagc tgggattaaa ggtgcacacc accacacctg gctaattttt  11820
gtatttttag tagagacagg gtttcatcat gttggccagg ctggtttcga actcctgacc  11880
tcaggtgatc ggcctgcctc agcctcccaa agtatgctgg aattataggc atgagccact  11940
gtgcccggct ttttgttttg ttttgttttt cctttggaca gggtctcgct ctgtcaccca  12000
ggctggagtg taggggcatg atcatggttc ctacagcctc acccttccag gctcaagcaa  12060
tccttctccc tcagcctccc aagtaactgg gactacaggt gcagccacca tgcccggcta  12120
attttacagt ttttttctag agagagtttt gctgtgttgc ccaggctggt ctcaaactcc  12180
taggcttaag tgatcctccc gcctcagtct cccgaagtgc tgagattaca ggcgtgagcc  12240
actgcacctg gccccttgtc cattttctac actgccttac cattgtctac actggctctc  12300
ctgggccaca gacagcacta accccattgt ctacaccacc tattttggcc accagctgtg  12360
gggtgttttc actgtctccc atagtgtcta cactggctcc tatgaccact gtctatgtaa  12420
acaccccact ttttctacac tggttctcct aggcactctc taaagtgccc cctgacactg  12480
tctacactga ctccctggag aactgtctgc attcacctcc cacattgtat cgaccagttc  12540
ccctgagcca cgatcaactg tctccgccgg gtgctagttg cattgatctt ctcacattgt  12600
ttgtgctggc tcccctaagc agtgtctgca gagtccccca gtgtagtctc catgttcctc  12660
tgcccaatat tgtctacact ggctcatcta caggctatcc agtctcaccc cacatcacca  12720
cactggcctc cttgtgttct gtctgcacag ccccctgaca gcatctgtcc tgattctcct  12780
gcacagcgtt acctccacca gctccctcat ggcatcatcg acattgacac ccacacattt  12840
atctccactg acagccccag gactctctaa ccagtgctgt ctaacagaaa tagcatgcaa  12900
gctgcatata ggattttaaa ttctccagcg gccaccccat taaaaaatta aaagaaagag  12960
gccaggcacg gtggctcacg cctgtaatcc cagcactttg ggaggccgag gcaggtggat  13020
cacctgaggt caggcattca agaccagcct gatcaatgtg gtgaaactct gtcttcacta  13080
aaaaatacaa aaattagcca ggcacggtgg cgggtgcctg taatcccagc tactcgggag  13140
actgaggcag gagaatcact tgaacctggg aggcggagat tgcaatgagc gagattacgc  13200
cattgcactc cagcctgggc agcagagcaa aactccatct caaaaacaag aaaagaaaga  13260
gatgaaattt atttgtttat ttatttatct atttatttat ttgagacggg gtcttactct  13320
gtcacccaga ctggagtgca gtggcacagc tccctgcagc ctcaacctcc tgggcttaag  13380
tgatcctccc acctcagcct cagtctcctg agtagctggg actacaggcg tgtgacacca  13440
tgcctagcta atttttgttt ttgtttttgt ttttgttttt ttgttttgtg atgaagtctt  13500
gctctgtcac ccaggctaga gtgcagtggc acgatctcaa ctcactgcag cctccgcctc  13560
tcgggttcaa gtgattctcc tgcctcagcc tcccgagtag ctgggattac aagccctggc  13620
```

```
cacagtgccc agctaatttt tgtatttgtg gtagagacgg gatttcacca tgttggccag  13680
gctggtctca aactcctgac ctcgtgatcc acccaccttg gcctcccaaa ttgctgggat  13740
tacagacgtg agccaccgca cccggcctat ttttattttt tctggagaca ggatctccct  13800
atgttgccca ggctggtctc aaactcctgg gctcaagtga tcctcctgcc tcaacctccc  13860
aaggtactgg gattacaggc atgagccact gtgcctggcc aaaattaatt tttaataatt  13920
gcctttactt aacccaatat acctaaaata ttatttcaac ttgtaattgt tttttaaaa  13980
ttattcttga gatctttccc atttattttg tcctagtaaa gcctttgaaa tctggtgtgt  14040
atttcggcct ggctatattt cgagtgctca gtagtcacat gtggccagta ggtgccatat  14100
tggacagcac agatctagac taagctccca catcatctac actggctcat ccaaatactg  14160
tctacacaca tacacagagc ctgtcttaat ttcgtcagct cccggggaca cactgtatat  14220
gtgggggtga tctcaccccc accaccacat tttcaacact ggcccgacaa tatagcatct  14280
gctgtaatat tccaacaccc tgtctacact gaacccatca gtaatatcca cacaagctct  14340
tctagacatc attcatactg ttcctcccac cattgtctat actgcttact ccccgccagg  14400
caattggtac acagattccc tcaggtactg tctatactgg agtccctcaa cactgtcact  14460
gggtctgagc gaggaggaga tctacactga ctcctacccc tcgcccccga ataaaaccct  14520
gtcccattgg cctgccccca aggacattga aaggtcttcg ctgtcaatca cgtatgggat  14580
ggctgagcag cagcctagag cagggttatc tgggactctt tcctgcagga cttgtcagaa  14640
ccttgaatac actgctgtgt gttgtgagtg gtcattgcct atgagtgaga aaaggaggag  14700
gcattttcct gcaggacacc caagacatgc ctggtccagg ctacccagga aagctagtgg  14760
agaaaagcag ctcctcagaa gccttctcca tgtccccact gaccaaggac tcctaggctt  14820
ctgctctctg tggcacccca tctacctaga ctcctcctag gcctctccag ctcccgctgt  14880
tttccaaata tccccgggcc ttttcctgca gtgtcgtgaa tcccgcgtag ccccaggccc  14940
cccaaagcct cccagtctct gaacctctgt atccatttcc tgcagacccc ccagaggtat  15000
ccatctctgg ctatgataac aactggtacc ttggccagaa tgaggccacc ctgacctgcg  15060
atgctcgcag caacccagag cccacaggct ataattggag cacgtgagtc ctgggtctca  15120
gggaggaggg gctgggggtc tggatttcta gcactgaggg aggaggggct gggggcctgg  15180
actcctggga ctgagggaga aggggctggg ggcccggacc cctgggtctg agggacgaga  15240
ggctgggagc ccggactcct gggtctgagg gaagaggggc tgggggtctg gacccctggg  15300
actgagagag gaggggctgg gcctggaccc ctgggtctga gggaggaggg gctgggggt  15360
ctggacccct gggtctgagg gaggagaagc tgggagcctg gacccctggg tctgaggcag  15420
gacagactgg ggcctggact cctggtctaa gagaggaggg agattcagaa aagagaaaaa  15480
gaggaggttg acttcgggcc cccagtgggg ggcatctctg ttttgacatc tctgttttgc  15540
ggttgaggcg tttagcaggt ggttgaatcc tggctggtgg atgcacctgc tttttggggt  15600
gtgcctgctc tgtgcccggt acttcccccg aatcccatgt gaccccatgc tgtgcacagt  15660
cagcagctgt tgccctgccc aggttaaaga ccagccacga gagggcagaa gcggcccttg  15720
aatcagcgct cggctccaaa gctggtcctc cgcctcttgg ccaagcttgt ctaacctgca  15780
ggccacatca tttgtaaact ttcttaaaac attatgagac ttttttttg cgaatttttt  15840
tagctcatta gctattgtta gtgttagtgt attttatgta tggcccagga cagttcttct  15900
tcttccaatg tggcccgggg aagccaaaag attggacacc cccactctag actgtaacca  15960
```

cctcaccgtc accttgtgta acctacttgg ttatctctgg atggagcaag tactatatat 16020
ccccattgtc tagatgagaa agttgaggct cacagcaata agatttcccc agattcacac 16080
tgaggctgag atcaagagca aggtaagaaa aaggcaaaga gataatacat aattttataa 16140
tacataattt tacataaatt acataatttt actgaaccgc cctttttttt taaagaaggg 16200
gctctgttgc cgaggctgga gtgcagtggc gtgatcatag ctcactgcag cctggacctc 16260
cctgggctca ggtgatcctc ccacctcagc ctcctgagta gctgggacta caggcacacg 16320
ccaccacact cagctaattt tgttgtattt tttttgcaga gacagggttt tgccacattg 16380
cccaggctgg tctgcaactc ctgggctcaa gcaatcaacc cacctcagcc tcctaaagtg 16440
ctgggattac aggcgtgagc cacctcgccc agccttaggt ctttttcctt attacaaaaa 16500
taacttgtgt ccactgtaga aatatcaaac aatttagtta tgagcaaaaa gaagaaagta 16560
gtgcctatag ttcaagtgta cccagccacc tccagaaata cccagtgacc ccttattata 16620
catcctgtct tttttctctc tgtttctaaa caaagactgg aattatgctg tacatataat 16680
tttgaacctt ttcgtctgtc ttgtgaatac ctttccatgt caaagcacat agatccacaa 16740
ctccattttc ccccacgttg tattaggaag actgtcaaac atacagaaaa atcataggaa 16800
ttttccagtg aacacttaag attccaccac gtggattccc ctgctaacat tttactgtgc 16860
ttgctttatc acgtttctgt gattccttca gtccctctat tcatccatca atcatattat 16920
gcatttcaga gcacccccag ctctcctgct tttttttttt tttttttttt tttgaggcag 16980
ggcctcactc tgttgctcag gctgtagtgc cgtggcacaa tcacagctca ctgcagcctt 17040
gaattcctgg gctcaagcga tcctccagct tcagcctccc agatagctgg gactacaggc 17100
acacaccacc acgcctggct aacctggccc ctttttttagt gttgctggga ttccaccact 17160
ttaaaaaaaa aattcaaaga atagagacag gatctcacta tgttgcccag gctggtcttg 17220
aactcctgta ctcaagcagt catctcacct gggcctccca aagggcaggg aagggattcc 17280
aacatatgtg gatgtcatca gttatttaac cagtccctag tagaggacac agatgtcatt 17340
ttccattttc aactctgcaa atgccatggt ggtgtccatc cccactggtc acttgtcagc 17400
agttgtccgt ggaaggaatt gccggtcaaa ggttttcaac tggtgtgatg gtgcctttac 17460
tgtcctgcct caaagcaccg caattcaggc tcttgagcca gatagctgcg tttgcatccc 17520
agctctgcgg agcacccaaa gcctgatgct tccatctcct ccacctctgt tcattaaacc 17580
agtgttcctt gactacttac tgtgtgccgg gtgcaattaa ccaacatacg ttggtcgata 17640
aaacagacca aatttcctcc ccatatagag cttccattct agtggtgaaa gaaacaagaa 17700
gcaagataaa gtgtgtagtg tgtgtgcaat ggtgataaat accatggaga agacaaagca 17760
gagaagggaa tgggactggg cgccatgact catacctgta atcccagcac tttgggaggc 17820
agagatggga ggatcacttg aggctaggag ttcaagacca gcctggccaa catggcgaaa 17880
ccccatctct accaaaaaag atacaaaaat tggccgggtg tggtggcatg cacctgtagt 17940
cccagctact caggaggctg aggtgggaag attccatgca cccaggaggt ggaggttgca 18000
gtgagtcaag atggtgccac tgcactccag cctgggtgac agagtgagac gctgtctcaa 18060
aaaaataata attaaataaa ttaaagagaa ggggatggga agggtgatca tcacagttga 18120
aatagggtgg ccaagtgagg tgttactaag gtgacatccc agcagaggcc tgaaggagat 18180
gagggtgagc tctgcgggtg cctaggggga aagcattcca gcagagggaa cagcatgggc 18240
aaacccattt ctatccatca gtccctgcat aagcaaacac cctggacacc taactggaga 18300
gtttgaggac caacaaagag gccactgtgg atgcagaggc gggagcaaag gggagagtaa 18360
tggaaaacgt gggcagaggt agcaggggcc agatcacgtg gggcctgtga caccagaaga 18420
cttcggttta actctgagcc aggctaggcc cccagagggt actgagctga ggtatgggaa 18480
ctgacttagg gttcacaggc gacctctggt ggccatgtgg ggaacagacg agggggcgag 18540
ggcagaaacg gagcccagcg tggaggcggc tgctgggggc cgggatgcac agcgccagag 18600
cagggaggta ccgtggaagc cctgaggaga ggtgggattc tggatggatc ttaaggcggg 18660
gccgacatga ttggctaatg ggttgggtgt gggcatgaga ggaagggaag agttgggggg 18720
cctccagagt tgctctccgc ttatgctata gagggcgtga gggtttctgg gcacgtagtg 18780
cgtgctcaat cactgtcact ccggacctgc agcagaggcc acctcctcac ctttctgtct 18840
ctcccaggac catgggtccc ctgccaccct ttgctgtggc ccagggcgcc cagctcctga 18900
tccgtcctgt ggacaaacca atcaacacaa ctttaatctg caacgtcacc aatgccctag 18960
gagctcgcca ggcagaactg accgtccagg tcaaaggtga ggaactccct gggtgggaag 19020
aacagggacc aaaggaagag gtcgaggcag ggttccctgt ctaatgctct ctggctccca 19080
tccttctcct aagccttctc acaaaaggac cagtggggcc agctttactc ccctgttaac 19140
tccataccta tatcactggt accgttgttc agctgcctgg atacactccc tccacacaca 19200
caggttggga tagatgtgga atccctctct ctcagggact caggcctttc caaatatatt 19260
aggcagacct ctatcaattg caattgacag aaacacaaag tagtctaagc aaaaaaaacc 19320
aaacaaaaca ggactttatt gaaaattcac cttcaggtat ggttagatcc aggggctcca 19380
accttgtaac ccaggaactt ttattttata catctcttgt ctctgctttt cgttatactg 19440
gctttattct caggcaggct ctgaagcaag atggccctcg gcagggacag gctcacattc 19500
taccagaatg gcaacagcag gagaaaaaac ataccacttt cagtaactgt agccatagtc 19560
ccagggctgg ctctcattgg cccagcttag gccacagccc acctatgaac caatcatagc 19620
agccagggag aatggaatat tctgattggc caggcctgtg tcaaagtccc attctgggca 19680
ccagagggtg ggatccattc cacctgaatt aaatagactg aggcagtgga gtggtggctc 19740
cctaaggaaa ttcaagatgc catttcaaga atgagggata aaccccaaga gtttccttac 19800
ctaaatacct gtttccttct ctttcagagg gacctcccag tgagcactca ggcatgtccc 19860
gtaacgccat catcttcctg gttctgggaa tcctggtttt tctgatcctg ctggggatcg 19920
ggatttattt ctattggtcc aaatgttccc gtgaggtcct ttggcactgt catctgtgtc 19980
cctcgagtga gcatcaccag agctgccgta attgagcacc tactacgggc tctgtgctga 20040
gtccttccag tgtgcctctc actgaatcct caccccactg ccatgaggtt tcccccattt 20100
gactgatgag ggtgcagagc cagggagcct tgttcactgg ttcattgatt acatttacaa 20160
atattattta cagagtggga gaagagcgta tagggtctta atgccatggt agggactttg 20220
gaatttaatt caggtgatgt gggagtccct gccagatgga tggagggtga aataatgctt 20280
aagccctcag ccttactcca tctgccttgt tcaggagtga ctcctaggag gaggtggcag 20340
gaactggcac ctctgatcct cagctctaaa agggtctgat gctttcacac ctcaagagat 20400
ttgcacaggc cgttcccctg cctggagcac cctcccatgg ctccttctgg agaagtgtgc 20460
cagctcattc tgtaatcaga ggaacgatgc tttgctgagc actgtctaca tgccactttg 20520
tatgtataac cccctcgatt ttaattttta atttttttta ttatttatgt atttatttat 20580
ttatttttga gacaggctct cactgtcgcc caggctggag tgcagtggtg cgatctcggc 20640
tcactgtagc cttcacctcc caggttcaag cgattctcat gcctcagcct cccaaggagc 20700
ggggattaca ggcacgcact actatgccca gcaatttttg tatttttagg agagacagcg 20760
tttcgccatg ttggccaggc tggtctcaaa cccctggtct cctgtgatcc acccgcctca 20820
gcctcccaaa gtgctgggat tacaggcatg agccaccaca cctggcctgt acaatctcct 20880
tgaatgccca caaccaccca gcaaagtggt tctcccgtga gccccatgtt acagaggagg 20940
aagtatttgc tttgagagat gaagttacct gccaatggtc aaacagctgg acatggttgt 21000
tggggagaag aagccagatc tttgactacc aagcttttcc ttcaaccact aaacaaagct 21060
gctcccttac aacccaggcg gatactgcct cgtccaggaa gccctccctg acccccaagc 21120
atgagccaag catccactag gctctcccac tccagccttg cccattctgg gtcatcaccg 21180
tgggggactt gtttgtcatc cccagtggac tgtgagcccc aagatagcag acctgaggct 21240
gtcactgtca tgactgtgtc cccaggaccg cctaccactg ggccgggcat aaaagaggca 21300
ctcgaggaag tgtttgctga gtgattcaat gtgtcagctc cagagccaga ctgcctgtat 21360
ctgggcccta aagctactgc ttgattagtg atgtcaccat aggcaaatag cttaagctgt 21420
atgactcagt ttcctcatct gtaaaatggg gtgatggtac ctaataatac agtagagcac 21480
ttaacacagt aggtggcaca tggtaagcca catactgagt atgtatttgc tatgattgtt 21540
attgctatta ttactattat tgttattatt aacataaact gcacaagagc aggctttttg 21600
tttgtttgtt tgtgttttgt tttgagacaa gatcttgctc tgttgcccag actggagtag 21660
tgcagtgatg tgatcttggc tcactgcagc ctcaacctcc caggctcagg tgattctccc 21720
acctcagcct ctcgagtagc tgggattata ggcgtgcact cccacgcctg gctaattttt 21780
tatattttta gtagagatgg agtttcgttg tgttgcccaa gctggtctca aactcctaga 21840
ctccagcaat ccgcccacct cagcctccca gagtgctgga attataggtg tgagccacca 21900
cgcctggcca agagcaggca tttttatctg ttttgttcac agctgtgtcc ccagcaccta 21960
gaatgtacct ggcacaaagt agacattcac catttgctga ataatactac tatttgctaa 22020
ataaacccct gttgaatagt ctaggaaact gaacacagag aggttaagtc acttgtccaa 22080
gttcacacag ctcctaaagg acagagatgg aatttgaacc catccatctg gttccagagc 22140
caggctcgat atttatggat atttcataac caagtgaata actggatggc taaatcctta 22200
gaaagcacac cctccatccc tgtctgacac acgtgtatac cattaaggga aatggcaccc 22260
ccatgtaata gcagaggcag aacttgacat tttcagggcc ctgacaccca ggcatgtctt 22320
cttcccatgc ttcccagcat tattccttcc tgacgacttc ccctcctatt tccccaggta 22380
cagagcatgc cagcgcctca gctaatgggg taagtgcagt gttggagcta aggagggtgt 22440
ggggtctgca cgaactacag accagacgtc ttcagatgcc cacggcccgg cctcaggagc 22500
ctgggtcttt tctcctggtg cctcgagcag catttcccaa cccttcctgc tgggcggaat 22560
cccctgtaga gtttgctaag acgcagcccc agacagtctg gtctgtgatg gggccaggga 22620
atctgcattt taatatccgc tctctccccc ctgccccacg ccccttcaat tccacccatg 22680
gccacacctt gagaagcact gccctggctt ccagggagag aggaggggac gggcctgcag 22740
ttctttgcac atggggcttc agtgggaaga tgtttgattt tgttcaaaag agccccaagg 22800
ctaaaatttg aaaaccctct tctagcatgt ctcctattca gctgtgagca gagagaacag 22860
ctcttcccag gatccacaga cagagggcac aaggtgacag cgtcgggact gagaggggag 22920
agagactgga gctggcaagg acgtgggcct ccagagttgg acccgacccc aatggatgaa 22980
gaccccctcc aaagagacca gcctccctcc ctgtgccaga cctcaaaacg acgggggcag 23040
gtgcaagttc ataggtctcc aagaccaccc tcctttcatt tgctagaagg actcactaga 23100
ctcaggaaag ctgttaggct cacagttaca gtttattaca gtaaaaggac agagattaag 23160
atcagcaaag ggaggaggtg cacagcacac gttccacgac agatgaggcg acggcttcca 23220
tctgccctct cccagtggag ccatataggc agcacctgat tctcacagca acatgtgaca 23280
acatgcaaga agtactgcca atactgccaa ccagagcagc tcactcgaga tctttgtgtc 23340
cagagttttt tgtttgtctt gagacagggt ctggctctgt tggcagacta gagtacagtg 23400
gtgagatcac agttcattgc agccttgact tctcaacgcc aagtcatcct cccacctcag 23460
cctcctgagt agctatgact acaggtatgt gccaccacgt ctggctaatc tttttattat 23520
ttgtaaagtc gaggtttccc tgtgttgccc aggctggtct tgaactcttg gctccaagtg 23580
atacttctgc cttggcctcc caaagtgctg aattaagcag ctcaccatcc acacggctga 23640
cctcatacat caagccaata ccgtgtggcc caagaccccc accataaatc acatcattag 23700
catgaaccac ccagagtggc ccaagactcc aagatcagct accaggcagg atattccaag 23760
ggcttagaga tgaatgccca ggagctgagg ataaagggcc cgatctttct ttgggcaagg 23820
ttaagccttt actgcatagc agaccacaca gaagggtgtg ggccaccaga gaattttggt 23880
aaaaatttgg cctctggcct tgagcttcta aatctctgta tccgtcagat ctctgtggtt 23940
acaagaaaca gccactgacc ctggtcacca gaggctgcaa ttcaggccgc aagcagctgc 24000
ctggggggtg tccaaggagc agagaaaact actagatgtg aacttgaaga aggttgtcag 24060
ctgcagccac tttctgccag catctgcagc cactttctgc cagcatctgc agccagcaag 24120
ctgggactgg caggaaataa cccacaaaag aagcaaatgc aatttccaac acaaggggga 24180
agggatgcag gggaggcag cgctgcagtt gctcaggaca cgctcctata ggaccaagat 24240
ggatgcgacc caagacccag gaggcccagc tgctcagtgc aactgacaag ttaaaaaggt 24300
ctatgatctt gagggcagac agcagaattc ctcttataaa gaaaactgtt tgggaaaata 24360
cgttgaggga gagaagacct tgggccaaga tgctaaatgg gaatgcaaag cttgagctgc 24420
tctgcaagag aaaataagca ggacagagga tttgctctgg acagagatgg aagagccggg 24480
aacagagaag tgtggggaag agataggaac cagcaggatg gcaggggcaa agggctcaag 24540
ggtgaggagg ccagtgggac cccacagagt tggggagata aaggaacatt ggttgctttg 24600
gtggcacgta agctccttgt ctgtctccag cacccagaat ctcattaaag cttatttatt 24660
gtacctccag cggctgtgtg caatggggtc ttttgtggaa atcaaggagc agacaggttt 24720
catgtgtact gtcaccacgt gggatggaac cagaggcatg gaagcaagac gctaaatgaa 24780
gagggccata agggctggga ttcccaggca ccttaggaac agcttgtctt tttttttttc 24840
ctctccaaaa aaaatgttta agggacggtg tctcctgtca cccaggctgg agtgcaatgg 24900
cacgatcata gctcattgca gcctctaact ccggggctca agcaatcctc ccacctcagc 24960
ctaccaagta gctgtgacca cagctgcccc tcaccatgct aagctaattt ttttaattag 25020
atagtacata aacgtcccaa aattagaaga taaaaagaca tgagggatcc attctaattt 25080
gtgtttggag tgtaatggtc cagctccatt cttctgcaca tggatatcca gttttacaca 25140
acactgtgaa tgtaatgaat gccactgaat catacactca aaaatagcta aaatggcaaa 25200
ttgtctgtta tctcttttta accaccattt ttgaaaatta attataccaa aaaaccattg 25260
aatagtgcac tttatttatt tatttatttg tttatttatt tatttatttt agaaataaga 25320
gtctcacttt gttgcccagg ctggagtgca gtggcgtgat catggctcat tgcagcctcg 25380
acctgctggg ctcgggctat ccttccatct cagcctcccg agtagctggg actataggtg 25440

```
ggcgccaccc cacctggcta aatctctttt taacttttgt agagataggc atctcgctat  25500
gttgcctagg ctgggctgga actcctgggc tcaagtgctc ctcctgcctt ggcctcccaa  25560
agcgctagga ttacagatgt gagccaccgc gcccaccctg aaccttactt tttttgctca  25620
gtttctggta attcagagaa tgcctcctga gttgttctac acccacctca tattccatgg  25680
gagggctgta cagggctttt ttaacgaggc ctctaaggac aggcatttgt atcctttcca  25740
gcctttcact attacaatgt tgtagtgaat aactttacac actgtcattt attttacttt  25800
ttttttttt tattttagag aaaggaatct tgccatcttg cccaggctgg tctcaaattc  25860
ctgggcccaa acaatcctcc cgccttggcc tcctaaagta ctgggattta taggcataag  25920
ccaccgtgcc tggccaatgc acactgtcat ttagctcatg ttaacacctg agtgtaggac  25980
acactcctgg aggtggaatt gctgggccaa agagtatgtt tcttgtcatt gtgatagata  26040
ttgacaaatg aaccctcaca gaagttgtgc tgagttctgt tcccaccagc gacgtaggcg  26100
atgacctttt tctggaggga gggggcatcc ttggagtcca cagagccagg aatggagagt  26160
gggcccagaa ttttggtata ggtgttgtat aaacttatag taaggttaag aaaaccgcaa  26220
ctatccttat cagagacttg gcggggggca gggtatgatg gagatcataa ggaggctaaa  26280
acactccaca ccctccctct gcattgctcc tgcacgggag tcgggaatct tttcaggttg  26340
atacgatctc accttgagga gctgtgaggt cccagaagcc tctgggttgc agattgcttg  26400
gggtgaaaat gtctgtgcta ctgaaatcta actttttaca aaaaattacg ggctgggcgc  26460
agtggctcac gcctgtaatc ccagcacttt gggaggctgc agcgggtgga tcacttgagg  26520
taaggagttc aagaccagac catagtgaaa ccgtgtctct acaaaaaaaa ttagccaggt  26580
gtggtggtgc atgcttgtaa tcccagctac tcagaaggct gaggtgggag aatcccttga  26640
acccgggaag tggaggctgg agtaaaccat gatcgagtta ctgcactcca gcctgggtga  26700
caagagtgag actctgtctc caaaaaaaaa aaaaaaaaaa aaaaaactgg attgcctggc  26760
tctactccgg gcacagcatg caggcccagt tctgctgctc tgctgtttgt tctgctttcc  26820
tccacatatt ggcatcaccc tctggtgcca agatggctgc tgcattccag gcatcacatc  26880
cagactcaga cccagagaag ctgcccatcc ctacctgggt gagcctttgt aggaacgaga  26940
aaccgcatcc agcagcagaa acctcaccca gcagcgtctt ttccggtctc attcaccagc  27000
gccgcccacc gctcaaccaa tccctggcca aaagaatggg accgcctgga aggctggacc  27060
aaacaggacc tgccctctgg ggctggggag aggcccagat gaaggctgca ggacaggatg  27120
gactcctaga cctctgttac cagcagtgac tacctctgtc tgggtggttg gaacatgttt  27180
gaattttatt ctaagtactg tctacaagtt ctgcaataaa ccttgactct tcttttaata  27240
atgcaaaagg aatcgaagtg attgtttgaa agggagagga agaaagagag agggagggag  27300
ggaagaatgg agggaggcag ggaaggagac agagagagta gaatccagcc accggaaaat  27360
ccagaatagc tggctttgct taatccatgc ctggaaataa ctgctgggtt tgcaacaact  27420
tctctcccgg agacagacca aggaaactac aaaactgcag gaaggattga agggccgggc  27480
acagtggctc acgcctgtaa tcccaacact ttgggaggcc gaggtggatt ggatcacctg  27540
agatcaggag ttcgagacca gcctggccaa catggtgaaa cctcgtctct gctagaaata  27600
caaaaataag ccgggcgtgg tggcgtgcgc ctatagtccc agctactcgg gaggctgagg  27660
caagagaatc gcttgaacct gggaggtgga ggttgcagtg agctgagatc gtgccactgc  27720
actccagctt gggcgacaga gtgagaatct gtcaggtgga ttctgagggt actctgaccc  27780
cacgaaccca gcatgaaatc ttccaggcat taaggaacat tgaggatgtg gaggattgga  27840
```

```
aatccctcca gggaaaatac acttctcttg agcagggtca cgaggggtgg gggcaatgtg  27900
ggaggtgggg caaatccaaa gacaaggtca acagcaataa taataataac aatgacaggc  27960
atttgttgct tgttggctgg gcctcttgca tacagttctc ccaacatccc tgtgaggtgg  28020
tgatgcttat ccccattctc caggggagga ggctgaggcc cagagaggtg aagtcgtgtg  28080
ccacaaaata ccccagccat atggtggtag aaccaagttt tcagccagac tcaccagctc  28140
acagcagagc tgccctggac tctacagcca ttcagtgtat agctgggcca ctccatcatt  28200
caaggcagtt caacgtcaag attcctgatt tgcctcaacc tggggcctct agaagatacc  28260
atcacccca acaagctgaa gacgtgtgtc cggaacactc agacacacac aaagtgctat  28320
ggatacacca caccccgacc tagctgtctc ttcctgatgg acctcactgg gtagaaatgc  28380
ctggcaccgc ctgcctcaga tccctaggtc agctctcact ccccaataga agtttctgag  28440
atgatgatga aaacgttctc catctgtgct gtccaatgga gtagccactg atcacttgag  28500
gctagtgagc acttgaaggt ggctagtttg aggaactgca ttttttaatg catttaattt  28560
tagttacttt gaatatatat acacatatat acatttatat atacatattc atacacatac  28620
attttacata tattttatat gtatatgtaa tatatatata aattatatat gtatatattt  28680
ttatatataa atatatatta tatatttata aatatataaa tatataatat atattatata  28740
gatatataaa tataaatata tattatatat ataaatatat aatatatatt atataaatat  28800
atataaatta tatatttata tatataatat ataaattata taaattatat atatttatat  28860
ataatatata aatatatata aattatataa tttatatatt atatataaat tatatatttt  28920
atatataata tatacaatat atataaatta tatataatat ataaatatat ataaattata  28980
tataatatat aaaatatata taaattatat ataatatata aaatatatat aaattatata  29040
aatctatata aatatatact atattataaa tatagtatat atttatatag atttatatta  29100
tttatatagt atatattata tatttatatg tttatgtata tataaatata taatatataa  29160
atatatttat atattatata tttatataat attttatata atatgttata tatttttata  29220
taatatatta tatatattta tat                                          29243
```

<210> SEQ ID NO 9
<211> LENGTH: 29261
<212> TYPE: DNA
<213> ORGANISM: Artificial Sequence
<220> FEATURE:
<223> OTHER INFORMATION: modified gene

<400> SEQUENCE: 9

```
aataaataac tttttagacc atatatttct tttttttttt tttttttttt tgagacagag     60
tctcactctg ttgcccagac tggaatgcag tggcatgacg ttgactcact gtaacctcca    120
cctcaagtga ttcagcctcc caagtagctg ggattacagg tgtgcacgac taccacccag    180
ctaatttttg tgtttttagt acagatgggg tttcaccatg ttggccaggc tggtcttgaa    240
ctcctgacct caaaagtgtg ggggaaagaa agagagatca gactgttact gtgtctatgt    300
agaaaaagga agacataaga aactccattt tgatctgtac taagaaaaat tcttctgcct    360
tgagatgctg ttaatctgta accctagccc caaccctgtg ctcgcagaaa cgtgtgctgt    420
attgactcaa ggtttaatgg atttagggct gtgcaggatg tgctttggta aaaatgtgtt    480
tgcaggcagt atgcttggta aaagtcattg ccattctcca gtctcaagta accagggaca    540
ccatacactg cggaaggcag cagggacctc tgcccaagaa aacctgggta ttgtccaaga    600
```

tttcccccac tgagacagcc tgagagatgg cctcgtggga agggaaagac ctgaccgtcc 660
cccagcccga cacccataaa aggtctgtgc tgaggaggat tagtgaaaga ggaaggcctc 720
tctgcagttg agataagagg agggcatctg tctgctgctc gtccctggga atggaatatc 780
tcggtgtaaa acccgatcgt acattctatt tactgagata ggagaaaact gccttatggc 840
tggaggtgag acacactggc agcaatactg ctctttactg cactgagata tttgtgtaaa 900
gtcaaacata aatctggcct acgtgcacat ccaggcacag ctcctttcct taaatttatc 960
tatgacaccg agtcctttgc tcacgttttc ctgctgaccc tctccccacc attaccctat 1020
agtcctgcca catcccccctc accgagatag tagggatagt gatcaataaa tactgaggga 1080
actcagagac cagtgccggt gcaggtcctc acttgctgag caccggtccc ctgggcccac 1140
ttttcttcct ctatactttg tctctgtgtc ttatttcttt tctcagtctc tcgtctccac 1200
cttgtgagaa atactcagag gtgtggaggg gcaggccccc ttcaaaatga tccacccacc 1260
tcagcctccc aaagtgctgg gattacaggc atgagccacc atgcccagcc acatataact 1320
tatttctaaa taacttattt aactaacacc acatgatttt atgacccccct attttatgga 1380
tgagaaaaaa gaggcaagag aagcgatacc agttgcttag gattcccagc taccaattag 1440
tggaagcaga atttgaacca agggagtctc tggagccctc gttcccaatc tccttttctt 1500
cctctccatg tctttctttc tccccctgct cccaggcctc ctacatcaca cccttctgga 1560
caaagcttca catctgacat tttctttttt ggggtggaca gagtcttact ctgtcaccga 1620
ggctggaggg ccgtggcgca atcatggctc atggcagcct caaactcctg ggcttgaggg 1680
atcctccagc ctcagcctcc caagtagctg ggactatggg catgtgccac cacacctggc 1740
taattttttta atttttttgta gaaatacagg gggtgggggc atatctgaaa attttaaacc 1800
ttccctgact gccgtgagca tttctgggta gaagccactc cacgacctta ctttgctggc 1860
atgagtgctg gacagcaatt tggcaacatc ctctagacca caaatgtgca tggcctttgg 1920
cccagcaaat cagcttctgg gaataaatat gacagatact gttacataca tgggaaatgc 1980
catggacatg atgacccagg gaagcacagt ttgcaagtac aaaagggctg gaaacaccca 2040
aaaagcccat cccctgaaga cagtttcaaa aatgacggtg cattcatgta atggaatagt 2100
acacatttgt gaatgaatga atgaggtagc tcaatatatc tgcctatggg aaaatcacca 2160
agatatgttg ctaagtgaaa aacagaaaga tacagaataa tgctaccatt ttattttttta 2220
atgggagagg gaagaataag gaaatggatt catatttgct taattacaca agcttcctga 2280
tgatcctttt ggatccagaa gtttgaaaac cacagcatca agaggatgcc cattgggcat 2340
ggtggctcac gcctgtaatc ccagcacttt gggaggctga ggagggtgga tcgcctaagt 2400
tcaggagttc gagaccagcc tggccaacat ggtgaaaccc catctctact aaaaacacaa 2460
aaaaattagc tgggtatggt ggtgcaggcc tgtaattcca gctacttggg aggctgaggc 2520
gcaagaatca cttaagcctg ggaggcggag gctgccgtga gccgagatca cgccattgca 2580
ctccagcttg ggagacagag caagactgtc tcaaaacaaa caaacacaca caaaaaaataa 2640
gatgcccatt ggagatctcc attcactatt ttatcagatg atatttcagc acttgagtga 2700
agaaaatgtc tacaactggt ccaaacactc aaggaattta gactcttgac agagaaacac 2760
acagaagcaa gcagatatgc cccgaaccaa acttgctttt tcttctaagc ctgcttcttc 2820
ggagcagcct ctgaccctcc agggccctga gaggagtccc tggagccaca ggagcttggg 2880
agcccagaga agtgggggaa tcccagatgg tgacagcatc atccagagga ggaacataac 2940
gatggccaca gattcccaat ttggaaataa ctcagcaaaa caacactgac agaaaattca 3000
gagatttcca agagactagc ctccctgttt ccatttagaa attcacctac atacatccag 3060
ggtgagagac cccaagcatc agatgtgtca tacacaagca tcagatccaa gttagagagg 3120
gcacccgggg acagaaacct ccaagccagc caaaagccaa aggaaggatt ttacagaaag 3180
atacaggaat gtggggccag gcacagtggc tcatgcctgc aatcctagca ctttgggagg 3240
ccgaggtggg aggatcgctt gcggccagga attcaaggcc agcctgagca acatagcgag 3300
atcctatctc tacaacaaat ttaaaaacta gctgggtgtg atcacatatg cctgtggtcc 3360
caactaccca ggaggctgag gcaggagttg agcccaggag gtggaggctg caatgagcaa 3420
tgatggcgcc acttcactcc agcctcagtg aaatagtgag accctgtcta aaaataataa 3480
taaaaataaa aaacatataa agatgtcaga gcacagggac cagagctgtt agtcggcctc 3540
atggagaccc tggccaggac agccacctct ggggaccagg aagtctctca gtttctgtct 3600
ctgagggttt ggctctctga gtctctctgt cacctctcat ttctctctca tctccctctg 3660
tctatgctgt gtctctatct ctttcaatct ctctgtctct gtctcccagc ccttatctct 3720
gagtgtgtct gtttctctct catttctctc tctctctctc tctctttctc tctctctctt 3780
tctctctctc tctttctctc tccccccctcc ctcctcccct ctccctactg caggctggtc 3840
cataaccctt atcttcccca gacctgatgg agttctggta ttaatctgtt tatggtctgt 3900
ttccctccac tagaacacgg tcttcattaa aggcagagat tttgtctgt cttattttct 3960
gctgtatacc cagtgcctgg gatactggct ggatcaataa atatatgctg aatgaagaat 4020
gaatgaatga ccattctcat gaacattatt atttgatgcc aactgtaaag caacaataat 4080
aataattgtc actgccactg ctgctattgt tggtatatca gctttttatt tagtacaaac 4140
tatatccccg aaattgagct aggcagtttc ttgtttaagt tttacagacc acgctgtgag 4200
gtaagtactg ttagtatgcc ctttttttctt tctttttgag acagagtctc actctgtcgc 4260
ccaggctgga gtgcagaggc ccgatcttgg ctcactgcaa cctctgcctc ccgggtacaa 4320
gtgattttcc tgtcttagcc tccccagtag ctgggattac aggcatgtgc caccatgccg 4380
gctaattttt gtatttttag taaagatggg tttttgccat gttggccagg ctggtcttga 4440
actcctggac ctctggtgat cctcctgcct cggcctccca aagtgctggg attacaggcg 4500
tcagccactg cgcttgctcc cccagccccc aaactttttt tttttttttt gagacaggtc 4560
tggctctgcc acccaagctg tagtgtagtg gcgcaatggt agctcactga agcctctaac 4620
tcctgggttc acacagtcct cctgcctcag cctcccaaaa tgctggaatt caggcctgag 4680
ccaccgcgcc ctactatgcc catttttcag ataaagaatc tgagggccct cgaggagaaa 4740
ccacttgccc aacatgagcc ctggtcttgt ctgaccccaa agcccatggg aagtttaggc 4800
tgcgtggaag gacagcctgg tgggctcagg atctgtccca tcacgagttg gaacctcagc 4860
tctgccactc ggcaaccgcg agccgttagt aagttgctga atctctccgt gtgcctccgt 4920
ttcctcacct ggaatgtggg cgacctcaca caggaagccg cctcttctag tgggcaccga 4980
cggagcgagc gcgcgtctgc agcgggactg agcgccggga gagacctgcg caggcgcagg 5040
cgcgcgggga gggccagcct gggtggccca ccccgcgcct ggcgggactg gccgccaact 5100
cccctccgct ccagtcactt gtctggagct tgaagaagtg ggtattcccc ttcccacccc 5160
aggcactgga ggagcggccc cccggggatt ccaggacctg agctccggga gctggactcg 5220
cagcgaccgc ggcagagcga gcgggcgccg ggaagcgagg agacgcccgc gggaggccca 5280
gctgctcgga gcaactggca tggcccgagc catggccgcc gcgtggccgc tgctgctggt 5340

-continued

```
ggcgctactg gtgctgtcct ggccaccccc aggaaccggt gagtgacccc cgcgcagtcc   5400
ggtggcccct gtctggctcc cagctccgca tccaggccgg gtactcgccc ccttgggttc   5460
ccgaagatga cggccccgcc cggcgccacc caccccccat ctctgccccg gggttggaag   5520
gaacacggtg cgagggtgcg agggcaggac cctcctcttg gccacccgga gagcggtcgg   5580
agttgggtac agaaattcct cgaaattggc agcaacacgg gtcgggcaca agaccctcct   5640
ctgggcccct cggaaagggg atggagttgg gtgaggaaat ttcccaaaaa ggcaagtgaa   5700
tcccggaaaa tcagcagatg gtgacgcatg ccggattacc ttacccaggt tcctgctcag   5760
catacccagg ccataaccca gcagcgtgct ggcaggctgg gtctggacgg aggggatggt   5820
tgatgttggg gaggaggaca gtgggtgaca cttgacacca ttacccctct gacccccaat   5880
gtctgactcc aggggcctgg ccattcattc attctttcat tctttttttt ttttttttga   5940
gacagtctca ctccatcacc caggctggag tgcagtgtcc tgctctcggc tcactgcagc   6000
ctcctcctcc cgagttcaag cgattctcct gcttcagcct cccgagtagc tcggattaca   6060
gacatgtgcc actatgcctg gctaatattt ttgtattttt agtagataca ggatttcacc   6120
atgttggcca ggctggtctc aaactcctga taaatatata tattatatat tattattata   6180
tattacatat tatagtaata tataataaaa atatataata tatattatag taatatataa   6240
tatataataa aatatataat atatattata gtaatatata atatataata aaatatataa   6300
tatatattat agtaatatat aatatattat aatatattat atatattatt ataatatata   6360
atatgtatat tatatattat atatattatt ataatatata atatgtatat tatatattat   6420
atatattatt ataatatata atatgtatta tgtattatat aattgataat atataataat   6480
atatttctta ataaatatat attaaatata ttatatattt ataacatata ttatttatat   6540
aataaataat atatatttta ttatacattt aaagagtaaa tagataacat attttattat   6600
ttatttatat gttttgtgta tatatatata tatatatata tatatatagt gcgtgtgtgc   6660
gtgtatgtgt gtgtgtgtat gagagagaca aggtcttgct ttgttgccca ggctggagtg   6720
cagtggtaca atcccggctc attgcaaact cgacttccca ggctcaagcg atcctctcac   6780
tgtggcttct ggagtagctg ggattatagg tgctcacctg gctaattttt tttgtatttt   6840
tggtagagac agggtttcgc tatgctgccc aggctggttg cagccaagca cagtggctca   6900
tgcctgtaat cccaacactt tgggaggctg tggtgggagg atcacttgag cttaggaatt   6960
caaaaccagc ctgggcaata tggcaagacc ccatctctac aaaaataatt aactaaataa   7020
aaatttaaaa ataaaaaaga atgcatagga ccatgtttat tagtgtcaat aagcgctgtc   7080
acattttgag gacctactat gtgctagggc ccttagcaga aagattttta tataggacct   7140
gggggattag aggtcagtct ctgaccgccc aagttcaaat cccacctctg ccactaaacc   7200
tctgtatgac ttggaggaca ctatactctg tgtcagtttc cctgtctgta aaatgatgtt   7260
aacagtagtg cttgcctcag gggggctatt tgaggattaa atgccaagat atatgtgaag   7320
cacccagaat agcccctgat ctgtgtcagc accctgtgag tgtccactgt tctaagtctc   7380
attttacaaa ctaggaaaaa gaatcagaga ggttaagtaa ccggcctgaa gctccacagc   7440
agaaaactga agggacccaa aactcctggg ctataattgc cttcctctcg tgcctcaatc   7500
ccccacattc ttccaaccag gacccaccca gagtaataat gcagtgtttc atggatttga   7560
agacccaaga tttctccccg ttttctacat tggggttatt ctaaccccta atggcaagtt   7620
gtgctataaa tgacaacagt catggtatgt gaaacctacg acactggtgc gatgaaaaag   7680
ttctgggcca ggtgcggtgg ctcatacctg taatcccagc actttgggag gccgtagtgg   7740
```

```
gaggatcact tgaggtcagg agttcaagac cagcctggcc aacatggtga aaccccatct   7800
ctgctaaaaa caaaaataca aaaaattagc caggtgtggt ggtgggagcc tgtcatccca   7860
gctacgcgga aagctgaggc aggagaaccg cttgaacccc agaggcagag cttgcagtga   7920
gcagagatcg cgccactgca ctccccctgg gcgacagaga gagactccgt ctcaaaaaaa   7980
aaagagaaga aaagaaaaag ttctggcgct atatagtagt aacggttgca caatatcgtg   8040
aaatgtacat agtgccactg aactgtatgc tttaaatgac ttaaatggta aatttagttt   8100
tttaaccaca atatttacca caattttttta aatcagtgat gttgagattc agggaaatac   8160
ggtaataata gaagaaatac ggtaataaat agccaaagtg aaggagcacg gccaagttgc   8220
agaccatccc agacgccctt accctcctcg cctgccatgg ccccaactag tgccccagtt   8280
cccccctcccc ccacacccca cggtccaccg gggatccagg gccccagcgt gcaagtgcac   8340
gcccaggtgc ccgggctcct ggagcccctc cctatctagt ccaagaacgc cccgggtctg   8400
acaccttctc ttcggttctc cgcaggggac gtcgtcgtgc aggcgcccac ccaggtgccc   8460
ggcttcttgg gcgactccgt gacgctgccc tgctacctac aggtgcccaa catggaggtg   8520
acgcatgtgt cacagctgac ttgggcgcgg catggtgaat ctggcagcat ggccgtcttc   8580
caccaaacgc agggccccag ctattcggag tccaaacggc tggaattcgt ggcagccaga   8640
ctgggcgcgg agctgcggaa tgcctcgctg aggatgttcg ggttgcgcgt agaggatgaa   8700
ggcaactaca cctgcctgtt cgtcacgttc ccgcagggca gcaggagcgt ggatatctgg   8760
ctccgagtgc ttggtgagca gggggttttg gggaggctga atgaaaggca gagacttggt   8820
gggaggatca gggaagttgg caaagagcgg ggaggcctgg gagggaggga gattccctcc   8880
acagcagatc ccctggggac aaaaggaggg ggcagcgcaa tgatgtgggg tggggtgggg   8940
ggaggtgagt ggggggaggg gctgcagggc aggaagaaag cagagatctc agggagtaag   9000
gacccccaag cctgggatca gaaagccctg agggaggagg aggggtatat tggaaaggga   9060
gctgggaggg gactgggaag gaagggagga ggcctgggtg gcctcttctg ggtccctcct   9120
ttcctcatct gtaaaagggt tggtgacaac agcatcaccc ttggaaagct gtcctgagtg   9180
tcatcactgc ctaggaaaga gtctgtctgc ccccttggac tgtgtaccca tgagggcaga   9240
accggggcta ttttgatcac tgctgggccc cagcactttc caccaaacaa tatttattga   9300
gcacttatta tgtgccattc taagagcttt acctgcatat tctaattgcc tgtgattcca   9360
tcattatcac ctgttgacag acaaggaaac tgaggcacag acttgcccaa gaccaaagct   9420
gcagccttag ggcagcggcg cttcaccgct ggcccatgtg agccccttag agctgtcggt   9480
tactgttact ttatctggtg aagaaggaga aagttgaaac agacagacag gaaagcaagg   9540
atcctgatac ccaaaagagg aggggatcat gctttcattt tcatgagctc catgaagcct   9600
tcctcttgga acttgagcaa gaagtctctg tgcctcagtt tcctcatctg tgggataggg   9660
atcaccatga ggattcaaaa aaactgaccc ttttttttt tttgagatag tttagttctg   9720
tcgcccaggc tggagtgcag tggtgtgatc atagtaggtc ctcactgcag cctggaactc   9780
ctgggctcaa gggatgttcc taccctccct gtagctggaa ttacaggaat gtgccaccat   9840
gcccaacttg ttttctgttt tgttttgttt tgttttgttt tcttttcttt ttaagcttat   9900
gtgccaagaa ctattccaag cctgtgcatg agaaactcat gaaatgtcaa gggcttggaa   9960
ctgtgcctag cacacaacac ccaaccaaag gcagctgttg tcactccagc aagcctggga  10020
ttctgggtat catggtttag gatgagggta aaacagaaac agtgagtcaa gttaaggaga  10080
```

aatcttcggt aaataatata ggtaatgatg gggaaggaag ttccaggttt gggaatcacc 10140
aggatgatga ttaagagatg gtcaaggtgg ttttggagtc agacagactt tatgtgaaag 10200
cccagctctg ctgcttacag ctgtgtgacc atgggcaagt cacttccctt ctcaacttca 10260
gggctcaggc ttcctctcct ccactgagcc ccagaccagg ataacccccct ttgggtttcc 10320
cctttccagc cctgccctct ccgagtcatc actgcctagg aaagagtccg tctgcccccct 10380
tggactgtgt acccatgagg gcagaaccag ggctattttg gtcactgctg ggctccagca 10440
ctttccacca aacaatattt attgagcgct tattatatac cattctaaga gctttacctg 10500
catattctca ttgcctgtga tcccatcact atcccctgtc aacagacaag gaaactgagg 10560
cacagacttg cccaagacca cacagctgct cagggacaca gctgggattt aaaccatgcc 10620
attctgtatc tttttttttt tttttttttt gagacagaat ctcactctgt cgcccaggct 10680
ggagagcagt gacacaatct cagctcactg caacctccgc ctcccgagtt caagcaattc 10740
tctggtctca gcctcccaag taactgggat tactggcgtg tgccaccata ccctggctaa 10800
tttttaatag agacagtttc tccatgttgg ccaggctggt ctcgaactcc tgaccccaag 10860
tgatccaccc acctcagccc cccaaagttc tgggattata ggcgtgagcc accccgccca 10920
gcaaccatgc catcctgtac ccttaatgaa tgcccccttc tgccacggag gggttcattg 10980
aatgacttgt tgcttttgtt cctcttccca gccaagcccc agaacacaga cctgggcggg 11040
atgcccaata cgagccaggt gccagggttc ctgtctggca cagtcactgt caccagcctc 11100
tggatattgg tgccctcaag ccaggtggac ggcaagaatg tgacctgcaa ggtggagcac 11160
gagagctttg agaagcctca gctgctgact gtgaacctca ccgtgtactg tgagtgtgcc 11220
caagtcagcg atggcaagaa cccctgccgg gctgccccca ccactgtcta cactgactcc 11280
ccaaggcact gtaggcattg cttccatcat ctgcaccggc tcccctgact cctgtctaca 11340
cgacccaccc ccattgtctg caccagctcc cctgggccgt aaacaacact gtccctattg 11400
tctacaccag tttacttggg ccatagtcaa tgctggtacc cagactgtct gccctggctc 11460
ctctagcggc tgtctgcacg gatacctgac actctgttga ctcccttgag cacagtctac 11520
actgccccta aactgcctac acccatttcc ccaggcaagt atccacaatg accctcccca 11580
cattgctaca ctggttcttc tggccacgat caacactgcc tcccttattg tctacaccca 11640
ctcccttgtc cttttcttc tttcctttt tttttttttt ttttgaaata gagtctcact 11700
ctgttaccca ggctgcagta cagtggcatg ttctcggctc actgtaacct ctgcctccca 11760
aattcaggtg gttctcctac ctcagcctcc caaatagctg ggattaaagg tgcacaccac 11820
cacacctggc taatttttgt atttttagta gagacagggt ttcatcatgt tggccaggct 11880
ggtttcgaac tcctgacctc aggtgatcgg cctgcctcag cctcccaaag tatgctggaa 11940
ttataggcat gagccactgt gcccggcttt ttgttttgtt ttgtttttcc tttggacagg 12000
gtctcgctct gtcacccagg ctggagtgta ggggcatgat catggttcct acagcctcac 12060
ccttccaggc tcaagcaatc cttctccctc agcctcccaa gtaactggga ctacaggtgc 12120
agccaccatg cccggctaat tttacagttt ttttctagag agagttttgc tgtgttgccc 12180
aggctggtct caaactccta ggcttaagtg atcctcccgc ctcagtctcc cgaagtgctg 12240
agattacagg cgtgagccac tgcacctggc cccttgtcca ttttctacac tgccttacca 12300
ttgtctacac tggctctcct gggccacaga cagcactaac cccattgtct acaccaccta 12360
ttttggccac cagctgtggg gtgttttcac tgtctcccat agtgtctaca ctggctccta 12420
tgaccactgt ctatgtaaac accccacttt ttctacactg gttctcctag gcactctcta 12480
aagtgccccc tgacactgtc tacactgact ccctggagaa ctgtctgcat tcacctccca 12540
cattgtatcg accagttccc ctgagccacg atcaactgtc tccgccgggt gctagttgca 12600
ttgatcttct cacattgttt gtgctggctc ccctaagcag tgtctgcaga gtcccccagt 12660
gtagtctcca tgttcctctg cccaatattg tctacactgg ctcatctaca ggctatccag 12720
tctcacccca catcaccaca ctggcctcct tgtgttctgt ctgcacagcc ccctgacagc 12780
atctgtcctg attctcctgc acagcgttac ctccaccagc tccctcatgg catcatcgac 12840
attgacaccc acacatttat ctccactgac agccccagga ctctctaacc agtgctgtct 12900
aacagaaata gcatgcaagc tgcatatagg attttaaatt ctccagcggc caccccatta 12960
aaaaattaaa agaaagaggc caggcacggt ggctcacgcc tgtaatccca gcactttggg 13020
aggccgaggc aggtggatca cctgaggtca ggcattcaag accagcctga tcaatgtggt 13080
gaaactctgt cttcactaaa aaatacaaaa attagccagg cacggtggcg ggtgcctgta 13140
atcccagcta ctcgggagac tgaggcagga gaatcacttg aacctgggag gcggagattg 13200
caatgagcga gattacgcca ttgcactcca gcctgggcag cagagcaaaa ctccatctca 13260
aaaacaagaa aagaaagaga tgaaatttat ttgtttattt atttatctat ttatttattt 13320
gagacggggt cttactctgt cacccagact ggagtgcagt ggcacagctc cctgcagcct 13380
caacctcctg ggcttaagtg atcctcccac ctcagcctca gtctcctgag tagctgggac 13440
tacaggcgtg tgacaccatg cctagctaat ttttgttttt gtttttgttt ttgttttttt 13500
gttttgtgat gaagtcttgc tctgtcaccc aggctagagt gcagtggcac gatctcaact 13560
cactgcagcc tccgcctctc gggttcaagt gattctcctg cctcagcctc ccgagtagct 13620
gggattacaa gccctggcca cagtgcccag ctaatttttg tatttgtggt agagacggga 13680
tttcaccatg ttggccaggc tggtctcaaa ctcctgacct cgtgatccac ccaccttggc 13740
ctcccaaatt gctgggatta cagacgtgag ccaccgcacc cggcctattt ttattttttc 13800
tggagacagg atctccctat gttgcccagg ctggtctcaa actcctgggc tcaagtgatc 13860
ctcctgcctc aacctcccaa ggtactggga ttacaggcat gagccactgt gcctggccaa 13920
aattaatttt taataattgc ctttacttaa cccaatatac ctaaaatatt atttcaactt 13980
gtaattgttt ttttaaaatt attcttgaga tctttcccat ttattttgtc ctagtaaagc 14040
ctttgaaatc tggtgtgtat ttcggcctgg ctatatttcg agtgctcagt agtcacatgt 14100
ggccagtagg tgccatattg gacagcacag atctagacta agctcccaca tcatctacac 14160
tggctcatcc aaatactgtc tacacacata cacagagcct gtcttaattt cgtcagctcc 14220
cggggacaca ctgtatatgt gggggtgatc tcacccccac caccacattt tcaacactgg 14280
cccgacaata tagcatctgc tgtaatattc caacaccctg tctacactga acccatcagt 14340
aatatccaca caagctcttc tagacatcat tcatactgtt cctcccacca ttgtctatac 14400
tgcttactcc ccgccaggca attggtacac agattccctc aggtactgtc tatactggag 14460
tccctcaaca ctgtcactgg gtctgagcga ggaggagatc tacactgact cctacccctc 14520
gcccccgaat aaaaccctgt cccattggcc tgcccccaag gacattgaaa ggtcttcgct 14580
gtcaatcacg tatgggatgg ctgagcagca gcctagagca gggttatctg ggactctttc 14640
ctgcaggact tgtcagaacc ttgaatacac tgctgtgtgt tgtgagtggt cattgcctat 14700
gagtgagaaa aggaggaggc attttcctgc aggacaccca agacatgcct ggtccaggct 14760
acccaggaaa gctagtggag aaaagcagct cctcagaagc cttctccatg tccccactga 14820
ccaaggactc ctaggcttct gctctctgtg gcaccccatc tacctagact cctcctaggc 14880
ctctccagct cccgctgttt tccaaatatc cccgggcctt ttcctgcagt gtcgtgaatc 14940
ccgcgtagcc ccaggccccc caaagcctcc cagtctctga acctctgtat ccatttcctg 15000
cagaccccc agaggtatcc atctctggct atgataacaa ctggtacctt ggccasmmtg 15060
aggccaccct gacctgcgat gctcgcagca acccagagcc cacaggctat aattggagca 15120
cgtgagtcct gggtctcagg gaggaggggc tgggggtctg gatttctagc actgagggag 15180
gaggggctgg gggcctggac tcctgggact gagggagaag gggctggggg cccggacccc 15240
tgggtctgag ggacgagagg ctgggagccc ggactcctgg gtctgaggga agaggggctg 15300
ggggtctgga cccctgggac tgagagagga ggggctgggc ctggacccct gggtctgagg 15360
gaggaggggc tggggggtct ggacccctgg gtctgaggga ggagaagctg ggagcctgga 15420
cccctgggtc tgaggcagga cagactgggg cctggactcc tggtctaaga gaggagggag 15480
attcagaaaa gagaaaaaga ggaggttgac ttcgggcccc cagtgggggg catctctgtt 15540
ttgacatctc tgttttgcgg ttgaggcgtt tagcaggtgg ttgaatcctg gctggtggat 15600
gcacctgctt tttggggtgt gcctgctctg tgcccggtac ttcccccgaa tcccatgtga 15660
ccccatgctg tgcacagtca gcagctgttg ccctgcccag gttaaagacc agccacgaga 15720
gggcagaagc ggcccttgaa tcagcgctcg gctccaaagc tggtcctccg cctcttggcc 15780
aagcttgtct aacctgcagg ccacatcatt tgtaaacttt cttaaaacat tatgagactt 15840
ttttttgcg aattttttta gctcattagc tattgttagt gttagtgtat tttatgtatg 15900
gcccaggaca gttcttcttc ttccaatgtg gcccggggaa gccaaaagat tggacacccc 15960
cactctagac tgtaaccacc tcaccgtcac cttgtgtaac ctacttggtt atctctggat 16020
ggagcaagta ctatatatcc ccattgtcta gatgagaaag ttgaggctca cagcaataag 16080
atttccccag attcacactg aggctgagat caagagcaag gtaagaaaaa ggcaaagaga 16140
taatacataa ttttataata cataatttta cataaattac ataattttac tgaaccgccc 16200
ttttttttta aagaaggggc tctgttgccg aggctggagt gcagtggcgt gatcatagct 16260
cactgcagcc tggacctccc tgggctcagg tgatcctccc acctcagcct cctgagtagc 16320
tgggactaca ggcacacgcc accacactca gctaattttg ttgtattttt tttgcagaga 16380
cagggttttg ccacattgcc caggctggtc tgcaactcct gggctcaagc aatcaaccca 16440
cctcagcctc ctaaagtgct gggattacag gcgtgagcca cctcgcccag ccttaggtct 16500
ttttccttat tacaaaaata acttgtgtcc actgtagaaa tatcaaacaa tttagttatg 16560
agcaaaaaga agaaagtagt gcctatagtt caagtgtacc cagccacctc cagaaatacc 16620
cagtgacccc ttattataca tcctgtcttt tttctctctg tttctaaaca aagactggaa 16680
ttatgctgta catataattt tgaacctttt cgtctgtctt gtgaatacct ttccatgtca 16740
aagcacatag atccacaact ccattttccc ccacgttgta ttaggaagac tgtcaaacat 16800
acagaaaaat catagaaatt ttccagtgaa cacttaagat tccaccacgt ggattcccct 16860
gctaacattt tactgtgctt gctttatcac gtttctgtga ttccttcagt ccctctattc 16920
atccatcaat catattatgc atttcagagc acccccagct ctcctgcttt tttttttttt 16980
tttttttttt tgaggcaggg cctcactctg ttgctcaggc tgtagtgccg tggcacaatc 17040
acagctcact gcagccttga attcctgggc tcaagcgatc ctccagcttc agcctcccag 17100
atagctggga ctacaggcac acaccaccac gcctggctaa cctggcccct tttttagtgt 17160
tgctgggatt ccaccacttt aaaaaaaaaa ttcaaagaat agagacagga tctcactatg 17220
ttgcccaggc tggtcttgaa ctcctgtact caagcagtca tctcacctgg gcctcccaaa 17280
gggcagggaa gggattccaa catatgtgga tgtcatcagt tatttaacca gtccctagta 17340
gaggacacag atgtcatttt ccattttcaa ctctgcaaat gccatggtgg tgtccatccc 17400
cactggtcac ttgtcagcag ttgtccgtgg aaggaattgc cggtcaaagg ttttcaactg 17460
gtgtgatggt gcctttactg tcctgcctca aagcaccgca attcaggctc ttgagccaga 17520
tagctgcgtt tgcatcccag ctctgcggag cacccaaagc ctgatgcttc catctcctcc 17580
acctctgttc attaaaccag tgttccttga ctacttactg tgtgccgggt gcaattaacc 17640
aacatacgtt ggtcgataaa acagaccaaa tttcctcccc atatagagct tccattctag 17700
tggtgaaaga aacaagaagc aagataaagt gtgtagtgtg tgtgcaatgg tgataaatac 17760
catggagaag acaaagcaga gaagggaatg ggactgggcg ccatgactca tacctgtaat 17820
cccagcactt tgggaggcag agatgggagg atcacttgag gctaggagtt caagaccagc 17880
ctggccaaca tggcgaaacc ccatctctac caaaaaagat acaaaaattg gccgggtgtg 17940
gtggcatgca cctgtagtcc cagctactca ggaggctgag gtgggaagat tccatgcacc 18000
caggaggtgg aggttgcagt gagtcaagat ggtgccactg cactccagcc tgggtgacag 18060
agtgagacgc tgtctcaaaa aaataataat taaataaatt aaagagaagg ggatgggaag 18120
ggtgatcatc acagttgaaa tagggtggcc aagtgaggtg ttactaaggt gacatcccag 18180
cagaggcctg aaggagatga gggtgagctc tgcgggtgcc tagggggaaa gcattccagc 18240
agagggaaca gcatgggcaa acccatttct atccatcagt ccctgcataa gcaaacaccc 18300
tggacaccta actggagagt ttgaggacca acaaagaggc cactgtggat gcagaggcgg 18360
gagcaaaggg gagagtaatg gaaaacgtgg gcagaggtag caggggccag atcacgtggg 18420
gcctgtgaca ccagaagact tcggtttaac tctgagccag gctaggcccc cagagggtac 18480
tgagctgagg tatgggaact gacttagggt tcacaggcga cctctggtgg ccatgtgggg 18540
aacagacgag gggcgaggg cagaaacgga gcccagcgtg gaggcggctg ctgggggccg 18600
ggatgcacag cgccagagca gggaggtacc gtggaagccc tgaggagagg tgggattctg 18660
gatggatctt aaggcggggc cgacatgatt ggctaatggg ttgggtgtgg gcatgagagg 18720
aagggaagag ttggggggcc tccagagttg ctctccgctt atgctataga gggcgtgagg 18780
gtttctgggc acgtagtgcg tgctcaatca ctgtcactcc ggacctgcag cagaggccac 18840
ctcctcacct ttctgtctct cccaggacca tgggtcccct gccacccttt gctgtggccc 18900
agggcgccca gctcctgatc cgtcctgtgg acaaaccaat caacacaact ttaatctgca 18960
acgtcaccaa tgccctagga gctcgccagg cagaactgac cgtccaggtc aaaggtgagg 19020
aactccctgg gtgggaagaa cagggaccaa aggaagaggt cgaggcaggg ttccctgtct 19080
aatgctctct ggctcccatc cttctcctaa gccttctcac aaaaggacca gtggggccag 19140
ctttactccc ctgttaactc catacctata tcactggtac cgttgttcag ctgcctggat 19200
acactccctc cacacacaca ggttgggata gatgtggaat ccctctctct cagggactca 19260
ggcctttcca aatatattag gcagacctct atcaattgca attgacagaa acacaaagta 19320
gtctaagcaa aaaaaaccaa acaaaacagg actttattga aaattcacct tcaggtatgg 19380
ttagatccag ggctccaac cttgtaaccc aggaactttt attttataca tctcttgtct 19440
ctgcttttcg ttatactggc tttattctca ggcaggctct gaagcaagat ggccctcggc 19500
agggacaggc tcacattcta ccagaatggc aacagcagga gaaaaaacat accactttca 19560

```
gtaactgtag ccatagtccc agggctggct ctcattggcc cagcttaggc cacagcccac  19620
ctatgaacca atcatagcag ccagggagaa tggaatattc tgattggcca ggcctgtgtc  19680
aaagtcccat tctgggcacc agagggtggg atccattcca cctgaattaa atagactgag  19740
gcagtggagt ggtggctccc taaggaaatt caagatgcca tttcaagaat gagggataaa  19800
ccccaagagt ttccttacct aaatacctgt ttccttctct ttcagaggga cctcccagtg  19860
agcactcagg catgtcccgt aacgccatca tcttcctggt tctgggaatc ctggtttttc  19920
tgatcctgct ggggatcggg atttatttct attggtccaa atgttcccgt gaggtccttt  19980
ggcactgtca tctgtgtccc tcgagtgagc atcaccagag ctgccgtaat tgagcaccta  20040
ctacgggctc tgtgctgagt ccttccagtg tgcctctcac tgaatcctca ccccactgcc  20100
atgaggtttc ccccatttga ctgatgaggg tgcagagcca gggagccttg ttcactggtt  20160
cattgattac atttacaaat attatttaca gagtgggaga agagcgtata gggtcttaat  20220
gccatggtag ggactttgga atttaattca ggtgatgtgg gagtccctgc cagatggatg  20280
gagggtgaaa taatgcttaa gccctcagcc ttactccatc tgccttgttc aggagtgact  20340
cctaggagga ggtggcagga actggcacct ctgatcctca gctctaaaag ggtctgatgc  20400
tttcacacct caagagattt gcacaggccg ttcccctgcc tggagcaccc tcccatggct  20460
ccttctggag aagtgtgcca gctcattctg taatcagagg aacgatgctt tgctgagcac  20520
tgtctacatg ccactttgta tgtataaccc cctcgatttt aatttttaat ttttttttatt  20580
atttatgtat ttatttattt atttttgaga caggctctca ctgtcgccca ggctggagtg  20640
cagtggtgcg atctcggctc actgtagcct tcacctccca ggttcaagcg attctcatgc  20700
ctcagcctcc caaggagcgg ggattacagg cacgcactac tatgcccagc aatttttgta  20760
tttttaggag agacagcgtt tcgccatgtt ggccaggctg gtctcaaacc cctggtctcc  20820
tgtgatccac ccgcctcagc ctcccaaagt gctgggatta caggcatgag ccaccacacc  20880
tggcctgtac aatctccttg aatgcccaca accacccagc aaagtggttc tcccgtgagc  20940
cccatgttac agaggaggaa gtatttgctt tgagagatga agttacctgc caatggtcaa  21000
acagctggac atggttgttg gggagaagaa gccagatctt tgactaccaa gcttttcctt  21060
caaccactaa acaaagctgc tcccttacaa cccaggcgga tactgcctcg tccaggaagc  21120
cctccctgac ccccaagcat gagccaagca tccactaggc tctcccactc cagccttgcc  21180
cattctgggt catcaccgtg ggggacttgt ttgtcatccc cagtggactg tgagccccaa  21240
gatagcagac ctgaggctgt cactgtcatg actgtgtccc caggaccgcc taccactggg  21300
ccgggcataa aagaggcact cgaggaagtg tttgctgagt gattcaatgt gtcagctcca  21360
gagccagact gcctgtatct gggccctaaa gctactgctt gattagtgat gtcaccatag  21420
gcaaatagct taagctgtat gactcagttt cctcatctgt aaaatggggt gatggtacct  21480
aataatacag tagagcactt aacacagtag gtggcacatg gtaagccaca tactgagtat  21540
gtatttgcta tgattgttat tgctattatt actattattg ttattattaa cataaactgc  21600
acaagagcag gctttttgtt tgtttgtttg tgttttgttt tgagacaaga tcttgctctg  21660
ttgcccagac tggagtagtg cagtgatgtg atcttggctc actgcagcct caacctccca  21720
ggctcaggtg attctcccac ctcagcctct cgagtagctg ggattatagg cgtgcactcc  21780
cacgcctggc taattttttta tatttttagt agagatggag tttcgttgtg ttgcccaagc  21840
tggtctcaaa ctcctagact ccagcaatcc gcccacctca gcctcccaga gtgctggaat  21900
tataggtgtg agccaccacg cctggccaag agcaggcatt tttatctgtt ttgttcacag  21960
```

```
ctgtgtcccc agcacctaga atgtacctgg cacaaagtag acattcacca tttgctgaat  22020
aatactacta tttgctaaat aaacccctgt tgaatagtct aggaaactga acacagagag  22080
gttaagtcac ttgtccaagt tcacacagct cctaaaggac agagatggaa tttgaaccca  22140
tccatctggt tccagagcca ggctcgatat ttatggatat ttcataacca agtgaataac  22200
tggatggcta aatccttaga aagcacaccc tccatccctg tctgacacac gtgtatacca  22260
ttaagggaaa tggcaccccc atgtaatagc agaggcagaa cttgacattt tcagggccct  22320
gacacccagg catgtcttct tcccatgctt cccagcatta ttccttcctg acgacttccc  22380
ctcctatttc cccaggtaca gagcatgcca gcgcctcagc taatggggta agtgcagtgt  22440
tggagctaag gagggtgtgg ggtctgcacg aactacagac cagacgtctt cagatgccca  22500
cggcccggcc tcaggagcct gggtcttttc tcctggtgcc tcgagcagca tttcccaacc  22560
cttcctgctg ggcggaatcc cctgtagagt ttgctaagac gcagccccag acagtctggt  22620
ctgtgatggg gccagggaat ctgcatttta atatccgctc tctccccccct gccccacgcc  22680
ccttcaattc cacccatggc cacaccttga gaagcactgc cctggcttcc agggagagag  22740
gaggggacgg gcctgcagtt ctttgcacat ggggcttcag tgggaagatg tttgattttg  22800
ttcaaaagag ccccaaggct aaaatttgaa aaccctcttc tagcatgtct cctattcagc  22860
tgtgagcaga gagaacagct cttcccagga tccacagaca gagggcacaa ggtgacagcg  22920
tcgggactga gaggggagag agactggagc tggcaaggac gtgggcctcc agagttggac  22980
ccgaccccaa tggatgaaga ccccctccaa agagaccagc ctccctccct gtgccagacc  23040
tcaaaacgac gggggcaggt gcaagttcat aggtctccaa gaccaccctc ctttcatttg  23100
ctagaaggac tcactagact caggaaagct gttaggctca cagttacagt ttattacagt  23160
aaaaggacag agattaagat cagcaaaggg aggaggtgca cagcacacgt tccacgacag  23220
atgaggcgac ggcttccatc tgccctctcc cagtggagcc atataggcag cacctgattc  23280
tcacagcaac atgtgacaac atgcaagaag tactgccaat actgccaacc agagcagctc  23340
actcgagatc tttgtgtcca gagttttttg tttgtcttga gacagggtct ggctctgttg  23400
gcagactaga gtacagtggt gagatcacag ttcattgcag ccttgacttc tcaacgccaa  23460
gtcatcctcc cacctcagcc tcctgagtag ctatgactac aggtatgtgc caccacgtct  23520
ggctaatctt tttattattt gtaaagtcga ggtttccctg tgttgcccag gctggtcttg  23580
aactcttggc tccaagtgat acttctgcct tggcctccca aagtgctgaa ttaagcagct  23640
caccatccac acggctgacc tcatacatca agccaatacc gtgtggccca agaccccccac  23700
cataaatcac atcattagca tgaaccaccc agagtggccc aagactccaa gatcagctac  23760
caggcaggat attccaaggg cttagagatg aatgcccagg agctgaggat aaagggcccg  23820
atctttcttt gggcaaggtt aagcctttac tgcatagcag accacacaga agggtgtggg  23880
ccaccagaga attttggtaa aaatttggcc tctggccttg agcttctaaa tctctgtatc  23940
cgtcagatct ctgtggttac aagaaacagc cactgaccct ggtcaccaga ggctgcaatt  24000
caggccgcaa gcagctgcct ggggggtgtc caaggagcag agaaaactac tagatgtgaa  24060
cttgaagaag gttgtcagct gcagccactt tctgccagca tctgcagcca ctttctgcca  24120
gcatctgcag ccagcaagct gggactggca ggaaataacc cacaaaagaa gcaaatgcaa  24180
tttccaacac aagggggaag ggatgcaggg ggaggcagcg ctgcagttgc tcaggacacg  24240
ctcctatagg accaagatgg atgcgaccca agacccagga ggcccagctg ctcagtgcaa  24300
```

```
ctgacaagtt aaaaaggtct atgatcttga gggcagacag cagaattcct cttataaaga  24360
aaactgtttg ggaaaatacg ttgagggaga gaagaccttg ggccaagatg ctaaatggga  24420
atgcaaagct tgagctgctc tgcaagagaa aataagcagg acagaggatt tgctctggac  24480
agagatggaa gagccgggaa cagagaagtg tggggaagag ataggaacca gcaggatggc  24540
aggggcaaag ggctcaaggg tgaggaggcc agtgggaccc cacagagttg gggagataaa  24600
ggaacattgg ttgctttggt ggcacgtaag ctccttgtct gtctccagca cccagaatct  24660
cattaaagct tatttattgt acctccagcg gctgtgtgca atggggtctt ttgtggaaat  24720
caaggagcag acaggtttca tgtgtactgt caccacgtgg gatggaacca gaggcatgga  24780
agcaagacgc taaatgaaga gggccataag ggctgggatt cccaggcacc ttaggaacag  24840
cttgtctttt ttttttttcct ctccaaaaaa aatgtttaag ggacggtgtc tcctgtcacc  24900
caggctggag tgcaatggca cgatcatagc tcattgcagc ctctaactcc ggggctcaag  24960
caatcctccc acctcagcct accaagtagc tgtgaccaca gctgcccctc accatgctaa  25020
gctaattttt ttaattagat agtacataaa cgtcccaaaa ttagaagata aaaagacatg  25080
agggatccat tctaatttgt gtttggagtg taatggtcca gctccattct tctgcacatg  25140
gatatccagt tttacacaac actgtgaatg taatgaatgc cactgaatca tacactcaaa  25200
aatagctaaa atggcaaatt gtctgttatc tctttttaac caccattttt gaaaattaat  25260
tataccaaaa aaccattgaa tagtgcactt tatttattta tttatttgtt tatttattta  25320
tttattttag aaataagagt ctcactttgt tgcccaggct ggagtgcagt ggcgtgatca  25380
tggctcattg cagcctcgac ctgctgggct cgggctatcc ttccatctca gcctcccgag  25440
tagctgggac tataggtggg cgccacccca cctggctaaa tctcttttta actttttgtag  25500
agataggcat ctcgctatgt tgcctaggct gggctggaac tcctgggctc aagtgctcct  25560
cctgccttgg cctcccaaag cgctaggatt acagatgtga gccaccgcgc ccaccctgaa  25620
ccttactttt tttgctcagt ttctggtaat tcagagaatg cctcctgagt tgttctacac  25680
ccacctcata ttccatggga gggctgtaca gggctttttt aacgaggcct ctaaggacag  25740
gcatttgtat cctttccagc ctttcactat tacaatgttg tagtgaataa ctttacacac  25800
tgtcatttat tttacttttt ttttttttta ttttagagaa aggaatcttg ccatcttgcc  25860
caggctggtc tcaaattcct gggcccaaac aatcctcccg ccttggcctc ctaaagtact  25920
gggatttata ggcataagcc accgtgcctg gccaatgcac actgtcattt agctcatgtt  25980
aacacctgag tgtaggacac actcctggag gtggaattgc tgggccaaag agtatgtttc  26040
ttgtcattgt gatagatatt gacaaatgaa ccctcacaga agttgtgctg agttctgttc  26100
ccaccagcga cgtaggcgat gacctttttc tggagggagg gggcatcctt ggagtccaca  26160
gagccaggaa tggagagtgg gcccagaatt ttggtatagg tgttgtataa acttatagta  26220
aggttaagaa aaccgcaact atccttatca gagacttggc ggggggcagg gtatgatgga  26280
gatcataagg aggctaaaac actccacacc ctccctctgc attgctcctg cacgggagtc  26340
gggaatcttt tcaggttgat acgatctcac cttgaggagc tgtgaggtcc cagaagcctc  26400
tgggttgcag attgcttggg gtgaaaatgt ctgtgctact gaaatctaac tttttacaaa  26460
aaattacggg ctgggcgcag tggctcacgc ctgtaatccc agcactttgg gaggctgcag  26520
cgggtggatc acttgaggta aggagttcaa gaccagacca tagtgaaacc gtgtctctac  26580
aaaaaaaatt agccaggtgt ggtggtgcat gcttgtaatc ccagctactc agaaggctga  26640
ggtgggagaa tcccttgaac ccgggaagtg gaggctggag taaaccatga tcgagttact  26700
```

gcactccagc ctgggtgaca agagtgagac tctgtctcca aaaaaaaaaa aaaaaaaaaa 26760
aaaactggat tgcctggctc tactccgggc acagcatgca ggcccagttc tgctgctctg 26820
ctgtttgttc tgctttcctc cacatattgg catcaccctc tggtgccaag atggctgctg 26880
cattccaggc atcacatcca gactcagacc cagagaagct gcccatccct acctgggtga 26940
gcctttgtag gaacgagaaa ccgcatccag cagcagaaac ctcacccagc agcgtctttt 27000
ccggtctcat tcaccagcgc cgcccaccgc tcaaccaatc cctggccaaa agaatgggac 27060
cgcctggaag gctggaccaa acaggacctg ccctctgggg ctggggagag gcccagatga 27120
aggctgcagg acaggatgga ctcctagacc tctgttacca gcagtgacta cctctgtctg 27180
ggtggttgga acatgtttga attttattct aagtactgtc tacaagttct gcaataaacc 27240
ttgactcttc ttttaataat gcaaaaggaa tcgaagtgat tgtttgaaag ggagaggaag 27300
aaagagagag ggagggaggg aagaatggag ggaggcaggg aaggagacag agagagtaga 27360
atccagccac cggaaaatcc agaatagctg gctttgctta atccatgcct ggaaataact 27420
gctgggtttg caacaacttc tctcccggag acagaccaag gaaactacaa aactgcagga 27480
aggattgaag ggccgggcac agtggctcac gcctgtaatc ccaacacttt gggaggccga 27540
ggtggattgg atcacctgag atcaggagtt cgagaccagc ctggccaaca tggtgaaacc 27600
tcgtctctgc tagaaataca aaaataagcc gggcgtggtg gcgtgcgcct atagtcccag 27660
ctactcggga ggctgaggca agagaatcgc ttgaacctgg gaggtggagg ttgcagtgag 27720
ctgagatcgt gccactgcac tccagcttgg gcgacagagt gagaatctgt caggtggatt 27780
ctgagggtac tctgacccca cgaacccagc atgaaatctt ccaggcatta aggaacattg 27840
aggatgtgga ggattggaaa tccctccagg gaaaatacac ttctcttgag cagggtcacg 27900
aggggtgggg gcaatgtggg aggtggggca aatccaaaga caaggtcaac agcaataata 27960
ataataacaa tgacaggcat ttgttgcttg ttggctgggc ctcttgcata cagttctccc 28020
aacatccctg tgaggtggtg atgcttatcc ccattctcca ggggaggagg ctgaggccca 28080
gagaggtgaa gtcgtgtgcc acaaaatacc ccagccatat ggtggtagaa ccaagttttc 28140
agccagactc accagctcac agcagagctg ccctggactc tacagccatt cagtgtatag 28200
ctgggccact ccatcattca aggcagttca acgtcaagat tcctgatttg cctcaacctg 28260
gggcctctag aagataccat cacccccaac aagctgaaga cgtgtgtccg gaacactcag 28320
acacacacaa agtgctatgg atacaccaca ccccgaccta gctgtctctt cctgatggac 28380
ctcactgggt agaaatgcct ggcaccgcct gcctcagatc cctaggtcag ctctcactcc 28440
ccaatagaag tttctgagat gatgatgaaa acgttctcca tctgtgctgt ccaatggagt 28500
agccactgat cacttgaggc tagtgagcac ttgaaggtgg ctagtttgag gaactgcatt 28560
ttttaatgca tttaatttta gttactttga atatatatac acatatatac atttatatat 28620
acatattcat acacatacat tttacatata ttttatatgt atatgtaata tatatataaa 28680
ttatatatgt atatattttt atatataaat atatattata tatttataaa tatataaata 28740
tataatatat attatataga tatataaata taaatatata ttatatatat aaatatataa 28800
tatatattat ataaatatat ataaattata tatttatata tataatatat aaattatata 28860
aattatatat atttatatat aatatataaa tatatataaa ttatataatt tatatattat 28920
atataaatta tatattttat atataatata tacaatatat ataaattata tataatatat 28980
aaatatatat aaattatata taatatataa aatatatata aattatatat aatatataaa 29040
atatatataa attatataaa tctatataaa tatatactat attataaata tagtatatat 29100
ttatatagat ttatattatt tatatagtat atattatata tttatatgtt tatgtatata 29160
taaatatata atatataaat atatttatat attatatatt tatataatat tttatataat 29220
atgttatata tttttatata atatattata tatatttata t 29261

<210> SEQ ID NO 10
<211> LENGTH: 29220
<212> TYPE: DNA
<213> ORGANISM: Artificial Sequence
<220> FEATURE:
<223> OTHER INFORMATION: modified gene

<400> SEQUENCE: 10
aataaataac tttttagacc atatatttct tttttttttt tttttttttt tgagacagag 60
tctcactctg ttgcccagac tggaatgcag tggcatgacg ttgactcact gtaacctcca 120
cctcaagtga ttcagcctcc caagtagctg ggattacagg tgtgcacgac taccacccag 180
ctaatttttg tgtttttagt acagatgggg tttcaccatg ttggccaggc tggtcttgaa 240
ctcctgacct caaaagtgtg ggggaaagaa agagagatca gactgttact gtgtctatgt 300
agaaaaagga agacataaga aactccattt tgatctgtac taagaaaaat tcttctgcct 360
tgagatgctg ttaatctgta accctagccc caaccctgtg ctcgcagaaa cgtgtgctgt 420
attgactcaa ggtttaatgg atttagggct gtgcaggatg tgctttggta aaaatgtgtt 480
tgcaggcagt atgcttggta aaagtcattg ccattctcca gtctcaagta accagggaca 540
ccatacactg cggaaggcag cagggacctc tgcccaagaa aacctgggta ttgtccaaga 600
tttcccccac tgagacagcc tgagagatgg cctcgtggga agggaaagac ctgaccgtcc 660
cccagcccga cacccataaa aggtctgtgc tgaggaggat tagtgaaaga ggaaggcctc 720
tctgcagttg agataagagg agggcatctg tctgctgctc gtccctggga atggaatatc 780
tcggtgtaaa acccgatcgt acattctatt tactgagata ggagaaaact gccttatggc 840
tggaggtgag acacactggc agcaatactg ctctttactg cactgagata tttgtgtaaa 900
gtcaaacata aatctggcct acgtgcacat ccaggcacag ctcctttcct taaatttatc 960
tatgacaccg agtcctttgc tcacgttttc ctgctgaccc tctccccacc attaccctat 1020
agtcctgcca catccccctc accgagatag tagggatagt gatcaataaa tactgaggga 1080
actcagagac cagtgccggt gcaggtcctc acttgctgag caccggtccc ctgggcccac 1140
ttttcttcct ctatactttg tctctgtgtc ttatttcttt tctcagtctc tcgtctccac 1200
cttgtgagaa atactcagag gtgtggaggg gcaggccccc ttcaaaatga tccacccacc 1260
tcagcctccc aaagtgctgg gattacaggc atgagccacc atgcccagcc acatataact 1320
tatttctaaa taacttattt aactaacacc acatgatttt atgacccccct attttatgga 1380 tgagaaaaaa gaggcaagag aagcgatacc agttgcttag gattcccagc taccaattag 1440
tggaagcaga atttgaacca agggagtctc tggagccctc gttcccaatc tccttttctt 1500
cctctccatg tctttctttc tccccctgct cccaggcctc ctacatcaca cccttctgga 1560
caaagcttca catctgacat tttctttttt ggggtggaca gagtcttact ctgtcaccga 1620
ggctggaggg ccgtggcgca atcatggctc atggcagcct caaactcctg ggcttgaggg 1680
atcctccagc ctcagcctcc caagtagctg ggactatggg catgtgccac cacacctggc 1740
taatttttta attttttgta gaaatacagg gggtgggggc atatctgaaa attttaaacc 1800
ttccctgact gccgtgagca tttctgggta gaagccactc cacgacctta ctttgctggc 1860

```
atgagtgctg gacagcaatt tggcaacatc ctctagacca caaatgtgca tggcctttgg   1920
cccagcaaat cagcttctgg gaataaatat gacagatact gttacataca tgggaaatgc   1980
catggacatg atgacccagg gaagcacagt ttgcaagtac aaaagggctg gaaacaccca   2040
aaaagcccat cccctgaaga cagtttcaaa aatgacggtg cattcatgta atggaatagt   2100
acacatttgt gaatgaatga atgaggtagc tcaatatatc tgcctatggg aaaatcacca   2160
agatatgttg ctaagtgaaa aacagaaaga tacagaataa tgctaccatt ttattttta   2220
atgggagagg gaagaataag gaaatggatt catatttgct taattacaca agcttcctga   2280
tgatcctttt ggatccagaa gtttgaaaac cacagcatca agaggatgcc cattgggcat   2340
ggtggctcac gcctgtaatc ccagcacttt gggaggctga ggagggtgga tcgcctaagt   2400
tcaggagttc gagaccagcc tggccaacat ggtgaaaccc catctctact aaaaacacaa   2460
aaaaattagc tgggtatggt ggtgcaggcc tgtaattcca gctacttggg aggctgaggc   2520
gcaagaatca cttaagcctg ggaggcggag gctgccgtga gccgagatca cgccattgca   2580
ctccagcttg ggagacagag caagactgtc tcaaaacaaa caaacacaca caaaaaataa   2640
gatgcccatt ggagatctcc attcactatt ttatcagatg atatttcagc acttgagtga   2700
agaaaatgtc tacaactggt ccaaacactc aaggaattta gactcttgac agagaaacac   2760
acagaagcaa gcagatatgc cccgaaccaa acttgctttt tcttctaagc ctgcttcttc   2820
ggagcagcct ctgaccctcc agggccctga gaggagtccc tggagccaca ggagcttggg   2880
agcccagaga agtgggggaa tcccagatgg tgacagcatc atccagagga ggaacataac   2940
gatggccaca gattcccaat ttggaaataa ctcagcaaaa caacactgac agaaaattca   3000
gagatttcca agagactagc ctccctgttt ccatttagaa attcacctac atacatccag   3060
ggtgagagac cccaagcatc agatgtgtca tacacaagca tcagatccaa gttagagagg   3120
gcacccgggg acagaaacct ccaagccagc caaaagccaa aggaaggatt ttacagaaag   3180
atacaggaat gtggggccag gcacagtggc tcatgcctgc aatcctagca ctttgggagg   3240
ccgaggtggg aggatcgctt gcggccagga attcaaggcc agcctgagca acatagcgag   3300
atcctatctc tacaacaaat ttaaaaacta gctgggtgtg atcacatatg cctgtggtcc   3360
caactaccca ggaggctgag gcaggagttg agcccaggag gtggaggctg caatgagcaa   3420
tgatggcgcc acttcactcc agcctcagtg aaatagtgag accctgtcta aaaataataa   3480
taaaaataaa aaacatataa agatgtcaga gcacagggac cagagctgtt agtcggcctc   3540
atggagaccc tggccaggac agccacctct ggggaccagg aagtctctca gtttctgtct   3600
ctgagggttt ggctctctga gtctctctgt cacctctcat ttctctctca tctccctctg   3660
tctatgctgt gtctctatct ctttcaatct ctctgtctct gtctcccagc ccttatctct   3720
gagtgtgtct gtttctctct catttctctc tctctctctc tctctttctc tctctctctt   3780
tctctctctc tctttctctc tccccctcc ctcctcccct ctccctactg caggctggtc   3840
cataaccctt atcttcccca gacctgatgg agttctggta ttaatctgtt tatggtctgt   3900
ttccctccac tagaacacgg tcttcattaa aggcagagat ttttgtctgt cttattttct   3960
gctgtatacc cagtgcctgg gatactggct ggatcaataa atatatgctg aatgaagaat   4020
gaatgaatga ccattctcat gaacattatt atttgatgcc aactgtaaag caacaataat   4080
aataattgtc actgccactg ctgctattgt tggtatatca gctttttatt tagtacaaac   4140
tatatccccg aaattgagct aggcagtttc ttgtttaagt tttacagacc acgctgtgag   4200
```

gtaagtactg ttagtatgcc ctttttttctt tctttttgag acagagtctc actctgtcgc 4260
ccaggctgga gtgcagaggc ccgatcttgg ctcactgcaa cctctgcctc ccgggtacaa 4320
gtgattttcc tgtcttagcc tccccagtag ctgggattac aggcatgtgc caccatgccg 4380
gctaattttt gtatttttag taaagatggg tttttgccat gttggccagg ctggtcttga 4440
actcctggac ctctggtgat cctcctgcct cggcctccca aagtgctggg attacaggcg 4500
tcagccactg cgcttgctcc cccagccccc aaactttttt tttttttttt gagacaggtc 4560
tggctctgcc acccaagctg tagtgtagtg gcgcaatggt agctcactga agcctctaac 4620
tcctgggttc acacagtcct cctgcctcag cctcccaaaa tgctggaatt caggcctgag 4680
ccaccgcgcc ctactatgcc catttttcag ataaagaatc tgagggccct cgaggagaaa 4740
ccacttgccc aacatgagcc ctggtcttgt ctgaccccaa agcccatggg aagtttaggc 4800
tgcgtggaag gacagcctgg tgggctcagg atctgtccca tcacgagttg gaacctcagc 4860
tctgccactc ggcaaccgcg agccgttagt aagttgctga atctctccgt gtgcctccgt 4920
ttcctcacct ggaatgtggg cgacctcaca caggaagccg cctcttctag tgggcaccga 4980
cggagcgagc gcgcgtctgc agcgggactg agcgccggga gagacctgcg caggcgcagg 5040
cgcgcgggga gggccagcct gggtggccca ccccgcgcct ggcgggactg gccgccaact 5100
cccctccgct ccagtcactt gtctggagct tgaagaagtg ggtattcccc ttcccacccc 5160
aggcactgga ggagcggccc cccggggatt ccaggacctg agctccggga gctggactcg 5220
cagcgaccgc ggcagagcga gcgggcgccg ggaagcgagg agacgcccgc gggaggccca 5280
gctgctcgga gcaactggca tggcccgagc catggccgcc gcgtggccgc tgctgctggt 5340
ggcgctactg gtgctgtcct ggccaccccc aggaaccggt gagtgacccc cgcgcagtcc 5400
ggtggcccct gtctggctcc cagctccgca tccaggccgg gtactcgccc ccttgggttc 5460
ccgaagatga cggccccgcc cggcgccacc caccccccat ctctgccccg gggttggaag 5520
gaacacggtg cgagggtgcg agggcaggac cctcctcttg gccacccgga gagcggtcgg 5580
agttgggtac agaaattcct cgaaattggc agcaacacgg gtcgggcaca agaccctcct 5640
ctgggcccct cggaaagggg atggagttgg gtgaggaaat ttcccaaaaa ggcaagtgaa 5700
tcccggaaaa tcagcagatg gtgacgcatg ccggattacc ttacccaggt tcctgctcag 5760
catacccagg ccataaccca gcagcgtgct ggcaggctgg gtctggacgg aggggatggt 5820
tgatgttggg gaggaggaca gtgggtgaca cttgacacca ttacccctct gacccccaat 5880
gtctgactcc aggggcctgg ccattcattc attctttcat tcttttttttt ttttttttga 5940
gacagtctca ctccatcacc caggctggag tgcagtgtcc tgctctcggc tcactgcagc 6000
ctcctcctcc cgagttcaag cgattctcct gcttcagcct cccgagtagc tcggattaca 6060
gacatgtgcc actatgcctg gctaatattt ttgtattttt agtagataca ggatttcacc 6120
atgttggcca ggctggtctc aaactcctga taaatatata tattatatat tattattata 6180
tattacatat tatagtaata tataataaaa atatataata tatattatag taatatataa 6240
tatataataa aatatataat atatattata gtaatatata atatataata aaatatataa 6300
tatatattat agtaatatat aatatattat aatatattat atatattatt ataatatata 6360
atatgtatat tatatattat atatattatt ataatatata atatgtatat tatatattat 6420
atatattatt ataatatata atatgtatta tgtattatat aattgataat atataataat 6480
atatttctta ataaatatat attaaatata ttatatattt ataacatata ttatttatat 6540
aataaataat atatatttta ttatacattt aaagagtaaa tagataacat attttattat 6600
ttatttatat gttttgtgta tatatatata tatatatata tatatatagt gcgtgtgtgc 6660
gtgtatgtgt gtgtgtgtat gagagagaca aggtcttgct ttgttgccca ggctggagtg 6720
cagtggtaca atcccggctc attgcaaact cgacttccca ggctcaagcg atcctctcac 6780
tgtggcttct ggagtagctg ggattatagg tgctcacctg gctaattttt tttgtatttt 6840
tggtagagac agggtttcgc tatgctgccc aggctggttg cagccaagca cagtggctca 6900
tgcctgtaat cccaacactt tgggaggctg tggtgggagg atcacttgag cttaggaatt 6960
caaaaccagc ctgggcaata tggcaagacc ccatctctac aaaaataatt aactaaataa 7020
aaatttaaaa ataaaaaaga atgcatagga ccatgtttat tagtgtcaat aagcgctgtc 7080
acattttgag gacctactat gtgctagggc ccttagcaga aagattttta tataggacct 7140
gggggattag aggtcagtct ctgaccgccc aagttcaaat cccacctctg ccactaaacc 7200
tctgtatgac ttggaggaca ctatactctg tgtcagtttc cctgtctgta aaatgatgtt 7260
aacagtagtg cttgcctcag gggggctatt tgaggattaa atgccaagat atatgtgaag 7320
cacccagaat agcccctgat ctgtgtcagc accctgtgag tgtccactgt tctaagtctc 7380
attttacaaa ctaggaaaaa gaatcagaga ggttaagtaa ccggcctgaa gctccacagc 7440
agaaaactga agggacccaa aactcctggg ctataattgc cttcctctcg tgcctcaatc 7500
ccccacattc ttccaaccag gacccaccca gagtaataat gcagtgtttc atggatttga 7560
agacccaaga tttctccccg ttttctacat tggggttatt ctaaccccta atggcaagtt 7620
gtgctataaa tgacaacagt catggtatgt gaaacctacg acactggtgc gatgaaaaag 7680
ttctgggcca ggtgcggtgg ctcatacctg taatcccagc actttgggag gccgtagtgg 7740
gaggatcact tgaggtcagg agttcaagac cagcctggcc aacatggtga aaccccatct 7800
ctgctaaaaa caaaaataca aaaaattagc caggtgtggt ggtgggagcc tgtcatccca 7860
gctacgcgga aagctgaggc aggagaaccg cttgaacccc agaggcagag cttgcagtga 7920
gcagagatcg cgccactgca ctccccctgg gcgacagaga gagactccgt ctcaaaaaaa 7980
aaagagaaga aaagaaaaag ttctggcgct atatagtagt aacggttgca caatatcgtg 8040
aaatgtacat agtgccactg aactgtatgc tttaaatgac ttaaatggta aatttagttt 8100
tttaaccaca atatttacca caatttttta aatcagtgat gttgagattc agggaaatac 8160
ggtaataata gaagaaatac ggtaataaat agccaaagtg aaggagcacg gccaagttgc 8220
agaccatccc agacgccctt accctcctcg cctgccatgg ccccaactag tgccccagtt 8280
ccccctcccc ccacacccca cggtccaccg gggatccagg gccccagcgt gcaagtgcac 8340
gcccaggtgc ccgggctcct ggagcccctc cctatctagt ccaagaacgc cccgggtctg 8400
acaccttctc ttcggttctc cgcaggggac gtcgtcgtgc aggcgcccac ccaggttaca 8460
ggtgcccaac atggaggtga cgcatgtgtc acagctgact tgggcgcggc atggtgaatc 8520
tggcagcatg gccgtcttcc accaaacgca gggccccagc tattcggagt ccaaacggct 8580
ggaattcgtg gcagccagac tgggcgcgga gctgcggaat gcctcgctga ggatgttcgg 8640
gttgcgcgta gaggatgaag gcaactacac ctgcctgttc gtcacgttcc cgcagggcag 8700
caggagcgtg gatatctggc tccgagtgct tggtgagcag gggtttttgg ggaggctgaa 8760
tgaaaggcag agacttggtg ggaggatcag ggaagttggc aaagagcggg gaggcctggg 8820
agggagggag attccctcca cagcagatcc cctggggaca aaaggagggg gcagcgcaat 8880
gatgtggggt ggggtggggg gaggtgagtg gggggagggg ctgcagggca ggaagaaagc 8940

```
agagatctca gggagtaagg acccccaagc ctgggatcag aaagccctga gggaggagga   9000
ggggtatatt ggaaagggag ctgggagggg actgggaagg aagggaggag gcctgggtgg   9060
cctcttctgg gtccctcctt tcctcatctg taaaagggtt ggtgacaaca gcatcaccct   9120
tggaaagctg tcctgagtgt catcactgcc taggaaagag tctgtctgcc cccttggact   9180
gtgtacccat gagggcagaa ccggggctat tttgatcact gctgggcccc agcactttcc   9240
accaaacaat atttattgag cacttattat gtgccattct aagagcttta cctgcatatt   9300
ctaattgcct gtgattccat cattatcacc tgttgacaga caaggaaact gaggcacaga   9360
cttgcccaag accaaagctg cagccttagg gcagcggcgc ttcaccgctg gcccatgtga   9420
gccccttaga gctgtcggtt actgttactt tatctggtga agaaggagaa agttgaaaca   9480
gacagacagg aaagcaagga tcctgatacc caaaagagga ggggatcatg ctttcatttt   9540
catgagctcc atgaagcctt cctcttggaa cttgagcaag aagtctctgt gcctcagttt   9600
cctcatctgt gggataggga tcaccatgag gattcaaaaa aactgaccct ttttttttt   9660
ttgagatagt ttagttctgt cgcccaggct ggagtgcagt ggtgtgatca tagtaggtcc   9720
tcactgcagc ctggaactcc tgggctcaag ggatgttcct accctccctg tagctggaat   9780
tacaggaatg tgccaccatg cccaacttgt tttctgtttt gttttgtttt gttttgtttt   9840
cttttctttt taagcttatg tgccaagaac tattccaagc ctgtgcatga gaaactcatg   9900
aaatgtcaag ggcttggaac tgtgcctagc acacaacacc caaccaaagg cagctgttgt   9960
cactccagca agcctgggat tctgggtatc atggtttagg atgagggtaa aacagaaaca  10020
gtgagtcaag ttaaggagaa atcttcggta aataatatag gtaatgatgg ggaaggaagt  10080
tccaggtttg ggaatcacca ggatgatgat taagagatgg tcaaggtggt tttggagtca  10140
gacagacttt atgtgaaagc ccagctctgc tgcttacagc tgtgtgacca tgggcaagtc  10200
acttcccttc tcaacttcag ggctcaggct tcctctcctc cactgagccc cagaccagga  10260
taaccccctt tgggtttccc ctttccagcc ctgccctctc cgagtcatca ctgcctagga  10320
aagagtccgt ctgccccctt ggactgtgta cccatgaggg cagaaccagg gctattttgg  10380
tcactgctgg gctccagcac tttccaccaa acaatattta ttgagcgctt attatatacc  10440
attctaagag ctttacctgc atattctcat tgcctgtgat cccatcacta tcccctgtca  10500
acagacaagg aaactgaggc acagacttgc ccaagaccac acagctgctc agggacacag  10560
ctgggattta aaccatgcca ttctgtatct tttttttttt tttttttttg agacagaatc  10620
tcactctgtc gcccaggctg gagagcagtg acacaatctc agctcactgc aacctccgcc  10680
tcccgagttc aagcaattct ctggtctcag cctcccaagt aactgggatt actggcgtgt  10740
gccaccatac cctggctaat ttttaataga gacagtttct ccatgttggc caggctggtc  10800
tcgaactcct gaccccaagt gatccaccca cctcagcccc ccaaagttct gggattatag  10860
gcgtgagcca ccccgcccag caaccatgcc atcctgtacc cttaatgaat gccccccttct  10920
gccacggagg ggttcattga atgacttgtt gcttttgttc ctcttcccag ccaagcccca  10980
gaacacagac ctgggcggga tgcccaatac gagccaggtg ccagggttcc tgtctggcac  11040
agtcactgtc accagcctct ggatattggt gccctcaagc caggtggacg gcaagaatgt  11100
gacctgcaag gtggagcacg agagctttga gaagcctcag ctgctgactg tgaacctcac  11160
cgtgtactgt gagtgtgccc aagtcagcga tggcaagaac ccctgccggg ctgcccccac  11220
cactgtctac actgactccc caaggcactg taggcattgc ttccatcatc tgcaccggct  11280
cccctgactc ctgtctacac gacccacccc cattgtctgc accagctccc ctgggccgta  11340
```

aacaacactg tccctattgt ctacaccagt ttacttgggc catagtcaat gctggtaccc 11400
agactgtctg ccctggctcc tctagcggct gtctgcacgg atacctgaca ctctgttgac 11460
tcccttgagc acagtctaca ctgcccctaa actgcctaca cccatttccc caggcaagta 11520
tccacaatga ccctccccac attgctacac tggttcttct ggccacgatc aacactgcct 11580
cccttattgt ctacacccac tcccttgtcc ttttctttct ttcctttttt tttttttttt 11640
tttgaaatag agtctcactc tgttacccag gctgcagtac agtggcatgt tctcggctca 11700
ctgtaacctc tgcctcccaa attcaggtgg ttctcctacc tcagcctccc aaatagctgg 11760
gattaaaggt gcacaccacc acacctggct aatttttgta tttttagtag agacagggtt 11820
tcatcatgtt ggccaggctg gtttcgaact cctgacctca ggtgatcggc ctgcctcagc 11880
ctcccaaagt atgctggaat tataggcatg agccactgtg cccggctttt tgttttgttt 11940
tgtttttcct ttggacaggg tctcgctctg tcacccaggc tggagtgtag gggcatgatc 12000
atggttccta cagcctcacc cttccaggct caagcaatcc ttctccctca gcctcccaag 12060
taactgggac tacaggtgca gccaccatgc ccggctaatt ttacagtttt tttctagaga 12120
gagttttgct gtgttgccca ggctggtctc aaactcctag gcttaagtga tcctcccgcc 12180
tcagtctccc gaagtgctga gattacaggc gtgagccact gcacctggcc ccttgtccat 12240
tttctacact gccttaccat tgtctacact ggctctcctg ggccacagac agcactaacc 12300
ccattgtcta caccacctat tttggccacc agctgtgggg tgttttcact gtctcccata 12360
gtgtctacac tggctcctat gaccactgtc tatgtaaaca ccccactttt tctacactgg 12420
ttctcctagg cactctctaa agtgcccccct gacactgtct acactgactc cctggagaac 12480
tgtctgcatt cacctcccac attgtatcga ccagttcccc tgagccacga tcaactgtct 12540
ccgccgggtg ctagttgcat tgatcttctc acattgtttg tgctggctcc cctaagcagt 12600
gtctgcagag tcccccagtg tagtctccat gttcctctgc ccaatattgt ctacactggc 12660
tcatctacag gctatccagt ctcaccccac atcaccacac tggcctcctt gtgttctgtc 12720
tgcacagccc cctgacagca tctgtcctga ttctcctgca cagcgttacc tccaccagct 12780
ccctcatggc atcatcgaca ttgacaccca cacatttatc tccactgaca gccccaggac 12840
tctctaacca gtgctgtcta acagaaatag catgcaagct gcatatagga ttttaaattc 12900
tccagcggcc accccattaa aaaattaaaa gaaagaggcc aggcacggtg gctcacgcct 12960
gtaatcccag cactttggga ggccgaggca ggtggatcac ctgaggtcag gcattcaaga 13020
ccagcctgat caatgtggtg aaactctgtc ttcactaaaa aatacaaaaa ttagccaggc 13080
acggtggcgg gtgcctgtaa tcccagctac tcgggagact gaggcaggag aatcacttga 13140
acctgggagg cggagattgc aatgagcgag attacgccat tgcactccag cctgggcagc 13200
agagcaaaac tccatctcaa aaacaagaaa agaaagagat gaaatttatt tgtttattta 13260
tttatctatt tatttatttg agacggggtc ttactctgtc acccagactg gagtgcagtg 13320
gcacagctcc ctgcagcctc aacctcctgg gcttaagtga tcctcccacc tcagcctcag 13380
tctcctgagt agctgggact acaggcgtgt gacaccatgc ctagctaatt tttgtttttg 13440
tttttgtttt tgtttttttg ttttgtgatg aagtcttgct ctgtcaccca ggctagagtg 13500
cagtggcacg atctcaactc actgcagcct ccgcctctcg ggttcaagtg attctcctgc 13560
ctcagcctcc cgagtagctg ggattacaag ccctggccac agtgcccagc taatttttgt 13620
atttgtggta gagacgggat ttcaccatgt tggccaggct ggtctcaaac tcctgacctc 13680
gtgatccacc caccttggcc tcccaaattg ctgggattac agacgtgagc caccgcaccc 13740
ggcctatttt tattttttct ggagacagga tctccctatg ttgcccaggc tggtctcaaa 13800
ctcctgggct caagtgatcc tcctgcctca acctcccaag gtactgggat tacaggcatg 13860
agccactgtg cctggccaaa attaattttt aataattgcc tttacttaac ccaatatacc 13920
taaaatatta tttcaacttg taattgtttt tttaaaatta ttcttgagat ctttcccatt 13980
tattttgtcc tagtaaagcc tttgaaatct ggtgtgtatt tcggcctggc tatatttcga 14040
gtgctcagta gtcacatgtg gccagtaggt gccatattgg acagcacaga tctagactaa 14100
gctcccacat catctacact ggctcatcca aatactgtct acacacatac acagagcctg 14160
tcttaatttc gtcagctccc ggggacacac tgtatatgtg ggggtgatct cacccccacc 14220
accacatttt caacactggc ccgacaatat agcatctgct gtaatattcc aacaccctgt 14280
ctacactgaa cccatcagta atatccacac aagctcttct agacatcatt catactgttc 14340
ctcccaccat tgtctatact gcttactccc cgccaggcaa ttggtacaca gattccctca 14400
ggtactgtct atactggagt ccctcaacac tgtcactggg tctgagcgag gaggagatct 14460
acactgactc ctacccctcg cccccgaata aaaccctgtc ccattggcct gcccccaagg 14520
acattgaaag gtcttcgctg tcaatcacgt atgggatggc tgagcagcag cctagagcag 14580
ggttatctgg gactctttcc tgcaggactt gtcagaacct tgaatacact gctgtgtgtt 14640
gtgagtggtc attgcctatg agtgagaaaa ggaggaggca ttttcctgca ggacacccaa 14700
gacatgcctg gtccaggcta cccaggaaag ctagtggaga aaagcagctc ctcagaagcc 14760
ttctccatgt ccccactgac caaggactcc taggcttctg ctctctgtgg caccccatct 14820
acctagactc ctcctaggcc tctccagctc ccgctgtttt ccaaatatcc ccgggccttt 14880
tcctgcagtg tcgtgaatcc cgcgtagccc caggcccccc aaagcctccc agtctctgaa 14940
cctctgtatc catttcctgc agaccccccca gaggtatcca tctctggcta tgataacaac 15000
tggtaccttg gccagaatga ggccaccctg acctgcgatg ctcgcagcaa cccagagccc 15060
acaggctata attggagcac gtgagtcctg ggtctcaggg aggaggggct gggggtctgg 15120
atttctagca ctgagggagg aggggctggg ggcctggact cctgggactg agggagaagg 15180
ggctgggggc ccggacccct gggtctgagg gacgagaggc tgggagcccg gactcctggg 15240
tctgagggaa gaggggctgg gggtctggac ccctgggact gagagaggag gggctgggcc 15300
tggacccctg ggtctgaggg aggaggggct ggggggtctg gacccctggg tctgagggag 15360
gagaagctgg gagcctggac ccctgggtct gaggcaggac agactggggc ctggactcct 15420
ggtctaagag aggagggaga ttcagaaaag agaaaaagag gaggttgact tcgggccccc 15480 agtgggggc atctctgttt tgacatctct gttttgcggt tgaggcgttt agcaggtggt 15540
tgaatcctgg ctggtggatg cacctgcttt ttggggtgtg cctgctctgt gcccggtact 15600
tcccccgaat cccatgtgac cccatgctgt gcacagtcag cagctgttgc cctgcccagg 15660
ttaaagacca gccacgagag ggcagaagcg gcccttgaat cagcgctcgg ctccaaagct 15720
ggtcctccgc ctcttggcca agcttgtcta acctgcaggc cacatcattt gtaaactttc 15780
ttaaaacatt atgagacttt ttttttgcga attttttag ctcattagct attgttagtg 15840
ttagtgtatt ttatgtatgg cccaggacag ttcttcttct tccaatgtgg cccggggaag 15900
ccaaaagatt ggacaccccc actctagact gtaaccacct caccgtcacc ttgtgtaacc 15960
tacttggtta tctctggatg gagcaagtac tatatatccc cattgtctag atgagaaagt 16020
tgaggctcac agcaataaga tttccccaga ttcacactga ggctgagatc aagagcaagg 16080
taagaaaaag gcaaagagat aatacataat tttataatac ataattttac ataaattaca 16140
taattttact gaaccgccct ttttttttaa agaaggggct ctgttgccga ggctggagtg 16200
cagtggcgtg atcatagctc actgcagcct ggacctccct gggctcaggt gatcctccca 16260
cctcagcctc ctgagtagct gggactacag gcacacgcca ccacactcag ctaattttgt 16320
tgtatttttt ttgcagagac agggttttgc cacattgccc aggctggtct gcaactcctg 16380
ggctcaagca atcaacccac ctcagcctcc taaagtgctg ggattacagg cgtgagccac 16440
ctcgcccagc cttaggtctt tttccttatt acaaaaataa cttgtgtcca ctgtagaaat 16500
atcaaacaat ttagttatga gcaaaaagaa gaaagtagtg cctatagttc aagtgtaccc 16560
agccacctcc agaaataccc agtgacccct tattatacat cctgtctttt ttctctctgt 16620
ttctaaacaa agactggaat tatgctgtac atataatttt gaaccttttc gtctgtcttg 16680
tgaatacctt tccatgtcaa agcacataga tccacaactc cattttcccc cacgttgtat 16740
taggaagact gtcaaacata cagaaaaatc ataggaattt tccagtgaac acttaagatt 16800
ccaccacgtg gattcccctg ctaacatttt actgtgcttg ctttatcacg tttctgtgat 16860
tccttcagtc cctctattca tccatcaatc atattatgca tttcagagca cccccagctc 16920
tcctgctttt tttttttttt tttttttttt gaggcagggc ctcactctgt tgctcaggct 16980
gtagtgccgt ggcacaatca cagctcactg cagccttgaa ttcctgggct caagcgatcc 17040
tccagcttca gcctcccaga tagctgggac tacaggcaca caccaccacg cctggctaac 17100
ctggcccctt ttttagtgtt gctgggattc caccacttta aaaaaaaaat tcaaagaata 17160
gagacaggat ctcactatgt tgcccaggct ggtcttgaac tcctgtactc aagcagtcat 17220
ctcacctggg cctcccaaag ggcagggaag ggattccaac atatgtggat gtcatcagtt 17280
atttaaccag tccctagtag aggacacaga tgtcattttc cattttcaac tctgcaaatg 17340
ccatggtggt gtccatcccc actggtcact tgtcagcagt tgtccgtgga aggaattgcc 17400
ggtcaaaggt tttcaactgg tgtgatggtg cctttactgt cctgcctcaa agcaccgcaa 17460
ttcaggctct tgagccagat agctgcgttt gcatcccagc tctgcggagc acccaaagcc 17520
tgatgcttcc atctcctcca cctctgttca ttaaaccagt gttccttgac tacttactgt 17580
gtgccgggtg caattaacca acatacgttg gtcgataaaa cagaccaaat ttcctcccca 17640
tatagagctt ccattctagt ggtgaaagaa acaagaagca agataaagtg tgtagtgtgt 17700
gtgcaatggt gataaatacc atggagaaga caaagcagag aagggaatgg gactgggcgc 17760
catgactcat acctgtaatc ccagcacttt gggaggcaga gatgggagga tcacttgagg 17820
ctaggagttc aagaccagcc tggccaacat ggcgaaaccc catctctacc aaaaaagata 17880
caaaaattgg ccgggtgtgg tggcatgcac ctgtagtccc agctactcag gaggctgagg 17940
tgggaagatt ccatgcaccc aggaggtgga ggttgcagtg agtcaagatg gtgccactgc 18000
actccagcct gggtgacaga gtgagacgct gtctcaaaaa aataataatt aaataaatta 18060
aagagaaggg gatgggaagg gtgatcatca cagttgaaat agggtggcca agtgaggtgt 18120
tactaaggtg acatcccagc agaggcctga aggagatgag ggtgagctct gcgggtgcct 18180
agggggaaag cattccagca gagggaacag catgggcaaa cccatttcta tccatcagtc 18240
cctgcataag caaacaccct ggacacctaa ctggagagtt tgaggaccaa caaagaggcc 18300
actgtggatg cagaggcggg agcaaagggg agagtaatgg aaaacgtggg cagaggtagc 18360
aggggccaga tcacgtgggg cctgtgacac cagaagactt cggtttaact ctgagccagg 18420
ctaggccccc agagggtact gagctgaggt atgggaactg acttagggtt cacaggcgac 18480
ctctggtggc catgtgggga acagacgagg gggcgagggc agaaacggag cccagcgtgg 18540
aggcggctgc tgggggccgg gatgcacagc gccagagcag ggaggtaccg tggaagccct 18600
gaggagaggt gggattctgg atggatctta aggcggggcc gacatgattg gctaatgggt 18660
tgggtgtggg catgagagga agggaagagt tggggggcct ccagagttgc tctccgctta 18720
tgctatagag ggcgtgaggg tttctgggca cgtagtgcgt gctcaatcac tgtcactccg 18780
gacctgcagc agaggccacc tcctcacctt tctgtctctc ccaggaccat gggtcccctg 18840
ccaccctttg ctgtggccca gggcgcccag ctcctgatcc gtcctgtgga caaaccaatc 18900
aacacaactt taatctgcaa cgtcaccaat gccctaggag ctcgccaggc agaactgacc 18960
gtccaggtca aaggtgagga actccctggg tgggaagaac agggaccaaa ggaagaggtc 19020
gaggcagggt tccctgtcta atgctctctg gctcccatcc ttctcctaag ccttctcaca 19080
aaaggaccag tggggccagc tttactcccc tgttaactcc atacctatat cactggtacc 19140
gttgttcagc tgcctggata cactccctcc acacacacag gttgggatag atgtggaatc 19200
cctctctctc agggactcag gcctttccaa atatattagg cagacctcta tcaattgcaa 19260
ttgacagaaa cacaaagtag tctaagcaaa aaaaaccaaa caaaacagga ctttattgaa 19320
aattcacctt caggtatggt tagatccagg ggctccaacc ttgtaaccca ggaactttta 19380
ttttatacat ctcttgtctc tgcttttcgt tatactggct ttattctcag gcaggctctg 19440
aagcaagatg gccctcggca gggacaggct cacattctac cagaatggca acagcaggag 19500
aaaaaacata ccactttcag taactgtagc catagtccca gggctggctc tcattggccc 19560
agcttaggcc acagcccacc tatgaaccaa tcatagcagc cagggagaat ggaatattct 19620
gattggccag gcctgtgtca aagtcccatt ctgggcacca gagggtggga tccattccac 19680
ctgaattaaa tagactgagg cagtggagtg gtggctccct aaggaaattc aagatgccat 19740
ttcaagaatg agggataaac cccaagagtt tccttaccta aatacctgtt tccttctctt 19800
tcagagggac ctcccagtga gcactcaggc atgtcccgta acgccatcat cttcctggtt 19860
ctgggaatcc tggtttttct gatcctgctg gggatcggga tttatttcta ttggtccaaa 19920
tgttcccgtg aggtcctttg gcactgtcat ctgtgtccct cgagtgagca tcaccagagc 19980
tgccgtaatt gagcacctac tacgggctct gtgctgagtc cttccagtgt gcctctcact 20040
gaatcctcac cccactgcca tgaggtttcc cccatttgac tgatgagggt gcagagccag 20100
ggagccttgt tcactggttc attgattaca tttacaaata ttatttacag agtgggagaa 20160
gagcgtatag ggtcttaatg ccatggtagg gactttggaa tttaattcag gtgatgtggg 20220
agtccctgcc agatggatgg agggtgaaat aatgcttaag ccctcagcct tactccatct 20280
gccttgttca ggagtgactc ctaggaggag gtggcaggaa ctggcacctc tgatcctcag 20340
ctctaaaagg gtctgatgct ttcacacctc aagagatttg cacaggccgt tcccctgcct 20400
ggagcaccct cccatggctc cttctggaga agtgtgccag ctcattctgt aatcagagga 20460
acgatgcttt gctgagcact gtctacatgc cactttgtat gtataacccc ctcgatttta 20520
atttttaatt ttttttatta tttatgtatt tatttattta tttttgagac aggctctcac 20580
tgtcgcccag gctggagtgc agtggtgcga tctcggctca ctgtagcctt cacctcccag 20640
gttcaagcga ttctcatgcc tcagcctccc aaggagcggg gattacaggc acgcactact 20700
atgcccagca atttttgtat ttttaggaga gacagcgttt cgccatgttg gccaggctgg 20760
tctcaaaccc ctggtctcct gtgatccacc cgcctcagcc tcccaaagtg ctgggattac 20820

```
aggcatgagc caccacacct ggcctgtaca atctccttga atgcccacaa ccacccagca  20880
aagtggttct cccgtgagcc ccatgttaca gaggaggaag tatttgcttt gagagatgaa  20940
gttacctgcc aatggtcaaa cagctggaca tggttgttgg ggagaagaag ccagatcttt  21000
gactaccaag cttttccttc aaccactaaa caaagctgct cccttacaac ccaggcggat  21060
actgcctcgt ccaggaagcc ctccctgacc cccaagcatg agccaagcat ccactaggct  21120
ctcccactcc agccttgccc attctgggtc atcaccgtgg gggacttgtt tgtcatcccc  21180
agtggactgt gagccccaag atagcagacc tgaggctgtc actgtcatga ctgtgtcccc  21240
aggaccgcct accactgggc cgggcataaa agaggcactc gaggaagtgt ttgctgagtg  21300
attcaatgtg tcagctccag agccagactg cctgtatctg ggccctaaag ctactgcttg  21360
attagtgatg tcaccatagg caaatagctt aagctgtatg actcagtttc ctcatctgta  21420
aaatggggtg atggtaccta ataatacagt agagcactta acacagtagg tggcacatgg  21480
taagccacat actgagtatg tatttgctat gattgttatt gctattatta ctattattgt  21540
tattattaac ataaactgca caagagcagg ctttttgttt gtttgtttgt gttttgtttt  21600
gagacaagat cttgctctgt tgcccagact ggagtagtgc agtgatgtga tcttggctca  21660
ctgcagcctc aacctcccag gctcaggtga ttctcccacc tcagcctctc gagtagctgg  21720
gattataggc gtgcactccc acgcctggct aatttttttat atttttagta gagatggagt  21780
ttcgttgtgt tgcccaagct ggtctcaaac tcctagactc cagcaatccg cccacctcag  21840
cctcccagag tgctggaatt ataggtgtga gccaccacgc ctggccaaga gcaggcattt  21900
ttatctgttt tgttcacagc tgtgtcccca gcacctagaa tgtacctggc acaaagtaga  21960
cattcaccat ttgctgaata atactactat ttgctaaata aacccctgtt gaatagtcta  22020
ggaaactgaa cacagagagg ttaagtcact tgtccaagtt cacacagctc ctaaaggaca  22080
gagatggaat ttgaacccat ccatctggtt ccagagccag gctcgatatt tatggatatt  22140
tcataaccaa gtgaataact ggatggctaa atccttagaa agcacaccct ccatccctgt  22200
ctgacacacg tgtataccat taagggaaat ggcacccccca tgtaatagca gaggcagaac  22260
ttgacatttt cagggccctg acacccaggc atgtcttctt cccatgcttc ccagcattat  22320
tccttcctga cgacttcccc tcctatttcc ccaggtacag agcatgccag cgcctcagct  22380
aatggggtaa gtgcagtgtt ggagctaagg agggtgtggg gtctgcacga actacagacc  22440
agacgtcttc agatgcccac ggcccggcct caggagcctg ggtcttttct cctggtgcct  22500
cgagcagcat ttcccaaccc ttcctgctgg gcggaatccc ctgtagagtt tgctaagacg  22560
cagccccaga cagtctggtc tgtgatgggg ccagggaatc tgcattttaa tatccgctct  22620
ctccccccctg ccccacgccc cttcaattcc acccatggcc acaccttgag aagcactgcc  22680
ctggcttcca gggagagagg aggggacggg cctgcagttc tttgcacatg gggcttcagt  22740
gggaagatgt ttgattttgt tcaaaagagc cccaaggcta aatttgaaa accctcttct  22800
agcatgtctc ctattcagct gtgagcagag agaacagctc ttcccaggat ccacagacag  22860
agggcacaag gtgacagcgt cgggactgag aggggagaga gactggagct ggcaaggacg  22920
tgggcctcca gagttggacc cgaccccaat ggatgaagac cccctccaaa gagaccagcc  22980
tccctccctg tgccagacct caaaacgacg ggggcaggtg caagttcata ggtctccaag  23040
accaccctcc tttcatttgc tagaaggact cactagactc aggaaagctg ttaggctcac  23100
agttacagtt tattacagta aaaggacaga gattaagatc agcaaaggga ggaggtgcac  23160
```

agcacacgtt ccacgacaga tgaggcgacg gcttccatct gccctctccc agtggagcca 23220
tataggcagc acctgattct cacagcaaca tgtgacaaca tgcaagaagt actgccaata 23280
ctgccaacca gagcagctca ctcgagatct ttgtgtccag agttttttgt ttgtcttgag 23340
acagggtctg gctctgttgg cagactagag tacagtggtg agatcacagt tcattgcagc 23400
cttgacttct caacgccaag tcatcctccc acctcagcct cctgagtagc tatgactaca 23460
ggtatgtgcc accacgtctg gctaatcttt ttattatttg taaagtcgag gtttccctgt 23520
gttgcccagg ctggtcttga actcttggct ccaagtgata cttctgcctt ggcctcccaa 23580
agtgctgaat taagcagctc accatccaca cggctgacct catacatcaa gccaataccg 23640
tgtggcccaa gacccccacc ataaatcaca tcattagcat gaaccaccca gagtggccca 23700
agactccaag atcagctacc aggcaggata ttccaagggc ttagagatga atgcccagga 23760
gctgaggata aagggcccga tctttctttg ggcaaggtta agcctttact gcatagcaga 23820
ccacacagaa gggtgtgggc caccagagaa ttttggtaaa aatttggcct ctggccttga 23880
gcttctaaat ctctgtatcc gtcagatctc tgtggttaca agaaacagcc actgaccctg 23940
gtcaccagag gctgcaattc aggccgcaag cagctgcctg gggggtgtcc aaggagcaga 24000
gaaaactact agatgtgaac ttgaagaagg ttgtcagctg cagccacttt ctgccagcat 24060
ctgcagccac tttctgccag catctgcagc cagcaagctg ggactggcag gaaataaccc 24120
acaaaagaag caaatgcaat ttccaacaca agggggaagg gatgcagggg gaggcagcgc 24180
tgcagttgct caggacacgc tcctatagga ccaagatgga tgcgacccaa gacccaggag 24240
gcccagctgc tcagtgcaac tgacaagtta aaaaggtcta tgatcttgag ggcagacagc 24300
agaattcctc ttataaagaa aactgtttgg gaaaatacgt tgagggagag aagaccttgg 24360
gccaagatgc taaatgggaa tgcaaagctt gagctgctct gcaagagaaa ataagcagga 24420
cagaggattt gctctggaca gagatggaag agccgggaac agagaagtgt ggggaagaga 24480
taggaaccag caggatggca ggggcaaagg gctcaagggt gaggaggcca gtgggacccc 24540
acagagttgg ggagataaag gaacattggt tgctttggtg gcacgtaagc tccttgtctg 24600
tctccagcac ccagaatctc attaaagctt atttattgta cctccagcgg ctgtgtgcaa 24660
tggggtcttt tgtggaaatc aaggagcaga caggtttcat gtgtactgtc accacgtggg 24720
atggaaccag aggcatggaa gcaagacgct aaatgaagag ggccataagg gctgggattc 24780
ccaggcacct taggaacagc ttgtcttttt ttttttcctc tccaaaaaaa atgtttaagg 24840
gacggtgtct cctgtcaccc aggctggagt gcaatggcac gatcatagct cattgcagcc 24900
tctaactccg gggctcaagc aatcctccca cctcagccta ccaagtagct gtgaccacag 24960
ctgcccctca ccatgctaag ctaatttttt taattagata gtacataaac gtcccaaaat 25020
tagaagataa aaagacatga gggatccatt ctaatttgtg tttggagtgt aatggtccag 25080
ctccattctt ctgcacatgg atatccagtt ttacacaaca ctgtgaatgt aatgaatgcc 25140
actgaatcat acactcaaaa atagctaaaa tggcaaattg tctgttatct ctttttaacc 25200 accattttttg aaaattaatt ataccaaaaa accattgaat agtgcacttt atttatttat 25260
ttatttgttt atttatttat ttattttaga aataagagtc tcactttgtt gcccaggctg 25320
gagtgcagtg gcgtgatcat ggctcattgc agcctcgacc tgctgggctc gggctatcct 25380
tccatctcag cctcccgagt agctgggact ataggtgggc gccaccccac ctggctaaat 25440
ctctttttaa cttttgtaga gataggcatc tcgctatgtt gcctaggctg ggctggaact 25500
cctgggctca agtgctcctc ctgccttggc ctcccaaagc gctaggatta cagatgtgag 25560
ccaccgcgcc caccctgaac cttacttttt ttgctcagtt tctggtaatt cagagaatgc 25620
ctcctgagtt gttctacacc cacctcatat tccatgggag ggctgtacag ggcttttttta 25680
acgaggcctc taaggacagg catttgtatc ctttccagcc tttcactatt acaatgttgt 25740
agtgaataac tttacacact gtcatttatt ttactttttt ttttttttat tttagagaaa 25800
ggaatcttgc catcttgccc aggctggtct caaattcctg ggcccaaaca atcctcccgc 25860
cttggcctcc taaagtactg ggatttatag gcataagcca ccgtgcctgg ccaatgcaca 25920
ctgtcattta gctcatgtta acacctgagt gtaggacaca ctcctggagg tggaattgct 25980
gggccaaaga gtatgtttct tgtcattgtg atagatattg acaaatgaac cctcacagaa 26040
gttgtgctga gttctgttcc caccagcgac gtaggcgatg accttttttct ggagggaggg 26100
ggcatccttg gagtccacag agccaggaat ggagagtggg cccagaattt tggtataggt 26160
gttgtataaa cttatagtaa ggttaagaaa accgcaacta tccttatcag agacttggcg 26220
gggggcaggg tatgatggag atcataagga ggctaaaaca ctccacaccc tccctctgca 26280
ttgctcctgc acgggagtcg ggaatctttt caggttgata cgatctcacc ttgaggagct 26340
gtgaggtccc agaagcctct gggttgcaga ttgcttgggg tgaaaatgtc tgtgctactg 26400
aaatctaact ttttacaaaa aattacgggc tgggcgcagt ggctcacgcc tgtaatccca 26460
gcactttggg aggctgcagc gggtggatca cttgaggtaa ggagttcaag accagaccat 26520
agtgaaaccg tgtctctaca aaaaaaatta gccaggtgtg gtggtgcatg cttgtaatcc 26580
cagctactca gaaggctgag gtgggagaat cccttgaacc cgggaagtgg aggctggagt 26640
aaaccatgat cgagttactg cactccagcc tgggtgacaa gagtgagact ctgtctccaa 26700
aaaaaaaaaa aaaaaaaaaa aaactggatt gcctggctct actccgggca cagcatgcag 26760
gcccagttct gctgctctgc tgtttgttct gctttcctcc acatattggc atcaccctct 26820
ggtgccaaga tggctgctgc attccaggca tcacatccag actcagaccc agagaagctg 26880
cccatcccta cctgggtgag cctttgtagg aacgagaaac cgcatccagc agcagaaacc 26940
tcacccagca gcgtcttttc cggtctcatt caccagcgcc gcccaccgct caaccaatcc 27000
ctggccaaaa gaatgggacc gcctggaagg ctggaccaaa caggacctgc cctctggggc 27060
tggggagagg cccagatgaa ggctgcagga caggatggac tcctagacct ctgttaccag 27120
cagtgactac ctctgtctgg gtggttggaa catgtttgaa ttttattcta agtactgtct 27180
acaagttctg caataaacct tgactcttct tttaataatg caaaaggaat cgaagtgatt 27240
gtttgaaagg gagaggaaga aagagagagg gagggaggga agaatggagg gaggcaggga 27300
aggagacaga gagagtagaa tccagccacc ggaaaatcca gaatagctgg ctttgcttaa 27360
tccatgcctg gaaataactg ctgggtttgc aacaacttct ctcccggaga cagaccaagg 27420
aaactacaaa actgcaggaa ggattgaagg gccgggcaca gtggctcacg cctgtaatcc 27480
caacactttg ggaggccgag gtggattgga tcacctgaga tcaggagttc gagaccagcc 27540
tggccaacat ggtgaaacct cgtctctgct agaaatacaa aaataagccg ggcgtggtgg 27600
cgtgcgccta tagtcccagc tactcgggag gctgaggcaa gagaatcgct tgaacctggg 27660
aggtggaggt tgcagtgagc tgagatcgtg ccactgcact ccagcttggg cgacagagtg 27720
agaatctgtc aggtggattc tgagggtact ctgaccccac gaacccagca tgaaatcttc 27780
caggcattaa ggaacattga ggatgtggag gattggaaat ccctccaggg aaaatacact 27840
tctcttgagc agggtcacga ggggtggggg caatgtggga ggtggggcaa atccaaagac 27900

```
aaggtcaaca gcaataataa taataacaat gacaggcatt tgttgcttgt tggctgggcc  27960
tcttgcatac agttctccca acatccctgt gaggtggtga tgcttatccc cattctccag  28020
gggaggaggc tgaggcccag agaggtgaag tcgtgtgcca caaaataccc agccatatg  28080
gtggtagaac caagttttca gccagactca ccagctcaca gcagagctgc cctggactct  28140
acagccattc agtgtatagc tgggccactc catcattcaa ggcagttcaa cgtcaagatt  28200
cctgatttgc ctcaacctgg ggcctctaga agataccatc acccccaaca agctgaagac  28260
gtgtgtccgg aacactcaga cacacacaaa gtgctatgga tacaccacac cccgacctag  28320
ctgtctcttc ctgatggacc tcactgggta gaaatgcctg gcaccgcctg cctcagatcc  28380
ctaggtcagc tctcactccc caatagaagt ttctgagatg atgatgaaaa cgttctccat  28440
ctgtgctgtc caatggagta gccactgatc acttgaggct agtgagcact tgaaggtggc  28500
tagtttgagg aactgcattt tttaatgcat ttaattttag ttactttgaa tatatataca  28560
catatataca tttatatata catattcata cacatacatt ttacatatat tttatatgta  28620
tatgtaatat atatataaat tatatatgta tatattttta tatataaata tatattatat  28680
atttataaat atataaatat ataatatata ttatatagat atataaatat aaatatatat  28740
tatatatata aatatataat atatattata taaatatata taaattatat atttatatat  28800
ataatatata aattatataa attatatata tttatatata atatataaat atatataaat  28860
tatataattt atatattata tataaattat atattttata tataatatat acaatatata  28920
taaattatat ataatatata aatatatata aattatatat aatatataaa atatatataa  28980
attatatata atatataaaa tatatataaa ttatataaat ctatataaat atatactata  29040
ttataaatat agtatatatt tatatagatt tatattattt atatagtata tattatatat  29100
ttatatgttt atgtatatat aaatatataa tatataaata tatttatata ttatatattt  29160
atataatatt ttatataata tgttatatat ttttatataa tatattatat atatttatat  29220
```

<210> SEQ ID NO 11
<211> LENGTH: 378
<212> TYPE: DNA
<213> ORGANISM: Homo sapiens

<400> SEQUENCE: 11

```
agcgggactg agcgccggga gagacctgcg caggcgcagg cgcgcgggga gggccagcct     60
gggtggccca ccccgcgcct ggcgggactg gccgccaact cccctccgct ccagtcactt    120
gtctggagct tgaagaagtg ggtattcccc ttcccacccc aggcactgga ggagcggccc    180
cccggggatt ccaggacctg agctccggga gctggactcg cagcgaccgc ggcagagcga    240
gcgggcgccg ggaagcgagg agacgcccgc gggaggccca gctgctcgga gcaactggca    300
tggcccgagc catggccgcc gcgtggccgc tgctgctggt ggcgctactg gtgctgtcct    360
ggccaccccc aggaaccg                                                  378
```

<210> SEQ ID NO 12
<211> LENGTH: 348
<212> TYPE: DNA
<213> ORGANISM: Homo sapiens

<400> SEQUENCE: 12

```
gggacgtcgt cgtgcaggcg cccacccagg tgcccggctt cttgggcgac tccgtgacgc     60
tgccctgcta cctacaggtg cccaacatgg aggtgacgca tgtgtcacag ctgacttggg    120
cgcggcatgg tgaatctggc agcatggccg tcttccacca aacgcagggc cccagctatt    180
```

cggagtccaa acggctggaa ttcgtggcag ccagactggg cgcggagctg cggaatgcct 240
cgctgaggat gttcgggttg cgcgtagagg atgaaggcaa ctacacctgc ctgttcgtca 300
cgttcccgca gggcagcagg agcgtggata tctggctccg agtgcttg 348

<210> SEQ ID NO 13
<211> LENGTH: 297
<212> TYPE: DNA
<213> ORGANISM: Homo sapiens

<400> SEQUENCE: 13
ccaagcccca gaacacagct gaggttcaga aggtccagct cactggagag ccagtgccca 60
tggcccgctg cgtctccaca gggggtcgcc cgccagccca aatcacctgg cactcagacc 120
tgggcgggat gcccaatacg agccaggtgc cagggttcct gtctggcaca gtcactgtca 180
ccagcctctg gatattggtg ccctcaagcc aggtggacgg caagaatgtg acctgcaagg 240
tggagcacga gagctttgag aagcctcagc tgctgactgt gaacctcacc gtgtact 297

<210> SEQ ID NO 14
<211> LENGTH: 118
<212> TYPE: DNA
<213> ORGANISM: Homo sapiens

<400> SEQUENCE: 14
accccccaga ggtatccatc tctggctatg ataacaactg gtaccttggc cagaatgagg 60
ccaccctgac ctgcgatgct cgcagcaacc cagagcccac aggctataat tggagcac 118

<210> SEQ ID NO 15
<211> LENGTH: 149
<212> TYPE: DNA
<213> ORGANISM: Homo sapiens

<400> SEQUENCE: 15
gaccatgggt cccctgccac cctttgctgt ggcccagggc gcccagctcc tgatccgtcc 60
tgtggacaaa ccaatcaaca caactttaat ctgcaacgtc accaatgccc taggagctcg 120
ccaggcagaa ctgaccgtcc aggtcaaag 149

<210> SEQ ID NO 16
<211> LENGTH: 159
<212> TYPE: DNA
<213> ORGANISM: Homo sapiens

<400> SEQUENCE: 16
agggacctcc cagtgagcac tcaggcatgt cccgtaacgc catcatcttc ctggttctgg 60
gaatcctggt ttttctgatc ctgctgggga tcgggattta tttctattgg tccaaatgtt 120
cccgtgaggt cctttggcac tgtcatctgt gtccctcga 159

<210> SEQ ID NO 17
<211> LENGTH: 32
<212> TYPE: DNA
<213> ORGANISM: Homo sapiens

<400> SEQUENCE: 17
gtacagagca tgccagcgcc tcagctaatg gg 32

<210> SEQ ID NO 18
<211> LENGTH: 4422
<212> TYPE: DNA

<213> ORGANISM: Homo sapiens

<400> SEQUENCE: 18

```
catgtctcct attcagctgt gagcagagag aacagctctt cccaggatcc acagacagag     60
ggcacaaggt gacagcgtcg ggactgagag gggagagaga ctggagctgg caaggacgtg    120
ggcctccaga gttggacccg accccaatgg atgaagaccc cctccaaaga gaccagcctc    180
cctccctgtg ccagacctca aaacgacggg ggcaggtgca agttcatagg tctccaagac    240
caccctcctt tcatttgcta gaaggactca ctagactcag gaaagctgtt aggctcacag    300
ttacagttta ttacagtaaa aggacagaga ttaagatcag caaagggagg aggtgcacag    360
cacacgttcc acgacagatg aggcgacggc ttccatctgc cctctcccag tggagccata    420
taggcagcac ctgattctca cagcaacatg tgacaacatg caagaagtac tgccaatact    480
gccaaccaga gcagctcact cgagatcttt gtgtccagag ttttttgttt gtcttgagac    540
agggtctggc tctgttggca gactagagta cagtggtgag atcacagttc attgcagcct    600
tgacttctca acgccaagtc atcctcccac ctcagcctcc tgagtagcta tgactacagg    660
tatgtgccac cacgtctggc taatcttttt attatttgta aagtcgaggt ttccctgtgt    720
tgcccaggct ggtcttgaac tcttggctcc aagtgatact tctgccttgg cctcccaaag    780
tgctgaatta agcagctcac catccacacg gctgacctca tacatcaagc caataccgtg    840
tggcccaaga cccccaccat aaatcacatc attagcatga accacccaga gtggcccaag    900
actccaagat cagctaccag gcaggatatt ccaagggctt agagatgaat gcccaggagc    960
tgaggataaa gggcccgatc tttctttggg caaggttaag cctttactgc atagcagacc   1020
acacagaagg gtgtgggcca ccagagaatt ttggtaaaaa tttggcctct ggccttgagc   1080
ttctaaatct ctgtatccgt cagatctctg tggttacaag aaacagccac tgaccctggt   1140
caccagaggc tgcaattcag gccgcaagca gctgcctggg gggtgtccaa ggagcagaga   1200
aaactactag atgtgaactt gaagaaggtt gtcagctgca gccactttct gccagcatct   1260
gcagccactt tctgccagca tctgcagcca gcaagctggg actggcagga aataacccac   1320
aaaagaagca aatgcaattt ccaacacaag gggaaggga tgcagggggga ggcagcgctg   1380
cagttgctca ggacacgctc ctataggacc aagatggatg cgacccaaga cccaggaggc   1440
ccagctgctc agtgcaactg acaagttaaa aggtctatg atcttgaggg cagacagcag   1500
aattcctctt ataaagaaaa ctgtttggga aaatacgttg agggagagaa gaccttgggc   1560
caagatgcta aatgggaatg caaagcttga gctgctctgc aagagaaaat aagcaggaca   1620
gaggatttgc tctggacaga gatggaagag ccgggaacag agaagtgtgg ggaagagata   1680
ggaaccagca ggatggcagg ggcaaagggc tcaagggtga ggaggccagt gggaccccac   1740
agagttgggg agataaagga acattggttg ctttggtggc acgtaagctc cttgtctgtc   1800
tccagcaccc agaatctcat taaagcttat ttattgtacc tccagcggct gtgtgcaatg   1860
gggtcttttg tggaaatcaa ggagcagaca ggtttcatgt gtactgtcac cacgtgggat   1920
ggaaccagag gcatggaagc aagacgctaa atgaagaggg ccataagggc tgggattccc   1980
aggcacctta ggaacagctt gtcttttttt ttttcctctc caaaaaaaat gtttaaggga   2040
cggtgtctcc tgtcacccag gctggagtgc aatggcacga tcatagctca ttgcagcctc   2100
taactccggg gctcaagcaa tcctcccacc tcagcctacc aagtagctgt gaccacagct   2160
gcccctcacc atgctaagct aatttttta attagatagt acataaacgt cccaaaatta   2220
gaagataaaa agacatgagg gatccattct aatttgtgtt tggagtgtaa tggtccagct   2280
```

```
ccattcttct gcacatggat atccagtttt acacaacact gtgaatgtaa tgaatgccac   2340
tgaatcatac actcaaaaat agctaaaatg gcaaattgtc tgttatctct ttttaaccac   2400
catttttgaa aattaattat accaaaaaac cattgaatag tgcactttat ttatttattt   2460
atttgtttat ttatttattt attttagaaa taagagtctc actttgttgc ccaggctgga   2520
gtgcagtggc gtgatcatgg ctcattgcag cctcgacctg ctgggctcgg gctatccttc   2580
catctcagcc tcccgagtag ctgggactat aggtgggcgc caccccacct ggctaaatct   2640
ctttttaact tttgtagaga taggcatctc gctatgttgc ctaggctggg ctggaactcc   2700
tgggctcaag tgctcctcct gccttggcct cccaaagcgc taggattaca gatgtgagcc   2760
accgcgccca ccctgaacct tacttttttt gctcagtttc tggtaattca gagaatgcct   2820
cctgagttgt tctacaccca cctcatattc catgggaggg ctgtacaggg ctttttttaac  2880
gaggcctcta aggacaggca tttgtatcct ttccagcctt tcactattac aatgttgtag   2940
tgaataactt tacacactgt catttatttt actttttttt ttttttattt tagagaaagg   3000
aatcttgcca tcttgcccag gctggtctca aattcctggg cccaaacaat cctcccgcct   3060
tggcctccta aagtactggg atttataggc ataagccacc gtgcctggcc aatgcacact   3120
gtcatttagc tcatgttaac acctgagtgt aggacacact cctggaggtg gaattgctgg   3180
gccaaagagt atgtttcttg tcattgtgat agatattgac aaatgaaccc tcacagaagt   3240
tgtgctgagt tctgttccca ccagcgacgt aggcgatgac ctttttctgg agggaggggg   3300
catccttgga gtccacagag ccaggaatgg agagtgggcc cagaattttg gtataggtgt   3360
tgtataaact tatagtaagg ttaagaaaac cgcaactatc cttatcagag acttggcggg   3420
gggcagggta tgatggagat cataaggagg ctaaaacact ccacaccctc cctctgcatt   3480
gctcctgcac gggagtcggg aatcttttca ggttgatacg atctcacctt gaggagctgt   3540
gaggtcccag aagcctctgg gttgcagatt gcttggggtg aaaatgtctg tgctactgaa   3600
atctaacttt ttacaaaaaa ttacgggctg ggcgcagtgg ctcacgcctg taatcccagc   3660
actttgggag gctgcagcgg gtggatcact tgaggtaagg agttcaagac cagaccatag   3720
tgaaaccgtg tctctacaaa aaaaattagc caggtgtggt ggtgcatgct tgtaatccca   3780
gctactcaga aggctgaggt gggagaatcc cttgaacccg ggaagtggag gctggagtaa   3840
accatgatcg agttactgca ctccagcctg ggtgacaaga gtgagactct gtctccaaaa   3900
aaaaaaaaaa aaaaaaaaaa actggattgc ctggctctac tccgggcaca gcatgcaggc   3960
ccagttctgc tgctctgctg tttgttctgc tttcctccac atattggcat caccctctgg   4020
tgccaagatg gctgctgcat tccaggcatc acatccagac tcagacccag agaagctgcc   4080
catccctacc tgggtgagcc tttgtaggaa cgagaaaccg catccagcag cagaaacctc   4140
acccagcagc gtcttttccg gtctcattca ccagcgccgc ccaccgctca accaatccct   4200
ggccaaaaga atgggaccgc ctggaaggct ggaccaaaca ggacctgccc tctggggctg   4260
gggagaggcc cagatgaagg ctgcaggaca ggatggactc ctagacctct gttaccagca   4320
gtgactacct ctgtctgggt ggttggaaca tgtttgaatt ttattctaag tactgtctac   4380
aagttctgca ataaaccttg actcttcttt taataatgca aa                      4422
```

<210> SEQ ID NO 19
<211> LENGTH: 20
<212> TYPE: DNA
<213> ORGANISM: Artificial Sequence
<220> FEATURE:

<223> OTHER INFORMATION: Target Exon: Exon 3

<400> SEQUENCE: 19
aatcacctgg cactcagacc 20

<210> SEQ ID NO 20
<211> LENGTH: 20
<212> TYPE: DNA
<213> ORGANISM: Artificial Sequence
<220> FEATURE:
<223> OTHER INFORMATION: Target Exon: Exon 2

<400> SEQUENCE: 20
caggcgccca cccaggtgcc 20

<210> SEQ ID NO 21
<211> LENGTH: 20
<212> TYPE: DNA
<213> ORGANISM: Artificial Sequence
<220> FEATURE:
<223> OTHER INFORMATION: Target Exon: Exon 2

<400> SEQUENCE: 21
gacgctgccc tgctacctac 20

<210> SEQ ID NO 22
<211> LENGTH: 20
<212> TYPE: DNA
<213> ORGANISM: Artificial Sequence
<220> FEATURE:
<223> OTHER INFORMATION: Target Exon: Exon 3

<400> SEQUENCE: 22
caagccccag aacacagctg 20

<210> SEQ ID NO 23
<211> LENGTH: 20
<212> TYPE: DNA
<213> ORGANISM: Artificial Sequence
<220> FEATURE:
<223> OTHER INFORMATION: Target Exon: Exon 4

<400> SEQUENCE: 23
ctggtacctt ggccagaatg 20

<210> SEQ ID NO 24
<211> LENGTH: 25
<212> TYPE: DNA
<213> ORGANISM: Artificial Sequence
<220> FEATURE:
<223> OTHER INFORMATION: 1st sgRNA NIV (Exon 3): Forward Sequence

<400> SEQUENCE: 24
caccgaatca cctggcactc agacc 25

<210> SEQ ID NO 25
<211> LENGTH: 25
<212> TYPE: DNA
<213> ORGANISM: Artificial Sequence
<220> FEATURE:
<223> OTHER INFORMATION: 1st sgRNA NIV (Exon 3) : Reverse Sequence

<400> SEQUENCE: 25
aaacggtctg agtgccaggt gattc 25

```
<210> SEQ ID NO 26
<211> LENGTH: 25
<212> TYPE: DNA
<213> ORGANISM: Artificial Sequence
<220> FEATURE:
<223> OTHER INFORMATION: 2nd sgRNA NIV (Exon 2): Forward sequence

<400> SEQUENCE: 26

caccgcaggc gcccacccag gtgcc                                          25


<210> SEQ ID NO 27
<211> LENGTH: 25
<212> TYPE: DNA
<213> ORGANISM: Artificial Sequence
<220> FEATURE:
<223> OTHER INFORMATION: 2nd sgRNA NIV (Exon 2) : Reverse Sequence

<400> SEQUENCE: 27

aaacggcacc tgggtgggcg cctgc                                          25


<210> SEQ ID NO 28
<211> LENGTH: 24
<212> TYPE: DNA
<213> ORGANISM: Artificial Sequence
<220> FEATURE:
<223> OTHER INFORMATION: 3rd sgRNA NIV (Exon 2) : Forward Sequence

<400> SEQUENCE: 28

caccgacgct gccctgctac ctac                                           24


<210> SEQ ID NO 29
<211> LENGTH: 25
<212> TYPE: DNA
<213> ORGANISM: Artificial Sequence
<220> FEATURE:
<223> OTHER INFORMATION: 3rd sgRNA NIV (Exon 2) : Reverse Sequence

<400> SEQUENCE: 29

aaacgtaggt agcagggcag cgtcc                                          25


<210> SEQ ID NO 30
<211> LENGTH: 25
<212> TYPE: DNA
<213> ORGANISM: Artificial Sequence
<220> FEATURE:
<223> OTHER INFORMATION: 4th sgRNA NIV (Exon 3) : Forward Sequence

<400> SEQUENCE: 30

caccgcaagc cccagaacac agctg                                          25


<210> SEQ ID NO 31
<211> LENGTH: 25
<212> TYPE: DNA
<213> ORGANISM: Artificial Sequence
<220> FEATURE:
<223> OTHER INFORMATION: 4th sgRNA NIV (Exon 3) : Reverse Sequence

<400> SEQUENCE: 31

aaaccagctg tgttctgggg cttgc                                          25


<210> SEQ ID NO 32
<211> LENGTH: 25
<212> TYPE: DNA
<213> ORGANISM: Artificial Sequence
<220> FEATURE:
<223> OTHER INFORMATION: 5th sgRNA NIV (Exon 4) : Forward Sequence
```

<400> SEQUENCE: 32
caccgctggt accttggcca gaatg 25

<210> SEQ ID NO 33
<211> LENGTH: 25
<212> TYPE: DNA
<213> ORGANISM: Artificial Sequence
<220> FEATURE:
<223> OTHER INFORMATION: 5th sgRNA NIV (Exon 4) : Reverse Sequence

<400> SEQUENCE: 33
aaaccattct ggccaaggta ccagc 25

<210> SEQ ID NO 34
<211> LENGTH: 19
<212> TYPE: DNA
<213> ORGANISM: Artificial Sequence
<220> FEATURE:
<223> OTHER INFORMATION: Exon2: Forward 1

<400> SEQUENCE: 34
gcaagtgcac gcccaggtg 19

<210> SEQ ID NO 35
<211> LENGTH: 22
<212> TYPE: DNA
<213> ORGANISM: Artificial Sequence
<220> FEATURE:
<223> OTHER INFORMATION: Exon2: Reverse 1

<400> SEQUENCE: 35
gatctgctgt ggagggaatc tc 22

<210> SEQ ID NO 36
<211> LENGTH: 20
<212> TYPE: DNA
<213> ORGANISM: Artificial Sequence
<220> FEATURE:
<223> OTHER INFORMATION: Exon2: Forward 2

<400> SEQUENCE: 36
ctatctagtc caagaacgcc 20

<210> SEQ ID NO 37
<211> LENGTH: 18
<212> TYPE: DNA
<213> ORGANISM: Artificial Sequence
<220> FEATURE:
<223> OTHER INFORMATION: Exon2: Reverse 2

<400> SEQUENCE: 37
acgctcctgc tgccctgc 18

<210> SEQ ID NO 38
<211> LENGTH: 18
<212> TYPE: DNA
<213> ORGANISM: Artificial Sequence
<220> FEATURE:
<223> OTHER INFORMATION: Exon3: Forward 1

<400> SEQUENCE: 38
tgaccccaag tgatccac 18

<210> SEQ ID NO 39
<211> LENGTH: 16

<212> TYPE: DNA
<213> ORGANISM: Artificial Sequence
<220> FEATURE:
<223> OTHER INFORMATION: Exon3: Reverse 1

<400> SEQUENCE: 39
cagtggtggg ggcagc 16

<210> SEQ ID NO 40
<211> LENGTH: 16
<212> TYPE: DNA
<213> ORGANISM: Artificial Sequence
<220> FEATURE:
<223> OTHER INFORMATION: Exon3: Forward 2

<400> SEQUENCE: 40
tcttcccagc caagcc 16

<210> SEQ ID NO 41
<211> LENGTH: 19
<212> TYPE: DNA
<213> ORGANISM: Artificial Sequence
<220> FEATURE:
<223> OTHER INFORMATION: Exon3: Reverse 2

<400> SEQUENCE: 41
ttcttgccat cgctgactt 19

<210> SEQ ID NO 42
<211> LENGTH: 20
<212> TYPE: DNA
<213> ORGANISM: Artificial Sequence
<220> FEATURE:
<223> OTHER INFORMATION: Exon4: Forward

<400> SEQUENCE: 42
gacatgcctg gtccaggcta 20

<210> SEQ ID NO 43
<211> LENGTH: 18
<212> TYPE: DNA
<213> ORGANISM: Artificial Sequence
<220> FEATURE:
<223> OTHER INFORMATION: Exon4: Reverse

<400> SEQUENCE: 43
agcccctcct ccctcaga 18

<210> SEQ ID NO 44
<211> LENGTH: 20
<212> TYPE: DNA
<213> ORGANISM: Artificial Sequence
<220> FEATURE:
<223> OTHER INFORMATION: Exon2: Forward 3

<400> SEQUENCE: 44
aactagtgcc ccagttcccc 20

<210> SEQ ID NO 45
<211> LENGTH: 22
<212> TYPE: DNA
<213> ORGANISM: Artificial Sequence
<220> FEATURE:
<223> OTHER INFORMATION: Exon2: Reverse 3

<400> SEQUENCE: 45
catgctgcca gattcaccat gc 22

<210> SEQ ID NO 46
<211> LENGTH: 20
<212> TYPE: DNA
<213> ORGANISM: Artificial Sequence
<220> FEATURE:
<223> OTHER INFORMATION: Exon2: Forward 4

<400> SEQUENCE: 46
ttaccctcct cgcctgccat 20

<210> SEQ ID NO 47
<211> LENGTH: 22
<212> TYPE: DNA
<213> ORGANISM: Artificial Sequence
<220> FEATURE:
<223> OTHER INFORMATION: Exon2: Reverse 4

<400> SEQUENCE: 47
caacccgaac atcctcagcg ag 22

<210> SEQ ID NO 48
<211> LENGTH: 5790
<212> TYPE: DNA
<213> ORGANISM: Homo sapiens

<400> SEQUENCE: 48
agtcacttgt ctggagcttg aagaagtggg tattcccctt cccaccccag gcactggagg 60
agcggccccc cggggattcc aggacctgag ctccggggagc tggactcgca gcgaccgcgg 120
cagagcgagc gggcgccggg aagcgaggag acgcccgcgg gaggcccagc tgctcggagc 180
aactggcatg gcccgagcca tggccgccgc gtggccgctg ctgctggtgg cgctactggt 240
gctgtcctgg ccacccccag gaaccgggga cgtcgtcgtg caggcgccca cccaggtgcc 300
cggcttcttg ggcgactccg tgacgctgcc ctgctaccta caggtgccca acatggaggt 360
gacgcatgtg tcacagctga cttgggcgcg gcatggtgaa tctggcagca tggccgtctt 420
ccaccaaacg cagggcccca gctattcgga gtccaaacgg ctggaattcg tggcagccag 480
actgggcgcg gagctgcgga atgcctcgct gaggatgttc gggttgcgcg tagaggatga 540
aggcaactac acctgcctgt tcgtcacgtt cccgcagggc agcaggagcg tggatatctg 600
gctccgagtg cttgccaagc cccagaacct tctgaggttc agaaggtcca gctcactgga 660
gagccagtgc ccatggcccg ctgcgtctcc acagggggtc gcccgccagc ccaaatcacc 720
tggcactcag cccaaatcac ctgcccaata cgagccaggt gccagggttc ctgtctggca 780
cagtcactgt caccagcctc tggatattgg tgccctcaag ccaggtggac ggcaagaatg 840
tgacctgcaa ggtggagcac gagagctttg agaagcctca gctgctgact gtgaacctca 900
ccgtgtacta ccccccagag gtatccatct ctggctatga taacaactgg taccttggcc 960
agaatgaggc caccctgacc tgcgatgctc gcagcaaccc agagcccaca ggctataatt 1020
ggagcacgac catgggtccc ctgccaccct ttgctgtggc ccagggcgcc cagctcctga 1080
tccgtcctgt ggacaaacca atcaacacaa ctttaatctg caacgtcacc aatgccctag 1140
gagctcgcca ggcagaactg accgtccagg tcaaagaggg acctcccagt gagcactcag 1200
gcatgtcccg taacgccatc atcttcctgg ttctgggaat cctggttttt ctgatcctgc 1260
tggggatcgg gatttatttc tattggtcca aatgttcccg tgaggtcctt tggcactgtc 1320
atctgtgtcc ctcgagtaca gagcatgcca gcgcctcagc taatgggcat gtctcctatt 1380

```
cagctgtgag cagagagaac agctcttccc aggatccaca gacagagggc acaaggtgac   1440
agcgtcggga ctgagagggg agagagactg gagctggcaa ggacgtgggc ctccagagtt   1500
ggacccgacc ccaatggatg aagaccccct ccaaagagac cagcctccct ccctgtgcca   1560
gacctcaaaa cgacgggggc aggtgcaagt tcataggtct ccaagaccac cctcctttca   1620
tttgctagaa ggactcacta gactcaggaa agctgttagg ctcacagtta cagtttatta   1680
cagtaaaagg acagagatta agatcagcaa agggaggagg tgcacagcac acgttccacg   1740
acagatgagg cgacggcttc catctgccct ctcccagtgg agccatatag gcagcacctg   1800
attctcacag caacatgtga caacatgcaa gaagtactgc caatactgcc aaccagagca   1860
gctcactcga gatctttgtg tccagagttt tttgtttgtc ttgagacagg gtctggctct   1920
gttggcagac tagagtacag tggtgagatc acagttcatt gcagccttga cttctcaacg   1980
ccaagtcatc ctcccacctc agcctcctga gtagctatga ctacaggtat gtgccaccac   2040
gtctggctaa tctttttatt atttgtaaag tcgaggtttc cctgtgttgc ccaggctggt   2100
cttgaactct tggctccaag tgatacttct gccttggcct cccaaagtgc tgaattaagc   2160
agctcaccat ccacacggct gacctcatac atcaagccaa taccgtgtgg cccaagaccc   2220
ccaccataaa tcacatcatt agcatgaacc acccagagtg gcccaagact ccaagatcag   2280
ctaccaggca ggatattcca agggcttaga gatgaatgcc caggagctga ggataaaggg   2340
cccgatcttt ctttgggcaa ggttaagcct ttactgcata gcagaccaca cagaagggtg   2400
tgggccacca gagaattttg gtaaaaattt ggcctctggc cttgagcttc taaatctctg   2460
tatccgtcag atctctgtgg ttacaagaaa cagccactga ccctggtcac cagaggctgc   2520
aattcaggcc gcaagcagct gcctgggggg tgtccaagga gcagagaaaa ctactagatg   2580
tgaacttgaa gaaggttgtc agctgcagcc actttctgcc agcatctgca gccactttct   2640
gccagcatct gcagccagca agctgggact ggcaggaaat aacccacaaa agaagcaaat   2700
gcaatttcca acacaagggg gaagggatgc agggggaggc agcgctgcag ttgctcagga   2760
cacgctccta taggaccaag atggatgcga cccaagaccc aggaggccca gctgctcagt   2820
gcaactgaca agttaaaaag gtctatgatc ttgagggcag acagcagaat tcctcttata   2880
aagaaaactg tttgggaaaa tacgttgagg gagagaagac cttgggccaa gatgctaaat   2940
gggaatgcaa agcttgagct gctctgcaag agaaaataag caggacagag gatttgctct   3000
ggacagagat ggaagagccg ggaacagaga agtgtgggga agagatagga accagcagga   3060
tggcaggggc aaagggctca agggtgagga ggccagtggg accccacaga gttggggaga   3120
taaaggaaca ttggttgctt tggtggcacg taagctcctt gtctgtctcc agcacccaga   3180
atctcattaa agcttattta ttgtacctcc agcggctgtg tgcaatgggg tcttttgtgg   3240
aaatcaagga gcagacaggt ttcatgtgta ctgtcaccac gtgggatgga accagaggca   3300
tggaagcaag acgctaaatg aagagggcca taagggctgg gattcccagg caccttagga   3360
acagcttgtc tttttttttt tcctctccaa aaaaaatgtt taagggacgg tgtctcctgt   3420
cacccaggct ggagtgcaat ggcacgatca tagctcattg cagcctctaa ctccggggct   3480
caagcaatcc tcccacctca gcctaccaag tagctgtgac cacagctgcc cctcaccatg   3540
ctaagctaat ttttttaatt agatagtaca taaacgtccc aaaattagaa gataaaaaga   3600
catgagggat ccattctaat ttgtgtttgg agtgtaatgg tccagctcca ttcttctgca   3660
catggatatc cagttttaca caacactgtg aatgtaatga atgccactga atcatacact   3720
```

caaaaatagc taaaatggca aattgtctgt tatctctttt taaccaccat ttttgaaaat 3780
taattatacc aaaaaaccat tgaatagtgc actttattta tttatttatt tgtttattta 3840
tttatttatt ttagaaataa gagtctcact ttgttgccca ggctggagtg cagtggcgtg 3900
atcatggctc attgcagcct cgacctgctg ggctcgggct atccttccat ctcagcctcc 3960
cgagtagctg ggactatagg tgggcgccac cccacctggc taaatctctt tttaactttt 4020
gtagagatag gcatctcgct atgttgccta ggctgggctg gaactcctgg gctcaagtgc 4080
tcctcctgcc ttggcctccc aaagcgctag gattacagat gtgagccacc gcgcccaccc 4140
tgaaccttac ttttttgct cagtttctgg taattcagag aatgcctcct gagttgttct 4200
acacccacct catattccat gggagggctg tacagggctt ttttaacgag gcctctaagg 4260
acaggcattt gtatcctttc cagcctttca ctattacaat gttgtagtga ataactttac 4320
acactgtcat ttattttact tttttttttt tttattttag agaaaggaat cttgccatct 4380
tgcccaggct ggtctcaaat tcctgggccc aaacaatcct cccgccttgg cctcctaaag 4440
tactgggatt tataggcata agccaccgtg cctggccaat gcacactgtc atttagctca 4500
tgttaacacc tgagtgtagg acacactcct ggaggtggaa ttgctgggcc aaagagtatg 4560
tttcttgtca ttgtgataga tattgacaaa tgaaccctca cagaagttgt gctgagttct 4620
gttcccacca gcgacgtagg cgatgacctt tttctggagg gagggggcat ccttggagtc 4680
cacagagcca ggaatggaga gtgggcccag aattttggta taggtgttgt ataaacttat 4740
agtaaggtta agaaaaccgc aactatcctt atcagagact tggcgggggg cagggtatga 4800
tggagatcat aaggaggcta aaacactcca caccctccct ctgcattgct cctgcacggg 4860
agtcgggaat cttttcaggt tgatacgatc tcaccttgag gagctgtgag gtcccagaag 4920
cctctgggtt gcagattgct tggggtgaaa atgtctgtgc tactgaaatc taacttttta 4980
caaaaaatta cgggctgggc gcagtggctc acgcctgtaa tcccagcact ttgggaggct 5040
gcagcgggtg gatcacttga ggtaaggagt tcaagaccag accatagtga aaccgtgtct 5100
ctacaaaaaa aattagccag gtgtggtggt gcatgcttgt aatcccagct actcagaagg 5160
ctgaggtggg agaatccctt gaacccggga agtggaggct ggagtaaacc atgatcgagt 5220
tactgcactc cagcctgggt gacaagagtg agactctgtc tccaaaaaaa aaaaaaaaaa 5280
aaaaaaaact ggattgcctg gctctactcc gggcacagca tgcaggccca gttctgctgc 5340
tctgctgttt gttctgcttt cctccacata ttggcatcac cctctggtgc caagatggct 5400
gctgcattcc aggcatcaca tccagactca gacccagaga agctgcccat ccctacctgg 5460
gtgagccttt gtaggaacga gaaaccgcat ccagcagcag aaacctcacc cagcagcgtc 5520
ttttccggtc tcattcacca gcgccgccca ccgctcaacc aatccctggc caaaagaatg 5580
ggaccgcctg gaaggctgga ccaaacagga cctgccctct ggggctgggg agaggcccag 5640
atgaaggctg caggacagga tggactccta gacctctgtt accagcagtg actacctctg 5700
tctgggtggt tggaacatgt ttgaatttta ttctaagtac tgtctacaag ttctgcaata 5760
aaccttgact cttcttttaa taatgcaaaa 5790

<210> SEQ ID NO 49
<211> LENGTH: 5693
<212> TYPE: DNA
<213> ORGANISM: Homo sapiens

<400> SEQUENCE: 49
agtcacttgt ctggagcttg aagaagtggg tattcccctt cccaccccag gcactggagg 60

```
agcggccccc cggggattcc aggacctgag ctccgggagc tggactcgca gcgaccgcgg    120
cagagcgagc gggcgccggg aagcgaggag acgcccgcgg gaggcccagc tgctcggagc    180
aactggcatg gcccgagcca tggccgccgc gtggccgctg ctgctggtgg cgctactggt    240
gctgtcctgg ccacccccag gaaccgggga cgtcgtcgtg caggcgccca cccaggtgcc    300
cggcttcttg ggcgactccg tgacgctgcc ctgctaccta caggtgccca acatggaggt    360
gacgcatgtg tcacagctga cttgggcgcg gcatggtgaa tctggcagca tggccgtctt    420
ccaccaaacg cagggcccca gctattcgga gtccaaacgg ctggaattcg tggcagccag    480
actgggcgcg gagctgcgga atgcctcgct gaggatgttc gggttgcgcg tagaggatga    540
aggcaactac acctgcctgt tcgtcacgtt cccgcagggc agcaggagcg tggatatctg    600
gctccgagtg cttgccaagc cccagaacac agacctgggc gggatgccca atacgagcca    660
ggtgccaggg ttcctgtctg gcacagtcac tgtcaccagc ctctggatat tggtgccctc    720
aagccaggtg gacggcaaga atgtgacctg caaggtggag cacgagagct ttgagaagcc    780
tcagctgctg actgtgaacc tcaccgtgta ctacccccca gaggtatcca tctctggcta    840
tgataacaac tggtaccttg gccagaatga ggccaccctg acctgcgatg ctcgcagcaa    900
cccagagccc acaggctata attggagcac gaccatgggt cccctgccac cctttgctgt    960
ggcccagggc gcccagctcc tgatccgtcc tgtggacaaa ccaatcaaca caactttaat   1020
ctgcaacgtc accaatgccc taggagctcg ccaggcagaa ctgaccgtcc aggtcaaaga   1080
gggacctccc agtgagcact caggcatgtc ccgtaacgcc atcatcttcc tggttctggg   1140
aatcctggtt tttctgatcc tgctggggat cgggatttat ttctattggt ccaaatgttc   1200
ccgtgaggtc ctttggcact gtcatctgtg tccctcgagt acagagcatg ccagcgcctc   1260
agctaatggg catgtctcct attcagctgt gagcagagag aacagctctt cccaggatcc   1320
acagacagag ggcacaaggt gacagcgtcg ggactgagag gggagagaga ctggagctgg   1380
caaggacgtg ggcctccaga gttggacccg accccaatgg atgaagaccc cctccaaaga   1440
gaccagcctc cctccctgtg ccagacctca aaacgacggg ggcaggtgca agttcatagg   1500
tctccaagac caccctcctt tcatttgcta gaaggactca ctagactcag gaaagctgtt   1560
aggctcacag ttacagttta ttacagtaaa aggacagaga ttaagatcag caaagggagg   1620
aggtgcacag cacacgttcc acgacagatg aggcgacggc ttccatctgc cctctcccag   1680
tggagccata taggcagcac ctgattctca cagcaacatg tgacaacatg caagaagtac   1740
tgccaatact gccaaccaga gcagctcact cgagatcttt gtgtccagag tttttgttt    1800
gtcttgagac agggtctggc tctgttggca gactagagta cagtggtgag atcacagttc   1860
attgcagcct tgacttctca acgccaagtc atcctcccac ctcagcctcc tgagtagcta   1920
tgactacagg tatgtgccac cacgtctggc taatcttttt attatttgta aagtcgaggt   1980
ttccctgtgt tgcccaggct ggtcttgaac tcttggctcc aagtgatact tctgccttgg   2040
cctcccaaag tgctgaatta agcagctcac catccacacg gctgacctca tacatcaagc   2100
caataccgtg tggcccaaga cccccaccat aaatcacatc attagcatga accacccaga   2160
gtggcccaag actccaagat cagctaccag gcaggatatt ccaagggctt agagatgaat   2220
gcccaggagc tgaggataaa gggcccgatc tttctttggg caaggttaag cctttactgc   2280
atagcagacc acacagaagg gtgtgggcca ccagagaatt ttggtaaaaa tttggcctct   2340
ggccttgagc ttctaaatct ctgtatccgt cagatctctg tggttacaag aaacagccac   2400
```

```
tgaccctggt caccagaggc tgcaattcag gccgcaagca gctgcctggg gggtgtccaa   2460
ggagcagaga aaactactag atgtgaactt gaagaaggtt gtcagctgca gccactttct   2520
gccagcatct gcagccactt tctgccagca tctgcagcca gcaagctggg actggcagga   2580
aataacccac aaaagaagca aatgcaattt ccaacacaag gggaaggga tgcaggggga    2640
ggcagcgctg cagttgctca ggacacgctc ctataggacc aagatggatg cgacccaaga   2700
cccaggaggc ccagctgctc agtgcaactg acaagttaaa aaggtctatg atcttgaggg   2760
cagacagcag aattcctctt ataaagaaaa ctgtttggga aaatacgttg agggagagaa   2820
gaccttgggc caagatgcta aatgggaatg caaagcttga gctgctctgc aagagaaaat   2880
aagcaggaca gaggatttgc tctggacaga gatggaagag ccgggaacag agaagtgtgg   2940
ggaagagata ggaaccagca ggatggcagg ggcaaagggc tcaagggtga ggaggccagt   3000
gggaccccac agagttgggg agataaagga acattggttg ctttggtggc acgtaagctc   3060
cttgtctgtc tccagcaccc agaatctcat taaagcttat ttattgtacc tccagcggct   3120
gtgtgcaatg ggtcttttg tggaaatcaa ggagcagaca ggtttcatgt gtactgtcac    3180
cacgtgggat ggaaccagag gcatggaagc aagacgctaa atgaagaggg ccataagggc   3240
tgggattccc aggcacctta ggaacagctt gtcttttttt ttttcctctc caaaaaaaat   3300
gtttaaggga cggtgtctcc tgtcacccag gctggagtgc aatggcacga tcatagctca   3360
ttgcagcctc taactccggg gctcaagcaa tcctcccacc tcagcctacc aagtagctgt   3420
gaccacagct gcccctcacc atgctaagct aatttttta attagatagt acataaacgt    3480
cccaaaatta gaagataaaa agacatgagg gatccattct aatttgtgtt tggagtgtaa   3540
tggtccagct ccattcttct gcacatggat atccagtttt acacaacact gtgaatgtaa   3600
tgaatgccac tgaatcatac actcaaaaat agctaaaatg gcaaattgtc tgttatctct   3660
ttttaaccac catttttgaa aattaattat accaaaaaac cattgaatag tgcactttat   3720
ttatttattt atttgtttat ttatttattt attttagaaa taagagtctc actttgttgc   3780
ccaggctgga gtgcagtggc gtgatcatgg ctcattgcag cctcgacctg ctgggctcgg   3840
gctatccttc catctcagcc tcccgagtag ctgggactat aggtgggcgc caccccacct   3900
ggctaaatct ctttttaact tttgtagaga taggcatctc gctatgttgc ctaggctggg   3960
ctggaactcc tgggctcaag tgctcctcct gccttggcct cccaaagcgc taggattaca   4020
gatgtgagcc accgcgccca ccctgaacct tacttttttt gctcagtttc tggtaattca   4080
gagaatgcct cctgagttgt tctacaccca cctcatattc catgggaggg ctgtacaggg   4140
ctttttaac gaggcctcta aggacaggca tttgtatcct ttccagcctt tcactattac    4200
aatgttgtag tgaataactt tacacactgt catttatttt actttttttt tttttattt    4260
tagagaaagg aatcttgcca tcttgcccag gctggtctca aattcctggg cccaaacaat   4320
cctcccgcct tggcctccta aagtactggg atttataggc ataagccacc gtgcctggcc   4380
aatgcacact gtcatttagc tcatgttaac acctgagtgt aggacacact cctggaggtg   4440
gaattgctgg gccaaagagt atgtttcttg tcattgtgat agatattgac aaatgaaccc   4500
tcacagaagt tgtgctgagt tctgttccca ccagcgacgt aggcgatgac ctttttctgg   4560
agggaggggg catccttgga gtccacagag ccaggaatgg agagtgggcc cagaattttg   4620
gtataggtgt tgtataaact tatagtaagg ttaagaaaac cgcaactatc cttatcagag   4680
acttggcggg gggcagggta tgatggagat cataaggagg ctaaaacact ccacaccctc   4740
cctctgcatt gctcctgcac gggagtcggg aatcttttca ggttgatacg atctcacctt   4800
```

```
gaggagctgt gaggtcccag aagcctctgg gttgcagatt gcttggggtg aaaatgtctg   4860
tgctactgaa atctaacttt ttacaaaaaa ttacgggctg ggcgcagtgg ctcacgcctg   4920
taatcccagc actttgggag gctgcagcgg gtggatcact tgaggtaagg agttcaagac   4980
cagaccatag tgaaaccgtg tctctacaaa aaaaattagc caggtgtggt ggtgcatgct   5040
tgtaatccca gctactcaga aggctgaggt gggagaatcc cttgaacccg ggaagtggag   5100
gctggagtaa accatgatcg agttactgca ctccagcctg ggtgacaaga gtgagactct   5160
gtctccaaaa aaaaaaaaaa aaaaaaaaaa actggattgc ctggctctac tccgggcaca   5220
gcatgcaggc ccagttctgc tgctctgctg tttgttctgc tttcctccac atattggcat   5280
caccctctgg tgccaagatg gctgctgcat tccaggcatc acatccagac tcagacccag   5340
agaagctgcc catccctacc tgggtgagcc tttgtaggaa cgagaaaccg catccagcag   5400
cagaaacctc acccagcagc gtcttttccg gtctcattca ccagcgccgc ccaccgctca   5460
accaatccct ggccaaaaga atgggaccgc ctggaaggct ggaccaaaca ggacctgccc   5520
tctggggctg gggagaggcc cagatgaagg ctgcaggaca ggatggactc ctagacctct   5580
gttaccagca gtgactacct ctgtctgggt ggttggaaca tgtttgaatt ttattctaag   5640
tactgtctac aagttctgca ataaaccttg actcttcttt taataatgca aaa          5693
```

```
<210> SEQ ID NO 50
<211> LENGTH: 5653
<212> TYPE: DNA
<213> ORGANISM: Homo sapiens

<400> SEQUENCE: 50
```

```
agtcacttgt ctggagcttg aagaagtggg tattcccctt cccaccccag gcactggagg     60
agcggccccc cggggattcc aggacctgag ctccgggagc tggactcgca gcgaccgcgg    120
cagagcgagc gggcgccggg aagcgaggag acgcccgcgg gaggcccagc tgctcggagc    180
aactggcatg gcccgagcca tggccgccgc gtggccgctg ctgctggtgg cgctactggt    240
gctgtcctgg ccacccccag gaaccgggga cgtcgtcgtg caggcgccca cccaggtcta    300
caggtgccca acatggaggt gacgcatgtg tcacagctga cttgggcgcg gcatggtgaa    360
tctggcagca tggccgtctt ccaccaaacg cagggcccca gctattcgga gtccaaacgg    420
ctggaattcg tggcagccag actgggcgcg gagctgcgga atgcctcgct gaggatgttc    480
gggttgcgcg tagaggatga aggcaactac acctgcctgt tcgtcacgtt cccgcagggc    540
agcaggagcg tggatatctg gctccgagtg cttgccaagc cccagaacac agacctgggc    600
gggatgccca atacgagcca ggtgccaggg ttcctgtctg gcacagtcac tgtcaccagc    660
ctctggatat tggtgccctc aagccaggtg gacggcaaga atgtgacctg caaggtggag    720
cacgagagct ttgagaagcc tcagctgctg actgtgaacc tcaccgtgta ctacccccca    780
gaggtatcca tctctggcta tgataacaac tggtaccttg gccagaatga ggccaccctg    840
acctgcgatg ctcgcagcaa cccagagccc acaggctata attggagcac gaccatgggt    900
cccctgccac cctttgctgt ggcccagggc gcccagctcc tgatccgtcc tgtggacaaa    960
ccaatcaaca caactttaat ctgcaacgtc accaatgccc taggagctcg ccaggcagaa   1020
ctgaccgtcc aggtcaaaga gggacctccc agtgagcact caggcatgtc ccgtaacgcc   1080
atcatcttcc tggttctggg aatcctggtt tttctgatcc tgctggggat cgggatttat   1140
ttctattggt ccaaatgttc ccgtgaggtc ctttggcact gtcatctgtg tccctcgagt   1200
```

```
acagagcatg ccagcgcctc agctaatggg catgtctcct attcagctgt gagcagagag   1260
aacagctctt cccaggatcc acagacagag ggcacaaggt gacagcgtcg ggactgagag   1320
gggagagaga ctggagctgg caaggacgtg ggcctccaga gttggacccg accccaatgg   1380
atgaagaccc cctccaaaga gaccagcctc cctccctgtg ccagacctca aaacgacggg   1440
ggcaggtgca agttcatagg tctccaagac caccctcctt tcatttgcta gaaggactca   1500
ctagactcag gaaagctgtt aggctcacag ttacagttta ttacagtaaa aggacagaga   1560
ttaagatcag caaagggagg aggtgcacag cacacgttcc acgacagatg aggcgacggc   1620
ttccatctgc cctctcccag tggagccata taggcagcac ctgattctca cagcaacatg   1680
tgacaacatg caagaagtac tgccaatact gccaaccaga gcagctcact cgagatcttt   1740
gtgtccagag tttttgttt gtcttgagac agggtctggc tctgttggca gactagagta   1800
cagtggtgag atcacagttc attgcagcct tgacttctca acgccaagtc atcctcccac   1860
ctcagcctcc tgagtagcta tgactacagg tatgtgccac cacgtctggc taatcttttt   1920
attatttgta aagtcgaggt ttccctgtgt tgcccaggct ggtcttgaac tcttggctcc   1980
aagtgatact tctgccttgg cctcccaaag tgctgaatta agcagctcac catccacacg   2040
gctgacctca tacatcaagc caataccgtg tggcccaaga cccccaccat aaatcacatc   2100
attagcatga accacccaga gtggcccaag actccaagat cagctaccag gcaggatatt   2160
ccaagggctt agagatgaat gcccaggagc tgaggataaa gggcccgatc tttctttggg   2220
caaggttaag cctttactgc atagcagacc acacagaagg gtgtgggcca ccagagaatt   2280
ttggtaaaaa tttggcctct ggccttgagc ttctaaatct ctgtatccgt cagatctctg   2340
tggttacaag aaacagccac tgaccctggt caccagaggc tgcaattcag gccgcaagca   2400
gctgcctggg gggtgtccaa ggagcagaga aaactactag atgtgaactt gaagaaggtt   2460
gtcagctgca gccactttct gccagcatct gcagccactt tctgccagca tctgcagcca   2520
gcaagctggg actggcagga aataacccac aaaagaagca aatgcaattt ccaacacaag   2580
ggggaaggga tgcaggggga ggcagcgctg cagttgctca ggacacgctc ctataggacc   2640
aagatggatg cgacccaaga cccaggaggc ccagctgctc agtgcaactg acaagttaaa   2700
aaggtctatg atcttgaggg cagacagcag aattcctctt ataaagaaaa ctgtttggga   2760
aaatacgttg agggagagaa gaccttgggc caagatgcta aatgggaatg caaagcttga   2820
gctgctctgc aagagaaaat aagcaggaca gaggatttgc tctggacaga gatggaagag   2880
ccgggaacag agaagtgtgg ggaagagata ggaaccagca ggatggcagg ggcaaagggc   2940
tcaagggtga ggaggccagt gggaccccac agagttgggg agataaagga acattggttg   3000
ctttggtggc acgtaagctc cttgtctgtc tccagcaccc agaatctcat taaagcttat   3060
ttattgtacc tccagcggct gtgtgcaatg gggtcttttg tggaaatcaa ggagcagaca   3120
ggtttcatgt gtactgtcac cacgtgggat ggaaccagag gcatggaagc aagacgctaa   3180
atgaagaggg ccataagggc tgggattccc aggcacctta ggaacagctt gtcttttttt   3240
ttttcctctc caaaaaaaat gtttaaggga cggtgtctcc tgtcacccag gctggagtgc   3300
aatggcacga tcatagctca ttgcagcctc taactccggg gctcaagcaa tcctcccacc   3360
tcagcctacc aagtagctgt gaccacagct gcccctcacc atgctaagct aattttttta   3420
attagatagt acataaacgt cccaaaatta gaagataaaa agacatgagg gatccattct   3480
aatttgtgtt tggagtgtaa tggtccagct ccattcttct gcacatggat atccagtttt   3540
acacaacact gtgaatgtaa tgaatgccac tgaatcatac actcaaaaat agctaaaatg   3600
```

gcaaattgtc tgttatctct ttttaaccac catttttgaa aattaattat accaaaaaac 3660
cattgaatag tgcactttat ttatttattt atttgtttat ttatttattt attttagaaa 3720
taagagtctc actttgttgc ccaggctgga gtgcagtggc gtgatcatgg ctcattgcag 3780
cctcgacctg ctgggctcgg gctatccttc catctcagcc tcccgagtag ctgggactat 3840
aggtgggcgc caccccacct ggctaaatct ctttttaact tttgtagaga taggcatctc 3900
gctatgttgc ctaggctggg ctggaactcc tgggctcaag tgctcctcct gccttggcct 3960
cccaaagcgc taggattaca gatgtgagcc accgcgccca ccctgaacct tacttttttt 4020
gctcagtttc tggtaattca gagaatgcct cctgagttgt tctacaccca cctcatattc 4080
catgggaggg ctgtacaggg ctttttttaac gaggcctcta aggacaggca tttgtatcct 4140
ttccagcctt tcactattac aatgttgtag tgaataactt tacacactgt catttatttt 4200
actttttttt ttttttattt tagagaaagg aatcttgcca tcttgcccag gctggtctca 4260
aattcctggg cccaaacaat cctcccgcct tggcctccta aagtactggg atttataggc 4320
ataagccacc gtgcctggcc aatgcacact gtcatttagc tcatgttaac acctgagtgt 4380
aggacacact cctggaggtg gaattgctgg gccaaagagt atgtttcttg tcattgtgat 4440
agatattgac aaatgaaccc tcacagaagt tgtgctgagt tctgttccca ccagcgacgt 4500
aggcgatgac ctttttctgg agggaggggg catccttgga gtccacagag ccaggaatgg 4560
agagtgggcc cagaattttg gtataggtgt tgtataaact tatagtaagg ttaagaaaac 4620
cgcaactatc cttatcagag acttggcggg gggcagggta tgatggagat cataaggagg 4680
ctaaaacact ccacaccctc cctctgcatt gctcctgcac gggagtcggg aatcttttca 4740
ggttgatacg atctcacctt gaggagctgt gaggtcccag aagcctctgg gttgcagatt 4800
gcttggggtg aaaatgtctg tgctactgaa atctaacttt ttacaaaaaa ttacgggctg 4860
ggcgcagtgg ctcacgcctg taatcccagc actttgggag gctgcagcgg gtggatcact 4920
tgaggtaagg agttcaagac cagaccatag tgaaaccgtg tctctacaaa aaaaattagc 4980
caggtgtggt ggtgcatgct tgtaatccca gctactcaga aggctgaggt gggagaatcc 5040
cttgaacccg ggaagtggag gctggagtaa accatgatcg agttactgca ctccagcctg 5100
ggtgacaaga gtgagactct gtctccaaaa aaaaaaaaaa aaaaaaaaaa actggattgc 5160
ctggctctac tccgggcaca gcatgcaggc ccagttctgc tgctctgctg tttgttctgc 5220
tttcctccac atattggcat caccctctgg tgccaagatg gctgctgcat tccaggcatc 5280
acatccagac tcagacccag agaagctgcc catccctacc tgggtgagcc tttgtaggaa 5340
cgagaaaccg catccagcag cagaaacctc acccagcagc gtcttttccg gtctcattca 5400
ccagcgccgc ccaccgctca accaatccct ggccaaaaga atgggaccgc ctggaaggct 5460
ggaccaaaca ggacctgccc tctggggctg gggagaggcc cagatgaagg ctgcaggaca 5520
ggatggactc ctagacctct gttaccagca gtgactacct ctgtctgggt ggttggaaca 5580
tgtttgaatt ttattctaag tactgtctac aagttctgca ataaaccttg actcttcttt 5640
taataatgca aaa 5653

<210> SEQ ID NO 51
<211> LENGTH: 5692
<212> TYPE: DNA
<213> ORGANISM: Homo sapiens

<400> SEQUENCE: 51

-continued

```
agtcacttgt ctggagcttg aagaagtggg tattcccctt cccaccccag gcactggagg     60
agcggccccc cggggattcc aggacctgag ctccgggagc tggactcgca gcgaccgcgg    120
cagagcgagc gggcgccggg aagcgaggag acgcccgcgg gaggcccagc tgctcggagc    180
aactggcatg gcccgagcca tggccgccgc gtggccgctg ctgctggtgg cgctactggt    240
gctgtcctgg ccacccccag gaaccgggga cgtcgtcgtg caggcgccca cccaggtgcc    300
cggcttcttg ggcgactccg tgacgctgcc ctgctactac aggtgcccaa catggaggtg    360
acgcatgtgt cacagctgac ttgggcgcgg catggtgaat ctggcagcat ggccgtcttc    420
caccaaacgc agggccccag ctattcggag tccaaacggc tggaattcgt ggcagccaga    480
ctgggcgcgg agctgcggaa tgcctcgctg aggatgttcg ggttgcgcgt agaggatgaa    540
ggcaactaca cctgcctgtt cgtcacgttc ccgcagggca gcaggagcgt ggatatctgg    600
ctccgagtgc ttgccaagcc ccagaacaca gacctgggcg ggatgcccaa tacgagccag    660
gtgccagggt tcctgtctgg cacagtcact gtcaccagcc tctggatatt ggtgccctca    720
agccaggtgg acggcaagaa tgtgacctgc aaggtggagc acgagagctt tgagaagcct    780
cagctgctga ctgtgaacct caccgtgtac taccccccag aggtatccat ctctggctat    840
gataacaact ggtaccttgg ccagaatgag gccaccctga cctgcgatgc tcgcagcaac    900
ccagagccca caggctataa ttggagcacg accatgggtc ccctgccacc ctttgctgtg    960
gcccagggcg cccagctcct gatccgtcct gtggacaaac caatcaacac aactttaatc   1020
tgcaacgtca ccaatgccct aggagctcgc caggcagaac tgaccgtcca ggtcaaagag   1080
ggacctccca gtgagcactc aggcatgtcc cgtaacgcca tcatcttcct ggttctggga   1140
atcctggttt ttctgatcct gctggggatc gggatttatt tctattggtc caaatgttcc   1200
cgtgaggtcc tttggcactg tcatctgtgt ccctcgagta cagagcatgc cagcgcctca   1260
gctaatgggc atgtctccta ttcagctgtg agcagagaga acagctcttc ccaggatcca   1320
cagacagagg gcacaaggtg acagcgtcgg gactgagagg ggagagagac tggagctggc   1380
aaggacgtgg gcctccagag ttggacccga ccccaatgga tgaagacccc ctccaaagag   1440
accagcctcc ctccctgtgc cagacctcaa aacgacgggg gcaggtgcaa gttcataggt   1500
ctccaagacc accctccttt catttgctag aaggactcac tagactcagg aaagctgtta   1560
ggctcacagt tacagtttat tacagtaaaa ggacagagat taagatcagc aaagggagga   1620
ggtgcacagc acacgttcca cgacagatga ggcgacggct tccatctgcc ctctcccagt   1680
ggagccatat aggcagcacc tgattctcac agcaacatgt gacaacatgc aagaagtact   1740
gccaatactg ccaaccagag cagctcactc gagatctttg tgtccagagt tttttgtttg   1800
tcttgagaca gggtctggct ctgttggcag actagagtac agtggtgaga tcacagttca   1860
ttgcagcctt gacttctcaa cgccaagtca tcctcccacc tcagcctcct gagtagctat   1920
gactacaggt atgtgccacc acgtctggct aatcttttta ttatttgtaa agtcgaggtt   1980
tccctgtgtt gcccaggctg gtcttgaact cttggctcca agtgatactt ctgccttggc   2040
ctcccaaagt gctgaattaa gcagctcacc atccacacgg ctgacctcat acatcaagcc   2100
aataccgtgt ggcccaagac ccccaccata aatcacatca ttagcatgaa ccacccagag   2160
tggcccaaga ctccaagatc agctaccagg caggatattc caagggctta gagatgaatg   2220
cccaggagct gaggataaag ggcccgatct ttctttgggc aaggttaagc ctttactgca   2280
tagcagacca cacagaaggg tgtgggccac cagagaattt tggtaaaaat ttggcctctg   2340
gccttgagct tctaaatctc tgtatccgtc agatctctgt ggttacaaga aacagccact   2400
```

```
gaccctggtc accagaggct gcaattcagg ccgcaagcag ctgcctgggg ggtgtccaag   2460
gagcagagaa aactactaga tgtgaacttg aagaaggttg tcagctgcag ccactttctg   2520
ccagcatctg cagccacttt ctgccagcat ctgcagccag caagctggga ctggcaggaa   2580
ataacccaca aaagaagcaa atgcaatttc caacacaagg gggaagggat gcagggggag   2640
gcagcgctgc agttgctcag gacacgctcc tataggacca agatggatgc gacccaagac   2700
ccaggaggcc cagctgctca gtgcaactga caagttaaaa aggtctatga tcttgagggc   2760
agacagcaga attcctctta taaagaaaac tgtttgggaa aatacgttga gggagagaag   2820
accttgggcc aagatgctaa atgggaatgc aaagcttgag ctgctctgca agagaaaata   2880
agcaggacag aggatttgct ctggacagag atggaagagc cgggaacaga gaagtgtggg   2940
gaagagatag gaaccagcag gatggcaggg gcaaagggct caagggtgag gaggccagtg   3000
ggaccccaca gagttgggga gataaaggaa cattggttgc tttggtggca cgtaagctcc   3060
ttgtctgtct ccagcaccca gaatctcatt aaagcttatt tattgtacct ccagcggctg   3120
tgtgcaatgg ggtcttttgt ggaaatcaag gagcagacag gtttcatgtg tactgtcacc   3180
acgtgggatg gaaccagagg catggaagca agacgctaaa tgaagagggc cataagggct   3240
gggattccca ggcaccttag gaacagcttg tcttttttt tttcctctcc aaaaaaaatg   3300
tttaagggac ggtgtctcct gtcacccagg ctggagtgca atggcacgat catagctcat   3360
tgcagcctct aactccgggg ctcaagcaat cctcccacct cagcctacca agtagctgtg   3420
accacagctg cccctcacca tgctaagcta atttttttaa ttagatagta cataaacgtc   3480
ccaaaattag aagataaaaa gacatgaggg atccattcta atttgtgttt ggagtgtaat   3540
ggtccagctc cattcttctg cacatggata tccagtttta cacaacactg tgaatgtaat   3600
gaatgccact gaatcataca ctcaaaaata gctaaaatgg caaattgtct gttatctctt   3660
tttaaccacc atttttgaaa attaattata ccaaaaaacc attgaatagt gcactttatt   3720
tatttattta tttgtttatt tatttattta ttttagaaat aagagtctca ctttgttgcc   3780
caggctggag tgcagtggcg tgatcatggc tcattgcagc ctcgacctgc tgggctcggg   3840
ctatccttcc atctcagcct cccgagtagc tgggactata ggtgggcgcc accccacctg   3900
gctaaatctc tttttaactt ttgtagagat aggcatctcg ctatgttgcc taggctgggc   3960
tggaactcct gggctcaagt gctcctcctg ccttggcctc ccaaagcgct aggattacag   4020
atgtgagcca ccgcgcccac cctgaacctt actttttttg ctcagtttct ggtaattcag   4080
agaatgcctc ctgagttgtt ctacacccac ctcatattcc atgggagggc tgtacagggc   4140
ttttttaacg aggcctctaa ggacaggcat ttgtatcctt tccagccttt cactattaca   4200
atgttgtagt gaataacttt acacactgtc atttatttta cttttttttt tttttatttt   4260
agagaaagga atcttgccat cttgcccagg ctggtctcaa attcctgggc ccaaacaatc   4320
ctcccgcctt ggcctcctaa agtactggga tttataggca taagccaccg tgcctggcca   4380
atgcacactg tcatttagct catgttaaca cctgagtgta ggacacactc ctggaggtgg   4440
aattgctggg ccaaagagta tgtttcttgt cattgtgata gatattgaca aatgaaccct   4500
cacagaagtt gtgctgagtt ctgttcccac cagcgacgta ggcgatgacc tttttctgga   4560
gggagggggc atccttggag tccacagagc caggaatgga gagtgggccc agaattttgg   4620
tataggtgtt gtataaactt atagtaaggt taagaaaacc gcaactatcc ttatcagaga   4680
cttggcgggg ggcagggtat gatggagatc ataaggaggc taaaacactc cacaccctcc   4740
```

```
ctctgcattg ctcctgcacg ggagtcggga atcttttcag gttgatacga tctcaccttg   4800

aggagctgtg aggtcccaga agcctctggg ttgcagattg cttggggtga aaatgtctgt   4860

gctactgaaa tctaactttt tacaaaaaat tacgggctgg gcgcagtggc tcacgcctgt   4920

aatcccagca ctttgggagg ctgcagcggg tggatcactt gaggtaagga gttcaagacc   4980

agaccatagt gaaaccgtgt ctctacaaaa aaaattagcc aggtgtggtg gtgcatgctt   5040

gtaatcccag ctactcagaa ggctgaggtg ggagaatccc ttgaacccgg gaagtggagg   5100

ctggagtaaa ccatgatcga gttactgcac tccagcctgg gtgacaagag tgagactctg   5160

tctccaaaaa aaaaaaaaaa aaaaaaaaaa ctggattgcc tggctctact ccgggcacag   5220

catgcaggcc cagttctgct gctctgctgt ttgttctgct ttcctccaca tattggcatc   5280

accctctggt gccaagatgg ctgctgcatt ccaggcatca catccagact cagacccaga   5340

gaagctgccc atccctacct gggtgagcct ttgtaggaac gagaaaccgc atccagcagc   5400

agaaacctca cccagcagcg tcttttccgg tctcattcac cagcgccgcc caccgctcaa   5460

ccaatccctg gccaaaagaa tggaccgcc tggaaggctg gaccaaacag gacctgccct   5520

ctggggctgg ggagaggccc agatgaaggc tgcaggacag gatggactcc tagacctctg   5580

ttaccagcag tgactacctc tgtctgggtg gttggaacat gtttgaattt tattctaagt   5640

actgtctaca agttctgcaa taaaccttga ctcttctttt aataatgcaa aa           5692
```

<210> SEQ ID NO 52
<211> LENGTH: 5693
<212> TYPE: DNA
<213> ORGANISM: Homo sapiens

<400> SEQUENCE: 52

```
agtcacttgt ctggagcttg aagaagtggg tattcccctt cccaccccag gcactggagg     60

agcggccccc cggggattcc aggacctgag ctccgggagc tggactcgca gcgaccgcgg    120

cagagcgagc gggcgccggg aagcgaggag acgcccgcgg gaggcccagc tgctcggagc    180

aactggcatg gcccgagcca tggccgccgc gtggccgctg ctgctggtgg cgctactggt    240

gctgtcctgg ccaccccccag gaaccgggga cgtcgtcgtg caggcgccca cccaggtgcc    300

cggcttcttg ggcgactccg tgacgctgcc ctgctaccta caggtgccca acatggaggt    360

gacgcatgtg tcacagctga cttgggcgcg gcatggtgaa tctggcagca tggccgtctt    420

ccaccaaacg cagggcccca gctattcgga gtccaaacgg ctggaattcg tggcagccag    480

actgggcgcg gagctgcgga atgcctcgct gaggatgttc gggttgcgcg tagaggatga    540

aggcaactac acctgcctgt tcgtcacgtt cccgcagggc agcaggagcg tggatatctg    600

gctccgagtg cttgccaagc cccagaacac agacctgggc gggatgccca atacgagcca    660

ggtgccaggg ttcctgtctg gcacagtcac tgtcaccagc ctctggatat tggtgccctc    720

aagccaggtg gacggcaaga atgtgacctg caaggtggag cacgagagct ttgagaagcc    780

tcagctgctg actgtgaacc tcaccgtgta ctaccccccca gaggtatcca tctctggcta    840

tgataacaac tggtaccttg gccagaatga ggccaccctg acctgcgatg ctcgcagcaa    900

cccagagccc acaggctata attggagcac gaccatgggt cccctgccac cctttgctgt    960

ggcccagggc gcccagctcc tgatccgtcc tgtggacaaa ccaatcaaca caactttaat   1020

ctgcaacgtc accaatgccc taggagctcg ccaggcagaa ctgaccgtcc aggtcaaaga   1080

gggacctccc agtgagcact caggcatgtc ccgtaacgcc atcatcttcc tggttctggg   1140

aatcctggtt tttctgatcc tgctggggat cgggatttat ttctattggt ccaaatgttc   1200
```

ccgtgaggtc ctttggcact gtcatctgtg tccctcgagt acagagcatg ccagcgcctc 1260
agctaatggg catgtctcct attcagctgt gagcagagag aacagctctt cccaggatcc 1320
acagacagag ggcacaaggt gacagcgtcg ggactgagag gggagagaga ctggagctgg 1380
caaggacgtg ggcctccaga gttggacccg accccaatgg atgaagaccc cctccaaaga 1440
gaccagcctc cctccctgtg ccagacctca aaacgacggg ggcaggtgca agttcatagg 1500
tctccaagac caccctcctt tcatttgcta gaaggactca ctagactcag gaaagctgtt 1560
aggctcacag ttacagttta ttacagtaaa aggacagaga ttaagatcag caaagggagg 1620
aggtgcacag cacacgttcc acgacagatg aggcgacggc ttccatctgc cctctcccag 1680
tggagccata taggcagcac ctgattctca cagcaacatg tgacaacatg caagaagtac 1740
tgccaatact gccaaccaga gcagctcact cgagatcttt gtgtccagag tttttttgttt 1800
gtcttgagac agggtctggc tctgttggca gactagagta cagtggtgag atcacagttc 1860
attgcagcct tgacttctca acgccaagtc atcctcccac ctcagcctcc tgagtagcta 1920
tgactacagg tatgtgccac cacgtctggc taatcttttt attatttgta aagtcgaggt 1980
ttccctgtgt tgcccaggct ggtcttgaac tcttggctcc aagtgatact tctgccttgg 2040
cctcccaaag tgctgaatta agcagctcac catccacacg gctgacctca tacatcaagc 2100
caataccgtg tggcccaaga cccccaccat aaatcacatc attagcatga accacccaga 2160
gtggcccaag actccaagat cagctaccag gcaggatatt ccaagggctt agagatgaat 2220
gcccaggagc tgaggataaa gggcccgatc tttctttggg caaggttaag cctttactgc 2280
atagcagacc acacagaagg gtgtgggcca ccagagaatt ttggtaaaaa tttggcctct 2340
ggccttgagc ttctaaatct ctgtatccgt cagatctctg tggttacaag aaacagccac 2400
tgaccctggt caccagaggc tgcaattcag gccgcaagca gctgcctggg gggtgtccaa 2460
ggagcagaga aaactactag atgtgaactt gaagaaggtt gtcagctgca gccactttct 2520
gccagcatct gcagccactt tctgccagca tctgcagcca gcaagctggg actggcagga 2580
aataacccac aaaagaagca aatgcaattt ccaacacaag ggggaaggga tgcaggggga 2640
ggcagcgctg cagttgctca ggacacgctc ctataggacc aagatggatg cgacccaaga 2700
cccaggaggc ccagctgctc agtgcaactg acaagttaaa aaggtctatg atcttgaggg 2760
cagacagcag aattcctctt ataaagaaaa ctgtttggga aaatacgttg agggagagaa 2820
gaccttgggc caagatgcta aatgggaatg caaagcttga gctgctctgc aagagaaaat 2880
aagcaggaca gaggatttgc tctggacaga gatggaagag ccgggaacag agaagtgtgg 2940
ggaagagata ggaaccagca ggatggcagg ggcaaagggc tcaagggtga ggaggccagt 3000
gggaccccac agagttgggg agataaagga acattggttg ctttggtggc acgtaagctc 3060
cttgtctgtc tccagcaccc agaatctcat taaagcttat ttattgtacc tccagcggct 3120
gtgtgcaatg gggtcttttg tggaaatcaa ggagcagaca ggtttcatgt gtactgtcac 3180
cacgtgggat ggaaccagag gcatggaagc aagacgctaa atgaagaggg ccataagggc 3240
tgggattccc aggcacctta ggaacagctt gtcttttttt ttttcctctc caaaaaaaat 3300
gtttaaggga cggtgtctcc tgtcacccag gctggagtgc aatggcacga tcatagctca 3360
ttgcagcctc taactccggg gctcaagcaa tcctcccacc tcagcctacc aagtagctgt 3420
gaccacagct gcccctcacc atgctaagct aattttttta attagatagt acataaacgt 3480
cccaaaatta gaagataaaa agacatgagg gatccattct aatttgtgtt tggagtgtaa 3540

```
tggtccagct ccattcttct gcacatggat atccagtttt acacaacact gtgaatgtaa   3600

tgaatgccac tgaatcatac actcaaaaat agctaaaatg gcaaattgtc tgttatctct   3660

ttttaaccac catttttgaa aattaattat accaaaaaac cattgaatag tgcactttat   3720

ttatttattt atttgtttat ttatttattt attttagaaa taagagtctc actttgttgc   3780

ccaggctgga gtgcagtggc gtgatcatgg ctcattgcag cctcgacctg ctgggctcgg   3840

gctatccttc catctcagcc tcccgagtag ctgggactat aggtgggcgc caccccacct   3900

ggctaaatct ctttttaact tttgtagaga taggcatctc gctatgttgc ctaggctggg   3960

ctggaactcc tgggctcaag tgctcctcct gccttggcct cccaaagcgc taggattaca   4020

gatgtgagcc accgcgccca ccctgaacct tacttttttt gctcagtttc tggtaattca   4080

gagaatgcct cctgagttgt tctacaccca cctcatattc catgggaggg ctgtacaggg   4140

ctttttaac gaggcctcta aggacaggca tttgtatcct ttccagcctt tcactattac   4200

aatgttgtag tgaataactt tacacactgt catttatttt actttttttt tttttatttt   4260

tagagaaagg aatcttgcca tcttgcccag gctggtctca aattcctggg cccaaacaat   4320

cctcccgcct tggcctccta aagtactggg atttataggc ataagccacc gtgcctggcc   4380

aatgcacact gtcatttagc tcatgttaac acctgagtgt aggacacact cctggaggtg   4440

gaattgctgg gccaaagagt atgtttcttg tcattgtgat agatattgac aaatgaaccc   4500

tcacagaagt tgtgctgagt tctgttccca ccagcgacgt aggcgatgac ctttttctgg   4560

agggaggggg catccttgga gtccacagag ccaggaatgg agagtgggcc cagaattttg   4620

gtataggtgt tgtataaact tatagtaagg ttaagaaaac cgcaactatc cttatcagag   4680

acttggcggg gggcagggta tgatggagat cataaggagg ctaaaacact ccacaccctc   4740

cctctgcatt gctcctgcac gggagtcggg aatcttttca ggttgatacg atctcacctt   4800

gaggagctgt gaggtcccag aagcctctgg gttgcagatt gcttggggtg aaaatgtctg   4860

tgctactgaa atctaacttt ttacaaaaaa ttacgggctg ggcgcagtgg ctcacgcctg   4920

taatcccagc actttgggag gctgcagcgg gtggatcact tgaggtaagg agttcaagac   4980

cagaccatag tgaaaccgtg tctctacaaa aaaaattagc caggtgtggt ggtgcatgct   5040

tgtaatccca gctactcaga aggctgaggt gggagaatcc cttgaacccg ggaagtggag   5100

gctggagtaa accatgatcg agttactgca ctccagcctg ggtgacaaga gtgagactct   5160

gtctccaaaa aaaaaaaaaa aaaaaaaaaa actggattgc ctggctctac tccgggcaca   5220

gcatgcaggc ccagttctgc tgctctgctg tttgttctgc tttcctccac atattggcat   5280

caccctctgg tgccaagatg gctgctgcat tccaggcatc acatccagac tcagacccag   5340

agaagctgcc catccctacc tgggtgagcc tttgtaggaa cgagaaaccg catccagcag   5400

cagaaacctc acccagcagc gtcttttccg gtctcattca ccagcgccgc ccaccgctca   5460

accaatccct ggccaaaaga atgggaccgc ctggaaggct ggaccaaaca ggacctgccc   5520

tctggggctg gggagaggcc cagatgaagg ctgcaggaca ggatggactc ctagacctct   5580

gttaccagca gtgactacct ctgtctgggt ggttggaaca tgtttgaatt ttattctaag   5640

tactgtctac aagttctgca ataaaccttg actcttcttt taataatgca aaa          5693
```

<210> SEQ ID NO 53
<211> LENGTH: 5693
<212> TYPE: DNA
<213> ORGANISM: Homo sapiens

<400> SEQUENCE: 53

```
agtcacttgt ctggagcttg aagaagtggg tattcccctt cccaccccag gcactggagg     60
agcggccccc cggggattcc aggacctgag ctccgggagc tggactcgca gcgaccgcgg    120
cagagcgagc gggcgccggg aagcgaggag acgcccgcgg gaggcccagc tgctcggagc    180
aactggcatg gcccgagcca tggccgccgc gtggccgctg ctgctggtgg cgctactggt    240
gctgtcctgg ccacccccag gaaccgggga cgtcgtcgtg caggcgccca cccaggtgcc    300
cggcttcttg ggcgactccg tgacgctgcc ctgctaccta caggtgccca acatggaggt    360
gacgcatgtg tcacagctga cttgggcgcg gcatggtgaa tctggcagca tggccgtctt    420
ccaccaaacg cagggcccca gctattcgga gtccaaacgg ctggaattcg tggcagccag    480
actgggcgcg gagctgcgga atgcctcgct gaggatgttc gggttgcgcg tagaggatga    540
aggcaactac acctgcctgt tcgtcacgtt cccgcagggc agcaggagcg tggatatctg    600
gctccgagtg cttgccaagc cccagaacac agacctgggc gggatgccca atacgagcca    660
ggtgccaggg ttcctgtctg gcacagtcac tgtcaccagc ctctggatat tggtgccctc    720
aagccaggtg gacggcaaga atgtgacctg caaggtggag cacgagagct ttgagaagcc    780
tcagctgctg actgtgaacc tcaccgtgta ctacccccca gaggtatcca tctctggcta    840
tgataacaac tggtaccttg gccagaatga ggccaccctg acctgcgatg ctcgcagcaa    900
cccagagccc acaggctata attggagcac gaccatgggt cccctgccac cctttgctgt    960
ggcccagggc gcccagctcc tgatccgtcc tgtggacaaa ccaatcaaca caactttaat   1020
ctgcaacgtc accaatgccc taggagctcg ccaggcagaa ctgaccgtcc aggtcaaaga   1080
gggacctccc agtgagcact caggcatgtc ccgtaacgcc atcatcttcc tggttctggg   1140
aatcctggtt tttctgatcc tgctggggat cgggatttat ttctattggt ccaaatgttc   1200
ccgtgaggtc ctttggcact gtcatctgtg tccctcgagt acagagcatg ccagcgcctc   1260
agctaatggg catgtctcct attcagctgt gagcagagag aacagctctt cccaggatcc   1320
acagacagag ggcacaaggt gacagcgtcg ggactgagag gggagagaga ctggagctgg   1380
caaggacgtg ggcctccaga gttggacccg accccaatgg atgaagaccc cctccaaaga   1440
gaccagcctc cctccctgtg ccagacctca aaacgacggg ggcaggtgca agttcatagg   1500
tctccaagac caccctcctt tcatttgcta gaaggactca ctagactcag gaaagctgtt   1560
aggctcacag ttacagttta ttacagtaaa aggacagaga ttaagatcag caaagggagg   1620
aggtgcacag cacacgttcc acgacagatg aggcgacggc ttccatctgc cctctcccag   1680
tggagccata taggcagcac ctgattctca cagcaacatg tgacaacatg caagaagtac   1740
tgccaatact gccaaccaga gcagctcact cgagatcttt gtgtccagag tttttttgttt   1800
gtcttgagac agggtctggc tctgttggca gactagagta cagtggtgag atcacagttc   1860
attgcagcct tgacttctca acgccaagtc atcctcccac ctcagcctcc tgagtagcta   1920
tgactacagg tatgtgccac cacgtctggc taatcttttt attatttgta aagtcgaggt   1980
ttccctgtgt tgcccaggct ggtcttgaac tcttggctcc aagtgatact tctgccttgg   2040
cctcccaaag tgctgaatta agcagctcac catccacacg gctgacctca tacatcaagc   2100
caataccgtg tggcccaaga cccccaccat aaatcacatc attagcatga accacccaga   2160
gtggcccaag actccaagat cagctaccag gcaggatatt ccaagggctt agagatgaat   2220
gcccaggagc tgaggataaa gggcccgatc tttctttggg caaggttaag cctttactgc   2280
atagcagacc acacagaagg gtgtgggcca ccagagaatt ttggtaaaaa tttggcctct   2340
```

-continued

```
ggccttgagc ttctaaatct ctgtatccgt cagatctctg tggttacaag aaacagccac   2400
tgaccctggt caccagaggc tgcaattcag gccgcaagca gctgcctggg gggtgtccaa   2460
ggagcagaga aaactactag atgtgaactt gaagaaggtt gtcagctgca gccactttct   2520
gccagcatct gcagccactt tctgccagca tctgcagcca gcaagctggg actggcagga   2580
aataacccac aaaagaagca aatgcaattt ccaacacaag gggaaggga tgcaggggga   2640
ggcagcgctg cagttgctca ggacacgctc ctataggacc aagatggatg cgacccaaga   2700
cccaggaggc ccagctgctc agtgcaactg acaagttaaa aaggtctatg atcttgaggg   2760
cagacagcag aattcctctt ataaagaaaa ctgtttggga aaatacgttg agggagagaa   2820
gaccttgggc caagatgcta aatgggaatg caaagcttga gctgctctgc aagagaaaat   2880
aagcaggaca gaggatttgc tctggacaga gatggaagag ccgggaacag agaagtgtgg   2940
ggaagagata ggaaccagca ggatggcagg ggcaaagggc tcaagggtga ggaggccagt   3000
gggaccccac agagttgggg agataaagga acattggttg ctttggtggc acgtaagctc   3060
cttgtctgtc tccagcaccc agaatctcat taaagcttat ttattgtacc tccagcggct   3120
gtgtgcaatg gggtcttttg tggaaatcaa ggagcagaca ggtttcatgt gtactgtcac   3180
cacgtgggat ggaaccagag gcatggaagc aagacgctaa atgaagaggg ccataagggc   3240
tgggattccc aggcacctta ggaacagctt gtcttttttt ttttcctctc caaaaaaaat   3300
gtttaaggga cggtgtctcc tgtcacccag gctggagtgc aatggcacga tcatagctca   3360
ttgcagcctc taactccggg gctcaagcaa tcctcccacc tcagcctacc aagtagctgt   3420
gaccacagct gcccctcacc atgctaagct aattttttta attagatagt acataaacgt   3480
cccaaaatta gaagataaaa agacatgagg gatccattct aatttgtgtt tggagtgtaa   3540
tggtccagct ccattcttct gcacatggat atccagtttt acacaacact gtgaatgtaa   3600
tgaatgccac tgaatcatac actcaaaaat agctaaaatg gcaaattgtc tgttatctct   3660
ttttaaccac catttttgaa aattaattat accaaaaaac cattgaatag tgcactttat   3720
ttatttattt atttgtttat ttatttattt attttagaaa taagagtctc actttgttgc   3780
ccaggctgga gtgcagtggc gtgatcatgg ctcattgcag cctcgacctg ctgggctcgg   3840
gctatccttc catctcagcc tcccgagtag ctgggactat aggtgggcgc caccccacct   3900
ggctaaatct ctttttaact tttgtagaga taggcatctc gctatgttgc ctaggctggg   3960
ctggaactcc tgggctcaag tgctcctcct gccttggcct cccaaagcgc taggattaca   4020
gatgtgagcc accgcgccca ccctgaacct tacttttttt gctcagtttc tggtaattca   4080
gagaatgcct cctgagttgt tctacaccca cctcatattc catgggaggg ctgtacaggg   4140
ctttttttaac gaggcctcta aggacaggca tttgtatcct ttccagcctt tcactattac   4200
aatgttgtag tgaataactt tacacactgt catttatttt actttttttt ttttttattt   4260
tagagaaagg aatcttgcca tcttgcccag gctggtctca aattcctggg cccaaacaat   4320
cctcccgcct tggcctccta aagtactggg atttataggc ataagccacc gtgcctggcc   4380
aatgcacact gtcatttagc tcatgttaac acctgagtgt aggacacact cctggaggtg   4440
gaattgctgg gccaaagagt atgtttcttg tcattgtgat agatattgac aaatgaaccc   4500
tcacagaagt tgtgctgagt tctgttccca ccagcgacgt aggcgatgac ctttttctgg   4560
agggaggggg catccttgga gtccacagag ccaggaatgg agagtgggcc cagaattttg   4620
gtataggtgt tgtataaact tatagtaagg ttaagaaaac cgcaactatc cttatcagag   4680
acttggcggg gggcagggta tgatggagat cataaggagg ctaaaacact ccacaccctc   4740
```

cctctgcatt gctcctgcac gggagtcggg aatcttttca ggttgatacg atctcacctt 4800
gaggagctgt gaggtcccag aagcctctgg gttgcagatt gcttggggtg aaaatgtctg 4860
tgctactgaa atctaacttt ttacaaaaaa ttacgggctg ggcgcagtgg ctcacgcctg 4920
taatcccagc actttgggag gctgcagcgg gtggatcact tgaggtaagg agttcaagac 4980
cagaccatag tgaaaccgtg tctctacaaa aaaaattagc caggtgtggt ggtgcatgct 5040
tgtaatccca gctactcaga aggctgaggt gggagaatcc cttgaacccg ggaagtggag 5100
gctggagtaa accatgatcg agttactgca ctccagcctg ggtgacaaga gtgagactct 5160
gtctccaaaa aaaaaaaaaa aaaaaaaaaa actggattgc ctggctctac tccgggcaca 5220
gcatgcaggc ccagttctgc tgctctgctg tttgttctgc tttcctccac atattggcat 5280
caccctctgg tgccaagatg gctgctgcat tccaggcatc acatccagac tcagacccag 5340
agaagctgcc catccctacc tgggtgagcc tttgtaggaa cgagaaaccg catccagcag 5400
cagaaacctc acccagcagc gtcttttccg gtctcattca ccagcgccgc ccaccgctca 5460
accaatccct ggccaaaaga atgggaccgc ctggaaggct ggaccaaaca ggacctgccc 5520
tctggggctg gggagaggcc cagatgaagg ctgcaggaca ggatggactc ctagacctct 5580
gttaccagca gtgactacct ctgtctgggt ggttggaaca tgtttgaatt ttattctaag 5640
tactgtctac aagttctgca ataaaccttg actcttcttt taataatgca aaa 5693

<210> SEQ ID NO 54
<211> LENGTH: 5675
<212> TYPE: DNA
<213> ORGANISM: Homo sapiens

<400> SEQUENCE: 54
agtcacttgt ctggagcttg aagaagtggg tattcccctt cccaccccag gcactggagg 60
agcggccccc cggggattcc aggacctgag ctccgggagc tggactcgca gcgaccgcgg 120
cagagcgagc gggcgccggg aagcgaggag acgcccgcgg gaggcccagc tgctcggagc 180
aactggcatg gcccgagcca tggccgccgc gtggccgctg ctgctggtgg cgctactggt 240
gctgtcctgg ccaccccccag gaaccgggga cgtcgtcgtg caggcgccca cccaggtgcc 300
cggcttcttg ggcgactcct tacaggtgcc caacatggag gtgacgcatg tgtcacagct 360
gacttgggcg cggcatggtg aatctggcag catggccgtc ttccaccaaa cgcagggccc 420
cagctattcg gagtccaaac ggctggaatt cgtggcagcc agactgggcg cggagctgcg 480
gaatgcctcg ctgaggatgt tcgggttgcg cgtagaggat gaaggcaact acacctgcct 540
gttcgtcacg ttcccgcagg gcagcaggag cgtggatatc tggctccgag tgcttgccaa 600
gccccagaac acagacctgg gcgggatgcc caatacgagc caggtgccag ggttcctgtc 660
tggcacagtc actgtcacca gcctctggat attggtgccc tcaagccagg tggacggcaa 720
gaatgtgacc tgcaaggtgg agcacgagag ctttgagaag cctcagctgc tgactgtgaa 780
cctcaccgtg tactaccccc cagaggtatc catctctggc tatgataaca actggtacct 840
tggccagaat gaggccaccc tgacctgcga tgctcgcagc aacccagagc ccacaggcta 900
taattggagc acgaccatgg gtcccctgcc accctttgct gtggcccagg gcgcccagct 960
cctgatccgt cctgtggaca aaccaatcaa cacaacttta atctgcaacg tcaccaatgc 1020
cctaggagct cgccaggcag aactgaccgt ccaggtcaaa gagggacctc ccagtgagca 1080
ctcaggcatg tcccgtaacg ccatcatctt cctggttctg ggaatcctgg tttttctgat 1140
cctgctgggg atcgggattt atttctattg gtccaaatgt tcccgtgagg tcctttggca 1200
ctgtcatctg tgtccctcga gtacagagca tgccagcgcc tcagctaatg ggcatgtctc 1260
ctattcagct gtgagcagag agaacagctc ttcccaggat ccacagacag agggcacaag 1320
gtgacagcgt cgggactgag aggggagaga gactggagct ggcaaggacg tgggcctcca 1380
gagttggacc cgaccccaat ggatgaagac cccctccaaa gagaccagcc tccctccctg 1440
tgccagacct caaaacgacg gggcaggtg caagttcata ggtctccaag accaccctcc 1500
tttcatttgc tagaaggact cactagactc aggaaagctg ttaggctcac agttacagtt 1560
tattacagta aaaggacaga gattaagatc agcaaaggga ggaggtgcac agcacacgtt 1620
ccacgacaga tgaggcgacg gcttccatct gccctctccc agtggagcca tataggcagc 1680
acctgattct cacagcaaca tgtgacaaca tgcaagaagt actgccaata ctgccaacca 1740
gagcagctca ctcgagatct ttgtgtccag agtttttgt ttgtcttgag acagggtctg 1800
gctctgttgg cagactagag tacagtggtg agatcacagt tcattgcagc cttgacttct 1860
caacgccaag tcatcctccc acctcagcct cctgagtagc tatgactaca ggtatgtgcc 1920
accacgtctg gctaatcttt ttattatttg taaagtcgag gtttccctgt gttgcccagg 1980
ctggtcttga actcttggct ccaagtgata cttctgcctt ggcctcccaa agtgctgaat 2040
taagcagctc accatccaca cggctgacct catacatcaa gccaataccg tgtggcccaa 2100
gacccccacc ataaatcaca tcattagcat gaaccaccca gagtggccca agactccaag 2160
atcagctacc aggcaggata ttccaagggc ttagagatga atgcccagga gctgaggata 2220
aagggcccga tctttctttg ggcaaggtta agcctttact gcatagcaga ccacacagaa 2280
gggtgtgggc caccagagaa ttttggtaaa aatttggcct ctggccttga gcttctaaat 2340
ctctgtatcc gtcagatctc tgtggttaca agaaacagcc actgaccctg gtcaccagag 2400
gctgcaattc aggccgcaag cagctgcctg gggggtgtcc aaggagcaga gaaaactact 2460
agatgtgaac ttgaagaagg ttgtcagctg cagccacttt ctgccagcat ctgcagccac 2520
tttctgccag catctgcagc cagcaagctg ggactggcag gaaataaccc acaaaagaag 2580
caaatgcaat ttccaacaca agggggaagg gatgcagggg gaggcagcgc tgcagttgct 2640
caggacacgc tcctatagga ccaagatgga tgcgacccaa gacccaggag gcccagctgc 2700
tcagtgcaac tgacaagtta aaaaggtcta tgatcttgag ggcagacagc agaattcctc 2760
ttataaagaa aactgtttgg gaaaatacgt tgagggagag aagaccttgg gccaagatgc 2820
taaatgggaa tgcaaagctt gagctgctct gcaagagaaa ataagcagga cagaggattt 2880
gctctggaca gagatggaag agccgggaac agagaagtgt ggggaagaga taggaaccag 2940
caggatggca ggggcaaagg gctcaagggt gaggaggcca gtgggacccc acagagttgg 3000
ggagataaag gaacattggt tgctttggtg gcacgtaagc tccttgtctg tctccagcac 3060
ccagaatctc attaaagctt atttattgta cctccagcgg ctgtgtgcaa tggggtcttt 3120
tgtggaaatc aaggagcaga caggtttcat gtgtactgtc accacgtggg atggaaccag 3180
aggcatggaa gcaagacgct aaatgaagag ggccataagg gctgggattc ccaggcacct 3240
taggaacagc ttgtcttttt tttttcctc tccaaaaaaa atgtttaagg gacggtgtct 3300
cctgtcaccc aggctggagt gcaatggcac gatcatagct cattgcagcc tctaactccg 3360
gggctcaagc aatcctccca cctcagccta ccaagtagct gtgaccacag ctgcccctca 3420
ccatgctaag ctaatttttt taattagata gtacataaac gtcccaaaat tagaagataa 3480
aaagacatga gggatccatt ctaatttgtg tttggagtgt aatggtccag ctccattctt 3540
ctgcacatgg atatccagtt ttacacaaca ctgtgaatgt aatgaatgcc actgaatcat 3600
acactcaaaa atagctaaaa tggcaaattg tctgttatct ctttttaacc accatttttg 3660
aaaattaatt ataccaaaaa accattgaat agtgcacttt atttatttat ttatttgttt 3720
atttatttat ttattttaga aataagagtc tcactttgtt gcccaggctg gagtgcagtg 3780
gcgtgatcat ggctcattgc agcctcgacc tgctgggctc gggctatcct tccatctcag 3840
cctcccgagt agctgggact ataggtgggc gccaccccac ctggctaaat ctctttttaa 3900
cttttgtaga gataggcatc tcgctatgtt gcctaggctg ggctggaact cctgggctca 3960
agtgctcctc ctgccttggc ctcccaaagc gctaggatta cagatgtgag ccaccgcgcc 4020
caccctgaac cttacttttt ttgctcagtt tctggtaatt cagagaatgc ctcctgagtt 4080
gttctacacc cacctcatat tccatgggag ggctgtacag ggctttttta acgaggcctc 4140
taaggacagg catttgtatc ctttccagcc tttcactatt acaatgttgt agtgaataac 4200
tttacacact gtcatttatt ttactttttt ttttttttat tttagagaaa ggaatcttgc 4260
catcttgccc aggctggtct caaattcctg ggcccaaaca atcctcccgc cttggcctcc 4320
taaagtactg ggatttatag gcataagcca ccgtgcctgg ccaatgcaca ctgtcattta 4380
gctcatgtta acacctgagt gtaggacaca ctcctggagg tggaattgct gggccaaaga 4440
gtatgtttct tgtcattgtg atagatattg acaaatgaac cctcacagaa gttgtgctga 4500
gttctgttcc caccagcgac gtaggcgatg accttttttct ggagggaggg ggcatccttg 4560
gagtccacag agccaggaat ggagagtggg cccagaattt tggtataggt gttgtataaa 4620
cttatagtaa ggttaagaaa accgcaacta tccttatcag agacttggcg gggggcaggg 4680
tatgatggag atcataagga ggctaaaaca ctccacaccc tccctctgca ttgctcctgc 4740
acgggagtcg ggaatctttt caggttgata cgatctcacc ttgaggagct gtgaggtccc 4800
agaagcctct gggttgcaga ttgcttgggg tgaaaatgtc tgtgctactg aaatctaact 4860
ttttacaaaa aattacgggc tgggcgcagt ggctcacgcc tgtaatccca gcactttggg 4920
aggctgcagc gggtggatca cttgaggtaa ggagttcaag accagaccat agtgaaaccg 4980
tgtctctaca aaaaaaatta gccaggtgtg gtggtgcatg cttgtaatcc cagctactca 5040
gaaggctgag gtgggagaat cccttgaacc cgggaagtgg aggctggagt aaaccatgat 5100
cgagttactg cactccagcc tgggtgacaa gagtgagact ctgtctccaa aaaaaaaaaa 5160
aaaaaaaaaa aaactggatt gcctggctct actccgggca cagcatgcag gcccagttct 5220
gctgctctgc tgtttgttct gctttcctcc acatattggc atcaccctct ggtgccaaga 5280
tggctgctgc attccaggca tcacatccag actcagaccc agagaagctg cccatcccta 5340
cctgggtgag cctttgtagg aacgagaaac cgcatccagc agcagaaacc tcacccagca 5400
gcgtcttttc cggtctcatt caccagcgcc gcccaccgct caaccaatcc ctggccaaaa 5460
gaatgggacc gcctggaagg ctggaccaaa caggacctgc cctctggggc tggggagagg 5520
cccagatgaa ggctgcagga caggatggac tcctagacct ctgttaccag cagtgactac 5580
ctctgtctgg gtggttggaa catgtttgaa ttttattcta agtactgtct acaagttctg 5640
caataaacct tgactcttct tttaataatg caaaa 5675

<210> SEQ ID NO 55
<211> LENGTH: 5693
<212> TYPE: DNA
<213> ORGANISM: Homo sapiens

<400> SEQUENCE: 55

```
agtcacttgt ctggagcttg aagaagtggg tattcccctt cccaccccag gcactggagg     60
agcggccccc cggggattcc aggacctgag ctccgggagc tggactcgca gcgaccgcgg    120
cagagcgagc gggcgccggg aagcgaggag acgcccgcgg gaggcccagc tgctcggagc    180
aactggcatg gcccgagcca tggccgccgc gtggccgctg ctgctggtgg cgctactggt    240
gctgtcctgg ccacccccag gaaccgggga cgtcgtcgtg caggcgccca cccaggtgcc    300
cggcttcttg ggcgactccg tgacgctgcc ctgctaccta caggtgccca acatggaggt    360
gacgcatgtg tcacagctga cttgggcgcg gcatggtgaa tctggcagca tggccgtctt    420
ccaccaaacg cagggcccca gctattcgga gtccaaacgg ctggaattcg tggcagccag    480
actgggcgcg gagctgcgga atgcctcgct gaggatgttc gggttgcgcg tagaggatga    540
aggcaactac acctgcctgt tcgtcacgtt cccgcagggc agcaggagcg tggatatctg    600
gctccgagtg cttgccaagc cccagaacac agacctgggc gggatgccca atacgagcca    660
ggtgccaggg ttcctgtctg gcacagtcac tgtcaccagc ctctggatat tggtgccctc    720
aagccaggtg gacggcaaga atgtgacctg caaggtggag cacgagagct ttgagaagcc    780
tcagctgctg actgtgaacc tcaccgtgta ctacccccca gaggtatcca tctctggcta    840
tgataacaac tggtaccttg gccasmmtga ggccaccctg acctgcgatg ctcgcagcaa    900
cccagagccc acaggctata attggagcac gaccatgggt cccctgccac cctttgctgt    960
ggcccagggc gcccagctcc tgatccgtcc tgtggacaaa ccaatcaaca caactttaat   1020
ctgcaacgtc accaatgccc taggagctcg ccaggcagaa ctgaccgtcc aggtcaaaga   1080
gggacctccc agtgagcact caggcatgtc ccgtaacgcc atcatcttcc tggttctggg   1140
aatcctggtt tttctgatcc tgctggggat cgggatttat ttctattggt ccaaatgttc   1200
ccgtgaggtc ctttggcact gtcatctgtg tccctcgagt acagagcatg ccagcgcctc   1260
agctaatggg catgtctcct attcagctgt gagcagagag aacagctctt cccaggatcc   1320
acagacagag ggcacaaggt gacagcgtcg ggactgagag gggagagaga ctggagctgg   1380
caaggacgtg ggcctccaga gttggacccg accccaatgg atgaagaccc cctccaaaga   1440
gaccagcctc cctccctgtg ccagacctca aaacgacggg ggcaggtgca agttcatagg   1500
tctccaagac caccctcctt tcatttgcta gaaggactca ctagactcag gaaagctgtt   1560
aggctcacag ttacagttta ttacagtaaa aggacagaga ttaagatcag caaagggagg   1620
aggtgcacag cacacgttcc acgacagatg aggcgacggc ttccatctgc cctctcccag   1680
tggagccata taggcagcac ctgattctca cagcaacatg tgacaacatg caagaagtac   1740
tgccaatact gccaaccaga gcagctcact cgagatcttt gtgtccagag ttttttgttt   1800
gtcttgagac agggtctggc tctgttggca gactagagta cagtggtgag atcacagttc   1860
attgcagcct tgacttctca acgccaagtc atcctcccac ctcagcctcc tgagtagcta   1920
tgactacagg tatgtgccac cacgtctggc taatcttttt attatttgta aagtcgaggt   1980
ttccctgtgt tgcccaggct ggtcttgaac tcttggctcc aagtgatact tctgccttgg   2040
cctcccaaag tgctgaatta agcagctcac catccacacg gctgacctca tacatcaagc   2100
caataccgtg tggcccaaga cccccaccat aaatcacatc attagcatga accacccaga   2160
gtggcccaag actccaagat cagctaccag gcaggatatt ccaagggctt agagatgaat   2220
gcccaggagc tgaggataaa gggcccgatc tttctttggg caaggttaag cctttactgc   2280
atagcagacc acacagaagg gtgtgggcca ccagagaatt ttggtaaaaa tttggcctct   2340
```

ggccttgagc ttctaaatct ctgtatccgt cagatctctg tggttacaag aaacagccac 2400
tgaccctggt caccagaggc tgcaattcag gccgcaagca gctgcctggg gggtgtccaa 2460
ggagcagaga aaactactag atgtgaactt gaagaaggtt gtcagctgca gccactttct 2520
gccagcatct gcagccactt tctgccagca tctgcagcca gcaagctggg actggcagga 2580
aataacccac aaaagaagca aatgcaattt ccaacacaag ggggaaggga tgcagggga 2640
ggcagcgctg cagttgctca ggacacgctc ctataggacc aagatggatg cgacccaaga 2700
cccaggaggc ccagctgctc agtgcaactg acaagttaaa aaggtctatg atcttgaggg 2760
cagacagcag aattcctctt ataaagaaaa ctgtttggga aaatacgttg agggagagaa 2820
gaccttgggc caagatgcta aatgggaatg caaagcttga gctgctctgc aagagaaaat 2880
aagcaggaca gaggatttgc tctggacaga gatggaagag ccgggaacag agaagtgtgg 2940
ggaagagata ggaaccagca ggatggcagg ggcaaagggc tcaagggtga ggaggccagt 3000
gggaccccac agagttgggg agataaagga acattggttg ctttggtggc acgtaagctc 3060
cttgtctgtc tccagcaccc agaatctcat taaagcttat ttattgtacc tccagcggct 3120
gtgtgcaatg gggtcttttg tggaaatcaa ggagcagaca ggtttcatgt gtactgtcac 3180
cacgtgggat ggaaccagag gcatggaagc aagacgctaa atgaagaggg ccataagggc 3240
tgggattccc aggcacctta ggaacagctt gtcttttttt ttttcctctc caaaaaaaat 3300
gtttaaggga cggtgtctcc tgtcacccag gctggagtgc aatggcacga tcatagctca 3360
ttgcagcctc taactccggg gctcaagcaa tcctcccacc tcagcctacc aagtagctgt 3420
gaccacagct gcccctcacc atgctaagct aattttttta attagatagt acataaacgt 3480
cccaaaatta gaagataaaa agacatgagg gatccattct aatttgtgtt tggagtgtaa 3540
tggtccagct ccattcttct gcacatggat atccagtttt acacaacact gtgaatgtaa 3600
tgaatgccac tgaatcatac actcaaaaat agctaaaatg gcaaattgtc tgttatctct 3660
ttttaaccac catttttgaa aattaattat accaaaaaac cattgaatag tgcactttat 3720
ttatttattt atttgtttat ttatttattt attttagaaa taagagtctc actttgttgc 3780
ccaggctgga gtgcagtggc gtgatcatgg ctcattgcag cctcgacctg ctgggctcgg 3840
gctatccttc catctcagcc tcccgagtag ctgggactat aggtgggcgc caccccacct 3900
ggctaaatct ctttttaact tttgtagaga taggcatctc gctatgttgc ctaggctggg 3960
ctggaactcc tgggctcaag tgctcctcct gccttggcct cccaaagcgc taggattaca 4020
gatgtgagcc accgcgccca ccctgaacct tacttttttt gctcagtttc tggtaattca 4080
gagaatgcct cctgagttgt tctacaccca cctcatattc catgggaggg ctgtacaggg 4140
ctttttttaac gaggcctcta aggacaggca tttgtatcct ttccagcctt tcactattac 4200
aatgttgtag tgaataactt tacacactgt catttatttt actttttttt ttttttattt 4260
tagagaaagg aatcttgcca tcttgcccag gctggtctca aattcctggg cccaaacaat 4320
cctcccgcct tggcctccta aagtactggg atttataggc ataagccacc gtgcctggcc 4380
aatgcacact gtcatttagc tcatgttaac acctgagtgt aggacacact cctggaggtg 4440
gaattgctgg gccaaagagt atgtttcttg tcattgtgat agatattgac aaatgaaccc 4500
tcacagaagt tgtgctgagt tctgttccca ccagcgacgt aggcgatgac ctttttctgg 4560
agggaggggg catccttgga gtccacagag ccaggaatgg agagtgggcc cagaattttg 4620
gtataggtgt tgtataaact tatagtaagg ttaagaaaac cgcaactatc cttatcagag 4680
acttggcggg gggcagggta tgatggagat cataaggagg ctaaaacact ccacaccctc 4740
cctctgcatt gctcctgcac gggagtcggg aatcttttca ggttgatacg atctcacctt 4800
gaggagctgt gaggtcccag aagcctctgg gttgcagatt gcttggggtg aaaatgtctg 4860
tgctactgaa atctaacttt ttacaaaaaa ttacgggctg ggcgcagtgg ctcacgcctg 4920
taatcccagc actttgggag gctgcagcgg gtggatcact tgaggtaagg agttcaagac 4980
cagaccatag tgaaaccgtg tctctacaaa aaaaattagc caggtgtggt ggtgcatgct 5040
tgtaatccca gctactcaga aggctgaggt gggagaatcc cttgaacccg ggaagtggag 5100
gctggagtaa accatgatcg agttactgca ctccagcctg ggtgacaaga gtgagactct 5160
gtctccaaaa aaaaaaaaaa aaaaaaaaaa actggattgc ctggctctac tccgggcaca 5220
gcatgcaggc ccagttctgc tgctctgctg tttgttctgc tttcctccac atattggcat 5280
caccctctgg tgccaagatg gctgctgcat tccaggcatc acatccagac tcagacccag 5340
agaagctgcc catccctacc tgggtgagcc tttgtaggaa cgagaaaccg catccagcag 5400
cagaaacctc acccagcagc gtcttttccg gtctcattca ccagcgccgc ccaccgctca 5460
accaatccct ggccaaaaga atgggaccgc ctggaaggct ggaccaaaca ggacctgccc 5520
tctggggctg gggagaggcc cagatgaagg ctgcaggaca ggatggactc ctagacctct 5580
gttaccagca gtgactacct ctgtctgggt ggttggaaca tgtttgaatt ttattctaag 5640
tactgtctac aagttctgca ataaaccttg actcttcttt taataatgca aaa 5693

<210> SEQ ID NO 56
<211> LENGTH: 5652
<212> TYPE: DNA
<213> ORGANISM: Homo sapiens

<400> SEQUENCE: 56
agtcacttgt ctggagcttg aagaagtggg tattcccctt cccaccccag gcactggagg 60
agcggccccc cggggattcc aggacctgag ctccgggagc tggactcgca gcgaccgcgg 120
cagagcgagc gggcgccggg aagcgaggag acgcccgcgg gaggcccagc tgctcggagc 180
aactggcatg gcccgagcca tggccgccgc gtggccgctg ctgctggtgg cgctactggt 240
gctgtcctgg ccacccccag gaaccgggga cgtcgtcgtg caggcgccca cccaggttac 300
aggtgcccaa catggaggtg acgcatgtgt cacagctgac ttgggcgcgg catggtgaat 360
ctggcagcat ggccgtcttc caccaaacgc agggccccag ctattcggag tccaaacggc 420
tggaattcgt ggcagccaga ctgggcgcgg agctgcggaa tgcctcgctg aggatgttcg 480
ggttgcgcgt agaggatgaa ggcaactaca cctgcctgtt cgtcacgttc ccgcagggca 540
gcaggagcgt ggatatctgg ctccgagtgc ttgccaagcc ccagaacaca gacctgggcg 600
ggatgcccaa tacgagccag gtgccagggt tcctgtctgg cacagtcact gtcaccagcc 660
tctggatatt ggtgccctca agccaggtgg acggcaagaa tgtgacctgc aaggtggagc 720
acgagagctt tgagaagcct cagctgctga ctgtgaacct caccgtgtac tacccccccag 780 aggtatccat ctctggctat gataacaact ggtaccttgg ccagaatgag gccaccctga 840
cctgcgatgc tcgcagcaac ccagagccca caggctataa ttggagcacg accatgggtc 900
ccctgccacc ctttgctgtg gcccagggcg cccagctcct gatccgtcct gtggacaaac 960
caatcaacac aactttaatc tgcaacgtca ccaatgccct aggagctcgc caggcagaac 1020
tgaccgtcca ggtcaaagag ggacctccca gtgagcactc aggcatgtcc cgtaacgcca 1080
tcatcttcct ggttctggga atcctggttt ttctgatcct gctggggatc gggatttatt 1140

```
tctattggtc caaatgttcc cgtgaggtcc tttggcactg tcatctgtgt ccctcgagta   1200
cagagcatgc cagcgcctca gctaatgggc atgtctccta ttcagctgtg agcagagaga   1260
acagctcttc ccaggatcca cagacagagg gcacaaggtg acagcgtcgg gactgagagg   1320
ggagagagac tggagctggc aaggacgtgg gcctccagag ttggacccga ccccaatgga   1380
tgaagacccc ctccaaagag accagcctcc ctccctgtgc cagacctcaa aacgacgggg   1440
gcaggtgcaa gttcataggt ctccaagacc accctccttt catttgctag aaggactcac   1500
tagactcagg aaagctgtta ggctcacagt tacagtttat tacagtaaaa ggacagagat   1560
taagatcagc aaagggagga ggtgcacagc acacgttcca cgacagatga ggcgacggct   1620
tccatctgcc ctctcccagt ggagccatat aggcagcacc tgattctcac agcaacatgt   1680
gacaacatgc aagaagtact gccaatactg ccaaccagag cagctcactc gagatctttg   1740
tgtccagagt tttttgtttg tcttgagaca gggtctggct ctgttggcag actagagtac   1800
agtggtgaga tcacagttca ttgcagcctt gacttctcaa cgccaagtca tcctcccacc   1860
tcagcctcct gagtagctat gactacaggt atgtgccacc acgtctggct aatcttttta   1920
ttatttgtaa agtcgaggtt tccctgtgtt gcccaggctg gtcttgaact cttggctcca   1980
agtgatactt ctgccttggc ctcccaaagt gctgaattaa gcagctcacc atccacacgg   2040
ctgacctcat acatcaagcc aataccgtgt ggcccaagac ccccaccata aatcacatca   2100
ttagcatgaa ccacccagag tggcccaaga ctccaagatc agctaccagg caggatattc   2160
caagggctta gagatgaatg cccaggagct gaggataaag ggcccgatct ttctttgggc   2220
aaggttaagc ctttactgca tagcagacca cacagaaggg tgtgggccac cagagaattt   2280
tggtaaaaat ttggcctctg gccttgagct tctaaatctc tgtatccgtc agatctctgt   2340
ggttacaaga aacagccact gaccctggtc accagaggct gcaattcagg ccgcaagcag   2400
ctgcctgggg ggtgtccaag gagcagagaa aactactaga tgtgaacttg aagaaggttg   2460
tcagctgcag ccactttctg ccagcatctg cagccacttt ctgccagcat ctgcagccag   2520
caagctggga ctggcaggaa ataacccaca aaagaagcaa atgcaatttc caacacaagg   2580
gggaagggat gcagggggag gcagcgctgc agttgctcag gacacgctcc tataggacca   2640
agatggatgc gacccaagac ccaggaggcc cagctgctca gtgcaactga caagttaaaa   2700
aggtctatga tcttgagggc agacagcaga attcctctta taaagaaaac tgtttgggaa   2760
aatacgttga gggagagaag accttgggcc aagatgctaa atgggaatgc aaagcttgag   2820
ctgctctgca agagaaaata agcaggacag aggatttgct ctggacagag atggaagagc   2880
cgggaacaga gaagtgtggg gaagagatag gaaccagcag gatggcaggg gcaaagggct   2940
caagggtgag gaggccagtg ggaccccaca gagttgggga gataaaggaa cattggttgc   3000
tttggtggca cgtaagctcc ttgtctgtct ccagcaccca gaatctcatt aaagcttatt   3060
tattgtacct ccagcggctg tgtgcaatgg ggtcttttgt ggaaatcaag gagcagacag   3120
gtttcatgtg tactgtcacc acgtgggatg gaaccagagg catggaagca agacgctaaa   3180
tgaagagggc cataagggct gggattccca ggcaccttag gaacagcttg tctttttttt   3240
tttcctctcc aaaaaaaatg tttaagggac ggtgtctcct gtcacccagg ctggagtgca   3300
atggcacgat catagctcat tgcagcctct aactccgggg ctcaagcaat cctcccacct   3360
cagcctacca agtagctgtg accacagctg cccctcacca tgctaagcta atttttttaa   3420
ttagatagta cataaacgtc ccaaaattag aagataaaaa gacatgaggg atccattcta   3480
```

```
atttgtgttt ggagtgtaat ggtccagctc cattcttctg cacatggata tccagtttta   3540
cacaacactg tgaatgtaat gaatgccact gaatcataca ctcaaaaata gctaaaatgg   3600
caaattgtct gttatctctt tttaaccacc atttttgaaa attaattata ccaaaaaacc   3660
attgaatagt gcactttatt tatttattta tttgtttatt tatttattta ttttagaaat   3720
aagagtctca ctttgttgcc caggctggag tgcagtggcg tgatcatggc tcattgcagc   3780
ctcgacctgc tgggctcggg ctatccttcc atctcagcct cccgagtagc tgggactata   3840
ggtgggcgcc accccacctg gctaaatctc tttttaactt ttgtagagat aggcatctcg   3900
ctatgttgcc taggctgggc tggaactcct gggctcaagt gctcctcctg ccttggcctc   3960
ccaaagcgct aggattacag atgtgagcca ccgcgcccac cctgaacctt actttttttg   4020
ctcagtttct ggtaattcag agaatgcctc ctgagttgtt ctacacccac ctcatattcc   4080
atgggagggc tgtacagggc ttttttaacg aggcctctaa ggacaggcat ttgtatcctt   4140
tccagccttt cactattaca atgttgtagt gaataacttt acacactgtc atttatttta   4200
cttttttttt tttttatttt agagaaagga atcttgccat cttgcccagg ctggtctcaa   4260
attcctgggc ccaaacaatc ctcccgcctt ggcctcctaa agtactggga tttataggca   4320
taagccaccg tgcctggcca atgcacactg tcatttagct catgttaaca cctgagtgta   4380
ggacacactc ctggaggtgg aattgctggg ccaaagagta tgtttcttgt cattgtgata   4440
gatattgaca aatgaaccct cacagaagtt gtgctgagtt ctgttcccac cagcgacgta   4500
ggcgatgacc tttttctgga gggagggggc atccttggag tccacagagc caggaatgga   4560
gagtgggccc agaattttgg tataggtgtt gtataaactt atagtaaggt taagaaaacc   4620
gcaactatcc ttatcagaga cttggcgggg ggcagggtat gatggagatc ataaggaggc   4680
taaaacactc cacaccctcc ctctgcattg ctcctgcacg ggagtcggga atcttttcag   4740
gttgatacga tctcaccttg aggagctgtg aggtcccaga agcctctggg ttgcagattg   4800
cttggggtga aaatgtctgt gctactgaaa tctaactttt tacaaaaaat tacgggctgg   4860
gcgcagtggc tcacgcctgt aatcccagca ctttgggagg ctgcagcggg tggatcactt   4920
gaggtaagga gttcaagacc agaccatagt gaaaccgtgt ctctacaaaa aaaattagcc   4980
aggtgtggtg gtgcatgctt gtaatcccag ctactcagaa ggctgaggtg ggagaatccc   5040
ttgaacccgg gaagtggagg ctggagtaaa ccatgatcga gttactgcac tccagcctgg   5100
gtgacaagag tgagactctg tctccaaaaa aaaaaaaaaa aaaaaaaaaa ctggattgcc   5160
tggctctact ccgggcacag catgcaggcc cagttctgct gctctgctgt ttgttctgct   5220
ttcctccaca tattggcatc accctctggt gccaagatgg ctgctgcatt ccaggcatca   5280
catccagact cagacccaga gaagctgccc atccctacct gggtgagcct ttgtaggaac   5340
gagaaaccgc atccagcagc agaaacctca cccagcagcg tcttttccgg tctcattcac   5400
cagcgccgcc caccgctcaa ccaatccctg gccaaaagaa tgggaccgcc tggaaggctg   5460
gaccaaacag gacctgccct ctggggctgg ggagaggccc agatgaaggc tgcaggacag   5520
gatggactcc tagacctctg ttaccagcag tgactacctc tgtctgggtg gttggaacat   5580
gtttgaattt tattctaagt actgtctaca agttctgcaa taaaccttga ctcttctttt   5640
aataatgcaa aa                                                       5652
```